United States Patent
Zhu et al.

(10) Patent No.: US 8,119,784 B2
(45) Date of Patent: Feb. 21, 2012

(54) DELTA-4 DESATURASE AND ITS USE IN MAKING POLYUNSATURATED FATTY ACIDS

(75) Inventors: Quinn Qun Zhu, West Chester, PA (US); Zhixiong Xue, Chadds Ford, PA (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 284 days.

(21) Appl. No.: 12/408,860

(22) Filed: Mar. 23, 2009

(65) Prior Publication Data

US 2009/0253188 A1  Oct. 8, 2009

Related U.S. Application Data

(60) Provisional application No. 61/041,716, filed on Apr. 2, 2008.

(51) Int. Cl.
C07H 21/04 (2006.01)
C12N 1/20 (2006.01)
C12N 5/10 (2006.01)

(52) U.S. Cl. .................. 536/23.2; 435/410; 435/254.11; 435/419

(58) Field of Classification Search .................. None
See application file for complete search history.

(56) References Cited

U.S. PATENT DOCUMENTS 7,087,432 B2 * 8/2006 Qiu et al. .................. 435/468

FOREIGN PATENT DOCUMENTS

| JP | 2005525780 T | 9/2005 |
| WO | 02/090493 | 11/2002 |
| WO | 02090493 A | 11/2002 |
| WO | 2004090123 A | 10/2004 |
| WO | 2007096387 A | 8/2007 |

OTHER PUBLICATIONS

Meyer et al., Biochemistry, 42(32): 9779-9788 (2003).
Tonon et al., FEBS J., 272(13): 3401-3412 (2005).
Pereira et al., Biochem. J., 384(2):357-366 (2004).

* cited by examiner

*Primary Examiner* — Elizabeth McElwain

(57) ABSTRACT

Described here are Δ4 desaturases that convert all-cis-7,10,13,16,19-docosapentaenoic acid ["DPA"; 22:5 ω-3] to docosahexaenoic acid ["DHA"; 22:6 ω-3], with secondary activity in converting docosatetraenoic acid ["DTA"; 22:4 ω-6] to all-cis-4,7,10,13,16-docosapentaenoic acid ["DPAn-6"; 22:5 ω-6]. Also, described here are isolated nuclei acid fragments and recombinant constructs comprising such fragments encoding Δ4 desaturases as well as methods of making long chain polyunsaturated fatty acids ["PUFAs"] using this Δ4 desaturase in oleaginous yeast.

15 Claims, 12 Drawing Sheets

Figure 1A:
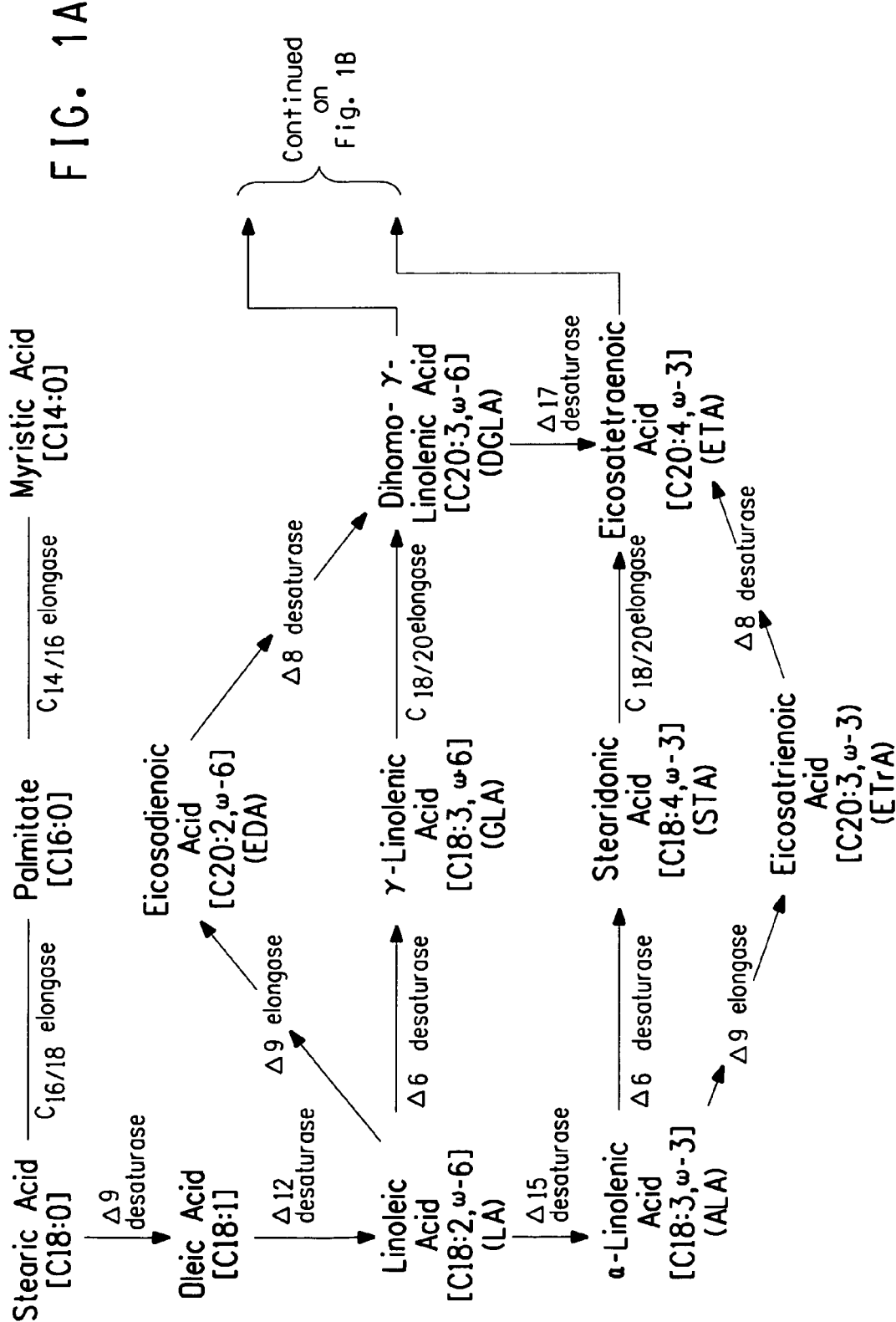

| | | 1 | | | 50 |
|---|---|---|---|---|---|
| SEQ ID NO:13 | (1) | MLVLFGNFYVKQYSQKNGKPENGATPENGAKPQPCENGTVEKRENDTANV | | | |
| SEQ ID NO:37 | (1) | ----------MGNGNLPASTAQLKSTSKPQ------------------- | | | |
| SEQ ID NO:38 | (1) | ----------------------------M-------------------- | | | |
| SEQ ID NO:42 | (1) | -------MPPSAASEG--------------------------------- | | | |

| | | 51 | | | 100 |
|---|---|---|---|---|---|
| SEQ ID NO:13 | (51) | RPTRPAGPPPATYDSLAVSGQGKERLFTTDEVRRHILPTDGWLTCHEG-- | | | |
| SEQ ID NO:37 | (21) | ---------------QQHEHRTISKSELAQHNTPKSAWCAVHSTP | | | |
| SEQ ID NO:38 | (2)  | -------------------TVGYDGEIPFEQVRAHNKPDDAWCAIHG-- | | | |
| SEQ ID NO:42 | (10) | -------------------GVAELRAAEVASYTRKAVDERPDLTIVG-- | | | |

| | | 101 | | | 150 |
|---|---|---|---|---|---|
| SEQ ID NO:13 | (100) | ---------------VYDVTDFLAKHPGGG--VITLGLGRDCTILIESYHP | | | |
| SEQ ID NO:37 | (51)  | ATDPSHSNNKQHAHLVLDITDFASRHPGGD-LILLASGKDASVLFETYHP | | | |
| SEQ ID NO:38 | (30)  | ---------------HVYDVTKFASVHPGGD-IILLAAGKDATVLYETYHV | | | |
| SEQ ID NO:42 | (38)  | ---------DAVYDAKAFRDEHPGAHFVSLFGGRDATEAFMEYHR | | | |

| | | 151 | | | 200 |
|---|---|---|---|---|---|
| SEQ ID NO:13 | (134) | AGRPDKVMEKYRIGTLQDP-------------------KTFYAWGESDFYPEL | | | |
| SEQ ID NO:37 | (100) | RGVPTSLIQKLQIGVMEE----------------EAFRDSFYSWTDSDFYTVL | | | |
| SEQ ID NO:38 | (65)  | RGVSDAVLRKYRIGKLPDGQGGANEKEKRTLSGLSSASYYTWNSDFYRVM | | | |
| SEQ ID NO:42 | (75)  | RAWPKARMSKFFVGSLDAS--------------EKP-TQADSAYLRL | | | |

| | | 201 | | | 250 |
|---|---|---|---|---|---|
| SEQ ID NO:13 | (168) | KRRALARLKEAGQARRGG--LGVKALLVLTLFFVSWYMWVA-----HKS | | | |
| SEQ ID NO:37 | (137) | KRRVVERLEERGLDRRGSKEIWIKALFLLVGFWYCLYKMYTTSDIDQYGI | | | |
| SEQ ID NO:38 | (115) | RERVVARLKERGKARRGYELWIKALLLLVGFWSSLCWMCT---LDPSFG | | | |
| SEQ ID NO:42 | (107) | CAEVNALLPK-GSGGFAPPSYWLKAAALVVAAVSIEGYMLLR-----GK | | | |

FIG. 2A

```
SEQ ID NO:13  (210)        FLWA-AVWGFAGSHVGLS QHDGNH GA FSRNTLVNRLAGWGMDLIGASST
SEQ ID NO:37  (187)        AIAYSIGMGTFAAFIGTC QHDGNH GA FAQNKLLNKLAGWTLDMIGASAF
SEQ ID NO:38  (162)        AILAAMSLGVFAAFVGTC QHDGNH GA FAQSRWVNKVAGWTLDMIGASGM
SEQ ID NO:42  (150)        TLLLSVFLGLVFAWIGLN QHDANH GA LSRHSVINYCLGYAQDWIGGNMV
                                           251                                        300

SEQ ID NO:13  (259)        VWEYQHVI GHHQYTN LVS--------DTLFSLPENDPDVFSSYPL
SEQ ID NO:37  (237)        TWELQHML GHHPYTN VLDGVEEERKERGEDVALEEKDQESDPDVFSSFPL
SEQ ID NO:38  (212)        TWEFQHAL GHHPYTN LIEEENGLQKVSGKKMDTKLADQESDPDVFSTYPM
SEQ ID NO:42  (200)        LWLQEHVV MHHLHTN DVD------------ADPDQKAHG-V
                                           301                                        350

SEQ ID NO:13  (296)        MRMHPDTAWQPHHRFQHLFAFPLFALMTISKVLTSDFAVCLSMKKGSIDC
SEQ ID NO:37  (287)        MRMHPHHTTSWYHKYQHLYAPPLFALMTLAKVFQQDFEVATSGRLYHIDA
SEQ ID NO:38  (262)        MRLHPWHQKRWYHRFQHIYGPFIFGEMTINKVVTQDVGVVFRKRLFQIDA
SEQ ID NO:42  (228)        LRLKPTDGWMPHHALQQLYILPGEAMYAFKLLFLDALELLAWRWEG--EK
                                           351                                        400

SEQ ID NO:13  (346)        SSRLVPLEGQLLFWGAKLANEFLLQIVLPCYLHGTAMGLALFSVAHLVSGE
SEQ ID NO:37  (337)        NVRYGSVWNVMRFWAMKVITMGYMMGLPIYFHGVLRGVGLFVIGHLACGE
SEQ ID NO:38  (312)        ECRYASPMYVARFWIMKALTVLYMVALPCYMQGPWHGLKLFAIAHFTCGE
SEQ ID NO:42  (276)        -ISPLARALFAPAVACKLGFWARFVALPLWLQPTVHTALCICATVCTGSF
                                           401                                        450
```

FIG. 2B

```
                                                                          500
SEQ ID NO:13  (396)  YLAICFIINHISESCEFMNTSFQTAAR------R---TEMLQAA
SEQ ID NO:37  (387)  LLATMFIVNHVIEGVSYGTKDLVGGASHGDEKKIVKPTTVLGDTPMEKTR
SEQ ID NO:38  (362)  VLATMFIVNHVIEGVSYASKDAVKGT------MAPPKTMHGVTPMNNTR
SEQ ID NO:42  (325)  YLAFFFFISHNFDGVGSVGPKGSLPR-----------------------

451                                                  550
SEQ ID NO:13  (431)  HQAAEAKK----------VKPTPPPNDWAVTQVQCCVNWRSGGVLANHLS
SEQ ID NO:37  (437)  EEALKSNSNNNKKKGEKNSVPSVPFNDWAAVQCQTSVNWSPGSWFWNHFS
SEQ ID NO:38  (405)  KEVEAEAS-----KSG--AVVKSVPLDDWAAVQCQTSANWSVGSWFWNHFS
SEQ ID NO:42  (351)  -----------------SATFVQRQVETSSNVGGYWLGVLN 501                                                  600
SEQ ID NO:13  (471)  GGLNHQIEHHLFPSISHANYPTIAPVVKEVCEEYGLPYKNYVTFWDAVCG
SEQ ID NO:37  (487)  GGLSHQIEHHLFPSICHTNYCHIQDVVESTCAEYGVPYQSESNLFVAYGK
SEQ ID NO:38  (449)  GGLNHQIEHHLFPGLSHETYYHIQDVVQSTCAEYGVPYQHEPSLWTAYWK
SEQ ID NO:42  (375)  GGLNFQIEHHLFPRLHHSYYAQIAPVVRTHIEKLGFKYRHFPTVGSNLSS

551
SEQ ID NO:13  (521)  MVQHLRLMGAPPVPTNGDKKS
SEQ ID NO:37  (537)  MISHLKFLGKAKCE-------
SEQ ID NO:38  (499)  MLEHLRRLGNEETHESWQRAA
SEQ ID NO:42  (425)  MLQHMGKMGTRPGAEKGGKAE

601
```

FIG. 2C

```
E1594D4  (SEQ ID NO:1)      1 ATG---CAGTCAACCAAGGCGGCCGACACCGCCGCTACCGACAAGAGTCT              50
E1594D4S (SEQ ID NO:3)    (1) ATGGCTCAGTCCACCAAGGCTGCCGACACTGCTGCCACCGACAAGTCTCT

E1594D4  (SEQ ID NO:1)   (48) CGACAAGAGAACCGCCTCATCTCTCGGGATGAGCTTCGTTCTCACAATGTCC           100
E1594D4S (SEQ ID NO:3)   (51) CGACAAGAACCGACTCATCTCTCCCGAGACGAGCTGCGTCTCACAACGTTC

E1594D4  (SEQ ID NO:1)   (98) CCCAGGATGCGTGGGCTGCTGTCCACGGGAGGGTCATCAACATCACGGAG            150
E1594D4S (SEQ ID NO:3)  (101) CCCAGGATGCCTGGGCTGCCGTCTCCACGGCCAGAGTCATCAACATTACCGAG

E1594D4  (SEQ ID NO:1)  (148) TTCGCCCCGACGTCATCCTGGCGGGCGACATCATCCTCCTTGCCGCAGGGAA            200
E1594D4S (SEQ ID NO:3)  (151) TTCGCCCCGACGGCATCCTGGTGGCGACATCATTCTGCTTGCCGCAGGAAA

E1594D4  (SEQ ID NO:1)  (198) GGATGCCACAGTCCTCTTCGAGACCTACCATCCCCGCGGTGTCCCCACCT            250
E1594D4S (SEQ ID NO:3)  (201) GGATGCCACCGTCCTCTTCGAGACTTACCATCCTCGAGGTGTTCCCACCT

E1594D4  (SEQ ID NO:1)  (248) CCATCCTCGACAAGCTCCAGGTGGGAAAGATGAAGGACGGGGAGCTGCCC            300
E1594D4S (SEQ ID NO:3)  (251) CGATCCTCGACAAGCTGCAGGTCGGCAAGATGAAGGACGAAGGAACTTCCC

E1594D4  (SEQ ID NO:1)  (298) TCCTCCTTCTACTCGTGGGATTCTGACTTTTACAAGACCCTGCGCCCG              350
E1594D4S (SEQ ID NO:3)  (301) TCCTCGTTCTACTCGTGGGATTCCGACTTTTACAAGACCCTGCGAGCTCG

FIG. 3A
```

```
E1594D4  (SEQ ID NO:1)    (348)  CGTTGTTGAGAGGTTGGACAAGCTCAACCTGCCGCGAAGGGAGGGTATG   400
E1594D4S (SEQ ID NO:3)    (351)  AGTGGTCGAGCGATTGGACAAGCTCAACCTGCCTCGAAGAGGTGGCTACG

E1594D4  (SEQ ID NO:1)    (398)  AGATCTGGGTCAAGGCAGTATTCCTCCTGGCAGGATTCTGGTTCAGCCTC   450
E1594D4S (SEQ ID NO:3)    (401)  AGATTGGGTCAAGGCAGTATTCCTCCTGGCTGGATTCTGGTTCAGCCTC

E1594D4  (SEQ ID NO:1)    (448)  TACAAGAGATGTCTGTGAACGAGACCTACTGGGCCGCATCGCTCTGGTCCGT   500
E1594D4S (SEQ ID NO:3)    (451)  TACAAGAGATGTCCGTCAACGAGACCTACTGGGCTGCCTCGCTGTGGTCCGT

E1594D4  (SEQ ID NO:1)    (498)  GTCCATGGGAGTGTTCGCCGCCTTCATCGGCACTTGCATCCAGCACGATG   550
E1594D4S (SEQ ID NO:3)    (501)  GTCTATGGGAGTCTTTGCTGCCTTCATCGGCACTTGCATTCAACACGATG

E1594D4  (SEQ ID NO:1)    (548)  GAAACCATGGCGCCTTCTGACCAGCCCGGCTCTGAACAAGGTGGCGGGC   600
E1594D4S (SEQ ID NO:3)    (551)  GAAACCACGGTGCCTTGCCTTCTCGACCAGCCCTGCTCTCAACAAGGTTGCAGGC

E1594D4  (SEQ ID NO:1)    (598)  TGGACTCTGGACATGATTGGGCGTCAGGTTTCACGTGGGAAATCCAACA   650
E1594D4S (SEQ ID NO:3)    (601)  TGGACTCTGGACATGATCGGTGCTTCTGGCTTTACATGGAGATTCAGCA

E1594D4  (SEQ ID NO:1)    (648)  TATGCTCGGCCATCATCCCTACACCAACGTTCTTGACGTGGACGAAGAAA   700
E1594D4S (SEQ ID NO:3)    (651)  TATGCTCGGACACCATCCCTACACCAACGTCCTGACGTGGACGAAGAGA
```

FIG. 3B

```
E1594D4  (SEQ ID NO:1)   701  AGAGGAAGGAAGCTGGCGACGACTGCCGATGGAAGACAAGGACCAGGAG  750
E1594D4S (SEQ ID NO:3)  (698) AGCGAAAGGAAGCTGGCGACGATTGTCCTATGGAGGACAAGGATCAGGAG

E1594D4  (SEQ ID NO:1)   751  TCCGACCCAGATGTCTTCTCCCTCTCCCTCATGGCATGCACCCATA      800
E1594D4S (SEQ ID NO:3)  (748) TCCGACCCAGATGTCTTCTTCTTCGTTTCCTCTCATGCGAATGCACCCCTA (751)

E1594D4  (SEQ ID NO:1)   801  CCACAAGGCTGAGTGGTACCATCGCTATCAGCACCTGTACGCGCCCGTTC  850
E1594D4S (SEQ ID NO:3)  (798) CCACAAGGCCGAGTGGTACCAGTATCAGCACCTGTACGCACCCGTTC     (801)

E1594D4  (SEQ ID NO:1)   851  TCTTCGCGTTCATGACGCTAGCCAAGTGTGTTCCAGCAGGATATCGAGTC  900
E1594D4S (SEQ ID NO:3)  (848) TCTTTGCTTTCATGACTCTTGCCAAGGTGTTCCAACAGACAGACATCGAAGTC (851)

E1594D4  (SEQ ID NO:1)   901  GCCACCACCCAGAGATTGTACCATATGCGATGCCAAGTGCCGATACAATTC  950
E1594D4S (SEQ ID NO:3)  (898) GCTACCACCTCAGCGACTGTACCACATCGACGCCAAGTGCCGATACAATTC (901)

E1594D4  (SEQ ID NO:1)   951  TATTCTGAAATGTCTTGCGCTTTTGGTCGATGAAGGTGCTTTCGATCGGAT 1000
E1594D4S (SEQ ID NO:3)  (948) CATTCTCAATGTCCTTCGGTTTTGGTTTGGTCGATGAAGGTGCTCTCCATCGGCT (951)

E1594D4  (SEQ ID NO:1)  1001  ATATGCTGGCTGTGCCCTGCTACTTCCACGGCATTCTTGGTGGCCTTGGC 1050
E1594D4S (SEQ ID NO:3)  (998) ACATGCTGGCTGTCCCTGCTACTTCCACGGAATCCTTGGTGGCCTTGGA (1001)
```

FIG. 3C

```
E1594D4  (SEQ ID NO:1)   (1048)  CTTTTCCTTATCGGCCACTTTGCCTGCGGTGAGCTTCTGGCGACCATGTT  1100
E1594D4S (SEQ ID NO:3)   (1051)  CTGTTTCTCATCGGCCACTTTGCCTTGCCTGTGAGAGCTTCTGGCAACCATGTT

E1594D4  (SEQ ID NO:1)   (1098)  CATTGTCAATCACGTCATTGAGGGAGTCTCCTTTGGCAAGAAGGGTGAAT  1150
E1594D4S (SEQ ID NO:3)   (1101)  CATTGTCAATCACGTCATCGAGGGTGTGTCCTTTGGCAAAAAGGGAGAAT

E1594D4  (SEQ ID NO:1)   (1148)  CGCTGGGACTTTCCAAGGACGTGGAGTTCAAGCCCACCACCGTTTCGGGC  1200
E1594D4S (SEQ ID NO:3)   (1151)  CTCTCGGTCTGTCTGTCCAAGGACGTGGAGTTCAAGCCTACAACCGTTTCTGGA

E1594D4  (SEQ ID NO:1)   (1198)  CGCACGCCCATGGAACAGAGACCCGTGCCGAAGCCAAGAAGGCGGCCAACGG  1250
E1594D4S (SEQ ID NO:3)   (1201)  CGAACTCCAATGGAGCCAGACCCGTGCCGAGGCCAAAAAGGCTGCCAATGG

E1594D4  (SEQ ID NO:1)   (1248)  CGGAAACGTGAAGGATGTCCCCTACAACGACTGGGCGGCCGTTCAATGCC  1300
E1594D4S (SEQ ID NO:3)   (1251)  AGGCAAACGTCAAGGATGTTCCCTACAACGACTGGGCTGCCGTTCAGTGTC

E1594D4  (SEQ ID NO:1)   (1298)  CGGAAACGAGTGTGAACTGGAGTCCTGGAGTCGTGGTTCTGGAATCACTTCAGC  1350
E1594D4S (SEQ ID NO:3)   (1301)  AAACGAGCGTCAACTGGTCTCCTGGATCGTGGTTCTGGAATCACTTCTCC

E1594D4  (SEQ ID NO:1)   (1348)  GGCGGTCTATCGCATCAGATTGAGCACCATCTTTCCCTAGCATTGCCA  1400
E1594D4S (SEQ ID NO:3)   (1351)  GGTGGCCCTCTCCCACCAGATCGAGCACCACCATCTCGTTTCCCAGCATTGTCA
```

FIG. 3D

```
                                                1450
E1594D4  (SEQ ID NO:1)  (1398)  CACCAATTACGCTCATATCCAAGACGTTGTCCAAAGACTTGCGAGGAGT
E1594D4S (SEQ ID NO:3)  (1401)  CACCAACTACGCTCACATCCAGGACGTTGTCCAGAAGACTTGCGAAGAGT
                                                1500
E1594D4  (SEQ ID NO:1)  (1448)  ASGGCGTTCCTTACCAAAGCGAGCCCTCTTTGTAYTCCGCCTATGGCAAG
E1594D4S (SEQ ID NO:3)  (1451)  ACGGTGTTCCTTACCAGTCCGAACCCTCTTTGTTCTCCGCCTATGGCAAG
                                                1548
E1594D4  (SEQ ID NO:1)  (1498)  ATGTTGAGCCATCTCAAGTACCTCGGAAACGAGAAGAAGGTGGCTTAG
E1594D4S (SEQ ID NO:3)  (1501)  ATGCTGTCTCATCTCAAGTACCTCGGAAACGAGAAAAAGTCGCTTAA
```

FIG. 3E

DELTA-4 DESATURASE AND ITS USE IN MAKING POLYUNSATURATED FATTY ACIDS

This application claims the benefit of priority of U.S. Provisional Application No. 61/041,716, filed Apr. 2, 2008, currently pending, and hereby incorporated herein by reference in its entirety.

FIELD OF THE INVENTION

This invention is in the field of biotechnology. More specifically, this invention pertains to the identification of nucleic acid fragments encoding a Δ4 fatty acid desaturase enzyme and the use of this desaturase in making long chain polyunsaturated fatty acids ["PUFAs"].

BACKGROUND OF THE INVENTION

The health benefits associated with polyunsaturated fatty acids ["PUFAs"], especially ω-3 and ω-6 PUFAs, have been well documented. In order to find ways to produce large-scale quantities of ω-3 and ω-6 PUFAs, researchers have directed their work toward the discovery of genes and the understanding of the encoded biosynthetic pathways that result in lipids and fatty acids.

A variety of different hosts including plants, algae, fungi, stramenopiles and yeast are being investigated as means for commercial PUFA production. Genetic engineering has demonstrated that the natural abilities of some hosts, even those natively limited to linoleic acid ["LA"; 18:2 ω-6] or α-linolenic acid ["ALA"; 18:3 ω-3] fatty acid production, can be substantially altered to result in high-level production of various long-chain ω-3/ω-6 PUFAs. Whether this is the result of natural abilities or recombinant technology, production of docosahexaenoic acid ["DHA"; 22:6 ω-3] from docosapentaenoic acid ["DPA"; 22:5 ω-3] may require expression of a Δ4 desaturase. More specifically, most Δ4 desaturase enzymes identified so far have the primary ability to convert DPA to DHA, with secondary activity in converting docosatetraenoic acid ["DTA"; 22:4 ω-6] to ω-6 docosapentaenoic acid ["DPAn-6"; 22:5 ω-6].

Based on the role Δ4 desaturase enzymes play in the synthesis of DHA, there has been considerable effort to identify and characterize these enzymes from various sources. Numerous Δ4 desaturases have been disclosed in both the open literature and the patent literature. Some examples include: *Euglena gracilis* (SEQ ID NO: 13; GenBank Accession No. AY278558; Meyer et al., *Biochemistry*, 42(32): 9779-9788 (2003)); *Thalassiosira pseudonana* (SEQ ID NO:37; GenBank Accession No. AAX14506; Tonon et al., *FEBS J.*, 272(13):3401-3412 (2005)); *Thraustochytrium aureum* (SEQ ID NO:14; GenBank Accession No. AAN75707); *Thraustochytrium* sp. (GenBank Accession No. CAD42496; U.S. Pat. No. 7,087,432); *Schizochytrium aggregatum* (SEQ ID NO:41; Int'l. App. Pub. No. WO 2002/090493); *Pavlova lutheri* (SEQ ID NO:42; GenBank Accession No. AAQ98793); and, *Isochrysis galbana* (SEQ ID NO:43; GenBank Accession No. AAV33631; Pereira et al., *Biochem. J.*, 384(2):357-366 (2004); Int'l. App. Pub. No. WO 2002/090493). There is need for the identification and isolation of additional genes encoding Δ4 desaturases that will be suitable for heterologous expression in a variety of host organisms for use in the production of ω-3/ω-6 fatty acids.

Applicants have solved the stated problem by isolating genes encoding Δ4 fatty acid desaturases from *Eutreptiella cf_gymnastica* CCMP1594.

SUMMARY OF THE INVENTION

Described herein are new genetic constructs encoding polypeptides having Δ4 desaturase activity, and their use in algae, bacteria, yeast, euglenoids, stramenopiles, fungi, plants and animals for the production of polyunsaturated fatty acids ["PUFAs"].

Described herein are isolated nucleic acid molecules selected from the group consisting of:
  (a) an isolated nucleotide sequence encoding a Δ4 desaturase enzyme selected from the group consisting of SEQ ID NO:2 and SEQ ID NO:4;
  (b) an isolated nucleotide sequence that hybridizes with (a) under the following hybridization conditions: 0.1×SSC, 0.1% SDS, 65° C. and washed with 2×SSC, 0.1% SDS followed by 0.1×SSC, 0.1% SDS; and,
  (c) an isolated nucleotide sequence that is completely complementary to (a) or (b).

Other isolated nucleic acid molecules described herein comprise a first nucleotide sequence encoding a Δ4 desaturase enzyme of at least 514 amino acids that has at least 68% identity based on the Clustal W method of alignment when compared to a polypeptide having the sequence as set forth in SEQ ID NO:2; or a second nucleotide sequence comprising the complement of the first nucleotide sequence.

Also described herein are genetic chimera of the nucleic acid molecules described herein and transformed host cells comprising them. In addition, described herein are methods for the production of docosahexaenoic acid is provided herein, comprising:
  a) providing a host cell comprising:
    (i) an isolated nucleotide molecule encoding a Δ4 desaturase polypeptide having at least 68% identity when compared to a polypeptide having the amino acid sequence as set forth in SEQ ID NO:2, based on the Clustal W method of alignment; and,
    (ii) a source of all-cis-7,10,13,16,19-docosapentaenoic acid (22:5, ω3);
  b) growing the host cell of step (a) under conditions wherein the nucleic acid fragment encoding the Δ4 desaturase polypeptide is expressed and the all-cis-7,10, 13,16,19-docosapentaenoic acid (22:5, ω3) is converted to docosahexaenoic acid; and,
  c) optionally recovering the docosahexaenoic acid of step (b).

Similarly, a method for the production of all-cis-4,7,10,13, 16-docosapentaenoic acid (22:5, ω-6) is provided, comprising:
  a) providing a host cell comprising:
    (i) an isolated nucleotide molecule encoding a Δ4 desaturase polypeptide having at least 68% identity when compared to a polypeptide having the amino acid sequence as set forth in SEQ ID NO:2, based on the Clustal W method of alignment; and,
    (ii) a source of docosatetraenoic acid;
  b) growing the host cell of step (a) under conditions wherein the nucleic acid fragment encoding the Δ4 desaturase polypeptide is expressed and the docosatetraenoic acid is converted to all-cis-4,7,10,13,16-docosapentaenoic acid (22:5, ω-6); and,
  c) optionally recovering the all-cis-4,7,10,13,16-docosapentaenoic acid (22:5, ω-6) of step (b).

Biological Deposits

The following biological material was made under the terms of the Budapest Treaty on the International Recognition of the Deposit of Microorganisms for the Purposes of Patent Procedure:

| Biological Material | Accession Number | Date of Deposit |
|---|---|---|
| *Yarrowia lipolytica* Y4127 | ATCC PTA-8802 | Nov. 29, 2007 |

As used herein, "ATCC" refers to the American Type Culture Collection International Depository Authority located at ATCC, 10801 University Blvd., Manassas, Va. 20110-2209, U.S.A. The listed deposit will be maintained in the indicated international depository for at least 30 years and will be made available to the public upon the grant of a patent disclosing it. The availability of a deposit does not constitute a license to practice the subject invention in derogation of patent rights granted by government action.

BRIEF DESCRIPTION OF THE DRAWINGS AND SEQUENCE LISTINGS

The invention can be more fully understood from the following detailed description and the accompanying sequence descriptions, which form a part of this application.

Figure 1B:
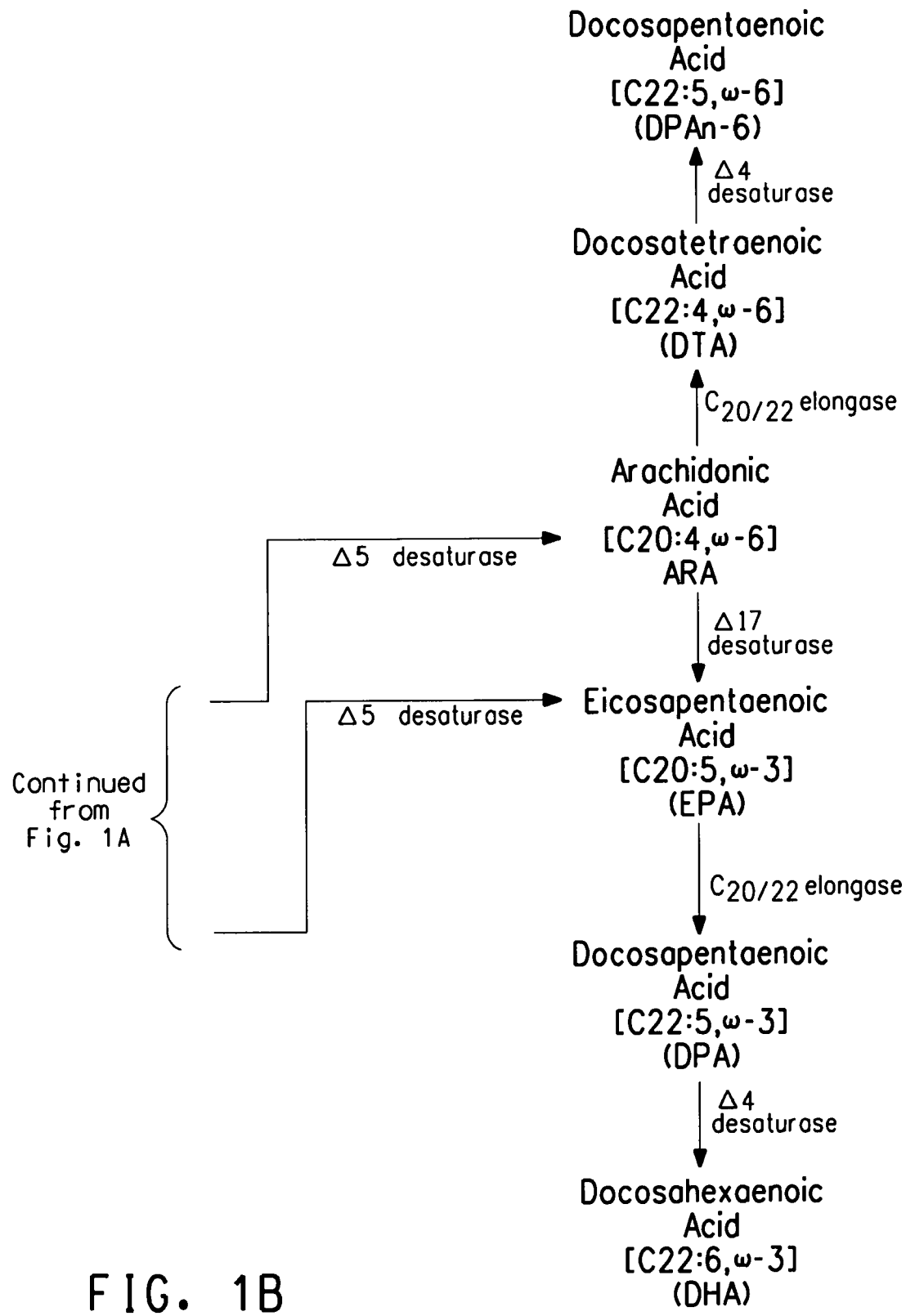

FIG. 1 includes FIG. 1A and FIG. 1B, which together illustrate the ω-3/ω-6 fatty acid biosynthetic pathway, and should be viewed together when considering the description of this pathway.

FIG. 2 includes FIG. 2A, FIG. 2B and FIG. 2C, which together show an alignment between and among the *Euglena gracilis* Δ4 fatty acid desaturase (SEQ ID NO:13; GenBank Accession No. AY278558), *Thalassiosira pseudonana* Δ4 fatty acid desaturase (SEQ ID NO:37; GenBank Accession No. AAX14506), *Thraustochytrium* sp. FJN-10 Δ4 fatty acid desaturase (SEQ ID NO:38; GenBank Accession No. AAZ43257), and *Pavlova lutheri* Δ4 fatty acid desaturase (SEQ ID NO:42; GenBank Accession No. AAQ98793), using a Clustal W analysis (MegAlign™ program of DNASTAR software). Degenerate primers were designed to correspond to the boxed regions.

FIG. 3 consists of FIG. 3A, FIG. 3B, FIG. 3C, FIG. 3D and FIG. 3E, which together show a comparison of the DNA sequence of the *Eutreptiella* cf_*gymnastica* CCMP1594 Δ4 desaturase gene (designated as E1594D4; SEQ ID NO:1) and the synthetic gene (designated as E1594D4S; SEQ ID NO:3) codon-optimized for expression in *Yarrowia lipolytica*.

Figure 4A:
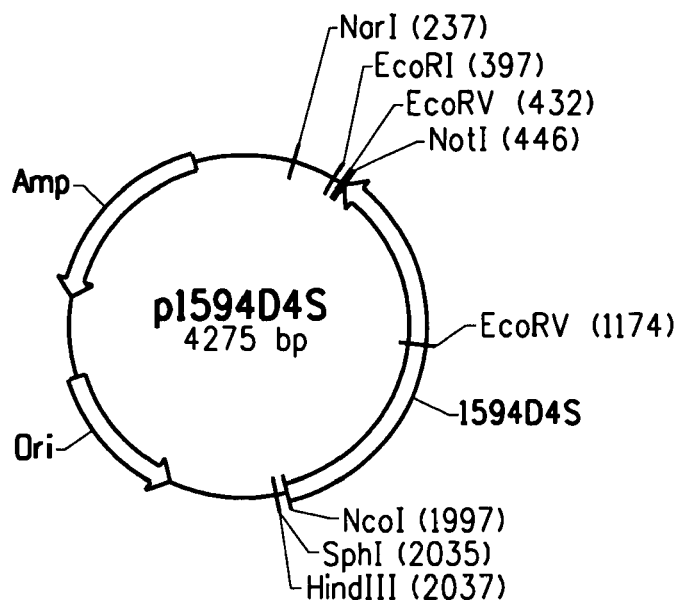
Figure 4B:
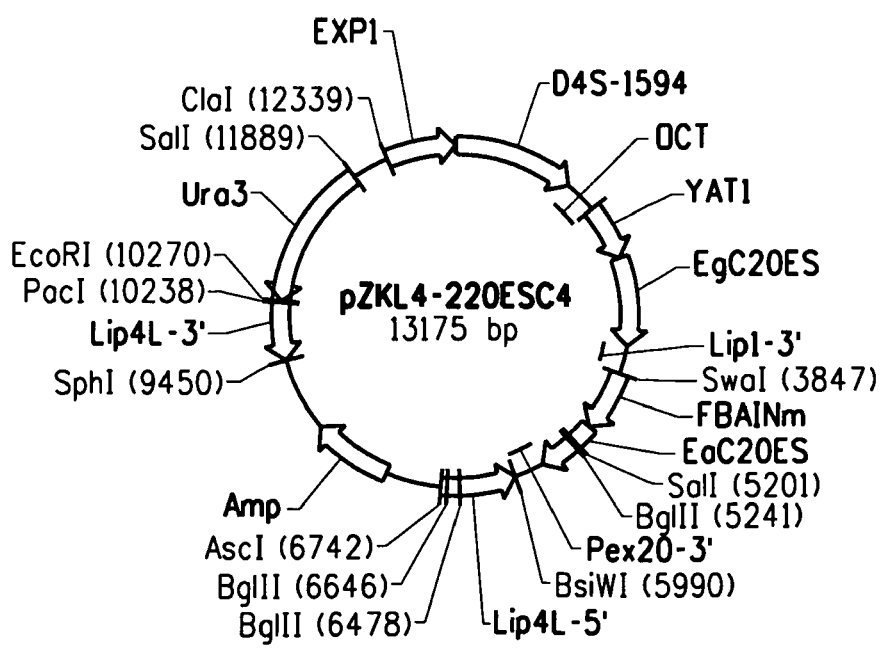

FIG. 4 provides plasmid maps for the following: (A) p1594D4S; and, (B) pZKL4-220ESC4.

Figure 5:
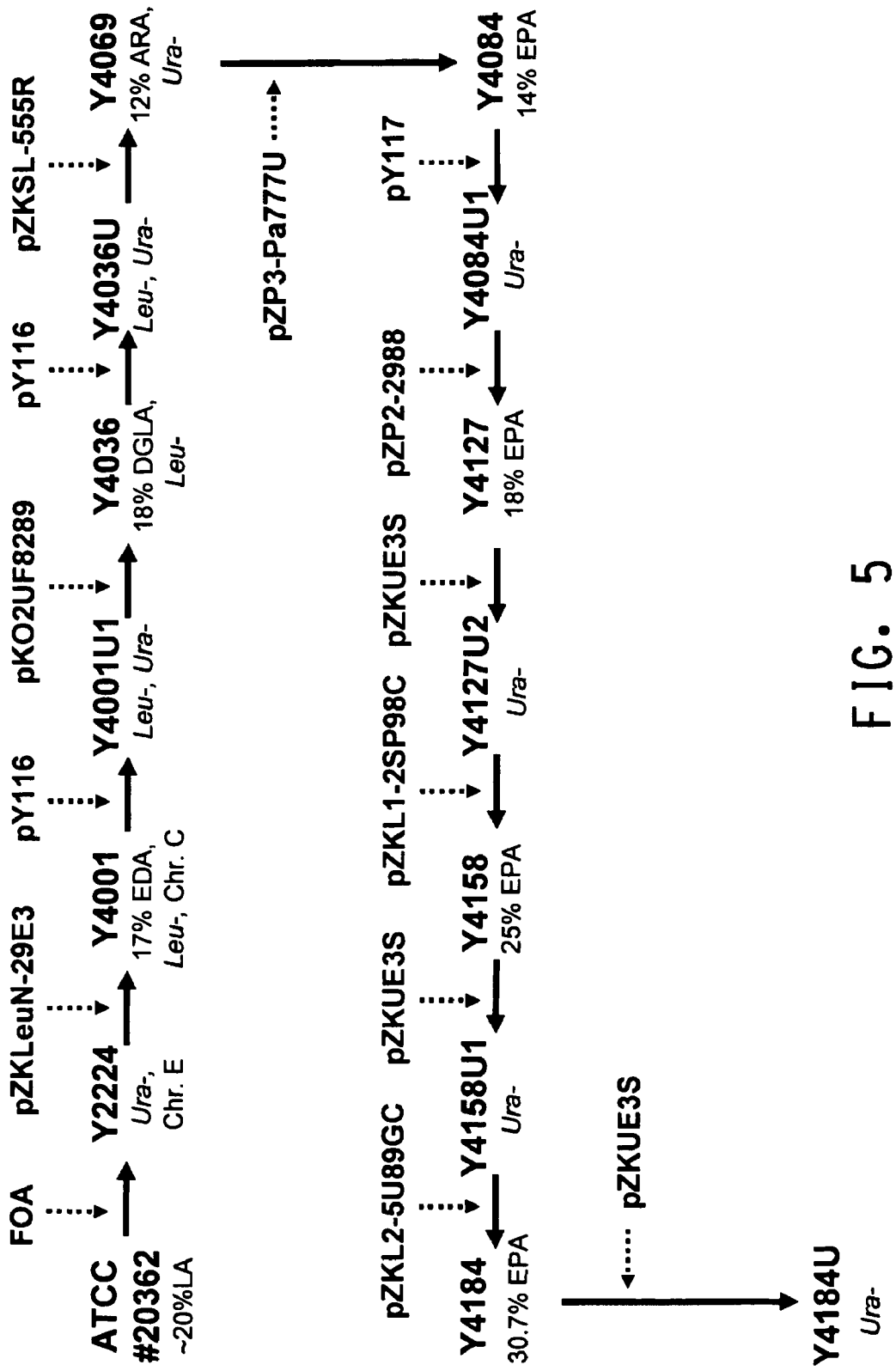

FIG. 5 diagrams the development of *Yarrowia lipolytica* strain Y4184U, producing about 31% EPA in the total lipid fraction.

The following sequences comply with 37 C.F.R. §1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1-9, 13-14, 37-47 are ORFs encoding genes or proteins (or portions thereof, or plasmids, as identified in Table 1.

TABLE 1

Summary Of Nucleic Acid And Protein SEQ ID Numbers

| Description and Abbreviation | Nucleic acid SEQ ID NO. | Protein SEQ ID NO. |
|---|---|---|
| *Eutreptiella* cf_*gymnastica* CCMP1594 Δ4 desaturase ("E1594D4") | 1 (1545 bp) | 2 (514 AA) |
| Synthetic Δ4 desaturase derived from *Eutreptiella* cf_*gymnastica* CCMP1594, codon-optimized for expression in *Yarrowia lipolytica* ("E1594D4S") | 3 (1548 bp) | 4 (515 AA) |
| *Eutreptiella* cf_*gymnastica* CCMP1594 Δ4 desaturase partial fragment | 5 (847 bp) | — |
| *Eutreptiella* cf_*gymnastica* CCMP1594 Δ4 desaturase E1594D4-5'-A fragment | 6 (359 bp) | — |
| *Eutreptiella* cf_*gymnastica* CCMP1594 Δ4 desaturase E1594D4-5'-B fragment | 7 (395 bp) | — |
| *Eutreptiella* cf_*gymnastica* CCMP1594 Δ4 desaturase E1594D4-3' fragment | 8 (873 bp) | — |
| *Eutreptiella* cf_*gymnastica* CCMP1594 Δ4 desaturase E1594D4-cDNA fragment | 9 (2070 bp) | — |
| *Euglena gracilis* Δ4 fatty acid desaturase (GenBank Accession No. AY278558) | — | 13 (541 AA) |
| *Thraustochytrium aureum* Δ4 desaturase (GenBank Accession No. AAN75707) | — | 14 (515 AA) |
| *Thalassiosira pseuduonana* Δ4 fatty acid desaturase (GenBank Accession No. AAX14506) | — | 37 (550 AA) |
| *Thraustochytrium* sp. FJN-10 Δ4 fatty acid desaturase (GenBank Accession No. AAZ43257) | — | 38 (519 AA) |
| Plasmid p1594D4S | 39 (4275 bp) | — |
| Plasmid pZKL4-220ESC4 | 40 (13175 bp) | — |
| *Schizochytrium aggregatum* Δ4 desaturase (Int'l. App. Pub. No. WO 2002/090493) | — | 41 (509 AA) |
| *Pavlova lutheri* Δ4 desaturase (GenBank Accession No. AAQ98793) | — | 42 (445 AA) |
| *Isochrysis galbana* Δ4 desaturase (GenBank Accession No. AAV33631) | — | 43 (433 AA) |
| Synthetic C20 elongase derived from *Euglena gracilis*, codon-optimized for expression in *Yarrowia lipolytica* (U.S. Pat. Appl. Pub. No. 2008-0254191) ("EgC20ES") | 44 (912 bp) | 45 (303 AA) |
| Synthetic C20 elongase derived from *Euglena anabaena*, codon-optimized for expression in *Yarrowia lipolytica* (U.S. Pat. Appl. Pub. No. 2008-0254191) ("EaC20ES") | 46 (900 bp) | 47 (299 AA) |

SEQ ID NOs:10-12 correspond to SMART™ IV oligonucleotide primer, CDSIII/3' PCR primer and 5' CDSIII PCR primer, respectively, used for *Eutreptiella* cf_*gymnastica* CCMP1594 cDNA synthesis.

SEQ ID NOs:15-17 correspond to degenerate oligonucleotide primers D4-F1, D4-F2 and D4-F3, respectively, all of which encode the peptide set forth in SEQ ID NO:18.

SEQ ID NO:19 corresponds to degenerate oligonucleotide primer D4-F4, which encodes the peptide set forth in SEQ ID NO:20.

SEQ ID NO:21 corresponds to degenerate oligonucleotide primer D4-F5, which encodes the peptide set forth in SEQ ID NO:22.

SEQ ID NOs:23-25 correspond to degenerate oligonucleotide primers D4-F6, D4-F7 and D4-F8, respectively, all of which encode the peptide set forth in SEQ ID NO:26.

SEQ ID NOs:27 and 28 correspond to degenerate oligonucleotide primers D4-R1 and D4-R2, both of which encode the peptide set forth in SEQ ID NO:29.

SEQ ID NOs:30-34 correspond to primers 1594D4-5-1, 1594D4-5-2, DNR CDS 5-2, 1594D4-5-4 and 1594D4-5-5, respectively, used to amplify the 5' coding region of the *Eutreptiella* cf_*gymnastica* CCMP1594 Δ4 desaturase gene.

SEQ ID NOs:35 and 36 correspond to primers 1594D4-3-1 and 1594D4-3-2, respectively, used to amplify the 3' coding region of the *Eutreptiella* cf_*gymnastica* CCMP1594 Δ4 desaturase gene.

DETAILED DESCRIPTION OF THE INVENTION

Applicants have identified a novel *Eutreptiella* cf_*gymnastica* CCMP1594 Δ4 desaturase enzyme and gene encoding the same that may be used for the manipulation of biochemical pathways for the production of healthful PUFAs. Thus, the subject invention finds many applications.

PUFAs, or derivatives thereof, are used as dietary substitutes, or supplements, particularly infant formulas, for patients undergoing intravenous feeding or for preventing or treating malnutrition. Alternatively, the purified PUFAs and derivatives thereof may be incorporated into cooking oils, fats or margarines and ingested as part of a consumer's typical diet, thereby giving the consumer desired dietary supplementation. Further, PUFAs may also be incorporated into infant formulas, nutritional supplements or other food products and may find use as anti-inflammatory or cholesterol lowering agents. Optionally, the compositions may be used for pharmaceutical use, either human or veterinary.

DEFINITIONS

In this disclosure, a number of terms and abbreviations are used. The following definitions are provided.

"Open reading frame" is abbreviated as "ORF".
"Polymerase chain reaction" is abbreviated as "PCR".
"American Type Culture Collection" is abbreviated as "ATCC".
"Polyunsaturated fatty acid(s)" is abbreviated as "PUFA(s)".
"Triacylglycerols" are abbreviated as "TAGs".
"Total fatty acids" are abbreviated as "TFAs".
"Dry cell weight" is abbreviated as "DCW".

The term "invention" or "present invention" as used herein is not meant to be limiting but applies generally to any of the inventions in the claims or described herein.

The term "fatty acids" refers to long chain aliphatic acids (alkanoic acids) of varying chain lengths, from about $C_{12}$ to $C_{22}$, although both longer and shorter chain-length acids are known. The predominant chain lengths are between $C_{16}$ and $C_{22}$. The structure of a fatty acid is represented by a simple notation system of "X:Y", where X is the total number of carbon ["C"] atoms in the particular fatty acid and Y is the number of double bonds. Additional details concerning the differentiation between "saturated fatty acids" versus "unsaturated fatty acids", "monounsaturated fatty acids" versus "polyunsaturated fatty acids" ["PUFAs"], and "omega-6 fatty acids" ["ω-6" or "n-6"] versus "omega-3 fatty acids" ["ω-3" or "n-3"] are provided in U.S. Pat. No. 7,238,482, which is hereby incorporated herein by reference.

Nomenclature used to describe PUFAs herein is given in Table 2. In the column titled "Shorthand Notation", the omega-reference system is used to indicate the number of carbons, the number of double bonds and the position of the double bond closest to the omega carbon, counting from the omega carbon, which is numbered 1 for this purpose. The remainder of the Table summarizes the common names of ω-3 and ω-6 fatty acids and their precursors, the abbreviations that are used throughout the specification and the chemical name of each compound.

TABLE 2

Nomenclature of Polyunsaturated Fatty Acids And Precursors

| Common Name | Abbreviation | Chemical Name | Shorthand Notation |
|---|---|---|---|
| Myristic | — | tetradecanoic | 14:0 |
| Palmitic | Palmitate | hexadecanoic | 16:0 |
| Palmitoleic | — | 9-hexadecenoic | 16:1 |
| Stearic | — | octadecanoic | 18:0 |
| Oleic | — | cis-9-octadecenoic | 18:1 |
| Linoleic | LA | cis-9,12-octadecadienoic | 18:2 ω-6 |
| ☐Linolenic | GLA | cis-6,9,12-octadecatrienoic | 18:3 ω-6 |
| Eicosadienoic | EDA | cis-11,14-eicosadienoic | 20:2 ω-6 |
| Dihomo-☐-Linolenic | DGLA | cis-8,11,14-eicosatrienoic | 20:3 ω-6 |
| Arachidonic | ARA | cis-5,8,11,14-eicosatetraenoic | 20:4 ω-6 |
| ☐Linolenic | ALA | cis-9,12,15-octadecatrienoic | 18:3 ω-3 |
| Stearidonic | STA | cis-6,9,12,15-octadecatetraenoic | 18:4 ω-3 |
| Eicosatrienoic | ETrA | cis-11,14,17-eicosatrienoic | 20:3 ω-3 |
| Sciadonic | SCI | cis-5,11,14-eicosatrienoic | 20:3b ω-6 |
| Juniperonic | JUP | cis-5,11,14,17-eicosatetraenoic | 20:4b ω-3 |
| Eicosa-tetraenoic | ETA | cis-8,11,14,17-eicosatetraenoic | 20:4 ω-3 |
| Eicosa-pentaenoic | EPA | cis-5,8,11,14,17-eicosapentaenoic | 20:5 ω-3 |
| Docosatrienoic | DRA | cis-10,13,16-docosatrienoic | 22:3 ω-6 |
| Docosa-tetraenoic | DTA | cis-7,10,13,16-docosatetraenoic | 22:4 ω-6 |
| Docosa-pentaenoic | DPAn-6 | cis-4,7,10,13,16-docosapentaenoic | 22:5 ω-6 |
| Docosa-pentaenoic | DPA | cis-7,10,13,16,19-docosapentaenoic | 22:5 ω-3 |
| Docosa-hexaenoic | DHA | cis-4,7,10,13,16,19-docosahexaenoic | 22:6 ω-3 |

Although the ω-3/ω-6 PUFAs listed in Table 2 are the most likely to be accumulated in the oil fractions of oleaginous yeast using the methods described herein, this list should not be construed as limiting or as complete.

The term "total lipid fraction" of cells herein refers to all esterified fatty acids of the cell. Various subfractions within the total lipid fraction can be isolated, including the triacylglycerol ["oil"] fraction, phosphatidylcholine fraction and the phosphatidyletanolamine fraction, although this is by no means inclusive of all sub-fractions.

The terms "triacylglycerols" ["TAGs"] and "oil" are interchangeable and refer to neutral lipids composed of three fatty acyl residues esterified to a glycerol molecule. TAGs can contain long chain PUFAs, as well as shorter saturated and unsaturated fatty acids and longer chain saturated fatty acids. The TAG fraction of cells is also referred to as the "oil fraction", and "oil biosynthesis" generically refers to the synthesis of TAGs in the cell. The oil or TAG fraction is a subfraction of the total lipid fraction, although also it constitutes a major part of the total lipid content, measured as the weight of total fatty acids in the cell as a percent of the dry cell weight [see below], in oleaginous organisms. The fatty acid composition in the oil ["TAG"] fraction and the fatty acid composition of the total lipid fraction are generally similar. Thus, an increase or decrease in the concentration of PUFAs in the total lipid fraction will correspond with an increase or decrease in the concentration of PUFAs in the oil ["TAG"] fraction, and vice versa.

The term "total fatty acids" ["TFAs"] herein refer to the sum of all cellular fatty acids that can be derivitized to fatty acid methyl esters ["FAMEs"] by the base transesterification method (as known in the art) in a given sample, which may be the total lipid fraction or the oil fraction, for example. Thus, total fatty acids include fatty acids from neutral and polar lipid fractions, including the phosphatidylcholine fraction, the phosphatidyletanolamine fraction and the diacylglycerol, monoacylglycerol and triacylglycerol ["TAG or oil"] fractions but not free fatty acids.

The term "total lipid content" of cells is a measure of TFAs as a percent of the dry cell weight ["DCW"]. Thus, total lipid content ["TFAs % DCW"] is equivalent to, e.g., milligrams of total fatty acids per 100 milligrams of DCW.

Generally, the concentration of a fatty acid is expressed herein as a weight percent of TFAs ["% TFAs"], e.g., milligrams of the given fatty acid per 100 milligrams of TFAs. Unless otherwise specifically stated in the disclosure herein, reference to the percent of a given fatty acid with respect to total lipids is equivalent to concentration of the fatty acid as % TFAs, e.g., % DHA of total lipids is equivalent to DHA % TFAs.

In some cases, it is useful to express the content of a given fatty acid(s) in a cell as its percent of the dry cell weight ["% DCW"]. Thus, for example, docosahexaenoic acid % DCW would be determined according to the following formula: (docosahexaenoic acid % TFAs)*(TFA % DCW)]/100.

The terms "lipid profile" and "lipid composition" are interchangeable and refer to the amount of an individual fatty acid contained in a particular lipid fraction, such as in the total lipid fraction or the oil ["TAG"] fraction; wherein the amount is expressed as a percent of TFAs. The sum of each individual fatty acid present in the mixture should be 100.

A metabolic pathway, or biosynthetic pathway, in a biochemical sense, can be regarded as a series of chemical reactions occurring within a cell, catalyzed by enzymes, to achieve either the formation of a metabolic product to be used or stored by the cell, or the initiation of another metabolic pathway, which is termed "flux generating step". Many of these pathways are elaborate, and involve a step by step modification of the initial substance to shape it into a product having the exact chemical structure desired.

The term "PUFA biosynthetic pathway" refers to a metabolic process that converts oleic acid to ω-6 fatty acids such as LA, EDA, GLA, DGLA, ARA, DRA, DTA and DPAn-6 and ω-3 fatty acids such as ALA, STA, ETrA, ETA, EPA, DPA and DHA. This process is well described in the literature. See e.g., Int'l. App. Pub. No. WO 2006/052870. Briefly, this process involves elongation of the carbon chain through the addition of carbon atoms and desaturation of the elongated molecule through the addition of double bonds, via a series of special elongation and desaturation enzymes termed "PUFA biosynthetic pathway enzymes" that are present in the endoplasmic reticulum membrane. More specifically, "PUFA biosynthetic pathway enzymes" refer to any of the following enzymes (and genes which encode said enzymes) associated with the biosynthesis of a PUFA, including: a Δ9 elongase, a $C_{14/16}$ elongase, a $C_{16/18}$ elongase, a $C_{18/20}$ elongase, a $C_{20/22}$ elongase. a Δ4 desaturase, a Δ5 desaturase, a Δ6 desaturase, a Δ8 desaturase, Δ9 desaturase, a Δ12 desaturase, a Δ5 desaturase and/or a Δ17 desaturase. The term "ω-3/ω-6 fatty acid biosynthetic pathway" refers to a set of genes which, when expressed under the appropriate conditions encode enzymes that catalyze the production of either or both ω-3 and ω-6 fatty acids. Typically the genes involved in the ω-3/ω-6 fatty acid biosynthetic pathway encode PUFA biosynthetic pathway enzymes. A representative pathway is illustrated in FIG. 1, providing for the conversion of myristic acid through various intermediates to DHA, which demonstrates how both ω-3 and ω-6 fatty acids may be produced from a common source. The pathway is naturally divided into two portions, such that one portion generates only ω-3 fatty acids and the other portion, only ω-6 fatty acids. That portion that only generates only ω-3 fatty acids is referred to herein as the ω-3 fatty acid biosynthetic pathway, whereas that portion that generates only ω-6 fatty acids is referred to herein as the ω-6 fatty acid biosynthetic pathway.

The term "functional" as used herein relating to the ω-3/ω-6 fatty acid biosynthetic pathway, means that some (or all) of the genes in the pathway express active enzymes, resulting in in vivo catalysis or substrate conversion. It should be understood that "ω-3/ω-6 fatty acid biosynthetic pathway" or "functional ω-3/ω-6 fatty acid biosynthetic pathway" does not imply that all of the genes listed in the above paragraph are required, as a number of fatty acid products require only the expression of a subset of the genes of this pathway.

The term "ω6 desaturase/ω6 elongase pathway" refers to a PUFA biosynthetic pathway that minimally includes at least one ω6 desaturase and at least one $C_{18/20}$ elongase, thereby enabling biosynthesis of DGLA and/or ETA from LA and ALA, respectively, with GLA and/or STA as intermediate fatty acids. With expression of other desaturases and elongases, ARA, DTA, DPAn-6, EPA, DPA and DHA may also be synthesized.

The term "Δ9 elongase/Δ8 desaturase pathway" refers to a PUFA biosynthetic pathway that minimally includes at least one Δ9 elongase and at least one Δ8 desaturase, thereby enabling biosynthesis of DGLA and/or ETA from LA and ALA, respectively, with EDA and/or ETrA as intermediate fatty acids. With expression of other desaturases and elongases, ARA, DTA, DPAn-6, EPA, DPA and DHA may also be synthesized.

The term "intermediate fatty acid" refers to any fatty acid produced in a fatty acid metabolic pathway that can be further converted to an intended product fatty acid in this pathway by the action of other metabolic pathway enzymes. For instance, when EPA is produced using the Δ9 elongase/Δ8 desaturase pathway, EDA, ETrA, DGLA, ETA and ARA can be produced and are considered "intermediate fatty acids" since these fatty acids can be further converted to EPA via action of other metabolic pathway enzymes.

The term "desaturase" refers to a polypeptide that can desaturate adjoining carbons in a fatty acid by removing a hydrogen from one of the adjoining carbons and thereby introducing a double bond between them. Desaturation produces a fatty acid or precursor of interest. Despite use of the omega-reference system throughout the specification to refer to specific fatty acids, it is more convenient to indicate the activity of a desaturase by counting from the carboxyl end of the substrate using the delta-system. Of particular interest herein are Δ4 desaturases that catalyze the conversion of the substrate fatty acid, DPA, to DHA and/or or the conversion of the substrate fatty acid, DTA, to DPAn-6. Other desaturases include: 1) Δ17 desaturases that desaturate a fatty acid between the $17^{th}$ and $18^{th}$ carbon atom numbered from the carboxyl-terminal end of the molecule and which, for example, catalyze the conversion of the substrate fatty acid, ARA, to EPA and/or the conversion of the substrate fatty acid, DGLA, to ETA; 2) Δ6 desaturases that catalyze the conversion of the substrate fatty acid, LA, to GLA and/or the conversion of the substrate fatty acid, ALA, to STA; 3) Δ12 desaturases that catalyze the conversion of the substrate fatty acid, oleic acid, to LA; 4) Δ15 desaturases that catalyze the conversion of the substrate fatty acid, LA, to ALA and/or the conversion of the substrate fatty acid, GLA, to STA; 5) Δ5 desaturases that catalyze the conversion of the substrate fatty acid, DGLA, to ARA and/or the conversion of the substrate fatty acid, ETA, to EPA; 6) Δ8 desaturases that catalyze the conversion of the substrate fatty acid, EDA, to DGLA and/or the conversion of the substrate fatty acid, ETrA, to ETA; and, 7) Δ9 desaturases that catalyze the conversion of the substrate fatty acid, palmitate, to palmitoleic acid (16:1) and/or the conversion of the substrate fatty acid, stearic acid, to oleic acid. In the art, Δ15 and Δ17 desaturases are also occasionally referred to as "omega-3 desaturases", "w-3 desaturases", and/ or "ω-3 desaturases", based on their ability to convert ω-6 fatty acids into their ω-3 counterparts (e.g., conversion of LA into ALA and ARA into EPA, respectively). It may be desirable to empirically determine the specificity of a particular fatty acid desaturase by transforming a suitable host with the gene for the fatty acid desaturase and determining its effect on the fatty acid profile of the host.

The term "E1594D4" refers to a Δ4 desaturase enzyme (SEQ ID NO:2) isolated from *Eutreptiella cf_gymnastica* CCMP1594, encoded by SEQ ID NO:1 herein. Similarly, the term "E1594D4S" refers to a synthetic Δ4 desaturase derived from *Eutreptiella cf_gymnastica* CCMP1594 that is codon-optimized for expression in *Yarrowia lipolytica* (i.e., SEQ ID NOs:3 and 4).

The terms "conversion efficiency" and "percent substrate conversion" refer to the efficiency by which a particular enzyme, such as a desaturase, can convert substrate to product. The conversion efficiency is measured according to the following formula: ([product]/[substrate+ product])*100, where 'product' includes the immediate product and all products in the pathway derived from it.

The term "elongase" refers to a polypeptide that can elongate a fatty acid carbon chain to produce an acid that is 2 carbons longer than the fatty acid substrate that the elongase acts upon. This process of elongation occurs in a multi-step mechanism in association with fatty acid synthase, as described in Int'l App. Pub. No. WO 2005/047480. Examples of reactions catalyzed by elongase systems are the conversion of GLA to DGLA, ARA to DTA, STA to ETA and EPA to DPA. In general, the substrate selectivity of elongases is somewhat broad but segregated by both chain length and the degree and type of unsaturation. For example, a $C_{14/16}$ elongase utilizes a $C_{14}$ substrate e.g., myristic acid; a $C_{16/18}$ elongase utilizes a $C_{16}$ substrate e.g., palmitate; a $C_{18/20}$ elongase [also known as a Δ6 elongase as the terms can be used interchangeably] utilizes a $C_{18}$ substrate e.g., GLA, STA; and, a $C_{20/22}$ elongase [also known as a $C_{20}$ elongase as the terms can be used interchangeably] utilizes a $C_{20}$ substrate e.g., ARA, EPA. In like manner, a Δ9 elongase is able to catalyze the conversion of LA and ALA to EDA and ETrA, respectively.

It is important to note that some elongases have broad specificity and thus a single enzyme may be capable of catalyzing several elongase reactions. For example, a single enzyme may thus act as both a $C_{16/18}$ elongase and a $C_{18/20}$ elongase. It may be desirable to empirically determine the specificity of a fatty acid elongase by transforming a suitable host with the gene for the fatty acid elongase and determining its effect on the fatty acid profile of the host.

The term "oleaginous" refers to those organisms that tend to store their energy source in the form of lipid (Weete, In: Fungal Lipid Biochemistry, $2^{nd}$ Ed., Plenum, 1980). The term "oleaginous yeast" refers to those microorganisms classified as yeasts that can make oil, that is, TAGs. Generally, the cellular oil or TAG content of oleaginous microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.*, 57:419-25 (1991)). It is not uncommon for oleaginous microorganisms to accumulate in excess of about 25% of their dry cell weight as oil. Examples of oleaginous yeast include, but are no means limited to, the following genera: *Yarrowia, Candida, Rhodotorula, Rhodosporidium, Cryptococcus, Trichosporon* and *Lipomyces*.

The term "Euglenophyceae" refers to a group of unicellular colorless or photosynthetic flagellates ["euglenoids"] found living in freshwater, marine, soil and parasitic environments. The class is characterized by solitary unicells, wherein most are free-swimming and have two flagella, one of which may be nonemergent, arising from an anterior invagination known as a reservoir. Photosynthetic euglenoids contain one to many chloroplasts, which vary from minute disks to expanded plates or ribbons. Colorless euglenoids depend on osmotrophy or phagotrophy for nutrient assimilation. About 1000 species have been described and classified into about 40 genera and 6 orders. Examples of Euglenophyceae include, but are no means limited to, the following genera: *Euglena, Eutreptiella* and *Tetruetreptia*.

As used herein the term "biomass" refers specifically to spent or used yeast cellular material from the fermentation of a recombinant production host producing PUFAs in commercially significant amounts, wherein the preferred production host is a recombinant strain of the oleaginous yeast, *Yarrowia lipolytica*. The biomass may be in the form of whole cells, whole cell lysates, homogenized cells, partially hydrolyzed cellular material, and/or partially purified cellular material e.g., microbially produced oil.

As used herein, the terms "isolated nucleic acid fragment" and "isolated nucleic acid molecule" are used interchangeably and refer to a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual, $2^{nd}$* ed., Cold Spring Harbor Laboratory: Cold Spring Harbor, N.Y. (1989), which is hereby incorporated herein by reference, particularly Chapter 11 and Table 11.1. The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability, corresponding to higher Tm, of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.*, 215: 403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The disclosure herein teaches the complete amino acid and nucleotide sequence encoding particular euglenoid proteins. The skilled artisan, having the benefit of the sequences as reported herein, may now use all or a substantial portion of the disclosed sequences for purposes known to those skilled in this art. Accordingly, the complete sequences as reported in the accompanying Sequence Listing, as well as substantial portions of those sequences as defined above, are encompassed in the present disclosure.

The term "complementary" is used to describe the relationship between nucleotide bases that are capable of hybridizing to one another. For example, with respect to DNA, adenosine is complementary to thymine and cytosine is complementary to guanine. Accordingly, isolated nucleic acid fragments that are complementary to the complete sequences as reported in the accompanying Sequence Listing, as well as those substantially similar nucleic acid sequences, are encompassed in the present disclosure.

The terms "homology" and "homologous" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments described herein, such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that homologous nucleic acid sequences encompassed by this invention are also defined by their ability to hybridize, under moderately stringent conditions, such as 0.5×SSC, 0.1% SDS, 60° C., with the sequences exemplified herein, or to any portion of the nucleotide sequences disclosed herein and which are functionally equivalent thereto.

"Codon degeneracy" refers to the nature in the genetic code permitting variation of the nucleotide sequence without effecting the amino acid sequence of an encoded polypeptide. Accordingly, described herein is any nucleic acid fragment that encodes all or a substantial portion of the amino acid sequence encoding the euglenoid polypeptide as set forth in SEQ ID NO:2 and/or SEQ ID NO:4. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These oligonucleotide building blocks are annealed and then ligated to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available. For example, the codon usage profile for *Yarrowia lipolytica* is provided in U.S. Pat. No. 7,125,672.

"Gene" refers to a nucleic acid fragment that expresses a specific protein, and which may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene that is introduced into the host organism by gene transfer. Foreign genes can comprise native genes inserted into a non-native organism, native genes introduced into a new location within the native host, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence (or located within an intron thereof, and which influence the transcription, RNA processing or stability, or translation of the associated coding sequence. Regulatory sequences may include promoters, enhancers, silencers, 5' untranslated leader sequence (e.g., between the transcription start site and the translation initiation codon), introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The terms "3' non-coding sequences" and "transcription terminator" refer to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and which can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; Int'l. App. Pub. No. WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated and yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence, i.e. the coding sequence is under the transcriptional control of the promoter. Coding sequences can be operably linked to regulatory sequences in sense or antisense orientation.

The term "expression", as used herein, refers to the transcription and stable accumulation of sense (mRNA) or antisense RNA derived from nucleic acid fragments. Expression may also refer to translation of mRNA into a polypeptide.

"Transformation" refers to the transfer of a nucleic acid molecule into a host organism, resulting in genetically stable inheritance. The nucleic acid molecule may be a plasmid that replicates autonomously, for example, or, it may integrate into the genome of the host organism. Host organisms containing the transformed nucleic acid fragments are referred to as "transgenic" or "recombinant" or "transformed" organisms.

The terms "plasmid" and "vector" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing an expression cassette(s) into a cell.

The term "expression cassette" refers to a fragment of DNA comprising the coding sequence of a selected gene and regulatory sequences preceding (5' non-coding sequences) and following (3' non-coding sequences) the coding sequence that are required for expression of the selected gene product. Thus, an expression cassette is typically composed of: 1) a promoter sequence; 2) a coding sequence, i.e., open reading frame ["ORF"]; and, 3) a 3' untranslated region, i.e., a terminator that in eukaryotes usually contains a polyadenylation site. The expression cassette(s) is usually included within a vector, to facilitate cloning and transformation. Different expression cassettes can be transformed into different organisms including bacteria, yeast, plants and mammalian cells, as long as the correct regulatory sequences are used for each host.

The term "percent identity" refers to a relationship between two or more polypeptide sequences or two or more polynucleotide sequences, as determined by comparing the sequences. "Percent identity" also means the degree of sequence relatedness between polypeptide or polynucleotide sequences, as the case may be, as determined by the percentage of match between compared sequences. "Percent identity" and "percent similarity" can be readily calculated by known methods, including but not limited to those described in: 1) *Computational Molecular Biology* (Lesk, A. M., Ed.) Oxford University: NY (1988); 2) *Biocomputing: Informatics and Genome Projects* (Smith, D. W., Ed.) Academic: NY (1993); 3) *Computer Analysis of Sequence Data, Part I* (Griffin, A. M., and Griffin, H. G., Eds.) Humania: N.J. (1994); 4) *Sequence Analysis in Molecular Biology* (von Heinje, G., Ed.) Academic (1987); and, 5) *Sequence Analysis Primer* (Gribskov, M. and Devereux, J., Eds.) Stockton: N.Y. (1991).

Preferred methods to determine percent identity are designed to give the best match between the sequences tested. Methods to determine percent identity and percent similarity are codified in publicly available computer programs.

Sequence alignments and percent identity calculations may be performed using the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" and the "Clustal W method of alignment" (described by Higgins and Sharp, *CABIOS*, 5:151-153 (1989); Higgins, D. G. et al., *Comput. Appl. Biosci.*, 8:189-191 (1992)) and found in the MegAlign™ program of the LASERGENE bioinformatics computing suite (DNASTAR Inc.). After alignment of the sequences using either Clustal program, it is possible to obtain a "percent identity" by viewing the "sequence distances" table in the program.

For multiple alignments using the Clustal V method of alignment, the default values correspond to GAP PENALTY=10 and GAP LENGTH PENALTY=10. Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. Default parameters for multiple alignment using the Clustal W method of alignment correspond to GAP PENALTY=10, GAP LENGTH PENALTY=0.2, Delay Divergent Seqs(%)=30, DNA Transition Weight=0.5, Protein Weight Matrix=Gonnet Series, DNA Weight Matrix=IUB.

It is well understood by one skilled in the art that various measures of sequence percent identity are useful in identifying polypeptides, from other species, wherein such polypeptides have the same or similar function or activity. Suitable nucleic acid fragments, i.e., isolated polynucleotides according to the disclosure herein, encode polypeptides that are at least about 70% identical, preferably at least about 75% identical, and more preferably at least about 80% identical to the amino acid sequences reported herein. Preferred nucleic acid fragments encode amino acid sequences that are at least about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Although preferred ranges are described above, any integer amino acid identity from 68% to 100% may be useful in describing the present invention, such as 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

The term "sequence analysis software" refers to any computer algorithm or software program that is useful for the analysis of nucleotide or amino acid sequences. "Sequence analysis software" may be commercially available or independently developed. Typical sequence analysis software include, but is not limited to: 1) the GCG suite of programs (Wisconsin Package Version 9.0, Genetics Computer Group (GCG), Madison, Wis.); 2) BLASTP, BLASTN, BLASTX (Altschul et al., *J. Mol. Biol.*, 215:403-410 (1990)); 3) DNASTAR (DNASTAR, Inc. Madison, Wis.); 4) Sequencher (Gene Codes Corporation, Ann Arbor, Mich.); and, 5) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within this description, whenever sequence analysis software is used for analysis, the analytical results are based on the "default values" of the program referenced, unless otherwise specified. As used herein "default values" will mean any set of values or parameters that originally load with the software when first initialized.

Standard recombinant DNA and molecular cloning techniques used herein are well known in the art and are described by Sambrook, J., Fritsch, E. F. and Maniatis, T., *Molecular Cloning: A Laboratory Manual*, 2$^{nd}$ ed., Cold Spring Harbor Laboratory: Cold Spring Harbor, N.Y. (1989) (hereinafter "Maniatis"); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987).

An Overview: Microbial Biosynthesis of Fatty Acids and Triacylglycerols

In general, lipid accumulation in oleaginous microorganisms is triggered in response to the overall carbon to nitrogen ratio present in the growth medium. This process, leading to the de novo synthesis of free palmitate (16:0) in oleaginous microorganisms, is described in detail in U.S. Pat. No. 7,238, 482. Palmitate is the precursor of longer-chain saturated and unsaturated fatty acid derivates, which are formed through the action of elongases and desaturases (FIG. 1).

TAGs, the primary storage unit for fatty acids, are formed by a series of reactions that involve: 1) esterification of one molecule of acyl-CoA to glycerol-3-phosphate via an acyltransferase to produce lysophosphatidic acid; 2) esterification of a second molecule of acyl-CoA via an acyltransferase to yield 1,2-diacylglycerol phosphate, commonly identified as phosphatidic acid; 3) removal of a phosphate by phosphatidic acid phosphatase to yield 1,2-diacylglycerol ["DAG"]; and, 4) addition of a third fatty acid by the action of an acyltransferase to form TAG. A wide spectrum of fatty acids can be incorporated into TAGs, including saturated and unsaturated fatty acids and short-chain and long-chain fatty acids.

Biosynthesis of Omega Fatty Acids

The metabolic process wherein oleic acid is converted to ω-3/ω-6 fatty acids involves elongation of the carbon chain through the addition of carbon atoms and desaturation of the molecule through the addition of double bonds. This requires a series of special desaturation and elongation enzymes present in the endoplasmic reticulum membrane. However, as seen in FIG. 1 and as described below, there are often multiple alternate pathways for production of a specific ω-3/ω-6 fatty acid.

Specifically, FIG. 1 depicts the pathways described below. All pathways require the initial conversion of oleic acid to linoleic acid ["LA"], the first of the ω-6 fatty acids, by a Δ12 desaturase. Then, using the "Δ9 elongase/Δ8 desaturase pathway" and LA as substrate, long-chain ω-6 and ω-3 fatty acids are formed as follows: 1) LA is converted to eicosadienoic acid ["EDA"] by a Δ9 elongase; 2) EDA is converted to dihomo-γ-linolenic acid ["DGLA"] by a Δ8 desaturase; 3) DGLA is converted to arachidonic acid ["ARA"] by a Δ5 desaturase; 4) ARA is converted to docosatetraenoic acid ["DTA"] by a $C_{20/22}$ elongase; and, 5) DTA is converted to docosapentaenoic acid ["DPAn-6"] by a Δ4 desaturase. Alternatively, the "Δ9 elongase/Δ8 desaturase pathway" can use α-linolenic acid ["ALA"] as substrate to produce long-chain ω-3 fatty acids as follows: 1) LA is converted to ALA, the first of the ω-3 fatty acids, by a Δ15 desaturase; 2) ALA is converted to eicosatrienoic acid ["ETrA"] by a Δ9 elongase; 3) ETrA is converted to eicosatetraenoic acid ["ETA"] by a Δ8 desaturase; 4) ETA is converted to eicosapentaenoic acid ["EPA"] by a Δ5 desaturase; 5) EPA is converted to docosapentaenoic acid ["DPA"] by a $C_{20/22}$ elongase; and, 6) DPA is converted to docosahexaenoic acid ["DHA"] by a Δ4 desaturase. Optionally, ω-6 fatty acids may be converted to ω-3 fatty acids. For example, ETA and EPA are produced from DGLA and ARA, respectively, by Δ17 desaturase activity.

Alternate pathways for the biosynthesis of ω-3/ω-6 fatty acids utilize a Δ6 desaturase and $C_{18/20}$ elongase, that is, the "Δ6 desaturase/Δ6 elongase pathway". More specifically, LA and ALA may be converted to γ-linolenic acid ["GLA"] and stearidonic acid ["STA"], respectively, by a Δ6 desaturase; then, a $C_{18/20}$ elongase converts GLA to DGLA and/or STA to ETA. Downstream PUFAs are subsequently formed as described above.

It is contemplated that the particular functionalities required to be expressed in a specific host organism for production of ω-3/ω-6 fatty acids will depend on the host cell (and its native PUFA profile and/or desaturase/elongase profile), the availability of substrate, and the desired end product(s). One skilled in the art will be able to identify various candidate genes encoding each of the enzymes desired for ω-3/ω-6 fatty acid biosynthesis. Useful desaturase and elongase sequences may be derived from any source, e.g., isolated from a natural source such as from bacteria, algae, fungi, oomycete, yeast, stramenopiles, plants, animals, etc., produced via a semi-synthetic route or synthesized de novo. Although the particular source of the desaturase and elongase genes introduced into the host is not critical, considerations for choosing a specific polypeptide having desaturase or elongase activity include: 1) the substrate specificity and activity of the polypeptide; 2) whether the polypeptide or a component thereof is a rate-limiting enzyme; 3) whether the desaturase or elongase is essential for synthesis of a desired PUFA; 4) co-factors required by the polypeptide; and/or, 5) whether the polypeptide was modified after its production, such as by a kinase or a prenyltransferase. The expressed polypeptide preferably has parameters compatible with the biochemical environment of its location in the host cell. See U.S. Pat. No. 7,238,482.

It may also be useful to consider the conversion efficiency of each particular desaturase and/or elongase. More specifically, since each enzyme rarely functions with 100% efficiency to convert substrate to product, the final lipid profile of un-purified oils produced in a host cell is typically a mixture of various PUFAs consisting of the desired ω-3/ω-6 fatty acid, as well as various upstream intermediary PUFAs. Thus, the conversion efficiency of each enzyme is also a variable to consider when optimizing biosynthesis of a desired fatty acid.

With each of the considerations above in mind, candidate genes having the appropriate desaturase and elongase activities (e.g., Δ6 desaturases, $C_{18/20}$ elongases, Δ5 desaturases, Δ17 desaturases, Δ15 desaturases, Δ9 desaturases, Δ12 desaturases, $C_{14/16}$ elongases, $C_{16/18}$ elongases, Δ9 elongases, Δ8 desaturases, Δ4 desaturases and $C_{20/22}$ elongases) can be identified according to publicly available literature such as e.g. GenBank, the patent literature, and experimental analysis of organisms having the ability to produce PUFAs. These genes will be suitable for introduction into a specific host organism, to enable or enhance the organism's synthesis of PUFAs.

Sequence Identification of a Novel Eutreptiella cf_gymnastica CCMP1594 Δ4 Desaturase The present disclosure relates to a nucleotide sequence (SEQ ID NO:1) isolated from Eutreptiella cf_gymnastica CCMP1594, encoding a Δ4 desaturase (SEQ ID NO:2). This sequence is designated herein as "E1594D4".

Comparison of the E1594D4 nucleotide base and deduced amino acid sequences to public databases reveals that the most similar known sequences are about 68% identical to the amino acid sequence of E1594D4 reported herein over a length of 514 amino acids using the Clustal W method of alignment (described by Higgins and Sharp, CABIOS, 5:151-153 (1989); Higgins, D. G. et al., Comput. Appl. Biosci., 8:189-191(1992); found in the MegAlign™ v6.1 program of the LASERGENE bioinformatics computing suite (DNASTAR Inc.)). More preferred amino acid fragments are at least about 70%-80% identical to the sequences herein, where those sequences that are at least about 80%-90% identical are particularly suitable and those sequences that are at least about 90%-95% identical are most preferred. Similarly, preferred E1594D4 encoding nucleic acid sequences corresponding to the ORF are those encoding active proteins and which are at least about 70%-80% identical to the nucleic acid sequences of E1594D4 reported herein, where those sequences that are at least about 80%-90% identical are particularly suitable and those sequences that are at least about 90%-95% identical are most preferred.

In alternate embodiments, the E1594D4 desaturase sequence can be codon-optimized for expression in a particular host organism. As is well known in the art, this can be a useful means to further optimize the expression of the enzyme in the alternate host, since use of host-preferred codons can substantially enhance the expression of the foreign gene encoding the polypeptide. In general, host-preferred codons can be determined within a particular host species of interest by examining codon usage in proteins, preferably those expressed in the largest amount, and determining which codons are used with highest frequency. Then, the coding sequence for a polypeptide of interest having e.g., desaturase activity can be synthesized in whole or in part using the codons preferred in the host species.

Thus, E1594D4 was codon-optimized for expression in Yarrowia lipolytica. This was possible based on previous determination of the Y. lipolytica codon usage profile, identification of those codons that were preferred, and determination of the consensus sequence around the 'ATG' initiation codon (see U.S. Pat. No. 7,238,482 and U.S. Pat. No. 7,125,672). The codon-optimized synthetic gene, designated herein as "E1594D4S", had one additional alanine amino acid inserted between amino acid residues 1 and 2 of the wildtype E1594D4; thus, the total length of E1594D4S is 1548 nucleotides (SEQ ID NO:3), while the encoded protein set forth as SEQ ID NO:4 is 515 amino acids in length.

One skilled in the art would be able to use the teachings herein to create various other codon-optimized Δ4 desaturase proteins suitable for optimal expression in alternate hosts (i.e., other than Yarrowia lipolytica), based on the wildtype E1594D4 sequence. Accordingly, the disclosure herein relates to any codon-optimized Δ4 desaturase protein that is derived from the wildtype E1594D4, that is, encoded by SEQ ID NO:2. This includes, but is not limited to, the nucleotide sequence set forth in SEQ ID NO:3, which encodes a synthetic Δ4 desaturase protein (i.e., E1594D4S as set forth in SEQ ID NO:4) that was codon-optimized for expression in *Yarrowia lipolytica*.

Identification and Isolation of Homologs

Any of the instant desaturase sequences (i.e., E1594D4, E1594D4S) or portions thereof may be used to search for Δ4 desaturase homologs in the same or other bacterial, algal, fungal, oomycete, yeast, stramenopiles, euglenoid, plant or animal species using sequence analysis software. In general, such computer software matches similar sequences by assigning degrees of homology to various substitutions, deletions, and other modifications.

Alternatively, any of the instant desaturase sequences or portions thereof may also be employed as hybridization reagents for the identification of Δ4 homologs. The basic components of a nucleic acid hybridization test include a probe, a sample suspected of containing the gene or gene fragment of interest and a specific hybridization method. Probes of the present invention are typically single-stranded nucleic acid sequences that are complementary to the nucleic acid sequences to be detected. Probes are "hybridizable" to the nucleic acid sequence to be detected. Although the probe length can vary from 5 bases to tens of thousands of bases, typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added (e.g., guanidinium chloride, guanidinium thiocyanate, sodium thiocyanate, lithium tetrachloroacetate, sodium perchlorate, rubidium tetrachloroacetate, potassium iodide, cesium trifluoroacetate). If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal), and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

In additional embodiments, any of the Δ4 desaturase nucleic acid fragments described herein (or any homologs identified thereof) may be used to isolate genes encoding homologous proteins from the same or other bacterial, algal, fungal, oomycete, yeast, stramenopiles, euglenoid, plant or animal species. Isolation of homologous genes using sequence-dependent protocols is well known in the art. Examples of sequence-dependent protocols include, but are not limited to: 1) methods of nucleic acid hybridization; 2) methods of DNA and RNA amplification, as exemplified by various uses of nucleic acid amplification technologies such as polymerase chain reaction ["PCR"] (U.S. Pat. No. 4,683, 202); ligase chain reaction ["LCR"] (Tabor, S. et al., *Proc. Natl. Acad. Sci. U.S.A.*, 82:1074 (1985)); or strand displacement amplification ["SDA"] (Walker, et al., *Proc. Natl. Acad. Sci. U.S.A.*, 89:392 (1992)); and, 3) methods of library construction and screening by complementation.

For example, genes encoding similar proteins or polypeptides to the Δ4 desaturases described herein could be isolated directly by using all or a portion of the nucleic acid fragments as DNA hybridization probes to screen libraries from any desired organism using well known methods, wherein those organisms producing DPAn-6 or DHA would be preferred. Specific oligonucleotide probes based upon the nucleic acid sequences can be designed and synthesized by methods known in the art (Maniatis, supra). Moreover, the entire sequences can be used directly to synthesize DNA probes by methods known to the skilled artisan, such as random primers DNA labeling, nick translation or end-labeling techniques, or RNA probes using available in vitro transcription systems. In addition, specific primers can be designed and used to amplify a part of or the full length of the Δ4 desaturase sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known (Thein and Wallace, "The use of oligonucleotides as specific hybridization probes in the Diagnosis of Genetic Disorders", in *Human Genetic Diseases: A Practical Approach*, K. E. Davis Ed., (1986) pp 33-50, IRL: Herndon, Va.; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the Δ4 desaturase sequences may be used in PCR protocols to amplify longer nucleic acid fragments encoding homologous genes from DNA or RNA. PCR may also be performed on a library of cloned nucleic acid fragments wherein the sequence of one primer is derived from the disclosed nucleic acid fragments. The sequence of the other primer takes advantage of the presence of the polyadenylic acid tracts to the 3' end of the mRNA precursor encoding eukaryotic genes.

Alternatively, the second primer sequence may be based upon sequences derived from the cloning vector. For example, the skilled artisan can follow the RACE protocol (Frohman et al., *Proc. Natl Acad. Sci. U.S.A.*, 85:8998 (1988)) to generate cDNAs by using PCR to amplify copies of the region between a single point in the transcript and the 3' or 5' end. Primers oriented in the 3' and 5' directions can be designed from the disclosed sequences. Using commercially available 3' RACE or 5' RACE systems (e.g., Gibco/BRL, Gaithersburg, Md.), specific 3' or 5' cDNA fragments can be isolated (Ohara et al., *Proc. Natl Acad. Sci. U.S.A.*, 86:5673 (1989); Loh et al., *Science*, 243:217 (1989)).

Alternately, any of the Δ4 desaturase nucleic acid fragments described herein (or any homologs identified thereof) may be used for creation of new and improved fatty acid desaturases. As is well known in the art, in vitro mutagenesis and selection, chemical mutagenesis, "gene shuffling" methods or other means can be employed to obtain mutations of naturally occurring desaturase genes. Furthermore, improved fatty acids may be synthesized by domain swapping, wherein a functional domain from any of the Δ4 desaturase nucleic acid fragments described herein is exchanged with a functional domain in an alternate desaturase gene to thereby result in a novel protein.

Methods for Production of Various ω-3 and/or ω-6 Fatty Acids

It is expected that introduction of chimeric genes encoding the Δ4 desaturases described herein (i.e., E1594D4, E1594D4S or other mutant enzymes, codon-optimized enzymes or homologs thereof), under the control of the appropriate promoters, will result in increased production of DPAn-6 and/or DHA in the transformed host organism, respectively. As such, described herein is a method for the direct production of PUFAs comprising exposing a fatty acid substrate (i.e., DTA or DPA) to the desaturase enzymes described herein (e.g., E1594D4, E1594D4S), such that the substrate is converted to the desired fatty acid product (i.e., DPAn-6 or DHA, respectively).

More specifically, a method for the production of DHA in a host cell is provided herein, wherein the host cell comprises:
  (i) an isolated nucleotide molecule encoding a Δ4 desaturase polypeptide having at least 68% identity when compared to a polypeptide having an amino acid sequence as set forth in SEQ ID NO:2, based on the Clustal W method of alignment; and,
  (ii) a source of DPA;
wherein the host cell is grown under conditions such that the Δ4 desaturase is expressed and the DPA is converted to DHA, and wherein the DHA is optionally recovered.

The person of skill in the art will recognize that the broad substrate range of the Δ4 desaturase may additionally allow for the use of the enzyme for the conversion DTA to DPAn-6. Accordingly, described herein is also a method for the production of DPAn-6, wherein the host cell comprises:
  (i) an isolated nucleotide molecule encoding a Δ4 desaturase polypeptide having at least 68% identity when compared to a polypeptide having an amino acid sequence as set forth in SEQ ID NO:2, based on the Clustal W method of alignment; and,
  (ii) a source of DTA;
wherein the host cell is grown under conditions such that the Δ4 desaturase is expressed and the DTA is converted to DPAn-6, and wherein the DPAn-6 is optionally recovered.

The source of the DTA or DPA used as substrate in either of the methods above may be produced by the host either naturally or transgenically, or the substrate may be provided exogenously. In particular, it is contemplated that the Δ4 desaturases described herein (e.g., E1594D4, E1594D4S or other mutant enzymes, codon-optimized enzymes or homologs thereof) may be expressed in conjunction with additional genes encoding enzymes of the PUFA biosynthetic pathway, such as Δ6 desaturases, $C_{18/20}$ elongases, Δ17 desaturases, Δ15 desaturases, Δ9 desaturases, Δ12 desaturases, $C_{14/16}$ elongases, $C_{16/18}$ elongases, Δ9 elongases, Δ8 desaturases, Δ5 desaturases and/or $C_{20/22}$ elongases, to result in production of DPAn-6 and/or DHA. The particular genes included within a particular expression cassette will depend on the host cell (and its PUFA profile and/or desaturase/elongase profile), the availability of substrate and the desired end product(s).

In alternative embodiments, it may be useful to disrupt a host organism's native Δ4 desaturase, based on the complete sequences described herein, the complement of those complete sequences, substantial portions of those sequences, codon-optimized desaturases derived therefrom and those sequences that are substantially homologous thereto.

Expression Systems, Cassettes And Vectors

The genes and gene products described herein may be expressed in heterologous host cells. Expression in recombinant hosts may be useful for the production of various PUFA pathway intermediates, or for the modulation of PUFA pathways already existing in the host for the synthesis of new products heretofore not possible using the host.

Expression systems and expression vectors containing regulatory sequences that direct high level expression of foreign proteins are well known. Any of these could be used to construct chimeric genes for production of any of the gene products of the instant sequences. These chimeric genes could then be introduced into appropriate host cells via transformation to provide high-level expression of the encoded enzymes.

Vectors (e.g., constructs, plasmids) and DNA expression cassettes useful for the transformation of suitable host cells are well known. The specific choice of sequences present in the construct is dependent upon the desired expression products (supra), the nature of the host cell, and the proposed means of separating transformed cells versus non-transformed cells. Typically, however, the vector contains at least one expression cassette, a selectable marker and sequences allowing autonomous replication or chromosomal integration. Suitable expression cassettes comprise a region 5' of the gene that controls transcriptional initiation, i.e., a promoter, the gene coding sequence, and a region 3' of the DNA fragment that controls transcriptional termination, i.e., a terminator. It is most preferred when both control regions are derived from genes from the transformed host cell, although it is to be understood that such control regions need not be derived from the genes native to the specific species chosen as a production host.

Transcriptional control regions or promoters useful for driving expression of Δ4 desaturase ORFs in the desired host cell are numerous and well known. These control regions may comprise a promoter, enhancer, silencer, intron sequences, 3' UTR and/or 5' UTR regions, and protein and/or RNA stabilizing elements. Such elements may vary in their strength and specificity. Virtually any promoter (i.e., native, synthetic, or chimeric) capable of directing expression of these genes in the selected host cell is suitable, although transcriptional and translational regions from the host species are particularly useful. Expression in a host cell can occur in an induced or constitutive fashion. Induced expression occurs by inducing the activity of a regulatable promoter operably linked to the gene of interest, while constitutive expression occurs by the use of a constitutive promoter operably linked to the gene of interest.

When the host cell is, for example, yeast, transcriptional and translational regions functional in yeast cells are provided, particularly from the host species. See Int'l. App. Pub. No. WO 2006/052870 for preferred transcriptional initiation regulatory regions for use in *Yarrowia lipolytica*. Any of a number of regulatory sequences may be used, depending upon whether constitutive or induced transcription is desired, the efficiency of the promoter in expressing the ORF of interest, the ease of construction, etc.

3' non-coding sequences encoding transcription termination signals, i.e., a "termination region", must be provided in a recombinant construct and may be derived from the 3' region of the gene from which the initiation region was obtained or from a different gene. A large number of termination regions are known and function satisfactorily in a variety of hosts when utilized in both the same and different genera and species from which they were derived. The termination region usually is selected more as a matter of convenience rather than because of any particular property. Termination control regions may also be derived from various genes native to the preferred hosts. The 3'-region can also be synthetic, as one of skill in the art can utilize available information to design and synthesize a 3'-region sequence that functions as a transcription terminator. A termination region may be unnecessary, but is highly preferred.

Merely inserting a gene, such as a desaturase, into a cloning vector does not ensure its expression at the desired rate, concentration, amount, etc. In response to the need for a high expression rate, many specialized expression vectors have been created by manipulating a number of different genetic elements that control transcription, RNA stability, translation, protein stability and location, oxygen limitation, and secretion from the host cell. Some of the manipulated features include: the nature of the relevant transcriptional promoter and terminator sequences, the number of copies of the cloned gene (wherein additional copies may be cloned within a single expression construct and/or additional copies may be introduced into the host cell by increasing the plasmid copy number or by multiple integration of the cloned gene into the genome), whether the gene is plasmid-borne or integrated into the genome of the host cell, the final cellular location of the synthesized foreign protein, the efficiency of translation and correct folding of the protein in the host organism, the intrinsic stability of the mRNA and protein of the cloned gene within the host cell, and the codon usage within the cloned gene such that its frequency approaches the frequency of preferred codon usage of the host cell. Each of these may be used in the methods and host cells described herein to further optimize expression of the Δ4 desaturases.

Transformation Of Host Cells

After a recombinant construct is created, e.g., comprising a chimeric gene comprising a promoter, ORF and terminator, it is placed in a plasmid vector capable of autonomous replication in the host cell or it is directly integrated into the genome of the host cell. Integration of expression cassettes can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

When two or more genes are expressed from separate replicating vectors, each vector may have a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene(s) of interest may be introduced into a host cell by any standard technique. These techniques include transformation, e.g., lithium acetate transformation (*Methods in Enzymology*, 194:186-187 (1991)), protoplast fusion, biolistic impact, electroporation, microinjection, vacuum filtration or any other method that introduces the gene(s) of interest into the host cell.

For convenience, a host cell that has been manipulated by any method to take up a DNA sequence, for example, in an expression cassette, is referred to herein as "transformed" or "recombinant". The transformed host will have at least one copy of the expression cassette and may have two or more, depending upon whether the expression cassette is integrated into the genome amplified, or is present on an extrachromosomal element having multiple copy numbers. The transformed host cell can be identified by various selection techniques, as described in U.S. Pat. No. 7,238,482 and U.S. Pat. No. 7,259,255.

Following transformation, substrates suitable for Δ4 desaturases (and, optionally other PUFA enzymes that are co-expressed within the host cell) may be produced by the host either naturally or transgenically, or they may be provided exogenously.

Metabolic Engineering of ω-3 and/or ω-6 Fatty Acid Biosynthesis

Knowledge of the sequences of the present Δ4 desaturases will be useful for manipulating ω-3 and/or ω-6 fatty acid biosynthesis in various host cells. This may require metabolic engineering directly within the PUFA biosynthetic pathway or additional manipulation of pathways that contribute carbon to the PUFA biosynthetic pathway.

Techniques useful for up-regulating desirable biochemical pathways and down-regulating undesirable biochemical pathways are well known in the art. For example, biochemical pathways competing with the ω-3 and/or ω-6 fatty acid biosynthetic pathways for energy or carbon, or native PUFA biosynthetic pathway enzymes that interfere with production of a particular PUFA end-product, may be eliminated by gene disruption or down-regulated by other means, such as antisense mRNA and zinc-finger targeting technologies.

The following discuss altering the PUFA biosynthetic pathway as a means to increase GLA, ARA, EPA or DHA, respectively, and desirable manipulations in the TAG biosynthetic pathway and in the TAG degradation pathway: Int'l. App. Pub. No. WO 2006/033723, Int'l. App. Pub. No. WO 2006/055322 [U.S. Pat. Appl. Pub. No. 2006-0094092-A1], Int'l. App. Pub. No. WO 2006/052870 [U.S. Pat. Appl. Pub. No. 2006-0115881-A1] and Int'l. App. Pub. No. WO 2006/052871 [U.S. Pat. Appl. Pub. No. 2006-0110806-A1], respectively.

Preferred Hosts for Recombinant Expression of Δ4 Desaturases

A variety of eukaryotic organisms are suitable as host, to thereby yield a transformant host organism comprising a Δ4 desaturase as described herein. These may include hosts that grow on a variety of feedstocks, including simple or complex carbohydrates, fatty acids, organic acids, oils, glycerols and alcohols, and/or hydrocarbons over a wide range of temperature and pH values. Based on the needs of the Applicants' Assignee, the genes described herein were initially isolated for expression in an oleaginous yeast (and in particular *Yar-*

*rowia lipolytica*); however, it is contemplated that because transcription, translation and the protein biosynthetic apparatus are highly conserved, any bacteria, yeast, algae, stramenopile, oomycete, euglenoid and/or fungus will be a suitable host for expression of the present nucleic acid fragments.

Preferred hosts are oleaginous organisms, such as oleaginous yeast. These oleaginous organisms are naturally capable of oil synthesis and accumulation, wherein the total oil content can comprise greater than about 25% of the cellular dry weight, more preferably greater than about 30% of the cellular dry weight, and most preferably greater than about 40% of the cellular dry weight. Various algae, moss, fungi, yeast and stramenopiles are naturally classified as oleaginous. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeast include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis* and *Yarrowia lipolytica* (formerly classified as *Candida lipolytica*).

Most preferred is the oleaginous yeast *Yarrowia lipolytica*; and, in a further embodiment, most preferred are the *Y. lipolytica* strains designated as ATCC #76982, ATCC #20362, ATCC #8862, ATCC #18944 and/or LGAM S(7)1 (Papanikolaou S., and Aggelis G., *Bioresour. Technol.*, 82(1):43-9 (2002)).

Specific teachings relating to transformation of *Yarrowia lipolytica* include U.S. Pat. No. 4,880,741, U.S. Pat. No. 5,071,764 and Chen, D. C. et al. (*Appl. Microbiol. Biotechnol.*, 48(2):232-235 (1997)). Specific teachings applicable for engineering ARA, EPA and DHA in *Y. lipolytica* are provided in Int'l. App. Pub. No. WO 2006/055322, Int'l. App. Pub. No. WO 2006/052870 and Int'l. App. Pub. No. WO 2006/052871, respectively. Detailed means for the synthesis and transformation of expression vectors comprising Δ4 desaturases in oleaginous yeast (i.e., *Yarrowia lipolytica*) are provided in Int'l. App. Pub. No. WO 2006/052871.

The preferred method of expressing genes in *Yarrowia lipolytica* is by integration of linear DNA into the genome of the host. Integration into multiple locations within the genome can be particularly useful when high level expression of genes are desired, such as in the Ura3 locus (GenBank Accession No. AJ306421), the Leu2 gene locus (GenBank Accession No. AF260230), the Lys5 gene locus (GenBank Accession No. M34929), the Aco2 gene locus (GenBank Accession No. AJ001300), the Pox3 gene locus (Pox3: GenBank Accession No. XP_503244; or, Aco3: GenBank Accession No. AJ001301), the Δ12 desaturase gene locus (Int'l. App. Pub. No. WO 2004/104167), the Lip1 gene locus (GenBank Accession No. Z50020), the Lip2 gene locus (GenBank Accession No. AJ012632), the SCP2 gene locus (GenBank Accession No. AJ431362), the Pex3 gene locus (GenBank Accession No. CAG78565), the Pex16 gene locus (GenBank Accession No. CAG79622) and/or the Pex10 gene locus (GenBank Accession No. CAG81606).

Preferred selection methods for use in *Yarrowia lipolytica* are resistance to kanamycin, hygromycin and the amino glycoside G418, as well as ability to grow on media lacking uracil, leucine, lysine, tryptophan or histidine. 5-fluoroorotic acid [5-fluorouracil-6-carboxylic acid monohydrate; "5-FOA"] may also be used for selection of yeast Ura⁻ mutants. This compound is toxic to yeast cells that possess a functioning URA3 gene encoding orotidine 5'-monophosphate decarboxylase [OMP decarboxylase]; thus, based on this toxicity, 5-FOA is especially useful for the selection and identification of Ura⁻ mutant yeast strains (Bartel, P. L. and Fields, S., Yeast 2-Hybrid System, Oxford University: New York, v. 7, pp 109-147, 1997; see also Int'l. App. Pub. No. WO 2006/052870 for 5-FOA use in *Yarrowia*).

Other microbial hosts include oleaginous bacteria, algae, euglenoids, stramenopiles and other fungi; and, within this broad group of microbial hosts, of particular interest are microorganisms that naturally produce ω-3/ω-6 fatty acids. For example, ARA, EPA and/or DHA is produced via *Cyclotella* sp., *Nitzschia* sp., *Pythium, Thraustochytrium* sp., *Schizochytrium* sp. and *Mortierella*. Thus, for example, transformation of *Mortierella alpine*, which is commercially used for production of ARA, with any of the present Δ4 desaturase genes under the control of inducible or regulated promoters (in addition to a Δ17 desaturase and a $C_{20/22}$ elongase) could yield a transformant organism capable of synthesizing DHA. The method of transformation of *M. alpina* is described by Mackenzie et al. (*Appl. Environ. Microbiol.*, 66:4655 (2000)). Similarly, methods for transformation of Thraustochytriales microorganisms (e.g., *Thraustochytrium, Schizochytrium*) are disclosed in U.S. Pat. No. 7,001,772.

In alternate embodiments, hosts may be plants or other animals. For example, using oilseed plants that can be readily engineered for PUFA production include: soybean (*Glycine* and *Soja* sp.), corn (*Zea mays*), flax (*Linum* sp.), rapeseed (*Brassica* sp.), primrose, canola, maize, cotton, safflower (*Carthamus* sp.) and sunflower (*Helianthus* sp.). See, for example, U.S. Pat. Appl. Pub. No. 2007-0237876 A1.

Regardless of the selected host or expression construct, multiple transformants must be screened to obtain a strain displaying the desired expression level, regulation and pattern. Such screening may be accomplished by Southern analysis of DNA blots (Southern, *J. Mol. Biol.*, 98:503 (1975)), Northern analysis of mRNA expression (Kroczek, *J. Chromatogr. Biomed. Appl.*, 618(1-2):133-145 (1993)), Western and/or Elisa analyses of protein expression, phenotypic analysis or GC analysis of the PUFA products.

Fermentation Processes for Omega Fatty Acid Production

The transformed host cell is grown under conditions that optimize expression of chimeric desaturase genes and produce the greatest and most economical yield of desired PUFAs. In general, media conditions may be optimized by modifying the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest. Oleaginous yeast of interest, such as *Yarrowia lipolytica*, are generally grown in complex media such as yeast extract-peptone-dextrose broth (YPD) or a defined minimal media that lacks a component necessary for growth and thereby forces selection of the desired expression cassettes (e.g., Yeast Nitrogen Base (DIFCO Laboratories, Detroit, Mich.)).

Fermentation media for the methods and host cells described herein must contain a suitable carbon source such as are taught in U.S. Pat. No. 7,238,482. Suitable sources of carbon encompass a wide variety of sources, with sugars, glycerol and/or fatty acids being preferred. Most preferred is glucose and/or fatty acids containing between 10-22 carbons.

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the oleaginous host and promotion of the enzymatic pathways of PUFA production. Particular attention is given to several metal ions, such as $Fe^{+2}$, $Cu^{+2}$, $Mn^{+2}$, $Co^{+2}$, $Zn^{+2}$, $M^{+2}$, that promote synthesis of lipids and PUFAs (Nakahara, T. et al., *Ind. Appl. Single Cell Oils*, D. J. Kyle and R. Colin, eds. pp 61-97 (1992)).

Preferred growth media for the methods and host cells described herein are common commercially prepared media, such as Yeast Nitrogen Base (DIFCO Laboratories, Detroit, Mich.). Other defined or synthetic growth media may also be used and the appropriate medium for growth of the transformant host cells is well known in microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of increased amounts of PUFAs and TAGs in oleaginous yeast cells requires a two-stage process, since the metabolic state must be "balanced" between growth and synthesis/storage of fats. Thus, most preferably, a two-stage fermentation process is necessary for the production of oils comprising PUFAs in oleaginous yeast. This approach is described in U.S. Pat. No. 7,238,482, as are various suitable fermentation process designs (i.e., batch, fed-batch and continuous) and considerations during growth.

Purification and Processing of PUFAs

Fatty acids, including PUFAs, may be found in the host microorganisms as free fatty acids or in esterified forms such as acylglycerols, phospholipids, sulfolipids or glycolipids. These fatty acids may be extracted from the host cells through a variety of means well-known in the art. One review of extraction techniques, quality analysis and acceptability standards for yeast lipids is that of Z. Jacobs (*Critical Reviews in Biotechnology*, 12(5/6):463-491 (1992)). A brief review of downstream processing is also available by A. Singh and O. Ward (*Adv. Appl. Microbiol.*, 45:271-312 (1997)).

In general, means for the purification of fatty acids (including PUFAs) may include extraction (e.g., U.S. Pat. No. 6,797,303 and U.S. Pat. No. 5,648,564) with organic solvents, sonication, supercritical fluid extraction (e.g., using carbon dioxide), saponification and physical means such as presses, or combinations thereof. See U.S. Pat. No. 7,238,482.

PUFAs for use in Foodstuffs, Health Food Products, Pharmaceuticals and Animal Feeds The market place contains many food and feed products, incorporating ω-3 and/or ω-6 fatty acids, particularly ALA, GLA, ARA, EPA, DPA and DHA. It is contemplated that oleaginous yeast biomass comprising long-chain PUFAs, partially purified biomass comprising PUFAs, purified oil comprising PUFAs, and/or purified PUFAs made by the methods and host cells described herein impart the health benefits, upon ingestion of foods or feed improved by their addition. These oils can be added to food analogs, drinks, meat products, cereal products, baked foods, snack foods and dairy products, to name a few. See U.S. Pat. Appl. Pub. No. 2006-0094092.

These compositions may impart health benefits by being added to medical foods including medical nutritionals, dietary supplements, infant formula and pharmaceuticals. The skilled artisan will appreciate the amount of the oils to be added to food, feed, dietary supplements, nutriceuticals, pharmaceuticals, and other ingestible products as to impart health benefits. Health benefits from ingestion of these oils are described in the art, known to the skilled artisan and continuously investigated. Such an amount is referred to herein as an "effective" amount and depends on, among other things, the nature of the ingested products containing these oils and the physical conditions they are intended to address.

EXAMPLES

The present invention is further described in the following Examples, which illustrate reductions to practice of the invention but do not completely define all of its possible variations.

General Methods

Standard recombinant DNA and molecular cloning techniques used in the Examples are well known in the art and are described by: 1) Sambrook, J., Fritsch, E. F. and Maniatis, T., *Molecular Cloning: A Laboratory Manual*; Cold Spring Harbor Laboratory: Cold Spring Harbor, N.Y. (1989) (Maniatis); 2) T. J. Silhavy, M. L. Bennan, and L. W. Enquist, Experiments with Gene Fusions; Cold Spring Harbor Laboratory: Cold Spring Harbor, N.Y. (1984); and, 3) Ausubel, F. M. et al., Current Protocols in Molecular Biology, published by Greene Publishing Assoc. and Wiley-Interscience, Hoboken, N.J. (1987).

Materials and methods suitable for the maintenance and growth of microbial cultures are well known in the art. Techniques suitable for use in the following examples may be found as set out in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in Biotechnology: A Textbook of Industrial Microbiology, 2$^{nd}$ ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.), unless otherwise specified. *E. coli* strains were typically grown at 37° C. on Luria Bertani (LB) plates.

General molecular cloning was performed according to standard methods (Sambrook et al., supra). DNA sequence was generated on an ABI Automatic sequencer using dye terminator technology (U.S. Pat. No. 5,366,860; EP 272,007) using a combination of vector and insert-specific primers. Sequence editing was performed in Sequencher (Gene Codes Corporation, Ann Arbor, Mich.). All sequences represent coverage at least two times in both directions. Comparisons of genetic sequences were accomplished using DNASTAR software (DNASTAR Inc., Madison, Wis.) unless otherwise specified.

The meaning of abbreviations is as follows: "sec" means second(s), "min" means minute(s), "h" means hour(s), "d" means day(s), "μL" means microliter(s), "mL" means milliliter(s), "L" means liter(s), "μM" means micromolar, "mM" means millimolar, "M" means molar, "mmol" means millimole(s), "μmole" mean micromole(s), "g" means gram(s), "μg" means microgram(s), "ng" means nanogram(s), "U" means unit(s), "bp" means base pair(s) and "kB" means kilobase(s).

Nomenclature for Expression Cassettes

The structure of an expression cassette is represented by a simple notation system of "X::Y::Z", wherein X describes the promoter fragment, Y describes the gene fragment, and Z describes the terminator fragment, which are all operably linked to one another.

Transformation and Cultivation of *Yarrowia lipolytica*

*Yarrowia lipolytica* strain ATCC #20362 was purchased from the American Type Culture Collection (Rockville, Md.). *Yarrowia lipolytica* strains were routinely grown at 28-30° C.

in several media, according to the recipes shown below. Agar plates were prepared as required by addition of 20 g/L agar to each liquid media, according to standard methodology.

YPD agar medium (per liter): 10 g of yeast extract [Difco]; 20 g of Bacto peptone [Difco]; and 20 g of glucose.

Basic Minimal Media (MM) (per liter): 20 g glucose; 1.7 g yeast nitrogen base without amino acids; 1.0 g proline; and pH 6.1 (not adjusted).

High Glucose Media (HGM) (per liter): 80 glucose; 2.58 g $KH_2PO_4$; 5.36 g $K_2HPO_4$; pH 7.5 (do not need to adjust).

Transformation of *Y. lipolytica* was performed according to the method of Chen, D. C. et al. (*Appl. Microbiol. Biotechnol.*, 48(2):232-235 (1997)), unless otherwise noted. Briefly, *Yarrowia* was streaked onto a YPD plate and grown at 30° C. for approximately 18 hr. Several large loopfuls of cells were scraped from the plate and resuspended in 1 mL of transformation buffer containing: 2.25 mL of 50% PEG, average MW 3350; 0.125 mL of 2 M Li acetate, pH 6.0; and 0.125 mL of 2 M DTT. Then, approximately 500 ng of linearized plasmid DNA was incubated in 100 µl of resuspended cells, and maintained at 39° C. for 1 hr with vortex mixing at 15 min intervals. The cells were plated onto selection media plates and maintained at 30° C. for 2 to 3 days.

Isolation of *Yarrowia lipolytica* Strain Y4184U

*Yarrowia lipolytica* strain Y4184, producing EPA relative to the total lipids via expression of a Δ9 elongase/Δ8 desaturase pathway, was generated as described in Example 7 of Int'l. App. Pub. No. WO 2008/073367, hereby incorporated herein by reference. Briefly, as diagrammed in FIG. 5, strain Y4184 was derived from *Y. lipolytica* ATCC #20362 via construction of strain Y2224 (a FOA resistant mutant from an autonomous mutation of the Ura3 gene of wildtype *Yarrowia* strain ATCC #20362), strain Y4001 (producing 17% EDA with a Leu-phenotype), strain Y4001U1 (Leu- and Ura-), strain Y4036 (producing 18% DGLA with a Leu-phenotype), strain Y4036U (Leu- and Ura-), strain Y4069 (producing 12% ARA with a Ura-phenotype), strain Y4084 (producing 14% EPA), strain Y4084U1 (Ura-), strain Y4127 (producing 18% EPA and deposited with the American Type Culture Collection on Nov. 29, 2007, under accession number ATCC PTA-8802), strain Y4127U2 (Ura-), strain Y4158 (producing 25% EPA), strain Y4158U1 (producing Ura-) and strain Y4184 (producing 30.7% EPA relative to the total TFAs).

The final genotype of strain Y4184 with respect to wildtype *Yarrowia lipolytica* ATCC #20362 was unknown 1-, unknown 2-, unknown 3-, unknown 4-, unknown 5-, unknown 6-, YAT1::ME3S::Pex16, EXP1::ME3S::Pex20 (2 copies), GPAT::EgD9e::Lip2, FBAINm::EgD9eS::Lip2, EXP1::EgD9eS::Lip1, FBA::EgD9eS::Pex20, YAT1::EgD9eS::Lip2, GPD::EgD9eS::Lip2, GPDIN::EgD8M::Lip1, YAT1::EgD8M::Aco, EXP1::EgD8M::Pex16, FBAINm::EgD8M::Pex20, FBAIN::EgD8M::Lip1 (2 copies), GPM/FBAIN::FmD12S::Oct, EXP1::FmD12S::Aco, YAT1::FmD12::Oct, GPD::FmD12::Pex20, EXP1::EgD5S::Pex20, YAT1::EgD5S::Aco, YAT1::RD5S::Oct, FBAIN::EgD5::Aco, FBAINm::PaD17::Aco, EXP1::PaD17::Pex16, YAT1::PaD17S::Lip1, YAT1::YlCPT1::Aco, GPD::YlCPT1::Aco (wherein FmD12 is a *Fusarium moniliforme* Δ12 desaturase gene [Int'l. App. Pub. No. WO 2005/047485]; FmD12S is a codon-optimized Δ12 desaturase gene, derived from *Fusarium moniliforme* [Int'l. App. Pub. No. WO 2005/047485]; ME3S is a codon-optimized $C_{16/18}$ elongase gene, derived from *Mortierella alpina* [Int'l. App. Pub. No. WO 2007/046817]; EgD9e is a *Euglena gracilis* Δ9 elongase gene [Int'l. App. Pub. No. WO 2007/061742]; EgD9eS is a codon-optimized Δ9 elongase gene, derived from *Euglena gracilis* [Int'l. App. Pub. No. WO 2007/061742]; EgD8M is a synthetic mutant Δ8 desaturase [Int'l. App. Pub. No. WO 2008/073271], derived from *Euglena gracilis* [U.S. Pat. No. 7,256,033]; EgD5 is a *Euglena gracilis* Δ5 desaturase [U.S. Pat. App. Pub. US 2007-0292924-A1]; EgD5S is a codon-optimized Δ5 desaturase gene, derived from *Euglena gracilis* [U.S. Pat. App. Pub. No. 2007-0292924]; RD5S is a codon-optimized Δ5 desaturase, derived from *Peridinium* sp. CCMP626 [U.S. Pat. App. Pub. No. 2007-0271632]; PaD17 is a *Pythium aphanidermatum* Δ17 desaturase [Int'l. App. Pub. No. WO 2008/054565]; PaD17S is a codon-optimized Δ17 desaturase, derived from *Pythium aphanidermatum* [Int'l. App. Pub. No. WO 2008/054565]; and, YlCPT1 is a *Yarrowia lipolytica* diacylglycerol cholinephosphotransferase gene [Int'l. App. Pub. No. WO 2006/052870]).

Finally, in order to disrupt the Ura3 gene in strain Y4184, construct pZKUE3S (described in Table 22 of Int'l. App. Pub. No. WO 2008/073367, hereby incorporated herein by reference) was used to integrate a EXP1::ME3S::Pex20 chimeric gene into the Ura3 gene of strain Y4184 to result in strains Y4184U1 (11.2% EPA of total lipids), Y4184U2 (10.6% EPA of total lipids) and Y4184U4 (15.5% EPA of total lipids), respectively (collectively, Y4184U).

Fatty Acid Analysis of *Yarrowia lipolytica*

For fatty acid analysis, cells were collected by centrifugation and lipids were extracted as described in Bligh, E. G. & Dyer, W. J. (*Can. J. Biochem. Physiol.*, 37:911-917 (1959)). Fatty acid methyl esters ["FAMEs"] were prepared by transesterification of the lipid extract with sodium methoxide (Roughan, G., and Nishida I., *Arch Biochem Biophys.*, 276 (1):38-46 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5-10 min. Sodium methoxide (100 µl of 1%) was added to the sample, and then the sample was vortexed and rocked for 20 min. After adding 3 drops of 1 M NaCl and 400 µl hexane, the sample was vortexed and spun. The upper layer was removed and analyzed by GC as described above.

Example 1

*Eutreptiella* cf_*gymnastica* CCMP1594 Lipid Profile, Total RNA Isolation and Genomic DNA Isolation

*Eutreptiella* cf_*gymnastica* CCMP1594 cells (1 liter of culture) were purchased from the Provasoli-Guillard National Center for Culture of Marine Phytoplankton (CCMP) (Bigelow Laboratory for Ocean Sciences, West Boothbay Harbor, Me.). Cells from 50 mL culture were resuspended in 600 µl of sodium methoxide dissolved in methanol. The sample was shaken for 20 min, and 50 µl of 1 M NaCl was added. After mixing, 600 µl of heptane was added. The sample was vortexed and centrifuged in an Eppendorf microfuge for 1 min. The upper layer was carefully separated from the lower layer and placed in a glass vial for GC analysis. The results of the analysis are shown below in Table 3. Fatty acids are identified as 16:0 (palmitate), 16:1 (palmitoleic acid), 18:0, 18:1 (oleic acid), 18:2, GLA, ALA, DGLA, ARA, EPA, DPA and DHA; and the composition of each is presented as the weight percent of total fatty acids ["TFAs"].

TABLE 3

Lipid Profile Of *Eutreptiella* cf *gymnastica* CCMP1594 Cells

| 16:0 | 16:1 | 18:0 | 18:1 | 18:2 | GLA | ALA | DGLA | ARA | EPA | DPA | DHA |
|---|---|---|---|---|---|---|---|---|---|---|---|
| 18.5 | 2.5 | 10 | 27.5 | 5 | 0 | 10.2 | 0.1 | 0.3 | 5.3 | 4.7 | 10.7 |

Based on the presence of EPA, DPA and DHA, it was concluded that the *Eutreptiella* cf_*gymnastica* CCMP1594 had a functional Δ4 desaturase capable of converting DPA (22:5, ω-3) to DHA (22:6, ω-3).

Total RNA and genomic DNA were isolated from *Eutreptiella* cf_*gymnastica* CCMP1594 using the trizol reagent (Invitrogen, Carlsbad, Calif.), according to the manufacturer's protocol. Cell pellet from the 1 L culture (~0.25 mL in volume) was resuspended in 0.75 mL of trizol reagent, mixed with 0.5 mL of 0.5 mm glass beads, and homogenized in a Biospec mini beadbeater (Bartlesville, Okla.) at the highest setting for 3 min. The mixture was centrifuged in an Eppendorf centrifuge for 30 sec at 14,000 rpm to remove debri and glass beads. The supernatant was extracted with 150 µL of 24:1 chloroform:isoamy alcohol. The upper aqueous phase was used for RNA isolation, while the lower organic phase was used for DNA isolation.

For RNA isolation, the aqueous phase was mixed with 0.375 mL of isopropyl alcohol and allowed to incubate at room temperature for 5 min. Precipitated RNA was collected by centrifugation at 8,000 rpm and 4° C. for 5 min. The pellet was washed once with 0.7 mL of 80% ethanol and air dried. Thus, 720 µg of total RNA were obtained.

For genomic DNA isolation, the lower organic phase was mixed with 75 µL of ethanol and incubated at room temperature for 5 min. The sample was then centrifuged at 5,000 rpm for 2 min in an Eppendorf centrifuge. The pellet was washed with 0.75 mL of 0.1 M sodium citrate in 10% ethanol twice. Each time, the sample was incubated for 15 min at room temperature in the wash solution, followed by centrifugation at 5,000 rpm for 5 min at 4° C. in an Eppendorf centrifuge. The pellet was air dried and re-dissolved in 300 µL of 8 mM NaOH. The pH of the sample was adjusted to 7.5 with 1 M HEPES. The DNA sample was then further purified with the Qiagen PCR purification kit according to the manufacturer's protocol. In this way, 45 µg genomic DNA were obtained from *Eutreptiella* cf_*gymnastica* CCMP1594.

Example 2

*Eutreptiella* cf_*gymnastica* CCMP1594 cDNA Synthesis cDNA was synthesized directly from the *Eutreptiella* cf_*gymnastica* CCMP1594 mRNA as follows. Total RNA (2.4 µg) from *Eutreptiella* cf_*gymnastica* CCMP1594 was used as template to synthesize double stranded cDNA. The Creator™ SMART™ cDNA Library Construction Kit from BD Bioscience Clontech (Palo Alto, Calif.) was used. One (1) µL of the total RNA sample was mixed with 1 µL of SMART IV oligonucleotide (SEQ ID NO:10), 1 µL CDSIII/3' PCR primer (SEQ ID NO:11) and 2 µL of water. The mixture was heated to 75° C. for 5 min and then cooled on ice for 5 min. To the sample were added 2 µL of 5× first strand buffer, 1 µL 20 mM DTT, 1 µL of dNTP mix (10 mM each of dATP, dCTP, dGTP and dTTP) and 1 µL of PowerScript reverse transcriptase. The sample was incubated at 42° C. for 1 h. The resulting first strand cDNA was then used as template for amplification. The reaction mixture contained 2 µL of the above first strand cDNA sample, 80 µL of water, 10 µL of 10× Advantage 2 PCR buffer, 2 µL 50× dNTP mix (10 mM each of dATP, dCTP, dGTP and dTTP), 2 µL of 5' CDSIII PCR primer (SEQ ID NO:12), 2 µL CDSIII/3' PCR primer (SEQ ID NO:11) and 2 µL 50× Advantage 2 polymerase mix. PCR amplification was performed using the following conditions: 95° C. for 1 min, followed by 20 cycles of 95° C. for 10 sec and 68° C. for 6 min. Amplification product was purified with a Qiagen PCR purification kit according to the manufacturer's protocol. Purified product was eluted with 50 µL of water.

Example 3

Isolation of a Portion of the Coding Region of the *Eutreotiella* cf_*gymnastica* CCMP1594 Δ4 Desaturase Gene The present Example describes the identification of a portion of the *Eutreptiella* cf_*gymnastica* CCMP1594 gene encoding Δ4 desaturase (designated herein as "E1594D4" (SEQ ID NOs:1 and 2)), by use of primers derived from conserved regions of other known Δ4 desaturase sequences.

The *Euglena gracilis* Δ4 fatty acid desaturase (SEQ ID NO:13; GenBank Accession No. AY278558; Meyer et al., *Biochemistry*, 42(32):9779-9788 (2003)), *Thalassiosira pseudonana* Δ4 fatty acid desaturase (SEQ ID NO:37; GenBank Accession No. AAX14506; Tonon et al., *FEBS J.*, 272 (13):3401-3412 (2005)), *Thraustochytrium* sp. FJN-10 Δ4 fatty acid desaturase (SEQ ID NO:38; GenBank Accession No. AAZ43257), and *Pavlova lutheri* (SEQ ID NO:42; GenBank Accession No. AAQ98793; Tonon et al., *FEBS Lett*, 553(3):440-444 (2003)) were aligned as shown in FIG. 2, using the method of Clustal W (slow, accurate, Gonnet option; Thompson et al., *Nucleic Acids Res.*, 22:4673-4680 (1994)) of the MegAlign™ program of DNASTAR software. Based on this alignment, degenerate primers were designed as shown in Table 4 (location of primers with respect to SEQ ID NOs:13, 37, 38 and 42 are shown within the boxed regions of FIG. 2).

TABLE 4

Degenerate Oligonucleotides Used To Amplify The Δ4 Desaturase Gene From *Eutreptiella* of *gymnastica* CCMP1594

| Primer | Nucleotide Sequence | Amino Acid Sequence |
|---|---|---|
| D4-F1 | TTCCTNGCNAARCAYCCNGG (SEQ ID NO: 15) | FLAKHPG (SEQ ID NO: 18) |
| D4-F2 | TTTCTNGCNAARCAYCCNGG (SEQ ID NO: 16) | FLAKHPG (SEQ ID NO: 18) |
| D4-F3 | TTYTTRGCNAARCAYCCNGG (SEQ ID NO: 17) | FLAKHPG (SEQ ID NO: 18) |
| D4-F4 | ATHCARCAYGAYGGNAAYCA (SEQ ID NO: 19) | IQHDGNH (SEQ ID NO: 20) |

TABLE 4-continued

Degenerate Oligonucleotides Used To Amplify
The Δ4 Desaturase Gene From *Eutreptiella*
cf_*gymnastica* CCMP1594

| Primer | Nucleotide Sequence | Amino Acid Sequence |
|---|---|---|
| D4-F5 | CAYGAYGGNAAYCAYGGNGC (SEQ ID NO: 21) | HDGNHGA (SEQ ID NO: 22) |
| D4-F6 | GGNCAYCAYAGYTTYACNAA (SEQ ID NO: 23) | GHHQYTN (SEQ ID NO: 26) |
| D4-F7 | GGYCAYCAYTCNTTYACNAA (SEQ ID NO: 24) | GHHQYTN (SEQ ID NO: 26) |
| D4-F8 | GGRCAYCAYTCNTTYACNAA (SEQ ID NO: 25) | GHHQYTN (SEQ ID NO: 26) |
| D4-R1 | AANAGRTGRTGYTCDATYTG (SEQ ID NQ: 27) | QIEHHLF (SEQ ID NO: 29) |
| D4-R2 | AAYAARTGRTGYTCDATYTG (SEQ ID NO: 28) | QIEHHLF SEQ ID NO: 29 |

[Note: The nucleic acid degeneracy code used for SEQ ID NOs: 15-29 was as follows: R = A/G; Y = C/T; H = A/C/T; D = A/G/T; and N = A/C/T/G.]

A total of 16 different PCR amplification reactions were performed, using all possible combinations of the 8 forward and 2 reverse primers. Each reaction mixture contained 1 μl of 1:10 diluted *Eutreptiella* cf_*gymnastica* CCMP1594 cDNA (from Example 2), 5 μl each of the forward and reverse primers (20 μM), 14 μl water and 25 μl of TaKaRa ExTaq 2× premix (TaKaRa Bio, Mountain View, Calif.). The thermocycler conditions were set for 94° C. for 1 min, then 30 cycles of 94° C. for 20 sec, 55° C. for 20 sec and 72° C. for 1 min, followed by a final extension at 72° C. for 7 min. PCR products were analyzed by electrophoresis on standard agarose gels, and putative Δ4 desaturase fragments were detected as shown below in Table 5.

TABLE 5

Detected Putative Δ4 Desaturase Fragments

| Product | Forward Primer | Reverse Primer |
|---|---|---|
| ~800 bp fragment | D4-F3 or D4-F4 | D4-R1 |
| ~800 bp fragment | D4-F3 | D4-R2 |
| ~700 bp fragment | D4-F6, D4-F7 or D4-F8 | D4-R1 or D4-R2 |

Each of the fragments described above in Table 5 were purified with a Qiagen PCR purification kit (Valencia, Calif.), cloned into pCR2.1-TOPO (Invitrogen) and sequenced.

Identity of the *Eutreptiella* cf_*gymnastica* CCMP1594 sequences were determined by conducting BLAST (Basic Local Alignment Search Tool; Altschul, S. F., et al., *J. Mol. Biol.*, 215:403-410 (1993)) searches for similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL and DDBJ databases). The sequences were analyzed for similarity to all publicly available DNA sequences contained in the "nr" database using the BLASTN algorithm provided by the National Center for Biotechnology Information ["NCBI"].

BLAST sequence analysis showed that the fragments generated by primer pairs D4-F4/D4-R1 and D4-F7/D4-R1 were from a single gene that showed extensive homology to the known Δ4 desaturases from other organisms. The sequences were assembled into a 847 bp contig (SEQ ID NO:5), which was assumed to encode a portion of a putative Δ4 desaturase from *Eutreptiella* cf_*gymnastica* CCMP1594.

Example 4

Isolation of the Full-Length Δ4 Desaturase from *Eutreptiella* cf_*gymnastica* CCMP1594

Primers were designed to isolate the 5' and 3' ends of the putative Δ4 desaturase gene from cDNA samples of *Eutreptiella* cf_*gymnastica* CCMP1594, based on the partial 847 bp sequence set forth in SEQ ID NO:5 and described in Example 3.

Isolation of the Δ4 Desaturase 5' Coding Region

The 5' region of the putative Δ4 desaturase from *Eutreptiella* cf_*gymnastica* CCMP1594 was isolated by nested PCR amplification of cDNA ends. Based on the partial sequence of the putative Δ4 desaturase gene, primer 1594D4-5-1 (SEQ ID NO:30) was used in combination with 5' CDSIII PCR primer (SEQ ID NO:12) from the BD-Clontech Creator™ Smart™ cDNA library kit for the first round of amplification. The reaction mixture contained 1 μl of each primer (10 μM), 1 μl of *Eutreptiella* cf_*gymnastica* CCMP1594 cDNA (~50 ng), 22 μl water and 25 μl TaKaRa ExTaq 2× premix. The thermocycler conditions were set for 94° C. for 60 sec, then 30 cycles at 94° C. for 20 sec, 55° C. for 20 sec and 72° C. for 30 sec, followed by a final extension at 72° C. for 5 min.

The second round of PCR amplification used 1 μl of diluted product from the first round PCR reaction as template, wherein the PCR product was diluted 1:50 in water. Amplification was conducted as described above, with the exception that 1 μl each of primers 1594D4-5-2 (SEQ ID NO:31) and DNR CDS 5-2 (SEQ ID NO:32) were used (stock solution of 10 μM for each primer).

A 359 bp DNA fragment from the second round PCR product was cloned into pCR2.1-TOPO (Invitrogen) and sequenced. The fragment (SEQ ID NO:6) was designated "E1594D4-5'-A", as analysis showed that this fragment overlapped partly with the original E1594D4 partial fragment (SEQ ID NO:5) and extended further upstream. However, there was no translation initiation codon in the extended 359 bp fragment of SEQ ID NO:6. Based on sequence comparison with known Δ4 desaturases, approximately 400 bp was assumed to be missing from the 5'-end.

The methodology utilized above to obtain fragment E1594D4-5'-A was repeated to obtain an additional 5' region of the E1594D4 gene, utilizing identical PCR conditions to those described above. However, primer 1594D4-5-4 (SEQ ID NO:33) replaced primer 1594D4-5-1 (SEQ ID NO:30) in the first round of amplification. Following a 1:50 dilution of the first round product, a second round PCR was conducted using primer 1594D4-5-5 (SEQ ID NO:34) instead of primer 1594D4-5-2 (SEQ ID NO:31).

A ~400 bp DNA fragment in the second round PCR product was cloned into pCR2.1-TOPO and sequenced. Sequence analysis showed that this fragment contained the 5' end of the E1594D4 gene, including the start codon and 9 bp of the 5' untranslated region. The fragment was designated "1594D4-5'-B" (SEQ ID NO:7).

Isolation of the Δ4 Desaturase 3' Coding Region

The 3' region of the putative Δ4 desaturase was also isolated by nested PCR amplification. In the first round, the reaction mixture contained 1 μl each of primer 1594D4-3-1

(SEQ ID NO:35, 10 μM) and primer CDSIII/3' PCR primer (SEQ ID NO:11, 10 μM), 1 μl of *Eutreptiella* cf_*gymnastica* CCMP1594 cDNA (~50 ng), 22 μl water and 25 μl TaKaRa ExTaq 2× premix. The thermocycler conditions were set for 94° C. for 60 sec, then 30 cycles at 94° C. for 20 sec, 55° C. for 20 sec and 72° C. for 30 sec, followed by a final extension at 72° C. for 7 min. For the second round PCR, the reaction mixture contained 1 μl each of primer 1594D4-3-2 (SEQ ID NO:36, 10 μM) and CDSIII/3' PCR primer (SEQ ID NO:11, 10 μM), 1 μl of 1:50 diluted first round PCR product, 22 μl water and 25 μl TaKaRa ExTaq 2× premix. PCR conditions were otherwise identical to that used for the first round PCR.

A ~900 bp DNA fragment was generated by the second round of PCR. This fragment was cloned into pCR2.1-TOPO and sequenced. Sequence analysis showed that this fragment (designated as "1594D4-3" and set forth as SEQ ID NO:8) included the 3' region of the E1594D4 gene.

Assembly and Analysis of the Complete Δ4 Desaturase Coding Sequence

The cDNA sequence of the entire putative *Eutreptiella* cf_*gymnastica* CCMP1594 Δ4 desaturase (E1594D4) gene was determined by assembly of the E1594D4 partial fragment (SEQ ID NO:5), the 1594D4-5'-A fragment (SEQ ID NO:6), the 1594D4-5'-B fragment (SEQ ID NO:7) and the 1594D4-3' fragment (SEQ ID NO:8). The 2070 bp CDNA sequence, including 9 bp of the 5' untranslated region and 516 bp of 3' untranslated region, was designated "E1594D4-cDNA" (SEQ ID NO:9). The E1594D4 CDS was 1345 bp in length (SEQ ID NO:1) and encoded a polypeptide of 514 amino acids (SEQ ID NO:2).

The E1594D4 sequence (i.e., SEQ ID NO:2) was compared for similarity to all publicly available protein sequences contained in the "nr" database, using the BLASTX algorithm (Gish, W. and States, D. J., *Nature Genetics*, 3:266-272 (1993)) provided by the NCBI. The results of the BLASTX comparison summarizing the sequence to which SEQ ID NO:2 has the most similarity are reported according to the % identity, % similarity and Expectation value. "% Identity" is defined as the percentage of amino acids that are identical between the two proteins. "% Similarity" is defined as the percentage of amino acids that are identical or conserved between the two proteins. "Expectation value" estimates the statistical significance of the match, specifying the number of matches, with a given score, that are expected in a search of a database of this size absolutely by chance.

Thus, SEQ ID NO:2 was found to share 65% identity and 76% similarity with the amino acid sequence of the Δ4 fatty acid desaturase from *Thalassiosira pseuduonana* (SEQ ID NO:37; GenBank Accession No. AAX14506), with an Expectation value of 0.0. Additionally, the full length E1594D4 gene shared identity and similarity with other Δ4 fatty acid desaturases. More specifically, pairwise comparison between and among Δ4 desaturase proteins from *Eutreptiella* cf_*gymnastica* CCMP1594 (SEQ ID NO:2), *Thalassiosira pseduonana* (SEQ ID NO:37, supra), *Euglena gracilis* (SEQ ID NO:13; GenBank Accession No. AY278558) and *Thraustochytrium* sp. FJN-10 (SEQ ID NO:38; GenBank Accession No. AAZ43257) using a Clustal W analysis (MegAlign™ program of DNASTAR software) resulted in the percent similarities shown below in Table 6.

TABLE 6

Percent Similarities Between And Among Various Δ4 Desaturases

| | SEQ ID NO: 2 | SEQ ID NO: 37 | SEQ ID NO: 13 | SEQ ID NO: 38 |
|---|---|---|---|---|
| *Eutreptiella cf_gymnastica* CCMP1594 (SEQ ID NO: 2) | 100 | 68 | 40 | 59 |
| *Thalassiosira pseuduonana* (SEQ ID NO: 37) | — | 100 | 41 | 56 |
| *Euglena gracilis* (SEQ ID NO: 13) | — | — | 100 | 42 |
| *Thraustochytrium* sp. FJN-10 (SEQ ID NO: 38) | — | — | — | 100 |

Example 5

Synthesis of a Codon-Optimized Δ4 Desaturase Gene ["E1594D4S"] for *Yarrowia lipolytica*

The codon usage of the Δ4 desaturase gene of *Eutreptiella* cf_*gymnastica* CCMP1594 (SEQ ID NOs:1 and 2; "E1594D4") was optimized for expression in *Yarrowia lipolytica*, in a manner similar to that described in Int'l. App. Pub. No. WO 2004/101753 and U.S. Pat. No. 7,125,672. Specifically, a codon-optimized Δ4 desaturase gene (designated "E1594D4S", SEQ ID NOs:3 and 4) was designed based on the coding sequence of the Δ4 desaturase gene of E1594D4, according to the *Yarrowia* codon usage pattern (Int'l. App. Pub. No. WO 2004/101753), the consensus sequence around the 'ATG' translation initiation codon, and the general rules of RNA stability (Guhaniyogi, G. and J. Brewer, *Gene*, 265(1-2):11-23 (2001)). A total of 200 bp of the 1545 bp coding region were modified (12.9%; FIG. 3) and 191 codons were optimized (37.1%). The GC content was reduced from 56.1% within the wild type gene (i.e., E1594D4) to 54.6% within the synthetic gene (i.e., E1594D4S). A NcoI site and NotI sites were incorporated around the translation initiation codon and after the stop codon of E1594D4S, respectively. In order to add a NcoI site around the translation initiation codon, E1594D4S had one additional alanine amino acid inserted between amino acid residues 1 and 2 of the wildtype E1594D4; thus, the total length of E1594D4S is 515 amino acids (SEQ ID NO:4). The designed E1594D4S gene (SEQ ID NO:3; labeled as "1594D4S" in FIG. 4A) was synthesized by GenScript Corporation (Piscataway, N.J.) and cloned into pUC57 (GenBank Accession No. Y14837) to generate p1594D4S (FIG. 4A; SEQ ID NO:39).

Example 6

Generation of Construct pZKL4-220ESC4, Comprising E1594D4S

The present Example describes the construction of plasmid pZKL4-220ESC4. This plasmid was constructed to integrate two chimeric $C_{20/22}$ elongase genes and one chimeric E1594D4S gene into the lipase 4-like locus (GenBank Accession No. XM_503825) of *Yarrowia lipolytica*. This was designed to integrate the chimeric genes into the genome of *Yarrowia lipolytica* and then permit study of the function of the codon-optimized Δ4 desaturase derived from *Eutreptiella* cf_*gymnastica* CCMP1594 in *Yarrowia lipolytica*.

Plasmid pZKL4-220ESC4 (FIG. 4B) contained the following components:

TABLE 7

Components Of Plasmid pZKL4-220ESC4 (SEQ ID NO: 40)

| RE Sites And Nucleotides Within SEQ ID NO: 40 | Description Of Fragment And Chimeric Gene Components |
|---|---|
| Asc I/BsiW I (6742-5990) | 745 bp 5' portion of the *Yarrowia* Lipase 4-like gene (labeled as "Lip4L-5'" in Figure; GenBank Accession No. XM_503825) |
| PacI/SphI (10235-9450) | 782 bp 3' portion of *Yarrowia* Lipase 4-like gene (labeled as "Lip4L-3'" in Figure; GenBank Accession No. XM_503825) |
| Swa I/BsiW I (3847-5990) | FBAINm::EaC20ES::Pex20, comprising: FBAINm: *Yarrowia lipolytica* FBAINm promoter (U.S. Pat. No. 7,202,356); EaC20ES: codon-optimized C20 elongase gene (SEQ ID NO: 46), derived from *Euglena anabaena* (U.S. Pat. Appl. Pub. No. 2008/0254191-A1); Pex20: Pex20 terminator sequence from *Yarrowia* Pex20 gene (GenBank Accession No. AF054613) |
| Pme I/Swa I (1868-3847) | YAT1::EgC20ES::Lip1, comprising: YAT1: *Yarrowia lipolytica* YAT1 promoter (U.S. Pat. Appl. Pub. No. 2006/0094102-A1); EgC20ES: codon-optimized C20 elongase gene (SEQ ID NO: 44), derived from *Euglena gracilis* (U.S. Pat. Appl. Pub. No. 2008/0254191-A1); Lip1: Lip1 terminator sequence from *Yarrowia* Lip1 gene (GenBank Accession No. Z50020) |
| Cla I/Pme I (12339-1868) | EXP1::E1594D4S::Oct, comprising: EXP1: *Yarrowia lipolytica* export protein (EXP1) promoter (Int'l. App. Pub. No. WO 2006/052870); E1594D4S: codon-optimized Δ4 desaturase (SEQ ID NO: 3), derived from *Eutreptiella cf_gymnastica* CCMP1594 (labeled as "D4S-1594" in Figure); OCT: OCT terminator sequence of *Yarrowia* OCT gene (GenBank Accession No. X69988) |
| Sal I/EcoR I (11889-10270) | *Yarrowia* Ura3 gene (GenBank Accession No. AJ306421) |

Example 7

Expression of the Codon-Optimized Δ4 Desaturase ("E1594D4S") in *Yarrowia lipolytica* Strain Y4184U4

The pZKL4-220ESC4 plasmid comprising E1594D4S (Example 6) was digested with AscI/SphI, and then used for transformation of strain Y4184U4 (General Methods), using standard transformation procedures. The transformants were selected on MM plates. After 4 days growth at 30° C., 3 transformants grown on the MM plates were picked and re-streaked onto fresh MM plates. Once grown, these strains and the control strain were individually inoculated into 3 mL liquid MM at 30° C. and shaken at 250 rpm/min for 2 days. The cells were collected by centrifugation, resuspended in High Glucose Media ["HGM"] and then shaken at 250 rpm/min for 5 days. The cells were collected by centrifugation, lipids were extracted, and fatty acid methyl esters ["FAMEs"] were prepared by trans-esterification, and subsequently analyzed with a Hewlett-Packard 6890 GC.

Results are shown below in Table 8. Specifically, fatty acids are identified as 16:0 (palmitate), 16:1, 18:0 (stearic acid), 18:1 (oleic acid), LA, ALA, EDA, DGLA, ARA, ETrA, ETA, EPA, DPA and DHA; and, fatty acid compositions were expressed as the weight percent (wt. %) of total fatty acids ["TFAs"].

TABLE 8

Fatty Acid Composition In Transformants Expressing E1594D4S (SEQ ID NO: 3)

| | 16:0 | 16:1 | 18:0 | 18:1 | LA | ALA | EDA | DGLA | ARA | ETrA | ETA | EPA | DPA | DHA |
|---|---|---|---|---|---|---|---|---|---|---|---|---|---|---|
| Y4184-Control | | | | | | | | | | | | | | |
| 1 | 3.6 | 1.4 | 1.9 | 8.3 | 29.0 | 6.3 | 4.7 | 1.1 | 0.4 | 2.1 | 1.1 | 30.4 | 0.5 | 0.0 |
| 2 | 3.8 | 1.7 | 1.7 | 8.4 | 31.1 | 6.2 | 4.3 | 1.1 | 0.4 | 1.9 | 1.2 | 28.8 | 0.3 | 0.0 |
| 3 | 4.5 | 1.8 | 1.9 | 8.1 | 32.0 | 5.9 | 4.8 | 1.2 | 0.4 | 1.9 | 1.2 | 28.0 | 0.2 | 0.0 |
| Average | 4.0 | 1.6 | 1.8 | 8.3 | 30.7 | 6.2 | 4.6 | 1.1 | 0.4 | 2.0 | 1.2 | 29.1 | 0.3 | 0.0 |
| Vector pZKL4-220EC4-1 in Y4184U4 | | | | | | | | | | | | | | |
| 1 | 4.5 | 1.3 | 1.5 | 6.3 | 29.4 | 5.1 | 3.3 | 1.2 | 0.5 | 1.4 | 1.0 | 22.1 | 9.8 | 2.0 |
| 2 | 4.3 | 1.3 | 1.9 | 7.0 | 29.5 | 5.7 | 3.2 | 1.1 | 0.5 | 1.4 | 1.0 | 21.2 | 10.4 | 1.9 |
| 3 | 4.3 | 1.6 | 1.4 | 6.2 | 29.1 | 4.0 | 3.3 | 1.3 | 0.8 | 1.4 | 0.8 | 22.0 | 10.3 | 2.0 |
| Average | 4.4 | 1.4 | 1.6 | 6.5 | 29.3 | 4.9 | 3.2 | 1.2 | 0.6 | 1.4 | 0.9 | 21.7 | 10.2 | 2.0 |

The GC analyses of Table 8 showed that there were about 2% DHA and 10.2% DPA of total lipids produced in all three transformants, but not in the control Y4184 strain. Conversion efficiency of the substrate, DPA, to DHA in the three transformant strains expressing E1594D4S was determined to be about 16%. The conversion efficiency was measured according to the following formula: ([product]/[substrate+product])*100, where 'product' includes the immediate product and all products in the pathway derived from it. Thus, this experimental data demonstrated that the synthetic Δ4 desaturase derived from *Eutreptiella cf_gymnastica* CCMP1594 and codon-optimized for expression in *Yarrowia lipolytica* (E1594D4S, as set forth in SEQ ID NO:3) was active to convert the substrate, DPA, to DHA.

---

What is claimed is:

1. An isolated nucleic acid molecule selected from the group consisting of:
   (a) an isolated nucleotide sequence encoding a delta-4 desaturase enzyme selected from the group consisting of SEQ ID NO:2 and SEQ ID NO:4;
   (b) an isolated nucleotide sequence encoding a delta-4 desaturase enzyme that hybridizes with (a) under the following stringent hybridization conditions: 0.1×SSC, 0.1% SDS, 65° C. and washed with 2×SSC, 0.1% SDS followed by 0.1×SSC, 0.1% SDS;
   (c) an isolated nucleotide sequence encoding a delta-4 desaturase enzyme having at least 90% identity when compared to a polypeptide haying the amino acid sequence as set forth in SEQ ID NO:2, based on the Clustal W method of alignment; and,
   (d) an isolated nucleotide sequence that is completely complementary to
   (a), (b) or (c).

2. The isolated nucleic acid molecule of claim 1, wherein at least 191 codons are codon-optimized for expression in *Yarrowia*.

3. The isolated nucleic acid molecule of claim 1 selected from the group consisting of SEQ ID NO:1 and SEQ ID NO:3.

4. The isolated nucleic acid molecule of claim 1, wherein the nucleotide sequence encoding a delta-4 desaturase enzyme comprises at least 514 amino acids.

5. A chimeric gene comprising the isolated nucleic acid molecule of claim 1 operably linked to at least one regulatory sequence.

6. A host cell comprising the isolated nucleic acid sequence of claim 1.

7. The host cell of claim 6, wherein the host cell is selected from the group consisting of yeast; oleaginous yeast preferably selected from the group consisting of: *Yarrowia, Candida, Rhodotorula, Rhodosporidium, Cryptococcus, Trichosporon* and *Lipomyces*; algae; bacteria; euglenoids; stramenopiles, fungi; *Mortierella; Thraustochytrium*; and *Schizochytrium*.

8. The host cell of claim 6, wherein the cell is from a plant selected from the group consisting of soybean, corn, flax, rapeseed, primrose, canola, maize, cotton, safflower and sunflower.

9. A host cell comprising the isolated nucleic acid sequence of claim 1.

10. The host cell of claim 9, wherein the host cell is selected from the group consisting of yeast; oleaginous yeast preferably selected from the group consisting of: *Yarrowia, Can-* dida, *Rhodotorula, Rhodosporidium, Cryptococcus, Trichosporon* and *Lipomyces*; algae; bacteria; euglenoids; stramenopiles, fungi; *Mortierella; Thraustochytrium*; and *Schizochytrium*.

11. The host cell of claim 9, wherein the cell is from a plant selected from the group consisting of soybean, corn, flax, rapeseed, primrose, canola, maize, cotton, safflower and sunflower.

12. A transformed *Yarrowia* comprising the isolated nucleic acid molecule of claim 1.

13. A method of making a polyunsaturated fatty acid selected from the group consisting of docosahexaenoic acid and all-cis-4,7,10,13,16-docosapentaenoic acid (22:5, omega-6), comprising:
   (a) providing a host cell comprising:
      (i) an isolated nucleotide molecule encoding a delta-4 desaturase polypeptide having at least 90% identity when compared to a polypeptide having the amino acid sequence as set forth in SEQ ID NO:2, based on the Clustal W method of alignment; and,
      (ii) a source fatty acid selected from the group consisting of all-cis-7,10,13,16,19-docosapentaenoic acid (22:5, omega-3) and docosatetraenoic acid;
   (b) growing the host cell of step (a) under conditions to express the nucleic acid fragment encoding the delta-4 desaturase polypeptide and to convert the source fatty acid to a polyunsaturated fatty acid selected from the group consisting of all-cis-7,10,13,16,19-docosapentaenoic acid (22:5, omega-3) and docosatetraenoic acid, such that when all-cis-7,10,13,16,19-docosapentaenoic acid (22:5, omega-3) is the source fatty acid, then docosahexaenoic acid is the polyunsaturated fatty acid produced; and when docosatetraenoic acid is the source fatty acid, then all-cis-4,7,10,13,16-docosapentaenoic acid (22:5, omega-6) is the polyunsaturated fatty acid produced; and,
   (c) optionally recovering the polyunsaturated fatty acid produced in step (b).

14. The method of claim 13, wherein the isolated nucleic acid molecule encodes a delta-4 desaturase polypeptide having an amino acid sequence selected from the group consisting of SEQ ID NO:2 and SEQ ID NO:4.

15. The method of claim 13, wherein the isolated nucleic acid molecule has a nucleic acid sequence selected from the group consisting of SEQ ID NO:1 and SEQ ID NO:3 and the host cell is selected from the group consisting of: algae; bacteria; yeast; oleaginous yeast preferably selected from the group consisting of *Yarrowia, Candida, Rhodotorula, Rhodosporidium, Cryptococcus, Trichosporon* and *Lipomyces*; stramenopiles; euglenoids; fungi; plant cells; and animal cells.

* * * * *

SEQUENCE LISTING

<160> NUMBER OF SEQ ID NOS: 136

<210> SEQ ID NO 1
<211> LENGTH: 1545
<212> TYPE: DNA
<213> ORGANISM: Eutreptiella cf_gymnastica CCMP1594
<220> FEATURE:
<221> NAME/KEY: misc_feature
<222> LOCATION: (1)..(1545)
<223> OTHER INFORMATION: delta-4 desaturase ("E1594D4")

<400> SEQUENCE: 1

```
atgcagtcaa ccaaggcggc cgacaccgcc gctaccgaca agagtctcga caagaaccgc      60
ctcatctctc gggatgagct tcgttctcac aatgtccccc aggatgcgtg ggctgctgtc     120
cacgggaggg tcatcaacat cacggagttc gcccgacgtc atcctggcgg cgacatcatc     180
ctccttgccg cagggaagga tgccacagtc ctcttcgaga cctaccatcc ccgcggtgtc     240
cccacctcca tcctcgacaa gctccaggtg ggaaagatga aggacgggga gctgccctcc     300
tccttctact cgtgggattc tgacttttac aagaccctgc gcgcccgcgt tgttgagagg     360
ttggacaagc tcaacctgcc gcgaagggga gggtatgaga tctgggtcaa ggcagtattc     420
ctcctggcag gattctggtt cagcctctac aagatgtctg tgaacgagac ctactgggcc     480
gcatcgctct ggtccgtgtc catgggagtg ttcgccgcct tcatcggcac ttgcatccag     540
cacgatggaa accatggcgc cttctcgacc agcccggctc tgaacaaggt ggcgggctgg     600
actctggaca tgattggggc gtcaggtttc acgtgggaaa tccaacatat gctcggccat     660
catccctaca ccaacgttct tgacgtggac gaagaaaaga ggaaggaagc tggcgacgac     720
tgcccgatgg aagacaagga ccaggagtcc gacccagatg tcttctcctc cttccctctc     780
atgcgcatgc acccatacca caaggctgag tggtaccatc gctatcagca cctgtacgcg     840
cccgttctct tcgcgttcat gacgctagcc aaggtgttcc agcaggatat cgaggtcgcc     900
accacccaga gattgtacca tatcgatgcc aagtgccgat acaattctat tctgaatgtc     960
ttgcgctttt ggtcgatgaa ggtgctttcg atcggatata tgctggctgt gccctgctac    1020
ttccacggca ttcttggtgg ccttggcctt ttccttatcg gccactttgc ctgcggtgag    1080
cttctggcga ccatgttcat tgtcaatcac gtcattgagg agtctccctt tggcaagaag    1140
ggtgaatcgc tgggactttc caaggacgtg gagttcaagc ccaccaccgt ttcgggccgc    1200
acgcccatgg aacagacccg tgccgaagcc aagaaggcgg ccaacggcgg aaacgtgaag    1260
gatgtcccct acaacgactg ggcggccgtt caatgccaaa cgagtgtgaa ctggagtcct    1320
ggatcgtggt tctggaatca cttcagcggc ggtctatcgc atcagattga gcaccatctt    1380
ttccctagca tttgccacac caattacgct catatccaag acgttgtcca aaagacttgc    1440
gaggagtasg gcgttcctta ccaaagcgag ccctctttgt aytccgccta tggcaagatg    1500
ttgagccatc tcaagtacct cggaaacgag aagaaggtgg cttag                    1545
```

<210> SEQ ID NO 2

-continued

```
<211> LENGTH: 514
<212> TYPE: PRT
<213> ORGANISM: Eutreptiella cf_gymnastica CCMP1594
<220> FEATURE:
<221> NAME/KEY: MISC_FEATURE
<222> LOCATION: (1)..(514)
<223> OTHER INFORMATION: delta-4 desaturase ("E1594D4")

<400> SEQUENCE: 2

Met Gln Ser Thr Lys Ala Ala Asp Thr Ala Thr Asp Lys Ser Leu
1               5                   10                  15

Asp Lys Asn Arg Leu Ile Ser Arg Asp Glu Leu Arg Ser His Asn Val
            20                  25                  30

Pro Gln Asp Ala Trp Ala Ala Val His Gly Arg Val Ile Asn Ile Thr
        35                  40                  45

Glu Phe Ala Arg Arg His Pro Gly Gly Asp Ile Ile Leu Leu Ala Ala
    50                  55                  60

Gly Lys Asp Ala Thr Val Leu Phe Glu Thr Tyr His Pro Arg Gly Val
65              70                  75                  80

Pro Thr Ser Ile Leu Asp Lys Leu Gln Val Gly Lys Met Lys Asp Gly
                85                  90                  95

Glu Leu Pro Ser Ser Phe Tyr Ser Trp Asp Ser Asp Phe Tyr Lys Thr
            100                 105                 110

Leu Arg Ala Arg Val Val Glu Arg Leu Asp Lys Leu Asn Leu Pro Arg
        115                 120                 125

Arg Gly Gly Tyr Glu Ile Trp Val Lys Ala Val Phe Leu Leu Ala Gly
    130                 135                 140

Phe Trp Phe Ser Leu Tyr Lys Met Ser Val Asn Glu Thr Tyr Trp Ala
145             150                 155                 160

Ala Ser Leu Trp Ser Val Ser Met Gly Val Phe Ala Ala Phe Ile Gly
                165                 170                 175

Thr Cys Ile Gln His Asp Gly Asn His Gly Ala Phe Ser Thr Ser Pro
            180                 185                 190

Ala Leu Asn Lys Val Ala Gly Trp Thr Leu Asp Met Ile Gly Ala Ser
        195                 200                 205

Gly Phe Thr Trp Glu Ile Gln His Met Leu Gly His His Pro Tyr Thr
    210                 215                 220

Asn Val Leu Asp Val Asp Glu Glu Lys Arg Lys Glu Ala Gly Asp Asp
225                 230                 235                 240

Cys Pro Met Glu Asp Lys Asp Gln Glu Ser Asp Pro Asp Val Phe Ser
                245                 250                 255

Ser Phe Pro Leu Met Arg Met His Pro Tyr His Lys Ala Glu Trp Tyr
            260                 265                 270

His Arg Tyr Gln His Leu Tyr Ala Pro Val Leu Phe Ala Phe Met Thr
        275                 280                 285

Leu Ala Lys Val Phe Gln Gln Asp Ile Glu Val Ala Thr Thr Gln Arg
    290                 295                 300

Leu Tyr His Ile Asp Ala Lys Cys Arg Tyr Asn Ser Ile Leu Asn Val
305                 310                 315                 320

Leu Arg Phe Trp Ser Met Lys Val Leu Ser Ile Gly Tyr Met Leu Ala
                325                 330                 335

Val Pro Cys Tyr Phe His Gly Ile Leu Gly Leu Gly Leu Phe Leu
            340                 345                 350

Ile Gly His Phe Ala Cys Gly Glu Leu Leu Ala Thr Met Phe Ile Val
        355                 360                 365

Asn His Val Ile Glu Gly Val Ser Phe Gly Lys Lys Gly Glu Ser Leu
```

```
                370              375                 380
Gly Leu Ser Lys Asp Val Glu Phe Lys Pro Thr Thr Val Ser Gly Arg
385                 390                 395                 400

Thr Pro Met Glu Gln Thr Arg Ala Glu Ala Lys Lys Ala Ala Asn Gly
                405                 410                 415

Gly Asn Val Lys Asp Val Pro Tyr Asn Asp Trp Ala Ala Val Gln Cys
                420                 425                 430

Gln Thr Ser Val Asn Trp Ser Pro Gly Ser Trp Phe Trp Asn His Phe
            435                 440                 445

Ser Gly Gly Leu Ser His Gln Ile Glu His His Leu Phe Pro Ser Ile
    450                 455                 460

Cys His Thr Asn Tyr Ala His Ile Gln Asp Val Val Gln Lys Thr Cys
465                 470                 475                 480

Glu Glu Xaa Gly Val Pro Tyr Gln Ser Glu Pro Ser Leu Tyr Ser Ala
                485                 490                 495

Tyr Gly Lys Met Leu Ser His Leu Lys Tyr Leu Gly Asn Glu Lys Lys
            500                 505                 510

Val Ala

<210> SEQ ID NO 3
<211> LENGTH: 1548
<212> TYPE: DNA
<213> ORGANISM: Eutreptiella cf_gymnastica CCMP1594
<220> FEATURE:
<221> NAME/KEY: CDS
<222> LOCATION: (1)..(1548)
<223> OTHER INFORMATION: synthetic delta-4 desaturase (codon-optimized
      for Yarrowia lipolytica) ("E1594D4S")

<400> SEQUENCE: 3 atg gct cag tcc acc aag gct gcc gac act gct gcc acc gac aag tct        48
Met Ala Gln Ser Thr Lys Ala Ala Asp Thr Ala Ala Thr Asp Lys Ser
1               5                   10                  15 ctc gac aag aac cga ctc atc tcc cga gac gag ctg cgg tct cac aac        96
Leu Asp Lys Asn Arg Leu Ile Ser Arg Asp Glu Leu Arg Ser His Asn
            20                  25                  30 gtt ccc cag gat gcc tgg gct gcc gtc cac ggc aga gtc atc aac att       144
Val Pro Gln Asp Ala Trp Ala Ala Val His Gly Arg Val Ile Asn Ile
        35                  40                  45 acc gag ttc gcc cga cgg cat cct ggt ggc gac atc att ctg ctt gcc       192
Thr Glu Phe Ala Arg Arg His Pro Gly Gly Asp Ile Ile Leu Leu Ala
    50                  55                  60 gca gga aag gat gcc acc gtg ctc ttc gag act tac cat cct cga ggt       240
Ala Gly Lys Asp Ala Thr Val Leu Phe Glu Thr Tyr His Pro Arg Gly
65                  70                  75                  80 gtt ccc acc tcg atc ctc gac aag ctg cag gtc ggc aag atg aag gac       288
Val Pro Thr Ser Ile Leu Asp Lys Leu Gln Val Gly Lys Met Lys Asp
                85                  90                  95 gga gaa ctt ccc tcc tcg ttc tac tcg tgg gat tcc gac ttt tac aag       336
Gly Glu Leu Pro Ser Ser Phe Tyr Ser Trp Asp Ser Asp Phe Tyr Lys
            100                 105                 110 acc ctg cga gct cga gtg gtc gag cga ttg gac aag ctc aac ctg cct       384
Thr Leu Arg Ala Arg Val Val Glu Arg Leu Asp Lys Leu Asn Leu Pro
        115                 120                 125 cga aga ggt ggc tac gag att tgg gtc aag gca gta ttc ctc ctg gct       432
Arg Arg Gly Gly Tyr Glu Ile Trp Val Lys Ala Val Phe Leu Leu Ala
    130                 135                 140 gga ttc tgg ttc agc ctc tac aag atg tcc gtc aac gag acc tac tgg       480
Gly Phe Trp Phe Ser Leu Tyr Lys Met Ser Val Asn Glu Thr Tyr Trp
145                 150                 155                 160
```

```
gct gcc tcg ctg tgg tcc gtg tct atg gga gtc ttt gct gcc ttc atc        528
Ala Ala Ser Leu Trp Ser Val Ser Met Gly Val Phe Ala Ala Phe Ile
            165                 170                 175 ggc act tgc att caa cac gat gga aac cac ggt gcc ttc tcg acc agc        576
Gly Thr Cys Ile Gln His Asp Gly Asn His Gly Ala Phe Ser Thr Ser
        180                 185                 190 cct gct ctc aac aag gtt gca ggc tgg act ctg gac atg atc ggt gct        624
Pro Ala Leu Asn Lys Val Ala Gly Trp Thr Leu Asp Met Ile Gly Ala
    195                 200                 205 tct ggc ttt aca tgg gag att cag cat atg ctc gga cac cat ccc tac        672
Ser Gly Phe Thr Trp Glu Ile Gln His Met Leu Gly His His Pro Tyr
210                 215                 220 acc aac gtc ctg gac gtg gac gaa gag aag cga aag gaa gct ggc gac        720
Thr Asn Val Leu Asp Val Asp Glu Glu Lys Arg Lys Glu Ala Gly Asp
225                 230                 235                 240 gat tgt cct atg gag gac aag gat cag gag tcc gac cca gat gtc ttc        768
Asp Cys Pro Met Glu Asp Lys Asp Gln Glu Ser Asp Pro Asp Val Phe
                245                 250                 255 tct tcg ttt cct ctc atg cga atg cac ccc tac cac aag gcc gag tgg        816
Ser Ser Phe Pro Leu Met Arg Met His Pro Tyr His Lys Ala Glu Trp
            260                 265                 270 tac cac cga tat cag cac ctg tac gca ccc gtt ctc ttt gct ttc atg        864
Tyr His Arg Tyr Gln His Leu Tyr Ala Pro Val Leu Phe Ala Phe Met
        275                 280                 285 act ctt gcc aag gtg ttc caa cag gac atc gaa gtc gct acc act cag        912
Thr Leu Ala Lys Val Phe Gln Gln Asp Ile Glu Val Ala Thr Thr Gln
    290                 295                 300 cga ctg tac cac atc gac gcc aag tgc cga tac aat tcc att ctc aat        960
Arg Leu Tyr His Ile Asp Ala Lys Cys Arg Tyr Asn Ser Ile Leu Asn
305                 310                 315                 320 gtc ctt cgg ttt tgg tcg atg aag gtg ctc tcc atc ggc tac atg ctg       1008
Val Leu Arg Phe Trp Ser Met Lys Val Leu Ser Ile Gly Tyr Met Leu
                325                 330                 335 gct gtt ccc tgc tac ttc cac gga atc ctt ggt ggc ctt gga ctg ttt       1056
Ala Val Pro Cys Tyr Phe His Gly Ile Leu Gly Gly Leu Gly Leu Phe
            340                 345                 350 ctc atc ggc cac ttt gcc tgt gga gag ctt ctg gca acc atg ttc att       1104
Leu Ile Gly His Phe Ala Cys Gly Glu Leu Leu Ala Thr Met Phe Ile
        355                 360                 365 gtc aat cac gtc atc gag ggt gtg tcc ttt ggc aaa aag gga gaa tct       1152
Val Asn His Val Ile Glu Gly Val Ser Phe Gly Lys Lys Gly Glu Ser
    370                 375                 380 ctc ggt ctg tcc aag gac gtg gag ttc aag cct aca acc gtt tct gga       1200
Leu Gly Leu Ser Lys Asp Val Glu Phe Lys Pro Thr Thr Val Ser Gly
385                 390                 395                 400 cga act cca atg gag cag acc cgt gcc gag gcc aaa aag gct gcc aat       1248
Arg Thr Pro Met Glu Gln Thr Arg Ala Glu Ala Lys Lys Ala Ala Asn
                405                 410                 415 gga ggc aac gtc aag gat gtt ccc tac aac gac tgg gct gcc gtt cag       1296
Gly Gly Asn Val Lys Asp Val Pro Tyr Asn Asp Trp Ala Ala Val Gln
            420                 425                 430 tgt caa acg agc gtc aac tgg tct cct gga tcg tgg ttc tgg aat cac       1344
Cys Gln Thr Ser Val Asn Trp Ser Pro Gly Ser Trp Phe Trp Asn His
        435                 440                 445 ttc tcc ggt ggc ctc tcc cac cag atc gag cac atc ctg ttt ccc agc       1392
Phe Ser Gly Gly Leu Ser His Gln Ile Glu His His Leu Phe Pro Ser
    450                 455                 460 att tgt cac acc aac tac gct cac atc cag gac gtt gtc cag aag act       1440
Ile Cys His Thr Asn Tyr Ala His Ile Gln Asp Val Val Gln Lys Thr
465                 470                 475                 480
```

```
tgc gaa gag tac ggt gtt cct tac cag tcc gaa ccc tct ttg ttc tcc      1488
Cys Glu Glu Tyr Gly Val Pro Tyr Gln Ser Glu Pro Ser Leu Phe Ser
            485                 490                 495 gcc tat ggc aag atg ctg tct cat ctc aag tac ctc gga aac gag aaa      1536
Ala Tyr Gly Lys Met Leu Ser His Leu Lys Tyr Leu Gly Asn Glu Lys
        500                 505                 510 aag gtc gct taa                                                      1548
Lys Val Ala
        515

<210> SEQ ID NO 4
<211> LENGTH: 515
<212> TYPE: PRT
<213> ORGANISM: Eutreptiella cf_gymnastica CCMP1594

<400> SEQUENCE: 4

Met Ala Gln Ser Thr Lys Ala Ala Asp Thr Ala Ala Thr Asp Lys Ser
1               5                   10                  15

Leu Asp Lys Asn Arg Leu Ile Ser Arg Asp Glu Leu Arg Ser His Asn
            20                  25                  30

Val Pro Gln Asp Ala Trp Ala Val His Gly Arg Val Ile Asn Ile
        35                  40                  45

Thr Glu Phe Ala Arg Arg His Pro Gly Gly Asp Ile Ile Leu Leu Ala
    50                  55                  60

Ala Gly Lys Asp Ala Thr Val Leu Phe Glu Thr Tyr His Pro Arg Gly
65                  70                  75                  80

Val Pro Thr Ser Ile Leu Asp Lys Leu Gln Val Gly Lys Met Lys Asp
                85                  90                  95

Gly Glu Leu Pro Ser Ser Phe Tyr Ser Trp Asp Ser Asp Phe Tyr Lys
            100                 105                 110

Thr Leu Arg Ala Arg Val Val Glu Arg Leu Asp Lys Leu Asn Leu Pro
        115                 120                 125

Arg Arg Gly Gly Tyr Glu Ile Trp Val Lys Ala Val Phe Leu Leu Ala
    130                 135                 140

Gly Phe Trp Phe Ser Leu Tyr Lys Met Ser Val Asn Glu Thr Tyr Trp
145                 150                 155                 160

Ala Ala Ser Leu Trp Ser Val Ser Met Gly Val Phe Ala Ala Phe Ile
                165                 170                 175

Gly Thr Cys Ile Gln His Asp Gly Asn His Gly Ala Phe Ser Thr Ser
            180                 185                 190

Pro Ala Leu Asn Lys Val Ala Gly Trp Thr Leu Asp Met Ile Gly Ala
        195                 200                 205

Ser Gly Phe Thr Trp Glu Ile Gln His Met Leu Gly His His Pro Tyr
    210                 215                 220

Thr Asn Val Leu Asp Val Asp Glu Glu Lys Arg Lys Glu Ala Gly Asp
225                 230                 235                 240

Asp Cys Pro Met Glu Asp Lys Asp Gln Glu Ser Asp Pro Asp Val Phe
                245                 250                 255

Ser Ser Phe Pro Leu Met Arg Met His Pro Tyr His Lys Ala Glu Trp
            260                 265                 270

Tyr His Arg Tyr Gln His Leu Tyr Ala Pro Val Leu Phe Ala Phe Met
        275                 280                 285

Thr Leu Ala Lys Val Phe Gln Gln Asp Ile Glu Val Ala Thr Thr Gln
    290                 295                 300

Arg Leu Tyr His Ile Asp Ala Lys Cys Arg Tyr Asn Ser Ile Leu Asn
305                 310                 315                 320
```

```
Val Leu Arg Phe Trp Ser Met Lys Val Leu Ser Ile Gly Tyr Met Leu
                325                 330                 335

Ala Val Pro Cys Tyr Phe His Gly Ile Leu Gly Gly Leu Gly Leu Phe
            340                 345                 350

Leu Ile Gly His Phe Ala Cys Gly Glu Leu Leu Ala Thr Met Phe Ile
        355                 360                 365

Val Asn His Val Ile Glu Gly Val Ser Phe Gly Lys Lys Gly Glu Ser
    370                 375                 380

Leu Gly Leu Ser Lys Asp Val Glu Phe Lys Pro Thr Thr Val Ser Gly
385                 390                 395                 400

Arg Thr Pro Met Glu Gln Thr Arg Ala Glu Ala Lys Lys Ala Ala Asn
                405                 410                 415

Gly Gly Asn Val Lys Asp Val Pro Tyr Asn Asp Trp Ala Ala Val Gln
            420                 425                 430

Cys Gln Thr Ser Val Asn Trp Ser Pro Gly Ser Trp Phe Trp Asn His
        435                 440                 445

Phe Ser Gly Gly Leu Ser His Gln Ile Glu His His Leu Phe Pro Ser
    450                 455                 460

Ile Cys His Thr Asn Tyr Ala His Ile Gln Asp Val Val Gln Lys Thr
465                 470                 475                 480

Cys Glu Glu Tyr Gly Val Pro Tyr Gln Ser Glu Pro Ser Leu Phe Ser
                485                 490                 495

Ala Tyr Gly Lys Met Leu Ser His Leu Lys Tyr Leu Gly Asn Glu Lys
            500                 505                 510

Lys Val Ala
        515

<210> SEQ ID NO 5
<211> LENGTH: 847
<212> TYPE: DNA
<213> ORGANISM: Eutreptiella cf_gymnastica CCMP1594
<220> FEATURE:
<221> NAME/KEY: misc_feature
<222> LOCATION: (781)..(781)
<223> OTHER INFORMATION: n is a, c, g, or t
<220> FEATURE:
<221> NAME/KEY: misc_feature
<222> LOCATION: (789)..(789)
<223> OTHER INFORMATION: n is a, c, g, or t
<220> FEATURE:
<221> NAME/KEY: misc_feature
<222> LOCATION: (831)..(831)
<223> OTHER INFORMATION: n is a, c, g, or t

<400> SEQUENCE: 5
attcaacacg acgggaacca tggcgccttc tcgaccagcc cggctctgaa caaggtggcg    60
ggctggactc tggacatgat tggggcgtca ggtttcacgt gggaaatcca acatatgctc   120
ggccatcatc cctacaccaa cgttcttgac gtggacgaag aaaagaggaa ggaagctggc   180
gacgactgcc cgatggaaga caaggaccag gagtccgacc cagatgtctt ctcctccttc   240
cctctcatgc gcatgcaccc ataccacaag gctgagtggt accatcgcta tcagcacctg   300
tacgcgcccg ttctcttcgc gttcatgacg ctagccaagg tgttccagca ggatatcgag   360
gtcgccacca cccagagatt gtaccatatc gatgccaagt gccgatacaa ttctattctg   420
aatgtcttgc gcttttggtc gatgaaggtg ctttcgatcg gatatatgct ggctgtgccc   480
tgctacttcc acggcattct tggtggcctt ggcttttcc ttatcggcca ctttgcctgc   540
ggtgagcttc tggcgaccat gttcattgtc aatcacgtca ttgagggagt ctcctttggc   600
```

| | |
|---|---|
| aagaagggtg aatcgctggg actttccaag acgtggagt tcaagcccac caccgtttcg | 660 |
| ggccgcacgc ccatggaaca acccgtgcc aagccaaga aggcggccaa cggcggaaac | 720 |
| gtgaaggatg tcccctacaa cgactgggcg ccgttcaat gccaaacgag tgtgaactgg | 780 |
| ngtcctggnt cgtggttctg gaatcacttc agcggcggtc tatcgcatca nattgagcac | 840 |
| cacctgt | 847 |

<210> SEQ ID NO 6
<211> LENGTH: 359
<212> TYPE: DNA
<213> ORGANISM: Eutreptiella cf_gymnastica CCMP1594

<400> SEQUENCE: 6

| | |
|---|---|
| ctactcgtgg gattctgact tttacaagac cctgcgcgcc cgcgttgttg agaggttgga | 60 |
| caagctcaac ctgccgcgaa ggggagggta tgagatctgg gtcaaggcag tattcctcct | 120 |
| ggcaggattc tggttcagcc tctacaagat gtctgtgaac gagacctact gggccgcatc | 180 |
| gctctggtcc gtgtccatgg gagtgttcgc cgccttcatc ggcacttgca tccagcacga | 240 |
| tggaaaccat ggcgccttct cgaccagccc ggctctgaac aaggtggcgg gctgactct | 300 |
| ggacatgatt ggggcgtcag gtttcacgtg gaaatccaa catatgctcg gccatcatc | 359 |

<210> SEQ ID NO 7
<211> LENGTH: 395
<212> TYPE: DNA
<213> ORGANISM: Eutreptiella cf_gymnastica CCMP1594

<400> SEQUENCE: 7

| | |
|---|---|
| ggaggagaga tgcagtcaac caaggcggcc gacaccgccg ctaccgacaa gagtctcgac | 60 |
| aagaaccgcc tcatctctcg ggatgagctt cgttctcaca atgtccccca ggatgcgtgg | 120 |
| gctgctgtcc acgggagggt catcaacatc acggagttcg cccgacgtca tcctggcggc | 180 |
| gacatcatcc tccttgccgc agggaaggat gccacagtcc tcttcgagac ctaccatccc | 240 |
| cgcggtgtcc ccacctccat cctcgacgag ctccaggtgg aaagatgaa ggacggggag | 300 |
| ctgccctcct ccttctactc gtgggattct gacttttaca agaccctgcg cgcccgcgtt | 360 |
| gttgagaggt tggacaagct caacctgccg cgaag | 395 |

<210> SEQ ID NO 8
<211> LENGTH: 873
<212> TYPE: DNA
<213> ORGANISM: Eutreptiella cf_gymnastica CCMP1594

<400> SEQUENCE: 8

| | |
|---|---|
| gtttcgggcc gcacgccat ggaacagacc cgtgccgaag ccaagaaggc ggccaacggc | 60 |
| ggaaacgtga aggatgtccc ctacaacgac tgggsggccg ttcaatgcca aacgagtgtg | 120 |
| aactggagtc ctggatcgtg gttctggaat cacttcagcg gcggtctatc gcatcagatt | 180 |
| gagcaccatc ttttccctag catttgccac accaattacg ctcatatcca agacgttgtc | 240 |
| caaaagactt gcgaggagta sggcgttcct taccaaagcg agccctcttt gtaytccgcc | 300 |
| tatggcaaga tgttgagcca tctcaagtac ctcggaaacg agaagaaggt ggcttaggca | 360 |
| ttggcgaact gaaaataaat tgctattgat ttttaaaaga ttttagcgag gaaattttcg | 420 |
| accaaataca acgcgtgttc ctyttgggcg gtcctgattc ggcacactgt gttttgcagg | 480 |
| atcatgctgc ctcacagggt ggggtcccat ctggtggttg tgtgaggtgc tgccggctgc | 540 |
| gtgctggaac acacgcatgc tgtcctatgg ttgggccggt gaggggtgac ggtcgcgaat | 600 |

| | |
|---|---|
| atggtggtga tggcggcggc ggtgggggcc ctggttgcgt caagcggcac aaaactacag | 660 |
| agttatacga cgatgtacac tatgcccctc tcctagggcc acccttgcct acaaggtgca | 720 |
| ttaactggct aatggtactc cagccaatga tctatacccct tgcatggttg ttattgctgc | 780 |
| gccccmccgg csccgcatct ggcgttgcgc tttcctgcac cccagtgcaa cctctggcgt | 840 |
| ctctatattt ttcaaaaaaa aaaaaaaaaa aaa | 873 |

<210> SEQ ID NO 9
<211> LENGTH: 2070
<212> TYPE: DNA
<213> ORGANISM: Eutreptiella cf_gymnastica CCMP1594

<400> SEQUENCE: 9

| | |
|---|---|
| ggaggagaga tgcagtcaac caaggcggcc gacaccgccg ctaccgacaa gagtctcgac | 60 |
| aagaaccgcc tcatctctcg ggatgagctt cgttctcaca atgtccccca ggatgcgtgg | 120 |
| gctgctgtcc acgggagggt catcaacatc acggagttcg cccgacgtca tcctggcggc | 180 |
| gacatcatcc tccttgccgc agggaaggat gccacagtcc tcttcgagac ctaccatccc | 240 |
| cgcggtgtcc ccacctccat cctcgacaag ctccaggtgg aaagatgaa ggacggggag | 300 |
| ctgccctcct ccttctactc gtgggattct gacttttaca agaccctgcg cgcccgcgtt | 360 |
| gttgagaggt tggacaagct caacctgccg cgaaggggag ggtatgagat ctgggtcaag | 420 |
| gcagtattcc tcctggcagg attctggttc agcctctaca agatgtctgt gaacgagacc | 480 |
| tactgggccg catcgctctg gtccgtgtcc atgggagtgt tcgccgcctt catcggcact | 540 |
| tgcatccagc acgatggaaa ccatggcgcc ttctcgacca gcccggctct gaacaaggtg | 600 |
| gcgggctgga ctctggacat gattggggcg tcaggtttca cgtgggaaat ccaacatatg | 660 |
| ctcggccatc atccctacac caacgttctt gacgtggacg aagaaaagag gaaggaagct | 720 |
| ggcgacgact gcccgatgga agacaaggac caggagtccg acccagatgt cttctcctcc | 780 |
| ttccctctca tgcgcatgca cccataccac aaggctgagt ggtaccatcg ctatcagcac | 840 |
| ctgtacgcgc ccgttctctt cgcgttcatg acgctagcca aggtgttcca gcaggatatc | 900 |
| gaggtcgcca ccacccagag attgtaccat atcgatgcca agtgccgata caattctatt | 960 |
| ctgaatgtct tgcgcttttg gtcgatgaag gtgctttcga tcggatatat gctggctgtg | 1020 |
| ccctgctact tccacggcat tcttggtggc cttggcctt tccttatcgg ccactttgcc | 1080 |
| tgcggtgagc ttctggcgac catgttcatt gtcaatcacg tcattgaggg agtctccttt | 1140 |
| ggcaagaagg gtgaatcgct gggactttcc aaggacgtgg agttcaagcc caccaccgtt | 1200 |
| tcgggccgca cgcccatgga acagacccgt gccgaagcca agaaggcggc caacggcgga | 1260 |
| aacgtgaagg atgtcccccta caacgactgg gcggccgttc aatgccaaac gagtgtgaac | 1320 |
| tggagtcctg gatcgtggtt ctggaatcac ttcagcggcg gtctatcgca tcagattgag | 1380 |
| caccatcttt tccctagcat ttgccacacc aattacgctc atatccaaga cgttgtccaa | 1440 |
| aagacttgcg aggagtasgg cgttccttac caaagcgagc cctctttgta ytccgcctat | 1500 |
| ggcaagatgt tgagccatct caagtacctc ggaaacgaga agaaggtggc ttaggcattg | 1560 |
| gcgaactgaa aataaattgc tattgatttt taaaagattt tagcgaggaa attttcgacc | 1620 |
| aaatacaacg cgtgttccty ttgggcggtc ctgattcggc acactgtgtt ttgcaggatc | 1680 |
| atgctgcctc acagggtggg gtcccatctg gtggttgtgt gaggtgctgc cggctgcgtg | 1740 |
| ctggaacaca cgcatgctgt cctatggttg ggcggtgag gggtgacggt cgcgaatatg | 1800 |
| gtggtgatgg cggcggcggt gggggccctg gttgcgtcaa gcggcacaaa actacagagt | 1860 |

```
tatacgacga tgtacactat gcccctctcc tagggccacc cttgcctaca aggtgcatta    1920
actggctaat ggtactccag ccaatgatct atacccttgc atggttgtta ttgctgcgcc    1980
ccmccggcsc cgcatctggc gttgcgcttt cctgcacccc agtgcaacct ctggcgtctc    2040 tatattttc aaaaaaaaaa aaaaaaaaaa                                      2070
```

```
<210> SEQ ID NO 10
<211> LENGTH: 39
<212> TYPE: DNA
<213> ORGANISM: Artificial Sequence
<220> FEATURE:
<223> OTHER INFORMATION: Smart IV oligonucleotide primer

<400> SEQUENCE: 10
aagcagtggt atcaacgcag agtggccatt acggccggg                           39

<210> SEQ ID NO 11
<211> LENGTH: 59
<212> TYPE: DNA
<213> ORGANISM: Artificial Sequence
<220> FEATURE:
<223> OTHER INFORMATION: CDSIII/3'PCR primer
<220> FEATURE:
<221> NAME/KEY: misc_feature
<222> LOCATION: (28)..(57)
<223> OTHER INFORMATION: thymidine (dT); see BD Biosciences Clontech's
      SMART cDNA technology
<220> FEATURE:
<221> NAME/KEY: misc_feature
<222> LOCATION: (59)..(59)
<223> OTHER INFORMATION: n is a, c, g, or t

<400> SEQUENCE: 11
attctagagg ccgaggcggc cgacatgttt tttttttttt tttttttttt tttttttvn    59

<210> SEQ ID NO 12
<211> LENGTH: 23
<212> TYPE: DNA
<213> ORGANISM: Artificial Sequence
<220> FEATURE:
<223> OTHER INFORMATION: 5' CDSIII PCR primer

<400> SEQUENCE: 12
aagcagtggt atcaacgcag agt                                            23

<210> SEQ ID NO 13
<211> LENGTH: 541
<212> TYPE: PRT
<213> ORGANISM: Euglena gracilis
<220> FEATURE:
<221> NAME/KEY: MISC_FEATURE
<222> LOCATION: (1)..(541)
<223> OTHER INFORMATION: delta-4 desaturase; GenBank Accession No.
      AY278558

<400> SEQUENCE: 13
```

Met Leu Val Leu Phe Gly Asn Phe Tyr Val Lys Gln Tyr Ser Gln Lys
1               5                   10                  15

Asn Gly Lys Pro Glu Asn Gly Ala Thr Pro Glu Asn Gly Ala Lys Pro
            20                  25                  30

Gln Pro Cys Glu Asn Gly Thr Val Glu Lys Arg Glu Asn Asp Thr Ala
        35                  40                  45

Asn Val Arg Pro Thr Arg Pro Ala Gly Pro Pro Ala Thr Tyr Tyr
    50                  55                  60

Asp Ser Leu Ala Val Ser Gly Gln Gly Lys Glu Arg Leu Phe Thr Thr
65                  70                  75                  80

```
Asp Glu Val Arg Arg His Ile Leu Pro Thr Asp Gly Trp Leu Thr Cys
                    85                  90                  95

His Glu Gly Val Tyr Asp Val Thr Asp Phe Leu Ala Lys His Pro Gly
            100                 105                 110

Gly Gly Val Ile Thr Leu Gly Leu Gly Arg Asp Cys Thr Ile Leu Ile
            115                 120                 125

Glu Ser Tyr His Pro Ala Gly Arg Pro Asp Lys Val Met Glu Lys Tyr
        130                 135                 140

Arg Ile Gly Thr Leu Gln Asp Pro Lys Thr Phe Tyr Ala Trp Gly Glu
145                 150                 155                 160

Ser Asp Phe Tyr Pro Glu Leu Lys Arg Arg Ala Leu Ala Arg Leu Lys
                165                 170                 175

Glu Ala Gly Gln Ala Arg Arg Gly Gly Leu Gly Val Lys Ala Leu Leu
            180                 185                 190

Val Leu Thr Leu Phe Phe Val Ser Trp Tyr Met Trp Val Ala His Lys
        195                 200                 205

Ser Phe Leu Trp Ala Ala Val Trp Gly Phe Ala Gly Ser His Val Gly
        210                 215                 220

Leu Ser Ile Gln His Asp Gly Asn His Gly Ala Phe Ser Arg Asn Thr
225                 230                 235                 240

Leu Val Asn Arg Leu Ala Gly Trp Gly Met Asp Leu Ile Gly Ala Ser
                245                 250                 255

Ser Thr Val Trp Glu Tyr Gln His Val Ile Gly His His Gln Tyr Thr
            260                 265                 270

Asn Leu Val Ser Asp Thr Leu Phe Ser Leu Pro Glu Asn Asp Pro Asp
        275                 280                 285

Val Phe Ser Ser Tyr Pro Leu Met Arg Met His Pro Asp Thr Ala Trp
        290                 295                 300

Gln Pro His His Arg Phe Gln His Leu Phe Ala Phe Pro Leu Phe Ala
305                 310                 315                 320

Leu Met Thr Ile Ser Lys Val Leu Thr Ser Asp Phe Ala Val Cys Leu
                325                 330                 335

Ser Met Lys Lys Gly Ser Ile Asp Cys Ser Ser Arg Leu Val Pro Leu
            340                 345                 350

Glu Gly Gln Leu Leu Phe Trp Gly Ala Lys Leu Ala Asn Phe Leu Leu
        355                 360                 365

Gln Ile Val Leu Pro Cys Tyr Leu His Gly Thr Ala Met Gly Leu Ala
        370                 375                 380

Leu Phe Ser Val Ala His Leu Val Ser Gly Glu Tyr Leu Ala Ile Cys
385                 390                 395                 400

Phe Ile Ile Asn His Ile Ser Glu Ser Cys Glu Phe Met Asn Thr Ser
                405                 410                 415

Phe Gln Thr Ala Ala Arg Arg Thr Glu Met Leu Gln Ala Ala His Gln
            420                 425                 430

Ala Ala Glu Ala Lys Lys Val Lys Pro Thr Pro Pro Asn Asp Trp
        435                 440                 445

Ala Val Thr Gln Val Gln Cys Cys Val Asn Trp Arg Ser Gly Gly Val
        450                 455                 460

Leu Ala Asn His Leu Ser Gly Gly Leu Asn His Gln Ile Glu His His
465                 470                 475                 480

Leu Phe Pro Ser Ile Ser His Ala Asn Tyr Pro Thr Ile Ala Pro Val
                485                 490                 495

Val Lys Glu Val Cys Glu Glu Tyr Gly Leu Pro Tyr Lys Asn Tyr Val
```

```
            500                 505                 510
Thr Phe Trp Asp Ala Val Cys Gly Met Val Gln His Leu Arg Leu Met
        515                 520                 525

Gly Ala Pro Pro Val Pro Thr Asn Gly Asp Lys Lys Ser
        530                 535                 540
```

<210> SEQ ID NO 14

<400> SEQUENCE: 14

000

<210> SEQ ID NO 15
<211> LENGTH: 20
<212> TYPE: DNA
<213> ORGANISM: Artificial Sequence
<220> FEATURE:
<223> OTHER INFORMATION: Primer D4-F1
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 15
ttcctngcna arcayccngg                                            20

<210> SEQ ID NO 16
<211> LENGTH: 20
<212> TYPE: DNA
<213> ORGANISM: Artificial Sequence
<220> FEATURE:
<223> OTHER INFORMATION: Primer D4-F2
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 16
tttctngcna arcayccngg                                            20

<210> SEQ ID NO 17
<211> LENGTH: 20
<212> TYPE: DNA
<213> ORGANISM: Artificial Sequence
<220> FEATURE:
<223> OTHER INFORMATION: Primer D4-F3
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 17

```
ttyttrgcna arcayccngg                                        20

<210> SEQ ID NO 18
<211> LENGTH: 7
<212> TYPE: PRT
<213> ORGANISM: Artificial Sequence
<220> FEATURE:
<223> OTHER INFORMATION: Translation of primers D4-F1, D4-F2 and D4-F3

<400> SEQUENCE: 18

Phe Leu Ala Lys His Pro Gly
1               5

<210> SEQ ID NO 19
<211> LENGTH: 20
<212> TYPE: DNA
<213> ORGANISM: Artificial Sequence
<220> FEATURE:
<223> OTHER INFORMATION: Primer D4-F4
<220> FEATURE:
<221> NAME/KEY: misc_feature
<222> LOCATION: (15)..(15)
<223> OTHER INFORMATION: n is a, c, g, or t

<400> SEQUENCE: 19
athcarcayg ayggnaayca                                        20

<210> SEQ ID NO 20
<211> LENGTH: 7
<212> TYPE: PRT
<213> ORGANISM: Artificial Sequence
<220> FEATURE:
<223> OTHER INFORMATION: Translation of primer D4-F4

<400> SEQUENCE: 20

Ile Gln His Asp Gly Asn His
1               5

<210> SEQ ID NO 21
<211> LENGTH: 20
<212> TYPE: DNA
<213> ORGANISM: Artificial Sequence
<220> FEATURE:
<223> OTHER INFORMATION: Primer D4-F5
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 21
caygayggna aycayggngc                                        20

<210> SEQ ID NO 22
<211> LENGTH: 7
<212> TYPE: PRT
<213> ORGANISM: Artificial Sequence
<220> FEATURE:
<223> OTHER INFORMATION: Translation of primer D4-F5

<400> SEQUENCE: 22

His Asp Gly Asn His Gly Ala
1               5

<210> SEQ ID NO 23
```

```
<211> LENGTH: 20
<212> TYPE: DNA
<213> ORGANISM: Artificial Sequence
<220> FEATURE:
<223> OTHER INFORMATION: Primer D4-F6
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 23
ggncaycaya gyttyacnaa                                              20

<210> SEQ ID NO 24
<211> LENGTH: 20
<212> TYPE: DNA
<213> ORGANISM: Artificial Sequence
<220> FEATURE:
<223> OTHER INFORMATION: Primer D4-F7
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 24
ggycaycayt cnttyacnaa                                              20

<210> SEQ ID NO 25
<211> LENGTH: 20
<212> TYPE: DNA
<213> ORGANISM: Artificial Sequence
<220> FEATURE:
<223> OTHER INFORMATION: Primer D4-F8
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 25
ggrcaycayt cnttyacnaa                                              20

<210> SEQ ID NO 26
<211> LENGTH: 7
<212> TYPE: PRT
<213> ORGANISM: Artificial Sequence
<220> FEATURE:
<223> OTHER INFORMATION: Translation of primers D4-F6, D4-F7 and D4-F8

<400> SEQUENCE: 26

Gly His His Gln Tyr Thr Asn
1               5

<210> SEQ ID NO 27
<211> LENGTH: 20
<212> TYPE: DNA
<213> ORGANISM: Artificial Sequence
<220> FEATURE:
<223> OTHER INFORMATION: Primer D4-R1
<220> FEATURE:
<221> NAME/KEY: misc_feature
```

```
<222> LOCATION: (3)..(3)
<223> OTHER INFORMATION: n is a, c, g, or t

<400> SEQUENCE: 27
aanagrtgrt gytcdatytg                                               20

<210> SEQ ID NO 28
<211> LENGTH: 20
<212> TYPE: DNA
<213> ORGANISM: Artificial Sequence
<220> FEATURE:
<223> OTHER INFORMATION: Primer D4-R2

<400> SEQUENCE: 28
aayaartgrt gytcdatytg                                               20

<210> SEQ ID NO 29
<211> LENGTH: 7
<212> TYPE: PRT
<213> ORGANISM: Artificial Sequence
<220> FEATURE:
<223> OTHER INFORMATION: Translation of primers D4-R1 and D4-R2

<400> SEQUENCE: 29

Gln Ile Glu His His Leu Phe
1               5

<210> SEQ ID NO 30
<211> LENGTH: 22
<212> TYPE: DNA
<213> ORGANISM: Artificial Sequence
<220> FEATURE:
<223> OTHER INFORMATION: Primer 1594D4-5-1

<400> SEQUENCE: 30
gtccacgtca agaacgttgg tg                                            22

<210> SEQ ID NO 31
<211> LENGTH: 22
<212> TYPE: DNA
<213> ORGANISM: Artificial Sequence
<220> FEATURE:
<223> OTHER INFORMATION: Primer 1594D4-5-2

<400> SEQUENCE: 31
gatgatggcc gagcatatgt tg                                            22

<210> SEQ ID NO 32
<211> LENGTH: 22
<212> TYPE: DNA
<213> ORGANISM: Artificial Sequence
<220> FEATURE:
<223> OTHER INFORMATION: Primer DNR CDS 5-2

<400> SEQUENCE: 32
caacgcagag tggccattac gg                                            22

<210> SEQ ID NO 33
<211> LENGTH: 22
<212> TYPE: DNA
<213> ORGANISM: Artificial Sequence
<220> FEATURE:
<223> OTHER INFORMATION: Primer 1594D4-5-4

<400> SEQUENCE: 33
gaatactgcc ttgacccaga tc                                            22
```

```
<210> SEQ ID NO 34
<211> LENGTH: 23
<212> TYPE: DNA
<213> ORGANISM: Artificial Sequence
<220> FEATURE:
<223> OTHER INFORMATION: Primer 1594D4-5-5

<400> SEQUENCE: 34
cttcgcggca ggttgagctt gtc                                           23

<210> SEQ ID NO 35
<211> LENGTH: 22
<212> TYPE: DNA
<213> ORGANISM: Artificial Sequence
<220> FEATURE:
<223> OTHER INFORMATION: Primer 1594D4-3-1

<400> SEQUENCE: 35
acgtggagtt caagcccacc ac                                            22

<210> SEQ ID NO 36
<211> LENGTH: 21
<212> TYPE: DNA
<213> ORGANISM: Artificial Sequence
<220> FEATURE:
<223> OTHER INFORMATION: Primer 1594D4-3-2

<400> SEQUENCE: 36
gtttcgggcc gcacgcccat g                                             21

<210> SEQ ID NO 37
<211> LENGTH: 550
<212> TYPE: PRT
<213> ORGANISM: Thalassiosira pseudonana
<220> FEATURE:
<221> NAME/KEY: MISC_FEATURE
<222> LOCATION: (1)..(550)
<223> OTHER INFORMATION: delta-4 desaturase; GenBank Accession No.
      AAX14506

<400> SEQUENCE: 37
```

Met Gly Asn Gly Asn Leu Pro Ala Ser Thr Ala Gln Leu Lys Ser Thr
1               5                   10                  15

Ser Lys Pro Gln Gln Gln His Glu His Arg Thr Ile Ser Lys Ser Glu
            20                  25                  30

Leu Ala Gln His Asn Thr Pro Lys Ser Ala Trp Cys Ala Val His Ser
        35                  40                  45

Thr Pro Ala Thr Asp Pro Ser His Ser Asn Asn Lys Gln His Ala His
    50                  55                  60

Leu Val Leu Asp Ile Thr Asp Phe Ala Ser Arg His Pro Gly Gly Asp
65                  70                  75                  80

Leu Ile Leu Leu Ala Ser Gly Lys Asp Ala Ser Val Leu Phe Glu Thr
                85                  90                  95

Tyr His Pro Arg Gly Val Pro Thr Ser Leu Ile Gln Lys Leu Gln Ile
            100                 105                 110

Gly Val Met Glu Glu Glu Ala Phe Arg Asp Ser Phe Tyr Ser Trp Thr
        115                 120                 125

Asp Ser Asp Phe Tyr Thr Val Leu Lys Arg Arg Val Glu Arg Leu
    130                 135                 140

Glu Glu Arg Gly Leu Asp Arg Arg Gly Ser Lys Glu Ile Trp Ile Lys
145                 150                 155                 160

Ala Leu Phe Leu Leu Val Gly Phe Trp Tyr Cys Leu Tyr Lys Met Tyr

```
                    165                 170                 175
Thr Thr Ser Asp Ile Asp Gln Tyr Gly Ile Ala Ile Ala Tyr Ser Ile
            180                 185                 190
Gly Met Gly Thr Phe Ala Ala Phe Ile Gly Thr Cys Ile Gln His Asp
            195                 200                 205
Gly Asn His Gly Ala Phe Ala Gln Asn Lys Leu Leu Asn Lys Leu Ala
            210                 215                 220
Gly Trp Thr Leu Asp Met Ile Gly Ala Ser Ala Phe Thr Trp Glu Leu
225                 230                 235                 240
Gln His Met Leu Gly His His Pro Tyr Thr Asn Val Leu Asp Gly Val
            245                 250                 255
Glu Glu Glu Arg Lys Glu Arg Gly Glu Asp Val Ala Leu Glu Glu Lys
            260                 265                 270
Asp Gln Glu Ser Asp Pro Asp Val Phe Ser Ser Phe Pro Leu Met Arg
            275                 280                 285
Met His Pro His His Thr Thr Ser Trp Tyr His Lys Tyr Gln His Leu
            290                 295                 300
Tyr Ala Pro Pro Leu Phe Ala Leu Met Thr Leu Ala Lys Val Phe Gln
305                 310                 315                 320
Gln Asp Phe Glu Val Ala Thr Ser Gly Arg Leu Tyr His Ile Asp Ala
            325                 330                 335
Asn Val Arg Tyr Gly Ser Val Trp Asn Val Met Arg Phe Trp Ala Met
            340                 345                 350
Lys Val Ile Thr Met Gly Tyr Met Met Gly Leu Pro Ile Tyr Phe His
            355                 360                 365
Gly Val Leu Arg Gly Val Gly Leu Phe Val Ile Gly His Leu Ala Cys
            370                 375                 380
Gly Glu Leu Leu Ala Thr Met Phe Ile Val Asn His Val Ile Glu Gly
385                 390                 395                 400
Val Ser Tyr Gly Thr Lys Asp Leu Val Gly Gly Ala Ser His Gly Asp
            405                 410                 415
Glu Lys Lys Ile Val Lys Pro Thr Thr Val Leu Gly Asp Thr Pro Met
            420                 425                 430
Glu Lys Thr Arg Glu Glu Ala Leu Lys Ser Asn Ser Asn Asn Asn Lys
            435                 440                 445
Lys Lys Gly Glu Lys Asn Ser Val Pro Ser Val Pro Phe Asn Asp Trp
            450                 455                 460
Ala Ala Val Gln Cys Gln Thr Ser Val Asn Trp Ser Pro Gly Ser Trp
465                 470                 475                 480
Phe Trp Asn His Phe Ser Gly Gly Leu Ser His Gln Ile Glu His His
            485                 490                 495
Leu Phe Pro Ser Ile Cys His Thr Asn Tyr Cys His Ile Gln Asp Val
            500                 505                 510
Val Glu Ser Thr Cys Ala Glu Tyr Gly Val Pro Tyr Gln Ser Glu Ser
            515                 520                 525
Asn Leu Phe Val Ala Tyr Gly Lys Met Ile Ser His Leu Lys Phe Leu
            530                 535                 540
Gly Lys Ala Lys Cys Glu
545                 550

<210> SEQ ID NO 38
<211> LENGTH: 519
<212> TYPE: PRT
<213> ORGANISM: Thraustochytrium sp. FJN-10
<220> FEATURE:
```

<221> NAME/KEY: MISC_FEATURE
<222> LOCATION: (1)..(519)
<223> OTHER INFORMATION: delta-4 desaturase; GenBank Accession No. AAZ43257

<400> SEQUENCE: 38

| | | | | | | | | | | | | | | |
|---|---|---|---|---|---|---|---|---|---|---|---|---|---|---|
| Met | Thr | Val | Gly | Tyr | Asp | Gly | Glu | Ile | Pro | Phe | Glu | Gln | Val | Arg | Ala |
| 1 | | | | 5 | | | | | 10 | | | | | 15 | |
| His | Asn | Lys | Pro | Asp | Asp | Ala | Trp | Cys | Ala | Ile | His | Gly | His | Val | Tyr |
| | | | 20 | | | | | 25 | | | | | 30 | | |
| Asp | Val | Thr | Lys | Phe | Ala | Ser | Val | His | Pro | Gly | Gly | Asp | Ile | Ile | Leu |
| | | 35 | | | | | 40 | | | | | 45 | | | |
| Leu | Ala | Ala | Gly | Lys | Asp | Ala | Thr | Val | Leu | Tyr | Glu | Thr | Tyr | His | Val |
| | 50 | | | | | 55 | | | | | 60 | | | | |
| Arg | Gly | Val | Ser | Asp | Ala | Val | Leu | Arg | Lys | Tyr | Arg | Ile | Gly | Lys | Leu |
| 65 | | | | | 70 | | | | | 75 | | | | | 80 |
| Pro | Asp | Gly | Gln | Gly | Gly | Ala | Asn | Glu | Lys | Glu | Lys | Arg | Thr | Leu | Ser |
| | | | | 85 | | | | | 90 | | | | | 95 | |
| Gly | Leu | Ser | Ser | Ala | Ser | Tyr | Tyr | Thr | Trp | Asn | Ser | Asp | Phe | Tyr | Arg |
| | | | 100 | | | | | 105 | | | | | 110 | | |
| Val | Met | Arg | Glu | Arg | Val | Val | Ala | Arg | Leu | Lys | Glu | Arg | Gly | Lys | Ala |
| | | 115 | | | | | 120 | | | | | 125 | | | |
| Arg | Arg | Gly | Gly | Tyr | Glu | Leu | Trp | Ile | Lys | Ala | Leu | Leu | Leu | Leu | Val |
| | 130 | | | | | 135 | | | | | 140 | | | | |
| Gly | Phe | Trp | Ser | Ser | Leu | Cys | Trp | Met | Cys | Thr | Leu | Asp | Pro | Ser | Phe |
| 145 | | | | | 150 | | | | | 155 | | | | | 160 |
| Gly | Ala | Ile | Leu | Ala | Ala | Met | Ser | Leu | Gly | Val | Phe | Ala | Ala | Phe | Val |
| | | | | 165 | | | | | 170 | | | | | 175 | |
| Gly | Thr | Cys | Ile | Gln | His | Asp | Gly | Asn | His | Gly | Ala | Phe | Ala | Gln | Ser |
| | | | 180 | | | | | 185 | | | | | 190 | | |
| Arg | Trp | Val | Asn | Lys | Val | Ala | Gly | Trp | Thr | Leu | Asp | Met | Ile | Gly | Ala |
| | | 195 | | | | | 200 | | | | | 205 | | | |
| Ser | Gly | Met | Thr | Trp | Glu | Phe | Gln | His | Ala | Leu | Gly | His | His | Pro | Tyr |
| | 210 | | | | | 215 | | | | | 220 | | | | |
| Thr | Asn | Leu | Ile | Glu | Glu | Glu | Asn | Gly | Leu | Gln | Lys | Val | Ser | Gly | Lys |
| 225 | | | | | 230 | | | | | 235 | | | | | 240 |
| Lys | Met | Asp | Thr | Lys | Leu | Ala | Asp | Gln | Glu | Ser | Asp | Pro | Asp | Val | Phe |
| | | | | 245 | | | | | 250 | | | | | 255 | |
| Ser | Thr | Tyr | Pro | Met | Met | Arg | Leu | His | Pro | Trp | His | Gln | Lys | Arg | Trp |
| | | | 260 | | | | | 265 | | | | | 270 | | |
| Tyr | His | Arg | Phe | Gln | His | Ile | Tyr | Gly | Pro | Phe | Ile | Phe | Gly | Phe | Met |
| | | 275 | | | | | 280 | | | | | 285 | | | |
| Thr | Ile | Asn | Lys | Val | Val | Thr | Gln | Asp | Val | Gly | Val | Val | Phe | Arg | Lys |
| | 290 | | | | | 295 | | | | | 300 | | | | |
| Arg | Leu | Phe | Gln | Ile | Asp | Ala | Glu | Cys | Arg | Tyr | Ala | Ser | Pro | Met | Tyr |
| 305 | | | | | 310 | | | | | 315 | | | | | 320 |
| Val | Ala | Arg | Phe | Trp | Ile | Met | Lys | Ala | Leu | Thr | Val | Leu | Tyr | Met | Val |
| | | | | 325 | | | | | 330 | | | | | 335 | |
| Ala | Leu | Pro | Cys | Tyr | Met | Gln | Gly | Pro | Trp | His | Gly | Leu | Lys | Leu | Phe |
| | | | 340 | | | | | 345 | | | | | 350 | | |
| Ala | Ile | Ala | His | Phe | Thr | Cys | Gly | Glu | Val | Leu | Ala | Thr | Met | Phe | Ile |
| | | 355 | | | | | 360 | | | | | 365 | | | |
| Val | Asn | His | Val | Ile | Glu | Gly | Val | Ser | Tyr | Ala | Ser | Lys | Asp | Ala | Val |
| | 370 | | | | | 375 | | | | | 380 | | | | |
| Lys | Gly | Thr | Met | Ala | Pro | Pro | Lys | Thr | Met | His | Gly | Val | Thr | Pro | Met |

```
                385                 390                 395                 400
Asn Asn Thr Arg Lys Glu Val Glu Ala Glu Ala Ser Lys Ser Gly Ala
                405                 410                 415

Val Val Lys Ser Val Pro Leu Asp Asp Trp Ala Ala Val Gln Cys Gln
            420                 425                 430

Thr Ser Ala Asn Trp Ser Val Gly Ser Trp Phe Trp Asn His Phe Ser
        435                 440                 445

Gly Gly Leu Asn His Gln Ile Glu His His Leu Phe Pro Gly Leu Ser
    450                 455                 460

His Glu Thr Tyr Tyr His Ile Gln Asp Val Val Gln Ser Thr Cys Ala
465                 470                 475                 480

Glu Tyr Gly Val Pro Tyr Gln His Glu Pro Ser Leu Trp Thr Ala Tyr
                485                 490                 495

Trp Lys Met Leu Glu His Leu Arg Arg Leu Gly Asn Glu Glu Thr His
            500                 505                 510

Glu Ser Trp Gln Arg Ala Ala
        515

<210> SEQ ID NO 39
<211> LENGTH: 4275
<212> TYPE: DNA
<213> ORGANISM: Artificial Sequence
<220> FEATURE:
<223> OTHER INFORMATION: Plasmid p1594D4S

<400> SEQUENCE: 39
tcgcgcgttt cggtgatgac ggtgaaaacc tctgacacat gcagctcccg gagacggtca      60
cagcttgtct gtaagcggat gccgggagca gacaagcccg tcaggcgcgc tcagcgggtg     120
ttggcgggtg tcgggctgg cttaactatg cggcatcaga gcagattgta ctgagagtgc      180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgagctcggt acctcgcgaa     420
tgcatctaga tatcggatcc cgggcggccg cttaagcgac ctttttctcg tttccgaggt     480
acttgagatg agacagcatc ttgccatagg cggagaacaa agagggttcg actggtaagg    540 aacaccgta ctcttcgcaa gtcttctgga caacgtcctg gatgtgagcg tagttggtgt      600
gacaaatgct gggaaacaga tggtgctcga tctggtggga gaggccaccg agaagtgat     660 tccagaacca cgatccagga gaccagttga cgctcgtttg acactgaacg gcagcccagt    720
cgttgtaggg aacatccttg acgttgcctc cattggcagc cttttttggcc tcggcacggg    780 tctgctccat ggagttcgt ccagaaacgg ttgtaggctt gaactccacg tccttggaca     840
gaccgagaga ttctcccttt tgccaaagg acacacctc gatgacgtga ttgacaatga     900
acatggttgc cagaagctct ccacaggcaa agtggccgat gagaaacagt ccaaggccac     960
caaggattcc gtggaagtag cagggaacag ccagcatgta gccgatggag agcaccttca    1020
tcgaccaaaa ccgaaggaca ttgagaatgg aattgtatcg gcacttggcg tcgatgtggt    1080
acagtcgctg agtggtagcg acttcgatgt cctgttggaa caccttggca agagtcatga    1140
aagcaaagag aacgggtgcg tacaggtgct gatatcggtg gtaccactcg gccttgtggt    1200
aggggtgcat tcgcatgaga ggaaacgaag agaagacatc tgggtcggac tcctgatcct    1260
tgtcctccat aggacaatcg tcgccagctt cctttcgctt ctcttcgtcc acgtccagga    1320
```

```
cgttggtgta gggatggtgt ccgagcatat gctgaatctc ccatgtaaag ccagaagcac   1380
cgatcatgtc cagagtccag cctgcaacct tgttgagagc agggctggtc gagaaggcac   1440
cgtggtttcc atcgtgttga atgcaagtgc cgatgaaggc agcaaagact cccatagaca   1500
cggaccacag cgaggcagcc cagtaggtct cgttgacgga catcttgtag aggctgaacc   1560
agaatccagc caggaggaat actgccttga cccaaatctc gtagccacct cttcgaggca   1620
ggttgagctt gtccaatcgc tcgaccactc gagctcgcag ggtcttgtaa aagtcggaat   1680
cccacgagta gaacgaggag ggaagttctc cgtccttcat cttgccgacc tgcagcttgt   1740
cgaggatcga ggtgggaaca cctcgaggat ggtaagtctc gaagagcacg gtggcatcct   1800
ttcctgcggc aagcagaatg atgtcgccac caggatgccg tcgggcgaac tcggtaatgt   1860
tgatgactct gccgtggacg gcagcccagg catcctgggg aacgttgtga accgcagct   1920
cgtctcggga gatgagtcgg ttcttgtcga gagacttgtc ggtggcagca gtgtcggcag   1980
ccttggtgga ctgagccatg gattgggggc ccgtcgactg cagaggcctg catgcaagct   2040
tggcgtaatc atggtcatag ctgtttcctg tgtgaaattg ttatccgctc acaattccac   2100
acaacatacg agccggaagc ataaagtgta aagcctgggg tgcctaatga gtgagctaac   2160
tcacattaat tgcgttgcgc tcactgcccg ctttccagtc gggaaacctg tcgtgccagc   2220
tgcattaata atcggccaa cgcgcgggga gaggcggttt gcgtattggg cgctcttccg   2280
cttcctcgct cactgactcg ctgcgctcgg tcgttcggct gcggcgagcg gtatcagctc   2340
actcaaaggc ggtaatacgg ttatccacag aatcagggga taacgcagga agaacatgt   2400
gagcaaaagg ccagcaaaag gccaggaacc gtaaaaaggc cgcgttgctg gcgtttttcc   2460
ataggctccg cccccctgac gagcatcaca aaaatcgacg ctcaagtcag aggtggcgaa   2520
acccgacagg actataaaga taccaggcgt ttccccctgg aagctccctc gtgcgctctc   2580
ctgttccgac cctgccgctt accggatacc tgtccgcctt ctcccttcg ggaagcgtgg   2640
cgctttctca tagctcacgc tgtaggtatc tcagttcggt gtaggtcgtt cgctccaagc   2700
tgggctgtgt gcacgaaccc cccgttcagc ccgaccgctg cgccttatcc ggtaactatc   2760
gtcttgagtc aacccggta agacacgact tatcgccact ggcagcagcc actggtaaca   2820
ggattagcag agcgaggtat gtaggcggtg ctacagagtt cttgaagtgg tggcctaact   2880
acggctacac tagaagaaca gtatttggta tctgcgctct gctgaagcca gttaccttcg   2940
gaaaaagagt tggtagctct tgatccggca acaaaccac cgctggtagc ggtggttttt   3000
ttgtttgcaa gcagcagatt acgcgcagaa aaaaaggatc tcaagaagat cctttgatct   3060
tttctacggg gtctgacgct cagtggaacg aaaactcacg ttaagggatt ttggtcatga   3120
gattatcaaa aaggatcttc acctagatcc ttttaaatta aaaatgaagt tttaaatcaa   3180
tctaaagtat atatgagtaa acttggtctg acagttacca atgcttaatc agtgaggcac   3240
ctatctcagc gatctgtcta tttcgttcat ccatagttgc ctgactcccc gtcgtgtaga   3300
taactacgat acgggagggc ttaccatctg gccccagtgc tgcaatgata ccgcgagacc   3360
cacgctcacc ggctccagat ttatcagcaa taaaccagcc agccggaagg gccgagcgca   3420
gaagtggtcc tgcaacttta tccgcctcca tccagtctat taattgttgc cgggaagcta   3480
gagtaagtag ttcgccagtt aatagtttgc gcaacgttgt tgccattgct acaggcatcg   3540
tggtgtcacg ctcgtcgttt ggtatggctt cattcagctc cggttcccaa cgatcaaggc   3600
gagttacatg atcccccatg ttgtgcaaaa aagcggttag ctccttcggt cctccgatcg   3660
ttgtcagaag taagttggcc gcagtgttat cactcatggt tatggcagca ctgcataatt   3720
```

| | |
|---|---|
| ctcttactgt catgccatcc gtaagatgct tttctgtgac tggtgagtac tcaaccaagt | 3780 |
| cattctgaga atagtgtatg cggcgaccga gttgctcttg cccggcgtca atacgggata | 3840 |
| ataccgcgcc acatagcaga actttaaaag tgctcatcat tggaaaacgt tcttcggggc | 3900 |
| gaaaactctc aaggatctta ccgctgttga gatccagttc gatgtaaccc actcgtgcac | 3960 |
| ccaactgatc ttcagcatct tttactttca ccagcgtttc tgggtgagca aaaacaggaa | 4020 |
| ggcaaaatgc cgcaaaaaag gaataagggc gacacggaa atgttaata ctcatactct | 4080 |
| tcctttttca atattattga agcatttatc agggttattg tctcatgagc ggatacatat | 4140 |
| ttgaatgtat ttagaaaaat aaacaaatag gggttccgcg cacatttccc cgaaaagtgc | 4200 |
| cacctgacgt ctaagaaacc attattatca tgacattaac ctataaaaat aggcgtatca | 4260 |
| cgaggccctt tcgtc | 4275 |

<210> SEQ ID NO 40
<211> LENGTH: 13175
<212> TYPE: DNA
<213> ORGANISM: Artificial Sequence
<220> FEATURE:
<223> OTHER INFORMATION: Plasmid pZKL4-220ESC4

<400> SEQUENCE: 40

| | |
|---|---|
| catggctcag tccaccaagg ctgccgacac tgctgccacc gacaagtctc tcgacaagaa | 60 |
| ccgactcatc tcccgagacg agctgcggtc tcacaacgtt ccccaggatg cctgggctgc | 120 |
| cgtccacggc agagtcatca acattaccga gttcgcccga cggcatcctg gtggcgacat | 180 |
| cattctgctt gccgcaggaa aggatgccac cgtgctcttc gagacttacc atcctcgagg | 240 |
| tgttcccacc tcgatcctcg acaagctgca ggtcggcaag atgaaggacg agaacttcc | 300 |
| ctcctcgttc tactcgtggg attccgactt ttacaagacc ctgcgagctc gagtggtcga | 360 |
| gcgattggac aagctcaacc tgcctcgaag aggtggctac gagatttggg tcaaggcagt | 420 |
| attcctcctg gctggattct ggttcagcct ctacaagatg tccgtcaacg agacctactg | 480 |
| ggctgcctcg ctgtggtccg tgtctatggg agtcttttgct gccttcatcg gcacttgcat | 540 |
| tcaacacgat ggaaaccacg gtgccttctc gaccagccct gctctcaaca aggttgcagg | 600 |
| ctggactctg gacatgatcg gtgcttctgg ctttacatgg gagattcagc atatgctcgg | 660 |
| acaccatccc tacaccaacg tcctggacgt ggacgaagag aagcgaaagg aagctggcga | 720 |
| cgattgtcct atggaggaca aggatcagga gtccgaccca gatgtcttct cttcgtttcc | 780 |
| tctcatgcga atgcaccct accacaaggc cgagtggtac caccgatatc agcacctgta | 840 |
| cgcacccgtt ctctttgctt tcatgactct tgccaaggtg ttccaacagg acatcgaagt | 900 |
| cgctaccact cagcgactgt accacatcga cgccaagtgc cgatacaatt ccattctcaa | 960 |
| tgtccttcgg ttttggtcga tgaaggtgct ctccatcggc tacatgctgg ctgttccctg | 1020 |
| ctacttccac ggaatccttg gtggccttgg actgtttctc atcggccact tgcctgtgg | 1080 |
| agagcttctg gcaaccatgt tcattgtcaa tcacgtcatc gagggtgtgt cctttggcaa | 1140 |
| aaagggagaa tctctcggtc tgtccaagga cgtggagttc aagcctacaa ccgtttctgg | 1200 |
| acgaactcca atggagcaga cccgtgccga ggccaaaaag gctgccaatg gaggcaacgt | 1260 |
| caaggatgtt ccctacaacg actgggctgc cgttcagtgt caaacgagcg tcaactggtc | 1320 |
| tcctggatcg tggttctgga atcacttctc cggtggcctc tcccaccaga tcgagcacca | 1380 |
| tctgtttccc agcatttgtc acaccaacta cgctcacatc caggacgttg tccagaagac | 1440 |
| ttgcgaagag tacggtgttc cttaccagtc cgaaccctct ttgttctccg cctatggcaa | 1500 |

```
gatgctgtct catctcaagt acctcggaaa cgagaaaaag gtcgcttaag cggccgcatg    1560
tacatacaag attatttata gaaatgaatc gcgatcgaac aaagagtacg agtgtacgag    1620 tagggggatga tgataaaagt ggaagaagtt ccgcatcttt ggatttatca acgtgtagga    1680
cgatacttcc tgtaaaaatg caatgtcttt accataggtt ctgctgtaga tgttattaac    1740
taccattaac atgtctactt gtacagttgc agaccagttg gagtatagaa tggtacactt    1800
accaaaaagt gttgatggtt gtaactacga tatataaaac tgttgacggg atctgcgtac    1860
actgtttaaa cagagtgtga aagactcact atggtccggg cttatctcga ccaatagcca    1920
aagtctggag tttctgagag aaaaaggcaa gatacgtatg taacaaagcg acgcatggta    1980
caataatacc ggaggcatgt atcatagaga gttagtggtt cgatgatggc actggtgcct    2040
ggtatgactt tatacggctg actacatatt tgtcctcaga catacaatta cagtcaagca    2100 cttaccttg  gacatctgta ggtacccccc ggccaagacg atctcagcgt gtcgtatgtc    2160
ggattggcgt agctccctcg ctcgtcaatt ggctcccatc tactttcttc tgcttggcta    2220
cacccagcat gtctgctatg gctcgttttc gtgccttatc tatcctccca gtattaccaa    2280
ctctaaatga catgatgtga ttgggtctac actttcatat cagagataag gagtagcaca    2340
gttgcataaa aagcccaact ctaatcagct tcttcctttc ttgtaattag tacaaaggtg    2400
attagcgaaa tctggaagct tagttggccc taaaaaaatc aaaaaaagca aaaaacgaaa    2460
aacgaaaaac cacagttttg agaacaggga ggtaacgaag gatcgtatat atatatatat    2520
atatatatac ccacggatcc cgagaccggc ctttgattct tccctacaac caaccattct    2580
caccacccta attcacaacc atggctgact ctcccgtcat caacctctcc accatgtgga    2640
agcctctgtc gctcatggcc ttggatcttg ctgttctggg acacgtctgg aagcaggcac    2700
aacaggaggg ctccatctcg gcttacgccg actctgtgtg gactcccctc atcatgtccg    2760
gtctgtacct ctccatgatc ttcgtgggat gtcgatggat gaagaaccga gagcccttcg    2820
aaatcaagac ctacatgttt gcctacaacc tgtaccagac cctcatgaac cttgcattg    2880 tgctgggctt cctctaccag gtccacgcta ccggtatgcg attctgggga tctggcgtgg    2940
accgatcgcc caagggtctg ggaattggct ttttcatcta tgcccattac acaacaagt    3000 acgtcgagta cttcgacaca ctcttcatgg tgctgcggaa aaagaacaac cagatttcct    3060
ttcttcacgt ctaccatcac gctctgctca cctgggcttg gtttgccgtg gtctacttcg    3120
ctcctggagg tgacggctgg tttggagcct gctacaattc ctccattcat gtcctgatgt    3180
actcttacta tctgcttgcc accttcggca tctcctgtcc ctggaaaaag atcctcaccc    3240
agctgcaaat ggttcagttc tgcttttgct tcacccactc gatctacgtg tggatttgcg    3300
gttccgaaat ctaccctcga ccccttgactg ctctccagtc cttcgtgatg gtcaacatgc    3360
tggttctctt tggcaacttc tacgtcaagc agtattctca gaagaatgga aagcccgaga    3420
acggtgccac tcctgagaac ggtgccaagc ctcagccctg cgagaacggc accgtcgaga    3480
agcgagagaa cgacactgcc aacgttcgat aagcggccgc atgaagat aaatatataa    3540 atacattgag atattaaatg cgctagatta gagagcctca tactgctcgg agagaagcca    3600
agacgagtac tcaaagggga ttacaccatc catatccaca gacacaagct ggggaaaggt    3660
tctatataca ctttccggaa taccgtagtt ccgatgtta tcaatggggg cagccaggat    3720
ttcaggcact tcggtgtctc ggggtgaaat ggcgttcttg gcctccatca agtcgtacca    3780
tgtcttcatt tgcctgtcaa agtaaaacag aagcagatga agaatgaact tgaagtgaag    3840
gaatttaaat tgccccggag aagacggcca ggccgcctag atgacaaatt caacaactca    3900
```

```
cagctgactt tctgccattg ccactagggg ggggcctttt tatatggcca agccaagctc    3960
tccacgtcgg ttgggctgca cccaacaata aatgggtagg gttgcaccaa caaagggatg    4020
ggatgggggg tagaagatac gaggataacg gggctcaatg gcacaaataa gaacgaatac    4080
tgccattaag actcgtgatc cagcgactga caccattgca tcatctaagg gcctcaaaac    4140
tacctcggaa ctgctgcgct gatctggaca ccacagaggt tccgagcact ttaggttgca    4200
ccaaatgtcc caccaggtgc aggcagaaaa cgctggaaca gcgtgtacag tttgtcttaa    4260
caaaaagtga gggcgctgag gtcgagcagg gtggtgtgac ttgttatagc ctttagagct    4320
gcgaaagcgc gtatggattt ggctcatcag gccagattga gggtctgtgg acacatgtca    4380
tgttagtgta cttcaatcgc ccctggata  tagccccgac aataggccgt ggcctcattt    4440
ttttgccttc cgcacatttc cattgctcgg tacccacacc ttgcttctcc tgcacttgcc    4500
aaccttaata ctggtttaca ttgaccaaca tcttacaagc gggggcttg  tctagggtat    4560 atataaacag tggctctccc aatcggttgc cagtctcttt tttcctttct ttccccacag    4620
attcgaaatc taaactacac atcacagaac tccgagccgt gagtatccac gacaagatca    4680
gtgtcgagac gacgcgtttt gtgtaatgac acaatccgaa agtcgctagc aacacacact    4740
ctctacacaa actaacccag ctctggtacc atggccgagg gcaagtccga cggtcccgtc    4800
gttaccctcc agtccatgtg gaagcccctg gctctcatgg ccatcgacgt cggcatcctg    4860
gtcaacgtgc gacggaaggc cttcaccgag ttcgacggac actcgaacgt cttcgccgat    4920
cccgtgtaca ttccctttgt catgaacctg ttctacctca ccatgatctt tgctggctgc    4980
cgatggatga agactcgaga acccttcgag atcaagtcct acatgtttgc ctacaacgct    5040
taccagacaa tgatgaactt tctcattgtg gtcggcttca tgtatgaggt tcactccacc    5100
ggtatgcgat actgggatc  cagaatcgac acttctacca agggcttggg actgggtttc    5160
ctcatctatg cccattacca caacaagtac gtggagtacg tcgacaccct gttcatgatt    5220
ctgcggaaga aaaacaatca gatctcgttc cttcacgttt accaccattc cctgctcact    5280
tgggcatggt gggctgtggt ctactgggct cctggcggag atgcctggtt cggtgcctgt    5340
tacaactcct tcatccacgt tctcatgtac tcctactatc tgtttgccac cttcggcatt    5400
cgatgtccct ggaaaaagat gctcacccag ttgcaaatgg tccagttctg cttttgcttc    5460
gctcatgcca tgtacgttgg atggcttggt cacgaggtgt accctcgatg gctcactgct    5520
ctgcaggcct ttgtgatgct caacatgctg gtcctctttg gcaacttcta catgaagtct    5580
tactccaagg cgagcaagct cgaaccagcc tctcccgtgt cgcctgcctc tcttgctcag    5640
aagcccttcg agaacgccaa ggtcaagtaa gcggccgcaa gtgtggatgg ggaagtgagt    5700
gcccggttct gtgtgcacaa ttggcaatcc aagatggatg gattcaacac agggatatag    5760
cgagctacgt ggtggtgcga ggatatagca acggatattt atgtttgaca cttgagaatg    5820
tacgatacaa gcactgtcca agtacaatac taaacatact gtacatactc atactcgtac    5880
ccgggcaacg gtttcacttg agtgcagtgg ctagtgctct tactcgtaca gtgtgcaata    5940
ctgcgtatca tagtctttga tgtatatcgt attcattcat gttagttgcg tacgtaggga    6000
tcaggtgctt aggaagctcg accaaccacg gagactgttg aaactggatg tcggtaacag    6060
catctggaat gctgaatgtt cctcgaataa caacatattt ctccttgttg aggtgatcat    6120
aagctatgta tccggtgatt gaagtggaat agaagtctcc tccgaagact gagtccaacg    6180
tcatgttcgg gaaataccga caactctctc cacatgtaaa atcagttcgt agaggagtga    6240
ctggcgcatt gacacagtag gcgatgtttg caatccgaga aaacttggcc gtaaagttgt    6300
```

```
acagctcctg ggaggcttga actcgagttt ttgaaagtgt cgctggtggc tcgccgaaga    6360
gggaggcata gaggtacgca accacttgcc cgagcgtgag gttcatgatg ccaatagtga    6420
atgtcattta tcaccgtact gcgcagtatt tatatagggc tcatcggtcc atgtatagat    6480
ctgtccactt atgacacccc catgtctcat taatgtgtaa aggtggagac gggtggagta    6540
caggtacaga gttggaggaa atcaggatag tggggttaag acatgctccg agtccaaatt    6600
tcaactctcc attgtcacaa gacctctggt ttcagagtta ttacagatct aggcctgttt    6660
caaggtgagg ggacctcatc tggatcggca cgacgatcgt caccttacag aggacgtctg    6720
tcgcagggaa aggtgatgtg gcgcgccagc tgcattaatg aatcggccaa cgcgcgggga    6780
gaggcggttt gcgtattggg cgctcttccg cttcctcgct cactgactcg ctgcgctcgg    6840
tcgttcggct gcggcgagcg gtatcagctc actcaaaggc ggtaatacgg ttatccacag    6900
aatcagggga taacgcagga agaacatgt gagcaaaagg ccagcaaaag gccaggaacc    6960
gtaaaaaggc cgcgttgctg gcgttttcc ataggctccg ccccctgac gagcatcaca    7020 aaaatcgacg ctcaagtcag aggtggcgaa acccgacagg actataaaga taccaggcgt    7080
ttccccctgg aagctccctc gtgcgctctc ctgttccgac cctgccgctt accggatacc    7140
tgtccgcctt tctcccttcg ggaagcgtgg cgctttctca tagctcacgc tgtaggtatc    7200
tcagttcggt gtaggtcgtt cgctccaagc tgggctgtgt gcacgaaccc cccgttcagc    7260
ccgaccgctg cgccttatcc ggtaactatc gtcttgagtc caacccggta agacacgact    7320
tatcgccact ggcagcagcc actggtaaca ggattagcag agcgaggtat gtaggcggtg    7380
ctacagagtt cttgaagtgg tggcctaact acggctacac tagaagaaca gtatttggta    7440
tctgcgctct gctgaagcca gttaccttcg gaaaaagagt tggtagctct tgatccggca    7500
aacaaaccac cgctggtagc ggtggttttt tgtttgcaa gcagcagatt acgcgcagaa    7560
aaaaaggatc tcaagaagat cctttgatct tttctacggg gtctgacgct cagtggaacg    7620
aaaactcacg ttaagggatt ttggtcatga gattatcaaa aaggatcttc acctagatcc    7680
ttttaaatta aaaatgaagt tttaaatcaa tctaaagtat atatgagtaa acttggtctg    7740
acagttacca atgcttaatc agtgaggcac ctatctcagc gatctgtcta tttcgttcat    7800
ccatagttgc ctgactcccc gtcgtgtaga taactacgat acgggagggc ttaccatctg    7860
gccccagtgc tgcaatgata ccgcgagacc cacgctcacc ggctccagat ttatcagcaa    7920
taaaccagcc agccggaagg gccgagcgca gaagtggtcc tgcaacttta tccgcctcca    7980
tccagtctat taattgttgc cgggaagcta gagtaagtag ttcgccagtt aatagtttgc    8040
gcaacgttgt tgccattgct acaggcatcg tggtgtcacg ctcgtcgttt ggtatggctt    8100
cattcagctc cggttcccaa cgatcaaggc gagttacatg atcccccatg ttgtgcaaaa    8160
aagcggttag ctccttcggt cctccgatcg ttgtcagaag taagttggcc gcagtgttat    8220
cactcatggt tatggcagca ctgcataatt ctcttactgt catgccatcc gtaagatgct    8280
tttctgtgac tggtgagtac tcaaccaagt cattctgaga atagtgtatg cggcgaccga    8340
gttgctcttg cccggcgtca atacgggata ataccgcgcc acatagcaga actttaaaag    8400
tgctcatcat tggaaaacgt tcttcgggc gaaaactctc aaggatctta ccgctgttga    8460
gatccagttc gatgtaaccc actcgtgcac ccaactgatc ttcagcatct tttactttca    8520
ccagcgtttc tgggtgagca aaaacaggaa ggcaaaatgc cgcaaaaaag gaataagggg    8580
cgacacggaa atgttgaata ctcatactct ccttttttca atattattga agcatttatc    8640
agggttattg tctcatgagc ggatacatat ttgaatgtat ttagaaaaat aaacaaatag    8700
```

```
gggttccgcg cacatttccc cgaaaagtgc cacctgatgc ggtgtgaaat accgcacaga   8760
tgcgtaagga gaaaataccg catcaggaaa ttgtaagcgt taatattttg ttaaaattcg   8820
cgttaaattt ttgttaaatc agctcatttt ttaaccaata ggccgaaatc ggcaaaatcc   8880
cttataaatc aaaagaatag accgagatag ggttgagtgt tgttccagtt tggaacaaga   8940
gtccactatt aaagaacgtg gactccaacg tcaagggcg aaaaaccgtc tatcagggcg    9000
atggcccact acgtgaacca tcaccctaat caagtttttt ggggtcgagg tgccgtaaag   9060
cactaaatcg gaaccctaaa gggagccccc gatttagagc ttgacgggga agccggcga    9120 acgtggcgag aaaggaaggg aagaaagcga aaggagcggg cgctagggcg ctggcaagtg   9180
tagcggtcac gctgcgcgta accaccacac ccgccgcgct taatgcgccg ctacagggcg   9240
cgtccattcg ccattcaggc tgcgcaactg ttgggaaggg cgatcggtgc gggcctcttc   9300
gctattacgc cagctggcga aggggggatg tgctgcaagg cgattaagtt gggtaacgcc   9360 aggggttttcc cagtcacgac gttgtaaaac gacggccagt gaattgtaat acgactcact   9420
atagggcgaa ttgggcccga cgtcgcatgc caaggcgtat attagttggt gggaaccagt   9480
gtacgaccgg gtcctgtata accaggttca gtggcatact tgtaggagtt gttcccgtgg   9540
tatttgggca tggctaagac atttcgccga ccaatgttaa gtgcacaata gccgatgtag   9600
tagatgtaag ccagatggtt ttggagcagg tcgattcgag accacagatt gaaagtgcct   9660
cgatggcagg cctcgttttc tcctccttca cagacagaca ctttgtcgag tgcagggtag   9720
acgctttctt ggtcaatgta cacttctcca atggcgtgtg tgtaattgga ccaatctggc   9780
agtccaacga agatatcgtt ccagtgggtg agcctgtagt ttcgtcgctt gtcgtttact   9840
tcaaggcctg tgtcattaaa ccacagctgg ttgatgtagt ttgcaaactc tgagtttcct   9900
actctcggct ggccaaagtt gatcatggta ggatcatgtc caagtaattt gaagtgagtt   9960
gcgaaaagaa gagcttgagc agcgcccagc gagtgaccag taacatacat tttgtagtca  10020
gtgtggttgg tgaggaactt ttcaaactga ggagcagcat tgaccatagt ttcgttgaag  10080
gccttggcga acccatcatg gatcatgcag cctttgcact cactagtttt gatgggaata  10140 agacggggt cttcaaccac cagagcccgc tctttgaggt tgtcaagacc tttgttctcc   10200
acttccaagt ctggtcggac tgcccatctc tgttaattaa gttgcgacac atgtcttgat  10260
agtatcttga attctctctc ttgagctttt ccataacaag ttcttctgcc tccaggaagt  10320
ccatgggtgg tttgatcatg gttttggtgt agtggtagtg cagtggtggt attgtgactg  10380
gggatgtagt tgagaataag tcatacacaa gtcagctttc ttcgagcctc atataagtat  10440
aagtagttca acgtattagc actgtaccca gcatctccgt atcgagaaac acaacaacat  10500
gccccattgg acagatcatg cggatacaca ggttgtgcag tatcatacat actcgatcag  10560
acaggtcgtc tgaccatcat acaagctgaa caagcgctcc atacttgcac gctctctata  10620
tacacagtta aattacatat ccatagtcta acctctaaca gttaatcttc tggtaagcct  10680
cccagccagc cttctggtat cgcttggcct cctcaatagg atctcggttc tggccgtaca  10740
gacctcggcc gacaattatg atatccgttc cggtagacat gacatcctca acagttcggt  10800
actgctgtcc gagagcgtct cccttgtcgt caagacccac cccgggggtc agaataagcc  10860
agtcctcaga gtcgcccttta ggtcggttct gggcaatgaa gccaaccaca aactcggggt  10920
cggatcgggc aagctcaatg gtctgcttgg agtactcgcc agtggccaga gagcccttgc  10980
aagacagctc ggccagcatg agcagacctc tggccagctt ctcgttggga gaggggacta  11040
ggaactcctt gtactgggag ttctcgtagt cagagacgtc ctccttcttc tgttcagaga  11100
```

```
cagtttcctc ggcaccagct cgcaggccag caatgattcc ggttccgggt acaccgtggg   11160
cgttggtgat atcggaccac tcggcgattc ggtgacaccg gtactggtgc ttgacagtgt   11220
tgccaatatc tgcgaacttt ctgtcctcga acaggaagaa accgtgctta agagcaagtt   11280
ccttgagggg gagcacagtg ccggcgtagg tgaagtcgtc aatgatgtcg atatgggttt   11340
tgatcatgca cacataaggt ccgaccttat cggcaagctc aatgagctcc ttggtggtgg   11400
taacatccag agaagcacac aggttggttt tcttggctgc cacgagcttg agcactcgag   11460
cggcaaaggc ggacttgtgg acgttagctc gagcttcgta ggagggcatt tggtggtga   11520 agaggagact gaaataaatt tagtctgcag aacttttat cggaacctta tctggggcag   11580
tgaagtatat gttatggtaa tagttacgag ttagttgaac ttatagatag actggactat   11640
acggctatcg gtccaaatta gaaagaacgt caatggctct ctgggcgtcg cctttgccga   11700
caaaaatgtg atcatgatga agccagcaa tgacgttgca gctgatattg ttgtcggcca   11760
accgcgccga aaacgcagct gtcagaccca cagcctccaa cgaagaatgt atcgtcaaag   11820
tgatccaagc acactcatag ttggagtcgt actccaaagg cggcaatgac gagtcagaca   11880
gatactcgtc gacctttcc ttgggaacca ccaccgtcag cccttctgac tcacgtattg   11940
tagccaccga cacaggcaac agtccgtgga tagcagaata tgtcttgtcg gtccatttct   12000
caccaacttt aggcgtcaag tgaatgttgc agaagaagta tgtgccttca ttgagaatcg   12060
gtgttgctga tttcaataaa gtcttgagat cagtttggcc agtcatgttg tgggggtaa   12120 ttggattgag ttatcgccta cagtctgtac aggtatactc gctgcccact ttatactttt   12180
tgattccgct gcacttgaag caatgtcgtt taccaaaagt gagaatgctc cacagaacac   12240
accccagggt atggttgagc aaaaaataaa cactccgata cggggaatcg aaccccggtc   12300
tccacggttc tcaagaagta ttcttgatga gagcgtatcg atggttaatg ctgctgtgtg   12360
ctgtgtgtgt gtgttgtttg gcgctcattg ttgcgttatg cagcgtacac cacaatattg   12420
gaagcttatt agccttctc ttttttcgtt tgcaaggctt aacaacattg ctgtggagag   12480
ggatggggat atggaggccg ctggagggag tcggagaggc gttttggagc ggcttggcct   12540
ggcgcccagc tcgcgaaacg cacctaggac cctttggcac gccgaaatgt gccacttttc   12600
agtctagtaa cgccttacct acgtcattcc atgcgtgcat gtttgcgcct ttttcccttt   12660
gcccttgatc gccacacagt acagtgcact gtacagtgga ggttttgggg gggtcttaga   12720
tgggagctaa aagcggccta gcggtacact agtgggattg tatggagtgg catggagcct   12780
aggtggagcc tgacaggacg cacgaccggc tagcccgtga cagacgatgg gtggctcctg   12840
ttgtccaccg cgtacaaatg tttgggccaa agtcttgtca gccttgcttg cgaacctaat   12900
tcccaatttt gtcacttcgc acccccattg atcgagccct aaccctgcc catcaggcaa   12960 tccaattaag ctcgcattgt ctgccttgtt tagtttggct cctgcccgtt tcggcgtcca   13020
cttgcacaaa cacaaacaag cattatatat aaggctcgtc tctccctccc aaccacactc   13080
acttttttgc ccgtcttccc ttgctaacac aaaagtcaag aacacaaaca accaccccaa   13140
cccccttaca cacaagacat atctacagca atggc                            13175
```

<210> SEQ ID NO 41
<211> LENGTH: 2987
<212> TYPE: DNA
<213> ORGANISM: Yarrowia lipolytica
<220> FEATURE:
<221> NAME/KEY: misc_feature
<223> OTHER INFORMATION: mutant acetohydroxyacid synthase (AHAS) with
    W497L mutation
<300> PUBLICATION INFORMATION:

```
<302> TITLE: HIGH EICOSAPENTAENOIC ACID PRODUCING STRAINS OF YARROWIA
      LIPOLYTICA
<310> PATENT DOCUMENT NUMBER: US 2006-0115881-A1
<311> PATENT FILING DATE: 2005-11-02
<312> PUBLICATION DATE: 2006-06-01
<313> RELEVANT RESIDUES: (1)..(2987)
<300> PUBLICATION INFORMATION:
<302> TITLE: HIGH EICOSAPENTAENOIC ACID PRODUCING STRAINS OF YARROWIA
      LIPOLYTICA
<310> PATENT DOCUMENT NUMBER: WO 2006/052870
<311> PATENT FILING DATE: 2005-11-03
<312> PUBLICATION DATE: 2006-05-18
<313> RELEVANT RESIDUES: (1)..(2987)

<400> SEQUENCE: 41
ttccctagtc ccagtgtaca cccgccgata tcgcttaccc tgcagccgga ttaaggttgg      60
caatttttca cgtccttgtc tccgcaatta ctcaccgggt ggtttataag attgcaagcg     120
tcttgatttg tctctgtata ctaacatgca atcgcgactc gcccgacggg ccactaacct     180
ggccagaatc tccagatcca agtattctct tggtctgcga tatgtttcca acacaaaagc     240
ccctgctgcc cagccggcaa ctgctgagtg agtattcctt gccataaacg acccagaacc     300
actgtatagt gtttggaagc actagtcaga agaccagcga aaacaggtgg aaaaaactga     360
gacgaaaagc aacgaccaga aatgtaatgt gtggaaaagc gacacacaca gagcagataa     420
agaggtgaca aataacgaca aatgaaatat cagtatcttc ccacaatcac tacctctcag     480
ctgtctgaag gtgcggctga tatatccatc ccacgtctaa cgtatggagt gtgatagaat     540
atgacgacac aagcatgaga actcgctctc tatccaacca ccgaaacact gtcactacag     600
ccgttcttgt tgctccattc gcttttgtga ttccatgcct tctctggtga ctgacaacat     660
tccttccttt tctccagccc tgttgttatc tgctcatgac ctacggccac tctctatcgc     720
atactaacat agacgatccc agcccgctcc ccacttccag ggcaccgttg gcaagcctcc     780
tatcctcaag aaggctgagg ctgccaacgc tgacatggac gagtccttca tcggaatgtc     840
tggaggagag atcttccacg agatgatgct gcgacacaac gtcgacactg tcttcggtta     900
ccccggtgga gccattctcc ccgtctttga cgccattcac aactctgagt acttcaactt     960
tgtgctccct cgacacgagc agggtgccgg ccacatggcc gagggctacg ctcgagcctc    1020
tggtaagccc ggtgtcgttc tcgtcacctc tggccccggt gccaccaacg tcatcacccc    1080
catgcaggac gctctttccg atggtacccc catggttgtc ttcaccggtc aggtcctgac    1140
ctccgttatc ggcactgacg ccttccagga ggccgatgtt gtcggcatct cccgatcttg    1200
caccaagtgg aacgtcatgg tcaagaacgt tgctgagctc ccccgacgaa tcaacgaggc    1260
ctttgagatt gctacttccg gccgacccgg tccgttctc gtcgatctgc caaggatgt     1320 tactgctgcc atcctgcgag agcccatccc caccaagtcc accattccct cgcattctct    1380
gaccaacctc acctctgccg ccgccaccga gttccagaag caggctatcc agcgagccgc    1440
caacctcatc aaccagtcca agaagcccgt cctttacgtc ggacagggta tccttggctc    1500
cgaggagggt cctaagctgc ttaaggagct ggctgagaag gccgagattc ccgtcaccac    1560
tactctgcag ggtcttggtg cctttgacga gcgagacccc aagtctctgc acatgctcgg    1620
tatgcacggt tccggctacg ccaacatggc catgcagaac gctgactgta tcattgctct    1680
cggcgcccga tttgatgacc gagttaccgg ctccatcccc aagtttgccc ccgaggctcg    1740
agccgctgcc cttgagggtc gaggtggtat tgttcacttt gagatccagg ccaagaacat    1800
caacaaggtt gttcaggcca ccgaagccgt tgagggagac gttaccgagt ctgtccgaca    1860
gctcatcccc ctcatcaaca aggtctctgc cgctgagcga gctccctgga ctgagactat    1920
```

```
ccagtcctgg aagcagcagt tccccttcct cttcgaggct gaaggtgagg atggtgttat    1980
caagccccag tccgtcattg ctctgctctc tgacctgaca gagaacaaca aggacaagac    2040
catcatcacc accggtgttg gtcagcatca gatgtggact gcccagcatt tccgatggcg    2100
acaccctcga accatgatca cttctggtgg tcttggaact atgggttacg gcctgcccgc    2160
cgctatcggc gccaaggttg cccgacctga ctgcgacgtc attgacatcg atggtgacgc    2220
ttctttcaac atgactctga ccgagctgtc caccgccgtt cagttcaaca ttggcgtcaa    2280
ggctattgtc ctcaacaacg aggaacaggg tatggtcacc cagctgcagt ctctcttcta    2340
cgagaaccga tactgccaca ctcatcagaa gaaccccgac ttcatgaagc tggccgagtc    2400
catgggcatg aagggtatcc gaatcactca cattgaccag ctggaggccg gtctcaagga    2460
gatgctcgca tacaagggcc ctgtgctcgt tgaggttgtt gtcgacaaga agatccccgt    2520
tcttcccatg gttcccgctg gtaaggcttt gcatgagttc cttgtctacg acgctgacgc    2580
cgaggctgct tctcgacccg atcgactgaa gaatgccccc gccccctcacg tccaccagac    2640 cacctttgag aactaagtgg aaaggaacac aagcaatccg aaccaaaaat aattggggtc    2700
ccgtgcccac agagtctagt gcagacctaa atgaccaca gtaaattata gctgttatta    2760
aacatgagat tttgaccaac aagagcgtag gaatgttatt agctactact tgtacataca    2820
cagcatttgt tttaaataat gttgcctcca ggggcagtga gatcaggacc cagatccgtg    2880
gccagctctc tgacttcaga ccgcttgtac ttaagcagct cgcaacactg ttgtcgagga    2940
ttgaacttgc catattcgat tttgtggtca tgaatccagc acacctc                  2987
```

<210> SEQ ID NO 42
<211> LENGTH: 14688
<212> TYPE: DNA
<213> ORGANISM: Artificial Sequence
<220> FEATURE:
<223> OTHER INFORMATION: Plasmid pZKLeuN-29E3

<400> SEQUENCE: 42

```
cgattgttgt ctactaacta tcgtacgata acttcgtata gcatacatta tacgaagtta     60
tcgcgtcgac gagtatctgt ctgactcgtc attgccgcct ttggagtacg actccaacta    120
tgagtgtgct tggatcactt tgacgataca ttcttcgttg gaggctgtgg gtctgacagc    180
tgcgttttcg gcgcggttgg ccgacaacaa tatcagctgc aacgtcattg ctggcttttca   240 tcatgatcac atttttgtcg gcaaaggcga cgcccagaga gccattgacg ttctttctaa    300
tttggaccga tagccgtata gtccagtcta tctataagtt caactaactc gtaactatta    360
ccataacata tacttcactg ccccagataa ggttccgata aaaagttctg cagactaaat    420
ttatttcagt ctcctcttca ccaccaaaat gccctcctac gaagctcgag ctaacgtcca    480
caagtccgcc tttgccgctc gagtgctcaa gctcgtggca gccaagaaaa ccaacctgtg    540
tgcttctctg gatgttacca ccaccaagga gctcattgag cttgccgata aggtcggacc    600
ttatgtgtgc atgatcaaaa cccatatcga catcattgac gacttcaccct acgccggcac    660 tgtgctcccc ctcaaggaac ttgctcttaa gcacggtttc ttcctgttcg aggacagaaa    720
gttcgcagat attggcaaca ctgtcaagca ccagtaccgg tgtcaccgaa tcgccgagtg    780
gtccgatatc accaacgccc acggtgtacc cggaaccgga atcattgctg gcctgcgagc    840
tggtgccgag gaaactgtct ctgaacagaa gaaggaggac gtctctgact acgagaactc    900
ccagtacaag gagttcctag tcccctctcc caacgagaag ctggcagag gtctgctcat    960 gctggccgag ctgtcttgca agggctctct ggccactggc gagtactcca agcagaccat   1020
```

```
tgagcttgcc cgatccgacc ccgagtttgt ggttggcttc attgcccaga accgacctaa    1080
gggcgactct gaggactggc ttattctgac ccccggggtg ggtcttgacg acaagggaga    1140
cgctctcgga cagcagtacc gaactgttga ggatgtcatg tctaccggaa cggatatcat    1200
aattgtcggc cgaggtctgt acggccagaa ccgagatcct attgaggagg ccaagcgata    1260
ccagaaggct ggctgggagg cttaccagaa gattaactgt tagaggttag actatggata    1320
tgtaatttaa ctgtgtatat agagagcgtg caagtatgga gcgcttgttc agcttgtatg    1380
atggtcagac gacctgtctg atcgagtatg tatgatactg cacaacctgt gtatccgcat    1440
gatctgtcca atggggcatg ttgttgtgtt tctcgatacg gagatgctgg gtacagtgct    1500
aatacgttga actacttata cttatatgag gctcgaagaa agctgacttg tgtatgactt    1560
attctcaact acatcsccag tcacaatacc accactgcac taccactaca ccaaaaccat    1620
gatcaaacca cccatggact tcctggaggc agaagaactt gttatggaaa agctcaagag    1680
agagatcata acttcgtata gcatacatta tacgaagtta tcctgcaggt aaaggaattc    1740
tggagtttct gagagaaaaa ggcaagatac gtatgtaaca aagcgacgca tggtacaata    1800
ataccggagg catgtatcat agagagttag tggttcgatg atggcactgg tgcctggtat    1860
gactttatac ggctgactac atatttgtcc tcagacatac aattacagtc aagcacttac    1920
ccttggacat ctgtaggtac cccccggcca agacgatctc agcgtgtcgt atgtcggatt    1980
ggcgtagctc cctcgctcgt caattggctc ccatctactt tcttctgctt ggctacaccc    2040
agcatgtctg ctatggctcg ttttcgtgcc ttatctatcc tcccagtatt accaactcta    2100
aatgacatga tgtgattggg tctacacttt catatcagag ataaggagta gcacagttgc    2160
ataaaaagcc caactctaat cagcttcttc ctttcttgta attagtacaa aggtgattag    2220
cgaaatctgg aagcttagtt ggccctaaaa aaatcaaaaa aagcaaaaaa cgaaaaacga    2280
aaaaccacag ttttgagaac agggaggtaa cgaaggatcg tatatatata tatatatata    2340
tataccacg gatcccgaga ccggcctttg attcttccct acaaccaacc attctcacca    2400
ccctaattca caaccatgga gtctggaccc atgcctgctg gcattccctt ccctgagtac    2460
tatgacttct ttatggactg gaagactccc ctggccatcg ctgccaccta cactgctgcc    2520
gtcggtctct tcaaccccaa ggttggcaag gtctcccgag tggttgccaa gtcggctaac    2580
gcaaagcctg ccgagcgaac ccagtccgga gctgccatga ctgccttcgt ctttgtgcac    2640
aacctcattc tgtgtgtcta ctctggcatc accttctact acatgtttcc tgctatggtc    2700
aagaacttcc gaacccacac actgcacgaa gcctactgcg acacggatca gtccctctgg    2760
aacaacgcac ttggctactg gggttacctc ttctacctgt ccaagttcta cgaggtcatt    2820
gacaccatca tcatcatcct gaagggacga cggtcctcgc tgcttcagac ctaccaccat    2880
gctggagcca tgattaccat gtggtctggc atcaactacc aagccactcc catttggatc    2940
tttgtggtct tcaactcctt cattcacacc atcatgtact gttactatgc cttcacctct    3000
atcggattcc atcctcctgg caaaaagtac ctgacttcga tgcagattac tcagtttctg    3060
gtcggtatca ccattgccgt gtcctacctc ttcgttcctg gctgcatccg aacacccggt    3120
gctcagatgg ctgtctggat caacgtcggc tacctgtttc ccttgaccta tctgttcgtg    3180
gactttgcca agcgaaccta ctccaagcga tctgccattg ccgctcagaa aaaggctcag    3240
taagcggccg cattgatgat tggaaacaca cacatgggtt atatctaggt gagagttagt    3300
tggacagtta tatattaaat cagctatgcc aacggtaact tcattcatgt caacgaggaa    3360
ccagtgactg caagtaatat agaatttgac caccttgcca ttctcttgca ctcctttact    3420
```

```
atatctcatt tatttcttat atacaaatca cttcttcttc ccagcatcga gctcggaaac   3480
ctcatgagca ataacatcgt ggatctcgtc aatagagggc ttttggact ccttgctgtt    3540 ggccaccttg tccttgctgt ctggctcatt ctgtttcaac gccttttaat taacggagta   3600
ggtctcggtg tcgaagcga cgccagatcc gtcatcctcc tttcgctctc caaagtagat    3660
acctccgacg agctctcgga caatgatgaa gtcggtgccc tcaacgtttc ggatggggga   3720
gagatcggcg agcttgggcg acagcagctg cagggtcgc aggttggcgt acaggttcag    3780
gtcctttcgc agcttgagga gaccctgctc gggtcgcacg tcggttcgtc cgtcgggagt   3840
ggtccatacg tgttggcag cgcctccgac agcaccgagc ataatagagt cagccttcg     3900 gcagatgtcg agagtagcgt cggtgatggg ctcgccctcc ttctcaatgg cagctcctcc   3960
aatgagtcgg tcctcaaaca caactcggt gccggaggcc tcagcaacag acttgagcac    4020
cttgacggcc tcggcaatca cctcggggcc acagaagtcg ccgccgagaa gaacaatctt   4080
cttggagtca gtcttggtct tcttagtttc gggttccatt gtggatgtgt gtggttgtat   4140
gtgtgatgtg gtgtgtggag tgaaaatctg tggctggcaa acgctcttgt atatatacgc   4200
acttttgccc gtgctatgtg gaagactaaa cctccgaaga ttgtgactca ggtagtgcgg   4260
tatcggctag ggacccaaac cttgtcgatg ccgatagcat gcgacgtcgg gcccaattcg   4320
ccctatagtg agtcgtatta caattcactg gccgtcgttt tacaacgtcg tgactgggaa   4380
aaccctggcg ttacccaact taatcgcctt gcagcacatc cccctttcgc cagctggcgt   4440
aatagcgaag aggcccgcac cgatcgccct tcccaacagt tgcgcagcct gaatggcgaa   4500
tggacgcgcc ctgtagcggc gcattaagcg cggcgggtgt ggtggttacg cgcagcgtga   4560
ccgctacact tgccagcgcc ctagcgcccg ctcctttcgc tttcttccct tcctttctcg   4620
ccacgttcgc cggctttccc cgtcaagctc taaatcgggg gctcccttta gggttccgat   4680
ttagtgcttt acggcacctc gaccccaaaa aacttgatta gggtgatggt tcacgtagtg   4740
ggccatcgcc ctgatagacg gtttttcgcc ctttgacgtt ggagtccacg ttctttaata   4800
gtggactctt gttccaaact ggaacaacac tcaaccctat ctcggtctat tcttttgatt   4860
tataagggat tttgccgatt tcggcctatt ggttaaaaaa tgagctgatt taacaaaaat   4920
ttaacgcgaa ttttaacaaa atattaacgc ttacaatttc ctgatgcggt attttctcct   4980
tacgcatctg tgcggtattt cacaccgcat caggtggcac ttttcgggga atgtgcgcg    5040 gaacccctat ttgtttattt ttctaaatac attcaaatat gtatccgctc atgagacaat   5100
aaccctgata aatgcttcaa taatattgaa aaggaagag tatgagtatt caacatttcc    5160
gtgtcgccct tattccctt tttgcggcat tttgccttcc tgtttttgct cacccagaaa    5220
cgctggtgaa agtaaaagat gctgaagatc agttgggtgc acgagtgggt tacatcgaac   5280
tggatctcaa cagcggtaag atccttgaga gttttcgccc cgaagaacgt tttccaatga   5340
tgagcacttt taaagttctg ctatgtggcg cggtattatc ccgtattgac gccgggcaag   5400
agcaactcgg tcgccgcata cactattctc agaatgactt ggttgagtac tcaccagtca   5460
cagaaaagca tcttacggat ggcatgacag taagagaatt atgcagtgct gccataacca   5520
tgagtgataa cactgcggcc aacttacttc tgacaacgat cggaggaccg aaggagctaa   5580 ccgcttttt gcacaacatg ggggatcatg taactcgcct tgatcgttgg aaccggagc     5640 tgaatgaagc cataccaaac gacgagcgtg acaccacgat gcctgtagca atggcaacaa   5700
cgttgcgcaa actattaact ggcgaactac ttactctagc ttcccggcaa caattaatag   5760
actggatgga ggcggataaa gttgcaggac cacttctgcg ctcggccctt ccggctggct   5820
```

```
ggtttattgc tgataaatct ggagccggtg agcgtgggtc tcgcggtatc attgcagcac   5880
tggggccaga tggtaagccc tcccgtatcg tagttatcta cacgacgggg agtcaggcaa   5940
ctatggatga acgaaataga cagatcgctg agataggtgc ctcactgatt aagcattggt   6000
aactgtcaga ccaagtttac tcatatatac tttagattga tttaaaactt cattttaat   6060 ttaaaaggat ctaggtgaag atcctttttg ataatctcat gaccaaaatc ccttaacgtg   6120
agttttcgtt ccactgagcg tcagaccccg tagaaaagat caaaggatct tcttgagatc   6180
ctttttttct gcgcgtaatc tgctgcttgc aaacaaaaaa accaccgcta ccagcggtgg   6240
tttgtttgcc ggatcaagag ctaccaactc tttttccgaa ggtaactggc ttcagcagag   6300
cgcagatacc aaatactgtt cttctagtgt agccgtagtt aggccaccac ttcaagaact   6360
ctgtagcacc gcctacatac ctcgctctgc taatcctgtt accagtggct gctgccagtg   6420
gcgataagtc gtgtcttacc gggttggact caagacgata gttaccggat aaggcgcagc   6480
ggtcgggctg aacggggggt tcgtgcacac agcccagctt ggagcgaacg acctacaccg   6540
aactgagata cctacagcgt gagctatgag aaagcgccac gcttcccgaa gggagaaagg   6600
cggacaggta tccggtaagc ggcagggtcg aacaggaga gcgcacgagg gagcttccag   6660
ggggaaacgc ctggtatctt tatagtcctg tcgggtttcg ccacctctga cttgagcgtc   6720
gatttttgtg atgctcgtca ggggggcgga gcctatggaa aaacgccagc aacgcggcct   6780
ttttacggtt cctggccttt tgctggcctt ttgctcacat gttctttcct gcgttatccc   6840
ctgattctgt ggataaccgt attaccgcct ttgagtgagc tgataccgct cgccgcagcc   6900
gaacgaccga gcgcagcgag tcagtgagcg aggaagcgga agagcgccca atacgcaaac   6960
cgcctctccc cgcgcgttgg ccgattcatt aatgcagctg gcgcgcccac tgagctcgtc   7020
taacggactt gatatacaac caattaaaac aaatgaaaag aaatacagtt ctttgtatca   7080
tttgtaacaa ttaccctgta caaactaagg tattgaaatc ccacaatatt cccaaagtcc   7140 accccttttcc aaattgtcat gcctacaact catataccaa gcactaacct accaaacacc   7200
actaaaaccc cacaaaatat atcttaccga atatacagta acaagctacc accacactcg   7260
ttgggtgcag tcgccagctt aaagatatct atccacatca gccacaactc ccttcctta   7320 ataaaccgac tacaccccttg gctattgagg ttatgagtga atatactgta gacaagacac   7380
tttcaagaag actgtttcca aaacgtacca ctgtcctcca ctacaaacac acccaatctg   7440
cttcttctag tcaaggttgc tacaccggta aattataaat catcatttca ttagcagggc   7500
agggcccttt ttatagagtc ttatacacta gcggaccctg ccggtagacc aacccgcagg   7560
cgcgtcagtt tgctccttcc atcaatgcgt cgtagaaacg acttactcct tcttgagcag   7620
ctccttgacc ttgttggcaa caagtctccg acctcggagg tggaggaaga gcctccgata   7680
tcggcggtag tgataccagc ctcgacggac tccttgacgg cagcctcaac agcgtcaccg   7740
gcgggcttca tgttaagaga gaacttgagc atcatggcgg cagacagaat ggtgcgtac   7800 gcaactaaca tgaatgaata cgatatacat caaagactat gatacgcagt attgcacact   7860
gtacgagtaa gagcactagc cactgcactc aagtgaaacc gttgcccggg tacgagtatg   7920
agtatgtaca gtatgtttag tattgtactt ggacagtgct tgtatcgtac attctcaagt   7980
gtcaaacata aatatccgtt gctatatcct cgcaccacca cgtagctcgc tatatccctg   8040
tgttgaatcc atccatcttg gattgccaat tgtgcacaca gaaccgggca ctcacttccc   8100
catccacact tgcggccgct taagcaacgg gcttgataac agcggggggg gtgcccacgt   8160
tgttgcggtt gcggaagaac agaacaccct taccagcacc ctcggcacca gcgctgggct   8220
```

```
caacccactg gcacatacgc gcactgcggt acatggcgcg gatgaagcca cgaggaccat    8280
cctggacatc agcccggtag tgcttgccca tgatgggctt aatggcctcg gtggcctcgt    8340
ccgcgttgta aaggggatg ctgctgacgt agtggtggag gacatgagtc tcgatgatgc    8400
cgtggagaag gtggcggccg atgaagccca tctcacggtc aatggtagca gcggcaccac    8460
ggacgaagtt ccactcgtcg ttggtgtagt ggggaagggt agggtcggtg tgctggagga    8520
aggtgatggc aacgagccag tggttaaccc agaggtaggg aacaaagtac cagatggcca    8580
tgttgtagaa accgaacttc tgaacgagga agtacagagc agtggccatc agaccgatac    8640
caatatcgct gaggacgatg agcttagcgt cactgttctc gtacagaggg ctgcggggat    8700
cgaagtggtt aacaccaccg ccgaggccgt tatgcttgcc cttgccgcga ccctcacgct    8760
ggcgctcgtg gtagttgtgg ccggtaacat tggtgatgag gtagttgggc cagccaacga    8820
gctgctgaag gacgagcatg agaagagtga aagcggggt ctcctcagta agatgagcga    8880
gctcgtgggt catcttttccg agacgagtag cctgctgctc gcgggttcgg ggaacgaaga    8940
ccatgtcacg ctccatgttg ccagtggcct tgtggtgctt tcggtgggag atttgccagc    9000
tgaagtaggg gacaaggagg gaagagtgaa gaacccagcc agtaatgtcg ttgatgatgc    9060
gagaatcgga gaaagcaccg tgaccgcact catgggcaat aacccagaga ccagtaccga    9120
aaagaccctg aagaacggtg tacacggccc acagaccagc gcgggcgggg gtggagggga    9180
tatattcggg ggtcacaaag ttgtaccaga tgctgaaagt ggtagtcagg aggacaatgt    9240
cgcggaggat ataaccgtat cccttgagag cggagcgctt gaagcagtgc ttagggatgg    9300
cattgtagat gtccttgatg gtaaagtcgg gaacctcgaa ctggttgccg taggtgtcga    9360
gcatgacacc atactcggac ttgggcttgg cgatatcaac ctcggacatg gacgagagcg    9420
atgtggaaga ggccgagtgg cggggagagt ctgaaggaga gacggcggca gactcagaat    9480
ccgtcacagt agttgaggtg acggtgcgtc taagcgcagg gttctgcttg ggcagagccg    9540
aagtggacgc catggttgat gtgtgtttaa ttcaagaatg aatatagaga agagaagaag    9600
aaaaaagatt caattgagcc ggcgatgcag acccttatat aaatgttgcc ttggacagac    9660
ggagcaagcc cgcccaaacc tacgttcggt ataatatgtt aagcttttta acacaaaggt    9720
ttggcttggg gtaacctgat gtggtgcaaa agaccgggcg ttggcgagcc attgcgcggg    9780
cgaatggggc cgtgactcgt ctcaaattcg agggcgtgcc tcaattcgtg ccccgtggc    9840 ttttcccgc cgtttccgcc ccgtttgcac cactgcagcc gcttctttgg ttcggacacc    9900
ttgctgcgag ctaggtgcct tgtgctactt aaaaagtggc ctcccaacac caacatgaca    9960
tgagtgcgtg ggccaagaca cgttggcggg gtcgcagtcg gctcaatggc ccggaaaaaa    10020
cgctgctgga gctggttcgg acgcagtccg ccgcggcgta tggatatccg caaggttcca    10080
tagcgccatt gccctccgtc ggcgtctatc ccgcaacctc taaatagagc gggaatataa    10140
cccaagcttc tttttttcc tttaacacgc acacccccaa ctatcatgtt gctgctgctg    10200
tttgactcta ctctgtggag gggtgctccc acccaaccca acctacaggt ggatccggcg    10260
ctgtgattgg ctgataagtc tcctatccgg actaattctg accaatggga catgcgcgca    10320
ggacccaaat gccgcaatta cgtaaccccca acgaaatgcc taccctctct tggagcccag    10380 cggcccaaa tccccccaag cagcccggtt ctaccggctt ccatctccaa gcacaagcag    10440
cccggttcta ccggcttcca tctccaagca ccctttctc cacaccccac aaaaagaccc    10500
gtgcaggaca tcctactgcg tcgacatcat ttaaattcct tcacttcaag ttcattcttc    10560
atctgcttct gttttacttt gacaggcaaa tgaagacatg gtacgacttg atggaggcca    10620
```

```
agaacgccat ttcaccccga gacaccgaag tgcctgaaat cctggctgcc cccattgata   10680
acatcggaaa ctacggtatt ccggaaagtg tatatagaac ctttccccag cttgtgtctg   10740
tggatatgga tggtgtaatc cccttgagt actcgtcttg gcttctctcc gagcagtatg   10800
aggctctcta atctagcgca tttaatatct caatgtattt atatatttat cttctcatgc   10860
ggccgctcac tgaatctttt tggctccctt gtgcttcctg acgatatacg tttgcacata   10920
gaaattcaag aacaaacaca agactgtgcc aacataaaag taattgaaga accagccaaa   10980
catcctcatc ccatcttggc gataacaggg aatgttcctg tacttccaga caatgtagaa   11040
accaacattg aattgaatga tctgcattga tgtaatcagg gattttggca tggggaactt   11100
cagcttgatc aatctggtcc aataataacc gtacatgatc cagtggatga aaccattcaa   11160
cagcacaaaa atccaaacag cttcatttcg gtaattatag aacagccaca tatccatcgg   11220
tgcccccaaa tgatggaaga attgcaacca ggtcagaggc ttgcccatca gtggcaaata   11280
gaaggagtca atatactcca ggaacttgct caaatagaac aactgcgtgg tgatcctgaa   11340
gacgttgttg tcaaaagcct tctcgcagtt gtcagacata acaccgatgg tgtacatggc   11400
atatgccatt gagaggaatg atcccaacga ataaatggac atgagaaggt tgtaattggt   11460
gaaaacaaac ttcatacgag actgaccttt tggaccaagg gggccaagag tgaacttcaa   11520
gatgacaaat gcgatggaca agtaaagcac ctcacagtga ctggcatcac tccagagttg   11580
ggcataatca actggttggg taaaacttcc tgcccaattg agactatttc attcaccacc   11640
tccatggcca ttgctgtaga tatgtcttgt gtgtaagggg gttggggtgg ttgtttgtgt   11700
tcttgacttt tgtgttagca agggaagacg ggcaaaaaag tgagtgtggt tgggaggag   11760 agacgagcct tatatataat gcttgtttgt gtttgtgcaa gtggacgccg aaacgggcag   11820
gagccaaact aaacaaggca gacaatgcga gcttaattgg attgcctgat gggcagggt   11880 tagggctcga tcaatggggg tgcgaagtga caaaattggg aattaggttc gcaagcaagg   11940
ctgacaagac tttggcccaa acatttgtac gcggtggaca acaggagcca cccatcgtct   12000
gtcacgggct agccggtcgt gcgtcctgtc aggctccacc taggctccat gccactccat   12060
acaatcccac tagtgtaccg ctaggccgct tttagctccc atctaagacc cccccaaaac   12120
ctccactgta cagtgcactg tactgtgtgg cgatcaaggg caagggaaaa aaggcgcaaa   12180
catgcacgca tggaatgacg taggtaaggc gttactagac tgaaaagtgg cacatttcgg   12240
cgtgccaaag ggtcctaggt gcgtttcgcg agctgggcgc caggccaagc cgctccaaaa   12300
cgcctctccg actccctcca gcggcctcca tatccccatc cctctccaca gcaatgttgt   12360
taagccttgc aaacgaaaaa atagaaaggc taataagctt ccaatattgt ggtgtacgct   12420
gcataacgca acaatgagcg ccaaacaaca cacacacaca gcacacagca gcattaacca   12480
cgatgaacag catgacatta caggtgggtg tgtaatcagg gccctgattg ctggtggtgg   12540
gagcccccat catgggcaga tctgcgtaca ctgtttaaac agtgtacgca gatctactat   12600
agaggaacat ttaaattgcc ccggagaaga cggccaggcc gcctagatga caaattcaac   12660
aactcacagc tgactttctg ccattgccac tagggggggg ccttttata tggccaagcc   12720 aagctctcca cgtcggttgg gctgcaccca acaataaatg ggtagggttg caccaacaaa   12780
gggatgggat gggggtaga agatacgagg ataacgggc tcaatggcac aaataagaac   12840
gaatactgcc attaagactc gtgatccagc gactgacacc attgcatcat ctaagggcct   12900
caaaactacc tcggaactgc tgcgctgatc tggacaccac agaggttccg agcactttag   12960
gttgcaccaa atgtcccacc aggtgcaggc agaaaacgct ggaacagcgt gtacagtttg   13020
```

-continued

```
tcttaacaaa aagtgagggc gctgaggtcg agcagggtgg tgtgacttgt tatagccttt      13080
agagctgcga aagcgcgtat ggatttggct catcaggcca gattgagggt ctgtggacac      13140
atgtcatgtt agtgtacttc aatcgccccc tggatatagc cccgacaata ggccgtggcc      13200
tcattttttt gccttccgca catttccatt gctcgatacc cacaccttgc ttctcctgca      13260
cttgccaacc ttaatactgg tttacattga ccaacatctt acaagcgggg ggcttgtcta      13320
gggtatatat aaacagtggc tctcccaatc ggttgccagt ctcttttttc ctttctttcc      13380
ccacagattc gaaatctaaa ctacacatca cagaattccg agccgtgagt atccacgaca      13440
agatcagtgt cgagacgacg cgttttgtgt aatgacacaa tccgaaagtc gctagcaaca      13500
cacactctct acacaaacta acccagctct ggtaccatgg aggtcgtgaa cgaaatcgtc      13560
tccattggcc aggaggttct tcccaaggtc gactatgctc agctctggtc tgatgcctcg      13620
cactgcgagg tgctgtacct ctccatcgcc ttcgtcatcc tgaagttcac ccttggtcct      13680
ctcggaccca agggtcagtc tcgaatgaag tttgtgttca ccaactacaa cctgctcatg      13740
tccatctact cgctgggctc cttcctctct atggcctacg ccatgtacac cattggtgtc      13800
atgtccgaca actgcgagaa ggctttcgac aacaatgtct tccgaatcac cactcagctg      13860
ttctacctca gcaagttcct cgagtacatt gactccttct atctgcccct catgggcaag      13920
cctctgacct ggttgcagtt cttcaccat ctcggagctc ctatggacat gtggctgttc       13980
tacaactacc gaaacgaagc cgtttggatc tttgtgctgc tcaacggctt cattcactgg      14040
atcatgtacg gctactattg gacccgactg atcaagctca gttccctat gcccaagtcc       14100 ctgattactt ctatgcagat cattcagttc aacgttggct tctacatcgt ctggaagtac      14160
cggaacattc cctgctaccg acaagatgga atgagaatgt ttggctggtt tttcaactac      14220
ttctacgttg gtactgtcct gtgtctgttc ctcaacttca cgtgcagac ctacatcgtc       14280 cgaaagcaca agggagccaa aaagattcag tgagcggccg catgtacata caagattatt      14340
tatagaaatg aatcgcgatc gaacaaagag tacgagtgta cgagtagggg atgatgataa      14400
aagtggaaga agttccgcat cttggattt atcaacgtgt aggacgatac ttcctgtaaa       14460
aatgcaatgt ctttaccata ggttctgctg tagatgttat taactaccat taacatgtct      14520
acttgtacag ttgcagacca gttggagtat agaatggtac acttaccaaa aagtgttgat      14580
ggttgtaact acgatatata aaactgttga cgggatcccc gctgatatgc ctaaggaaca      14640
atcaaagagg aagatattaa ttcagaatgc tagtatacag ttagggat                   14688
```

```
<210> SEQ ID NO 43
<211> LENGTH: 1434
<212> TYPE: DNA
<213> ORGANISM: Fusarium monoliforme
<220> FEATURE:
<221> NAME/KEY: CDS
<222> LOCATION: (1)..(1434)
<223> OTHER INFORMATION: delta-12 desaturase
<300> PUBLICATION INFORMATION:
<302> TITLE: DELTA-12 DESATURASES SUITABLE FOR ALTERING LEVELS OF
      POLYUNSATURATED FATTY ACIDS IN OLEAGINOUS YEAST
<310> PATENT DOCUMENT NUMBER: WO 2005/047485
<311> PATENT FILING DATE: 2004-11-12
<312> PUBLICATION DATE: 2005-05-26
<313> RELEVANT RESIDUES: (1)..(1434)
<300> PUBLICATION INFORMATION:
<302> TITLE: DELTA-12 DESATURASES SUITABLE FOR ALTERING LEVELS OF
      POLYUNSATURATED FATTY ACIDS IN OLEAGINOUS YEAST
<310> PATENT DOCUMENT NUMBER: US 2005-0216975-A1
<311> PATENT FILING DATE: 2004-11-10
<312> PUBLICATION DATE: 2005-09-29
<313> RELEVANT RESIDUES: (1)..(1434)
```

-continued

```
<400> SEQUENCE: 43 atg gcg tcc act tcg gct ctg ccc aag cag aac cct gcg ctt aga cgc      48
Met Ala Ser Thr Ser Ala Leu Pro Lys Gln Asn Pro Ala Leu Arg Arg
1               5                   10                  15 acc gtc acc tca act act gtg acg gat tct gag tct gcc gcc gtc tct      96
Thr Val Thr Ser Thr Thr Val Thr Asp Ser Glu Ser Ala Ala Val Ser
                20                  25                  30 cct tca gac tct ccc cgc cac tcg gcc tct tcc aca tcg ctc tcg tcc     144
Pro Ser Asp Ser Pro Arg His Ser Ala Ser Ser Thr Ser Leu Ser Ser
            35                  40                  45 atg tcc gag gtt gat atc gcc aag ccc aag tcc gag tat ggt gtc atg     192
Met Ser Glu Val Asp Ile Ala Lys Pro Lys Ser Glu Tyr Gly Val Met
    50                  55                  60 ctc gac acc tac ggc aac cag ttc gag gtt ccc gac ttt acc atc aag     240
Leu Asp Thr Tyr Gly Asn Gln Phe Glu Val Pro Asp Phe Thr Ile Lys
65                  70                  75                  80 gac atc tac aat gcc atc cct aag cac tgc ttc aag cgc tcc gct ctc     288
Asp Ile Tyr Asn Ala Ile Pro Lys His Cys Phe Lys Arg Ser Ala Leu
                85                  90                  95 aag gga tac ggt tat atc ctc cgc gac att gtc ctg ctg act acc act     336
Lys Gly Tyr Gly Tyr Ile Leu Arg Asp Ile Val Leu Leu Thr Thr Thr
            100                 105                 110 ttc agc atc tgg tac aac ttt gtg acc ccc gaa tat atc ccc tcc acc     384
Phe Ser Ile Trp Tyr Asn Phe Val Thr Pro Glu Tyr Ile Pro Ser Thr
    115                 120                 125 ccc gcc cgc gct ggt ctg tgg gcc gtg tac acc gtt ctt cag ggt ctt     432
Pro Ala Arg Ala Gly Leu Trp Ala Val Tyr Thr Val Leu Gln Gly Leu
130                 135                 140 ttc ggt act ggt ctc tgg gtt att gcc cat gag tgc ggt cac ggt gct     480
Phe Gly Thr Gly Leu Trp Val Ile Ala His Glu Cys Gly His Gly Ala
145                 150                 155                 160 ttc tcc gat tct cgc atc atc aac gac att act ggc tgg gtt ctt cac     528
Phe Ser Asp Ser Arg Ile Ile Asn Asp Ile Thr Gly Trp Val Leu His
                165                 170                 175 tct tcc ctc ctt gtc ccc tac ttc agc tgg caa atc tcc cac cga aag     576
Ser Ser Leu Leu Val Pro Tyr Phe Ser Trp Gln Ile Ser His Arg Lys
            180                 185                 190 cac cac aag gcc act ggc aac atg gag cgt gac atg gtc ttc gtt ccc     624
His His Lys Ala Thr Gly Asn Met Glu Arg Asp Met Val Phe Val Pro
    195                 200                 205 cga acc cgc gag cag cag gct act cgt ctc gga aag atg acc cac gag     672
Arg Thr Arg Glu Gln Gln Ala Thr Arg Leu Gly Lys Met Thr His Glu
210                 215                 220 ctc gct cat ctt act gag gag acc ccc gct ttc act ctt ctc atg ctc     720
Leu Ala His Leu Thr Glu Glu Thr Pro Ala Phe Thr Leu Leu Met Leu
225                 230                 235                 240 gtc ctt cag cag ctc gtt ggc tgg ccc aac tac ctc atc acc aat gtt     768
Val Leu Gln Gln Leu Val Gly Trp Pro Asn Tyr Leu Ile Thr Asn Val
                245                 250                 255 acc ggc cac aac tac cac gag cgc cag cgt gag ggt cgc ggc aag ggc     816
Thr Gly His Asn Tyr His Glu Arg Gln Arg Glu Gly Arg Gly Lys Gly
            260                 265                 270 aag cat aac ggc ctc ggc ggt gtt aac cac ttc gat ccc cgc agc     864
Lys His Asn Gly Leu Gly Gly Val Asn His Phe Asp Pro Arg Ser
    275                 280                 285 cct ctg tac gag aac agt gac gct aag ctc atc gtc ctc agc gat att     912
Pro Leu Tyr Glu Asn Ser Asp Ala Lys Leu Ile Val Leu Ser Asp Ile
290                 295                 300 ggt atc ggt ctg atg gcc act gct ctg tac ttc ctc gtt cag aag ttc     960
Gly Ile Gly Leu Met Ala Thr Ala Leu Tyr Phe Leu Val Gln Lys Phe
```

```
                    305                 310                 315                 320
ggt ttc tac aac atg gcc atc tgg tac ttt gtt ccc tac ctc tgg gtt      1008
Gly Phe Tyr Asn Met Ala Ile Trp Tyr Phe Val Pro Tyr Leu Trp Val
                325                 330                 335 aac cac tgg ctc gtt gcc atc acc ttc ctc cag cac acc gac cct acc      1056
Asn His Trp Leu Val Ala Ile Thr Phe Leu Gln His Thr Asp Pro Thr
            340                 345                 350 ctt ccc cac tac acc aac gac gag tgg aac ttc gtc cgt ggt gcc gct      1104
Leu Pro His Tyr Thr Asn Asp Glu Trp Asn Phe Val Arg Gly Ala Ala
        355                 360                 365 gct acc att gac cgt gag atg ggc ttc atc ggc cgc cac ctt ctc cac      1152
Ala Thr Ile Asp Arg Glu Met Gly Phe Ile Gly Arg His Leu Leu His
    370                 375                 380 ggc atc atc gag act cat gtc ctc cac cac tac gtc agc agc atc ccc      1200
Gly Ile Ile Glu Thr His Val Leu His His Tyr Val Ser Ser Ile Pro
385                 390                 395                 400 ttc tac aac gcg gac gag gcc acc gag gcc att aag ccc atc atg ggc      1248
Phe Tyr Asn Ala Asp Glu Ala Thr Glu Ala Ile Lys Pro Ile Met Gly
                405                 410                 415 aag cac tac cgg gct gat gtc cag gat ggt cct cgt ggc ttc atc cgc      1296
Lys His Tyr Arg Ala Asp Val Gln Asp Gly Pro Arg Gly Phe Ile Arg
            420                 425                 430 gcc atg tac cgc agt gcg cgt atg tgc cag tgg gtt gag ccc agc gct      1344
Ala Met Tyr Arg Ser Ala Arg Met Cys Gln Trp Val Glu Pro Ser Ala
        435                 440                 445 ggt gcc gag ggt gct ggt aag ggt gtt ctg ttc ttc cgc aac cgc aac      1392
Gly Ala Glu Gly Ala Gly Lys Gly Val Leu Phe Phe Arg Asn Arg Asn
    450                 455                 460 aac gtg ggc acc ccc ccc gct gtt atc aag ccc gtt gct taa              1434
Asn Val Gly Thr Pro Pro Ala Val Ile Lys Pro Val Ala
465                 470                 475

<210> SEQ ID NO 44
<211> LENGTH: 477
<212> TYPE: PRT
<213> ORGANISM: Fusarium monoliforme

<400> SEQUENCE: 44

Met Ala Ser Thr Ser Ala Leu Pro Lys Gln Asn Pro Ala Leu Arg Arg
1               5                   10                  15

Thr Val Thr Ser Thr Thr Val Thr Asp Ser Glu Ser Ala Ala Val Ser
                20                  25                  30

Pro Ser Asp Ser Pro Arg His

-continued

```
Phe Ser Asp Ser Arg Ile Ile Asn Asp Ile Thr Gly Trp Val Leu His
            165                 170                 175

Ser Ser Leu Leu Val Pro Tyr Phe Ser Trp Gln Ile Ser His Arg Lys
        180                 185                 190

His His Lys Ala Thr Gly Asn Met Glu Arg Asp Met Val Phe Val Pro
    195                 200                 205

Arg Thr Arg Glu Gln Gln Ala Thr Arg Leu Gly Lys Met Thr His Glu
210                 215                 220

Leu Ala His Leu Thr Glu Glu Thr Pro Ala Phe Thr Leu Leu Met Leu
225                 230                 235                 240

Val Leu Gln Gln Leu Val Gly Trp Pro Asn Tyr Leu Ile Thr Asn Val
                245                 250                 255

Thr Gly His Asn Tyr His Glu Arg Gln Arg Glu Gly Arg Gly Lys Gly
            260                 265                 270

Lys His Asn Gly Leu Gly Gly Val Asn His Phe Asp Pro Arg Ser
        275                 280                 285

Pro Leu Tyr Glu Asn Ser Asp Ala Lys Leu Ile Val Leu Ser Asp Ile
    290                 295                 300

Gly Ile Gly Leu Met Ala Thr Ala Leu Tyr Phe Leu Val Gln Lys Phe
305                 310                 315                 320

Gly Phe Tyr Asn Met Ala Ile Trp Tyr Phe Val Pro Tyr Leu Trp Val
                325                 330                 335

Asn His Trp Leu Val Ala Ile Thr Phe Leu Gln His Thr Asp Pro Thr
            340                 345                 350

Leu Pro His Tyr Thr Asn Asp Glu Trp Asn Phe Val Arg Gly Ala Ala
        355                 360                 365

Ala Thr Ile Asp Arg Glu Met Gly Phe Ile Gly Arg His Leu Leu His
    370                 375                 380

Gly Ile Ile Glu Thr His Val Leu His His Tyr Val Ser Ser Ile Pro
385                 390                 395                 400

Phe Tyr Asn Ala Asp Glu Ala Thr Glu Ala Ile Lys Pro Ile Met Gly
                405                 410                 415

Lys His Tyr Arg Ala Asp Val Gln Asp Gly Pro Arg Gly Phe Ile Arg
            420                 425                 430

Ala Met Tyr Arg Ser Ala Arg Met Cys Gln Trp Val Glu Pro Ser Ala
        435                 440                 445

Gly Ala Glu Gly Ala Gly Lys Gly Val Leu Phe Phe Arg Asn Arg Asn
    450                 455                 460

Asn Val Gly Thr Pro Pro Ala Val Ile Lys Pro Val Ala
465                 470                 475

<210> SEQ ID NO 45
<211> LENGTH: 777
<212> TYPE: DNA
<213> ORGANISM: Euglena gracilis
<220> FEATURE:
<221> NAME/KEY: CDS
<222> LOCATION: (1)..(777)
<223> OTHER INFORMATION: synthetic delta-9 elongase (codon-optimized for
      Yarrowia lipolytica)
<300> PUBLICATION INFORMATION:
<302> TITLE: DELTA-9 ELONGASES AND THEIR USE IN MAKING POLYUNSATURATED
      FATTY ACIDS
<310> PATENT DOCUMENT NUMBER: WO 2007/061742
<311> PATENT FILING DATE: 2006-11-16
<312> PUBLICATION DATE: 2007-05-31
<313> RELEVANT RESIDUES: (1)..(777)
<300> PUBLICATION INFORMATION:
<302> TITLE: DELTA-9 ELONGASES AND THEIR USE IN MAKING POLYUNSATURATED
      FATTY ACIDS
```

-continued

```
<310> PATENT DOCUMENT NUMBER: US-2007-0117190-A1
<311> PATENT FILING DATE: 2006-11-16
<312> PUBLICATION DATE: 2007-05-24
<313> RELEVANT RESIDUES: (1)..(777)

<400> SEQUENCE: 45 atg gag gtc gtg aac gaa atc gtc tcc att ggc cag gag gtt ctt ccc      48
Met Glu Val Val Asn Glu Ile Val Ser Ile Gly Gln Glu Val Leu Pro
1               5                   10                  15 aag gtc gac tat gct cag ctc tgg tct gat gcc tcg cac tgc gag gtg      96
Lys Val Asp Tyr Ala Gln Leu Trp Ser Asp Ala Ser His Cys Glu Val
            20                  25                  30 ctg tac ctc tcc atc gcc ttc gtc atc ctg aag ttc acc ctt ggt cct     144
Leu Tyr Leu Ser Ile Ala Phe Val Ile Leu Lys Phe Thr Leu Gly Pro
        35                  40                  45 ctc gga ccc aag ggt cag tct cga atg aag ttt gtg ttc acc aac tac     192
Leu Gly Pro Lys Gly Gln Ser Arg Met Lys Phe Val Phe Thr Asn Tyr
    50                  55                  60 aac ctg ctc atg tcc atc tac tcg ctg ggc tcc ttc ctc tct atg gcc     240
Asn Leu Leu Met Ser Ile Tyr Ser Leu Gly Ser Phe Leu Ser Met Ala
65                  70                  75                  80 tac gcc atg tac acc att ggt gtc atg tcc gac aac tgc gag aag gct     288
Tyr Ala Met Tyr Thr Ile Gly Val Met Ser Asp Asn Cys Glu Lys Ala
                85                  90                  95 ttc gac aac aat gtc ttc cga atc acc act cag ctg ttc tac ctc agc     336
Phe Asp Asn Asn Val Phe Arg Ile Thr Thr Gln Leu Phe Tyr Leu Ser
            100                 105                 110 aag ttc ctc gag tac att gac tcc ttc tat ctg ccc ctc atg ggc aag     384
Lys Phe Leu Glu Tyr Ile Asp Ser Phe Tyr Leu Pro Leu Met Gly Lys
        115                 120                 125 cct ctg acc tgg ttg cag ttc ttt cac cat ctc gga gct cct atg gac     432
Pro Leu Thr Trp Leu Gln Phe Phe His His Leu Gly Ala Pro Met Asp
    130                 135                 140 atg tgg ctg ttc tac aac tac cga aac gaa gcc gtt tgg atc ttt gtg     480
Met Trp Leu Phe Tyr Asn Tyr Arg Asn Glu Ala Val Trp Ile Phe Val
145                 150                 155                 160 ctg ctc aac ggc ttc att cac tgg atc atg tac ggc tac tat tgg acc     528
Leu Leu Asn Gly Phe Ile His Trp Ile Met Tyr Gly Tyr Tyr Trp Thr
                165                 170                 175 cga ctg atc aag ctc aag ttc cct atg ccc aag tcc ctg att act tct     576
Arg Leu Ile Lys Leu Lys Phe Pro Met Pro Lys Ser Leu Ile Thr Ser
            180                 185                 190 atg cag atc att cag ttc aac gtt ggc ttc tac atc gtc tgg aag tac     624
Met Gln Ile Ile Gln Phe Asn Val Gly Phe Tyr Ile Val Trp Lys Tyr
        195                 200                 205 cgg aac att ccc tgc tac cga caa gat gga atg aga atg ttt ggc tgg     672
Arg Asn Ile Pro Cys Tyr Arg Gln Asp Gly Met Arg Met Phe Gly Trp
    210                 215                 220 ttt ttc aac tac ttc tac gtt ggt act gtc ctg tgt ctg ttc ctc aac     720
Phe Phe Asn Tyr Phe Tyr Val Gly Thr Val Leu Cys Leu Phe Leu Asn
225                 230                 235                 240 ttc tac gtg cag acc tac atc gtc cga aag cac aag gga gcc aaa aag     768
Phe Tyr Val Gln Thr Tyr Ile Val Arg Lys His Lys Gly Ala Lys Lys
                245                 250                 255 att cag tga                                                         777
Ile Gln

<210> SEQ ID NO 46
<211> LENGTH: 258
<212> TYPE: PRT
<213> ORGANISM: Euglena gracilis
```

-continued

```
<400> SEQUENCE: 46

Met Glu Val Val Asn Glu Ile Val Ser Ile Gly Gln Glu Val Leu Pro
1               5                   10                  15

Lys Val Asp Tyr Ala Gln Leu Trp Ser Asp Ala Ser His Cys Glu Val
            20                  25                  30

Leu Tyr Leu Ser Ile Ala Phe Val Ile Leu Lys Phe Thr Leu Gly Pro
        35                  40                  45

Leu Gly Pro Lys Gly Gln Ser Arg Met Lys Phe Val Phe Thr Asn Tyr
    50                  55                  60

Asn Leu Leu Met Ser Ile Tyr Ser Leu Gly Ser Phe Leu Ser Met Ala
65                  70                  75                  80

Tyr Ala Met Tyr Thr Ile Gly Val Met Ser Asp Asn Cys Glu Lys Ala
                85                  90                  95

Phe Asp Asn Asn Val Phe Arg Ile Thr Thr Gln Leu Phe Tyr Leu Ser
            100                 105                 110

Lys Phe Leu Glu Tyr Ile Asp Ser Phe Tyr Leu Pro Leu Met Gly Lys
        115                 120                 125

Pro Leu Thr Trp Leu Gln Phe Phe His His Leu Gly Ala Pro Met Asp
    130                 135                 140

Met Trp Leu Phe Tyr Asn Tyr Arg Asn Glu Ala Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Ile Lys Leu Lys Phe Pro Met Pro Lys Ser Leu Ile Thr Ser
            180                 185                 190

Met Gln Ile Ile Gln Phe Asn Val Gly Phe Tyr Ile Val Trp Lys Tyr
        195                 200                 205

Arg Asn Ile Pro Cys Tyr Arg Gln Asp Gly Met Arg Met Phe Gly Trp
    210                 215                 220

Phe Phe Asn Tyr Phe Tyr Val Gly Thr Val Leu Cys Leu Phe Leu Asn
225                 230                 235                 240

Phe Tyr Val Gln Thr Tyr Ile Val Arg Lys His Lys Gly Ala Lys Lys
                245                 250                 255

Ile Gln

<210> SEQ ID NO 47
<211> LENGTH: 828
<212> TYPE: DNA
<213> ORGANISM: Mortierella alpina
<220> FEATURE:
<221> NAME/KEY: CDS
<222> LOCATION: (1)..(828)
<223> OTHER INFORMATION: synthetic C16/18 elongase (codon-optimized for
      Yarrowia lipolytica)
<300> PUBLICATION INFORMATION:
<302> TITLE: A MORTIERELLA ALPINA C16/18 FATTY ACID ELONGASE
<310> PATENT DOCUMENT NUMBER: US 2007-0087420-A1
<311> PATENT FILING DATE: 2005-10-19
<312> PUBLICATION DATE: 2007-04-19
<313> RELEVANT RESIDUES: (1)..(828)
<300> PUBLICATION INFORMATION:
<302> TITLE: A MORTIERELLA ALPINA C16/18 FATTY ACID ELONGASE
<310> PATENT DOCUMENT NUMBER: WO 2007/046817
<311> PATENT FILING DATE: 2005-11-04
<312> PUBLICATION DATE: 2007-04-26
<313> RELEVANT RESIDUES: (1)..(828)

<400> SEQUENCE: 47 atg gag tct gga ccc atg cct gct ggc att ccc ttc cct gag tac tat      48
Met Glu Ser Gly Pro Met Pro Ala Gly Ile Pro Phe Pro Glu Tyr Tyr
1               5                   10                  15
```

| | | |
|---|---|---|
| gac ttc ttt atg gac tgg aag act ccc ctg gcc atc gct gcc acc tac<br>Asp Phe Phe Met Asp Trp Lys Thr Pro Leu Ala Ile Ala Ala Thr Tyr<br>20 25 30 | | 96 |
| act gct gcc gtc ggt ctc ttc aac ccc aag gtt ggc aag gtc tcc cga<br>Thr Ala Ala Val Gly Leu Phe Asn Pro Lys Val Gly Lys Val Ser Arg<br>35 40 45 | | 144 |
| gtg gtt gcc aag tcg gct aac gca aag cct gcc gag cga acc cag tcc<br>Val Val Ala Lys Ser Ala Asn Ala Lys Pro Ala Glu Arg Thr Gln Ser<br>50 55 60 | | 192 |
| gga gct gcc atg act gcc ttc gtc ttt gtg cac aac ctc att ctg tgt<br>Gly Ala Ala Met Thr Ala Phe Val Phe Val His Asn Leu Ile Leu Cys<br>65 70 75 80 | | 240 |
| gtc tac tct ggc atc acc ttc tac tac atg ttt cct gct atg gtc aag<br>Val Tyr Ser Gly Ile Thr Phe Tyr Tyr Met Phe Pro Ala Met Val Lys<br>85 90 95 | | 288 |
| aac ttc cga acc cac aca ctg cac gaa gcc tac tgc gac acg gat cag<br>Asn Phe Arg Thr His Thr Leu His Glu Ala Tyr Cys Asp Thr Asp Gln<br>100 105 110 | | 336 |
| tcc ctc tgg aac aac gca ctt ggc tac tgg ggt tac ctc ttc tac ctg<br>Ser Leu Trp Asn Asn Ala Leu Gly Tyr Trp Gly Tyr Leu Phe Tyr Leu<br>115 120 125 | | 384 |
| tcc aag ttc tac gag gtc att gac acc atc atc atc ctg aag gga<br>Ser Lys Phe Tyr Glu Val Ile Asp Thr Ile Ile Ile Leu Lys Gly<br>130 135 140 | | 432 |
| cga cgg tcc tcg ctg ctt cag acc tac cac cat gct gga gcc atg att<br>Arg Arg Ser Ser Leu Leu Gln Thr Tyr His His Ala Gly Ala Met Ile<br>145 150 155 160 | | 480 |
| acc atg tgg tct ggc atc aac tac caa gcc act ccc att tgg atc ttt<br>Thr Met Trp Ser Gly Ile Asn Tyr Gln Ala Thr Pro Ile Trp Ile Phe<br>165 170 175 | | 528 |
| gtg gtc ttc aac tcc ttc att cac acc atc atg tac tgt tac tat gcc<br>Val Val Phe Asn Ser Phe Ile His Thr Ile Met Tyr Cys Tyr Tyr Ala<br>180 185 190 | | 576 |
| ttc acc tct atc gga ttc cat cct cct ggc aaa aag tac ctg act tcg<br>Phe Thr Ser Ile Gly Phe His Pro Pro Gly Lys Lys Tyr Leu Thr Ser<br>195 200 205 | | 624 |
| atg cag att act cag ttt ctg gtc ggt atc acc att gcc gtg tcc tac<br>Met Gln Ile Thr Gln Phe Leu Val Gly Ile Thr Ile Ala Val Ser Tyr<br>210 215 220 | | 672 |
| ctc ttc gtt cct ggc tgc atc cga aca ccc ggt gct cag atg gct gtc<br>Leu Phe Val Pro Gly Cys Ile Arg Thr Pro Gly Ala Gln Met Ala Val<br>225 230 235 240 | | 720 |
| tgg atc aac gtc ggc tac ctg ttt ccc ttg acc tat ctg ttc gtg gac<br>Trp Ile Asn Val Gly Tyr Leu Phe Pro Leu Thr Tyr Leu Phe Val Asp<br>245 250 255 | | 768 |
| ttt gcc aag cga acc tac tcc aag cga tct gcc att gcc gct cag aaa<br>Phe Ala Lys Arg Thr Tyr Ser Lys Arg Ser Ala Ile Ala Ala Gln Lys<br>260 265 270 | | 816 |
| aag gct cag taa<br>Lys Ala Gln<br>275 | | 828 |

<210> SEQ ID NO 48
<211> LENGTH: 275
<212> TYPE: PRT
<213> ORGANISM: Mortierella alpina

<400> SEQUENCE: 48

Met Glu Ser Gly Pro Met Pro Ala Gly Ile Pro Phe Pro Glu Tyr Tyr
1               5                   10                  15

Asp Phe Phe Met Asp Trp Lys Thr Pro Leu Ala Ile Ala Ala Thr Tyr
            20                  25                  30

Thr Ala Ala Val Gly Leu Phe Asn Pro Lys Val Gly Lys Val Ser Arg
        35                  40                  45

Val Val Ala Lys Ser Ala Asn Ala Lys Pro Ala Glu Arg Thr Gln Ser
 50                  55                  60

Gly Ala Ala Met Thr Ala Phe Val Phe Val His Asn Leu Ile Leu Cys
 65                  70                  75                  80

Val Tyr Ser Gly Ile Thr Phe Tyr Tyr Met Phe Pro Ala Met Val Lys
                85                  90                  95

Asn Phe Arg Thr His Thr Leu His Glu Ala Tyr Cys Asp Thr Asp Gln
            100                 105                 110

Ser Leu Trp Asn Asn Ala Leu Gly Tyr Trp Gly Tyr Leu Phe Tyr Leu
        115                 120                 125

Ser Lys Phe Tyr Glu Val Ile Asp Thr Ile Ile Ile Leu Lys Gly
    130                 135                 140

Arg Arg Ser Ser Leu Leu Gln Thr Tyr His His Ala Gly Ala Met Ile
145                 150                 155                 160

Thr Met Trp Ser Gly Ile Asn Tyr Gln Ala Thr Pro Ile Trp Ile Phe
                165                 170                 175

Val Val Phe Asn Ser Phe Ile His Thr Ile Met Tyr Cys Tyr Tyr Ala
            180                 185                 190

Phe Thr Ser Ile Gly Phe His Pro Pro Gly Lys Lys Tyr Leu Thr Ser
        195                 200                 205

Met Gln Ile Thr Gln Phe Leu Val Gly Ile Thr Ile Ala Val Ser Tyr
    210                 215                 220

Leu Phe Val Pro Gly Cys Ile Arg Thr Pro Gly Ala Gln Met Ala Val
225                 230                 235                 240

Trp Ile Asn Val Gly Tyr Leu Phe Pro Leu Thr Tyr Leu Phe Val Asp
                245                 250                 255

Phe Ala Lys Arg Thr Tyr Ser Lys Arg Ser Ala Ile Ala Ala Gln Lys
            260                 265                 270

Lys Ala Gln
        275

<210> SEQ ID NO 49
<211> LENGTH: 34
<212> TYPE: DNA
<213> ORGANISM: Escherichia coli

<400> SEQUENCE: 49
ataacttcgt ataatgtatg ctatacgaag ttat                            34

<210> SEQ ID NO 50
<211> LENGTH: 8739
<212> TYPE: DNA
<213> ORGANISM: Artificial Sequence
<220> FEATURE:
<223> OTHER INFORMATION: Plasmid pY116

<400> SEQUENCE: 50
ggccgccacc gcggcccgag attccggcct cttcggccgc caagcgaccc gggtggacgt     60
ctagaggtac ctagcaatta acagatagtt tgccggtgat aattctctta acctcccaca    120
ctcctttgac ataacgattt atgtaacgaa actgaaattt gaccagatat tgtgtccgcg    180
gtggagctcc agcttttgtt cccttttagt agggtttaaa cgagcttggc gtaatcatgg    240
tcatagctgt ttcctgtgtg aaattgttat ccgctcacaa ttccacacaa cgtacgagcc    300

```
ggaagcataa agtgtaaagc ctggggtgcc taatgagtga gctaactcac attaattgcg    360
ttgcgctcac tgcccgcttt ccagtcggga acctgtcgt gccagctgca ttaatgaatc    420
ggccaacgcg cggggagagg cggtttgcgt attgggcgct cttccgcttc ctcgctcact    480
gactcgctgc gctcggtcgt tcggctgcgg cgagcggtat cagctcactc aaaggcggta    540
atacggttat ccacagaatc aggggataac gcaggaaaga acatgtgagc aaaaggccag    600
caaaaggcca ggaaccgtaa aaaggccgcg ttgctggcgt ttttccatag gctccgcccc    660
cctgacgagc atcacaaaaa tcgacgctca agtcagaggt ggcgaaaccc gacaggacta    720
taaagatacc aggcgtttcc ccctggaagc tccctcgtgc gctctcctgt tccgaccctg    780
ccgcttaccg gatacctgtc cgcctttctc ccttcgggaa gcgtggcgct ttctcatagc    840
tcacgctgta ggtatctcag ttcggtgtag gtcgttcgct ccaagctggg ctgtgtgcac    900
gaaccccccg ttcagcccga ccgctgcgcc ttatccggta actatcgtct gagtccaac    960 ccggtaagac acgacttatc gccactggca gcagccactg gtaacaggat tagcagagcg   1020
aggtatgtag gcggtgctac agagttcttg aagtggtggc ctaactacgg ctacactaga   1080
aggacagtat ttggtatctg cgctctgctg aagccagtta ccttcggaaa aagagttggt   1140
agctcttgat ccggcaaaca aaccaccgct ggtagcggtg gttttttttgt ttgcaagcag   1200 cagattacgc gcagaaaaaa aggatctcaa gaagatcctt tgatctttc tacggggtct   1260 gacgctcagt ggaacgaaaa ctcacgttaa gggattttgg tcatgagatt atcaaaaagg   1320
atcttcacct agatcctttt aaattaaaaa tgaagtttta aatcaatcta agtatatat   1380 gagtaaactt ggtctgacag ttaccaatgc ttaatcagtg aggcacctat ctcagcgatc   1440
tgtctatttc gttcatccat agttgcctga ctccccgtcg tgtagataac tacgatacgg   1500
gagggcttac catctggccc cagtgctgca atgataccgc gagacccacg ctcaccggct   1560
ccagatttat cagcaataaa ccagccagcc ggaagggccg agcgcagaag tggtcctgca   1620
actttatccg cctccatcca gtctattaat tgttgccggg aagctagagt aagtagttcg   1680
ccagttaata gtttgcgcaa cgttgttgcc attgctacag gcatcgtggt gtcacgctcg   1740
tcgtttggta tggcttcatt cagctccggt tcccaacgat caaggcgagt tacatgatcc   1800
cccatgttgt gcaaaaaagc ggttagctcc ttcggtcctc cgatcgttgt cagaagtaag   1860
ttggccgcag tgttatcact catggttatg gcagcactgc ataattctct tactgtcatg   1920
ccatccgtaa gatgcttttc tgtgactggt gagtactcaa ccaagtcatt ctgagaatag   1980
tgtatgcggc gaccgagttg ctcttgcccg gcgtcaatac gggataatac cgcgccacat   2040
agcagaactt taaaagtgct catcattgga aaacgttctt cggggcgaaa actctcaagg   2100
atcttaccgc tgttgagatc cagttcgatg taacccactc gtgcacccaa ctgatcttca   2160
gcatctttta ctttcaccag cgtttctggg tgagcaaaaa caggaaggca aaatgccgca   2220
aaaaagggaa taagggcgac acggaaatgt tgaatactca tactcttcct ttttcaatat   2280
tattgaagca tttatcaggg ttattgtctc atgagcggat acatatttga atgtatttag   2340
aaaaataaac aaataggggt tccgcgcaca tttccccgaa aagtgccacc tgacgcgccc   2400
tgtagcggcg cattaagcgc ggcgggtgtg gtggttacgc gcagcgtgac cgctacactt   2460
gccagcgccc tagcgcccgc tcctttcgct ttcttccctt cctttctcgc cacgttcgcc   2520
ggctttcccc gtcaagctct aaatcggggg ctccctttag ggttccgatt tagtgcttta   2580
cggcacctcg accccaaaaa acttgattag ggtgatggtt cacgtagtgg gccatcgccc   2640
tgatagacgg ttttttcgccc tttgacgttg gagtccacgt tctttaatag tggactcttg   2700
```

```
ttccaaactg gaacaacact caaccctatc tcggtctatt cttttgattt ataagggatt    2760
ttgccgattt cggcctattg gttaaaaaat gagctgattt aacaaaaatt taacgcgaat    2820
tttaacaaaa tattaacgct tacaatttcc attcgccatt caggctgcgc aactgttggg    2880
aagggcgatc ggtgcgggcc tcttcgctat tacgccagct ggcgaaaggg ggatgtgctg    2940
caaggcgatt aagttgggta acgccagggt tttcccagtc acgacgttgt aaaacgacgg    3000
ccagtgaatt gtaatacgac tcactatagg gcgaattggg taccgggccc ccctcgagg    3060 tcgatggtgt cgataagctt gatatcgaat tcatgtcaca caaaccgatc ttcgcctcaa    3120
ggaaacctaa ttctacatcc gagagactgc cgagatccag tctacactga ttaattttcg    3180
ggccaataat ttaaaaaaat cgtgttatat aatattatat gtattatata tatacatcat    3240
gatgatactg acagtcatgt cccattgcta aatagacaga ctccatctgc cgcctccaac    3300
tgatgttctc aatatttaag gggtcatctc gcattgttta ataataaaca gactccatct    3360
accgcctcca aatgatgttc tcaaaatata ttgtatgaac ttatttttat tacttagtat    3420
tattagacaa cttacttgct ttatgaaaaa cacttcctat ttaggaaaca atttataatg    3480
gcagttcgtt catttaacaa tttatgtaga ataaatgtta taaatgcgta tgggaaatct    3540
taaatatgga tagcataaat gatatctgca ttgcctaatt cgaaatcaac agcaacgaaa    3600 aaaatcccett gtacaacata aatagtcatc gagaaatatc aactatcaaa gaacagctat    3660
tcacacgtta ctattgagat tattattgga cgagaatcac acactcaact gtctttctct    3720
cttctagaaa tacaggtaca agtatgtact attctcattg ttcatacttc tagtcatttc    3780
atcccacata ttccttggat ttctctccaa tgaatgacat tctatcttgc aaattcaaca    3840
attataataa gatataccaa agtagcggta tagtggcaat caaaaagctt ctctggtgtg    3900
cttctcgtat ttattttat tctaatgatc cattaaaggt atatatttat ttcttgttat    3960
ataatccttt tgtttattac atgggctgga tacataaagg tattttgatt taattttttg    4020
cttaaattca atcccccctc gttcagtgtc aactgtaatg gtaggaaatt accatacttt    4080
tgaagaagca aaaaaaatga aagaaaaaaa aaatcgtatt tccaggttag acgttccgca    4140
gaatctagaa tgcggtatgc ggtacattgt tcttcgaacg taaaagttgc gctccctgag    4200
atattgtaca ttttttgcttt tacaagtaca agtacatcgt acaactatgt actactgttg    4260
atgcatccac aacagtttgt tttgtttttt tttgttttt tttttctaa tgattcatta    4320 ccgctatgta tacctacttg tacttgtagt aagcccgggtt attggcgttc aattaatcat    4380
agacttatga atctgcacgg tgtgcgctgc gagttacttt tagcttatgc atgctacttg    4440
ggtgtaatat tgggatctgt tcggaaatca acggatgctc aaccgatttc gacagtaatt    4500
aattaatttg aatcgaatcg gagcctaaaa tgaacccgag tatatctcat aaaattctcg    4560
gtgagaggtc tgtgactgtc agtacaaggt gccttcatta tgccctcaac cttaccatac    4620
ctcactgaat gtagtgtacc tctaaaaatg aaatacagtg ccaaaagcca aggcactgag    4680
ctcgtctaac ggacttgata taaccaat taaacaaat gaaaagaaat acagttcttt    4740
gtatcatttg taacaattac cctgtacaaa ctaaggtatt gaaatcccac aatattccca    4800
aagtccaccc cttttccaaat tgtcatgcct acaactcata taccaagcac taacctacca    4860
aacaccacta aaacccccaca aaatatatct taccgaatat acagtaacaa gctaccacca    4920
cactcgttgg gtgcagtcgc cagcttaaag atatctatcc acatcagcca caactccctt    4980
cctttaataa accgactaca ccccttggcta ttgaggttat gagtgaatat actgtagaca    5040
agacactttc aagaagactg tttccaaaac gtaccactgt cctccactac aaacacaccc    5100
```

```
aatctgcttc ttctagtcaa ggttgctaca ccggtaaatt ataaatcatc atttcattag   5160
cagggcaggg ccctttttat agagtcttat acactagcgg accctgccgg tagaccaacc   5220
cgcaggcgcg tcagtttgct ccttccatca atgcgtcgta gaaacgactt actccttctt   5280
gagcagctcc ttgaccttgt tggcaacaag tctccgacct cggaggtgga ggaagagcct   5340
ccgatatcgg cggtagtgat accagcctcg acggactcct tgacggcagc ctcaacagcg   5400
tcaccggcgg gcttcatgtt aagagagaac ttgagcatca tggcggcaga cagaatggtg   5460
gcaatggggt tgaccttctg cttgccgaga tcggggcag atccgtgaca gggctcgtac    5520
agaccgaacg cctcgttggt gtcgggcaga gaagccagag aggcggaggg cagcagaccc   5580
agagaaccgg ggatgacgga ggcctcgtcg gagatgatat cgccaaacat gttggtggtg   5640
atgatgatac cattcatctt ggagggctgc ttgatgagga tcatggcggc cgagtcgatc   5700
agctggtggt tgagctcgag ctgggggaat tcgtccttga ggactcgagt gacagtcttt   5760
cgccaaagtc gagaggaggc cagcacgttg gccttgtcaa gagaccacac gggaagaggg   5820
gggttgtgct gaagggccag gaaggcggcc attcgggcaa ttcgctcaac ctcaggaacg   5880
gagtaggtct cggtgtcgga agcgacgcca gatccgtcat cctcctttcg ctctccaaag   5940
tagatacctc cgacgagctc tcggacaatg atgaagtcgg tgccctcaac gtttcggatg   6000
ggggagagat cggcgagctt gggcgacagc agctggcagg gtcgcaggtt ggcgtacagg   6060
ttcaggtcct ttcgcagctt gaggagaccc tgctcgggtc gcacgtcggt tcgtccgtcg   6120
ggagtggtcc atacggtgtt ggcagcgcct ccgacagcac cgagcataat agagtcagcc   6180
tttcggcaga tgtcgagagt agcgtcggtg atgggctcgc cctccttctc aatggcagct   6240
cctccaatga gtcggtcctc aaacacaaac tcggtgccgg aggcctcagc aacagacttg   6300
agcaccttga cggcctcggc aatcacctcg gggccacaga agtcgccgcc gagaagaaca   6360
atcttcttgg agtcagtctt ggtcttctta gtttcgggtt ccattgtgga tgtgtgtggt   6420
tgtatgtgtg atgtggtgtg tggagtgaaa atctgtggct ggcaaacgct cttgtatata   6480
tacgcacttt tgcccgtgct atgtggaaga ctaaacctcc gaagattgtg actcaggtag   6540
tgcggtatcg gctagggacc caaaccttgt cgatgccgat agcgctatcg aacgtacccc   6600
agccggccgg gagtatgtcg gaggggacat acgagatcgt caagggtttg tggccaactg   6660
gtatttaaat gtagctaacg gtagcaggcg aactactggt acataccteee cccggaatat   6720 gtacaggcat aatgcgtatc tgtgggacat gtggtcgttg cgccattatg taagcagcgt   6780
gtactcctct gactgtccat atggtttgct ccatctcacc ctcatcgttt tcattgttca   6840
caggcggcca caaaaaaact gtcttctctc cttctctctt cgccttagtc tactcggacc   6900
agttttagtt tagcttggcg ccactggata aatgagacct caggccttgt gatgaggagg   6960
tcacttatga agcatgttag gaggtgcttg tatggataga gaagcaccca aaataataag   7020
aataataata aaacagggg cgttgtcatt tcatatcgtg ttttcaccat caatacacct    7080
ccaaacaatg cccttcatgt ggccagcccc aatattgtcc tgtagttcaa ctctatgcag   7140
ctcgtatctt attgagcaag taaaactctg tcagccgata ttgcccgacc cgcgacaagg   7200
gtcaacaagg tggtgtaagg ccttcgcaga agtcaaaact gtgccaaaca aacatctaga   7260
gtctctttgg tgtttctcgc atatatttwa tcggctgtct tacgtatttg cgcctcgta    7320 ccggactaat ttcggatcat ccccaatacg cttttttcttc gcagctgtca acagtgtcca   7380
tgatctatcc acctaaatgg gtcatatgag gcgtataatt tcgtggtgct gataataatt   7440
cccatatatt tgacacaaaa cttccccccc tagacataca tctcacaatc tcacttcttg   7500
```

```
tgcttctgtc acacatctcc tccagctgac ttcaactcac acctctgccc cagttggtct    7560
acagcggtat aaggtttctc cgcatagagg tgcaccactc ctcccgatac ttgtttgtgt    7620
gacttgtggg tcacgacata tatatctaca cacattgcgc caccctttgg ttcttccagc    7680
acaacaaaaa cacgacacgc taaccatggc caatttactg accgtacacc aaaatttgcc    7740
tgcattaccg gtcgatgcaa cgagtgatga ggttcgcaag aacctgatgg acatgttcag    7800
ggatcgccag gcgttttctg agcatacctg gaaaatgctt ctgtccgttt gccggtcgtg    7860
ggcggcatgg tgcaagttga ataaccggaa atggtttccc gcagaacctg aagatgttcg    7920
cgattatctt ctatatcttc aggcgcgcgg tctggcagta aaaactatcc agcaacattt    7980
gggccagcta acatgcttc atcgtcggtc cgggctgcca cgaccaagtg acagcaatgc      8040
tgtttcactg gttatgcggc ggatccgaaa agaaaacgtt gatgccggtg aacgtgcaaa    8100
acaggctcta gcgttcgaac gcactgattt cgaccaggtt cgttcactca tggaaaatag    8160
cgatcgctgc caggatatac gtaatctggc atttctgggg attgcttata cacccctgtt    8220
acgtatagcc gaaattgcca ggatcagggt taaagatatc tcacgtactg acggtgggag    8280
aatgttaatc catattggca gaacgaaaac gctggttagc accgcaggtg tagagaaggc    8340
acttagcctg ggggtaacta aactggtcga gcgatggatt tccgtctctg gtgtagctga    8400
tgatccgaat aactacctgt tttgccgggt cagaaaaaat ggtgttgccg cgccatctgc    8460
caccagccag ctatcaactc gcgccctgga agggatttt gaagcaactc atcgattgat     8520
ttacggcgct aaggatgact ctggtcagag atacctggcc tggtctggac acagtgcccg    8580
tgtcggagcc gcgcgagata tggcccgcgc tggagtttca ataccggaga tcatgcaagc    8640
tggtggctgg accaatgtaa atattgtcat gaactatatc cgtaacctgg atagtgaaac    8700
aggggcaatg gtgcgcctgc tggaagatgg cgattaagc                           8739
```

<210> SEQ ID NO 51
<211> LENGTH: 15337
<212> TYPE: DNA
<213> ORGANISM: Artificial Sequence
<220> FEATURE:
<223> OTHER INFORMATION: Plasmid pKO2UF8289

<400> SEQUENCE: 51

```
cgatcgagga agaggacaag cggctgcttc ttaagtttgt gacatcagta tccaaggcac      60
cattgcaagg attcaaggct ttgaacccgt catttgccat tcgtaacgct ggtagacagg     120
ttgatcggtt ccctacggcc tccacctgtg tcaatcttct caagctgcct gactatcagg     180
acattgatca acttcggaag aaacttttgt atgccattcg atcacatgct ggtttcgatt     240
tgtcttagag gaacgcatat acagtaatca tagagaataa acgatattca tttattaaag     300
tagatagttg aggtagaagt tgtaaagagt gataaatagc ggccgctcac tgaatctttt     360 tggctcccctt gtgcttcctg acgatatacg tttgcacata gaaattcaag aacaaacaca    420
agactgtgcc aacataaaag taattgaaga accagccaaa catcctcatc ccatcttggc     480
gataacaggg aatgttcctg tacttccaga caatgtagaa accaacattg aattgaatga     540
tctgcattga tgtaatcagg gattttggca tggggaactt cagcttgatc aatctggtcc     600
aataataacc gtacatgatc cagtggatga accattcaa cagcacaaaa atccaaacag      660
cttcatttcg gtaattatag aacagccaca tatccatcgg tgcccccaaa tgatggaaga    720
attgcaacca ggtcagaggc ttgcccatca gtggcaaata gaaggagtca atatactcca    780
ggaacttgct caaatagaac aactgcgtgg tgatcctgaa gacgttgttg tcaaaagcct    840
```

```
tctcgcagtt gtcagacata acaccgatgg tgtacatggc atatgccatt gagaggaatg    900
atcccaacga ataaatggac atgagaaggt tgtaattggt gaaaacaaac ttcatacgag    960
actgaccttt tggaccaagg gggccaagag tgaacttcaa gatgacaaat gcgatggaca   1020
agtaaagcac ctcacagtga ctggcatcac tccagagttg gcataatcaa actggtttgg   1080
taaaacttcc tgcccaattg agactatttc attcaccacc tccatggtta gcgtgtcgtg   1140
tttttgttgt gctggaagaa ccaaagggtg gcgcaatgtg tgtagatata tatgtcgtga   1200
cccacaagtc acacaaacaa gtatcgggag gagtggtgca cctctatgcg gagaaacctt   1260
ataccgctgt agaccaactg gggcagaggt gtgagttgaa gtcagctgga ggagatgtgt   1320
gacagaagca caagaagtga gattgtgaga tgtatgtcta ggggggggaag ttttgtgtca   1380 aatatatggg aattattatc agcaccacga aattatacgc ctcatatgac ccatttaggt   1440
ggatagatca tggacactgt tgacagctgc gaagaaaaag cgtattgggg atgatccgaa   1500
attagtccgg taccgaggcg caaatacgta agacagccga twaaatatat gcgagaaaca   1560
ccaaagagac tctagatgtt tgtttggcac agttttgact tctgcgaagg ccttacacca   1620
ccttgttgac ccttgtcgcg ggtcgggcaa tatcggctga cagagttttta cttgctcaat   1680 aagatacgag ctgcatagag ttgaactaca ggacaatatt ggggctggcc acatgaaggg   1740
cattgtttgg aggtgtattg atggtgaaaa cacgatatga aatgacaacg cccctgttt    1800 tattattatt cttattattt tgggtgcttc tctatccata caagcacctc ctaacatgct   1860
tcataagtga cctcctcatc acaaggcctg aggtctcatt tatccagtgg cgccaagcta   1920
aactaaaact ggtccgagta gactaaggcg aagagagaag gagagaagac agttttttg    1980 tggccgcctg tgaacaatga aaacgatgag ggtgagatgg agcaaaccat atggtttaaa   2040
cagtcagagg agtacacgct gcttacataa tggcgcaacg accacatgtc ccacagatac   2100
gcatcgattc gattcaaatt aattaaaagg cgttgaaaca gaatgagcca gacagcaagg   2160
acaaggtggc caacagcaag gagtccaaaa agccctctat tgacgagatc cacgatgtta   2220
ttgctcatga ggtttccgag ctcgatgctg ggaagaagaa gtgatttgta tataagaaat   2280
aaatgagata tagtaaagga gtgcaagaga atggcaaggt ggtcaaattc tatattactt   2340
gcagtcactg gttcctcgtt gacatgaatg aagttaccgt tggcatagct gatttaatat   2400
ataactgtcc aactaactct cacctagata taacccatgt gtgtgtttcc aatcatcaat   2460
gcggccgctt actgagcctt ggcaccgggc tgcttctcgg ccattcgagc gaactgggac   2520
aggtatcgga gcaggatgac gagaccttca tggggcagag ggtttcggta ggggaggttg   2580
tgcttctggc acagctgttc cacctggtag gaaacggcag tgaggttgtg tcgaggcagg   2640
gtgggccaga tggtgctcc gatctggtag ttcaggcctc caaagaacca gtcagtaatg   2700
atgcctcgtc gaatgttcat ggtctcatgg atctgaccca cagagaagcc atgtccgtcc   2760
cagacggaat caccgatctt ctccagaggg tagtggttca tgaagaccac gatggcaatt   2820
ccgaagccac cgacgagctc ggaaacaaag aacaccagca tcgaggtcag gatggagggc   2880
ataaagaaga ggtggaacag ggtcttgaga gtccagtgca gagcgagtcc aatggcctct   2940
ttcttgtact gagatcggta gaactggttg tctcggtcct tgagggatcg aacggtcagc   3000
acagactgga aacaccagat gaatcgcagg agaaatacaga tgaccaggaa atagtactgt   3060
tggaactgaa tgagctttcg ggagatggga gaagctcgag tgacatcgtc ctcggaccag   3120
gcgagcagag gcaggttatc aatgtcggga tcgtgaccct gaacgttggt agcagaatga   3180
tgggcgttgt gtctgtcctt ccaccaggtc acggagaagc cctggagtcc gttgccaaag   3240
```

```
accagaccca ggacgttatt ccagtttcgg ttcttgaagg tctggtggtg gcagatgtca   3300
tgagacagcc atcccatttg ctggtagtgc ataccgagca cgagagcacc aatgaagtac   3360
aggtggtact ggaccagcat gaagaaggca agcacgccaa gacccagggt ggtcaagatc   3420
ttgtacgagt accagagggg agaggcgtca acatgccag tggcgatcag ctcttctcgg    3480
agctttcgga aatcctcctg agcttcgttg acggcagcct ggggaggcag ctcggaagcc   3540
tggttgatct tgggcattcg cttgagcttg tcgaaggctt cctgagagtg cataaccatg   3600
aaggcgtcag tagcatctcg tccctggtag ttctcaatga tttcagctcc accagggtgg   3660
aagttcaccc aagcggagac gtcgtacacc tttccgtcga tgacgagggg cagagcctgt   3720
cgagaagcct tcaccatggc cattgctgta gatatgtctt gtgtgtaagg gggttggggt   3780
ggttgtttgt gttcttgact tttgtgttag caagggaaga cggcaaaaa agtgagtgtg    3840 gttgggaggg agagacgagc cttatatata atgcttgttt gtgtttgtgc aagtggacgc   3900
cgaaacgggc aggagccaaa ctaaacaagg cagacaatgc gagcttaatt ggattgcctg   3960
atgggcaggg gttagggctc gatcaatggg ggtgcgaagt gacaaaattg ggaattaggt   4020
tcgcaagcaa ggctgacaag actttggccc aaacatttgt acgcggtgga caacaggagc   4080
cacccatcgt ctgtcacggg ctagccggtc gtgcgtcctg tcaggctcca cctaggctcc   4140
atgccactcc atacaatccc actagtgtac cgctaggccg cttttagctc ccatctaaga   4200
cccccccaaa acctccactg tacagtgcac tgtactgtgt ggcgatcaag gcaagggaa    4260 aaaaggcgca acatgcacg catggaatga cgtaggtaag gcgttactag actgaaaagt    4320
ggcacatttc ggcgtgccaa agggtcctag gtgcgtttcg cgagctgggc gccaggccaa   4380
gccgctccaa aacgcctctc cgactcccct cagcggcctc catatcccca tccctctcca   4440
cagcaatgtt gttaagcctt gcaaacgaaa aaatagaaag gctaataagc ttccaatatt   4500
gtggtgtacg ctgcataacg caacaatgag cgccaaacaa cacacacaca cagcacacag   4560
cagcattaac cacgatgttt aaacagtgta cgcagatccc gtcaacagtt ttatatatcg   4620
tagttacaac catcaacact ttttggtaag tgtaccattc tatactccaa ctggtctgca   4680
actgtacaag tagacatgtt aatggtagtt aataacatct acagcagaac ctatggtaaa   4740
gacattgcat ttttacagga agtatcgtcc tacacgttga taaatccaaa gatgcggaac   4800
ttcttccact tttatcatca tcccctactc gtacactcgt actctttgtt cgatcgcgat   4860
tcatttctat aaataatctt gtatgtacat gcggccgctt aagcaacggg cttgataaca   4920
gcgggggggg tgcccacgtt gttgcggttg cggaagaaca gaacacccctt accagcaccc  4980 tcggcaccag cgctgggctc aacccactgg cacatacgcg cactgcggta catgcgcgg    5040 atgaagccac gaggaccatc ctggacatca gcccggtagt gcttgcccat gatgggctta   5100
atggcctcgg tggcctcgtc cgcgttgtag aagggggatgc tgctgacgta gtggtggagg  5160
acatgagtct cgatgatgcc gtggagaagg tggcggccga tgaagcccat ctcacggtca   5220
atggtagcag cggcaccacg gacgaagttc cactcgtcgt tggtgtagtg gggaagggta   5280
gggtcggtgt gctggaggaa ggtgatggca acagagccagt ggttaaccca gaggtaggga  5340
acaaagtacc agatggccat gttgtagaaa ccgaacttct gaacgaggaa gtacagagca   5400
gtggccatca gaccgatacc aatatcgctg aggacgatga gcttagcgtc actgttctcg   5460
tacagagggc tgcggggatc gaagtggtta acaccaccgc cgaggccgtt atgcttgccc   5520
ttgccgcgac cctcacgctg gcgctcgtgg tagttgtggc cggtaacatt ggtgatgagg   5580
tagttgggcc agccaacgag ctgctgaagg acgagcatga gaagagtgaa agcgggggtc   5640
```

```
tcctcagtaa gatgagcgag ctcgtgggtc atctttccga gacgagtagc ctgctgctcg    5700
cgggttcggg gaacgaagac catgtcacgc tccatgttgc cagtggcctt gtggtgcttt    5760
cggtgggaga tttgccagct gaagtagggg acaaggaggg aagagtgaag aacccagcca    5820
gtaatgtcgt tgatgatgcg agaatcggag aaagcaccgt gaccgcactc atgggcaata    5880
acccagagac cagtaccgaa aagaccctga agaacggtgt acacggccca cagaccagcg    5940
cgggcggggg tggagggggat atattcgggg gtcacaaagt tgtaccagat gctgaaagtg    6000
gtagtcagga ggacaatgtc gcggaggata taaccgtatc ccttgagagc ggagcgcttg    6060
aagcagtgct tagggatggc attgtagatg tccttgatgg taaagtcggg aacctcgaac    6120
tggttgccgt aggtgtcgag catgacacca tactcggact tgggcttggc gatatcaacc    6180
tcggacatgg acgagagcga tgtggaagag gccgagtggc ggggagagtc tgaaggagag    6240
acggcggcag actcagaatc cgtcacagta gttgaggtga cggtgcgtct aagcgcaggg    6300
ttctgcttgg gcagagccga agtggacgcc atggttgtga attagggtgg tgagaatggt    6360
tggttgtagg gaagaatcaa aggccggtct cgggatccgt gggtatatat atatatatat    6420
atatatacga tccttcgtta cctccctgtt ctcaaaactg tggttttttcg ttttttcgttt    6480
tttgcttttt ttgatttttt tagggccaac taagcttcca gatttcgcta atcacctttg    6540
tactaattac aagaaaggaa gaagctgatt agagttgggc tttttatgca actgtgctac    6600
tccttatctc tgatatgaaa gtgtagaccc aatcacatca tgtcatttag agttggtaat    6660
actgggagga tagataaggc acgaaaacga gccatagcag acatgctggg tgtagccaag    6720
cagaagaaag tagatgggag ccaattgacg agcgagggag ctacgccaat ccgacatacg    6780
acacgctgag atcgtcttgg ccgggggggta cctacagatg tccaagggta agtgcttgac    6840
tgtaattgta tgtctgagga caaatatgta gtcagccgta taaagtcata ccaggcacca    6900
gtgccatcat cgaaccacta actctctatg atacatgcct ccggtattat tgtaccatgc    6960
gtcgctttgt tacatacgta tcttgccttt ttctctcaga aactccagac tttggctatt    7020
ggtcgagata agcccggacc atagtgagtc tttcacactc tacatttctc ccttgctcca    7080
actatttaaa ttgccccgga gaagacggcc aggccgccta gatgacaaat tcaacaactc    7140
acagctgact ttctgccatt gccactaggg ggggcctttt ttatatggcc aagccaagct    7200
ctccacgtcg gttgggctgc acccaacaat aaatgggtag ggttgcacca acaaagggat    7260
gggatggggg gtagaagata cgaggataac ggggctcaat ggcacaaata agaacgaata    7320
ctgccattaa gactcgtgat ccagcgactg acaccattgc atcatctaag ggcctcaaaa    7380
ctacctcgga actgctgcgc tgatctggac accacagagg ttccgagcac tttaggttgc    7440
accaaatgtc ccaccaggtg caggcagaaa acgctggaac agcgtgtaca gtttgtctta    7500
acaaaaagtg agggcgctga ggtcgagcag ggtggtgtga cttgttatag cctttagagc    7560
tgcgaaagcg cgtatggatt tggctcatca ggccagattg agggtctgtg gacacatgtc    7620
atgttagtgt acttcaatcg cccccctggat atagccccga caataggccg tggcctcatt    7680
tttttgcctt ccgcacattt ccattgctcg gtacccacac cttgcttctc ctgcacttgc    7740
caaccttaat actggtttac attgaccaac atcttacaag cggggggctt gtctagggta    7800
tatataaaca gtggctctcc caatcggttg ccagtctctt ttttcctttc tttccccaca    7860
gattcgaaat ctaaactaca catcacagaa ttccgagccg tgagtatcca cgacaagatc    7920
agtgtcgaga cgacgcgttt tgtgtaatga cacaatccga aagtcgctag caacacacac    7980
tctctacaca aactaaccca gctctggtac catggtgaag gcttctcgac aggctctgcc    8040
```

```
cctcgtcatc gacggaaagg tgtacgacgt ctccgcttgg gtgaacttcc accctggtgg    8100
agctgaaatc attgagaact accagggacg agatgctact gacgccttca tggttatgca    8160
ctctcaggaa gccttcgaca agctcaagcg aatgcccaag atcaaccagg cttccgagct    8220
gcctccccag gctgccgtca acgaagctca ggaggatttc cgaaagctcc gagaagagct    8280
gatcgccact ggcatgtttg acgcctctcc cctctggtac tcgtacaaga tcttgaccac    8340
cctgggtctt ggcgtgcttg ccttcttcat gctggtccag taccacctgt acttcattgg    8400
tgctctcgtg ctcggtatgc actaccagca aatgggatgg ctgtctcatg acatctgcca    8460
ccaccagacc ttcaagaacc gaaactggaa taacgtcctg ggtctggtct ttggcaacgg    8520
actccagggc ttctccgtga cctggtggaa ggacagacac aacgcccatc attctgctac    8580
caacgttcag ggtcacgatc ccgacattga taacctgcct ctgctcgcct ggtccgagga    8640
cgatgtcact cgagcttctc ccatctcccg aaagctcatt cagttccaac agtactattt    8700
cctggtcatc tgtattctcc tgcgattcat ctggtgtttc cagtctgtgc tgaccgttcg    8760
atccctcaag gaccgagaca accagttcta ccgatctcag tacaagaaag aggccattgg    8820
actcgctctg cactggactc tcaagaccct gttccacctc ttctttatgc cctccatcct    8880
gacctcgatg ctggtgttct tgtttccga gctcgtcggt ggcttcggaa ttgccatcgt    8940
ggtcttcatg aaccactacc ctctggagaa gatcggtgat tccgtctggg acggacatgg    9000
cttctctgtg ggtcagatcc atgagaccat gaacattcga cgaggcatca ttactgactg    9060
gttctttgga ggcctgaact accagatcga gcaccatctc tggcccaccc tgcctcgaca    9120
caacctcact gccgtttcct accaggtgga acagctgtgc cagaagcaca acctccccta    9180
ccgaaaccct ctgccccatg aaggtctcgt catcctgctc cgatacctgt cccagttcgc    9240
tcgaatggcc gagaagcagc ccggtgccaa ggctcagtaa gcggccgcaa gtgtggatgg    9300
ggaagtgagt gcccggttct gtgtgcacaa ttggcaatcc aagatggatg gattcaacac    9360
agggatatag cgagctacgt ggtggtgcga ggatatagca acggatattt atgtttgaca    9420
cttgagaatg tacgatacaa gcactgtcca agtacaatac taaacatact gtacatactc    9480
atactcgtac ccgggcaacg gtttcacttg agtgcagtgg ctagtgctct tactcgtaca    9540
gtgtgcaata ctgcgtatca tagtctttga tgtatatcgt attcattcat gttagttgcg    9600
tacgggtgaa gcttccactg gtcggcgtgg tagtggggca gagtggggtc ggtgtgctgc    9660
aggtaggtga tggccacgag ccagtggttg acccacaggt aggggatcag gtagtagagg    9720
gtgacggaag ccaggcccca tcggttgatg gagtatgcga tgacggacat ggtgatacca    9780
ataccgacgt tagagatcca gatgttgaac cagtccttct tctcaaacag cggggcgttg    9840
gggttgaagt ggttgacagc ccatttgttg agcttggggt acttctgtcc ggtaacgtaa    9900
gacagcagat acagaggcca tccaaacacc tgctgggtga tgaggccgta gagggtcatg    9960
aggggagcgt cctcagcaag ctcagaccag tcatgggcgc ctcggttctc cataaactcc    10020
tttcggtcct tgggcacaaa caccatatca cgggtgaggt gaccagtgga cttgtggtgc    10080
atggagtggg tcagcttcca ggcgtagtaa gggaccagca tggaggagtg cagaacccat    10140
ccggtgacgt tgttgacggt gttagagtcg gagaaagcag agtggccaca ctcgtgggca    10200
agaacccaca gaccggtgcc aaacagaccc tggacaatgg agtacatggc ccaggccaca    10260
gctcggccgg aagccgaggg aataagaggc aggtacgcgt aggccatgta ggcaaaaacg    10320
gcgataaaga agcaggcgcg ccagctgcat taatgaatcg ccaacgcgc ggggagaggc    10380 ggtttgcgta ttgggcgctc ttccgcttcc tcgctcactg actcgctgcg ctcggtcgtt    10440
```

```
cggctgcggc gagcggtatc agctcactca aaggcggtaa tacgttatc  cacagaatca   10500 ggggataacg caggaaagaa catgtgagca aaaggccagc aaaaggccag gaaccgtaaa   10560
aaggccgcgt tgctggcgtt tttccatagg ctccgcccc  ctgacgagca tcacaaaaat   10620
cgacgctcaa gtcagaggtg gcgaaacccg acaggactat aaagatacca ggcgtttccc   10680
cctggaagct ccctcgtgcg ctctcctgtt ccgaccctgc cgcttaccgg atacctgtcc   10740
gcctttctcc cttcgggaag cgtggcgctt tctcatagct cacgctgtag gtatctcagt   10800
tcggtgtagg tcgttcgctc caagctgggc tgtgtgcacg aaccccccgt tcagcccgac   10860
cgctgcgcct tatccggtaa ctatcgtctt gagtccaacc cggtaagaca cgacttatcg   10920
ccactggcag cagccactgg taacaggatt agcagagcga gtatgtagg  cggtgctaca   10980 gagttcttga agtggtggcc taactacggc tacactagaa gaacagtatt tggtatctgc   11040
gctctgctga agccagttac cttcggaaaa agagttggta gctcttgatc cggcaaacaa   11100
accaccgctg gtagcggtgg tttttttgtt tgcaagcagc agattacgcg cagaaaaaaa   11160
ggatctcaag aagatccttt gatcttttct acggggtctg acgctcagtg gaacgaaaac   11220
tcacgttaag ggattttggt catgagatta tcaaaaagga tcttcaccta gatccttta   11280 aattaaaaat gaagttttaa atcaatctaa agtatatatg agtaaacttg gtctgacagt   11340
taccaatgct taatcagtga ggcacctatc tcagcgatct gtctatttcg ttcatccata   11400
gttgcctgac tccccgtcgt gtagataact acgatacggg agggcttacc atctggcccc   11460
agtgctgcaa tgataccgcg agacccacgc tcaccggctc cagatttatc agcaataaac   11520
cagccagccg gaagggccga gcgcagaagt ggtcctgcaa ctttatccgc ctccatccag   11580
tctattaatt gttgccggga agctagagta agtagttcgc cagttaatag tttgcgcaac   11640
gttgttgcca ttgctacagg catcgtggtg tcacgctcgt cgtttggtat ggcttcattc   11700
agctccggtt cccaacgatc aaggcgagtt acatgatccc ccatgttgtg caaaaaagcg   11760
gttagctcct tcggtcctcc gatcgttgtc agaagtaagt tggccgcagt gttatcactc   11820
atggttatgg cagcactgca taattctctt actgtcatgc catccgtaag atgcttttct   11880
gtgactggtg agtactcaac caagtcattc tgagaatagt gtatgcggcg accgagttgc   11940
tcttgcccgg cgtcaatacg ggataatacc gcgccacata gcagaacttt aaaagtgctc   12000
atcattggaa aacgttcttc ggggcgaaaa ctctcaagga tcttaccgct gttgagatcc   12060
agttcgatgt aacccactcg tgcacccaac tgatcttcag catctttac  tttcaccagc   12120 gtttctgggt gagcaaaaac aggaaggcaa aatgccgcaa aaaagggaat aagggcgaca   12180
cggaaatgtt gaatactcat actcttcctt tttcaatatt attgaagcat ttatcagggt   12240
tattgtctca tgagcggata catatttgaa tgtatttaga aaaataaaca ataggggtt   12300 ccgcgcacat ttccccgaaa agtgccacct gatgcggtgt gaaataccgc acagatgcgt   12360
aaggagaaaa taccgcatca ggaaattgta agcgttaata ttttgttaaa attcgcgtta   12420
aatttttgtt aaatcagctc attttttaac caataggccg aaatcggcaa aatcccttat   12480
aaatcaaaag aatagaccga gatagggttg agtgttgttc cagtttggaa caagagtcca   12540
ctattaaaga acgtggactc caacgtcaaa gggcgaaaaa ccgtctatca gggcgatggc   12600
ccactacgtg aaccatcacc ctaatcaagt tttttggggt cgaggtgccg taaagcacta   12660
aatcggaacc ctaaagggag cccccgattt agagcttgac ggggaaagcc ggcgaacgtg   12720
gcgagaaagg aagggaagaa agcgaaagga gcgggcgcta gggcgctggc aagtgtagcg   12780
gtcacgctgc gcgtaaccac cacacccgcc gcgcttaatg cgccgctaca gggcgcgtcc   12840
```

```
attcgccatt caggctgcgc aactgttggg aagggcgatc ggtgcgggcc tcttcgctat   12900
tacgccagct ggcgaaaggg ggatgtgctg caaggcgatt aagttgggta acgccagggt   12960
tttcccagtc acgacgttgt aaaacgacgg ccagtgaatt gtaatacgac tcactatagg   13020
gcgaattggg cccgacgtcg catgcttgaa tctacaagta ggagggttgg agtgattaag   13080
tgaaacttct ttaacggctc tatgccagtt ctattgatat ccgaaacatc agtatgaagg   13140
tctgataagg gtgacttctt cccacagatt cgtatcagta cgagtacgag accggtactt   13200
gtaacagtat tgatactaaa gggaaactac aacggttgtc agcgtaatgt gacttcgccc   13260
atgaacgcag acacgcagtg ccgagtgcgg tgatatcgcc tactcgttac gtccatggac   13320
tacacaaccc ctcggcttcg cttggcttag cctcgggctc ggtgctgttc agttaaaaca   13380
caatcaaata acatttctac tttttagaag gcaggccgtc aggagcaact ccgactccat   13440
tgacgtttct aaacatctga atgccttcct taccttcaac aaactggcag gttcgggcga   13500
cagtgtaaag agacttgatg aagttggtgt cgtcgtgtcg gtagtgcttg cccatgacct   13560
tcttgatctt ctcagtggcg attcgggcgt tgtagaaggg aattccttta cctgcaggat   13620
aacttcgtat aatgtatgct atacgaagtt atgatctctc tcttgagctt ttccataaca   13680
agttcttctg cctccaggaa gtccatgggt ggtttgatca tggttttggt gtagtggtag   13740
tgcagtggtg gtattgtgac tggggatgta gttgagaata agtcatacac aagtcagctt   13800
tcttcgagcc tcatataagt ataagtagtt caacgtatta gcactgtacc cagcatctcc   13860
gtatcgagaa acacaacaac atgccccatt ggacagatca tgcggataca caggttgtgc   13920
agtatcatac atactcgatc agacaggtcg tctgaccatc atacaagctg aacaagcgct   13980
ccatacttgc acgctctcta tatacacagt taaattacat atccatagtc taacctctaa   14040
cagttaatct tctggtaagc ctcccagcca gccttctggt atcgcttggc ctcctcaata   14100
ggatctcggt tctggccgta cagacctcgg ccgacaatta tgatatccgt tccggtagac   14160
atgacatcct caacagttcg gtactgctgt ccgagagcgt ctcccttgtc gtcaagaccc   14220
accccggggg tcagaataag ccagtcctca gagtcgccct taggtcggtt ctgggcaatg   14280
aagccaacca caaactcggg gtcggatcgg gcaagctcaa tggtctgctt ggagtactcg   14340
ccagtggcca gagagccctt gcaagacagc tcggccagca tgagcagacc tctgccagc   14400 ttctcgttgg gagagggac taggaactcc ttgtactggg agttctcgta gtcagagacg   14460
tcctccttct tctgttcaga gacagtttcc tcggcaccag ctcgcaggcc agcaatgatt   14520
ccggttccgg gtacaccgtg ggcgttggtg atatcggacc actcggcgat tcggtgacac   14580
cggtactggt gcttgacagt gttgccaata tctgcgaact ttctgtcctc gaacaggaag   14640
aaaccgtgct taagagcaag ttccttgagg gggagcacag tgccggcgta ggtgaagtcg   14700
tcaatgatgt cgatatgggt tttgatcatg cacacataag gtccgacctt atcggcaagc   14760
tcaatgagct ccttggtggt ggtaacatcc agagaagcac acaggttggt tttcttggct   14820
gccacgagct tgagcactcg agcggcaaag gcggacttgt ggacgttagc tcgagcttcg   14880
taggagggca ttttggtggt gaagaggaga ctgaaataaa tttagtctgc agaacttttt   14940
atcggaacct tatctggggc agtgaagtat atgttatggt aatagttacg agttagttga   15000
acttatagat agactggact atacggctat cggtccaaat tagaaagaac gtcaatggct   15060
ctctgggcgt cgccttttgcc gacaaaaatg tgatcatgat gaaagccagc aatgacgttg   15120 cagctgtatat tgttgtcggc caaccgcgcc gaaaacgcag ctgtcagacc cacagcctcc   15180
aacgaagaat gtatcgtcaa agtgatccaa gcacactcat agttggagtc gtactccaaa   15240
```

```
ggcggcaatg acgagtcaga cagatactcg tcgacgcgat aacttcgtat aatgtatgct    15300
atacgaagtt atcgtacgat agttagtaga caacaat                             15337

<210> SEQ ID NO 52
<211> LENGTH: 777
<212> TYPE: DNA
<213> ORGANISM: Euglena gracilis
<220> FEATURE:
<221> NAME/KEY: CDS
<222> LOCATION: (1)..(777)
<223> OTHER INFORMATION: delta-9 elongase
<300> PUBLICATION INFORMATION:
<302> TITLE: DELTA-9 ELONGASES AND THEIR USE IN MAKING POLYUNSATURATED
      FATTY ACIDS
<310> PATENT DOCUMENT NUMBER: WO 2007/061742
<311> PATENT FILING DATE: 2006-11-16
<312> PUBLICATION DATE: 2007-05-31
<313> RELEVANT RESIDUES: (1)..(777)
<300> PUBLICATION INFORMATION:
<302> TITLE: DELTA-9 ELONGASES AND THEIR USE IN MAKING POLYUNSATURATED
      FATTY ACIDS
<310> PATENT DOCUMENT NUMBER: US 2007-0117190-A1
<311> PATENT FILING DATE: 2006-11-16
<312> PUBLICATION DATE: 2007-05-24
<313> RELEVANT RESIDUES: (1)..(777)

<400> SEQUENCE: 52 atg gag gtg gtg aat gaa ata gtc tca att ggg cag gaa gtt tta ccc     48
Met Glu Val Val Asn Glu Ile Val Ser Ile Gly Gln Glu Val Leu Pro
1               5                   10                  15 aaa gtt gat tat gcc caa ctc tgg agt gat gcc agt cac tgt gag gtg     96
Lys Val Asp Tyr Ala Gln Leu Trp Ser Asp Ala Ser His Cys Glu Val
            20                  25                  30 ctt tac ttg tcc atc gca ttt gtc atc ttg aag ttc act ctt ggc ccc    144
Leu Tyr Leu Ser Ile Ala Phe Val Ile Leu Lys Phe Thr Leu Gly Pro
        35                  40                  45 ctt ggt cca aaa ggt cag tct cgt atg aag ttt gtt ttc acc aat tac    192
Leu Gly Pro Lys Gly Gln Ser Arg Met Lys Phe Val Phe Thr Asn Tyr
    50                  55                  60 aac ctt ctc atg tcc att tat tcg ttg gga tca ttc ctc tca atg gca    240
Asn Leu Leu Met Ser Ile Tyr Ser Leu Gly Ser Phe Leu Ser Met Ala
65                  70                  75                  80 tat gcc atg tac acc atc ggt gtt atg tct gac aac tgc gag aag gct    288
Tyr Ala Met Tyr Thr Ile Gly Val Met Ser Asp Asn Cys Glu Lys Ala
                85                  90                  95 ttt gac aac aac gtc ttc agg atc acc acg cag ttg ttc tat ttg agc    336
Phe Asp Asn Asn Val Phe Arg Ile Thr Thr Gln Leu Phe Tyr Leu Ser
            100                 105                 110 aag ttc ctg gag tat att gac tcc ttc tat ttg cca ctg atg ggc aag    384
Lys Phe Leu Glu Tyr Ile Asp Ser Phe Tyr Leu Pro Leu Met Gly Lys
        115                 120                 125 cct ctg acc tgg ttg caa ttc ttc cat cat ttg ggg gca ccg atg gat    432
Pro Leu Thr Trp Leu Gln Phe Phe His His Leu Gly Ala Pro Met Asp
    130                 135                 140 atg tgg ctg ttc tat aat tac cga aat gaa gct gtt tgg att ttt gtg    480
Met Trp Leu Phe Tyr Asn Tyr Arg Asn Glu Ala Val Trp Ile Phe Val
145                 150                 155                 160 ctg ttg aat ggt ttc atc cac tgg atc atg tac ggt tat tat tgg acc    528
Leu Leu Asn Gly Phe Ile His Trp Ile Met Tyr Gly Tyr Tyr Trp Thr
                165                 170                 175 aga ttg atc aag ctg aag ttc ccc atg cca aaa tcc ctg att aca tca    576
Arg Leu Ile Lys Leu Lys Phe Pro Met Pro Lys Ser Leu Ile Thr Ser
            180                 185                 190 atg cag atc att caa ttc aat gtt ggt ttc tac att gtc tgg aag tac    624
Met Gln Ile Ile Gln Phe Asn Val Gly Phe Tyr Ile Val Trp Lys Tyr
```

```
Met Gln Ile Ile Gln Phe Asn Val Gly Phe Tyr Ile Val Trp Lys Tyr
        195                 200                 205 agg aac att ccc tgt tat cgc caa gat ggg atg agg atg ttt ggc tgg    672
Arg Asn Ile Pro Cys Tyr Arg Gln Asp Gly Met Arg Met Phe Gly Trp
    210                 215                 220 ttc ttc aat tac ttt tat gtt ggc aca gtc ttg tgt ttg ttc ttg aat    720
Phe Phe Asn Tyr Phe Tyr Val Gly Thr Val Leu Cys Leu Phe Leu Asn
225                 230                 235                 240 ttc tat gtg caa acg tat atc gtc agg aag cac aag gga gcc aaa aag    768
Phe Tyr Val Gln Thr Tyr Ile Val Arg Lys His Lys Gly Ala Lys Lys
                245                 250                 255 att cag tga                                                        777
Ile Gln

<210> SEQ ID NO 53
<211> LENGTH: 258
<212> TYPE: PRT
<213> ORGANISM: Euglena gracilis

<400> SEQUENCE: 53

Met Glu Val Val Asn Glu Ile Val Ser Ile Gly Gln Glu Val Leu Pro
1               5                   10                  15

Lys Val Asp Tyr Ala Gln Leu Trp Ser Asp Ala Ser His Cys Glu Val
            20                  25                  30

Leu Tyr Leu Ser Ile Ala Phe Val Ile Leu Lys Phe Thr Leu Gly Pro
        35                  40                  45

Leu Gly Pro Lys Gly Gln Ser Arg Met Lys Phe Val Phe Thr Asn Tyr
    50                  55                  60

Asn Leu Leu Met Ser Ile Tyr Ser Leu Gly Ser Phe Leu Ser Met Ala
65                  70                  75                  80

Tyr Ala Met Tyr Thr Ile Gly Val Met Ser Asp Asn Cys Glu Lys Ala
                85                  90                  95

Phe Asp Asn Asn Val Phe Arg Ile Thr Thr Gln Leu Pro Tyr Leu Ser
            100                 105                 110

Lys Phe Leu Glu Tyr Ile Asp Ser Phe Tyr Leu Pro Leu Met Gly Lys
        115                 120                 125

Pro Leu Thr Trp Leu Gln Phe Phe His His Leu Gly Ala Pro Met Asp
    130                 135                 140

Met Trp Leu Phe Tyr Asn Tyr Arg Asn Glu Ala Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Ile Lys Leu Lys Phe Pro Met Pro Lys Ser Leu Ile Thr Ser
            180                 185                 190

Met Gln Ile Ile Gln Phe Asn Val Gly Phe Tyr Ile Val Trp Lys Tyr
        195                 200                 205

Arg Asn Ile Pro Cys Tyr Arg Gln Asp Gly Met Arg Met Phe Gly Trp
    210                 215                 220

Phe Phe Asn Tyr Phe Tyr Val Gly Thr Val Leu Cys Leu Phe Leu Asn
225                 230                 235                 240

Phe Tyr Val Gln Thr Tyr Ile Val Arg Lys His Lys Gly Ala Lys Lys
                245                 250                 255

Ile Gln

<210> SEQ ID NO 54
<211> LENGTH: 1272
<212> TYPE: DNA
```

<213> ORGANISM: Artificial Sequence
<220> FEATURE:
<223> OTHER INFORMATION: mutant EgD8S-23 delta-8 desaturase
<220> FEATURE:
<221> NAME/KEY: CDS
<222> LOCATION: (2)..(1270)

<400> SEQUENCE: 54

```
c atg gtg aag gct tct cga cag gct ctg ccc ctc gtc atc gac gga aag      49
  Met Val Lys Ala Ser Arg Gln Ala Leu Pro Leu Val Ile Asp Gly Lys
  1               5                  10                  15 gtg tac gac gtc tcc gct tgg gtg aac ttc cac cct ggt gga gct gaa        97
Val Tyr Asp Val Ser Ala Trp Val Asn Phe His Pro Gly Gly Ala Glu
                 20                  25                  30 atc att gag aac tac cag gga cga gat gct act gac gcc ttc atg gtt       145
Ile Ile Glu Asn Tyr Gln Gly Arg Asp Ala Thr Asp Ala Phe Met Val
             35                  40                  45 atg cac tct cag gaa gcc ttc gac aag ctc aag cga atg ccc aag atc       193
Met His Ser Gln Glu Ala Phe Asp Lys Leu Lys Arg Met Pro Lys Ile
 50                  55                  60 aac cag gct tcc gag ctg cct ccc cag gct gcc gtc aac gaa gct cag       241
Asn Gln Ala Ser Glu Leu Pro Pro Gln Ala Ala Val Asn Glu Ala Gln
 65                  70                  75                  80 gag gat ttc cga aag ctc cga gaa gag ctg atc gcc act ggc atg ttt       289
Glu Asp Phe Arg Lys Leu Arg Glu Glu Leu Ile Ala Thr Gly Met Phe
                 85                  90                  95 gac gcc tct ccc ctc tgg tac tcg tac aag atc ttg acc acc ctg ggt       337
Asp Ala Ser Pro Leu Trp Tyr Ser Tyr Lys Ile Leu Thr Thr Leu Gly
                100                 105                 110 ctt ggc gtg ctt gcc ttc ttc atg ctg gtc cag tac cac ctg tac ttc       385
Leu Gly Val Leu Ala Phe Phe Met Leu Val Gln Tyr His Leu Tyr Phe
            115                 120                 125 att ggt gct ctc gtg ctc ggt atg cac tac cag caa atg gga tgg ctg       433
Ile Gly Ala Leu Val Leu Gly Met His Tyr Gln Gln Met Gly Trp Leu
        130                 135                 140 tct cat gac atc tgc cac cac cag acc ttc aag aac cga aac tgg aat       481
Ser His Asp Ile Cys His His Gln Thr Phe Lys Asn Arg Asn Trp Asn
145                 150                 155                 160 aac gtc ctg ggt ctg gtc ttt ggc aac gga ctc cag ggc ttc tcc gtg       529
Asn Val Leu Gly Leu Val Phe Gly Asn Gly Leu Gln Gly Phe Ser Val
                165                 170                 175 acc tgg tgg aag gac aga cac aac gcc cat cat tct gct acc aac gtt       577
Thr Trp Trp Lys Asp Arg His Asn Ala His His Ser Ala Thr Asn Val
                180                 185                 190 cag ggt cac gat ccc gac att gat aac ctg cct ctg ctc gcc tgg tcc       625
Gln Gly His Asp Pro Asp Ile Asp Asn Leu Pro Leu Leu Ala Trp Ser
            195                 200                 205 gag gac gat gtc act cga gct tct ccc atc tcc cga aag ctc att cag       673
Glu Asp Asp Val Thr Arg Ala Ser Pro Ile Ser Arg Lys Leu Ile Gln
        210                 215                 220 ttc caa cag tac tat ttc ctg gtc atc tgt att ctc ctg cga ttc atc       721
Phe Gln Gln Tyr Tyr Phe Leu Val Ile Cys Ile Leu Leu Arg Phe Ile
225                 230                 235                 240 tgg tgt ttc cag tct gtg ctg acc gtt cga tcc ctc aag gac cga gac       769
Trp Cys Phe Gln Ser Val Leu Thr Val Arg Ser Leu Lys Asp Arg Asp
                245                 250                 255 aac cag ttc tac cga tct cag tac aag aaa gag gcc att gga ctc gct       817
Asn Gln Phe Tyr Arg Ser Gln Tyr Lys Lys Glu Ala Ile Gly Leu Ala
                260                 265                 270 ctg cac tgg act ctc aag acc ctg ttc cac ctc ttc ttt atg ccc tcc       865
Leu His Trp Thr Leu Lys Thr Leu Phe His Leu Phe Phe Met Pro Ser
            275                 280                 285
```

```
atc ctg acc tcg atg ctg gtg ttc ttt gtt tcc gag ctc gtc ggt ggc      913
Ile Leu Thr Ser Met Leu Val Phe Phe Val Ser Glu Leu Val Gly Gly
    290             295                 300 ttc gga att gcc atc gtg gtc ttc atg aac cac tac cct ctg gag aag      961
Phe Gly Ile Ala Ile Val Val Phe Met Asn His Tyr Pro Leu Glu Lys
305             310                 315                 320 atc ggt gat tcc gtc tgg gac gga cat ggc ttc tct gtg ggt cag atc     1009
Ile Gly Asp Ser Val Trp Asp Gly His Gly Phe Ser Val Gly Gln Ile
                325                 330                 335 cat gag acc atg aac att cga cga ggc atc att act gac tgg ttc ttt     1057
His Glu Thr Met Asn Ile Arg Arg Gly Ile Ile Thr Asp Trp Phe Phe
            340                 345                 350 gga ggc ctg aac tac cag atc gag cac cat ctc tgg ccc acc ctg cct     1105
Gly Gly Leu Asn Tyr Gln Ile Glu His His Leu Trp Pro Thr Leu Pro
355                 360                 365 cga cac aac ctc act gcc gtt tcc tac cag gtg gaa cag ctg tgc cag     1153
Arg His Asn Leu Thr Ala Val Ser Tyr Gln Val Glu Gln Leu Cys Gln
    370                 375                 380 aag cac aac ctc ccc tac cga aac cct ctg ccc cat gaa ggt ctc gtc     1201
Lys His Asn Leu Pro Tyr Arg Asn Pro Leu Pro His Glu Gly Leu Val
385                 390                 395                 400 atc ctg ctc cga tac ctg tcc cag ttc gct cga atg gcc gag aag cag     1249
Ile Leu Leu Arg Tyr Leu Ser Gln Phe Ala Arg Met Ala Glu Lys Gln
                405                 410                 415 ccc ggt gcc aag gct cag taa gc                                      1272
Pro Gly Ala Lys Ala Gln
                420

<210> SEQ ID NO 55
<211> LENGTH: 422
<212> TYPE: PRT
<213> ORGANISM: Artificial Sequence
<220> FEATURE:
<223> OTHER INFORMATION: Synthetic Construct

<400> SEQUENCE: 55

Met Val Lys Ala Ser Arg Gln Ala Leu Pro Leu Val Ile Asp Gly Lys
1               5                   10                  15

Val Tyr Asp Val Ser Ala Trp Val Asn Phe His Pro Gly Gly Ala Glu
                20                  25                  30

Ile Ile Glu Asn Tyr Gln Gly Arg Asp Ala Thr Asp Ala Phe Met Val
            35                  40                  45

Met His Ser Gln Glu Ala Phe Asp Lys Leu Lys Arg Met Pro Lys Ile
        50                  55                  60

Asn Gln Ala Ser Glu Leu Pro Pro Gln Ala Ala Val Asn Glu Ala Gln
65                  70                  75                  80

Glu Asp Phe Arg Lys Leu Arg Glu Glu Leu Ile Ala Thr Gly Met Phe
                85                  90                  95

Asp Ala Ser Pro Leu Trp Tyr Ser Tyr Lys Ile Leu Thr Thr Leu Gly
            100                 105                 110

Leu Gly Val Leu Ala Phe Phe Met Leu Val Gln Tyr His Leu Tyr Phe
        115                 120                 125

Ile Gly Ala Leu Val Leu Gly Met His Tyr Gln Gln Met Gly Trp Leu
    130                 135                 140

Ser His Asp Ile Cys His His Gln Thr Phe Lys Asn Arg Asn Trp Asn
145                 150                 155                 160

Asn Val Leu Gly Leu Val Phe Gly Asn Gly Leu Gln Gly Phe Ser Val
                165                 170                 175
```

```
Thr Trp Trp Lys Asp Arg His Asn Ala His His Ser Ala Thr Asn Val
            180                 185                 190

Gln Gly His Asp Pro Asp Ile Asp Asn Leu Pro Leu Leu Ala Trp Ser
        195                 200                 205

Glu Asp Asp Val Thr Arg Ala Ser Pro Ile Ser Arg Lys Leu Ile Gln
210                 215                 220

Phe Gln Gln Tyr Tyr Phe Leu Val Ile Cys Ile Leu Leu Arg Phe Ile
225                 230                 235                 240

Trp Cys Phe Gln Ser Val Leu Thr Val Arg Ser Leu Lys Asp Arg Asp
                245                 250                 255

Asn Gln Phe Tyr Arg Ser Gln Tyr Lys Lys Glu Ala Ile Gly Leu Ala
            260                 265                 270

Leu His Trp Thr Leu Lys Thr Leu Phe His Leu Phe Phe Met Pro Ser
        275                 280                 285

Ile Leu Thr Ser Met Leu Val Phe Val Ser Glu Leu Val Gly Gly
290                 295                 300

Phe Gly Ile Ala Ile Val Val Phe Met Asn His Tyr Pro Leu Glu Lys
305                 310                 315                 320

Ile Gly Asp Ser Val Trp Asp Gly His Gly Phe Ser Val Gly Gln Ile
                325                 330                 335

His Glu Thr Met Asn Ile Arg Arg Gly Ile Ile Thr Asp Trp Phe Phe
            340                 345                 350

Gly Gly Leu Asn Tyr Gln Ile Glu His His Leu Trp Pro Thr Leu Pro
        355                 360                 365

Arg His Asn Leu Thr Ala Val Ser Tyr Gln Val Glu Gln Leu Cys Gln
370                 375                 380

Lys His Asn Leu Pro Tyr Arg Asn Pro Leu Pro His Glu Gly Leu Val
385                 390                 395                 400

Ile Leu Leu Arg Tyr Leu Ser Gln Phe Ala Arg Met Ala Glu Lys Gln
                405                 410                 415

Pro Gly Ala Lys Ala Gln
            420
```

<210> SEQ ID NO 56
<211> LENGTH: 1272
<212> TYPE: DNA
<213> ORGANISM: Euglena gracilis
<220> FEATURE:
<221> NAME/KEY: CDS
<222> LOCATION: (2)..(1270)
<223> OTHER INFORMATION: synthetic delta-8 desaturase (codon-optimized for Yarrowia lipolytica) ("D8SF" or "EgD8S")
<300> PUBLICATION INFORMATION:
<302> TITLE: DELTA-8 DESATURASE AND ITS USE IN MAKING POLYUNSATURATED FATTY ACIDS
<310> PATENT DOCUMENT NUMBER: WO 2006/012325 and WO 2006/012326
<311> PATENT FILING DATE: 2005-06-24
<312> PUBLICATION DATE: 2006-02-02
<313> RELEVANT RESIDUES: (1)..(1272)
<300> PUBLICATION INFORMATION:
<302> TITLE: DELTA-8 DESATURASE AND ITS USE IN MAKING POLYUNSATURATED FATTY ACIDS
<310> PATENT DOCUMENT NUMBER: US-2005-0287652-A1
<311> PATENT FILING DATE: 2005-06-24
<312> PUBLICATION DATE: 2005-12-29
<313> RELEVANT RESIDUES: (1)..(1272)

<400> SEQUENCE: 56

```
c atg gtg aag tcc aag cga cag gct ctg ccc ctc acc atc gac gga act      49
  Met Val Lys Ser Lys Arg Gln Ala Leu Pro Leu Thr Ile Asp Gly Thr
  1               5                   10                  15 acc tac gac gtc tcc gct tgg gtg aac ttc cac cct ggt gga gct gaa        97
```

```
          Thr Tyr Asp Val Ser Ala Trp Val Asn Phe His Pro Gly Gly Ala Glu
                  20                  25                  30 atc att gag aac tac cag gga cga gat gct act gac gcc ttc atg gtt          145
Ile Ile Glu Asn Tyr Gln Gly Arg Asp Ala Thr Asp Ala Phe Met Val
         35                  40                  45 atg cac tct cag gaa gcc ttc gac aag ctc aag cga atg ccc aag atc          193
Met His Ser Gln Glu Ala Phe Asp Lys Leu Lys Arg Met Pro Lys Ile
     50                  55                  60 aac ccc tcc tcc gag ctg cct ccc cag gct gcc gtc aac gaa gct cag          241
Asn Pro Ser Ser Glu Leu Pro Pro Gln Ala Ala Val Asn Glu Ala Gln
65                  70                  75                  80 gag gat ttc cga aag ctc cga gaa gag ctg atc gcc act ggc atg ttt          289
Glu Asp Phe Arg Lys Leu Arg Glu Glu Leu Ile Ala Thr Gly Met Phe
             85                  90                  95 gac gcc tct ccc ctc tgg tac tcg tac aag atc tcc acc acc ctg ggt          337
Asp Ala Ser Pro Leu Trp Tyr Ser Tyr Lys Ile Ser Thr Thr Leu Gly
                100                 105                 110 ctt ggc gtg ctt gga tac ttc ctg atg gtc cag tac cag atg tac ttc          385
Leu Gly Val Leu Gly Tyr Phe Leu Met Val Gln Tyr Gln Met Tyr Phe
            115                 120                 125 att ggt gct gtg ctg ctc ggt atg cac tac cag caa atg gga tgg ctg          433
Ile Gly Ala Val Leu Leu Gly Met His Tyr Gln Gln Met Gly Trp Leu
    130                 135                 140 tct cat gac atc tgc cac cac cag acc ttc aag aac cga aac tgg aat          481
Ser His Asp Ile Cys His His Gln Thr Phe Lys Asn Arg Asn Trp Asn
145                 150                 155                 160 aac ctc gtg ggt ctg gtc ttt ggc aac gga ctc cag ggc ttc tcc gtg          529
Asn Leu Val Gly Leu Val Phe Gly Asn Gly Leu Gln Gly Phe Ser Val
                165                 170                 175 acc tgg tgg aag gac aga cac aac gcc cat cat tct gct acc aac gtt          577
Thr Trp Trp Lys Asp Arg His Asn Ala His His Ser Ala Thr Asn Val
            180                 185                 190 cag ggt cac gat ccc gac att gat aac ctg cct ctg ctc gcc tgg tcc          625
Gln Gly His Asp Pro Asp Ile Asp Asn Leu Pro Leu Leu Ala Trp Ser
        195                 200                 205 gag gac gat gtc act cga gct tct ccc atc tcc cga aag ctc att cag          673
Glu Asp Asp Val Thr Arg Ala Ser Pro Ile Ser Arg Lys Leu Ile Gln
210                 215                 220 ttc caa cag tac tat ttc ctg gtc atc tgt att ctg ctg cga ttc atc          721
Phe Gln Gln Tyr Tyr Phe Leu Val Ile Cys Ile Leu Leu Arg Phe Ile
225                 230                 235                 240 tgg tgt ttc cag tct gtg ctg acc gtt cga tcc ctc aag gac cga gac          769
Trp Cys Phe Gln Ser Val Leu Thr Val Arg Ser Leu Lys Asp Arg Asp
                245                 250                 255 aac cag ttc tac cga tct cag tac aag aaa gag gcc att gga ctc gct          817
Asn Gln Phe Tyr Arg Ser Gln Tyr Lys Lys Glu Ala Ile Gly Leu Ala
            260                 265                 270 ctg cac tgg act ctc aag acc ctg ttc cac ctc ttc ttt atg ccc tcc          865
Leu His Trp Thr Leu Lys Thr Leu Phe His Leu Phe Phe Met Pro Ser
        275                 280                 285 atc ctg acc tcg ctc ctg gtg ttc ttt gtt tcc gag ctc gtc ggt ggc          913
Ile Leu Thr Ser Leu Leu Val Phe Phe Val Ser Glu Leu Val Gly Gly
    290                 295                 300 ttc gga att gcc atc gtg gtc ttc atg aac cac tac cct ctg gag aag          961
Phe Gly Ile Ala Ile Val Val Phe Met Asn His Tyr Pro Leu Glu Lys
305                 310                 315                 320 atc ggt gat tcc gtc tgg gac gga cat ggc ttc tct gtg ggt cag atc         1009
Ile Gly Asp Ser Val Trp Asp Gly His Gly Phe Ser Val Gly Gln Ile
                325                 330                 335 cat gag acc atg aac att cga cga ggc atc att act gac tgg ttc ttt         1057
```

```
His Glu Thr Met Asn Ile Arg Arg Gly Ile Ile Thr Asp Trp Phe Phe
            340                 345                 350 gga ggc ctg aac tac cag atc gag cac cat ctc tgg ccc acc ctg cct    1105
Gly Gly Leu Asn Tyr Gln Ile Glu His His Leu Trp Pro Thr Leu Pro
            355                 360                 365 cga cac aac ctc act gcc gtt tcc tac cag gtg gaa cag ctg tgc cag    1153
Arg His Asn Leu Thr Ala Val Ser Tyr Gln Val Glu Gln Leu Cys Gln
            370                 375                 380 aag cac aac ctc ccc tac cga aac cct ctg ccc cat gaa ggt ctc gtc    1201
Lys His Asn Leu Pro Tyr Arg Asn Pro Leu Pro His Glu Gly Leu Val
385                 390                 395                 400 atc ctg ctc cga tac ctg gcc gtg ttc gct cga atg gcc gag aag cag    1249
Ile Leu Leu Arg Tyr Leu Ala Val Phe Ala Arg Met Ala Glu Lys Gln
                405                 410                 415 ccc gct ggc aag gct ctc taa gc                                     1272
Pro Ala Gly Lys Ala Leu
            420

<210> SEQ ID NO 57
<211> LENGTH: 422
<212> TYPE: PRT
<213> ORGANISM: Euglena gracilis

<400> SEQUENCE: 57

Met Val Lys Ser Lys Arg Gln Ala Leu Pro Leu Thr Ile Asp Gly Thr
1               5                   10                  15

Thr Tyr Asp Val Ser Ala Trp Val Asn Phe His Pro Gly Gly Ala Glu
                20                  25                  30

Ile Ile Glu Asn Tyr Gln Gly Arg Asp Ala Thr Asp Ala Phe Met Val
            35                  40                  45

Met His Ser Gln Glu Ala Phe Asp Lys Leu Lys Arg Met Pro Lys Ile
        50                  55                  60

Asn Pro Ser Ser Glu Leu Pro Pro Gln Ala Ala Val Asn Glu Ala Gln
65                  70                  75                  80

Glu Asp Phe Arg Lys Leu Arg Glu Glu Leu Ile Ala Thr Gly Met Phe
                85                  90                  95

Asp Ala Ser Pro Leu Trp Tyr Ser Tyr Lys Ile Ser Thr Thr Leu Gly
            100                 105                 110

Leu Gly Val Leu Gly Tyr Phe Leu Met Val Gln Tyr Gln Met Tyr Phe
        115                 120                 125

Ile Gly Ala Val Leu Leu Gly Met His Tyr Gln Gln Met Gly Trp Leu
    130                 135                 140

Ser His Asp Ile Cys His His Gln Thr Phe Lys Asn Arg Asn Trp Asn
145                 150                 155                 160

Asn Leu Val Gly Leu Val Phe Gly Asn Gly Leu Gln Gly Phe Ser Val
                165                 170                 175

Thr Trp Trp Lys Asp Arg His Asn Ala His His Ser Ala Thr Asn Val
            180                 185                 190

Gln Gly His Asp Pro Asp Ile Asp Asn Leu Pro Leu Leu Ala Trp Ser
        195                 200                 205

Glu Asp Asp Val Thr Arg Ala Ser Pro Ile Ser Arg Lys Leu Ile Gln
    210                 215                 220

Phe Gln Gln Tyr Phe Leu Val Ile Cys Ile Leu Arg Phe Ile
225                 230                 235                 240

Trp Cys Phe Gln Ser Val Leu Thr Val Arg Ser Leu Lys Asp Arg Asp
                245                 250                 255

Asn Gln Phe Tyr Arg Ser Gln Tyr Lys Lys Glu Ala Ile Gly Leu Ala
```

-continued

```
                260                 265                 270
Leu His Trp Thr Leu Lys Thr Leu Phe His Leu Phe Met Pro Ser
            275                 280                 285

Ile Leu Thr Ser Leu Leu Val Phe Phe Val Ser Glu Leu Val Gly Gly
    290                 295                 300

Phe Gly Ile Ala Ile Val Val Phe Met Asn His Tyr Pro Leu Glu Lys
305                 310                 315                 320

Ile Gly Asp Ser Val Trp Asp Gly His Gly Phe Ser Val Gly Gln Ile
                325                 330                 335

His Glu Thr Met Asn Ile Arg Arg Gly Ile Ile Thr Asp Trp Phe Phe
                340                 345                 350

Gly Gly Leu Asn Tyr Gln Ile Glu His His Leu Trp Pro Thr Leu Pro
            355                 360                 365

Arg His Asn Leu Thr Ala Val Ser Tyr Gln Val Glu Gln Leu Cys Gln
            370                 375                 380

Lys His Asn Leu Pro Tyr Arg Asn Pro Leu Pro His Glu Gly Leu Val
385                 390                 395                 400

Ile Leu Leu Arg Tyr Leu Ala Val Phe Ala Arg Met Ala Glu Lys Gln
                405                 410                 415

Pro Ala Gly Lys Ala Leu
                420

<210> SEQ ID NO 58
<211> LENGTH: 13707
<212> TYPE: DNA
<213> ORGANISM: Artificial Sequence
<220> FEATURE:
<223> OTHER INFORMATION: Plasmid pZKSL-555R

<400> SEQUENCE: 58
aaacagtgta cgcagatctg cccatgatgg gggctcccac caccagcaat cagggccctg      60
attacacacc cacctgtaat gtcatgctgt tcatcgtggt taatgctgct gtgtgctgtg     120
tgtgtgtgtt gtttggcgct cattgttgct ttatgcagcg tacaccacaa tattggaagc     180
ttattagcct ttctattttt tcgtttgcaa ggcttaacaa cattgctgtg gagagggatg     240
gggatatgga ggccgctgga gggagtcgga gaggcgtttt ggagcggctt ggcctggcgc     300
ccagctcgcg aaacgcacct aggaccctt ggcacgccga aatgtgccac ttttcagtct     360
agtaacgcct tacctacgtc attccatgcg tgcatgtttg cgcctttttt cccttgccct     420
tgatcgccac acagtacagt gcactgtaca gtggaggttt tggggggggtc ttagatggga     480 gctaaaagcg gcctagcggt acactagtgg gattgtatgg agtggcatgg agcctaggtg     540
gagcctgaca ggacgcacga ccggctagcc cgtgacagac gatgggtggc tcctgttgtc     600
caccgcgtac aaatgtttgg gccaaagtct tgtcagcctt gcttgcgaac ctaattccca     660 atttttgtcac ttcgcaccc cattgatcga gccctaaccc ctgcccatca ggcaatccaa     720
ttaagctcgc attgtctgcc ttgtttagtt tggctcctgc ccgtttcggc gtccacttgc     780
acaaacacaa acaagcatta tatataaggc tcgtctctcc ctcccaacca cactcacttt     840
tttgcccgtc ttcccttgct aacacaaaag tcaagaacac aaacaaccac cccaaccccc     900
ttacacacaa gacatatcta cagcaatggc catggctctc tcccttacta ccgagcagct     960
gctcgagcga cccgacctgg ttgccatcga cggcattctc tacgatctgg aaggtcttgc    1020
caaggtccat cccggaggcg acttgatcct cgcttctggt gcctccgatg cttctcctct    1080
gttctactcc atgcacccctt acgtcaagcc cgagaactcg aagctgcttc aacagttcgt    1140
```

```
gcgaggcaag cacgaccgaa cctccaagga cattgtctac acctacgact ctcccttttgc    1200
acaggacgtc aagcgaacta tgcgagaggt catgaaaggt cggaactggt atgccacacc    1260
tggattctgg ctgcgaaccg ttggcatcat tgctgtcacc gccttttgcg agtggcactg    1320
ggctactacc ggaatggtgc tgtggggtct cttgactgga ttcatgcaca tgcagatcgg    1380
cctgtccatt cagcacgatg cctctcatgg tgccatcagc aaaaagccct gggtcaacgc    1440
tctctttgcc tacggcatcg acgtcattgg atcgtccaga tggatctggc tgcagtctca    1500
catcatgcga catcacacct acaccaatca gcatggtctc gacctggatg ccgagtccgc    1560
agaaccattc cttgtgttcc acaactaccc tgctgccaac actgctcgaa agtggtttca    1620
ccgattccag gcctggtaca tgtacctcgt gcttggagcc tacggcgttt cgctggtgta    1680
caaccctctc tacatcttcc gaatgcagca caacgacacc attcccgagt ctgtcacagc    1740
catgcgagag aacggctttc tgcgacggta ccgaaccctt gcattcgtta tgcgagcttt    1800
cttcatctttt cgaaccgcct tcttgccctg gtatctcact ggaacctccc tgctcatcac    1860
cattcctctg gtgcccactg ctaccggtgc cttcctcacc ttcttttttca tcttgtctca    1920
caacttcgat ggctcggagc gaatccccga caagaactgc aaggtcaaga gctccgagaa    1980
ggacgttgaa gccgatcaga tcgactggta cagagctcag gtggagacct cttccaccta    2040
cggtggaccc attgccatgt tctttactgg cggtctcaac ttccagatcg agcatcacct    2100
ctttcctcga atgtcgtctt ggcactatcc cttcgtgcag caagctgtcc gagagtgttg    2160
cgaacgacac ggagttcggt acgtcttcta ccctaccatt gtgggcaaca tcatttccac    2220
cctcaagtac atgcacaaag tcggtgtggt tcactgtgtc aaggacgctc aggattccta    2280
agcggccgca agtgtggatg gggaagtgag tgcccggttc tgtgtgcaca attggcaatc    2340
caagatggat ggattcaaca cagggatata gcgagctacg tggtggtgcg aggatatagc    2400
aacggatatt tatgtttgac acttgagaat gtacgataca agcactgtcc aagtacaata    2460
ctaaacatac tgtacatact catactcgta cccgggcaac ggtttcactt gagtgcagtg    2520
gctagtgctc ttactcgtac agtgtgcaat actgcgtatc atagtctttg atgtatatcg    2580
tattcattca tgttagttgc gtacgctgtg ttgttgtatg tggtgaagct tgacaatgga    2640
tggtgtgtcg tatcaggctg gggaacaatt gtgcttaagt atgctgcagt tgagtaagag    2700
tcatcgctcc accaaaataa agtttgccat tagggttgga gagagagatg gtggctggaa    2760
gaattaaatg acatcaagct gaggattgtg ggtgtgcaat aacacatgtt agggggtgacc    2820
tgtggctcga aatctgataa ttattttgta actttatgat tattcttaga tttttttaata    2880
ttcctctata taacacataa gtagctgtcg tctagttgtt catagcctga ctcctgcaat    2940
agattagtgc agagtgattt tgtgcaattg agagccacgg ttgagtcaag tgactttgtg    3000
tgtgaagtca tcttacgttt caagtctcac aggttactca attggttggt tgtctgccct    3060
ttacagatat ttacagtacc tgagcgtaaa gtcgttcatc cacggaatga ctgttcctgt    3120
cacgcagtca tgatcatgga tgtggctggt caggaaccat tttggatagg agacttaggg    3180
attggactat tattgaaaaa actgagccga atatgtata gttctattg aatgcagaac    3240
ttctgatggt caattcactt atttcaggca tatcggtcat ggtggcagct gccacgatgt    3300
tatctcgttg gaaaccctcgg cgcgccagct gcattaatga atcggccaac gcgcggggag    3360
aggcggtttg cgtattgggc gctcttccgc ttcctcgctc actgactcgc tgcgctcggt    3420
cgttcggctg cggcgagcgg tatcagctca ctcaaaggcg gtaatacggt tatccacaga    3480
atcaggggat aacgcaggaa agaacatgtg agcaaaaggc cagcaaaagg ccaggaaccg    3540
```

```
taaaaaggcc gcgttgctgg cgttttcca taggctccgc ccccctgacg agcatcacaa    3600
aaatcgacgc tcaagtcaga ggtggcgaaa cccgacagga ctataaagat accaggcgtt    3660
tccccctgga agctccctcg tgcgctctcc tgttccgacc ctgccgctta ccggatacct    3720
gtccgccttt ctcccttcgg gaagcgtggc gctttctcat agctcacgct gtaggtatct    3780
cagttcggtg taggtcgttc gctccaagct gggctgtgtg cacgaacccc ccgttcagcc    3840
cgaccgctgc gccttatccg gtaactatcg tcttgagtcc aacccggtaa gacacgactt    3900
atcgccactg gcagcagcca ctggtaacag gattagcaga gcgaggtatg taggcggtgc    3960
tacagagttc ttgaagtggt ggcctaacta cggctacact agaagaacag tatttggtat    4020
ctgcgctctg ctgaagccag ttaccttcgg aaaaagagtt ggtagctctt gatccggcaa    4080
acaaaccacc gctggtagcg tggttttttt gtttgcaag cagcagatta cgcgcagaaa    4140
aaaaggatct caagaagatc ctttgatctt ttctacgggg tctgacgctc agtggaacga    4200
aaactcacgt taagggattt tggtcatgag attatcaaaa aggatcttca cctagatcct    4260
tttaaattaa aaatgaagtt ttaaatcaat ctaaagtata tatgagtaaa cttggtctga    4320
cagttaccaa tgcttaatca gtgaggcacc tatctcagcg atctgtctat ttcgttcatc    4380
catagttgcc tgactccccg tcgtgtagat aactacgata cgggagggct taccatctgg    4440
ccccagtgct gcaatgatac cgcgagaccc acgctcaccg gctccagatt tatcagcaat    4500
aaaccagcca gccggaaggg ccgagcgcag aagtggtcct gcaactttat ccgcctccat    4560
ccagtctatt aattgttgcc gggaagctag agtaagtagt tcgccagtta atagtttgcg    4620
caacgttgtt gccattgcta caggcatcgt ggtgtcacgc tcgtcgtttg gtatggcttc    4680
attcagctcc ggttcccaac gatcaaggcg agttacatga tcccccatgt tgtgcaaaaa    4740
agcggttagc tccttcggtc ctccgatcgt tgtcagaagt aagttggccg cagtgttatc    4800
actcatggtt atggcagcac tgcataattc tcttactgtc atgccatccg taagatgctt    4860
ttctgtgact ggtgagtact caaccaagtc attctgagaa tagtgtatgc ggcgaccgag    4920
ttgctcttgc ccggcgtcaa tacgggataa taccgcgcca catagcagaa ctttaaaagt    4980
gctcatcatt ggaaaacgtt cttcggggcg aaaactctca aggatcttac cgctgttgag    5040
atccagttcg atgtaaccca ctcgtgcacc caactgatct tcagcatctt ttactttcac    5100
cagcgtttct gggtgagcaa aaacaggaag gcaaaatgcc gcaaaaaagg gaataagggc    5160
gacacggaaa tgttgaatac tcatactctt cctttttcaa tattattgaa gcatttatca    5220
gggttattgt ctcatgagcg gatacatatt tgaatgtatt tagaaaaata aacaaatagg    5280
ggttccgcgc acatttcccc gaaaagtgcc acctgatgcg gtgtgaaata ccgcacagat    5340
gcgtaaggag aaaataccgc atcaggaaat tgtaagcgtt aatattttgt taaaattcgc    5400
gttaaatttt tgttaaatca gctcattttt taaccaatag gccgaaatcg gcaaaatccc    5460
ttataaatca aaagaataga ccgagatagg gttgagtgtt gttccagttt ggaacaagag    5520
tccactatta agaacgtgg actccaacgt caaaggcga aaaccgtct atcagggcga    5580
tggcccacta cgtgaaccat cacctaatc aagttttttg gggtcgaggt gccgtaaagc    5640
actaaatcgg aaccctaaag ggagccccg atttagagct tgacggggaa agccggcgaa    5700
cgtggcgaga aggaaggga agaaagcgaa aggagcgggc gctagggcgc tggcaagtgt    5760
agcggtcacg ctgcgcgtaa ccaccacacc cgccgcgctt aatgcgccgc tacagggcgc    5820
gtccattcgc cattcaggct gcgcaactgt tgggaagggc gatcggtgcg ggcctcttcg    5880
ctattacgcc agctggcgaa agggggatgt gctgcaaggc gattaagttg ggtaacgcca    5940
```

```
gggttttccc agtcacgacg ttgtaaaacg acggccagtg aattgtaata cgactcacta    6000
tagggcgaat tgggcccgac gtcgcatgca ttccatagcc acacctttgc ctatggcttc    6060
acaaccgaag gcaattcgag aggtcgcgct tatggaatcg actcgtataa agctgaaggg    6120
aaagggagac gttccgagcg ctcagatgca atagtcgtcc agctaatgtg gattcaaaaa    6180 caacccaac agtaatcttg aaaatttgaa cggatcaatc tgaacactct tgctccaggt     6240
cattcttcta acgcacatcc ccagagtcta gagggagttg tgttgtgaac atcctaataa    6300
acaatgcaat ggattcggga tatcttctgt ctcgcccct actcgatgtc gagtaaaccg     6360
atcaccaact aacaatactc ctccgcgttc tgccattgac tctcaaacag acatcgctat    6420
caacggaaca gcatatttta gcttcttagg acaataaata ttgataatgc cggctctccc    6480
tcggtatatt aagcaatcca ttcatacact cattcatcag gttaatttta tatatataat    6540
ttgtctattc aaacaccgta aattactggt accatcatct cctccttttc aaatacacgt    6600
ctatttgcat taatgaaatt actcgccaat tcgcagaacg tgtttgtcga acagagcctt    6660
agctcgggtc cagacaggag cagtgtctcg ctgaggaagc tgcaggagag ttaattaact    6720
cacctgcagg attgagacta tgaatggatt cccgtgcccg tattactcta ctaatttgat    6780
cttggaacgc gaaaatacgt ttctaggact ccaaagaatc tcaactcttg tccttactaa    6840
atatactacc catagttgat ggtttacttg aacagagagg acatgttcac ttgacccaaa    6900
gtttctcgca tctcttggat atttgaacaa cggcgtccac tgaccgtcag ttatccagtc    6960
acaaaccccc cacattcata cattcccatg tacgtttaca aagttctcaa ttccatcgtg    7020
caaatcaaaa tcacatctat tcattcatca tatataaacc catcatgtct actaacactc    7080
acaactccat agaaaacatc gactcagaac acacgctcca tgcggccgct taggaatcct    7140
gtgcgtcctt cacgcagtgg acgacaccca ccttatgcat gtacttcagg gtggagatga    7200
tgttgccgac gatggtaggg tagaaaacat atcgcactcc atgtcgttcg caacactccc    7260
ggaccgcctg ctggacgaag gggtagtgcc aagacgacat ccggggaaag aggtggtgct    7320
cgatctggaa attgagaccg ccagtgaaga acatggcgat ggggccaccg tatgtggagg    7380
acgtctccac ctgcgcccga taccagtcaa tttggtcagc ctcaacgtcc ttctcagatc    7440
gcttaacctt gcagttcttg tcggggatcc gttcggagcc atcaaaattg tgggacaaaa    7500
tgaagaagaa cgtcaagaag gcaccagttg cggtgggcac cagaggaatg gtgatcagca    7560
atgaggtccc agtgaggtac cagggcaaga atgcggtccg gaagatgaag aaagctcgca    7620
tcacgaatgc aagtgtgcgg tagcgccgca gaaagccatt ttcccgcatg gccgtgacag    7680
actctgggat ggtgtcattg tgctgcatcc ggaaaatgta gagcgggttg tacaccagcg    7740
ataccccgta tgcccccagc acaaggtaca tgtaccaagc ctggaagcgg tggaaccact    7800
ttcgggcggt gtttgcggcg gggtagttgt ggaacaccag gaacggctct gccgactccg    7860
catccaggtc gaggccgtgc tggttggtgt aggtgtggtg ccgcatgatg tgcgactgca    7920
gccaaatcca ccgggacgat ccgatgacgt caatgccgta ggcgaagagg gcgttgaccc    7980
aaggcttctt gctgatggcc ccgtgggacg catcatgctg gatggataag ccgatctgca    8040
tgtgcatgaa tccagtcaac aggccccaca gcaccatccc cgtggtagcc cagtgccact    8100
cgcaaaaggc cgtcacggcg atgatcccaa cggtgcgcag ccagaagcca ggggttgcgt    8160
accagttcct ccctttcatc acctcgcgca ttgtccgctt aacgtcttgt gcgaagggag    8220
aatcatacgt gtagacaatg tccttcgagg tgcggtcatg cttccctcgg acgaactgtt    8280
gaagcaattt ggagttctcc ggtttgacgt atggatgcat tgaataaaag agaggggagg    8340
```

-continued

```
catcagaggc accagaagcg agaatcaaat ctcctcctgg atgaactttg gcaagcccttt    8400
caaggtcgta gaggatgcca tcaatcgcaa ccaaatcagg gcgttctaac agctgttctg    8460
tggtaagact gagagccatg gagagctggg ttagtttgtg tagagagtgt gtgttgctag    8520
cgactttcgg attgtgtcat tacacaaaac gcgtcgtctc gacactgatc ttgtcgtgga    8580
tactcacggc tcggacatcg tcgccgacga tgacaccgga cttttcgctta aggacgtcag    8640
taacaggcat tgtgtgatgt gtagtttaga tttcgaatct gtggggaaag aaaggaaaaa    8700
agagactggc aaccgattgg gagagccact gtttatatat accctagaca agccccccgc    8760
ttgtaagatg ttggtcaatg taaaccagta ttaaggttgg caagtgcagg agaagcaagg    8820
tgtgggtacc gagcaatgga aatgtgcgga aggcaaaaaa atgaggccac ggcctattgt    8880
cggggctata tccagggggc gattgaagta cactaacatg acatgtgtcc acagaccctc    8940
aatctggcct gatgagccaa atccatacgc gctttcgcag ctctaaaggc tataacaagt    9000
cacaccaccc tgctcgacct cagcgccctc acttttttgtt aagacaaaact gtacacgctg    9060
ttccagcgtt ttctgcctgc acctggtggg acatttggtg caacctaaag tgctcggaac    9120
ctctgtggtg tccagatcag cgcagcagtt ccgaggtagt tttgaggccc ttagatgatg    9180
caatggtgtc agtcgctgga tcacgagtct taatggcagt attcgttctt atttgtgcca    9240
ttgagccccg ttatcctcgt atcttctacc ccccatccca tcctttgtt ggtgcaaccc    9300
tacccattta ttgttgggtg cagcccaacc gacgtggaga gcttggcttg gccatataaa    9360
aaggcccccc cctagtggca atggcagaaa gtcagctgtg agttgttgaa tttgtcatct    9420
aggcggcctg gccgtcttct ccggggcaat tgggctgtt ttttgggaca caaatacgcc    9480
gccaacccgg tctctcctga attccgtcgt cgcctgagtc gacatcattt atttaccagt    9540
tggccacaaa cccttgacga tctcgtatgt cccctccgac atactcccgg ccggctgggg    9600
tacgttcgat agcgctatcg gcatcgacaa ggtttgggtc cctagccgat accgcactac    9660
ctgagtcaca atcttcggag gtttagtctt ccacatagca cgggcaaaag tgcgtatata    9720
tacaagagcg tttgccagcc acagattttc actccacaca ccacatcaca catacaacca    9780
cacacatcca caatggaacc cgaaactaag aagaccaaga ctgactccaa gaagattgtt    9840
cttctcggcg gcgacttctg tggccccgag gtgattgccg aggccgtcaa ggtgctcaag    9900
tctgttgctg aggcctccgg caccgagttt gtgtttgagg accgactcat ggaggagct    9960
gccattgaga aggagggcga gcccatcacc gacgctactc tcgacatctg ccgaaaggct   10020
gactctatta tgctcggtgc tgtcggaggc gctgccaaca ccgtatggac cactcccgac   10080
ggacgaaccg acgtgcgacc cgagcagggt ctcctcaagc tgcgaaagga cctgaacctg   10140
tacgccaacc tgcgacctg ccagctgctg tcgcccaagc tcgccgatct ctcccccatc   10200
cgaaacgttg agggcaccga cttcatcatt gtccgagagc tcgtcggagg tatctacttt   10260
ggagagcgaa aggaggatga cggatctggc gtcgcttccg acaccgagac ctactccgtt   10320
cctgaggttg agcgaattgc ccgaatggcc gccttcctgg cccttcagca aaccccccct   10380
cttcccgtgt ggtctcttga caaggccaac gtgctggcct cctctcgact ttggcgaaag   10440
actgtcactc gagtcctcaa ggacgaactc ccccagctcg agctcaacca ccagctgatc   10500
gactcggccg ccatgatcct catcaagcag ccctccaaga tgaatggtat catcatcacc   10560
accaacatgt ttggcgatat catctccgac gaggcctccg tcatccccgg ttctctgggt   10620
ctgctgccct ccgcctctct ggcttctctg cccgacacca acgaggcgtt cggtctgtac   10680
gagccctgtc acggatctgc ccccgatctc ggcaagcaga aggtcaaccc cattgccacc   10740
```

```
attctgtctg ccgccatgat gctcaagttc tctcttaaca tgaagcccgc cggtgacgct   10800
gttgaggctg ccgtcaagga gtccgtcgag gctggtatca ctaccgccga tatcggaggc   10860
tcttcctcca cctccgaggt cggagacttg ttgccaacaa ggtcaaggag ctgctcaaga   10920
aggagtaagt cgtttctacg acgcattgat ggaaggagca aactgacgcg cctgcgggtt   10980
ggtctaccgg cagggtccgc tagtgtataa gactctataa aaagggccct gccctgctaa   11040
tgaaatgatg atttataatt taccggtgta gcaaccttga ctagaagaag cagattgggt   11100
gtgtttgtag tggaggacag tggtacgttt tggaaacagt cttcttgaaa gtgtcttgtc   11160
tacagtatat tcactcataa cctcaatagc caagggtgta gtcggtttat taaaggaagg   11220
gagttgtggc tgatgtggat atcgatagtt ggagcaaggg agaaatgtag agtgtgaaag   11280
actcactatg gtccgggctt atctcgacca atagccaaag tctggagttt ctgagagaaa   11340
aaggcaagat acgtatgtaa caaagcgacg catggtacaa taataccgga ggcatgtatc   11400
atagagagtt agtggttcga tgatggcact ggtgcctggt atgactttat acggctgact   11460
acatatttgt cctcagacat acaattacag tcaagcactt acccttggac atctgtaggt   11520
acccccccggc caagacgatc tcagcgtgtc gtatgtcgga ttggcgtagc tccctcgctc   11580
gtcaattggc tcccatctac tttcttctgc ttggctacac ccagcatgtc tgctatggct   11640
cgttttcgtg ccttatctat cctcccagta ttaccaactc taaatgacat gatgtgattg   11700
ggtctacact ttcatatcag agataaggag tagcacagtt gcataaaaag cccaactcta   11760
atcagcttct tcctttcttg taattagtac aaaggtgatt agcgaaatct ggaagcttag   11820
ttggccctaa aaaaatcaaa aaaagcaaaa aacgaaaaac gaaaaaccac agttttgaga   11880
acagggaggt aacgaaggat cgtatatata tatatatata tatatacccca cggatcccga   11940
gaccggcctt tgattcttcc ctacaaccaa ccattctcac caccctaatt cacaaccatg   12000
gctcccgacg ccgacaagct gcgacagcga aaggctcagt ccatccagga cactgccgat   12060
tctcaggcta ccgagctcaa gattggcacc ctgaagggtc tccaaggcac cgagatcgtc   12120
attgatggcg acatctacga catcaaagac ttcgatcacc ctggaggcga atccatcatg   12180
acctttggtg gcaacgacgt tactgccacc tacaagatga ttcatcccta ccactcgaag   12240
catcacctgg agaagatgaa aaaggtcggt cgagtgcccg actacacctc cgagtacaag   12300
ttcgatactc ccttcgaacg agagatcaaa caggaggtct tcaagattgt gcgaagaggt   12360
cgagagtttg gaacacctgg ctacttcttt cgagccttct gctacatcgg tctcttcttt   12420
tacctgcagt atctctgggt taccactcct accactttcg cccttgctat cttctacggt   12480
gtgtctcagg ccttcattgg cctgaacgtc cagcacgacg ccaaccacgg agctgcctcc   12540
aaaaagccct ggatcaacaa tttgctcggc ctgggtgccg actttatcgg aggctccaag   12600
tggctctgga tgaaccagca ctggaccccat cacacttaca ccaaccatca cgagaaggat   12660
cccgacgccc tgggtgcaga gcctatgctg ctcttcaacg actatccctt gggtcaccc   12720
aagcgaaccc tcattcatca cttccaagcc ttctactatc tgtttgtcct tgctggctac   12780
tgggtgtctt cggtgttcaa ccctcagatc ctggacctcc agcaccgagg tgcccaggct   12840
gtcggcatga agatggagaa cgactacatt gccaagtctc gaaagtacgc tatcttcctg   12900
cgactcctgt acatctacac caacattgtg gctcccatcc agaaccaagg cttttcgctc   12960
accgtcgttg ctcacattct tactatgggt gtcgcctcca gcctgaccct cgctactctg   13020
ttcgccctct cccacaactt cgagaacgca gatcgggatc ccacctacga ggctcgaaag   13080
ggaggcgagc ctgtctgttg gttcaagtcg caggtggaaa cctcctctac ttacggtggc   13140
```

```
ttcatttccg gttgccttac aggcggactc aactttcagg tcgagcatca cctgtttcct    13200
cgaatgtcct ctgcctggta cccctacatc gctcctaccg ttcgagaggt ctgcaaaaag    13260
cacggcgtca agtacgccta ctatccctgg gtgtggcaga acctcatctc gaccgtcaag    13320
tacctgcatc agtccggaac tggctcgaac tggaagaacg gtgccaatcc ctactctggc    13380
aagctgtaag cggccgcatg tacatacaag attatttata gaaatgaatc gcgatcgaac    13440
aaagagtacg agtgtacgag taggggatga tgataaaagt ggaagaagtt ccgcatcttt    13500
ggatttatca acgtgtagga cgatacttcc tgtaaaaatg caatgtcttt accataggtt    13560
ctgctgtaga tgttattaac taccattaac atgtctactt gtacagttgc agaccagttg    13620
gagtatagaa tggtacactt accaaaaagt gttgatggtt gtaactacga tatataaaac    13680
tgttgacggg atctgcgtac actgttt                                        13707

<210> SEQ ID NO 59
<211> LENGTH: 1350
<212> TYPE: DNA
<213> ORGANISM: Euglena gracilis
<220> FEATURE:
<221> NAME/KEY: CDS
<222> LOCATION: (1)..(1350)
<223> OTHER INFORMATION: delta-5 desaturase

<400> SEQUENCE: 59 atg gct ctc agt ctt acc aca gaa cag ctg tta gaa cgc cct gat ttg      48
Met Ala Leu Ser Leu Thr Thr Glu Gln Leu Leu Glu Arg Pro Asp Leu
1               5                   10                  15 gtt gcg att gat ggc atc ctc tac gac ctt gaa ggg ctt gcc aaa gtt      96
Val Ala Ile Asp Gly Ile Leu Tyr Asp Leu Glu Gly Leu Ala Lys Val
            20                  25                  30 cat cca gga gga gat ttg att ctc gct tct ggt gcc tct gat gcc tcc     144
His Pro Gly Gly Asp Leu Ile Leu Ala Ser Gly Ala Ser Asp Ala Ser
        35                  40                  45 cct ctc ttt tat tca atg cat cca tac gtc aaa ccg gag aat tcc aaa     192
Pro Leu Phe Tyr Ser Met His Pro Tyr Val Lys Pro Glu Asn Ser Lys
    50                  55                  60 ttg ctt caa cag ttc gtc cga ggg aag cat gac cgc acc tcg aag gac     240
Leu Leu Gln Gln Phe Val Arg Gly Lys His Asp Arg Thr Ser Lys Asp
65                  70                  75                  80 att gtc tac acg tat gat tct ccc ttc gca caa gac gtt aag cgg aca     288
Ile Val Tyr Thr Tyr Asp Ser Pro Phe Ala Gln Asp Val Lys Arg Thr
                85                  90                  95 atg cgc gag gtg atg aaa ggg agg aac tgg tac gca acc cct ggc ttc     336
Met Arg Glu Val Met Lys Gly Arg Asn Trp Tyr Ala Thr Pro Gly Phe
            100                 105                 110 tgg ctg cgc acc gtt ggg atc atc gcc gtg acg gcc ttt tgc gag tgg     384
Trp Leu Arg Thr Val Gly Ile Ile Ala Val Thr Ala Phe Cys Glu Trp
        115                 120                 125 cac tgg gct acc acg ggg atg gtg ctg tgg ggc ctg ttg act gga ttc     432
His Trp Ala Thr Thr Gly Met Val Leu Trp Gly Leu Leu Thr Gly Phe
    130                 135                 140 atg cac atg cag atc ggc tta tcc atc cag cat gat gcg tcc cac ggg     480
Met His Met Gln Ile Gly Leu Ser Ile Gln His Asp Ala Ser His Gly
145                 150                 155                 160 gcc atc agc aag aag cct tgg gtc aac gcc ctc ttc gcc tac ggc att     528
Ala Ile Ser Lys Lys Pro Trp Val Asn Ala Leu Phe Ala Tyr Gly Ile
                165                 170                 175 gac gtc atc gga tcg tcc cgg tgg att tgg ctg cag tcg cac atc atg     576
Asp Val Ile Gly Ser Ser Arg Trp Ile Trp Leu Gln Ser His Ile Met
            180                 185                 190
```

```
cgg cac cac acc tac acc aac cag cac ggc ctc gac ctg gat gcg gag      624
Arg His His Thr Tyr Thr Asn Gln His Gly Leu Asp Leu Asp Ala Glu
        195                 200                 205 tcg gca gag ccg ttc ctg gtg ttc cac aac tac ccc gcc gca aac acc      672
Ser Ala Glu Pro Phe Leu Val Phe His Asn Tyr Pro Ala Ala Asn Thr
210                 215                 220 gcc cga aag tgg ttc cac cgc ttc caa gct tgg tac atg tac ctt gtg      720
Ala Arg Lys Trp Phe His Arg Phe Gln Ala Trp Tyr Met Tyr Leu Val
225                 230                 235                 240 ctg ggg gca tac ggg gta tcg ctg gtg tac aac ccg ctc tac att ttc      768
Leu Gly Ala Tyr Gly Val Ser Leu Val Tyr Asn Pro Leu Tyr Ile Phe
                245                 250                 255 cgg atg cag cac aat gac acc atc cca gag tct gtc acg gcc atg cgg      816
Arg Met Gln His Asn Asp Thr Ile Pro Glu Ser Val Thr Ala Met Arg
            260                 265                 270 gag aat ggc ttt ctg cgg cgc tac cgc aca ctt gca ttc gtg atg cga      864
Glu Asn Gly Phe Leu Arg Arg Tyr Arg Thr Leu Ala Phe Val Met Arg
        275                 280                 285 gct ttc ttc atc ttc cgg acc gca ttc ttg ccc tgg tac ctc act ggg      912
Ala Phe Phe Ile Phe Arg Thr Ala Phe Leu Pro Trp Tyr Leu Thr Gly
290                 295                 300 acc tca ttg ctg atc acc att cct ctg gtg ccc act gca act ggt gcc      960
Thr Ser Leu Leu Ile Thr Ile Pro Leu Val Pro Thr Ala Thr Gly Ala
305                 310                 315                 320 ttc ttg acg ttc ttc ttc att ttg tcc cac aat ttt gat ggc tcc gaa     1008
Phe Leu Thr Phe Phe Phe Ile Leu Ser His Asn Phe Asp Gly Ser Glu
                325                 330                 335 cgg atc ccc gac aag aac tgc aag gtt aag agc tct gag aag gac gtt     1056
Arg Ile Pro Asp Lys Asn Cys Lys Val Lys Ser Ser Glu Lys Asp Val
            340                 345                 350 gag gct gac caa att gac tgg tat cgg gcg cag gtg gag acg tcc tcc     1104
Glu Ala Asp Gln Ile Asp Trp Tyr Arg Ala Gln Val Glu Thr Ser Ser
        355                 360                 365 aca tac ggt ggc ccc atc gcc atg ttc ttc act ggc ggt ctc aat ttc     1152
Thr Tyr Gly Gly Pro Ile Ala Met Phe Phe Thr Gly Gly Leu Asn Phe
370                 375                 380 cag atc gag cac cac ctc ttt ccc cgg atg tcg tct tgg cac tac ccc     1200
Gln Ile Glu His His Leu Phe Pro Arg Met Ser Ser Trp His Tyr Pro
385                 390                 395                 400 ttc gtc cag cag gcg gtc cgg gag tgt tgc gaa cgc cat gga gtg cga     1248
Phe Val Gln Gln Ala Val Arg Glu Cys Cys Glu Arg His Gly Val Arg
                405                 410                 415 tat gtt ttc tac cct acc atc gtc ggc aac atc atc tcc acc ctg aag     1296
Tyr Val Phe Tyr Pro Thr Ile Val Gly Asn Ile Ile Ser Thr Leu Lys
            420                 425                 430 tac atg cat aag gtg ggt gtc gtc cac tgc gtg aag gac gca cag gat     1344
Tyr Met His Lys Val Gly Val Val His Cys Val Lys Asp Ala Gln Asp
        435                 440                 445 tcc tga                                                              1350
Ser

<210> SEQ ID NO 60
<211> LENGTH: 449
<212> TYPE: PRT
<213> ORGANISM: Euglena gracilis

<400> SEQUENCE: 60

Met Ala Leu Ser Leu Thr Thr Glu Gln Leu Leu Glu Arg Pro Asp Leu
1               5                   10                  15

Val Ala Ile Asp Gly Ile Leu Tyr Asp Leu Glu Gly Leu Ala Lys Val
            20                  25                  30
```

```
His Pro Gly Gly Asp Leu Ile Leu Ala Ser Gly Ala Ser Asp Ala Ser
         35                  40                  45

Pro Leu Phe Tyr Ser Met His Pro Tyr Val Lys Pro Glu Asn Ser Lys
 50                  55                  60

Leu Leu Gln Gln Phe Val Arg Gly Lys His Asp Arg Thr Ser Lys Asp
 65                  70                  75                  80

Ile Val Tyr Thr Tyr Asp Ser Pro Phe Ala Gln Asp Val Lys Arg Thr
                 85                  90                  95

Met Arg Glu Val Met Lys Gly Arg Asn Trp Tyr Ala Thr Pro Gly Phe
                100                 105                 110

Trp Leu Arg Thr Val Gly Ile Ala Val Thr Ala Phe Cys Glu Trp
            115                 120                 125

His Trp Ala Thr Thr Gly Met Val Leu Trp Gly Leu Leu Thr Gly Phe
        130                 135                 140

Met His Met Gln Ile Gly Leu Ser Ile Gln His Asp Ala Ser His Gly
145                 150                 155                 160

Ala Ile Ser Lys Lys Pro Trp Val Asn Ala Leu Phe Ala Tyr Gly Ile
                165                 170                 175

Asp Val Ile Gly Ser Ser Arg Trp Ile Trp Leu Gln Ser His Ile Met
                180                 185                 190

Arg His His Thr Tyr Thr Asn Gln His Gly Leu Asp Leu Asp Ala Glu
        195                 200                 205

Ser Ala Glu Pro Phe Leu Val Phe His Asn Tyr Pro Ala Ala Asn Thr
210                 215                 220

Ala Arg Lys Trp Phe His Arg Phe Gln Ala Trp Tyr Met Tyr Leu Val
225                 230                 235                 240

Leu Gly Ala Tyr Gly Val Ser Leu Val Tyr Asn Pro Leu Tyr Ile Phe
                245                 250                 255

Arg Met Gln His Asn Asp Thr Ile Pro Glu Ser Val Thr Ala Met Arg
                260                 265                 270

Glu Asn Gly Phe Leu Arg Arg Tyr Arg Thr Leu Ala Phe Val Met Arg
                275                 280                 285

Ala Phe Phe Ile Phe Arg Thr Ala Phe Leu Pro Trp Tyr Leu Thr Gly
290                 295                 300

Thr Ser Leu Leu Ile Thr Ile Pro Leu Val Pro Thr Ala Thr Gly Ala
305                 310                 315                 320

Phe Leu Thr Phe Phe Phe Ile Leu Ser His Asn Phe Asp Gly Ser Glu
                325                 330                 335

Arg Ile Pro Asp Lys Asn Cys Lys Val Lys Ser Ser Glu Lys Asp Val
                340                 345                 350

Glu Ala Asp Gln Ile Asp Trp Tyr Arg Ala Gln Val Glu Thr Ser Ser
                355                 360                 365

Thr Tyr Gly Gly Pro Ile Ala Met Phe Phe Thr Gly Gly Leu Asn Phe
        370                 375                 380

Gln Ile Glu His His Leu Phe Pro Arg Met Ser Ser Trp His Tyr Pro
385                 390                 395                 400

Phe Val Gln Gln Ala Val Arg Glu Cys Cys Glu Arg His Gly Val Arg
                405                 410                 415

Tyr Val Phe Tyr Pro Thr Ile Val Gly Asn Ile Ile Ser Thr Leu Lys
                420                 425                 430

Tyr Met His Lys Val Gly Val Val His Cys Val Lys Asp Ala Gln Asp
                435                 440                 445

Ser
```

<210> SEQ ID NO 61
<211> LENGTH: 1350
<212> TYPE: DNA
<213> ORGANISM: Euglena gracilis
<220> FEATURE:
<221> NAME/KEY: CDS
<222> LOCATION: (1)..(1350)
<223> OTHER INFORMATION: synthetic delta-5 desaturase (codon-optimized for Yarrowia lipolytica)

<400> SEQUENCE: 61

```
atg gct ctc tcc ctt act acc gag cag ctg ctc gag cga ccc gac ctg      48
Met Ala Leu Ser Leu Thr Thr Glu Gln Leu Leu Glu Arg Pro Asp Leu
1               5                   10                  15 gtt gcc atc gac ggc att ctc tac gat ctg gaa ggt ctt gcc aag gtc      96
Val Ala Ile Asp Gly Ile Leu Tyr Asp Leu Glu Gly Leu Ala Lys Val
                20                  25                  30 cat ccc gga ggc gac ttg atc ctc gct tct ggt gcc tcc gat gct tct     144
His Pro Gly Gly Asp Leu Ile Leu Ala Ser Gly Ala Ser Asp Ala Ser
            35                  40                  45 cct ctg ttc tac tcc atg cac cct tac gtc aag ccc gag aac tcg aag     192
Pro Leu Phe Tyr Ser Met His Pro Tyr Val Lys Pro Glu Asn Ser Lys
        50                  55                  60 ctg ctt caa cag ttc gtg cga ggc aag cac gac cga acc tcc aag gac     240
Leu Leu Gln Gln Phe Val Arg Gly Lys His Asp Arg Thr Ser Lys Asp
65                  70                  75                  80 att gtc tac acc tac gac tct ccc ttt gca cag gac gtc aag cga act     288
Ile Val Tyr Thr Tyr Asp Ser Pro Phe Ala Gln Asp Val Lys Arg Thr
                85                  90                  95 atg cga gag gtc atg aaa ggt cgg aac tgg tat gcc aca cct gga ttc     336
Met Arg Glu Val Met Lys Gly Arg Asn Trp Tyr Ala Thr Pro Gly Phe
                100                 105                 110 tgg ctg cga acc gtt ggc atc att gct gtc acc gcc ttt tgc gag tgg     384
Trp Leu Arg Thr Val Gly Ile Ile Ala Val Thr Ala Phe Cys Glu Trp
            115                 120                 125 cac tgg gct act acc gga atg gtg ctg tgg ggt ctc ttg act gga ttc     432
His Trp Ala Thr Thr Gly Met Val Leu Trp Gly Leu Leu Thr Gly Phe
        130                 135                 140 atg cac atg cag atc ggc ctg tcc att cag cac gat gcc tct cat ggt     480
Met His Met Gln Ile Gly Leu Ser Ile Gln His Asp Ala Ser His Gly
145                 150                 155                 160 gcc atc agc aaa aag ccc tgg gtc aac gct ctc ttt gcc tac ggc atc     528
Ala Ile Ser Lys Lys Pro Trp Val Asn Ala Leu Phe Ala Tyr Gly Ile
                165                 170                 175 gac gtc att gga tcg tcc aga tgg atc tgg ctg cag tct cac atc atg     576
Asp Val Ile Gly Ser Ser Arg Trp Ile Trp Leu Gln Ser His Ile Met
                180                 185                 190 cga cat cac acc tac acc aat cag cat ggt ctc gac ctg gat gcc gag     624
Arg His His Thr Tyr Thr Asn Gln His Gly Leu Asp Leu Asp Ala Glu
            195                 200                 205 tcc gca gaa cca ttc ctt gtg ttc cac aac tac cct gct gcc aac act     672
Ser Ala Glu Pro Phe Leu Val Phe His Asn Tyr Pro Ala Ala Asn Thr
        210                 215                 220 gct cga aag tgg ttt cac cga ttc cag gcc tgg tac atg tac ctc gtg     720
Ala Arg Lys Trp Phe His Arg Phe Gln Ala Trp Tyr Met Tyr Leu Val
225                 230                 235                 240 ctt gga gcc tac ggc gtt tcg ctg gtg tac aac cct ctc tac atc ttc     768
Leu Gly Ala Tyr Gly Val Ser Leu Val Tyr Asn Pro Leu Tyr Ile Phe
                245                 250                 255 cga atg cag cac aac gac acc att ccc gag tct gtc aca gcc atg cga     816
Arg Met Gln His Asn Asp Thr Ile Pro Glu Ser Val Thr Ala Met Arg
```

```
                  260                 265                 270
gag aac ggc ttt ctg cga cgg tac cga acc ctt gca ttc gtt atg cga      864
Glu Asn Gly Phe Leu Arg Arg Tyr Arg Thr Leu Ala Phe Val Met Arg
        275                 280                 285 gct ttc ttc atc ttt cga acc gcc ttc ttg ccc tgg tat ctc act gga      912
Ala Phe Phe Ile Phe Arg Thr Ala Phe Leu Pro Trp Tyr Leu Thr Gly
290                 295                 300 acc tcc ctg ctc atc acc att cct ctg gtg ccc act gct acc ggt gcc      960
Thr Ser Leu Leu Ile Thr Ile Pro Leu Val Pro Thr Ala Thr Gly Ala
305                 310                 315                 320 ttc ctc acc ttc ttt ttc atc ttg tct cac aac ttc gat ggc tcg gag     1008
Phe Leu Thr Phe Phe Phe Ile Leu Ser His Asn Phe Asp Gly Ser Glu
                325                 330                 335 cga atc ccc gac aag aac tgc aag gtc aag agc tcc gag aag gac gtt     1056
Arg Ile Pro Asp Lys Asn Cys Lys Val Lys Ser Ser Glu Lys Asp Val
            340                 345                 350 gaa gcc gat cag atc gac tgg tac aga gct cag gtg gag acc tct tcc     1104
Glu Ala Asp Gln Ile Asp Trp Tyr Arg Ala Gln Val Glu Thr Ser Ser
        355                 360                 365 acc tac ggt gga ccc att gcc atg ttc ttt act ggc ggt ctc aac ttc     1152
Thr Tyr Gly Gly Pro Ile Ala Met Phe Phe Thr Gly Gly Leu Asn Phe
370                 375                 380 cag atc gag cat cac ctc ttt cct cga atg tcg tct tgg cac tat ccc     1200
Gln Ile Glu His His Leu Phe Pro Arg Met Ser Ser Trp His Tyr Pro
385                 390                 395                 400 ttc gtg cag caa gct gtc cga gag tgt tgc gaa cga cac gga gtt cgg     1248
Phe Val Gln Gln Ala Val Arg Glu Cys Cys Glu Arg His Gly Val Arg
                405                 410                 415 tac gtc ttc tac cct acc att gtg ggc aac atc att tcc acc ctc aag     1296
Tyr Val Phe Tyr Pro Thr Ile Val Gly Asn Ile Ile Ser Thr Leu Lys
            420                 425                 430 tac atg cac aaa gtc ggt gtg gtt cac tgt gtc aag gac gct cag gat     1344
Tyr Met His Lys Val Gly Val Val His Cys Val Lys Asp Ala Gln Asp
        435                 440                 445 tcc taa                                                              1350
Ser

<210> SEQ ID NO 62
<211> LENGTH: 449
<212> TYPE: PRT
<213> ORGANISM: Euglena gracilis

<400> SEQUENCE: 62

Met Ala Leu Ser Leu Thr Thr Glu Gln Leu Glu Arg Pro Asp Leu
1               5                   10                  15

Val Ala Ile Asp Gly Ile Leu Tyr Asp Leu Glu Gly Leu Ala Lys Val
                20                  25                  30

His Pro Gly Gly Asp Leu Ile Leu Ala Ser Gly Ala Ser Asp Ala Ser
            35                  40                  45

Pro Leu Phe Tyr Ser Met His Pro Tyr Val Lys Pro Glu Asn Ser Lys
        50                  55                  60

Leu Leu Gln Gln Phe Val Arg Gly Lys His Asp Arg Thr Ser Lys Asp
65                  70                  75                  80

Ile Val Tyr Thr Tyr Asp Ser Pro Phe Ala Gln Asp Val Lys Arg Thr
                85                  90                  95

Met Arg Glu Val Met Lys Gly Arg Asn Trp Tyr Ala Thr Pro Gly Phe
            100                 105                 110

Trp Leu Arg Thr Val Gly Ile Ile Ala Val Thr Ala Phe Cys Glu Trp
        115                 120                 125
```

His Trp Ala Thr Thr Gly Met Val Leu Trp Gly Leu Leu Thr Gly Phe
    130                 135                 140

Met His Met Gln Ile Gly Leu Ser Ile Gln His Asp Ala Ser His Gly
145                 150                 155                 160

Ala Ile Ser Lys Lys Pro Trp Val Asn Ala Leu Phe Ala Tyr Gly Ile
                165                 170                 175

Asp Val Ile Gly Ser Ser Arg Trp Ile Trp Leu Gln Ser His Ile Met
            180                 185                 190

Arg His His Thr Tyr Thr Asn Gln His Gly Leu Asp Leu Asp Ala Glu
        195                 200                 205

Ser Ala Glu Pro Phe Leu Val Phe His Asn Tyr Pro Ala Ala Asn Thr
210                 215                 220

Ala Arg Lys Trp Phe His Arg Phe Gln Ala Trp Tyr Met Tyr Leu Val
225                 230                 235                 240

Leu Gly Ala Tyr Gly Val Ser Leu Val Tyr Asn Pro Leu Tyr Ile Phe
                245                 250                 255

Arg Met Gln His Asn Asp Thr Ile Pro Glu Ser Val Thr Ala Met Arg
            260                 265                 270

Glu Asn Gly Phe Leu Arg Arg Tyr Arg Thr Leu Ala Phe Val Met Arg
        275                 280                 285

Ala Phe Phe Ile Phe Arg Thr Ala Phe Leu Pro Trp Tyr Leu Thr Gly
290                 295                 300

Thr Ser Leu Leu Ile Thr Ile Pro Leu Val Pro Thr Ala Thr Gly Ala
305                 310                 315                 320

Phe Leu Thr Phe Phe Phe Ile Leu Ser His Asn Phe Asp Gly Ser Glu
                325                 330                 335

Arg Ile Pro Asp Lys Asn Cys Lys Val Lys Ser Ser Glu Lys Asp Val
            340                 345                 350

Glu Ala Asp Gln Ile Asp Trp Tyr Arg Ala Gln Val Glu Thr Ser Ser
        355                 360                 365

Thr Tyr Gly Gly Pro Ile Ala Met Phe Phe Thr Gly Gly Leu Asn Phe
    370                 375                 380

Gln Ile Glu His His Leu Phe Pro Arg Met Ser Ser Trp His Tyr Pro
385                 390                 395                 400

Phe Val Gln Gln Ala Val Arg Glu Cys Cys Glu Arg His Gly Val Arg
                405                 410                 415

Tyr Val Phe Tyr Pro Thr Ile Val Gly Asn Ile Ile Ser Thr Leu Lys
            420                 425                 430

Tyr Met His Lys Val Gly Val Val His Cys Val Lys Asp Ala Gln Asp
        435                 440                 445

Ser

<210> SEQ ID NO 63
<211> LENGTH: 1392
<212> TYPE: DNA
<213> ORGANISM: Peridinium sp. CCMP626
<220> FEATURE:
<221> NAME/KEY: CDS
<222> LOCATION: (1)..(1392)
<223> OTHER INFORMATION: synthetic delta-5 desaturase (codon-optimized for Yarrowia lipolytica)

<400> SEQUENCE: 63 atg gct ccc gac gcc gac aag ctg cga cag cga aag gct cag tcc atc    48
Met Ala Pro Asp Ala Asp Lys Leu Arg Gln Arg Lys Ala Gln Ser Ile
1               5                   10                  15

-continued

| | | |
|---|---|---|
| cag gac act gcc gat tct cag gct acc gag ctc aag att ggc acc ctg<br>Gln Asp Thr Ala Asp Ser Gln Ala Thr Glu Leu Lys Ile Gly Thr Leu<br>     20                   25                   30 | 96 |
| aag ggt ctc caa ggc acc gag atc gtc att gat ggc gac atc tac gac<br>Lys Gly Leu Gln Gly Thr Glu Ile Val Ile Asp Gly Asp Ile Tyr Asp<br>         35                   40                   45 | 144 |
| atc aaa gac ttc gat cac cct gga ggc gaa tcc atc atg acc ttt ggt<br>Ile Lys Asp Phe Asp His Pro Gly Gly Glu Ser Ile Met Thr Phe Gly<br>50                   55                   60 | 192 |
| ggc aac gac gtt act gcc acc tac aag atg att cat ccc tac cac tcg<br>Gly Asn Asp Val Thr Ala Thr Tyr Lys Met Ile His Pro Tyr His Ser<br>65                   70                75                  80 | 240 |
| aag cat cac ctg gag aag atg aaa aag gtc ggt cga gtg ccc gac tac<br>Lys His His Leu Glu Lys Met Lys Lys Val Gly Arg Val Pro Asp Tyr<br>                   85                   90                   95 | 288 |
| acc tcc gag tac aag ttc gat act ccc ttc gaa cga gag atc aaa cag<br>Thr Ser Glu Tyr Lys Phe Asp Thr Pro Phe Glu Arg Glu Ile Lys Gln<br>                100                105               110 | 336 |
| gag gtc ttc aag att gtg cga aga ggt cga gag ttt gga aca cct ggc<br>Glu Val Phe Lys Ile Val Arg Arg Gly Arg Glu Phe Gly Thr Pro Gly<br>              115                120               125 | 384 |
| tac ttc ttt cga gcc ttc tgc tac atc ggt ctc ttt tac ctg cag<br>Tyr Phe Phe Arg Ala Phe Cys Tyr Ile Gly Leu Phe Phe Tyr Leu Gln<br>130                   135                   140 | 432 |
| tat ctc tgg gtt acc act cct acc act ttc gcc ctt gct atc ttc tac<br>Tyr Leu Trp Val Thr Thr Pro Thr Thr Phe Ala Leu Ala Ile Phe Tyr<br>145                   150                   155               160 | 480 |
| ggt gtg tct cag gcc ttc att ggc ctg aac gtc cag cac gac gcc aac<br>Gly Val Ser Gln Ala Phe Ile Gly Leu Asn Val Gln His Asp Ala Asn<br>                    165                170               175 | 528 |
| cac gga gct gcc tcc aaa aag ccc tgg atc aac aat ttg ctc ggc ctg<br>His Gly Ala Ala Ser Lys Lys Pro Trp Ile Asn Asn Leu Leu Gly Leu<br>              180                185               190 | 576 |
| ggt gcc gac ttt atc gga ggc tcc aag tgg ctc tgg atg aac cag cac<br>Gly Ala Asp Phe Ile Gly Gly Ser Lys Trp Leu Trp Met Asn Gln His<br>                195                200               205 | 624 |
| tgg acc cat cac act tac acc aac cat cac gag aag gat ccc gac gcc<br>Trp Thr His His Thr Tyr Thr Asn His His Glu Lys Asp Pro Asp Ala<br>210                   215                   220 | 672 |
| ctg ggt gca gag cct atg ctg ctc ttc aac gac tat ccc ttg ggt cac<br>Leu Gly Ala Glu Pro Met Leu Leu Phe Asn Asp Tyr Pro Leu Gly His<br>225                   230                   235               240 | 720 |
| ccc aag cga acc ctc att cat cac ttc caa gcc ttc tac tat ctg ttt<br>Pro Lys Arg Thr Leu Ile His His Phe Gln Ala Phe Tyr Tyr Leu Phe<br>                    245                250               255 | 768 |
| gtc ctt gct ggc tac tgg gtg tct tcg gtg ttc aac cct cag atc ctg<br>Val Leu Ala Gly Tyr Trp Val Ser Ser Val Phe Asn Pro Gln Ile Leu<br>              260                265               270 | 816 |
| gac ctc cag cac cga ggt gcc cag gct gtc ggc atg aag atg gag aac<br>Asp Leu Gln His Arg Gly Ala Gln Ala Val Gly Met Lys Met Glu Asn<br>            275                280               285 | 864 |
| gac tac att gcc aag tct cga aag tac gct atc ttc ctg cga ctc ctg<br>Asp Tyr Ile Ala Lys Ser Arg Lys Tyr Ala Ile Phe Leu Arg Leu Leu<br>         290                295               300 | 912 |
| tac atc tac acc aac att gtg gct ccc atc cag aac caa ggc ttt tcg<br>Tyr Ile Tyr Thr Asn Ile Val Ala Pro Ile Gln Asn Gln Gly Phe Ser<br>305                   310                   315               320 | 960 |
| ctc acc gtc gtt gct cac att ctt act atg ggt gtc gcc tcc agc ctg<br>Leu Thr Val Val Ala His Ile Leu Thr Met Gly Val Ala Ser Ser Leu<br>                    325                330               335 | 1008 |

```
acc ctc gct act ctg ttc gcc ctc tcc cac aac ttc gag aac gca gat     1056
Thr Leu Ala Thr Leu Phe Ala Leu Ser His Asn Phe Glu Asn Ala Asp
        340                 345                 350 cgg gat ccc acc tac gag gct cga aag gga ggc gag cct gtc tgt tgg     1104
Arg Asp Pro Thr Tyr Glu Ala Arg Lys Gly Gly Glu Pro Val Cys Trp
            355                 360                 365 ttc aag tcg cag gtg gaa acc tcc tct act tac ggt ggc ttc att tcc     1152
Phe Lys Ser Gln Val Glu Thr Ser Ser Thr Tyr Gly Gly Phe Ile Ser
    370                 375                 380 ggt tgc ctt aca ggc gga ctc aac ttt cag gtc gag cat cac ctg ttt     1200
Gly Cys Leu Thr Gly Gly Leu Asn Phe Gln Val Glu His His Leu Phe
385                 390                 395                 400 cct cga atg tcc tct gcc tgg tac ccc tac atc gct cct acc gtt cga     1248
Pro Arg Met Ser Ser Ala Trp Tyr Pro Tyr Ile Ala Pro Thr Val Arg
                405                 410                 415 gag gtc tgc aaa aag cac ggc gtc aag tac gcc tac tat ccc tgg gtg     1296
Glu Val Cys Lys Lys His Gly Val Lys Tyr Ala Tyr Tyr Pro Trp Val
            420                 425                 430 tgg cag aac ctc atc tcg acc gtc aag tac ctg cat cag tcc gga act     1344
Trp Gln Asn Leu Ile Ser Thr Val Lys Tyr Leu His Gln Ser Gly Thr
    435                 440                 445 ggc tcg aac tgg aag aac ggt gcc aat ccc tac tct ggc aag ctg taa     1392
Gly Ser Asn Trp Lys Asn Gly Ala Asn Pro Tyr Ser Gly Lys Leu
450                 455                 460

<210> SEQ ID NO 64
<211> LENGTH: 463
<212> TYPE: PRT
<213> ORGANISM: Peridinium sp. CCMP626

<400> SEQUENCE: 64

Met Ala Pro Asp Ala Asp Lys Leu Arg Gln Arg Lys Ala Gln Ser Ile
1               5                   10                  15

Gln Asp Thr Ala Asp Ser Gln Ala Thr Glu Leu Lys Ile Gly Thr Leu
            20                  25                  30

Lys Gly Leu Gln Gly Thr Glu Ile Val Ile Asp Gly Asp Ile Tyr Asp
        35                  40                  45

Ile Lys Asp Phe Asp His Pro Gly Gly Glu Ser Ile Met Thr Phe Gly
    50                  55                  60

Gly Asn Asp Val Thr Ala Thr Tyr Lys Met Ile His Pro Tyr His Ser
65                  70                  75                  80

Lys His His Leu Glu Lys Met Lys Lys Val Gly Arg Val Pro Asp Tyr
                85                  90                  95

Thr Ser Glu Tyr Lys Phe Asp Thr Pro Phe Glu Arg Glu Ile Lys Gln
            100                 105                 110

Glu Val Phe Lys Ile Val Arg Arg Gly Arg Glu Phe Gly Thr Pro Gly
        115                 120                 125

Tyr Phe Phe Arg Ala Phe Cys Tyr Ile Gly Leu Phe Phe Tyr Leu Gln
    130                 135                 140

Tyr Leu Trp Val Thr Thr Pro Thr Thr Phe Ala Leu Ala Ile Phe Tyr
145                 150                 155                 160

Gly Val Ser Gln Ala Phe Ile Gly Leu Asn Val Gln His Asp Ala Asn
                165                 170                 175

His Gly Ala Ala Ser Lys Lys Pro Trp Ile Asn Asn Leu Leu Gly Leu
            180                 185                 190

Gly Ala Asp Phe Ile Gly Gly Ser Lys Trp Leu Trp Met Asn Gln His
        195                 200                 205

Trp Thr His His Thr Tyr Thr Asn His His Glu Lys Asp Pro Asp Ala
```

|       |     | 210 |     |     |     | 215 |     |     |     | 220 |     |
|-------|-----|-----|-----|-----|-----|-----|-----|-----|-----|-----|-----|

Leu Gly Ala Glu Pro Met Leu Leu Phe Asn Asp Tyr Pro Leu Gly His
225                 230                 235                 240

Pro Lys Arg Thr Leu Ile His His Phe Gln Ala Phe Tyr Leu Phe
                245                 250                 255

Val Leu Ala Gly Tyr Trp Val Ser Val Phe Asn Pro Gln Ile Leu
            260                 265                 270

Asp Leu Gln His Arg Gly Ala Gln Ala Val Gly Met Lys Met Glu Asn
            275                 280                 285

Asp Tyr Ile Ala Lys Ser Arg Lys Tyr Ala Ile Phe Leu Arg Leu Leu
    290                 295                 300

Tyr Ile Tyr Thr Asn Ile Val Ala Pro Ile Gln Asn Gln Gly Phe Ser
305                 310                 315                 320

Leu Thr Val Val Ala His Ile Leu Thr Met Gly Val Ala Ser Ser Leu
                325                 330                 335

Thr Leu Ala Thr Leu Phe Ala Leu Ser His Asn Phe Glu Asn Ala Asp
            340                 345                 350

Arg Asp Pro Thr Tyr Glu Ala Arg Lys Gly Gly Glu Pro Val Cys Trp
            355                 360                 365

Phe Lys Ser Gln Val Glu Thr Ser Ser Thr Tyr Gly Phe Ile Ser
370                 375                 380

Gly Cys Leu Thr Gly Leu Asn Phe Gln Val Glu His Leu Phe
385                 390                 395                 400

Pro Arg Met Ser Ser Ala Trp Tyr Pro Tyr Ile Ala Pro Thr Val Arg
                405                 410                 415

Glu Val Cys Lys Lys His Gly Val Lys Tyr Ala Tyr Tyr Pro Trp Val
            420                 425                 430

Trp Gln Asn Leu Ile Ser Thr Val Lys Tyr Leu His Gln Ser Gly Thr
            435                 440                 445

Gly Ser Asn Trp Lys Asn Gly Ala Asn Pro Tyr Ser Gly Lys Leu
    450                 455                 460

<210> SEQ ID NO 65
<211> LENGTH: 13066
<212> TYPE: DNA
<213> ORGANISM: Artificial Sequence
<220> FEATURE:
<223> OTHER INFORMATION: Plasmid pZP3-Pa777U

<400> SEQUENCE: 65
tctcggtcta ttcttttgat ttataaggga ttttgccgat ttcggcctat tggttaaaaa     60
atgagctgat ttaacaaaaa tttaacgcga atttttaacaa atattaacg cttacaattt    120 cctgatgcgg tattttctcc ttacgcatct gtgcggtatt tcacaccgca tcaggtggca    180
cttttcgggg aaatgtgcgc ggaaccccta tttgtttatt tttctaaata cattcaaata    240
tgtatccgct catgagacaa taaccctgat aaatgcttca ataatattga aaaggaaga    300 gtatgagtat tcaacatttc cgtgtcgccc ttattccctt ttttgcggca ttttgccttc    360 ctgttttgc tcacccagaa acgctggtga agtaaaaga tgctgaagat cagttgggtg    420
cacgagtggg ttacatcgaa ctggatctca acagcggtaa gatccttgag agttttcgcc    480
ccgaagaacg ttttccaatg atgagcactt ttaaagttct gctatgtggc gcggtattat    540
cccgtattga cgccgggcaa gagcaactcg gtcgccgcat acactattct cagaatgact    600
tggttgagta ctcaccagtc acagaaaagc atcttacgga tggcatgaca gtaagagaat    660
tatgcagtgc tgccataacc atgagtgata acactgcggc caacttactt ctgacaacga    720

```
tcggaggacc gaaggagcta accgcttttt tgcacaacat ggggatcat gtaactcgcc    780
ttgatcgttg ggaaccggag ctgaatgaag ccataccaaa cgacgagcgt gacaccacga    840
tgcctgtagc aatggcaaca acgttgcgca aactattaac tggcgaacta cttactctag    900
cttcccggca acaattaata gactggatgg aggcggataa agttgcagga ccacttctgc    960
gctcggccct tccggctggc tggtttattg ctgataaatc tggagccggt gagcgtgggt   1020
ctcgcggtat cattgcagca ctgggccag atggtaagcc ctcccgtatc gtagttatct   1080
acacgacggg gagtcaggca actatggatg aacgaaatag acagatcgct gagataggtg   1140
cctcactgat taagcattgg taactgtcag accaagttta ctcatatata ctttagattg   1200
atttaaaact tcattttaa tttaaaagga tctaggtgaa gatccttttt gataatctca   1260
tgaccaaaat cccttaacgt gagttttcgt tccactgagc gtcagacccc gtagaaaaga   1320
tcaaaggatc ttcttgagat cctttttttc tgcgcgtaat ctgctgcttg caaacaaaaa   1380
aaccaccgct accagcggtg gtttgtttgc cggatcaaga gctaccaact cttttccga    1440
aggtaactgg cttcagcaga gcgcagatac caaatactgt tcttctagtg tagccgtagt   1500
taggccacca cttcaagaac tctgtagcac cgcctacata cctcgctctg ctaatcctgt   1560
taccagtggc tgctgccagt ggcgataagt cgtgtcttac cgggttggac tcaagacgat   1620
agttaccgga taaggcgcag cggtcgggct gaacggggg ttcgtgcaca cagcccagct   1680
tggagcgaac gacctacacc gaactgagat acctacagcg tgagctatga aaagcgcca   1740
cgcttcccga agggagaaag gcggacaggt atccggtaag cggcagggtc ggaacaggag   1800
agcgcacgag ggagcttcca gggggaaacg cctggtatct ttatagtcct gtcgggtttc   1860
gccacctctg acttgagcgt cgatttttgt gatgctcgtc agggggggcgg agcctatgga   1920
aaaacgccag caacgcggcc ttttttacggt tcctggcctt tgctggcct tttgctcaca   1980
tgttctttcc tgcgttatcc cctgattctg tggataaccg tattaccgcc tttgagtgag   2040
ctgataccgc tcgccgcagc cgaacgaccg agcgcagcga gtcagtgagc gaggaagcgg   2100
aagagcgccc aatacgcaaa ccgcctctcc ccgcgcgttg gccgattcat taatgcagct   2160
ggcgcgccac caatcacaat tctgaaaagc acatcttgat ctcctcattg cggggagtcc   2220
aacggtggtc ttattccccc gaatttcccg ctcaatctcg ttccagaccg acccggacac   2280
agtgcttaac gccgttccga aactctaccg cagatatgct ccaacggact gggctgcata   2340
gatgtgatcc tcggcttgga gaaatggata aaagccggcc aaaaaaaaag cggaaaaaag   2400
cggaaaaaaa gagaaaaaaa atcgcaaaat ttgaaaaata gggggaaaag acgcaaaaac   2460
gcaaggaggg gggagtatat gacactgata agcaagctca caacggttcc tcttattttt   2520
ttcctcatct tctgcctagg ttcccaaaat cccagatgct tctctccagt gccaaaagta   2580
agtaccccac aggttttcgg ccgaaaattc cacgtgcagc aacgtcgtgt ggggtgttaa   2640
aatgtggggg ggggaacca ggacaagagg ctcttgtggg agccgaatga gagcacaaag   2700
cgggcgggtg tgataaggc atttttgccc attttcccctt ctcctgtctc tccgacggtg   2760
atggcgttgt gcgtcctcta tttctttta tttctttttg tttattcct ctgactaccg   2820
atttggtttg atttcctcaa ccccacacaa ataagctcgg gccgaggaat atatatatac   2880
acggacacag tcgccctgtg gacaacacgt cactacctct acgatacaca ccgtacgttg   2940
tgtggaagct tgtgagcgga taacaatttc acacaggaaa cagctatgac catgattacg   3000
ccaagctcga aattaaccct cactaaaggg aacaaaagct ggagctccac cgcggacaca   3060
atatctggtc aaatttcagt ttcgttacat ttaaattcct tcacttcaag ttcattcttc   3120
```

```
atctgcttct gttttacttt gacaggcaaa tgaagacatg gtacgacttg atggaggcca    3180
agaacgccat ttcaccccga gacaccgaag tgcctgaaat cctggctgcc cccattgata    3240
acatcggaaa ctacggtatt ccggaaagtg tatatagaac cttccccag cttgtgtctg    3300
tggatatgga tggtgtaatc ccctttgagt actcgtcttg gcttctctcc gagcagtatg    3360
aggctctcta atctagcgca tttaatatct caatgtattt atatatttat cttctcatgc    3420
ggccgcttag ttggctttgg tcttggcagc cttggcctcc ttgagggtaa acatcttggc    3480
atccttgtcg accacgccgt acttggcgta cataagacca attcggatga aggtgggaat    3540
gatgggagaa gccgactttc gcaccagttc gggaaaggcc tgagcgaagg cagcagtggc    3600
ctcgttgagc ttgtagtgag gaatgatggg aaacagatgg tggatctgat gtgtaccaat    3660
gttgtgggac aggttgtcga tgagggctcc gtagcttcgg tccacagagg acaagttgcc    3720
cttgacatag gtccactccg aatcggcgta ccagggagtt tcctcgtcgt tgtgatggag    3780
gaaggtagtg acaaccagca tggtggcgaa tccaaagaga ggtgcgaagt aatacagagc    3840
catggtcttg aggccgtaga cgtaggtaag gtaggcgtac agaccagcaa aggccacgag    3900
agagccgagg gaaatgatga cggcagacat tcttcgcagg tagagaggct cccagggatt    3960
gaagtggttg accttcggg gaggaaatcc agcaacgagg taggcaaacc aagccgaacc    4020
aagggagatg accatgtgtc gggacagggg atgagagtcg gcttctcgct gagggtagaa    4080
gatctcatcc ttgtcgatgt tgccggtgtt cttgtgatgg tgtcgatggc tgatcttcca    4140
cgactcgtag ggagtcagaa tgatggagtg aatgagtgtg ccaacagaga agttgagcag    4200
gtgggatcgc gagaaggcac catgtccaca gtcgtgaccg atggtaaaga atccccagaa    4260
cacgatacc tggagcagaa tgtagccagt gcaaaggacg gcatcgagca gtgcaaactc    4320
ctgcacgata gcaagggctc gagcatagta cagtccgaga gcaagggaac cggcaatgcc    4380
cagagctcgc acggtatagt agagggacca gggaacagag gcttcgaagc agtgggcagg    4440
cagggatcgc ttgatctcgg tgagagtagg gaactcgtag ggagcggcaa cggtagagga    4500
agccatggtt gtgaattagg gtggtgagaa tggttggttg tagggaagaa tcaaaggccg    4560
gtctcgggat ccgtgggtat atatatatat atatatatat acgatccttc gttacctccc    4620
tgttctcaaa actgtggttt tcgttttttc gtttttgct ttttttgatt tttttagggc     4680
caactaagct tccagatttc gctaatcacc tttgtactaa ttacaagaaa ggaagaagct    4740
gattagagtt gggcttttta tgcaactgtg ctactcctta tctctgatat gaaagtgtag    4800
acccaatcac atcatgtcat ttagagttgg taatactggg aggatagata aggcacgaaa    4860
acgagccata gcagacatgc tgggtgtagc caagcagaag aaagtagatg ggagccaatt    4920
gacgagcgag ggagctacgc caatccgaca tacgacacgc tgagatcgtc ttggccgggg    4980
ggtacctaca gatgtccaag ggtaagtgct tgactgtaat tgtatgtctg aggacaaata    5040
tgtagtcagc cgtataaagt cataccaggc accagtgcca tcatcgaacc actaactctc    5100
tatgatacat gcctccggta ttattgtacc atgcgtcgct ttgttacata cgtatcttgc    5160
cttttttctct cagaaactcc agactttggc tattggtcga gataagcccg gaccatagtg    5220
agtctttcac actctacatt tctcccttgc tccaactatc gattgttgtc tactaactat    5280
cgtacgataa cttcgtatag catacattat acgaagttat cgcgtcgacg agtatctgtc    5340
tgactcgtca ttgccgcctt tggagtacga ctccaactat gagtgtgctt ggatcacttt    5400
gacgatacat tcttcgttgg aggctgtggg tctgacagct gcgttttcgg cgcggttggc    5460
cgacaacaat atcagctgca acgtcattgc tggctttcat catgatcaca ttttgtcgg    5520
```

```
caaaggcgac gcccagagag ccattgacgt tctttctaat ttggaccgat agccgtatag   5580
tccagtctat ctataagttc aactaactcg taactattac cataacatat acttcactgc   5640
cccagataag gttccgataa aaagttctgc agactaaatt tatttcagtc tcctcttcac   5700
caccaaaatg ccctcctacg aagctcgagc taacgtccac aagtccgcct ttgccgctcg   5760
agtgctcaag ctcgtggcag ccaagaaaac caacctgtgt gcttctctgg atgttaccac   5820
caccaaggag ctcattgagc ttgccgataa ggtcggacct tatgtgtgca tgatcaaaac   5880
ccatatcgac atcattgacg acttcaccta cgccggcact gtgctccccc tcaaggaact   5940
tgctcttaag cacggtttct tcctgttcga ggacagaaag ttcgcagata ttggcaacac   6000
tgtcaagcac cagtaccggt gtcaccgaat cgccgagtgg tccgatatca ccaacgccca   6060
cggtgtaccc ggaaccggaa tcattgctgg cctgcgagct ggtgccgagg aaactgtctc   6120
tgaacagaag aaggaggacg tctctgacta cgagaactcc cagtacaagg agttcctagt   6180
cccctctccc aacgagaagc tggccagagg tctgctcatg ctggccgagc tgtcttgcaa   6240
gggctctctg gccactggcg agtactccaa gcagaccatt gagcttgccc gatccgaccc   6300
cgagtttgtg gttggcttca ttgcccagaa ccgacctaag ggcgactctg aggactggct   6360
tattctgacc cccggggtgg gtcttgacga caagggagac gctctcggac agcagtaccg   6420
aactgttgag gatgtcatgt ctaccggaac ggatatcata attgtcggcc gaggtctgta   6480
cggccagaac cgagatccta ttgaggaggc caagcgatac cagaaggctg ctgggaggc   6540
ttaccagaag attaactgtt agaggttaga ctatggatat gtaatttaac tgtgtatata   6600
gagagcgtgc aagtatggag cgcttgttca gcttgtatga tggtcagacg acctgtctga   6660
tcgagtatgt atgatactgc acaacctgtg tatccgcatg atctgtccaa tggggcatgt   6720
tgttgtgttt ctcgatacgg agatgctggg tacagtgcta atacgttgaa ctacttatac   6780
ttatatgagg ctcgaagaaa gctgacttgt gtatgactta ttctcaacta catccccagt   6840
cacaatacca ccactgcact accactacac caaaaccatg atcaaaccac ccatggactt   6900
cctggaggca gaagaacttg ttatggaaaa gctcaagaga gagatcataa cttcgtatag   6960
catacattat acgaagttat cctgcaggta aaggaattca tgctgttcat cgtggttaat   7020
gctgctgtgt gctgtgtgtg tgtgttgttt ggcgctcatt gttgcgttat gcagcgtaca   7080
ccacaatatt ggaagcttat tagccttcct atttttcgt ttgcaaggct taacaacatt   7140
gctgtggaga gggatgggga tatggaggcc gctggaggga gtcggagagg cgttttggag   7200
cggcttggcc tggcgcccag ctcgcgaaac gcacctagga ccctttggca cgccgaaatg   7260
tgccactttt cagtctagta acgccttacc tacgtcattc catgcgtgca tgtttgcgcc   7320
ttttttccct tgcccttgat cgccacacag tacagtgcac tgtacagtgg aggttttggg   7380
ggggtcttag atgggagcta aaagcggcct agcggtacac tagtgggatt gtatggagtg   7440
gcatggagcc taggtggagc ctgacaggac gcacgaccgg ctagcccgtg acagacgatg   7500
ggtggctcct gttgtccacc gcgtacaaat gtttgggcca aagtcttgtc agccttgctt   7560
gcgaacctaa ttcccaattt tgtcacttcg cacccccatt gatcgagccc taaccctgc    7620
ccatcaggca atccaattaa gctcgcattg tctgccttgt ttagtttggc tcctgcccgt   7680
ttcggcgtcc acttgcacaa acacaaacaa gcattatata taaggctcgt ctctccctcc   7740
caaccacact cacttttttg cccgtcttcc cttgctaaca caaaagtcaa gaacacaaac   7800
aaccacccca accccttac acacaagaca tatctacagc aatggccatg gcttcttcca    7860
ctgttgctgc gccgtacgag ttcccgacgc tgacggagat caagcgctcg ctgccagcgc   7920
```

```
actgctttga ggcctcggtc ccgtggtcgc tctactacac cgtgcgcgcg ctgggcatcg    7980
ccggctcgct cgcgctcggc ctctactacg cgcgcgcgct cgcgatcgtg caggagtttg    8040
ccctgctgga tgcggtgctc tgcacggggt acattctgct gcagggcatc gtattctggg    8100
ggttcttcac catcggccat gactgcggcc acggcgcgtt ctcgcgttcg cacctgctca    8160
acttcagcgt cggcacgctc attcactcga tcatcctcac gccgtacgag tcatggaaga    8220
tctcgcaccg ccaccaccac aagaacacgg gcaacatcga caaggacgag attttctacc    8280
cgcagcgcga ggccgactcg cacccactgt cccgacacat ggtgatctcg ctcggctcgg    8340
cctggttcgc gtacctcgtt gcgggcttcc ctcctcgcaa ggtgaaccac ttcaacccct    8400
gggaaccgtt gtacctgcgc cgcatgtctg ccgtcatcat ctcactcggc tcgctcgtgg    8460
cgttcgcggg cttgtatgcg tatctcacct acgtctatgg ccttaagacc atggcgctgt    8520
actacttcgc ccctctcttt gggttcgcca cgatgctcgt ggtcactacc ttttttgcacc    8580 acaatgacga ggaaacgcca tggtacgccg actcggagtg gacgtacgtc aagggcaacc    8640
tctcgtccgt ggaccgctcg tacgcgcgc tcatcgacaa cctgagccac aacatcggca    8700
cgcaccagat ccaccacctg tttccgatca tcccgcacta caagctgaac gaggcgacgg    8760
cagcgttcgc gcaggcgttc ccggagctcg tgcgcaagag cgcgtcgccg atcatcccga    8820
cgttcatccg catcgggctc atgtacgcca agtacgcgt cgtggacaag gacgccaaga    8880
tgtttacgct caaggaggcc aaggccgcca agaccaaggc caactaggcg gccgcattga    8940
tgattggaaa cacacacatg ggttatatct aggtgagagt tagttggaca gttatatatt    9000
aaatcagcta tgccaacggt aacttcattc atgtcaacga ggaaccagtg actgcaagta    9060
atatagaatt tgaccacctt gccattctct tgcactcctt tactatatct catttatttc    9120
ttatatacaa atcacttctt cttcccagca tcgagctcgg aaacctcatg agcaataaca    9180
tcgtggatct cgtcaataga gggcttttg gactccttgc tgttggccac cttgtccttg    9240
ctgtttaaac agtgtacgca gatctactat agaggaacat ttaaattgcc ccggagaaga    9300
cggccaggcc gcctagatga caaattcaac aactcacagc tgactttctg ccattgccac    9360
tagggggggg ccttttttata tggccaagcc aagctctcca cgtcggttgg gctgcaccca    9420
acaataaatg ggtagggttg caccaacaaa gggatgggat ggggggtaga agatacgagg    9480 ataacgggc tcaatggcac aaataagaac gaatactgcc attaagactc gtgatccagc    9540
gactgacacc attgcatcat ctaagggcct caaaactacc tcggaactgc tgcgctgatc    9600
tggacaccac agaggttccg agcactttag gttgcaccaa atgtcccacc aggtgcaggc    9660
agaaaacgct ggaacagcgt gtacagtttg tcttaacaaa aagtgagggc gctgaggtcg    9720
agcagggtgg tgtgacttgt tatagccttt agagctgcga aagcgcgtat ggatttggct    9780
catcaggcca gattgagggt ctgtggacac atgtcatgtt agtgtacttc aatcgccccc    9840
tggatatagc cccgacaata ggccgtggcc tcatttttt gccttccgca catttccatt    9900
gctcggtacc cacaccttgc ttctcctgca cttgccaacc ttaatactgg tttacattga    9960
ccaacatctt acaagcgggg ggcttgtcta gggtatatat aaacagtggc tctcccaatc    10020
ggttgccagt ctcttttttc ctttctttcc ccacagattc gaaatctaaa ctacacatca    10080
cagaattccg agccgtgagt atccacgaca agatcagtgt cgacgacgcg cgttttgtgt    10140
aatgacacaa tccgaaagtc gctagcaaca cacactctct acacaaacta acccagctct    10200
ggtaccatgg cttcttccac tgttgctgcg ccgtacgagt cccgacgct gacggagatc    10260 aagcgctcgc tgccagcgca ctgctttgag gcctcggtcc cgtggtcgct ctactacacc    10320
```

```
gtgcgcgcgc tgggcatcgc cggctcgctc gcgctcggcc tctactacgc gcgcgcgctc   10380
gcgatcgtgc aggagtttgc cctgctggat gcggtgctct gcacggggta cattctgctg   10440
cagggcatcg tattctgggg gttcttcacc atcggccatg actgcggcca cggcgcgttc   10500
tcgcgttcgc acctgctcaa cttcagcgtc ggcacgctca ttcactcgat catcctcacg   10560
ccgtacgagt catggaagat ctcgcaccgc caccaccaca agaacacggg caacatcgac   10620
aaggacgaga ttttctaccc gcagcgcgag gccgactcgc acccactgtc ccgacacatg   10680
gtgatctcgc tcggctcggc ctggttcgcg tacctcgttg cgggcttccc tcctcgcaag   10740
gtgaaccact tcaacccttg ggaaccgttg tacctgcgcc gcatgtctgc cgtcatcatc   10800
tcactcggct cgctcgtggc gttcgcgggc ttgtatgcgt atctcaccta cgtctatggc   10860
cttaagacca tggcgctgta ctacttcgcc cctctctttg ggttcgccac gatgctcgtg   10920
gtcactacct ttttgcacca caatgacgag gaaacgccat ggtacgccga ctcggagtgg   10980
acgtacgtca agggcaacct ctcgtccgtg gaccgctcgt acggcgcgct catcgacaac   11040
ctgagccaca acatcggcac gcaccagatc caccacctgt ttccgatcat cccgcactac   11100
aagctgaacg aggcgacggc agcgttcgcg caggcgttcc cggagctcgt gcgcaagagc   11160
gcgtcgccga tcatcccgac gttcatccgc atcgggctca tgtacgccaa gtacggcgtc   11220
gtggacaagg acgccaagat gtttacgctc aaggaggcca aggccgccaa gaccaaggcc   11280
aactaggcgg ccgcatggag cgtgtgttct gagtcgatgt tttctatgga gttgtgagtg   11340
ttagtagaca tgatgggttt atatatgatg aatgaataga tgtgattttg atttgcacga   11400
tggaattgag aactttgtaa acgtacatgg gaatgtatga atgtgggggt tttgtgactg   11460
gataactgac ggtcagtgga cgccgttgtt caaatatcca agagatgcga gaactttgg   11520 gtcaagtgaa catgtcctct ctgttcaagt aaaccatcaa ctatgggtag tatatttagt   11580
aaggacaaga gttgagattc tttggagtcc tagaaacgta ttttcgcgtt ccaagatcaa   11640
attagtagag taatacgggc acgggaatcc attcatagtc tcaatcctgc aggtgagtta   11700
attaagatga cgacatttgc gagctggacg aggaatagat ggagcgtgtg ttctgagtcg   11760
atgttttcta tggagttgtg agtgttagta gacatgatgg gtttatatat gatgaatgaa   11820
tagatgtgat tttgatttgc acgatggaat tgagaacttt gtaaacgtac atgggaatgt   11880
atgaatgtgg gggttttgtg actggataac tgacggtcag tggacgccgt tgttcaaata   11940
tccaagagat gcgagaaact ttgggtcaag tgaacatgtc ctctctgttc aagtaaacca   12000
tcaactatgg gtagtatatt tagtaaggac aagagttgag attctttgga gtcctagaaa   12060
cgtattttcg cgttccaaga tcaaattagt agagtaatac gggcacggga atccattcat   12120
agtctcaatt ttcccatagg tgtgctacaa ggtgttgaga tgtggtacag taccaccatg   12180
attcgaggta aagagcccag aagtcattga tgaggtcaag aaatacacag atctacagct   12240
caatacaatg aatatcttct ttcatattct tcaggtgaca ccaagggtgt ctattttccc   12300
cagaaatgcg tgaaaaggcg cgtgtgtagc gtggagtatg ggttcggttg gcgtatcctt   12360
catatatcga cgaaatagta gggcaagaga tgacaaaaag tatctatatg tagacagcgt   12420
agaatatgga tttgattggt ataaattcat ttattgcgtg tctcacaaat actctcgata   12480
agttggggtt aaactggaga tggaacaatg tcgatatctc gacgcatgcg acgtcgggcc   12540
caattcgccc tatagtgagt cgtattacaa ttcactggcc gtcgttttac aacgtcgtga   12600
ctgggaaaac cctggcgtta cccaacttaa tcgccttgca gcacatcccc ctttcgccag   12660
ctggcgtaat agcgaagagg cccgcaccga tcgcccttcc caacagttgc gcagcctgaa   12720
```

-continued

```
tggcgaatgg acgcgccctg tagcggcgca ttaagcgcgg cgggtgtggt ggttacgcgc   12780
agcgtgaccg ctacacttgc cagcgcccta gcgcccgctc ctttcgcttt cttcccttcc   12840
tttctcgcca cgttcgccgg ctttccccgt caagctctaa atcggggget ccctttaggg   12900 ttccgattta gtgctttacg gcacctcgac cccaaaaaac ttgattaggg tgatggttca   12960
cgtagtgggc catcgccctg atagacggtt tttcgccctt tgacgttgga gtccacgttc   13020
tttaatagtg gactcttgtt ccaaactgga acaacactca acccta                  13066
```

<210> SEQ ID NO 66
<211> LENGTH: 1080
<212> TYPE: DNA
<213> ORGANISM: Pythium aphanidermatum
<220> FEATURE:
<221> NAME/KEY: CDS
<222> LOCATION: (1)..(1080)
<223> OTHER INFORMATION: delta-17 desaturase

<400> SEQUENCE: 66

```
atg gct tct tcc act gtt gct gcg ccg tac gag ttc ccg acg ctg acg        48
Met Ala Ser Ser Thr Val Ala Ala Pro Tyr Glu Phe Pro Thr Leu Thr
1               5                   10                  15 gag atc aag cgc tcg ctg cca gcg cac tgc ttt gag gcc tcg gtc ccg        96
Glu Ile Lys Arg Ser Leu Pro Ala His Cys Phe Glu Ala Ser Val Pro
            20                  25                  30 tgg tcg ctc tac tac acc gtg cgc gcg ctg ggc atc gcc ggc tcg ctc       144
Trp Ser Leu Tyr Tyr Thr Val Arg Ala Leu Gly Ile Ala Gly Ser Leu
        35                  40                  45 gcg ctc ggc ctc tac tac gcg cgc gcg ctc gcg atc gtg cag gag ttt       192
Ala Leu Gly Leu Tyr Tyr Ala Arg Ala Leu Ala Ile Val Gln Glu Phe
    50                  55                  60 gcc ctg ctg gat gcg gtg ctc tgc acg ggg tac att ctg ctg cag ggc       240
Ala Leu Leu Asp Ala Val Leu Cys Thr Gly Tyr Ile Leu Leu Gln Gly
65                  70                  75                  80 atc gta ttc tgg ggg ttc ttc acc atc ggc cat gac tgc ggc cac ggc       288
Ile Val Phe Trp Gly Phe Phe Thr Ile Gly His Asp Cys Gly His Gly
                85                  90                  95 gcg ttc tcg cgt tcg cac ctg ctc aac ttc agc gtc ggc acg ctc att       336
Ala Phe Ser Arg Ser His Leu Leu Asn Phe Ser Val Gly Thr Leu Ile
            100                 105                 110 cac tcg atc atc ctc acg ccg tac gag tca tgg aag atc tcg cac cgc       384
His Ser Ile Ile Leu Thr Pro Tyr Glu Ser Trp Lys Ile Ser His Arg
        115                 120                 125 cac cac cac aag aac acg ggc aac atc gac aag gac gag att ttc tac       432
His His His Lys Asn Thr Gly Asn Ile Asp Lys Asp Glu Ile Phe Tyr
    130                 135                 140 ccg cag cgc gag gcc gac tcg cac cca ctg tcc cga cac atg gtg atc       480
Pro Gln Arg Glu Ala Asp Ser His Pro Leu Ser Arg His Met Val Ile
145                 150                 155                 160 tcg ctc ggc tcg gcc tgg ttc gcg tac ctc gtt gcg ggc ttc cct cct       528
Ser Leu Gly Ser Ala Trp Phe Ala Tyr Leu Val Ala Gly Phe Pro Pro
                165                 170                 175 cgc aag gtg aac cac ttc aac cct tgg gaa ccg ttg tac ctg cgc cgc       576
Arg Lys Val Asn His Phe Asn Pro Trp Glu Pro Leu Tyr Leu Arg Arg
            180                 185                 190 atg tct gcc gtc atc atc tca ctc ggc tcg ctc gtg gcg ttc gcg ggc       624
Met Ser Ala Val Ile Ile Ser Leu Gly Ser Leu Val Ala Phe Ala Gly
        195                 200                 205 ttg tat gcg tat ctc acc tac gtc tat ggc ctt aag acc atg gcg ctg       672
Leu Tyr Ala Tyr Leu Thr Tyr Val Tyr Gly Leu Lys Thr Met Ala Leu
    210                 215                 220
```

```
tac tac ttc gcc cct ctc ttt ggg ttc gcc acg atg ctc gtg gtc act       720
Tyr Tyr Phe Ala Pro Leu Phe Gly Phe Ala Thr Met Leu Val Val Thr
225                 230                 235                 240 acc ttt ttg cac cac aat gac gag gaa acg cca tgg tac gcc gac tcg       768
Thr Phe Leu His His Asn Asp Glu Glu Thr Pro Trp Tyr Ala Asp Ser
                245                 250                 255 gag tgg acg tac gtc aag ggc aac ctc tcg tcc gtg gac cgc tcg tac       816
Glu Trp Thr Tyr Val Lys Gly Asn Leu Ser Ser Val Asp Arg Ser Tyr
        260                 265                 270 ggc gcg ctc atc gac aac ctg agc cac aac atc ggc acg cac cag atc       864
Gly Ala Leu Ile Asp Asn Leu Ser His Asn Ile Gly Thr His Gln Ile
275                 280                 285 cac cac ctg ttt ccg atc atc ccg cac tac aag ctg aac gag gcg acg       912
His His Leu Phe Pro Ile Ile Pro His Tyr Lys Leu Asn Glu Ala Thr
        290                 295                 300 gca gcg ttc gcg cag gcg ttc ccg gag ctc gtg cgc aag agc gcg tcg       960
Ala Ala Phe Ala Gln Ala Phe Pro Glu Leu Val Arg Lys Ser Ala Ser
305                 310                 315                 320 ccg atc atc ccg acg ttc atc cgc atc ggg ctc atg tac gcc aag tac      1008
Pro Ile Ile Pro Thr Phe Ile Arg Ile Gly Leu Met Tyr Ala Lys Tyr
                325                 330                 335 ggc gtc gtg gac aag gac gcc aag atg ttt acg ctc aag gag gcc aag      1056
Gly Val Val Asp Lys Asp Ala Lys Met Phe Thr Leu Lys Glu Ala Lys
        340                 345                 350 gcc gcc aag acc aag gcc aac tag                                      1080
Ala Ala Lys Thr Lys Ala Asn
355

<210> SEQ ID NO 67
<211> LENGTH: 359
<212> TYPE: PRT
<213> ORGANISM: Pythium aphanidermatum

<400> SEQUENCE: 67

Met Ala Ser Ser Thr Val Ala Ala Pro Tyr Glu Phe Pro Thr Leu Thr
1               5                   10                  15

Glu Ile Lys Arg Ser Leu Pro Ala His Cys Phe Glu Ala Ser Val Pro
            20                  25                  30

Trp Ser Leu Tyr Tyr Thr Val Arg Ala Leu Gly Ile Ala Gly Ser Leu
        35                  40                  45

Ala Leu Gly Leu Tyr Tyr Ala Arg Ala Leu Ala Ile Val Gln Glu Phe
    50                  55                  60

Ala Leu Leu Asp Ala Val Leu Cys Thr Gly Tyr Ile Leu Leu Gln Gly
65                  70                  75                  80

Ile Val Phe Trp Gly Phe Phe Thr Ile Gly His Asp Cys Gly His Gly
                85                  90                  95

Ala Phe Ser Arg Ser His Leu Leu Asn Phe Ser Val Gly Thr Leu Ile
            100                 105                 110

His Ser Ile Ile Leu Thr Pro Tyr Glu Ser Trp Lys Ile Ser His Arg
        115                 120                 125

His His Lys Asn Thr Gly Asn Ile Asp Lys Asp Glu Ile Phe Tyr
    130                 135                 140

Pro Gln Arg Glu Ala Asp Ser His Pro Leu Ser Arg His Met Val Ile
145                 150                 155                 160

Ser Leu Gly Ser Ala Trp Phe Ala Tyr Leu Val Ala Gly Phe Pro Pro
                165                 170                 175

Arg Lys Val Asn His Phe Asn Pro Trp Glu Pro Leu Tyr Leu Arg Arg
            180                 185                 190
```

```
Met Ser Ala Val Ile Ile Ser Leu Gly Ser Leu Val Ala Phe Ala Gly
        195                 200                 205
Leu Tyr Ala Tyr Leu Thr Tyr Val Tyr Gly Leu Lys Thr Met Ala Leu
        210                 215                 220
Tyr Tyr Phe Ala Pro Leu Phe Gly Phe Ala Thr Met Leu Val Val Thr
225                 230                 235                 240
Thr Phe Leu His His Asn Asp Glu Glu Thr Pro Trp Tyr Ala Asp Ser
                245                 250                 255
Glu Trp Thr Tyr Val Lys Gly Asn Leu Ser Ser Val Asp Arg Ser Tyr
            260                 265                 270
Gly Ala Leu Ile Asp Asn Leu Ser His Asn Ile Gly Thr His Gln Ile
        275                 280                 285
His His Leu Phe Pro Ile Ile Pro His Tyr Lys Leu Asn Glu Ala Thr
        290                 295                 300
Ala Ala Phe Ala Gln Ala Phe Pro Glu Leu Val Arg Lys Ser Ala Ser
305                 310                 315                 320
Pro Ile Ile Pro Thr Phe Ile Arg Ile Gly Leu Met Tyr Ala Lys Tyr
                325                 330                 335
Gly Val Val Asp Lys Asp Ala Lys Met Phe Thr Leu Lys Glu Ala Lys
            340                 345                 350
Ala Ala Lys Thr Lys Ala Asn
        355

<210> SEQ ID NO 68
<211> LENGTH: 1080
<212> TYPE: DNA
<213> ORGANISM: Pythium aphanidermatum
<220> FEATURE:
<221> NAME/KEY: CDS
<222> LOCATION: (1)..(1080)
<223> OTHER INFORMATION: synthetic delta-17 desaturase (codon-optimized
      for Yarrowia lipolytica)

<400> SEQUENCE: 68 atg gct tcc tct acc gtt gcc gct ccc tac gag ttc cct act ctc acc      48
Met Ala Ser Ser Thr Val Ala Ala Pro Tyr Glu Phe Pro Thr Leu Thr
1               5                   10                  15 gag atc aag cga tcc ctg cct gcc cac tgc ttc gaa gcc tct gtt ccc      96
Glu Ile Lys Arg Ser Leu Pro Ala His Cys Phe Glu Ala Ser Val Pro
            20                  25                  30 tgg tcc ctc tac tat acc gtg cga gct ctg ggc att gcc ggt tcc ctt     144
Trp Ser Leu Tyr Tyr Thr Val Arg Ala Leu Gly Ile Ala Gly Ser Leu
        35                  40                  45 gct ctc gga ctg tac tat gct cga gcc ctt gct atc gtg cag gag ttt     192
Ala Leu Gly Leu Tyr Tyr Ala Arg Ala Leu Ala Ile Val Gln Glu Phe
    50                  55                  60 gca ctg ctc gat gcc gtc ctt tgc act ggc tac att ctg ctc cag ggt     240
Ala Leu Leu Asp Ala Val Leu Cys Thr Gly Tyr Ile Leu Leu Gln Gly
65                  70                  75                  80 atc gtg ttc tgg gga ttc ttt acc atc ggt cac gac tgt gga cat ggt     288
Ile Val Phe Trp Gly Phe Phe Thr Ile Gly His Asp Cys Gly His Gly
                85                  90                  95 gcc ttc tcg cga tcc cac ctg ctc aac ttc tct gtt ggc aca ctc att     336
Ala Phe Ser Arg Ser His Leu Leu Asn Phe Ser Val Gly Thr Leu Ile
            100                 105                 110 cac tcc atc att ctg act ccc tac gag tcg tgg aag atc agc cat cga     384
His Ser Ile Ile Leu Thr Pro Tyr Glu Ser Trp Lys Ile Ser His Arg
        115                 120                 125 cac cat cac aag aac acc ggc aac atc gac aag gat gag atc ttc tac     432
```

```
His His His Lys Asn Thr Gly Asn Ile Asp Lys Asp Glu Ile Phe Tyr
        130                 135                 140 cct cag cga gaa gcc gac tct cat ccc ctg tcc cga cac atg gtc atc      480
Pro Gln Arg Glu Ala Asp Ser His Pro Leu Ser Arg His Met Val Ile
145                 150                 155                 160 tcc ctt ggt tcg gct tgg ttt gcc tac ctc gtt gct gga ttt cct ccc      528
Ser Leu Gly Ser Ala Trp Phe Ala Tyr Leu Val Ala Gly Phe Pro Pro
                165                 170                 175 cga aag gtc aac cac ttc aat ccc tgg gag cct ctc tac ctg cga aga      576
Arg Lys Val Asn His Phe Asn Pro Trp Glu Pro Leu Tyr Leu Arg Arg
            180                 185                 190 atg tct gcc gtc atc att tcc ctc ggc tct ctc gtg gcc ttt gct ggt      624
Met Ser Ala Val Ile Ile Ser Leu Gly Ser Leu Val Ala Phe Ala Gly
        195                 200                 205 ctg tac gcc tac ctt acc tac gtc tac ggc ctc aag acc atg gct ctg      672
Leu Tyr Ala Tyr Leu Thr Tyr Val Tyr Gly Leu Lys Thr Met Ala Leu
    210                 215                 220 tat tac ttc gca cct ctc ttt gga ttc gcc acc atg ctg gtt gtc act      720
Tyr Tyr Phe Ala Pro Leu Phe Gly Phe Ala Thr Met Leu Val Val Thr
225                 230                 235                 240 acc ttc ctc cat cac aac gac gag gaa act ccc tgg tac gcc gat tcg      768
Thr Phe Leu His His Asn Asp Glu Glu Thr Pro Trp Tyr Ala Asp Ser
                245                 250                 255 gag tgg acc tat gtc aag ggc aac ttg tcc tct gtg gac cga agc tac      816
Glu Trp Thr Tyr Val Lys Gly Asn Leu Ser Ser Val Asp Arg Ser Tyr
            260                 265                 270 gga gcc ctc atc gac aac ctg tcc cac aac att ggt aca cat cag atc      864
Gly Ala Leu Ile Asp Asn Leu Ser His Asn Ile Gly Thr His Gln Ile
        275                 280                 285 cac cat ctg ttt ccc atc att cct cac tac aag ctc aac gag gcc act      912
His His Leu Phe Pro Ile Ile Pro His Tyr Lys Leu Asn Glu Ala Thr
    290                 295                 300 gct gcc ttc gct cag gcc ttt ccc gaa ctg gtg cga aag tcg gct tct      960
Ala Ala Phe Ala Gln Ala Phe Pro Glu Leu Val Arg Lys Ser Ala Ser
305                 310                 315                 320 ccc atc att ccc acc ttc atc cga att ggt ctt atg tac gcc aag tac     1008
Pro Ile Ile Pro Thr Phe Ile Arg Ile Gly Leu Met Tyr Ala Lys Tyr
                325                 330                 335 ggc gtg gtc gac aag gat gcc aag atg ttt acc ctc aag gag gcc aag     1056
Gly Val Val Asp Lys Asp Ala Lys Met Phe Thr Leu Lys Glu Ala Lys
            340                 345                 350 gct gcc aag acc aaa gcc aac taa                                     1080
Ala Ala Lys Thr Lys Ala Asn
        355

<210> SEQ ID NO 69
<211> LENGTH: 359
<212> TYPE: PRT
<213> ORGANISM: Pythium aphanidermatum

<400> SEQUENCE: 69

Met Ala Ser Ser Thr Val Ala Ala Pro Tyr Glu Phe Pro Thr Leu Thr
1               5                   10                  15

Glu Ile Lys Arg Ser Leu Pro Ala His Cys Phe Glu Ala Ser Val Pro
            20                  25                  30

Trp Ser Leu Tyr Tyr Thr Val Arg Ala Leu Gly Ile Ala Gly Ser Leu
        35                  40                  45

Ala Leu Gly Leu Tyr Tyr Ala Arg Ala Leu Ala Ile Val Gln Glu Phe
    50                  55                  60

Ala Leu Leu Asp Ala Val Leu Cys Thr Gly Tyr Ile Leu Leu Gln Gly
```

| | | | | 65 | | | | 70 | | | | 75 | | | | 80 |
|---|---|---|---|---|---|---|---|---|---|---|---|---|---|---|---|---|
| Ile | Val | Phe | Trp | Gly | Phe | Phe | Thr | Ile | Gly | His | Asp | Cys | Gly | His | Gly | |

Ile Val Phe Trp Gly Phe Phe Thr Ile Gly His Asp Cys Gly His Gly
65                  70                  75                  80

Ala Phe Ser Arg Ser His Leu Leu Asn Phe Ser Val Gly Thr Leu Ile
            85                  90                  95

His Ser Ile Ile Leu Thr Pro Tyr Glu Ser Trp Lys Ile Ser His Arg
    100                 105                 110

His His His Lys Asn Thr Gly Asn Ile Asp Lys Asp Glu Ile Phe Tyr
        115                 120                 125

Pro Gln Arg Glu Ala Asp Ser His Pro Leu Ser Arg His Met Val Ile
            130                 135                 140

Ser Leu Gly Ser Ala Trp Phe Ala Tyr Leu Val Ala Gly Phe Pro Pro
145                 150                 155                 160

Arg Lys Val Asn His Phe Asn Pro Trp Glu Pro Leu Tyr Leu Arg Arg
                165                 170                 175

Met Ser Ala Val Ile Ile Ser Leu Gly Ser Leu Val Ala Phe Ala Gly
            180                 185                 190

Leu Tyr Ala Tyr Leu Thr Tyr Val Tyr Gly Lys Thr Met Ala Leu
    195                 200                 205

Tyr Tyr Phe Ala Pro Leu Phe Gly Phe Ala Thr Met Leu Val Val Thr
225                 230                 235                 240

Thr Phe Leu His His Asn Asp Glu Glu Thr Pro Trp Tyr Ala Asp Ser
                245                 250                 255

Glu Trp Thr Tyr Val Lys Gly Asn Leu Ser Ser Val Asp Arg Ser Tyr
            260                 265                 270

Gly Ala Leu Ile Asp Asn Leu Ser His Asn Ile Gly Thr His Gln Ile
        275                 280                 285

His His Leu Phe Pro Ile Ile Pro His Tyr Lys Leu Asn Glu Ala Thr
    290                 295                 300

Ala Ala Phe Ala Gln Ala Phe Pro Glu Leu Val Arg Lys Ser Ala Ser
305                 310                 315                 320

Pro Ile Ile Pro Thr Phe Ile Arg Ile Gly Leu Met Tyr Ala Lys Tyr
                325                 330                 335

Gly Val Val Asp Lys Asp Ala Lys Met Phe Thr Leu Lys Glu Ala Lys
            340                 345                 350

Ala Ala Lys Thr Lys Ala Asn
        355

<210> SEQ ID NO 70
<211> LENGTH: 9570
<212> TYPE: DNA
<213> ORGANISM: Artificial Sequence
<220> FEATURE:
<223> OTHER INFORMATION: Plasmid pY117

<400> SEQUENCE: 70

```
ggccgccacc gcggcccgag attccggcct cttcggccgc caagcgaccc gggtggacgt      60
ctagaggtac ctagcaatta acagatagtt tgccggtgat aattctctta acctcccaca    120
ctcctttgac ataacgattt atgtaacgaa actgaaattt gaccagatat tgtgtccgcg    180
gtggagctcc agcttttgtt ccctttagtg agggtttaaa cgagcttggc gtaatcatgg    240
tcatagctgt ttcctgtgtg aaattgttat ccgctcacaa ttccacacaa cgtacgagcc    300
ggaagcataa agtgtaaagc ctggggtgcc taatgagtga gctaactcac attaattgcg    360
ttgcgctcac tgcccgcttt ccagtcggga acctgtcgt gccagctgca ttaatgaatc      420
```

```
ggccaacgcg cggggagagg cggtttgcgt attgggcgct cttccgcttc ctcgctcact    480
gactcgctgc gctcggtcgt tcggctgcgg cgagcggtat cagctcactc aaaggcggta    540
atacggttat ccacagaatc agggqataac gcaggaaaga acatgtgagc aaaaggccag    600
caaaaggcca ggaaccgtaa aaggccgcg ttgctggcgt ttttccatag gctccgcccc     660
cctgacgagc atcacaaaaa tcgacgctca agtcagaggt ggcgaaaccc gacaggacta    720
taaagatacc aggcgtttcc ccctggaagc tccctcgtgc gctctcctgt tccgaccctg    780
ccgcttaccg gatacctgtc cgcctttctc ccttcgggaa gcgtggcgct ttctcatagc    840
tcacgctgta ggtatctcag ttcggtgtag gtcgttcgct ccaagctggg ctgtgtgcac    900
gaaccccccg ttcagcccga ccgctgcgcc ttatccggta actatcgtct tgagtccaac    960
ccggtaagac acgacttatc gccactggca gcagccactg gtaacaggat tagcagagcg   1020
aggtatgtag gcggtgctac agagttcttg aagtggtggc ctaactacgg ctacactaga   1080
aggacagtat ttggtatctg cgctctgctg aagccagtta ccttcggaaa aagagttggt   1140
agctcttgat ccggcaaaca aaccaccgct ggtagcggtg gttttttgt ttgcaagcag   1200
cagattacgc gcagaaaaaa aggatctcaa gaagatcctt tgatctttc tacgggtct    1260
gacgctcagt ggaacgaaaa ctcacgttaa gggattttgg tcatgagatt atcaaaaagg   1320
atcttcacct agatcctttt aaattaaaaa tgaagtttta atcaatcta aagtatatat    1380
gagtaaactt ggtctgacag ttaccaatgc ttaatcagtg aggcacctat ctcagcgatc   1440
tgtctatttc gttcatccat agttgcctga ctccccgtcg tgtagataac tacgatacgg   1500
gagggcttac catctggccc cagtgctgca atgataccgc gagacccacg ctcaccggct   1560
ccagatttat cagcaataaa ccagccagcc ggaagggccg agcgcagaag tggtcctgca   1620
actttatccg cctccatcca gtctattaat tgttgccggg aagctagagt aagtagttcg   1680
ccagttaata gtttgcgcaa cgttgttgcc attgctacag gcatcgtggt gtcacgctcg   1740
tcgtttggta tggcttcatt cagctccggt tcccaacgat caaggcgagt tacatgatcc   1800
cccatgttgt gcaaaaaagc ggttagctcc ttcggtcctc cgatcgttgt cagaagtaag   1860
ttggccgcag tgttatcact catggttatg gcagcactgc ataattctct tactgtcatg   1920
ccatccgtaa gatgcttttc tgtgactggt gagtactcaa ccaagtcatt ctgagaatag   1980
tgtatgcggc gaccgagttg ctcttgcccg gcgtcaatac gggataatac cgcgccacat   2040
agcagaactt taaaagtgct catcattgga aaacgttctt cggggcgaaa actctcaagg   2100
atcttaccgc tgttgagatc cagttcgatg taacccactc gtgcacccaa ctgatcttca   2160
gcatctttta ctttcaccag cgtttctggg tgagcaaaaa caggaaggca aaatgccgca   2220
aaaaagggaa taagggcgac acggaaatgt tgaatactca tactcttcct ttttcaatat   2280
tattgaagca tttatcaggg ttattgtctc atgagcggat acatatttga atgtatttag   2340
aaaaataaac aaatagggqt tccgcgcaca tttccccgaa aagtgccacc tgacgcgccc   2400
tgtagcggcg cattaagcgc ggcgggtgtg gtggttacgc gcagcgtgac cgctacactt   2460
gccagcgccc tagcgcccgc tcctttcgct ttcttccctt cctttctcgc cacgttcgcc   2520
ggctttcccc gtcaagctct aaatcggggg ctcccttag ggttccgatt tagtgcttta   2580
cggcacctcg accccaaaaa acttgattag ggtgatggtt cacgtagtgg gccatcgccc   2640
tgatagacgg ttttttcgccc tttgacgttg gagtccacgt tctttaatag tggactcttg   2700
ttccaaactg gaacaacact caaccctatc tcggtctatt cttttgattt ataagggatt   2760
ttgccgattt cggcctattg gttaaaaaat gagctgattt aacaaaaatt taacgcgaat   2820
```

```
tttaacaaaa tattaacgct tacaatttcc attcgccatt caggctgcgc aactgttggg    2880
aagggcgatc ggtgcgggcc tcttcgctat tacgccagct ggcgaaaggg ggatgtgctg    2940
caaggcgatt aagttgggta acgccagggt tttcccagtc acgacgttgt aaaacgacgg    3000
ccagtgaatt gtaatacgac tcactatagg gcgaattggg taccgggccc ccctcgagg     3060 tcgatggtgt cgataagctt gatatcgaat tcatgtcaca caaaccgatc ttcgcctcaa    3120
ggaaacctaa ttctcatcc gagagactgc cgagatccag tctacactga ttaatttcg      3180 ggccaataat ttaaaaaaat cgtgttatat aatattatat gtattatata tatacatcat    3240
gatgatactg acagtcatgt cccattgcta aatagacaga ctccatctgc cgcctccaac    3300
tgatgttctc aatatttaag gggtcatctc gcattgttta ataataaaca gactccatct    3360
accgcctcca aatgatgttc tcaaaatata ttgtatgaac ttatttttat tacttagtat    3420
tattagacaa cttacttgct ttatgaaaaa cacttcctat ttaggaaaca atttataatg    3480
gcagttcgtt catttaacaa tttatgtaga ataaatgtta taaatgcgta tgggaaatct    3540
taaatatgga tagcataaat gatatctgca ttgcctaatt cgaaatcaac agcaacgaaa    3600
aaaatccctt gtacaacata aatagtcatc gagaaatatc aactatcaaa gaacagctat    3660
tcacacgtta ctattgagat tattattgga cgagaatcac acactcaact gtctttctct    3720
cttctagaaa tacaggtaca agtatgtact attctcattg ttcatacttc tagtcatttc    3780
atcccacata ttccttggat ttctctccaa tgaatgacat tctatcttgc aaattcaaca    3840
attataataa gatataccaa agtagcggta tagtggcaat caaaaagctt ctctggtgtg    3900
cttctcgtat ttattttat tctaatgatc cattaaaggt atatatttat ttcttgttat      3960
ataatccttt tgtttattac atgggctgga tacataaagg tattttgatt taattttttg    4020
cttaaattca atccccctc gttcagtgtc aactgtaatg gtaggaaatt accatacttt      4080
tgaagaagca aaaaaatga agaaaaaaa aaatcgtatt tccaggttag acgttccgca       4140
gaatctagaa tgcggtatgc ggtacattgt tcttcgaacg taaaagttgc gctccctgag    4200
atattgtaca tttttgcttt tacaagtaca agtacatcgt acaactatgt actactgttg    4260
atgcatccac aacagtttgt tttgttttt tttgtttttt tttttctaa tgattcatta       4320 ccgctatgta tacctacttg tacttgtagt aagccgggtt attggcgttc aattaatcat    4380
agacttatga atctgcacgg tgtgcgctgc gagttacttt tagcttatgc atgctacttg    4440
ggtgtaatat tgggatctgt tcggaaatca acggatgctc aaccgatttc gacagtaatt    4500
aattaattcc ctagtcccag tgtacacccg ccgatatcgc ttaccctgca gccgattaa     4560 ggttggcaat ttttcacgtc cttgtctccg caattactca ccgggtggtt tataagattg    4620
caagcgtctt gatttgtctc tgtatactaa catgcaatcg cgactcgccc gacgggccac    4680
taacctggcc agaatctcca gatccaagta ttctcttggt ctgcgatatg tttccaacac    4740
aaaagcccct gctgcccagc cggcaactgc tgagtgagta ttccttgcca taaacgaccc    4800
agaaccactg tatagtgttt ggaagcacta gtcagaagac cagcgaaaac aggtggaaaa    4860
aactgagacg aaaagcaacg accagaaatg taatgtgtgg aaaagcgaca cacacagagc    4920
agataaagag gtgacaaata acgacaaatg aaatatcagt atcttcccac aatcactacc    4980
tctcagctgt ctgaaggtgc ggctgatata tccatcccac gtctaacgta tggagtgtga    5040
tagaatatga cgacacaagc atgagaactc gctctctatc caaccaccga aacactgtca    5100
ctacagccgt tcttgttgct ccattcgctt ttgtgattcc atgccttctc tggtgactga    5160
caacattcct tccttttctc cagccctgtt gttatctgct catgacctac ggccactctc    5220
```

```
tatcgcatac taacatagac gatcccagcc cgctccccac ttccagggca ccgttggcaa    5280
gcctcctatc ctcaagaagg ctgaggctgc caacgctgac atggacgagt ccttcatcgg    5340
aatgtctgga ggagagatct tccacgagat gatgctgcga cacaacgtcg acactgtctt    5400
cggttacccc ggtggagcca ttctccccgt ctttgacgcc attcacaact ctgagtactt    5460
caactttgtg ctccctcgac acgagcaggg tgccggccac atggccgagg gctacgctcg    5520
agcctctggt aagcccggtg tcgttctcgt cacctctggc cccggtgcca ccaacgtcat    5580 caccccccatg caggacgctc tttccgatgg taccccccatg gttgtcttca ccggtcaggt    5640
```

```
tgactgtcca tatggtttgc tccatctcac cctcatcgtt ttcattgttc acaggcggcc    7680
acaaaaaaac tgtcttctct ccttctctct tcgccttagt ctactcggac cagttttagt    7740
ttagcttggc gccactggat aaatgagacc tcaggccttg tgatgaggag gtcacttatg    7800
aagcatgtta ggaggtgctt gtatggatag agaagcaccc aaaataataa gaataataat    7860
aaaacagggg gcgttgtcat ttcatatcgt gttttcacca tcaatacacc tccaaacaat    7920
gcccttcatg tggccagccc caatattgtc ctgtagttca actctatgca gctcgtatct    7980
tattgagcaa gtaaaactct gtcagccgat attgcccgac ccgcgacaag ggtcaacaag    8040
gtggtgtaag gccttcgcag aagtcaaaac tgtgccaaac aaacatctag agtctctttg    8100
gtgtttctcg catatatttw atcggctgtc ttacgtattt gcgcctcggt accggactaa    8160
tttcggatca tccccaatac gcttttcctt cgcagctgtc aacagtgtcc atgatctatc    8220
cacctaaatg ggtcatatga ggcgtataat ttcgtggtgc tgataataat tcccatatat    8280
ttgacacaaa acttccccccc ctagacatac atctcacaat ctcacttctt gtgcttctgt    8340
cacacatctc ctccagctga cttcaactca cacctctgcc ccagttggtc tacagcggta    8400 taaggttttct ccgcatagag gtgcaccact cctcccgata cttgtttgtg tgacttgtgg    8460
gtcacgacat atatatctac acacattgcg ccacccttttg gttcttccag cacaacaaaa    8520
acacgacacg ctaaccatgg ccaatttact gaccgtacac caaaatttgc ctgcattacc    8580
ggtcgatgca acgagtgatg aggttcgcaa gaacctgatg gacatgttca gggatcgcca    8640
ggcgttttct gagcataccct ggaaaatgct tctgtccgtt tgccggtcgt gggcggcatg    8700
gtgcaagttg aataaccgga aatggtttcc cgcagaacct gaagatgttc gcgattatct    8760
tctatatctt caggcgcgcg gtctggcagt aaaaactatc cagcaacatt tgggccagct    8820
aaacatgctt catcgtcggt ccgggctgcc acgaccaagt gacagcaatg ctgtttcact    8880
ggttatgcgg cggatccgaa aagaaaacgt tgatgccggt gaacgtgcaa acaggctct    8940 agcgttcgaa cgcactgatt tcgaccaggt tcgttcactc atggaaaata gcgatcgctg    9000
ccaggatata cgtaatctgg catttctggg gattgcttat aacaccctgt tacgtatagc    9060
cgaaattgcc aggatcaggg ttaaagatat ctcacgtact gacggtggga gaatgttaat    9120
ccatattggc agaacgaaaa cgctggttag caccgcaggt gtagagaagg cacttagcct    9180
gggggtaact aaaactggtcg agcgatggat ttccgtctct ggtgtagctg atgatccgaa    9240
taactacctg ttttgccggg tcagaaaaaa tggtgttgcc gcgccatctg ccaccagcca    9300
gctatcaact cgcgccctgg aagggatttt tgaagcaact catcgattga tttacggcgc    9360
taaggatgac tctggtcaga gatacctggc ctggtctgga cacagtgccc gtgtcggagc    9420
cgcgcgagat atggcccgcg ctggagtttc aataccggag atcatgcaag ctggtggctg    9480
gaccaatgta atattgtca tgaactatat ccgtaacctg gatagtgaaa caggggcaat    9540
ggtgcgcctg ctggaagatg gcgattaagc                                     9570
```

<210> SEQ ID NO 71
<211> LENGTH: 15743
<212> TYPE: DNA
<213> ORGANISM: Artificial Sequence
<220> FEATURE:
<223> OTHER INFORMATION: Plasmid pZP2-2988

<400> SEQUENCE: 71

```
ggccgcatgt acatacaaga ttatttatag aaatgaatcg cgatcgaaca aagagtacga      60
gtgtacgagt aggggatgat gataaaagtg gaagaagttc cgcatctttg gatttatcaa     120
```

```
cgtgtaggac gatacttcct gtaaaaatgc aatgtcttta ccataggttc tgctgtagat    180
gttattaact accattaaca tgtctacttg tacagttgca gaccagttgg agtatagaat    240
ggtacactta ccaaaaagtg ttgatggttg taactacgat atataaaact gttgacggga    300
tctgtatatt cggtaagata tattttgtgg ggttttagtg gtgtttaaac agtgtacgca    360
gtactataga ggaacaattg ccccggagaa gacggccagg ccgcctagat gacaaattca    420
acaactcaca gctgactttc tgccattgcc actagggggg ggccttttta tatggccaag    480
ccaagctctc cacgtcggtt gggctgcacc caacaataaa tgggtagggt tgcaccaaca    540
aagggatggg atgggggggta gaagatacga ggataacggg gctcaatggc acaaataaga    600
acgaatactg ccattaagac tcgtgatcca gcgactgaca ccattgcatc atctaagggc    660
ctcaaaacta cctcggaact gctgcgctga tctggacacc acagaggttc cgagcacttt    720
aggttgcacc aaatgtccca ccaggtgcag gcagaaaacg ctggaacagc gtgtacagtt    780
tgtcttaaca aaaagtgagg gcgctgaggt cgagcagggt ggtgtgactt gttatagcct    840
ttagagctgc gaaagcgcgt atggatttgg ctcatcaggc cagattgagg gtctgtggac    900
acatgtcatg ttagtgtact tcaatcgccc cctggatata gccccgacaa taggccgtgg    960
cctcattttt ttgccttccg cacatttcca ttgctcggta cccacacctt gcttctcctg    1020
cacttgccaa ccttaatact ggtttacatt gaccaacatc ttacaagcgg ggggcttgtc    1080
tagggtatat ataaacagtg gctctcccaa tcggttgcca gtctcttttt tcctttcttt    1140
ccccacagat tcgaaatcta aactacacat cacaccatgg aggtcgtgaa cgaaatcgtc    1200
tccattggcc aggaggttct tcccaaggtc gactatgctc agctctggtc tgatgcctcg    1260
cactgcgagg tgctgtacct ctccatcgcc ttcgtcatcc tgaagttcac ccttggtcct    1320
ctcggaccca agggtcagtc tcgaatgaag tttgtgttca ccaactacaa cctgctcatg    1380
tccatctact cgctgggctc cttcctctct atggcctacg ccatgtacac cattggtgtc    1440
atgtccgaca actgcgagaa ggcttttcgac aacaatgtct tccgaatcac cactcagctg    1500
ttctacctca gcaagttcct cgagtacatt gactccttct atctgcccct catgggcaag    1560
cctctgacct ggttgcagtt cttttcaccat ctcggagctc ctatggacat gtggctgttc    1620
tacaactacc gaaacgaagc cgtttggatc tttgtgctgc tcaacggctt cattcactgg    1680
atcatgtacg gctactattg gacccgactg atcaagctca gttccctat gcccaagtcc    1740
ctgattactt ctatgcagat cattcagttc aacgttggct tctacatcgt ctggaagtac    1800
cggaacattc cctgctaccg acaagatgga atgagaatgt ttggctggtt tttcaactac    1860
ttctacgttg gtactgtcct gtgtctgttc ctcaacttct acgtgcagac ctacatcgtc    1920
cgaaagcaca agggagccaa aaagattcag tgagcggccg caagtgtgga tggggaagtg    1980
agtgcccggt tctgtgtgca caattggcaa tccaagatgg atggattcaa cacagggata    2040
tagcgagcta cgtggtggtg cgaggatata gcaacggata tttatgtttg acacttgaga    2100
atgtacgata caagcactgt ccaagtacaa tactaaacat actgtacata ctcatactcg    2160
tacccgggca acgtttcac ttgagtcag tggctagtgc tcttactcgt acagtgtgca    2220
atactgcgta tcatagtctt tgatgtatat cgtattcatt catgttagtt gcgtacgggc    2280
gtcgttgctt gtgtgatttt tgaggaccca tccctttggt atataagtat actctggggt    2340
taaggttgcc cgtgtagtct aggttatagt tttcatgtga ataccgaga gccgagggag    2400
aataaacggg ggtatttgga cttgtttttt tcgcggaaaa gcgtcgaatc aaccctgcgg    2460
gccttgcacc atgtccacga cgtgtttctc gccccaattc gccccttgca cgtcaaaatt    2520
```

```
aggcctccat ctagacccct ccataacatg tgactgtggg gaaaagtata agggaaacca    2580
tgcaaccata gacgacgtga aagacgggga ggaaccaatg gaggccaaag aaatggggta    2640
gcaacagtcc aggagacaga caaggagaca aggagagggc gcccgaaaga tcggaaaaac    2700
aaacatgtcc aattggggca gtgacggaaa cgacacggac acttcagtac aatggaccga    2760
ccatctccaa gccagggtta ttccggtatc accttggccg taacctcccg ctggtacctg    2820
atattgtaca cgttcacatt caatatactt tcagctacaa taagagaggc tgtttgtcgg    2880
gcatgtgtgt ccgtcgtatg gggtgatgtc cgagggcgaa attcgctaca agcttaactc    2940
tggcgcttgt ccagtatgaa tagacaagtc aagaccagtg gtgccatgat tgacagggag    3000
gtacaagact tcgatactcg agcattactc ggacttgtgg cgattgaaca gacgggcgat    3060
cgcttctccc ccgtattgcc ggcgcgccag ctgcattaat gaatcggcca acgcgcgggg    3120
agaggcggtt tgcgtattgg gcgctcttcc gcttcctcgc tcactgactc gctgcgctcg    3180
gtcgttcggc tgcggcgagc ggtatcagct cactcaaagg cggtaatacg gttatccaca    3240
gaatcagggg ataacgcagg aaagaacatg tgagcaaaag gccagcaaaa ggccaggaac    3300
cgtaaaaagg ccgcgttgct ggcgtttttc cataggctcc gcccccctga cgagcatcac    3360
aaaaatcgac gctcaagtca gaggtggcga aacccgacag gactataaag ataccaggcg    3420
tttccccctg gaagctccct cgtgcgctct cctgttccga ccctgccgct taccggatac    3480
ctgtccgcct ttctcccttc gggaagcgtg gcgctttctc atagctcacg ctgtaggtat    3540
ctcagttcgg tgtaggtcgt tcgctccaag ctgggctgtg tgcacgaacc ccccgttcag    3600
cccgaccgct gcgccttatc cggtaactat cgtcttgagt ccaacccggt aagacacgac    3660
ttatcgccac tggcagcagc cactggtaac aggattagca gagcgaggta tgtaggcggt    3720
gctacagagt tcttgaagtg gtggcctaac tacggctaca ctagaagaac agtatttggt    3780
atctgcgctc tgctgaagcc agttaccttc ggaaaaagag ttggtagctc ttgatccggc    3840
aaacaaacca ccgctggtag cggtggtttt tttgtttgca agcagcagat tacgcgcaga    3900
aaaaaaggat ctcaagaaga tcctttgatc ttttctacgg ggtctgacgc tcagtggaac    3960
gaaaactcac gttaagggat tttggtcatg agattatcaa aaaggatctt cacctagatc    4020
cttttaaatt aaaaatgaag ttttaaatca atctaaagta tatatgagta aacttggtct    4080
gacagttacc aatgcttaat cagtgaggca cctatctcag cgatctgtct atttcgttca    4140
tccatagttg cctgactccc cgtcgtgtag ataactacga tacgggaggg cttaccatct    4200
ggccccagtg ctgcaatgat accgcgagac ccacgctcac cggctccaga tttatcagca    4260
ataaaccagc cagccggaag ggccgagcgc agaagtggtc ctgcaacttt atccgcctcc    4320
atccagtcta ttaattgttg ccgggaagct agagtaagta gttcgccagt taatagtttg    4380
cgcaacgttg ttgccattgc tacaggcatc gtggtgtcac gctcgtcgtt tggtatggct    4440
tcattcagct ccggttccca acgatcaagg cgagttacat gatcccccat gttgtgcaaa    4500
aaagcggtta gctccttcgg tcctccgatc gttgtcagaa gtaagttggc cgcagtgtta    4560
tcactcatgg ttatggcagc actgcataat tctcttactg tcatgccatc cgtaagatgc    4620
ttttctgtga ctggtgagta ctcaaccaag tcattctgag aatagtgtat gcggcgaccg    4680
agttgctctt gcccggcgtc aatacggat aataccgcgc cacatagcag aactttaaaa    4740
gtgctcatca ttggaaaacg ttcttcgggg cgaaaactct caaggatctt accgctgttg    4800
agatccagtt cgatgtaacc cactcgtgca cccaactgat cttcagcatc ttttactttc    4860
accagcgttt ctgggtgagc aaaaacagga aggcaaaatg ccgcaaaaaa gggaataagg    4920
```

```
gcgacacgga aatgttgaat actcatactc ttccttttc  aatattattg aagcatttat   4980
cagggttatt gtctcatgag cggatacata tttgaatgta tttagaaaaa taaacaaata   5040
ggggttccgc gcacatttcc ccgaaaagtg ccacctgatg cggtgtgaaa taccgcacag   5100
atgcgtaagg agaaaatacc gcatcaggaa attgtaagcg ttaatatttt gttaaaattc   5160
gcgttaaatt tttgttaaat cagctcattt tttaaccaat aggccgaaat cggcaaaatc   5220
ccttataaat caaagaata  gaccgagata gggttgagtg ttgttccagt ttggaacaag   5280
agtccactat taagaacgt  ggactccaac gtcaagggc  gaaaaaccgt ctatcagggc   5340
gatggcccac tacgtgaacc atcaccctaa tcaagttttt tggggtcgag gtgccgtaaa   5400
gcactaaatc ggaaccctaa agggagcccc cgatttagag cttgacgggg aaagccggcg   5460
aacgtggcga gaaggaagg  gaagaaagcg aaaggagcgg gcgctagggc gctggcaagt   5520
gtagcggtca cgctgcgcgt aaccaccaca cccgccgcgc ttaatgcgcc gctacagggc   5580
gcgtccattc gccattcagg ctgcgcaact gttgggaagg gcgatcggtg cgggcctctt   5640
cgctattacg ccagctggcg aaaggggat  gtgctgcaag gcgattaagt tgggtaacgc   5700
cagggttttc ccagtcacga cgttgtaaaa cgacggccag tgaattgtaa tacgactcac   5760
tatagggcga attgggcccg acgtcgcatg cgctgatgac actttggtct gaaagagatg   5820
cattttgaat cccaaacttg cagtgcccaa gtgacataca tctccgcgtt ttggaaaatg   5880
ttcagaaaca gttgattgtg ttggaatggg gaatgggaa  tggaaaaatg actcaagtat   5940
caattccaaa aacttctctg gctggcagta cctactgtcc atactactgc attttctcca   6000
gtcaggccac tctatactcg acgacacagt agtaaaaccc agataatttc gacataaaca   6060
agaaaacaga cccaataata tttatatata gtcagccgtt tgtccagttc agactgtaat   6120
agccgaaaaa aaatccaaag tttctattct aggaaaatat attccaatat ttttaattct   6180
taatctcatt tatttattc  tagcgaaata catttcagct acttgagaca tgtgataccc   6240
acaaatcgga ttcggactcg gttgttcaga agagcatatg gcattcgtgc tcgcttgttc   6300
acgtattctt cctgttccat ctcttggccg acaatcacac aaaaatgggg ttttttttt   6360
aattctaatg attcattaca gcaaaattga gatatagcag accacgtatt ccataatcac   6420
caaggaagtt cttgggcgtc ttaattaact cacctgcagg attgagacta tgaatggatt   6480
cccgtgcccg tattactcta ctaatttgat cttggaacgc gaaaatacgt ttctaggact   6540
ccaaagaatc tcaactcttg tccttactaa atatactacc catagttgat ggtttacttg   6600
aacagagagg acatgttcac ttgacccaaa gtttctcgca tctcttggat atttgaacaa   6660
cggcgtccac tgaccgtcag ttatccagtc acaaaacccc cacattcata cattcccatg   6720
tacgtttaca aagttctcaa ttccatcgtg caaatcaaaa tcacatctat tcattcatca   6780
tatataaacc catcatgtct actaacactc acaactccat agaaaacatc gactcagaac   6840
acacgctcca tgcggccgct tactgagcct tggcaccggg ctgcttctcg gccattcgag   6900
cgaactggga caggtatcgg agcaggatga cgagaccttc atggggcaga gggtttcggt   6960
aggggaggtt gtgcttctgg cacagctgtt ccacctggta ggaaacggca gtgaggttgt   7020
gtcgaggcag ggtgggccag agatggtgct cgatctggta gttcaggcct ccaaagaacc   7080
agtcagtaat gatgcctcgt cgaatgttca tggtctcatg gatctgaccc acagagaagc   7140
catgtccgtc ccagacggaa tcaccgatct tctccagagg gtagtggttc atgaagacca   7200
cgatggcaat tccgaagcca ccgacgagct cggaaacaaa gaacaccagc atcgaggtca   7260
ggatggaggg cataaagaag aggtggaaca gggtcttgag agtccagtgc agagcgagtc   7320
```

```
caatggcctc tttcttgtac tgagatcggt agaactggtt gtctcggtcc ttgagggatc   7380
gaacggtcag cacagactgg aaacaccaga tgaatcgcag gagaatacag atgaccagga   7440
aatagtactg ttggaactga atgagctttc gggagatggg agaagctcga gtgacatcgt   7500
cctcggacca ggcgagcaga ggcaggttat caatgtcggg atcgtgaccc tgaacgttgg   7560
tagcagaatg atgggcgttg tgtctgtcct tccaccaggt cacggagaag ccctggagtc   7620
cgttgccaaa gaccagaccc aggacgttat tccagtttcg gttcttgaag gtctggtggt   7680
ggcagatgtc atgagacagc catcccattt gctggtagtg cataccgagc acgagagcac   7740
caatgaagta caggtggtac tggaccagca tgaagaaggc aagcacgcca agacccaggg   7800
tggtcaagat cttgtacgag taccagaggg gagaggcgtc aaacatgcca gtggcgatca   7860
gctcttctcg gagctttcgg aaatcctcct gagcttcgtt gacggcagcc tgggaggca   7920
gctcggaagc ctggttgatc ttgggcattc gcttgagctt gtcgaaggct tcctgagagt   7980
gcataaccat gaaggcgtca gtagcatctc gtccctggta gttctcaatg atttcagctc   8040
caccagggtg gaagttcacc caagcggaga cgtcgtacac cttccgtcg atgacgaggg   8100
gcagagcctg tcgagaagcc ttcaccatgg ttgtgaatta gggtggtgag aatggttggt   8160
tgtagggaag aatcaaaggc cggtctcggg atccgtgggt atatatatat atatatatat   8220
atacgatcct tcgttacctc cctgttctca aaactgtggt ttttcgtttt tcgtttttg   8280
cttttttga tttttttagg gccaactaag cttccagatt tcgctaatca cctttgtact   8340
aattacaaga aaggaagaag ctgattagag ttgggctttt tatgcaactg tgctactcct   8400
tatctctgat atgaaagtgt agacccaatc acatcatgtc atttagagtt ggtaatactg   8460
ggaggataga taaggcacga aaacgagcca tagcagacat gctgggtgta gccaagcaga   8520
agaaagtaga tgggagccaa ttgacgagcg agggagctac gccaatccga catacgacac   8580
gctgagatcg tcttggccgg ggggtaccta cagatgtcca agggtaagtg cttgactgta   8640
attgtatgtc tgaggacaaa tatgtagtca gccgtataaa gtcataccag gcaccagtgc   8700
catcatcgaa ccactaactc tctatgatac atgcctccgg tattattgta ccatgcgtcg   8760
cttttgttaca tacgtatctt gccttttct ctcagaaact ccagactttg gctattggtc   8820
gagataagcc cggaccatag tgagtctttc acactctaca tttctccctt gctccaacta   8880
tttaaattcc ttcacttcaa gttcattctt catctgcttc tgttttactt tgacaggcaa   8940
atgaagacat ggtacgactt gatggaggcc aagaacgcca tttcaccccg agacaccgaa   9000
gtgcctgaaa tcctggctgc ccccattgat aacatcggaa actacggtat tccggaaagt   9060
gtatatagaa ccttttcccca gcttgtgtct gtggatatgg atggtgtaat cccctttgag   9120
tactcgtctt ggcttctctc cgagcagtat gaggctctct aatctagcgc atttaatatc   9180
tcaatgtatt tatatattta tcttctcatg cggccgctta ctgagccttg gcaccgggct   9240
gcttctcggc cattcgagcg aactgggaca ggtatcggag caggatgacg agaccttcat   9300
ggggcagagg gtttcggtag gggaggttgt gcttctggca cagctgttcc acctggtagg   9360
aaacggcagt gaggttgtgt cgaggcaggg tgggccagag atggtgctcg atctggtagt   9420
tcaggcctcc aaagaaccag tcagtaatga tgcctcgtcg aatgttcatg gtctcatgga   9480
tctgacccac agaaagcca tgtccgtccc agacggaatc accgatcttc tccagagggt   9540
agtggttcat gaagaccacg atggcaattc cgaagccacc gacgagctcg gaaacaaaga   9600
acaccagcat cgaggtcagg atggagggca taaagaagag gtggaacagg gtcttgagag   9660
tccagtgcag agcgagtcca atggcctctt tcttgtactg agatcggtag aactggttgt   9720
```

```
ctcggtcctt gagggatcga acggtcagca cagactggaa acaccagatg aatcgcagga      9780
gaatacagat gaccaggaaa tagtactgtt ggaactgaat gagctttcgg gagatgggag      9840
aagctcgagt gacatcgtcc tcggaccagg cgagcagagg caggttatca atgtcgggat      9900
cgtgaccctg aacgttggta gcagaatgat gggcgttgtg tctgtccttc caccaggtca      9960
cggagaagcc ctggagtccg ttgccaaaga ccagacccag gacgttattc cagtttcggt     10020
tcttgaaggt ctggtggtgg cagatgtcat gagacagcca tcccatttgc tggtagtgca     10080
taccgagcac gagagcacca atgaagtaca ggtggtactg gaccagcatg aagaaggcaa     10140
gcacgccaag acccagggtg gtcaagatct tgtacgagta ccagagggga gaggcgtcaa     10200
acatgccagt ggcgatcagc tcttctcgga gctttcggaa atcctcctga gcttcgttga     10260
cggcagcctg gggaggcagc tcggaagcct ggttgatctt gggcattcgc ttgagcttgt     10320
cgaaggcttc ctgagagtgc ataaccatga aggcgtcagt agcatctcgt ccctggtagt     10380
tctcaatgat ttcagctcca ccagggtgga agttcaccca agcggagacg tcgtacacct     10440
ttccgtcgat gacgaggggc agagcctgtc gagaagcctt caccatgggc aggacctgtg     10500
ttagtacatt gtcggggagt catcaattgg ttcgacaggt tgtcgactgt tagtatgagc     10560
tcaattgggc tctggtgggt cgatgacact tgtcatctgt ttctgttggg tcatgtttcc     10620
atcaccttct atggtactca caattcgtcc gattcgcccg aatccgttaa taccgacttt     10680
gatggccatg ttgatgtgtg tttaattcaa gaatgaatat agaagagaga agaagaaaaa     10740
agattcaatt gagccggcga tgcagaccct tatataaatg ttgccttgga cagacggagc     10800
aagcccgccc aaacctacgt tcggtataat atgttaagct ttttaacaca aaggtttggc     10860
ttggggtaac ctgatgtggt gcaaaagacc gggcgttggc gagccattgc gcgggcgaat     10920
ggggccgtga ctcgtctcaa attcgagggc gtgcctcaat tcgtgccccc gtggcttttt     10980
cccgccgttt ccgccccgtt tgcaccactg cagccgcttc tttggttcgg acaccttgct     11040
gcgagctagg tgccttgtgc tacttaaaaa gtggcctccc aacaccaaca tgacatgagt     11100
gcgtgggcca agacacgttg gcggggtcgc agtcggctca atggcccgga aaaaacgctg     11160
ctggagctgg ttcggacgca gtccgccgcg gcgtatggat atccgcaagg ttccatagcg     11220
ccattgccct ccgtcggcgt ctatcccgca acctctaaat agagcgggaa tataacccaa     11280
gcttcttttt tttcctttaa cacgcacacc cccaactatc atgttgctgc tgctgtttga     11340
ctctactctg tggaggggtg ctcccaccca acccaaccta caggtggatc cggcgctgtg     11400
attggctgat aagtctccta tccggactaa ttctgaccaa tgggacatgc gcgcaggacc     11460
caaatgccgc aattacgtaa ccccaacgaa atgcctaccc ctctttggag cccagcggcc     11520
ccaaatcccc ccaagcagcc cggttctacc ggcttccatc tccaagcaca agcagcccgg     11580
aattccttta cctgcaggat aacttcgtat aatgtatgct atacgaagtt atgatctctc     11640
tcttgagctt ttccataaca agttcttctg cctccaggaa gtccatgggt ggtttgatca     11700
tggttttggt gtagtggtag tgcagtggtg gtattgtgac tggggatgta gttgagaata     11760
agtcatacac aagtcagctt tcttcgagcc tcatataagt ataagtagtt caacgtatta     11820
gcactgtacc cagcatctcc gtatcgagaa acacaacaac atgccccatt ggacagatca     11880
tgcggataca caggttgtgc agtatcatac atactcgatc agacaggtcg tctgaccatc     11940
atacaagctg aacaagcgct ccatacttgc acgctctcta tatacacagt taaattacat     12000
atccatagtc taacctctaa cagttaatct tctggtaagc ctcccagcca gccttctggt     12060
atcgcttggc ctcctcaata ggatctcggt tctggccgta cagacctcgg ccgacaatta     12120
```

```
tgatatccgt tccggtagac atgacatcct caacagttcg gtactgctgt ccgagagcgt   12180
ctcccttgtc gtcaagaccc accccggggg tcagaataag ccagtcctca gagtcgccct   12240
taggtcggtt ctgggcaatg aagccaacca caaactcggg gtcggatcgg gcaagctcaa   12300
tggtctgctt ggagtactcg ccagtggcca gagagccctt gcaagacagc tcggccagca   12360
tgagcagacc tctggccagc ttctcgttgg gagagggac taggaactcc ttgtactggg    12420
agttctcgta gtcagagacg tcctccttct tctgttcaga gacagtttcc tcggcaccag   12480
ctcgcaggcc agcaatgatt ccggttccgg gtacaccgtg ggcgttggtg atatcggacc   12540
actcggcgat tcggtgacac cggtactggt gcttgacagt gttgccaata tctgcgaact   12600
ttctgtcctc gaacaggaag aaaccgtgct taagagcaag ttccttgagg gggagcacag   12660
tgccggcgta ggtgaagtcg tcaatgatgt cgatatgggg tttgatcatg cacacataag   12720
gtccgacctt atcggcaagc tcaatgagct ccttggtggt ggtaacatcc agagaagcac   12780
acaggttggt tttcttggct gccacgagct tgagcactcg agcggcaaag gcggacttgt   12840
ggacgttagc tcgagcttcg taggagggca ttttggtggt gaagaggaga ctgaaataaa   12900
tttagtctgc agaactttt atcggaacct tatctgggc agtgaagtat atgttatggt     12960
aatagttacg agttagttga acttatagat agactggact atacggctat cggtccaaat   13020
tagaaagaac gtcaatggct ctctgggcgt cgcctttgcc gacaaaaatg tgatcatgat   13080
gaaagccagc aatgacgttg cagctgatat tgttgtcggc caaccgcgcc gaaaacgcag   13140
ctgtcagacc cacagcctcc aacgaagaat gtatcgtcaa agtgatccaa gcacactcat   13200
agttggagtc gtactccaaa ggcggcaatg acgagtcaga cagatactcg tcgacgcgat   13260
aacttcgtat aatgtatgct atacgaagtt atcgtacgat agttagtaga caacaatcga   13320
taacgtctcg taccaaccac agattacgac ccattcgcag tcacagttca ctagggtttg   13380
ggttgcatcc gttgagagcg gtttgttttt aaccttctcc atgtgctcac tcaggttttg   13440
ggttcagatc aaatcaaggc gtgaaccact ttgtttgagg acaaatgtga cacaaccaac   13500
cagtgtcagg gcaagtccg tgacaaaggg gaagatacaa tgcaattact gacagttaca    13560
gactgcctcg atgccctaac cttgccccaa aataagacaa ctgtcctcgt ttaagcgcaa   13620
ccctattcag cgtcacgtca taatagcgtt tggatagcac tagtctatga ggagcgtttt   13680
atgttgcggt gagggcgatt ggtgctcata tgggttcaat tgaggtggcg gaacgagctt   13740
agtcttcaat tgaggtgcga gcgacacaat tgggtgtcac gtggcctaat tgacctcggg   13800
tcgtggagtc cccagttata cagcaaccac gaggtgcatg ggtaggagac gtcaccagac   13860
aatagggttt ttttggact ggagagggtt gggcaaaagc gctcaacggg ctgtttgggg    13920
agctgtgggg gaggaattgg cgatatttgt gaggttaacg gctccgattt gcgtgttttg   13980
tcgctcctgc atctccccat acccatatct tccctcccca cctctttcca cgataatttt   14040
acggatcagc aataaggttc cttctcctag tttccacgtc catatatatc tatgctgcgt   14100
cgtccttttc gtgacatcac caaaacacat acaacaatgg ctgttactga cgtccttaag   14160
cgaaagtccg gtgtcatcgt cggcgacgat gtccgagccg tgagtatcca cgacaagatc   14220
agtgtcgaga cgacgcgttt tgtgtaatga cacaatccga aagtcgctag caacacacac   14280
tctctacaca aactaaccca gctctccatg gcctccacct cggctctgcc caagcagaac   14340
cctgccctcc gacgaaccgt cacttccacc actgtgaccg actcggagtc tgctgccgtc   14400
tctccctccg attctcccag acactcggcc tcctctacat cgctgtcttc catgtccgag   14460
gtggacattg ccaagcccaa gtccgagtac ggtgtcatgc tggataccta cggcaaccag   14520
```

-continued

```
ttcgaagttc ccgacttcac catcaaggac atctacaacg ctattcccaa gcactgcttc    14580
aagcgatctg ctctcaaggg atacggctac attcttcgag acattgtcct cctgactacc    14640
actttcagca tctggtacaa ctttgtgaca cccgagtaca ttccctccac tcctgctcga    14700
gccggtctgt gggctgtgta caccgttctt cagggactct tcggtactgg actgtgggtc    14760
attgcccacg agtgtggaca tggtgctttc tccgattccc gaatcatcaa cgacattact    14820
ggctgggtgc ttcactcttc cctgcttgtt ccctacttca gctggcaaat ctcccaccgg    14880
aagcatcaca aggccactgg aaacatggag cgagacatgg tcttcgttcc tcgaacccga    14940
gagcagcaag ctactcgact cggcaagatg acccacgaac tcgcccatct taccgaggaa    15000
actcctgctt tcaccctgct catgcttgtg cttcagcaac tggtcggttg cccaactat     15060 ctcattacca acgttactgg acacaactac catgagcggc agcgagaggg tcgaggcaag    15120
ggaaagcaca acggtcttgg cggtggagtt aaccatttcg atccccgatc tcctctgtac    15180
gagaacagcg acgccaagct catcgtgctc tccgacattg gcattggtct tatggccacc    15240
gctctgtact ttctcgttca gaagttcgga ttctacaaca tggccatctg gtacttcgtt    15300
ccctacttgt gggttaacca ctggctcgtc gccattacct ttctgcagca cacagatcct    15360
actcttcccc actacaccaa cgacgagtgg aactttgtgc gaggtgccgc tgcaaccatc    15420
gaccgagaga tgggcttcat tggacgtcat ctgctccacg gcattatcga gactcacgtc    15480
ctgcatcact acgtctcttc cattcccttc tacaatgcgg acgaagctac cgaggccatc    15540
aaacctatca tgggcaagca ctatcgagct gatgtccagg acggtcctcg aggattcatt    15600
cgagccatgt accgatctgc acgaatgtgc cagtgggttg aaccctccgc tggtgccgag    15660
ggagctggca agggtgtcct gttctttcga aaccgaaaca atgtgggcac tcctcccgct    15720
gtcatcaagc ccgttgccta agc                                            15743
```

<210> SEQ ID NO 72
<211> LENGTH: 1434
<212> TYPE: DNA
<213> ORGANISM: Fusarium moniliforme
<220> FEATURE:
<221> NAME/KEY: CDS
<222> LOCATION: (1)..(1434)
<223> OTHER INFORMATION: synthetic delta-12 desaturase (codon-optimized for Yarrowia lipolytica)
<300> PUBLICATION INFORMATION:
<302> TITLE: DELTA-12 DESATURASES SUITABLE FOR ALTERING LEVELS OF POLYUNSATURATED FATTY ACIDS IN OLEAGINOUS YEAST
<310> PATENT DOCUMENT NUMBER: WO 2005/047485
<311> PATENT FILING DATE: 2004-11-12
<312> PUBLICATION DATE: 2005-05-26
<313> RELEVANT RESIDUES: (1)..(1434)
<300> PUBLICATION INFORMATION:
<302> TITLE: DELTA-12 DESATURASES SUITABLE FOR ALTERING LEVELS OF POLYUNSATURATED FATTY ACIDS IN OLEAGINOUS YEAST
<310> PATENT DOCUMENT NUMBER: US 2005-0216975-A1
<311> PATENT FILING DATE: 2004-11-10
<312> PUBLICATION DATE: 2005-09-29
<313> RELEVANT RESIDUES: (1)..(1434)

<400> SEQUENCE: 72

```
atg gcc tcc acc tcg gct ctg ccc aag cag aac cct gcc ctc cga cga    48
Met Ala Ser Thr Ser Ala Leu Pro Lys Gln Asn Pro Ala Leu Arg Arg
1               5                   10                  15 acc gtc act tcc acc act gtg acc gac tcg gag tct gct gcc gtc tct    96
Thr Val Thr Ser Thr Thr Val Thr Asp Ser Glu Ser Ala Ala Val Ser
            20                  25                  30 ccc tcc gat tct ccc aga cac tcg gcc tcc tct aca tcg ctg tct tcc   144
Pro Ser Asp Ser Pro Arg His Ser Ala Ser Ser Thr Ser Leu Ser Ser
        35                  40                  45
```

```
atg tcc gag gtg gac att gcc aag ccc aag tcc gag tac ggt gtc atg      192
Met Ser Glu Val Asp Ile Ala Lys Pro Lys Ser Glu Tyr Gly Val Met
 50              55                  60 ctg gat acc tac ggc aac cag ttc gaa gtt ccc gac ttc acc atc aag      240
Leu Asp Thr Tyr Gly Asn Gln Phe Glu Val Pro Asp Phe Thr Ile Lys
 65          70                  75                  80 gac atc tac aac gct att ccc aag cac tgc ttc aag cga tct gct ctc      288
Asp Ile Tyr Asn Ala Ile Pro Lys His Cys Phe Lys Arg Ser Ala Leu
                 85                  90                  95 aag gga tac ggc tac att ctt cga gac att gtc ctc ctg act acc act      336
Lys Gly Tyr Gly Tyr Ile Leu Arg Asp Ile Val Leu Leu Thr Thr Thr
            100                 105                 110 ttc agc atc tgg tac aac ttt gtg aca ccc gag tac att ccc tcc act      384
Phe Ser Ile Trp Tyr Asn Phe Val Thr Pro Glu Tyr Ile Pro Ser Thr
        115                 120                 125 cct gct cga gcc ggt ctg tgg gct gtg tac acc gtt ctt cag gga ctc      432
Pro Ala Arg Ala Gly Leu Trp Ala Val Tyr Thr Val Leu Gln Gly Leu
130                 135                 140 ttc ggt act gga ctg tgg gtc att gcc cac gag tgt gga cat ggt gct      480
Phe Gly Thr Gly Leu Trp Val Ile Ala His Glu Cys Gly His Gly Ala
145                 150                 155                 160 ttc tcc gat tcc cga atc atc aac gac att act ggc tgg gtg ctt cac      528
Phe Ser Asp Ser Arg Ile Ile Asn Asp Ile Thr Gly Trp Val Leu His
                165                 170                 175 tct tcc ctg ctt gtt ccc tac ttc agc tgg caa atc tcc cac cgg aag      576
Ser Ser Leu Leu Val Pro Tyr Phe Ser Trp Gln Ile Ser His Arg Lys
            180                 185                 190 cat cac aag gcc act gga aac atg gag cga gac atg gtc ttc gtt cct      624
His His Lys Ala Thr Gly Asn Met Glu Arg Asp Met Val Phe Val Pro
        195                 200                 205 cga acc cga gag cag caa gct act cga ctc ggc aag atg acc cac gaa      672
Arg Thr Arg Glu Gln Gln Ala Thr Arg Leu Gly Lys Met Thr His Glu
210                 215                 220 ctc gcc cat ctt acc gag gaa act cct gct ttc acc ctg ctc atg ctt      720
Leu Ala His Leu Thr Glu Glu Thr Pro Ala Phe Thr Leu Leu Met Leu
225                 230                 235                 240 gtg ctt cag caa ctg gtc ggt tgg ccc aac tat ctc att acc aac gtt      768
Val Leu Gln Gln Leu Val Gly Trp Pro Asn Tyr Leu Ile Thr Asn Val
                245                 250                 255 act gga cac aac tac cat gag cgg cag cga gag ggt cga ggc aag gga      816
Thr Gly His Asn Tyr His Glu Arg Gln Arg Glu Gly Arg Gly Lys Gly
            260                 265                 270 aag cac aac ggt ctt ggc ggt gga gtt aac cat ttc gat ccc cga tct      864
Lys His Asn Gly Leu Gly Gly Gly Val Asn His Phe Asp Pro Arg Ser
        275                 280                 285 cct ctg tac gag aac agc gac gcc aag ctc atc gtg ctc tcc gac att      912
Pro Leu Tyr Glu Asn Ser Asp Ala Lys Leu Ile Val Leu Ser Asp Ile
290                 295                 300 ggc att ggt ctt atg gcc acc gct ctg tac ttt ctc gtt cag aag ttc      960
Gly Ile Gly Leu Met Ala Thr Ala Leu Tyr Phe Leu Val Gln Lys Phe
305                 310                 315                 320 gga ttc tac aac atg gcc atc tgg tac ttc gtt ccc tac ttg tgg gtt     1008
Gly Phe Tyr Asn Met Ala Ile Trp Tyr Phe Val Pro Tyr Leu Trp Val
                325                 330                 335 aac cac tgg ctc gtc gcc att acc ttt ctg cag cac aca gat cct act     1056
Asn His Trp Leu Val Ala Ile Thr Phe Leu Gln His Thr Asp Pro Thr
            340                 345                 350 ctt ccc cac tac acc aac gac gag tgg aac ttt gtg cga ggt gcc gct     1104
Leu Pro His Tyr Thr Asn Asp Glu Trp Asn Phe Val Arg Gly Ala Ala
355                 360                 365
```

```
gca acc atc gac cga gag atg ggc ttc att gga cgt cat ctg ctc cac    1152
Ala Thr Ile Asp Arg Glu Met Gly Phe Ile Gly Arg His Leu Leu His
    370             375                 380 ggc att atc gag act cac gtc ctg cat cac tac gtc tct tcc att ccc    1200
Gly Ile Ile Glu Thr His Val Leu His His Tyr Val Ser Ser Ile Pro
385             390                 395                 400 ttc tac aat gcg gac gaa gct acc gag gcc atc aaa cct atc atg ggc    1248
Phe Tyr Asn Ala Asp Glu Ala Thr Glu Ala Ile Lys Pro Ile Met Gly
                405                 410                 415 aag cac tat cga gct gat gtc cag gac ggt cct cga gga ttc att cga    1296
Lys His Tyr Arg Ala Asp Val Gln Asp Gly Pro Arg Gly Phe Ile Arg
            420                 425                 430 gcc atg tac cga tct gca cga atg tgc cag tgg gtt gaa ccc tcc gct    1344
Ala Met Tyr Arg Ser Ala Arg Met Cys Gln Trp Val Glu Pro Ser Ala
        435                 440                 445 ggt gcc gag gga gct ggc aag ggt gtc ctg ttc ttt cga aac cga aac    1392
Gly Ala Glu Gly Ala Gly Lys Gly Val Leu Phe Phe Arg Asn Arg Asn
    450                 455                 460 aat gtg ggc act cct ccc gct gtc atc aag ccc gtt gcc taa            1434
Asn Val Gly Thr Pro Pro Ala Val Ile Lys Pro Val Ala
465                 470                 475

<210> SEQ ID NO 73
<211> LENGTH: 477
<212> TYPE: PRT
<213> ORGANISM: Fusarium moniliforme

<400> SEQUENCE: 73

Met Ala Ser Thr Ser Ala Leu Pro Lys Gln Asn Pro Ala Leu Arg Arg
1               5                   10                  15

Thr Val Thr Ser Thr Thr Val Thr Asp Ser Glu Ser Ala Ala Val Ser
            20                  25                  30

Pro Ser Asp Ser Pro Arg His Ser Ala Ser Ser Thr Ser Leu Ser Ser
        35                  40                  45

Met Ser Glu Val Asp Ile Ala Lys Pro Lys Ser Glu Tyr Gly Val Met
    50                  55                  60

Leu Asp Thr Tyr Gly Asn Gln Phe Glu Val Pro Asp Phe Thr Ile Lys
65                  70                  75                  80

Asp Ile Tyr Asn Ala Ile Pro Lys His Cys Phe Lys Arg Ser Ala Leu
                85                  90                  95

Lys Gly Tyr Gly Tyr Ile Leu Arg Asp Ile Val Leu Leu Thr Thr Thr
            100                 105                 110

Phe Ser Ile Trp Tyr Asn Phe Val Thr Pro Glu Tyr Ile Pro Ser Thr
        115                 120                 125

Pro Ala Arg Ala Gly Leu Trp Ala Val Tyr Thr Val Leu Gln Gly Leu
    130                 135                 140

Phe Gly Thr Gly Leu Trp Val Ile Ala His Glu Cys Gly His Gly Ala
145                 150                 155                 160

Phe Ser Asp Ser Arg Ile Ile Asn Asp Ile Thr Gly Trp Val Leu His
                165                 170                 175

Ser Ser Leu Leu Val Pro Tyr Phe Ser Trp Gln Ile Ser His Arg Lys
            180                 185                 190

His His Lys Ala Thr Gly Asn Met Glu Arg Asp Met Val Phe Val Pro
        195                 200                 205

Arg Thr Arg Glu Gln Gln Ala Thr Arg Leu Gly Lys Met Thr His Glu
    210                 215                 220

Leu Ala His Leu Thr Glu Glu Thr Pro Ala Phe Thr Leu Leu Met Leu
```

```
                 225                 230                 235                 240
Val Leu Gln Gln Leu Val Gly Trp Pro Asn Tyr Leu Ile Thr Asn Val
                245                 250                 255

Thr Gly His Asn Tyr His Glu Arg Gln Arg Glu Gly Arg Gly Lys Gly
            260                 265                 270

Lys His Asn Gly Leu Gly Gly Val Asn His Phe Asp Pro Arg Ser
    275                 280                 285

Pro Leu Tyr Glu Asn Ser Asp Ala Lys Leu Ile Val Leu Ser Asp Ile
        290                 295                 300

Gly Ile Gly Leu Met Ala Thr Ala Leu Tyr Phe Leu Val Gln Lys Phe
305                 310                 315                 320

Gly Phe Tyr Asn Met Ala Ile Trp Tyr Phe Val Pro Tyr Leu Trp Val
                325                 330                 335

Asn His Trp Leu Val Ala Ile Thr Phe Leu Gln His Thr Asp Pro Thr
            340                 345                 350

Leu Pro His Tyr Thr Asn Asp Glu Trp Asn Phe Val Arg Gly Ala Ala
        355                 360                 365

Ala Thr Ile Asp Arg Glu Met Gly Phe Ile Gly Arg His Leu Leu His
    370                 375                 380

Gly Ile Ile Glu Thr His Val Leu His His Tyr Val Ser Ser Ile Pro
385                 390                 395                 400

Phe Tyr Asn Ala Asp Glu Ala Thr Glu Ala Ile Lys Pro Ile Met Gly
                405                 410                 415

Lys His Tyr Arg Ala Asp Val Gln Asp Gly Pro Arg Gly Phe Ile Arg
            420                 425                 430

Ala Met Tyr Arg Ser Ala Arg Met Cys Gln Trp Val Glu Pro Ser Ala
        435                 440                 445

Gly Ala Glu Gly Ala Gly Lys Gly Val Leu Phe Phe Arg Asn Arg Asn
    450                 455                 460

Asn Val Gly Thr Pro Pro Ala Val Ile Lys Pro Val Ala
465                 470                 475

<210> SEQ ID NO 74
<211> LENGTH: 6303
<212> TYPE: DNA
<213> ORGANISM: Artificial Sequence
<220> FEATURE:
<223> OTHER INFORMATION: Plasmid pZKUE3S

<400> SEQUENCE: 74
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
aacatactgt acatactcat actcgtaccc gggcaacggt ttcacttgag tgcagtggct     240
agtgctctta ctcgtacagt gtgcaatact gcgtatcata gtctttgatg tatatcgtat     300
tcattcatgt tagttgcgta cgaggaaact gtctctgaac agaagaagga ggacgtctct     360
gactacgaga actcccagta caaggagttc ctagtcccct ctcccaacga gaagctggcc     420
agaggtctgc tcatgctggc cgagctgtct tgcaagggct ctctggccac tggcgagtac     480
tccaagcaga ccattgagct tgcccgatcc gaccccgagt ttgtggttgg cttcattgcc     540
cagaaccgac ctaagggcga ctctgaggac tggcttattc tgaccccgg ggtgggtctt     600 gacgacaagg gagacgctct cggacagcag taccgaactg ttgaggatgt catgtctacc     660
ggaacggata tcataattgt cggccgaggt ctgtacggcc agaaccgaga tcctattgag     720
```

```
gaggccaagc gataccagaa ggctggctgg gaggcttacc agaagattaa ctgttagagg    780
ttagactatg gatatgtaat ttaactgtgt atatagagag cgtgcaagta tggagcgctt    840
gttcagcttg tatgatggtc agacgacctg tctgatcgag tatgtatgat actgcacaac    900
ctgtgtatcc gcatgatctg tccaatgggg catgttgttg tgtttctcga tacgagatg     960
ctgggtacag tgctaatacg ttgaactact tatacttata tgaggctcga agaaagctga   1020
cttgtgtatg acttaattaa tcgagcttgg cgtaatcatg gtcatagctg tttcctgtgt   1080
gaaattgtta tccgctcaca attccacaca acatacgagc cggaagcata agtgtaaag    1140
cctggggtgc ctaatgagtg agctaactca cattaattgc gttgcgctca ctgcccgctt   1200
tccagtcggg aaacctgtcg tgccagctgc attaatgaat cggccaacgc gcgggagag    1260
gcggtttgcg tattgggcgc tcttccgctt cctcgctcac tgactcgctg cgctcggtcg   1320
ttcggctgcg gcgagcggta tcagctcact caaaggcggt aatacggtta ccacagaat    1380
caggggataa cgcaggaaag aacatgtgag caaaaggcca gcaaaaggcc aggaaccgta   1440
aaaaggccgc gttgctggcg ttttttccata ggctccgccc ccctgacgag catcacaaaa   1500
atcgacgctc aagtcagagg tggcgaaacc cgacaggact ataaagatac caggcgtttc   1560
ccctggaag ctccctcgtg cgctctcctg ttccgaccct gccgcttacc ggatacctgt    1620
ccgcctttct cccttcggga agcgtggcgc tttctcatag ctcacgctgt aggtatctca   1680
gttcggtgta ggtcgttcgc tccaagctgg gctgtgtgca cgaaccccc gttcagcccg    1740
accgctgcgc cttatccggt aactatcgtc ttgagtccaa cccggtaaga cacgacttat   1800
cgccactggc agcagccact ggtaacagga ttagcagagc gaggtatgta ggcggtgcta   1860
cagagttctt gaagtggtgg cctaactacg gctacactag aaggacagta tttggtatct   1920
gcgctctgct gaagccagtt accttcggaa aaagagttgg tagctcttga tccggcaaac   1980
aaaccaccgc tggtagcggt ggttttttg tttgcaagca gcagattacg cgcagaaaaa   2040
aaggatctca agaagatcct ttgatctttt ctacgggtc tgacgctcag tggaacgaaa    2100
actcacgtta agggattttg gtcatgagat tatcaaaaag gatcttcacc tagatccttt   2160
taaattaaaa atgaagtttt aaatcaatct aaagtatata tgagtaaact tggtctgaca   2220
gttaccaatg cttaatcagt gaggcaccta tctcagcgat ctgtctattt cgttcatcca   2280
tagttgcctg actccccgtc gtgtagataa ctacgatacg ggagggctta ccatctggcc   2340
ccagtgctgc aatgataccg cgagacccac gctcaccggc tccagattta tcagcaataa   2400
accagccagc cggaagggcc gagcgcagaa gtggtcctgc aactttatcc gcctccatcc   2460
agtctattaa ttgttgccgg gaagctagag taagtagttc gccagttaat agtttgcgca   2520
acgttgttgc cattgctaca ggcatcgtgg tgtcacgctc gtcgtttggt atggcttcat   2580
tcagctccgg ttcccaacga tcaaggcgag ttacatgatc ccccatgttg tgcaaaaaag   2640
cggttagctc cttcggtcct ccgatcgttg tcagaagtaa gttggccgca gtgttatcac   2700
tcatggttat ggcagcactg cataattctc ttactgtcat gccatccgta agatgctttt   2760
ctgtgactgg tgagtactca accaagtcat tctgagaata gtgtatgcgg cgaccgagtt   2820
gctcttgccc ggcgtcaata cgggataata ccgcgccaca tagcagaact ttaaaagtgc   2880
tcatcattgg aaaacgttct cggggcgaa aactctcaag gatcttaccg ctgttgagat    2940
ccagttcgat gtaacccact cgtgcaccca actgatcttc agcatctttt actttcacca   3000
gcgtttctgg gtgagcaaaa acaggaaggc aaaatgccgc aaaaaaggga ataagggcga   3060
cacggaaatg ttgaatactc atactcttcc ttttttcaata ttattgaagc atttatcagg   3120
```

```
gttattgtct catgagcgga tacatatttg aatgtattta gaaaaataaa caaatagggg    3180
ttccgcgcac atttccccga aaagtgccac ctgacgcgcc ctgtagcggc gcattaagcg    3240
cggcgggtgt ggtggttacg cgcagcgtga ccgctacact tgccagcgcc ctagcgcccg    3300
ctcctttcgc tttcttccct tcctttctcg ccacgttcgc cggctttccc cgtcaagctc    3360
taaatcgggg gctcccttta gggttccgat ttagtgcttt acggcacctc gaccccaaaa    3420
aacttgatta gggtgatggt tcacgtagtg ggccatcgcc ctgatagacg gtttttcgcc    3480
ctttgacgtt ggagtccacg ttctttaata gtggactctt gttccaaact ggaacaacac    3540
tcaaccctat ctcggtctat tcttttgatt tataagggat tttgccgatt tcggcctatt    3600
ggttaaaaaa tgagctgatt taacaaaaat ttaacgcgaa ttttaacaaa atattaacgc    3660
ttacaatttc cattcgccat tcaggctgcg caactgttgg gaagggcgat cggtgcgggc    3720
ctcttcgcta ttacgccagc tggcgaaagg gggatgtgct gcaaggcgat taagttgggt    3780
aacgccaggg ttttcccagt cacgacgttg taaaacgacg ccagtgaat tgtaatacga    3840 ctcactatag ggcgaattgg gtaccgggcc cccctcgag gtcgacgagt atctgtctga    3900
ctcgtcattg catgccttg gagtacgact ccaactatga gtgtgcttgg atcactttga    3960
cgatacattc ttcgttggag gctgtgggtc tgacagctgc gttttcggcg cggttggccg    4020
acaacaatat cagctgcaac gtcattgctg gctttcatca tgatcacatt tttgtcggca    4080
aaggcgacgc ccagagagcc attgacgttc tttctaattt ggaccgatag ccgtatagtc    4140
cagtctatct ataagttcaa ctaactcgta actattacca taacatatac ttcactgccc    4200
cagataaggt tccgataaaa agttctgcag actaaattta tttcagtctc ctcttcacca    4260
ccaaaatgcc ctcctacgaa gctcgagtgc tcaagctcgt ggcagccaag aaaaccaacc    4320
tgtgtgcttc tctggatgtt accaccacca aggagctcat tgagcttgcc gataaggtcg    4380
gaccttatgt gtgcatgatc aaaacccata tcgacatcat tgacgacttc acctacgccg    4440
gcactgtgct ccccctcaag gaacttgctc ttaagcacgg tttcttcctg ttcgaggaca    4500
gaaagttcgc agatattggc aacactgtca agcaccagta ccggtgtcac cgaatcgccg    4560
agtggtccga tatcaccaac gcccacggtg tttaaacccg gaaccggaat cgataagctt    4620
gatatcgaat tcatgctgtt catcgtggtt aatgctgctg tgtgctgtgt gtgtgtgttg    4680
tttggcgctc attgttgcgt tatgcagcgt acaccacaat attggaagct tattagcctt    4740
tctatttttt cgtttgcaag gcttaacaac attgctgtgg agagggatgg ggatatggag    4800
gccgctggag ggagtcggag aggcgttttg gagcggcttg gcctggcgcc cagctcgcga    4860
aacgcaccta ggaccctttg gcacgccgaa atgtgccact tttcagtcta gtaacgcctt    4920
acctacgtca ttccatgcgt gcatgtttgc gccttttttc ccttgccctt gatcgccaca    4980
cagtacagtg cactgtacag tggaggtttt gggggggtct tagatgggag ctaaaagcgg    5040
cctagcggta cactagtggg attgtatgga gtggcatgga gcctaggtgg agcctgacag    5100
gacgcacgac cggctagccc gtgacagacg atgggtggct cctgttgtcc accgcgtaca    5160
aatgtttggg ccaaagtctt gtcagccttg cttgcgaacc taattcccaa ttttgtcact    5220
tcgcaccccc attgatcgag ccctaacccc tgcccatcag gcaatccaat taagctcgca    5280
ttgtctgcct tgtttagttt ggctcctgcc cgtttcggcg tccacttgca caaacacaaa    5340
caagcattat atataaggct cgtctctccc tcccaaccac actcactttt tgcccgtct    5400 tcccttgcta acacaaaagt caagaacaca aacaaccacc caaccccct tacacacaag    5460 acatatctac accatggagt ctggacccat gcctgctggc attcccttcc ctgagtacta    5520
```

| | |
|---|---|
| tgacttctttt atggactgga agactcccct ggccatcgct gccacctaca ctgctgccgt | 5580 |
| cggtctcttc aaccccaagg ttggcaaggt ctcccgagtg gttgccaagt cggctaacgc | 5640 |
| aaagcctgcc gagcgaaccc agtccggagc tgccatgact gccttcgtct ttgtgcacaa | 5700 |
| cctcattctg tgtgtctact ctggcatcac cttctactac atgtttcctg ctatggtcaa | 5760 |
| gaacttccga acccacacac tgcacgaagc tactgcgac acggatcagt ccctctggaa | 5820 |
| caacgcactt ggctactggg gttacctctt ctacctgtcc aagttctacg aggtcattga | 5880 |
| caccatcatc atcatcctga agggacgacg gtcctcgctg cttcagacct accaccatgc | 5940 |
| tggagccatg attaccatgt ggtctggcat caactaccaa gccactccca tttggatctt | 6000 |
| tgtggtcttc aactccttca ttcacaccat catgtactgt tactatgcct tcacctctat | 6060 |
| cggattccat cctcctggca aaaagtacct gacttcgatg cagattactc agtttctggt | 6120 |
| cggtatcacc attgccgtgt cctacctctt cgttcctggc tgcatccgaa cacccggtgc | 6180 |
| tcagatggct gtctggatca acgtcggcta cctgtttccc ttgacctatc tgttcgtgga | 6240 |
| ctttgccaag cgaacctact ccaagcgatc tgccattgcc gctcagaaaa aggctcagta | 6300 |
| agc | 6303 |

<210> SEQ ID NO 75
<211> LENGTH: 15877
<212> TYPE: DNA
<213> ORGANISM: Artificial Sequence
<220> FEATURE:
<223> OTHER INFORMATION: Plasmid pZKL1-2SP98C

<400> SEQUENCE: 75

| | |
|---|---|
| aaatgatgtc gacgcagtag gatgtcctgc acgggtcttt ttgtgggtg tggagaaagg | 60 |
| ggtgcttgga tcgatggaag ccggtagaac cgggctgctt gtgcttggag atggaagccg | 120 |
| gtagaaccgg gctgcttggg gggatttggg gccgctgggc tccaaagagg ggtaggcatt | 180 |
| tcgttggggt tacgtaattg cggcatttgg gtcctgcgcg catgtcccat tggtcagaat | 240 |
| tagtccggat aggagactta tcagccaatc acagcgccgg atccacctgt aggttgggtt | 300 |
| gggtgggagc accccctcca cagagtagagt caaacagcag cagcaacatg atagttgggg | 360 |
| gtgtgcgtgt taaaggaaaa aaaagaagct tgggttatat tcccgctcta tttagaggtt | 420 |
| gcgggataga cgccgacgga gggcaatggc gctatggaac cttgcggata tccatacgcc | 480 |
| gcggcggact gcgtccgaac cagctccagc agcgttttt ccgggccatt gagccgactg | 540 |
| cgaccccgcc aacgtgtctt ggcccacgca ctcatgtcat gttggtgttg ggaggccact | 600 |
| ttttaagtag cacaaggcac ctagctcgca gcaaggtgtc cgaaccaaag aagcggctgc | 660 |
| agtggtgcaa acgggcgga aacggcggga aaaagccacg ggggcacgaa ttgaggcacg | 720 |
| ccctcgaatt tgagacgagt cacggcccca ttcgcccgcg caatggctcg ccaacgcccg | 780 |
| gtctttttgca ccacatcagg ttaccccaag ccaaaccttt gtgttaaaaa gcttaacata | 840 |
| ttataccgaa cgtaggtttg ggcgggcttg ctccgtctgt ccaaggcaac atttatataa | 900 |
| gggtctgcat cgccggctca attgaatctt ttttcttctt ctcttctcta tattcattct | 960 |
| tgaattaaac acacatcaac catgggcgta ttcattaaac aggagcagct tccggctctc | 1020 |
| aagaagtaca agtactccgc cgaggatcac tcgttcatct ccaacaacat tctgcgcccc | 1080 |
| ttctggcgac agtttgtcaa aatcttccct ctgtggatgg ccccaacat ggtgactctg | 1140 |
| ctgggcttct tctttgtcat tgtgaacttc atcaccatgc tcattgttga tcccaccac | 1200 |
| gaccgcgagc ctcccagatg ggtctacctc acctacgctc tgggtctgtt cctttaccag | 1260 |

```
acatttgatg cctgtgacgg atcccatgcc cgacgaactg gccagagtgg acccttgga   1320 gagctgtttg accactgtgt cgacgccatg aatacctctc tgattctcac ggtggtggtg   1380
tccaccaccc atatgggata taacatgaag ctactgattg tgcagattgc cgctctcgga   1440
aacttctacc tgtcgacctg ggagacctac cataccggaa ctctgtacct ttctggcttc   1500
tctggtcctg ttgaaggtat cttgattctg gtggctcttt tcgtcctcac cttcttcact   1560
ggtcccaacg tgtacgctct gaccgtctac gaggctcttc ccgagtccat cacttcgctg   1620
ctgcctgcca gcttcctgga cgtcaccatc acccagatct acattggatt cggagtgctg   1680
ggcatggtgt tcaacatcta cggcgcctgc ggaaacgtga tcaagtacta caacaacaag   1740
ggcaagagcg ctctccccgc cattctcgga atcgcccct ttggcatctt ctacgtcggc    1800
gtctttgcct gggcccatgt tgctcctctg cttctctcca gtacgccat cgtctatctg    1860 tttgccattg ggctgccctt tgccatgcaa gtcggccaga tgattcttgc ccatctcgtg   1920
cttgctccct ttccccactg gaacgtgctg ctcttcttcc cctttgtggg actggcagtg   1980
cactacattg cacccgtgtt tggctgggac gccgatatcg tgtcggttaa cactctcttc   2040
acctgttttg gcgccaccct ctccatttac gccttctttg tgcttgagat catcgacgag   2100
atcaccaact acctcgatat ctggtgtctg cgaatcaagt accctcagga gaagaagacc   2160
gaataagcgg ccgcatggag cgtgtgttct gagtcgatgt tttctatgga gttgtgagtg   2220
ttagtagaca tgatgggttt atatatgatg aatgaataga tgtgattttg atttgcacga   2280
tggaattgag aactttgtaa acgtacatgg gaatgtatga atgtgggggt tttgtgactg   2340
gataactgac ggtcagtgga cgccgttgtt caaatatcca agagatgcga gaaactttgg   2400
gtcaagtgaa catgtcctct ctgttcaagt aaaccatcaa ctatgggtag tatatttagt   2460
aaggacaaga gttgagattc tttggagtcc tagaaacgta ttttcgcgtt ccaagatcaa   2520
attagtagag taatacgggc acgggaatcc attcatagtc tcaatcctgc aggtgagtta   2580
attaatcgag cttggcgtaa tcatggtcat agctgtttcc tgtgtgaaat tgttatccgc   2640
tcacaattcc acacaacgta cgatagttag tagacaacaa tcagaacatc tccctcctta   2700
tataatcaca caggccagaa cgcgctaaac taaagcgctt tggacactat gttacattgg   2760
cattgattga actgaaacca cagtctccct cgcctgaatc gagcaatgga tgttgtcgga   2820
agtcaacttc actagaagag cggttctatg ccttgtcaag atcatatcat aaactcactc   2880
tgtattaccc catctataga acacttgtta tgaatgggcg gaaacattcc gctatatgca   2940
cctttccaca ctaatgcaaa gatgtgcatc ttcaacgggt agtaagactg gttccgactt   3000
ccgttgcatg gagagcaatg acctcgataa tgcgaacatc ccccacatat acactcttac   3060
acaggccaat ataatctgtg catttactaa atatttaagt ctatgcacct gcttgatgaa   3120
aagcggcacg gatggtatca tctagttttc gccaatccaa gaaccaactg tgttggcagt   3180
ggtgtagccc atgcacaca gaccaaagat gaaaatacag acatcggcgg ttcgagccgt    3240
ggtgcctcga gcaacaccct tgtaatgcaa aagaggaggg taaatgtaca ccagaggcac   3300
acatgcaaac gatccggtga gagcgacgaa ccgatcgaga tcgtcggcac ctccccatgc   3360
aacaaaggcg gtgacaaaca caaggaagaa ccggaaaatg ttcttctgcc acttgatggt   3420
agagttgtac ttgcctgatc gggtgaagag accattctcg atgattcgga tggcgcgcca   3480
gctgcattaa tgaatcggcc aacgcgcggg gagaggcggt ttgcgtattg ggcgctcttc   3540
cgcttcctcg ctcactgact cgctgcgctc ggtcgttcgg ctgcggcgag cggtatcagc   3600
tcactcaaag gcggtaatac ggttatccac agaatcaggg gataacgcag gaaagaacat   3660
```

```
gtgagcaaaa ggccagcaaa aggccaggaa ccgtaaaaag gccgcgttgc tggcgttttt    3720
ccataggctc cgccccctg acgagcatca caaaaatcga cgctcaagtc agaggtggcg    3780
aaacccgaca ggactataaa gataccaggc gtttccccct ggaagctccc tcgtgcgctc    3840
tcctgttccg accctgccgc ttaccggata cctgtccgcc tttctccctt cgggaagcgt    3900
ggcgctttct catagctcac gctgtaggta tctcagttcg gtgtaggtcg ttcgctccaa    3960
gctgggctgt gtgcacgaac cccccgttca gcccgaccgc tgcgccttat ccggtaacta    4020
tcgtcttgag tccaacccgg taagacacga cttatcgcca ctggcagcag ccactggtaa    4080
caggattagc agagcgaggt atgtaggcgg tgctacagag ttcttgaagt ggtggcctaa    4140
ctacggctac actagaagaa cagtatttgg tatctgcgct ctgctgaagc cagttacctt    4200
cggaaaaaga gttggtagct cttgatccgg caaacaaacc accgctggta gcggtggttt    4260
ttttgtttgc aagcagcaga ttacgcgcag aaaaaaagga tctcaagaag atcctttgat    4320
cttttctacg gggtctgacg ctcagtggaa cgaaaactca cgttaaggga ttttggtcat    4380
gagattatca aaaaggatct tcacctagat ccttttaaat taaaaatgaa gttttaaatc    4440
aatctaaagt atatatgagt aaacttggtc tgacagttac caatgcttaa tcagtgaggc    4500
acctatctca gcgatctgtc tatttcgttc atccatagtt gcctgactcc ccgtcgtgta    4560
gataactacg atacgggagg gcttaccatc tggccccagt gctgcaatga taccgcgaga    4620
cccacgctca ccggctccag atttatcagc aataaaccag ccagccggaa gggccgagcg    4680
cagaagtggt cctgcaactt tatccgcctc catccagtct attaattgtt gccgggaagc    4740
tagagtaagt agttcgccag ttaatagttt gcgcaacgtt gttgccattg ctacaggcat    4800
cgtggtgtca cgctcgtcgt ttggtatggc ttcattcagc tccggttccc aacgatcaag    4860
gcgagttaca tgatccccca tgttgtgcaa aaaagcggtt agctccttcg gtcctccgat    4920
cgttgtcaga agtaagttgg ccgcagtgtt atcactcatg gttatggcag cactgcataa    4980
ttctcttact gtcatgccat ccgtaagatg cttttctgtg actggtgagt actcaaccaa    5040
gtcattctga atagtgta tgcggcgacc gagttgctct tgcccggcgt caatacggga    5100
taataccgcg ccacatagca gaactttaaa agtgctcatc attggaaaac gttcttcggg    5160
gcgaaaactc tcaaggatct taccgctgtt gagatccagt tcgatgtaac ccactcgtgc    5220
acccaactga tcttcagcat cttttacttt caccagcgtt tctgggtgag caaaaacagg    5280
aaggcaaaat gccgcaaaaa agggaataag ggcgacacgg aaatgttgaa tactcatact    5340 cttcctttt caatattatt gaagcattta tcagggttat tgtctcatga gcggatacat    5400
atttgaatgt atttagaaaa ataaacaaat aggggttccg cgcacatttc cccgaaaagt    5460
gccacctgat gcggtgtgaa ataccgcaca gatgcgtaag gagaaaatac cgcatcagga    5520
aattgtaagc gttaatattt tgttaaaatt cgcgttaaat ttttgttaaa tcagctcatt    5580
ttttaaccaa taggccgaaa tcggcaaaat cccttataaa tcaaagaat agaccgagat    5640 agggttgagt gttgttccag tttggaacaa gagtccacta ttaaagaacg tggactccaa    5700
cgtcaaaggg cgaaaaaccg tctatcaggg cgatggccca ctacgtgaac catcacccta    5760
atcaagtttt tgggtcga ggtgccgtaa agcactaaat cggaaccct aagggagccc    5820 ccgatttaga gcttgacggg gaagccggc gaacgtggcg agaaaggaag ggaagaaagc    5880
gaaaggagcg ggcgctaggg cgctggcaag tgtagcggtc acgctgcgcg taaccaccac    5940
acccgccgcg cttaatgcgc cgctacaggg cgcgtccatt cgccattcag gctgcgcaac    6000
tgttgggaag ggcgatcggt gcgggcctct tcgctattac gccagctggc gaaagggggga    6060
```

```
tgtgctgcaa ggcgattaag ttgggtaacg ccagggtttt cccagtcacg acgttgtaaa    6120
acgacggcca gtgaattgta atacgactca ctatagggcg aattgggccc gacgtcgcat    6180
gcttagaagt gaggattaca agaagcctct ggatatcaat gatgaacgta ctcagcggct    6240
ggtcaagcat ttcgaccgtc gaatcgacga ggtgttcacc tttgacaagc gagggttccc    6300
aattgatcac gttctcgagt tgttcaaatc ttctctcaac atctctctgc atgaactatc    6360
tctgttgacg aacgtgtcac ccactgttcc tcgaacgccc ttctccgagt ttggtctgaa    6420
catcttcgat ctcaaactga cccccgcagt gatcaatagt gccatgccac tgccgatgcg    6480
gtgcgaacat ccctggaggg attctcggag ctctacacaa tgcagattct gtcgtcgagt    6540
actctctacc ttgctcgaat gacttattgt gctactactg cactcatgct tcgatcatgt    6600
gccctactgc accccaaatt tggtgatctg attgagacag agtaccctct tcagctgatt    6660
cagaagatca tcagcaacat gaatgatgtg gttgaccagg caggctgttg tagtcacgtc    6720
cttcacttca agttcattct tcatctgctt ctgttttact ttgacaggca aatgaagaca    6780
tggtacgact tgatggaggc caagaacgcc atttcacccc gagacaccga agtgcctgaa    6840
atcctggctg cccccattga taacatcgga aactacggta ttccggaaag tgtatataga    6900 accttttcccc agcttgtgtc tgtggatatg gatggtgtaa tcccctttaat taactcacct    6960 gcaggattga gactatgaat ggattcccgt gcccgtatta ctctactaat ttgatcttgg    7020
aacgcgaaaa tacgtttcta ggactccaaa gaatctcaac tcttgtcctt actaaatata    7080
ctacccatag ttgatggttt acttgaacag agaggacatg ttcacttgac ccaaagtttc    7140
tcgcatctct tggatatttg aacaacggcg tccactgacc gtcagttatc cagtcacaaa    7200
acccccacat tcatacattc ccatgtacgt ttacaaagtt ctcaattcca tcgtgcaaat    7260
caaaatcaca tctattcatt catcatatat aaacccatca tgtctactaa cactcacaac    7320
tccatagaaa acatcgactc agaacacacg ctccatgcgg ccgcttaggc aacgggcttg    7380
atgacagcgg gaggagtgcc cacattgttt cggtttcgaa agaacaggac acccttgcca    7440
gctccctcgg caccagcgga gggttcaacc cactggcaca ttcgtgcaga tcggtacatg    7500
gctcgaatga atcctcgagg accgtcctgg acatcagctc gatagtgctt gcccatgata    7560
ggtttgatgg cctcggtagc ttcgtccgca ttgtagaagg gaatggaaga gacgtagtga    7620
tgcaggacgt gagtctcgat aatgccgtgg agcagatgac gtccaatgaa gcccatctct    7680
cggtcgatgt tgcagcggc acctcgcaca aagttccact cgtcgttggt gtagtgggga    7740
agagtaggat ctgtgtgctg cagaaaggta atggcgacga gccagtggtt aacccacaag    7800
tagggaacga agtaccagat ggccatgttg tagaatccga acttctgaac gagaaagtac    7860
agagcggtgg ccataagacc aatgccaatg tcggagagca cgatgagctt ggcgtcgctg    7920
ttctcgtaca gaggagatcg gggatcgaaa tggttaactc caccgccaag accgttgtgc    7980
tttcccttgc ctcgaccctc tcgctgccgc tcatggtagt tgtgtccagt aacgttggta    8040
atgagatagt tgggccaacc gaccagttgc tgaagcacaa gcatgagcag ggtgaaagca    8100
ggagtttcct cggtaagatg ggcgagttcg tgggtcatct tgccgagtcg agtagcttgc    8160
tgctctcggg ttcgaggaac gaagaccatg tctcgctcca tgtttccagt ggccttgtga    8220
tgcttccggt gggagatttg ccagctgaag tagggaacaa gcagggaaga gtgaagcacc    8280
cagccagtaa tgtcgttgat gattcgggaa tcggagaaag caccatgtcc acactcgtgg    8340
gcaatgaccc acagtccagt accgaagagt ccctgaagaa cggtgtacac agcccacaga    8400
ccggctcgag caggagtgga gggaatgtac tcgggtgtca caaagttgta ccagatgctg    8460
```

```
aaagtggtag tcaggaggac aatgtctcga agaatgtagc cgtatcccct tgagagcagat      8520 cgcttgaagc agtgcttggg aatagcgttg tagatgtcct tgatggtgaa gtcgggaact      8580
tcgaactggt tgccgtaggt atccagcatg acaccgtact cggacttggg cttggcaatg      8640
tccacctcgg acatggaaga cagcgatgta gaggaggccg agtgtctggg agaatcggag      8700
ggagagacgg cagcagactc cgagtcggtc acagtggtgg aagtgacggt tcgtcggagg      8760
gcagggttct gcttgggcag agccgaggtg gaggccatgg ccattgctgt agatatgtct      8820
tgtgtgtaag ggggttgggg tggttgtttg tgttcttgac ttttgtgtta gcaagggaag      8880
acgggcaaaa aagtgagtgt ggttgggagg gagagacgag ccttatatat aatgcttgtt      8940
tgtgtttgtg caagtggacg ccgaaacggg caggagccaa actaaacaag gcagacaatg      9000
cgagcttaat tggattgcct gatgggcagg ggttagggct cgatcaatgg gggtgcgaag      9060
tgacaaaatt gggaattagg ttcgcaagca aggctgacaa gactttggcc caaacatttg      9120
tacgcggtgg acaacaggag ccacccatcg tctgtcacgg gctagccggt cgtgcgtcct      9180
gtcaggctcc acctaggctc catgccactc catacaatcc cactagtgta ccgctaggcc      9240
gcttttagct cccatctaag accccccccaa aacctccact gtacagtgca ctgtactgtg      9300
tggcgatcaa gggcaaggga aaaaaggcgc aaacatgcac gcatggaatg acgtaggtaa      9360
ggcgttacta gactgaaaag tggcacattt cggcgtgcca aagggtccta ggtgcgtttc      9420
gcgagctggg cgccaggcca agccgctcca aaacgcctct ccgactccct ccagcggcct      9480
ccatatcccc atccctctcc acagcaatgt tgttaagcct tgcaaacgaa aaaatagaaa      9540
ggctaataag cttccaatat tgtggtgtac gctgcataac gcaacaatga gcgccaaaca      9600
acacacacac acagcacaca gcagcattaa ccacgatgaa cagcatgaat tcctttacct      9660
gcaggataac ttcgtataat gtatgctata cgaagttatg atctctctct tgagcttttc      9720
cataacaagt tcttctgcct ccaggaagtc catgggtggt ttgatcatgg ttttggtgta      9780
gtggtagtgc agtggtggta ttgtgactgg ggatgtagtt gagaataagt catacacaag      9840
tcagctttct tcgagcctca tataagtata agtagttcaa cgtattagca ctgtacccag      9900
catctccgta tcgagaaaca caacaacatg ccccattgga cagatcatgc ggatacacag      9960
gttgtgcagt atcatacata ctcgatcaga caggtcgtct gaccatcata caagctgaac     10020
aagcgctcca tacttgcacg ctctctatat acacagttaa attacatatc catagtctaa     10080
cctctaacag ttaatcttct ggtaagcctc ccagccagcc ttctggtatc gcttggcctc     10140
ctcaatagga tctcggttct ggccgtacag acctcggccg acaattatga tatccgttcc     10200
ggtagacatg acatcctcaa cagttcggta ctgctgtccg agagcgtctc ccttgtcgtc     10260
aagacccacc ccggggtca gaataagcca gtcctcagag tcgcccttag gtcggttctg     10320
ggcaatgaag ccaaccacaa actcgggtc ggatcgggca agctcaatgg tctgcttgga     10380
gtactcgcca gtggccagag agcccttgca agacagctcg gccagcatga gcagacctct     10440
ggccagcttc tcgttgggag aggggactag gaactccttg tactgggagt tctcgtagtc     10500
agagacgtcc tccttcttct gttcagagac agtttcctcg gcaccagctc gcaggccagc     10560
aatgattccg gttccgggta caccgtgggc gttggtgata tcggaccact cggcgattcg     10620
gtgacaccgg tactggtgct tgacagtgtt gccaatatct gcgaactttc tgtcctcgaa     10680
caggaagaaa ccgtgcttaa gagcaagttc cttgaggggg agcacagtgc cggcgtaggt     10740
gaagtcgtca atgatgtcga tatgggtttt gatcatgcac acataaggtc cgaccttatc     10800
ggcaagctca atgagctcct tggtggtggt aacatccaga gaagcacaca ggttggtttt     10860
```

-continued

```
cttggctgcc acgagcttga gcactcgagc ggcaaaggcg gacttgtgga cgttagctcg   10920
agcttcgtag gagggcattt tggtggtgaa gaggagactg aaataaattt agtctgcaga   10980 acttttatc ggaaccttat ctggggcagt gaagtatatg ttatggtaat agttacgagt    11040
tagttgaact tatagataga ctggactata cggctatcgg tccaaattag aaagaacgtc   11100
aatggctctc tgggcgtcgc ctttgccgac aaaaatgtga tcatgatgaa agccagcaat   11160
gacgttgcag ctgatattgt tgtcggccaa ccgcgccgaa aacgcagctg tcagacccac   11220
agcctccaac gaagaatgta tcgtcaaagt gatccaagca cactcatagt tggagtcgta   11280
ctccaaaggc ggcaatgacg agtcagacag atactcgtcg acgcgataac ttcgtataat   11340
gtatgctata cgaagttatc gtacgatagt tagtagacaa caatcgatcg aggaagagga   11400
caagcggctg cttcttaagt ttgtgacatc agtatccaag gcaccattgc aaggattcaa   11460
ggctttgaac ccgtcatttg ccattcgtaa cgctggtaga caggttgatc ggttccctac   11520
ggcctccacc tgtgtcaatc ttctcaagct gcctgactat caggacattg atcaacttcg   11580
gaagaaactt ttgtatgcca ttcgatcaca tgctggtttc gatttgtctt agaggaacgc   11640
atatacagta atcatagaga ataaacgata ttcatttatt aaagtagata gttgaggtag   11700
aagttgtaaa gagtgataaa tagcggccgc tcactgaatc ttttttggctc ccttgtgctt   11760 tcggacgatg taggtctgca cgtagaagtt gaggaacaga cacaggacag taccaacgta   11820
gaagtagttg aaaaaccagc caaacattct cattccatct tgtcggtagc agggaatgtt   11880
ccggtacttc cagacgatgt agaagccaac gttgaactga atgatctgca tagaagtaat   11940
cagggacttg ggcataggga acttgagctt gatcagtcgg gtccaatagt agccgtacat   12000
gatccagtga atgaagccgt tgagcagcac aaagatccaa acggcttcgt ttcggtagtt   12060
gtagaacagc cacatgtcca taggagctcc gagatggtga agaactgca accaggtcag   12120 aggcttgccc atgaggggca gatagaagga gtcaatgtac tcgaggaact tgctgaggta   12180
gaacagctga gtggtgattc ggaagacatt gttgtcgaaa gccttctcgc agttgtcgga   12240
catgacacca atggtgtaca tggcgtaggc catagagagg aaggagccca gcgagtagat   12300
ggacatgagc aggttgtagt tggtgaacac aaacttcatt cgagactgac ccttgggtcc   12360
gagaggacca agggtgaact tcaggatgac gaaggcgatg gagaggtaca gcacctcgca   12420
gtgcgaggca tcagaccaga gctgagcata gtcgaccttg ggaagaacct cctggccaat   12480
ggagacgatt tcgttcacga cctccatggt tgtgaattag ggtggtgaga atggttggtt   12540
gtagggaaga atcaaaggcc ggtctcggga tccgtgggta tatatatata tatatatata   12600
tacgatcctt cgttacctcc ctgttctcaa aactgtggtt tttcgttttt cgttttttgc   12660
tttttttgat tttttaggg ccaactaagc ttccagattt cgctaatcac ctttgtacta    12720
attacaagaa aggaagaagc tgattagagt tgggcttttt atgcaactgt gctactcctt   12780
atctctgata tgaaagtgta gacccaatca catcatgtca tttagagttg gtaatactgg   12840
gaggatagat aaggcacgaa aacgagccat agcagacatg ctgggtgtag ccaagcagaa   12900
gaaagtagat gggagccaat tgacgagcga gggagctacg ccaatccgac atacgacacg   12960
ctgagatcgt cttggccggg gggtacctac agatgtccaa gggtaagtgc ttgactgtaa   13020
ttgtatgtct gaggacaaat atgtagtcag ccgtataaag tcataccagg caccagtgcc   13080
atcatcgaac cactaactct ctatgataca tgcctccggt attattgtac catgcgtcgc   13140
tttgttacat acgtatcttg ccttttctc tcagaaactc cagactttgg ctattggtcg    13200
agataagccc ggaccatagt gagtctttca cactctgttt aaacaccact aaaacccac    13260
```

```
aaaatatatc ttaccgaata tacagatcta ctatagagga acaattgccc cggagaagac    13320
ggccaggccg cctagatgac aaattcaaca actcacagct gactttctgc cattgccact    13380
aggggggggc cttttttatat ggccaagcca agctctccac gtcggttggg ctgcacccaa    13440
caataaatgg gtagggttgc accaacaaag ggatgggatg ggggtagaa gatacgagga     13500 taacggggct caatggcaca aataagaacg aatactgcca ttaagactcg tgatccagcg    13560
actgacacca ttgcatcatc taagggcctc aaaactacct cggaactgct gcgctgatct    13620
ggacaccaca gaggttccga gcactttagg ttgcaccaaa tgtcccacca ggtgcaggca    13680
gaaaacgctg aacagcgtg tacagtttgt cttaacaaaa agtgagggcg ctgaggtcga     13740
gcagggtggt gtgacttgtt atagccttta gagctgcgaa agcgcgtatg gatttggctc    13800
atcaggccag attgagggtc tgtggacaca tgtcatgtta gtgtacttca atcgcccct     13860 ggatatagcc ccgacaatag gccgtggcct cattttttg ccttccgcac atttccattg     13920
ctcggtaccc acaccttgct tctcctgcac ttgccaacct taatactggt ttacattgac    13980
caacatctta caagcggggg gcttgtctag ggtatatata aacagtggct ctcccaatcg    14040
gttgccagtc tcttttttcc tttctttccc cacagattcg aaatctaaac tacacatcac    14100
acaatgcctg ttactgacgt ccttaagcga aagtccggtg tcatcgtcgg cgacgatgtc    14160
cgagccgtga gtatccacga caagatcagt gtcgagacga cgcgttttgt gtaatgacac    14220
aatccgaaag tcgctagcaa cacacactct ctacacaaac taacccagct ctccatggtg    14280
aaggcttctc gacaggctct gccctcgtc atcgacggaa aggtgtacga cgtctccgct      14340
tgggtgaact tccaccctgg tggagctgaa atcattgaga actaccaggg acgagatgct    14400
actgacgcct tcatggttat gcactctcag gaagccttcg acaagctcaa gcgaatgccc    14460
aagatcaacc aggcttccga gctgcctccc caggctgccg tcaacgaagc tcaggaggat    14520
ttccgaaagc tccgagaaga gctgatcgcc actggcatgt ttgacgcctc tcccctctgg    14580
tactcgtaca agatcttgac cacctgggt cttggcgtgc ttgccttctt catgctggtc      14640
cagtaccacc tgtacttcat tggtgctctc gtgctcggta tgcactacca gcaaatggga    14700
tggctgtctc atgacatctg ccaccaccag accttcaaga accgaaactg gaataacgtc    14760
ctgggtctgg tctttggcaa cggactccag ggcttctccg tgacctggtg gaaggacaga    14820
cacaacgccc atcattctgc taccaacgtt cagggtcacg atcccgacat tgataacctg    14880
cctctgctcg cctggtccga ggacgatgtc actcgagctt ctcccatctc ccgaaagctc    14940
attcagttcc aacagtacta tttcctggtc atctgtattc tcctgcgatt catctggtgt    15000
ttccagtctg tgctgaccgt tcgatccctc aaggaccgag acaaccagtt ctaccgatct    15060
cagtacaaga aagaggccat tggactcgct ctgcactgga ctctcaagac cctgttccac    15120
ctcttcttta tgccctccat cctgacctcg atgctggtgt tctttgtttc cgagctcgtc    15180
ggtggcttcg gaattgccat cgtggtcttc atgaaccact accctctgga gaagatcggt    15240
gattccgtct gggacggaca tggcttctct gtgggtcaga tccatgagac catgaacatt    15300
cgacgaggca tcattactga ctggttcttt ggaggcctga actaccagat cgagcaccat    15360
ctctggccca ccctgcctcg acacaacctc actgccgttt cctaccaggt ggaacagctg    15420
tgccagaagc acaacctccc ctaccgaaac cctctgcccc atgaaggtct cgtcatcctg    15480
ctccgatacc tgtcccagtt cgctcgaatg gccgagaagc agcccggtgc caaggctcag    15540
taagcggcca catgagaaga taaatatata aatacattga gatattaaat gcgctagatt    15600
agagagcctc atactgctcg gagagaagcc aagacgagta ctcaaagggg attacaccat    15660
```

```
ccatatccac agacacaagc tgggggaaagg ttctatatac actttccgga ataccgtagt   15720
ttccgatgtt atcaatgggg gcagccagga tttcaggcac ttcggtgtct cggggtgaaa   15780
tggcgttctt ggcctccatc aagtcgtacc atgtcttcat ttgcctgtca aagtaaaaca   15840
gaagcagatg aagaatgaac ttgaagtgaa ggaattt                              15877

<210> SEQ ID NO 76
<211> LENGTH: 1185
<212> TYPE: DNA
<213> ORGANISM: Yarrowia lipolytica
<220> FEATURE:
<221> NAME/KEY: CDS
<222> LOCATION: (1)..(1185)
<223> OTHER INFORMATION: diacylglycerol cholinephosphotransferase
      (YlCPT1)
<300> PUBLICATION INFORMATION:
<302> TITLE: HIGH EICOSAPENTAENOIC ACID PRODUCING STRAINS OF
<310> PATENT DOCUMENT NUMBER: WO 2006/052870
<311> PATENT FILING DATE: 2005-11-03
<312> PUBLICATION DATE: 2006-05-18
<313> RELEVANT RESIDUES: (1)..(1185)
<300> PUBLICATION INFORMATION:
<302> TITLE: HIGH EICOSAPENTAENOIC ACID PRODUCING STRAINS OF
<310> PATENT DOCUMENT NUMBER: US 2006-0115881-A1
<311> PATENT FILING DATE: 2005-11-02
<312> PUBLICATION DATE: 2006-06-01
<313> RELEVANT RESIDUES: (1)..(1185)

<400> SEQUENCE: 76 atg ggc gta ttc att aaa cag gag cag ctt ccg gct ctc aag aag tac      48
Met Gly Val Phe Ile Lys Gln Glu Gln Leu Pro Ala Leu Lys Lys Tyr
1               5                   10                  15 aag tac tcc gcc gag gat cac tcg ttc atc tcc aac aac att ctg cgc      96
Lys Tyr Ser Ala Glu Asp His Ser Phe Ile Ser Asn Asn Ile Leu Arg
                20                  25                  30 ccc ttc tgg cga cag ttt gtc aaa atc ttc cct ctg tgg atg gcc ccc     144
Pro Phe Trp Arg Gln Phe Val Lys Ile Phe Pro Leu Trp Met Ala Pro
            35                  40                  45 aac atg gtg act ctg ttg ggc ttc ttt gtc att gtg aac ttc atc         192
Asn Met Val Thr Leu Leu Gly Phe Phe Phe Val Ile Val Asn Phe Ile
        50                  55                  60 acc atg ctc att gtt gat ccc acc cac gac cgc gag cct ccc aga tgg    240
Thr Met Leu Ile Val Asp Pro Thr His Asp Arg Glu Pro Pro Arg Trp
65                  70                  75                  80 gtc tac ctc acc tac gct ctg ggt ctg ttc ctt tac cag aca ttt gat    288
Val Tyr Leu Thr Tyr Ala Leu Gly Leu Phe Leu Tyr Gln Thr Phe Asp
                85                  90                  95 gcc tgt gac gga tcc cat gcc cga cga act ggc cag agt gga ccc ctt    336
Ala Cys Asp Gly Ser His Ala Arg Arg Thr Gly Gln Ser Gly Pro Leu
            100                 105                 110 gga gag ctg ttt gac cac tgt gtc gac gcc atg aat acc tct ctg att    384
Gly Glu Leu Phe Asp His Cys Val Asp Ala Met Asn Thr Ser Leu Ile
        115                 120                 125 ctc acg gtg gtg gtg tcc acc acc cat atg gga tat aac atg aag ctg    432
Leu Thr Val Val Val Ser Thr Thr His Met Gly Tyr Asn Met Lys Leu
    130                 135                 140 ctg att gtg cag att gcc gct ctc gga aac ttc tac ctg tcg acc tgg    480
Leu Ile Val Gln Ile Ala Ala Leu Gly Asn Phe Tyr Leu Ser Thr Trp
145                 150                 155                 160 gag acc tac cat acc gga act ctg tac ctt tct ggc ttc tct ggt cct    528
Glu Thr Tyr His Thr Gly Thr Leu Tyr Leu Ser Gly Phe Ser Gly Pro
                165                 170                 175 gtt gaa ggt atc ttg att ctg gtg gct ctt ttc gtc ctc acc ttc ttc    576
Val Glu Gly Ile Leu Ile Leu Val Ala Leu Phe Val Leu Thr Phe Phe
```

-continued

```
                180                 185                 190
act ggt ccc aac gtg tac gct ctg acc gtc tac gag gct ctt ccc gaa    624
Thr Gly Pro Asn Val Tyr Ala Leu Thr Val Tyr Glu Ala Leu Pro Glu
            195                 200                 205 tcc atc act tcg ctg ctg cct gcc agc ttc ctg gac gtc acc atc acc    672
Ser Ile Thr Ser Leu Leu Pro Ala Ser Phe Leu Asp Val Thr Ile Thr
    210                 215                 220 cag atc tac att gga ttc gga gtg ctg ggc atg gtg ttc aac atc tac    720
Gln Ile Tyr Ile Gly Phe Gly Val Leu Gly Met Val Phe Asn Ile Tyr
225                 230                 235                 240 ggc gcc tgc gga aac gtg atc aag tac tac aac aac aag ggc aag agc    768
Gly Ala Cys Gly Asn Val Ile Lys Tyr Tyr Asn Asn Lys Gly Lys Ser
                245                 250                 255 gct ctc ccc gcc att ctc gga atc gcc ccc ttt ggc atc ttc tac gtc    816
Ala Leu Pro Ala Ile Leu Gly Ile Ala Pro Phe Gly Ile Phe Tyr Val
            260                 265                 270 ggc gtc ttt gcc tgg gcc cat gtt gct cct ctg ctt ctc tcc aag tac    864
Gly Val Phe Ala Trp Ala His Val Ala Pro Leu Leu Leu Ser Lys Tyr
    275                 280                 285 gcc atc gtc tat ctg ttt gcc att ggg gct gcc ttt gcc atg caa gtc    912
Ala Ile Val Tyr Leu Phe Ala Ile Gly Ala Ala Phe Ala Met Gln Val
290                 295                 300 ggc cag atg att ctt gcc cat ctc gtg ctt gct ccc ttc ccc cac tgg    960
Gly Gln Met Ile Leu Ala His Leu Val Leu Ala Pro Phe Pro His Trp
305                 310                 315                 320 aac gtg ctg ctc ttc ttc ccc ttt gtg gga ctg gca gtg cac tac att   1008
Asn Val Leu Leu Phe Phe Pro Phe Val Gly Leu Ala Val His Tyr Ile
                325                 330                 335 gca ccc gtg ttt ggc tgg gac gcc gat atc gtg tcg gtt aac act ctc   1056
Ala Pro Val Phe Gly Trp Asp Ala Asp Ile Val Ser Val Asn Thr Leu
            340                 345                 350 ttc acc tgt ttt ggc gcc acc ctc tcc att tac gcc ttc ttt gtg ctt   1104
Phe Thr Cys Phe Gly Ala Thr Leu Ser Ile Tyr Ala Phe Phe Val Leu
    355                 360                 365 gag atc atc gac gag atc acc aac tac ctc gat atc tgg tgt ctg cga   1152
Glu Ile Ile Asp Glu Ile Thr Asn Tyr Leu Asp Ile Trp Cys Leu Arg
370                 375                 380 atc aag tac cct cag gag aag aag act gag taa                        1185
Ile Lys Tyr Pro Gln Glu Lys Lys Thr Glu
385                 390
```

<210> SEQ ID NO 77
<211> LENGTH: 394
<212> TYPE: PRT
<213> ORGANISM: Yarrowia lipolytica

<400> SEQUENCE: 77

```
Met Gly Val Phe Ile Lys Gln Glu Gln Leu Pro Ala Leu Lys Lys Tyr
1               5                   10                  15

Lys Tyr Ser Ala Glu Asp His Ser Phe Ile Ser Asn Asn Ile Leu Arg
            20                  25                  30

Pro Phe Trp Arg Gln Phe Val Lys Ile Phe Pro Leu Trp Met Ala Pro
        35                  40                  45

Asn Met Val Thr Leu Leu Gly Phe Phe Val Ile Val Asn Phe Ile
    50                  55                  60

Thr Met Leu Ile Val Asp Pro Thr His Asp Arg Glu Pro Pro Arg Trp
65                  70                  75                  80

Val Tyr Leu Thr Tyr Ala Leu Gly Leu Phe Leu Tyr Gln Thr Phe Asp
                85                  90                  95
```

```
Ala Cys Asp Gly Ser His Ala Arg Arg Thr Gly Gln Ser Gly Pro Leu
                100                 105                 110

Gly Glu Leu Phe Asp His Cys Val Asp Ala Met Asn Thr Ser Leu Ile
            115                 120                 125

Leu Thr Val Val Val Ser Thr Thr His Met Gly Tyr Asn Met Lys Leu
130                 135                 140

Leu Ile Val Gln Ile Ala Ala Leu Gly Asn Phe Tyr Leu Ser Thr Trp
145                 150                 155                 160

Glu Thr Tyr His Thr Gly Thr Leu Tyr Leu Ser Gly Phe Ser Gly Pro
                165                 170                 175

Val Glu Gly Ile Leu Ile Leu Val Ala Leu Phe Val Leu Thr Phe Phe
            180                 185                 190

Thr Gly Pro Asn Val Tyr Ala Leu Thr Val Tyr Glu Ala Leu Pro Glu
            195                 200                 205

Ser Ile Thr Ser Leu Leu Pro Ala Ser Phe Leu Asp Val Thr Ile Thr
            210                 215                 220

Gln Ile Tyr Ile Gly Phe Gly Val Leu Gly Met Val Phe Asn Ile Tyr
225                 230                 235                 240

Gly Ala Cys Gly Asn Val Ile Lys Tyr Tyr Asn Asn Lys Gly Lys Ser
                245                 250                 255

Ala Leu Pro Ala Ile Leu Gly Ile Ala Pro Phe Gly Ile Phe Tyr Val
            260                 265                 270

Gly Val Phe Ala Trp Ala His Val Ala Pro Leu Leu Leu Ser Lys Tyr
            275                 280                 285

Ala Ile Val Tyr Leu Phe Ala Ile Gly Ala Ala Phe Ala Met Gln Val
            290                 295                 300

Gly Gln Met Ile Leu Ala His Leu Val Leu Ala Pro Phe Pro His Trp
305                 310                 315                 320

Asn Val Leu Leu Phe Phe Pro Phe Val Gly Leu Ala Val His Tyr Ile
                325                 330                 335

Ala Pro Val Phe Gly Trp Asp Ala Asp Ile Val Ser Val Asn Thr Leu
            340                 345                 350

Phe Thr Cys Phe Gly Ala Thr Leu Ser Ile Tyr Ala Phe Phe Val Leu
            355                 360                 365

Glu Ile Ile Asp Glu Ile Thr Asn Tyr Leu Asp Ile Trp Cys Leu Arg
370                 375                 380

Ile Lys Tyr Pro Gln Glu Lys Lys Thr Glu
385                 390

<210> SEQ ID NO 78
<211> LENGTH: 15812
<212> TYPE: DNA
<213> ORGANISM: Artificial Sequence
<220> FEATURE:
<223> OTHER INFORMATION: Plasmid pZKL2-5U89GC

<400> SEQUENCE: 78
gtacgttatc atttgaacag tgaaaggcta cagtaacaga agcagttgta aacttcattc      60
cgttgattct gtactacagt accccactac gccgcttccg ctgacactgt tcaacccaaa     120
aactacatct gcgtgcgctg tgtaaggcta tcatcagata catactgtag attctgtaga     180
tgcgaacctg cttgtatcat atacatcccc ctccccctga cctgcacaag caagcaatgt     240
gacattgata ttgctgctta tctagtgccg aggatgtgaa agccgagact caaacatttc     300
ttttactctc ttgttcctga ccagacctgg cggagattac gccagtatga ttcttgcagg     360
tctgagacaa gcctggaaca gccaacattt attttttcgaa gcgagaaaca tgccacaccc     420
```

```
cggcacgttc agagatgcat atgatttgtt tttcgagtaa cagtacccccc cccccccccc    480
ccaatgaaac cagtattact cacaccatcc tcattcaaag cgttacactg attacgcgcc    540
catcaacgac agcatgaggg gactgctgat ctgatctaat caaatgacta caaaaatcgc    600
aataatgaag agcaaacgac aaaaaagaaa caggttaacc aatcccgctt caatgtctca    660
ccacaatcca gcactgtttc tcattacctc ctccctctaa tttcagagtt gcatcagggt    720
ccttgatggc gcgccagctg cattaatgaa tcggccaacg cgcggggaga ggcggtttgc    780
gtattgggcg ctcttccgct tcctcgctca ctgactcgct gcgctcggtc gttcggctgc    840
ggcgagcggt atcagctcac tcaaaggcgg taatacggtt atccacagaa tcagggggata   900
acgcaggaaa gaacatgtga gcaaaaggcc agcaaaaggc caggaaccgt aaaaaggccg    960
cgttgctggc gtttttccat aggctccgcc cccctgacga gcatcacaaa aatcgacgct   1020
caagtcagag gtggcgaaac ccgacaggac tataaagata ccaggcgttt ccccctggaa   1080
gctccctcgt gcgctctcct gttccgaccc tgccgcttac cggatacctg tccgcctttc   1140
tcccttcggg aagcgtggcg ctttctcata gctcacgctg taggtatctc agttcggtgt   1200
aggtcgttcg ctccaagctg gctgtgtgc acgaacccccc cgttcagccc gaccgctgcg   1260
ccttatccgg taactatcgt cttgagtcca acccggtaag acacgactta tcgccactgg   1320
cagcagccac tggtaacagg attagcagag cgaggtatgt aggcggtgct acagagttct   1380
tgaagtggtg gcctaactac ggctacacta agaacagt atttggtatc tgcgctctgc    1440
tgaagccagt taccttcgga aaaagagttg gtagctcttg atccggcaaa caaaccaccg   1500
ctggtagcgg tggtttttttt gtttgcaagc agcagattac gcgcagaaaa aaaggatctc   1560
aagaagatcc tttgatcttt tctacggggt ctgacgctca gtggaacgaa aactcacgtt   1620
aagggatttt ggtcatgaga ttatcaaaaa ggatcttcac ctagatcctt ttaaattaaa   1680
aatgaagttt taaatcaatc taaagtatat atgagtaaac ttggtctgac agttaccaat   1740
gcttaatcag tgaggcacct atctcagcga tctgtctatt tcgttcatcc atagttgcct   1800
gactccccgt cgtgtagata actacgatac gggagggctt accatctggc cccagtgctg   1860
caatgatacc gcgagaccca cgctcaccgg ctccagattt atcagcaata aaccagccag   1920
ccggaagggc cgagcgcaga agtggtcctg caactttatc cgcctccatc cagtctatta   1980
attgttgccg ggaagctaga gtaagtagtt cgccagttaa tagtttgcgc aacgttgttg   2040
ccattgctac aggcatcgtg gtgtcacgct cgtcgtttgg tatggcttca ttcagctccg   2100
gttcccaacg atcaaggcga gttacatgat cccccatgtt gtgcaaaaaa gcggttagct   2160
ccttcggtcc tccgatcgtt gtcagaagta agttggccgc agtgttatca ctcatggtta   2220
tggcagcact gcataattct cttactgtca tgccatccgt aagatgcttt tctgtgactg   2280
gtgagtactc aaccaagtca ttctgagaat agtgtatgcg gcgaccgagt tgctcttgcc   2340
cggcgtcaat acgggataat accgcgccac atagcagaac tttaaaagtg ctcatcattg   2400
gaaaacgttc ttcggggcga aaactctcaa ggatcttacc gctgttgaga tccagttcga   2460
tgtaacccac tcgtgcaccc aactgatctt cagcatcttt tactttcacc agcgtttctg   2520
ggtgagcaaa aacaggaagg caaaatgccg caaaaaaggg aataagggcg acacggaaat   2580
gttgaatact catactcttc cttttcaat attattgaag catttatcag ggttattgtc   2640
tcatgagcgg atacatattt gaatgtattt agaaaaataa acaaataggg gttccgcgca   2700
catttccccg aaaagtgcca cctgatgcgg tgtgaaatac cgcacagatg cgtaaggaga   2760
aaataccgca tcaggaaatt gtaagcgtta atattttgtt aaaattcgcg ttaaattttt   2820
```

```
gttaaatcag ctcattttt  aaccaatagg ccgaaatcgg caaaatccct tataaatcaa    2880
aagaatagac cgagataggg ttgagtgttg ttccagtttg gaacaagagt ccactattaa    2940
agaacgtgga ctccaacgtc aaagggcgaa aaaccgtcta tcagggcgat ggcccactac    3000
gtgaaccatc accctaatca agttttttgg ggtcgaggtg ccgtaaagca ctaaatcgga    3060
accctaaagg gagcccccga tttagagctt gacggggaaa gccggcgaac gtggcgagaa    3120
aggaagggaa gaaagcgaaa ggagcgggcg ctagggcgct ggcaagtgta gcggtcacgc    3180
tgcgcgtaac caccacaccc gccgcgctta atgcgccgct acagggcgcg tccattcgcc    3240
attcaggctg cgcaactgtt gggaagggcg atcggtgcgg gcctcttcgc tattacgcca    3300
gctggcgaaa gggggatgtg ctgcaaggcg attaagttgg gtaacgccag gttttccca     3360 gtcacgacgt tgtaaaacga cggccagtga attgtaatac gactcactat agggcgaatt    3420
gggcccgacg tcgcatgctg gtttcgattt gtcttagagg aacgcatata cagtaatcat    3480
agagaataaa cgatattcat ttattaaagt agatagttga ggtagaagtt gtaaagagtg    3540
ataaatagct tagataccac agacaccctc ggtgacgaag tactgcagat ggtttccaat    3600
cacattgacc tgctggagca gagtgttacc ggcagagcac tgtttattgc tctggccctg    3660
gcacatgaca acgttggaga gaggagggtg gatcaggggc cagtcaataa agacctcacc    3720
agagcagtgc tggtaaccgt cccagaaggg cacttgaggg acgatatctc ctcggtgggt    3780
gattcggtag agctttcggt cttttggacac cttggagaca tcggggttct cctggccaaa    3840
gaagagttta tcgacccagt tagcaaagcc agcgttaccg acaatgggct gaccaagagt    3900
aacaacgagg ggatcgtggc cgttaacctt gaggttgatt ccgaacagaa gggctgcagc    3960
tcctccgaga gagtgaccgg tgacagcaat ctggtagtcg ggatactgct caatcacaga    4020
gtcgagcttg gggccgatct gattgtaggt gttgttgtag gactggatga agccattgtg    4080
gacaagacag tcatcacaag tagcagtaga agagatgtta gcagcaagat caaagttaat    4140
taactcacct gcaggattga gactatgaat ggattcccgt gcccgtatta ctctactaat    4200
ttgatcttgg aacgcgaaaa tacgtttcta ggactccaaa gaatctcaac tcttgtcctt    4260
actaaatata ctacccatag ttgatggttt acttgaacag agaggacatg ttcacttgac    4320
ccaaagtttc tcgcatctct tggatatttg aacaacggcg tccactgacc gtcagttatc    4380
cagtcacaaa accccccacat tcatacattc ccatgtacgt ttacaaagtt ctcaattcca    4440
tcgtgcaaat caaatcaca  tctattcatt catcatatat aaacccatca tgtctactaa    4500
cactcacaac tccatagaaa acatcgactc agaacacacg ctccatgcgg ccgcttagga    4560
atcctgagcg tccttgacac agtgaaccac accgactttg tgcatgtact tgagggtgga    4620
aatgatgttg cccacaatgg tagggtagaa gacgtaccga actccgtgtc gttcgcaaca    4680
ctctcggaca gcttgctgca cgaagggata gtgccaagac gacattcgag gaaagaggtg    4740
atgctcgatc tggaagttga gaccgccagt aaagaacatg gcaatgggtc caccgtaggt    4800
ggaagaggtc tccacctgag ctctgtacca gtcgatctga tcggcttcaa cgtccttctc    4860
ggagctcttg accttgcagt tcttgtcggg gattcgctcc gagccatcga agttgtgaga    4920
caagatgaaa aagaaggtga ggaaggcacc ggtagcagtg ggcaccgagg aatggtgat     4980 gagcagggag gttccagtga gataccaggg caagaaggcg gttcgaaaga tgaagaaagc    5040
tcgcataacg aatgcaaggg ttcggtaccg tcgcagaaag ccgttctctc gcatggctgt    5100
gacagactcg ggaatggtgt cgttgtgctg cattcggaag atgtagagag ggttgtacac    5160
cagcgaaacg ccgtaggctc caagcacgag gtacatgtac caggcctgga atcggtgaaa    5220
```

```
ccactttcga gcagtgttgg cagcagggta gttgtggaac acaaggaatg gttctgcgga    5280
ctcggcatcc aggtcgagac catgctgatt ggtgtaggtg tgatgtcgca tgatgtgaga    5340
ctgcagccag atccatctgg acgatccaat gacgtcgatg ccgtaggcaa agagagcgtt    5400
gacccagggc tttttgctga tggcaccatg agaggcatcg tgctgaatgg acaggccgat    5460
ctgcatgtgc atgaatccag tcaagagacc ccacagcacc attccggtag tagcccagtg    5520
ccactcgcaa aaggcggtga cagcaatgat gccaacggtt cgcagccaga tccaggtgt     5580 ggcataccag ttccgacctt tcatgacctc tcgcatagtt cgcttgacgt cctgtgcaaa    5640
gggagagtcg taggtgtaga caatgtcctt ggaggttcgg tcgtgcttgc ctcgcacgaa    5700
ctgttgaagc agcttcgagt tctcgggctt gacgtaaggg tgcatggagt agaacagagg    5760
agaagcatcg gaggcaccag aagcgaggat caagtcgcct ccgggatgga ccttggcaag    5820
accttccaga tcgtagagaa tgccgtcgat ggcaaccagg tcgggtcgct cgagcagctg    5880
ctcggtagta agggagagag ccatggttgt gaattagggt ggtgagaatg gttggttgta    5940
gggaagaatc aaaggccggt ctcgggatcc gtgggtatat atatatatat atatatatac    6000
gatccttcgt tacctccctg ttctcaaaac tgtggttttt cgttttcgt tttttgcttt     6060 ttttgatttt tttagggcca actaagcttc cagatttcgc taatcacctt tgtactaatt    6120
acaagaaagg aagaagctga ttagagttgg gcttttatg caactgtgct actccttatc     6180
tctgatatga aagtgtagac ccaatcacat catgtcattt agagttggta atactgggag    6240
gatagataag gcacgaaaac gagccatagc agacatgctg ggtgtagcca agcagaagaa    6300
agtagatggg agccaattga cgagcgaggg agctacgcca atccgacata cgacacgctg    6360
agatcgtctt ggccgggggg tacctacaga tgtccaaggg taagtgcttg actgtaattg    6420
tatgtctgag gacaaatatg tagtcagccg tataaagtca taccaggcac cagtgccatc    6480
atcgaaccac taactctcta tgatacatgc ctccggtatt attgtaccat gcgtcgcttt    6540
gttacatacg tatcttgcct ttttctctca gaaactccag aattctctct cttgagcttt    6600
tccataacaa gttcttctgc ctccaggaag tccatgggtg gtttgatcat ggttttggtg    6660
tagtggtagt gcagtggtgg tattgtgact ggggatgtag ttgagaataa gtcatacaca    6720
agtcagcttt cttcgagcct catataagta taagtagttc aacgtattag cactgtaccc    6780
agcatctccg tatcgagaaa cacaacaaca tgccccattg gacagatcat gcggatacac    6840
aggttgtgca gtatcataca tactcgatca gacaggtcgt ctgaccatca tacaagctga    6900
acaagcgctc catacttgca cgctctctat atacacagtt aaattacata tccatagtct    6960
aacctctaac agttaatctt ctggtaagcc tcccagccag ccttctggta tcgcttggcc    7020
tcctcaatag gatctcggtt ctggccgtac agacctcggc cgacaattat gatatccgtt    7080
ccggtagaca tgcatcctc aacagttcgg tactgctgtc cgagagcgtc tcccttgtcg     7140
tcaagaccca ccccgggggt cagaataagc cagtcctcag agtcgccctt aggtcggttc    7200
tgggcaatga agccaaccac aaactcgggg tcggatcggg caagctcaat ggtctgcttg    7260
gagtactcgc cagtggccag agagcccttg caagacagcc cggccagcat gagcagacct    7320
ctggccagct tctcgttggg agaggggact aggaactcct tgtactggga gttctcgtag    7380
tcagagacgt cctccttctt ctgttcagag acagtttcct cggcaccagc tcgcaggcca    7440
gcaatgattc cggttccggg tacaccgtgg gcgttggtga tatcggacca ctcggcgatt    7500
cggtgacacc ggtactggtg cttgacagtg ttgccaatat ctgcgaactt tctgtcctcg    7560
aacaggaaga aaccgtgctt aagagcaagt tccttgaggg ggagcacagt gccggcgtag    7620
```

```
gtgaagtcgt caatgatgtc gatatgggtt ttgatcatgc acacataagg tccgacctta      7680
tcggcaagct caatgagctc cttggtggtg gtaacatcca gagaagcaca caggttggtt      7740
ttcttggctg ccacgagctt gagcactcga gcggcaaagg cggacttgtg gacgttagct      7800
cgagcttcgt aggagggcat tttggtggtg aagaggagac tgaaataaat ttagtctgca      7860
gaacttttta tcggaacctt atctggggca gtgaagtata tgttatggta atagttacga      7920
gttagttgaa cttatagata gactggacta tacggctatc ggtccaaatt agaaagaacg      7980
tcaatggctc tctgggcgtc gcctttgccg acaaaaatgt gatcatgatg aaagccagca      8040
atgacgttgc agctgatatt gttgtcggcc aaccgcgccg aaaacgcagc tgtcagaccc      8100
acagcctcca acgaagaatg tatcgtcaaa gtgatccaag cacactcata gttggagtcg      8160
tactccaaag gcggcaatga cgagtcagac agatactcgt cgaccttttc cttgggaacc      8220
accaccgtca gcccttctga ctcacgtatt gtagccaccg acacaggcaa cagtccgtgg      8280
atagcagaat atgtcttgtc ggtccatttc tcaccaactt taggcgtcaa gtgaatgttg      8340
cagaagaagt atgtgccttc attgagaatc ggtgttgctg atttcaataa agtcttgaga      8400
tcagtttggc cagtcatgtt gtgggggggta attggattga gttatcgcct acagtctgta      8460
caggtatact cgctgcccac tttatacttt ttgattccgc tgcacttgaa gcaatgtcgt      8520
ttaccaaaag tgagaatgct ccacagaaca caccccaggg tatggttgag caaaaaataa      8580
acactccgat acggggaatc gaaccccggt ctccacggtt ctcaagaagt attcttgatg      8640
agagcgtatc gatcgaggaa gaggacaagc ggctgcttct taagtttgtg acatcagtat      8700
ccaaggcacc attgcaagga ttcaaggctt tgaacccgtc atttgccatt cgtaacgctg      8760
gtagacaggt tgatcggttc cctacggcct ccacctgtgt caatcttctc aagctgcctg      8820
actatcagga cattgatcaa cttcggaaga aacttttgta tgccattcga tcacatgctg      8880
gtttcgattt gtcttagagg aacgcatata cagtaatcat agagaataaa cgatattcat      8940
ttattaaagt agatagttga ggtagaagtt gtaaagagtg ataaatagcg gccgctcact      9000
gaatcttttt ggctcccttg tgctttcgga cgatgtaggg ctgcacgtag aagttgagga      9060
acagacacag gacagtacca acgtagaagt agttgaaaaa ccagccaaac attctcattc      9120
catcttgtcg gtagcaggga atgttccggt acttccagac gatgtagaag ccaacgttga      9180
actgaatgat ctgcatagaa gtaatcaggg acttgggcat agggaacttg agcttgatca      9240
gtcgggtcca atagtagccg tacatgatcc agtgaatgaa gccgttgagc agcacaaaga      9300
tccaaacggc ttcgtttcgg tagttgtaga acagccacat gtccatagga gctccgagat      9360
ggtgaaagaa ctgcaaccag gtcagaggct gcccatgag gggcagatag aaggagtcaa      9420
tgtactcgag gaacttgctg aggtagaaca gctgagtggt gattcggaag acattgttgt      9480
cgaaagcctt ctcgcagttg tcggacatga caccaatggt gtacatggcg taggccatag      9540
agaggaagga gcccagcgag tagatggaca tgagcaggtt gtagttggtg aacacaaact      9600
tcattcgaga ctgacccttg gtccgagag gaccaagggt gaacttcagg atgacgaagg      9660
cgatggagag gtacagcacc tcgcagtgcg aggcatcaga ccagagctga gcatagtcga      9720
ccttgggaag aacctcctgg ccaatggaga cgatttcgtt cacgacctcc atggttgatg      9780
tgtgtttaat tcaagaatga atatagaaa gagaagaaga aaaagattc aattgagccg      9840 gcgatgcaga cccttatata aatgttgcct tggacagacg gagcaagccc gcccaaacct      9900
acgttccgta taatatgtta agcttttta cacaaaggt tggcttgggg taacctgatg      9960
tggtgcaaaa gaccgggcgt tggcgagcca ttgcgcgggc gaatgggcc gtgactcgtc     10020
```

```
tcaaattcga gggcgtgcct caattcgtgc ccccgtggct ttttcccgcc gtttccgccc   10080
cgtttgcacc actgcagccg cttctttggt tcggacacct tgctgcgagc taggtgcctt   10140
gtgctactta aaaagtggcc tcccaacacc aacatgacat gagtgcgtgg gccaagacac   10200
gttggcgggg tcgcagtcgg ctcaatggcc cggaaaaaac gctgctggag ctggttcgga   10260
cgcagtccgc cgcggcgtat ggatatccgc aaggttccat agcgccattg ccctccgtcg   10320
gcgtctatcc cgcaacctct aaatagagcg ggaatataac ccaagcttct ttttttttcct  10380 ttaacacgca cacccccaac tatcatgttg ctgctgctgt ttgactctac tctgtggagg   10440
ggtgctccca cccaacccaa cctacaggtg gatccggcgc tgtgattggc tgataagtct   10500
cctatccgga ctaattctga ccaatgggac atgcgcgcag gacccaaatg ccgcaattac   10560
gtaaccccaa cgaaatgcct acccctcttt ggagcccagc ggccccaaat ccccccaagc   10620
agcccggttc taccggcttc catctccaag cacaagcagc ccggttctac cggcttccat   10680
ctccaagcac ccctttctcc acacccacaa aaagacccg tgcaggacat cctactgcgt    10740
gtttaaacac cactaaaacc ccacaaaata tatcttaccg aatatacaga tctactatag   10800
aggaacaatt gccccggaga agacggccag gccgcctaga tgacaaattc aacaactcac   10860
agctgacttt ctgccattgc cactaggggg gggcctttt atatggccaa gccaagctct    10920
ccacgtcggt tgggctgcac ccaacaataa atgggtaggg ttgcaccaac aaagggatgg   10980 gatgggggt agaagatacg aggataacgg ggctcaatgg cacaaataag aacgaatact    11040
gccattaaga ctcgtgatcc agcgactgac accattgcat catctaaggg cctcaaaact   11100
acctcggaac tgctgcgctg atctggacac cacagaggtt ccgagcactt taggttgcac   11160
caaatgtccc accaggtgca ggcagaaaac gctggaacag cgtgtacagt ttgtcttaac   11220
aaaaagtgag ggcgctgagg tcgagcaggg tggtgtgact tgttatagcc tttagagctg   11280
cgaaagcgcg tatggatttg gctcatcagg ccagattgag ggtctgtgga cacatgtcat   11340
gttagtgtac ttcaatcgcc ccctggatat agccccgaca ataggccgtg gcctcatttt   11400
tttgccttcc gcacatttcc attgctcggt acccacacct tgcttctcct gcacttgcca   11460
accttaatac tggtttacat tgaccaacat cttacaagcg gggggcttgt ctagggtata   11520
tataaacagt ggctctccca atcggttgcc agtctctttt ttcctttctt tccccacaga   11580
ttcgaaatct aaactacaca tcacacaatg cctgttactg acgtccttaa gcgaaagtcc   11640
ggtgtcatcg tcggcgacga tgtccgagcc gtgagtatcc acgacaagat cagtgtcgag   11700
acgacgcgtt ttgtgtaatg acacaatccg aaagtcgcta gcaacacaca ctctctacac   11760 aaactaacccc agctctccat ggtgaaggct tctcgacagg ctctgcccct cgtcatcgac   11820
ggaaaggtgt acgacgtctc cgcttgggtg aacttccacc ctggtggagc tgaaatcatt   11880
gagaactacc agggacgaga tgctactgac gccttcatgg ttatgcactc tcaggaagcc   11940
ttcgacaagc tcaagcgaat gcccaagatc aaccaggctt ccgagctgcc tccccaggct   12000
gccgtcaacg aagctcagga ggatttccga aagctccgag aagagctgat cgccactggc   12060
atgtttgacg cctctccect ctggtactcg tacaagatct tgaccaccct gggtcttggc   12120
gtgcttgcct tcttcatgct ggtccagtac cacctgtact tcattggtgc tctcgtgctc   12180
ggtatgcact accagcaaat gggatggctg tctcatgaca tctgccacca ccagaccttc   12240
aagaaccgaa actggaataa cgtcctgggt ctggtctttg gcaacggact ccagggcttc   12300
tccgtgacct ggtggaagga cagacacaac gcccatcatt ctgctaccaa cgttcagggt   12360
cacgatcccg acattgataa cctgcctctg ctcgcctggt ccgaggacga tgtcactcga   12420
```

```
gcttctccca tctcccgaaa gctcattcag ttccaacagt actatttcct ggtcatctgt   12480
attctcctgc gattcatctg gtgtttccag tctgtgctga ccgttcgatc cctcaaggac   12540
cgagacaacc agttctaccg atctcagtac aagaaagagg ccattggact cgctctgcac   12600
tggactctca agaccctgtt ccacctcttc tttatgccct ccatcctgac ctcgatgctg   12660
gtgttctttg tttccgagct cgtcggtggc ttcggaattg ccatcgtggt cttcatgaac   12720
cactaccctc tggagaagat cggtgattcc gtctgggacg gacatggctt ctctgtgggt   12780
cagatccatg agaccatgaa cattcgacga ggcatcatta ctgactggtt ctttggaggc   12840
ctgaactacc agatcgagca ccatctctgg cccaccctgc ctcgacacaa cctcactgcc   12900
gtttcctacc aggtggaaca gctgtgccag aagcacaacc tccctaccg aaaccctctg   12960 ccccatgaag gtctcgtcat cctgctccga tacctgtccc agttcgctcg aatggccgag   13020
aagcagcccg gtgccaaggc tcagtaagcg gccgcatgag aagataaata tataaataca   13080
ttgagatatt aaatgcgcta gattagagag cctcatactg ctcggagaga agccaagacg   13140
agtactcaaa ggggattaca ccatccatat ccacagacac aagctgggga aaggttctat   13200
atacactttc cggaataccg tagttttccga tgttatcaat gggggcagcc aggatttcag   13260
gcacttcggt gtctcggggt gaaatggcgt tcttggcctc catcaagtcg taccatgtct   13320
tcatttgcct gtcaaagtaa aacagaagca gatgaagaat gaacttgaag tgaaggaatt   13380
taaatagttg gagcaaggga gaaatgtaga gtgtgaaaga ctcactatgg tccgggctta   13440
tctcgaccaa tagccaaagt ctggagtttc tgagagaaaa aggcaagata cgtatgtaac   13500
aaagcgacgc atggtacaat aataccggag gcatgtatca tagagagtta gtggttcgat   13560
gatggcactg gtgcctggta tgactttata cggctgacta catatttgtc ctcagacata   13620
caattacagt caagcactta cccttggaca tctgtaggta cccccggcc aagacgatct   13680 cagcgtgtcg tatgtcggat tggcgtagct ccctcgctcg tcaattggct cccatctact   13740
ttcttctgct tggctacacc cagcatgtct gctatggctc gttttcgtgc cttatctatc   13800
ctcccagtat taccaactct aaatgacatg atgtgattgg gtctacactt tcatatcaga   13860
gataaggagt agcacagttg cataaaaagc ccaactctaa tcagcttctt cctttcttgt   13920
aattagtaca aaggtgatta gcgaaatctg gaagcttagt tggccctaaa aaaatcaaaa   13980
aaagcaaaaa acgaaaaacg aaaaaccaca gttttgagaa cagggaggta acgaaggatc   14040
gtatatatat atatatatat atataccac ggatcccgag accggccttt gattcttccc   14100
tacaaccaac cattctcacc accctaattc acaaccatgg gcgtattcat taaacaggag   14160
cagcttccgg ctctcaagaa gtacaagtac tccgccgagg atcactcgtt catctccaac   14220
aacattctgc gcccttctg gcgacagttt gtcaaaatct tccctctgtg gatggccccc   14280
aacatggtga ctctgctggg cttcttcttt gtcattgtga acttcatcac catgctcatt   14340
gttgatccca cccgaccg cgagcctccc agatgggtct acctcaccta cgctctgggt   14400
ctgttccttt accagacatt tgatgcctgt gacggatccc atgcccgacg aactggccag   14460
agtggacccc ttggagagct gttgaccac tgtgtcgacg ccatgaatac ctctctgatt   14520
ctcacggtgg tggtgtccac cacccatatg ggatataaca tgaagctact gattgtgcag   14580
attgccgctc tcggaaactt ctacctgtcg acctgggaga cctaccatac cggaactctg   14640
tacctttctg gcttctctgg tcctgttgaa ggtatcttga ttctggtggc tcttttcgtc   14700
ctcaccttct tcactggtcc caacgtgtac gctctgaccg tctacgaggc tcttcccgag   14760
tccatcactt cgctgctgcc tgccagcttc ctggacgtca ccatcaccca gatctacatt   14820
```

-continued

```
ggattcggag tgctgggcat ggtgttcaac atctacggcg cctgcggaaa cgtgatcaag   14880
tactacaaca acaagggcaa gagcgctctc cccgccattc tcggaatcgc cccctttggc   14940
atcttctacg tcggcgtctt tgcctgggcc catgttgctc ctctgcttct ctccaagtac   15000
gccatcgtct atctgtttgc cattggggct gcctttgcca tgcaagtcgg ccagatgatt   15060
cttgcccatc tcgtgcttgc tccctttccc cactggaacg tgctgctctt cttccccttt   15120
gtgggactgg cagtgcacta cattgcaccc gtgtttggct gggacgccga tatcgtgtcg   15180
gttaacactc tcttcacctg ttttggcgcc accctctcca tttacgcctt ctttgtgctt   15240
gagatcatcg acgagatcac caactacctc gatatctggt gtctgcgaat caagtaccct   15300
caggagaaga agaccgaata agcggccgca tggagcgtgt gttctgagtc gatgttttct   15360
atggagttgt gagtgttagt agacatgatg ggtttatata tgatgaatga atagatgtga   15420
ttttgatttg cacgatggaa ttgagaactt tgtaaacgta catgggaatg tatgaatgtg   15480
ggggttttgt gactggataa ctgacggtca gtggacgccg ttgttcaaat atccaagaga   15540
tgcgagaaac tttgggtcaa gtgaacatgt cctctctgtt caagtaaacc atcaactatg   15600
ggtagtatat ttagtaagga caagagttga gattctttgg agtcctagaa acgtattttc   15660
gcgttccaag atcaaattag tagagtaata cgggcacggg aatccattca tagtctcaat   15720
cctgcaggtg agttaattaa tcgagcttgg cgtaatcatg gtcatagctg tttcctgtgt   15780
gaaattgtta tccgctcaca attccacaca ac                                 15812
```

<210> SEQ ID NO 79
<211> LENGTH: 18
<212> TYPE: DNA
<213> ORGANISM: Artificial Sequence
<220> FEATURE:
<223> OTHER INFORMATION: M13F universal primer

<400> SEQUENCE: 79

```
tgtaaaacga cggccagt                                                 18
```

<210> SEQ ID NO 80
<211> LENGTH: 277
<212> TYPE: PRT
<213> ORGANISM: Pavlova sp. CCMP459
<220> FEATURE:
<221> NAME/KEY: MISC_FEATURE
<222> LOCATION: (1)..(277)
<223> OTHER INFORMATION: C20-polyunsaturated fatty acid elongase;
      GenBank Accession No. AAV33630

<400> SEQUENCE: 80

```
Met Met Leu Ala Ala Gly Tyr Leu Leu Val Leu Ser Ala Ala Arg Gln
 1               5                  10                  15

Ser Phe Gln Gln Asp Ile Asp Asn Pro Asn Gly Ala Tyr Ser Thr Ser
            20                  25                  30

Trp Thr Gly Leu Pro Ile Val Met Ser Val Val Tyr Leu Ser Gly Val
        35                  40                  45

Phe Gly Leu Thr Lys Tyr Phe Glu Asn Arg Lys Pro Met Thr Gly Leu
    50                  55                  60

Lys Asp Tyr Met Phe Thr Tyr Asn Leu Tyr Gln Val Ile Ile Asn Val
65                  70                  75                  80

Trp Cys Val Val Ala Phe Leu Leu Glu Val Arg Arg Ala Gly Met Ser
                85                  90                  95

Leu Ile Gly Asn Lys Val Asp Leu Gly Pro Asn Ser Phe Arg Leu Gly
            100                 105                 110
```

```
Phe Val Thr Trp Val His Tyr Asn Asn Lys Tyr Val Glu Leu Leu Asp
            115                 120                 125

Thr Leu Trp Met Val Leu Arg Lys Lys Thr Gln Gln Val Ser Phe Leu
130                 135                 140

His Val Tyr His His Val Leu Leu Met Trp Ala Trp Phe Val Val Val
145                 150                 155                 160

Lys Leu Gly Asn Gly Gly Asp Ala Tyr Phe Gly Gly Leu Met Asn Ser
                165                 170                 175

Ile Ile His Val Met Met Tyr Ser Tyr Tyr Thr Met Ala Leu Leu Gly
                180                 185                 190

Trp Ser Cys Pro Trp Lys Arg Tyr Leu Thr Gln Ala Gln Leu Val Gln
            195                 200                 205

Phe Cys Ile Cys Leu Ala His Ser Thr Trp Ala Ala Val Thr Gly Ala
            210                 215                 220

Tyr Pro Trp Arg Ile Cys Leu Val Glu Val Trp Val Met Val Ser Met
225                 230                 235                 240

Leu Val Leu Phe Thr Arg Phe Tyr Arg Gln Ala Tyr Ala Lys Glu Ala
                245                 250                 255

Lys Ala Lys Glu Ala Lys Lys Leu Ala Gln Glu Ala Ser Gln Ala Lys
            260                 265                 270

Ala Val Lys Ala Glu
        275

<210> SEQ ID NO 81
<211> LENGTH: 608
<212> TYPE: DNA
<213> ORGANISM: Euglena gracilis

<400> SEQUENCE: 81
attgtattgc ctgcacaatg gcggatagcc cagtcatcaa cctcagcacc atgtggaaac      60
ccctttcact gatgggacat gtctggaagc aggcacaaca ggagggcagc atttcggcct     120
atgctgattc tgttcggatt cctctcatta tgtccgtttt atacttatca atgatcttcg     180
tggggtgccg ctggatgaag aaccgtgagc cctttgagat caaaacatac atgtttgcgt     240
ataacctgta tcagaccttg atgaaccttt gcatcgtgtt gggattcttg taccaggtgc     300
atgccactgg gatgcgcttt tggggaagtg tgtcgaccg aagcccgaaa ggtttgggca     360
ttggcttctt catttatgcc cactaccaca acaagtatgt ggatatttt gatacacttt     420 ttatggtgct gcgaaagaag aacaaccaga tttctttcct tcacgtgtat catcatgccc     480
tgttgacatg ggcttggttt gctgttgtgt atttcgcacc tggaggtgat ggctggtttg     540
gagcttgcta caattcttcc atccatgtcc tgatgtactc ttactacttg cttgcaactt     600
ttggcatc                                                              608

<210> SEQ ID NO 82
<211> LENGTH: 1327
<212> TYPE: DNA
<213> ORGANISM: Euglena gracilis

<400> SEQUENCE: 82
gcattgtatt gcctgcacaa tggcggatag cccagtcatc aacctcagca ccatgtggaa      60 accccttttca ctgatgggac atgtctggaa gcaggcacaa caggagggca gcatttcggc    120
ctatgctgat tctgttcgga ttcctctcat tatgtccgtt tttatactta tcaatgatct    180
cgtggggtgc gctggatga agaaccgtga gccctttgag atcaaaacat acatgtttgc    240
```

| | |
|---|---|
| gtataacctg tatcagacct tgatgaacct ttgcatcgtg ttgggattct tgtaccaggt | 300 |
| gcatgccact gggatgcgct tttggggaag tggtgtcgac cgaagcccga aaggtttggg | 360 |
| cattggcttc ttcatttatg cccactacca caacaagtat gtggaatatt ttgatacact | 420 |
| ttttatggtg ctgcgaaaga agaacaacca gatttctttc cttcacgtgt atcatcatgc | 480 |
| cctgttgaca tgggcttggt tgctgttgt gtatttcgca cctggaggtg atggctggtt | 540 |
| tggagcttgc tacaattctt ccatccatgt cctgatgtac tcttactact tgcttgcaac | 600 |
| ttttggcatc agttgcccat ggaagaagat cttgacacag ctccagatgg ttcagttctg | 660 |
| tttctgtttt acacattcca tttatgtgtg gatttgcggg tcagagatct acccacggcc | 720 |
| tctgactgct ttgcagtcgt tcgtgatggt caatatgttg gtgctgtttg gcaatttcta | 780 |
| tgtcaagcaa tactcccaaa agaacggcaa gccggagaac ggagccaccc ctgagaacgg | 840 |
| agcgaagccg caaccttgcg agaacggcac ggtggaaaag cgagaggcgc ccgatctgt | 900 |
| cggcatggga cgctgaggag tccaaatgca cggaaaggag ctagcgatgc ctcacgagct | 960 |
| aatctgcctc ggagtagact cccacatttc tcctgctctg tgttttgctc tcctcagtcc | 1020 |
| ccattggctc tccagtgacc gcgctttccc ctcttctgtc aagccaccct cctgcatggg | 1080 |
| ttccagcgga gcttctgacc gcttcgacat tttccttgcg cagccctgcc tcacgcagcg | 1140 |
| gacattttg ggcactgcgg tgcagtgttt atgtgtcctc ccaccccgtc ttaccctccc | 1200 |
| cctggcttgc tcggaccatc cagctcgttt atcctctcct ctcctgtggc agcgttgcct | 1260 |
| cggagtggaa agcttcagat aagcatcttt cctcctttgc attcaatgct ccacaagaaa | 1320 |
| ctctcaa | 1327 |

<210> SEQ ID NO 83
<211> LENGTH: 897
<212> TYPE: DNA
<213> ORGANISM: Euglena gracilis

<400> SEQUENCE: 83

| | |
|---|---|
| atggcggata gcccagtcat caacctcagc accatgtgga aacccctttc actgatggga | 60 |
| catgtctgga agcaggcaca acaggagggc agcatttcgg cctatgctga ttctgttcgg | 120 |
| attcctctca ttatgtccgt tttatactta tcaatgatct tcgtggggtg ccgctggatg | 180 |
| aagaaccgtg agccctttga gatcaaaaca tacatgtttg cgtataacct gtatcagacc | 240 |
| ttgatgaacc tttgcatcgt gttgggattc ttgtaccagg tgcatgccac tgggatgcgc | 300 |
| ttttggggaa gtggtgtcga ccgaagcccg aaaggtttgg gcattggctt cttcatttat | 360 |
| gcccactacc acaacaagta tgtggaatat tttgatacac ttttatggt gctgcgaaag | 420 |
| aagaacaacc agatttcttt ccttcacgtg tatcatcatg ccctgttgac atgggcttgg | 480 |
| tttgctgttg tgtatttcgc acctggaggt gatggctggt ttggagcttg ctacaattct | 540 |
| tccatccatg tcctgatgta ctcttactac ttgcttgcaa cttttggcat cagttgccca | 600 |
| tggaagaaga tcttgacaca gctccagatg gttcagttct gtttctgttt tacacattcc | 660 |
| atttatgtgt ggatttgcgg gtcagagatc tacccacggc ctctgactgc tttgcagtcg | 720 |
| ttcgtgatgg tcaatatgtt ggtgctgttt ggcaatttct atgtcaagca atactcccaa | 780 |
| aagaacggca gccggagaa cggagccacc cctgagaacg gagcgaagcc gcaaccttgc | 840 |
| gagaacggca cggtggaaaa gcgagaggcg cccgatctg tcggcatggg acgctga | 897 |

<210> SEQ ID NO 84
<211> LENGTH: 298
<212> TYPE: PRT

<213> ORGANISM: Euglena gracilis

<400> SEQUENCE: 84

Met Ala Asp Ser Pro Val Ile Asn Leu Ser Thr Met Trp Lys Pro Leu
1               5                   10                  15

Ser Leu Met Gly His Val Trp Lys Gln Ala Gln Gln Glu Gly Ser Ile
            20                  25                  30

Ser Ala Tyr Ala Asp Ser Val Arg Ile Pro Leu Ile Met Ser Val Leu
        35                  40                  45

Tyr Leu Ser Met Ile Phe Val Gly Cys Arg Trp Met Lys Asn Arg Glu
    50                  55                  60

Pro Phe Glu Ile Lys Thr Tyr Met Phe Ala Tyr Asn Leu Tyr Gln Thr
65                  70                  75                  80

Leu Met Asn Leu Cys Ile Val Leu Gly Phe Leu Tyr Gln Val His Ala
                85                  90                  95

Thr Gly Met Arg Phe Trp Gly Ser Gly Val Asp Arg Ser Pro Lys Gly
            100                 105                 110

Leu Gly Ile Gly Phe Phe Ile Tyr Ala His Tyr His Asn Lys Tyr Val
        115                 120                 125

Glu Tyr Phe Asp Thr Leu Phe Met Val Leu Arg Lys Lys Asn Asn Gln
    130                 135                 140

Ile Ser Phe Leu His Val Tyr His His Ala Leu Leu Thr Trp Ala Trp
145                 150                 155                 160

Phe Ala Val Val Tyr Phe Ala Pro Gly Gly Asp Gly Trp Phe Gly Ala
                165                 170                 175

Cys Tyr Asn Ser Ser Ile His Val Leu Met Tyr Ser Tyr Tyr Leu Leu
            180                 185                 190

Ala Thr Phe Gly Ile Ser Cys Pro Trp Lys Lys Ile Leu Thr Gln Leu
        195                 200                 205

Gln Met Val Gln Phe Cys Phe Cys Phe Thr His Ser Ile Tyr Val Trp
    210                 215                 220

Ile Cys Gly Ser Glu Ile Tyr Pro Arg Pro Leu Thr Ala Leu Gln Ser
225                 230                 235                 240

Phe Val Met Val Asn Met Leu Val Leu Phe Gly Asn Phe Tyr Val Lys
                245                 250                 255

Gln Tyr Ser Gln Lys Asn Gly Lys Pro Glu Asn Gly Ala Thr Pro Glu
            260                 265                 270

Asn Gly Ala Lys Pro Gln Pro Cys Glu Asn Gly Thr Val Glu Lys Arg
        275                 280                 285

Glu Ala Pro Arg Ser Val Gly Met Gly Arg
    290                 295

<210> SEQ ID NO 85
<211> LENGTH: 20
<212> TYPE: DNA
<213> ORGANISM: Artificial Sequence
<220> FEATURE:
<223> OTHER INFORMATION: sequencing primer SeqE

<400> SEQUENCE: 85
cgacacactc caatctttcc                                          20

<210> SEQ ID NO 86
<211> LENGTH: 20
<212> TYPE: DNA
<213> ORGANISM: Artificial Sequence
<220> FEATURE:
<223> OTHER INFORMATION: sequencing primer SeqW

<400> SEQUENCE: 86
ggtggctgga gttagacatc                                              20

<210> SEQ ID NO 87
<211> LENGTH: 742
<212> TYPE: DNA
<213> ORGANISM: Euglena gracilis

<400> SEQUENCE: 87
attttttttc ggtgcggcgc attgtattgc ctgcacaatg gcggatagcc cagtcatcaa     60
cctcagcacc atgtggaaac ccctttcact gatggctttg gaccttgccg tttttgggaca   120
tgtctggaag caggcacaac aggagggcag catttcggcc tatgctgatt ctgtttggac    180
tcctctcatt atgtccggtt tacttatc aatgatcttc gtggggtgcc gctggatgaa      240
gaaccgtgaa cccttttgaga tcaaaacata catgtttgcg tataacctgt atcagacctt   300
gatgaacctt tgcatcgtgt tgggattctt gtaccaggtg catgccactg ggatgcgctt    360
ttggggaagt ggtgtcgacc gaagcccaaa aggtttgggc attggcttct tcatttatgc    420
ccactaccac aacaagtatg tggaatattt tgatacactt tttatggtgc tgcgaaagaa    480
gaacaaccag atttctttcc ttcacgtgta tcatcatgcc ctgttgacat gggcttggtt    540
tgctgttgtg tatttcgcac ctggaggtga tggctggttt ggagcttgct acaattcttc    600
catccatgtc ctgatgtact cttactactt gcttgcaact tttggcatca gttgcccatg    660
gaagaagatc ttgacacagc tccagatggt tcaattctgt ttctgtttta cacattccat    720
ttatgtgtgg atttgcgggt ca                                             742

<210> SEQ ID NO 88
<211> LENGTH: 2630
<212> TYPE: DNA
<213> ORGANISM: Euglena gracilis

<400> SEQUENCE: 88
attttttttc ggtgcggcgc attgtattgc ctgcacaatg gcggatagcc cagtcatcaa     60
cctcagcacc atgtggaaac ccctttcact gatggctttg gaccttgccg tttttgggaca   120
tgtctggaag caggcacaac aggagggcag catttcggcc tatgctgatt ctgtttggac    180
tcctctcatt atgtccggtt tacttatc aatgatcttc gtggggtgcc gctggatgaa      240
gaaccgtgaa cccttttgaga tcaaaacata catgtttgcg tataacctgt atcagacctt   300
gatgaacctt tgcatcgtgt tgggattctt gtaccaggtg catgccactg ggatgcgctt    360
ttggggaagt ggtgtcgacc gaagcccaaa aggtttgggc attggcttct tcatttatgc    420
ccactaccac aacaagtatg tggaatattt tgatacactt tttatggtgc tgcgaaagaa    480
gaacaaccag atttctttcc ttcacgtgta tcatcatgcc ctgttgacat gggcttggtt    540
tgctgttgtg tatttcgcac ctggaggtga tggctggttt ggagcttgct acaattcttc    600
catccatgtc ctgatgtact cttactactt gcttgcaact tttggcatca gttgcccatg    660
gaagaagatc ttgacacagc tccagatggt tcaattctgt ttctgtttta cacattccat    720
ttatgtgtgg atttgcgggt cagagatcta cccacggcct ctgactgctt tgcagtcgtt    780
cgtgatggtc aatatgttgg tgctgtttgg caatttctat gtcaagcaat actcccaaaa    840
gaacggcaag ccggagaacg gagccacccc tgagaacgga gcgaagccgc aaccttgcga    900
gaacggcacg gtgaaaagc gagagaatga caccgccaac gttcggcccg ccgtccagc     960
tggactcccg ccggccacgt actacgactc cctggcagtg tcggggcagg gcaaggagcg   1020

-continued

```
gctgttcacc accgatgagg tgaggcggca catcctcccc accgatggct ggctgacgtg    1080
ccacgaagga gtctacgatg tcactgattt ccttgccaag cccctggtg gcggtgtcat     1140 cacgctgggc cttggaaggg actgcacaat cctcgtcgag tcataccacc ctgctgggcg    1200
cccggacaag gtgatggaga agtaccgcat tggtacgctg caggacccca agacgttcta    1260
tgcttgggga gagtccgatt tctaccctga gttgaagcgc cgggcccttg caaggctgaa    1320
ggaggctggt caggcgcggc gcggcggcct tggggtgaag gccctcctgg tgctcaccct    1380
cttcttcgtg tcgtggtaca tgtgggtggc ccacaagtcc ttcctctggg ccgccgtctg    1440
gggcttcgcc ggctcccacg tcgggctgag catccagcac gacggcaacc acggcgcgtt    1500
cagccgcagc acactggtga accgcctggc ggggtggggc atggacttga tcggcgcgtc    1560
gtcaacggtg tgggagtacc agcacgtcat cggccaccac cagtacacca acctcgtgtc    1620
ggacacgcta ttcagtctgc ctgagaacga tccggacgtc ttctccagct acccgctgat    1680
gcgcatgcac ccggatacgg cgtggcagcc gcaccaccgc ttccagcacc tgttcgcgtt    1740
cccactgttc gccctgatga caatcagcaa ggtgctgacc agcgatttcg ctgtctgcct    1800
cagcatgaag aaggggtcca tcgactgctc ctccaggctc gtcccactgg aggggcagct    1860
gctgttctgg ggggccaagc tggcgaactt cctgttgcag attgtgttgc atgctacct    1920 ccacgggaca gctatgggcc tggccctctt ctctgttgcc acccttgtgt cggggggagta   1980 cctcgcgatc tgcttcatca tcaaccacat cagcgagtct tgtgagttta tgaatacaag    2040
ctttcaaacc gccgcccgga ggacagagat gcttcaggca gcccatcagg cagcggaggc    2100
caagaaggtg aagcccaccc ctccaccgaa cgattgggct gtgacacagg tccaatgctg    2160
cgtgaattgg agatcaggtg gcgtgttggc caatcacctc tctggaggct gaaccacca    2220 gatcgagcat catctgttcc ccagcatctc gcatgccaac taccccatca tcgcccgtgt    2280
tgtgaaggag gtgtgcgagg agtatggggt gccgtacaag aactacgtca cgttctggga    2340
tgcagtctgt ggcatggttc agcacctccg gttgatgggt gctccaccgg tgccaacgaa    2400
cggggacaaa aagtcataag ccacgacatc atttgggggct cactccgtgc agccttttct    2460
tgggctgccc acgaagatgc gcgatgaggc acctggtggt tgccctccgc cggcctcgga    2520
aaacggttcg acgcctgctc cttcagccca gagcactccg gcgaagagtg aaagagcact    2580
gacctgaatt ttatgatgac ccatttttt aaaaaaaaaa aaaaaaaaaa                2630
```

```
<210> SEQ ID NO 89
<211> LENGTH: 2382
<212> TYPE: DNA
<213> ORGANISM: Euglena gracilis
<220> FEATURE:
<221> NAME/KEY: misc_feature
<222> LOCATION: (1)..(2382)
<223> OTHER INFORMATION: DHA synthase 1 (or "EgDHAsyn1")

<400> SEQUENCE: 89
```

```
atggcggata gcccagtcat caacctcagc accatgtgga aaccccttttc actgatggct     60 ttggaccttg ccgttttggg acatgtctgg aagcaggcac aacaggaggg cagcatttcg    120
gcctatgctg attctgtttg gactcctctc attatgtccg gtttatactt atcaatgatc    180
ttcgtggggt gccgctggat gaagaaccgt gaacccttg agatcaaaac atacatgttt     240
gcgtataacc tgtatcagac cttgatgaac cttcgcatcg tgttgggatt cttgtaccag    300
gtgcatgcca ctgggatgcg cttttgggga agtggtgtcg accgaagccc aaaaggtttg    360
ggcattggct tcttcatttta tgcccactac cacaacaagt atgtggaata ttttgataca    420
```

```
cttttatgg tgctgcgaaa gaagaacaac cagatttctt tccttcacgt gtatcatcat    480
gccctgttga catgggcttg gtttgctgtt gtgtatttcg cacctggagg tgatggctgg    540
tttggagctt gctacaattc ttccatccat gtcctgatgt actcttacta cttgcttgca    600
acttttggca tcagttgccc atggaagaag atcttgacac agctccagat ggttcaattc    660
tgtttctgtt ttacacattc catttatgtg tggatttgcg ggtcagagat ctacccacgg    720
cctctgactg ctttgcagtc gttcgtgatg gtcaatatgt tggtgctgtt tggcaatttc    780
tatgtcaagc aatactccca aaagaacggc aagccggaga acggagccac ccctgagaac    840
ggagcgaagc cgcaaccttg cgagaacggc acggtggaaa gcgagagaa tgacaccgcc    900 aacgttcggc cgcccgtcc agctggactc ccgccggcca cgtactacga ctccctggca    960
gtgtcggggc agggcaagga gcggctgttc accaccgatg aggtgaggcg gcacatcctc   1020
cccaccgatg gctggctgac gtgccacgaa ggagtctacg atgtcactga tttccttgcc   1080
aagcaccctg gtggcggtgt catcacgctg gccttggaa gggactgcac aatcctcgtc   1140
gagtcatacc accctgctgg gcgcccggac aaggtgatgg agaagtaccg cattggtacg   1200
ctgcaggacc ccaagacgtt ctatgcttgg ggagagtccg atttctaccc tgagttgaag   1260
cgccgggccc ttgcaaggct gaaggaggct ggtcaggcgc ggcgcggcgg ccttggggtg   1320
aaggccctcc tggtgctcac cctcttcttc gtgtcgtggt acatgtgggt ggcccacaag   1380
tccttcctct gggccgccgt ctggggcttc gccggctccc acgtcgggct gagcatccag   1440
cacgacggca accacggcgc gttcagccgc agcacactgg tgaaccgcct ggcggggtgg   1500
ggcatggact tgatcggcgc gtcgtcaacg gtgtgggagt accagcacgt catcggccac   1560
caccagtaca ccaacctcgt gtcggacacg ctattcagtc tgcctgagaa cgatccggac   1620
gtcttctcca gctacccgct gatgcgcatg cacccggata cggcgtggca gccgcaccac   1680
cgcttccagc acctgttcgc gttcccactg ttcgccctga tgacaatcag caaggtgctg   1740
accagcgatt tcgctgtctg cctcagcatg aagaagggt ccatcgactg ctcctccagg   1800
ctcgtcccac tggaggggca gctgctgttc tgggggggcca agctggcgaa cttcctgttg   1860
cagattgtgt tgccatgcta cctccacggg acagctatgg gcctggccct cttctctgtt   1920
gcccaccttg tgtcggggga gtacctcgcg atctgcttca tcatcaacca catcagcgag   1980
tcttgtgagt ttatgaatac aagctttcaa accgccgccc ggaggacaga gatgcttcag   2040
gcagcccatc aggcagcgga ggccaagaag gtgaagccca cccctccacc gaacgattgg   2100
gctgtgacac aggtccaatg ctgcgtgaat tggagatcag gtggcgtgtt ggccaatcac   2160
ctctctggag gcttgaacca ccagatcgag catcatctgt tccccagcat ctcgcatgcc   2220
aactacccca tcatcgcccg tgttgtgaag gaggtgtgcg aggagtatgg gttgccgtac   2280
aagaactacg tcacgttctg ggatgcagtc tgtggcatgg ttcagcacct ccggttgatg   2340
ggtgctccac cggtgccaac gaacggggac aaaaagtcat aa                       2382
```

<210> SEQ ID NO 90
<211> LENGTH: 793
<212> TYPE: PRT
<213> ORGANISM: Euglena gracilis
<220> FEATURE:
<221> NAME/KEY: MISC_FEATURE
<222> LOCATION: (1)..(793)
<223> OTHER INFORMATION: DHA synthase 1 (or "EgDHAsyn1")

<400> SEQUENCE: 90

Met Ala Asp Ser Pro Val Ile Asn Leu Ser Thr Met Trp Lys Pro Leu

-continued

```
1               5                   10                  15
Ser Leu Met Ala Leu Asp Leu Ala Val Leu Gly His Val Trp Lys Gln
            20                  25                  30

Ala Gln Gln Glu Gly Ser Ile Ser Ala Tyr Ala Asp Ser Val Trp Thr
            35                  40                  45

Pro Leu Ile Met Ser Gly Leu Tyr Leu Ser Met Ile Phe Val Gly Cys
50                  55                  60

Arg Trp Met Lys Asn Arg Glu Pro Phe Glu Ile Lys Thr Tyr Met Phe
65                  70                  75                  80

Ala Tyr Asn Leu Tyr Gln Thr Leu Met Asn Leu Cys Ile Val Leu Gly
            85                  90                  95

Phe Leu Tyr Gln Val His Ala Thr Gly Met Arg Phe Trp Gly Ser Gly
            100                 105                 110

Val Asp Arg Ser Pro Lys Gly Leu Gly Ile Gly Phe Phe Ile Tyr Ala
            115                 120                 125

His Tyr His Asn Lys Tyr Val Glu Tyr Phe Asp Thr Leu Phe Met Val
            130                 135                 140

Leu Arg Lys Lys Asn Asn Gln Ile Ser Phe Leu His Val Tyr His His
145                 150                 155                 160

Ala Leu Leu Thr Trp Ala Trp Phe Ala Val Val Tyr Phe Ala Pro Gly
            165                 170                 175

Gly Asp Gly Trp Phe Gly Ala Cys Tyr Asn Ser Ser Ile His Val Leu
            180                 185                 190

Met Tyr Ser Tyr Tyr Leu Leu Ala Thr Phe Gly Ile Ser Cys Pro Trp
            195                 200                 205

Lys Lys Ile Leu Thr Gln Leu Gln Met Val Gln Phe Cys Phe Cys Phe
            210                 215                 220

Thr His Ser Ile Tyr Val Trp Ile Cys Gly Ser Glu Ile Tyr Pro Arg
225                 230                 235                 240

Pro Leu Thr Ala Leu Gln Ser Phe Val Met Val Asn Met Leu Val Leu
            245                 250                 255

Phe Gly Asn Phe Tyr Val Lys Gln Tyr Ser Gln Lys Asn Gly Lys Pro
            260                 265                 270

Glu Asn Gly Ala Thr Pro Glu Asn Gly Ala Lys Pro Gln Pro Cys Glu
            275                 280                 285

Asn Gly Thr Val Glu Lys Arg Glu Asn Asp Thr Ala Asn Val Arg Pro
            290                 295                 300

Ala Arg Pro Ala Gly Leu Pro Pro Ala Thr Tyr Tyr Asp Ser Leu Ala
305                 310                 315                 320

Val Ser Gly Gln Gly Lys Glu Arg Leu Phe Thr Thr Asp Glu Val Arg
            325                 330                 335

Arg His Ile Leu Pro Thr Asp Gly Trp Leu Thr Cys His Glu Gly Val
            340                 345                 350

Tyr Asp Val Thr Asp Phe Leu Ala Lys His Pro Gly Gly Gly Val Ile
            355                 360                 365

Thr Leu Gly Leu Gly Arg Asp Cys Thr Ile Leu Val Glu Ser Tyr His
            370                 375                 380

Pro Ala Gly Arg Pro Asp Lys Val Met Glu Lys Tyr Arg Ile Gly Thr
385                 390                 395                 400

Leu Gln Asp Pro Lys Thr Phe Tyr Ala Trp Gly Glu Ser Asp Phe Tyr
            405                 410                 415

Pro Glu Leu Lys Arg Arg Ala Leu Ala Arg Leu Lys Glu Ala Gly Gln
            420                 425                 430
```

```
Ala Arg Arg Gly Gly Leu Gly Val Lys Ala Leu Leu Val Leu Thr Leu
        435                 440                 445

Phe Phe Val Ser Trp Tyr Met Trp Val Ala His Lys Ser Phe Leu Trp
450                 455                 460

Ala Ala Val Trp Gly Phe Ala Gly Ser His Val Gly Leu Ser Ile Gln
465                 470                 475                 480

His Asp Gly Asn His Gly Ala Phe Ser Arg Ser Thr Leu Val Asn Arg
                485                 490                 495

Leu Ala Gly Trp Gly Met Asp Leu Ile Gly Ala Ser Ser Thr Val Trp
                500                 505                 510

Glu Tyr Gln His Val Ile Gly His His Gln Tyr Thr Asn Leu Val Ser
                515                 520                 525

Asp Thr Leu Phe Ser Leu Pro Glu Asn Asp Pro Asp Val Phe Ser Ser
530                 535                 540

Tyr Pro Leu Met Arg Met His Pro Asp Thr Ala Trp Gln Pro His His
545                 550                 555                 560

Arg Phe Gln His Leu Phe Ala Phe Pro Leu Phe Ala Leu Met Thr Ile
                565                 570                 575

Ser Lys Val Leu Thr Ser Asp Phe Ala Val Cys Leu Ser Met Lys Lys
                580                 585                 590

Gly Ser Ile Asp Cys Ser Ser Arg Leu Val Pro Leu Glu Gly Gln Leu
                595                 600                 605

Leu Phe Trp Gly Ala Lys Leu Ala Asn Phe Leu Leu Gln Ile Val Leu
610                 615                 620

Pro Cys Tyr Leu His Gly Thr Ala Met Gly Leu Ala Leu Phe Ser Val
625                 630                 635                 640

Ala His Leu Val Ser Gly Glu Tyr Leu Ala Ile Cys Phe Ile Ile Asn
                645                 650                 655

His Ile Ser Glu Ser Cys Glu Phe Met Asn Thr Ser Phe Gln Thr Ala
                660                 665                 670

Ala Arg Arg Thr Glu Met Leu Gln Ala Ala His Gln Ala Ala Glu Ala
                675                 680                 685

Lys Lys Val Lys Pro Thr Pro Pro Asn Asp Trp Ala Val Thr Gln
690                 695                 700

Val Gln Cys Cys Val Asn Trp Arg Ser Gly Gly Val Leu Ala Asn His
705                 710                 715                 720

Leu Ser Gly Gly Leu Asn His Gln Ile Glu His His Leu Phe Pro Ser
                725                 730                 735

Ile Ser His Ala Asn Tyr Pro Ile Ile Ala Arg Val Val Lys Glu Val
                740                 745                 750

Cys Glu Glu Tyr Gly Leu Pro Tyr Lys Asn Tyr Val Thr Phe Trp Asp
                755                 760                 765

Ala Val Cys Gly Met Val Gln His Leu Arg Leu Met Gly Ala Pro Pro
770                 775                 780

Val Pro Thr Asn Gly Asp Lys Lys Ser
785                 790
```

<210> SEQ ID NO 91
<211> LENGTH: 300
<212> TYPE: PRT
<213> ORGANISM: Ostreococcus tauri
<220> FEATURE:
<221> NAME/KEY: MISC_FEATURE
<222> LOCATION: (1)..(300)
<223> OTHER INFORMATION: polyunsaturated fatty acid elongase 2; GenBank
      Accession No. AAV67798

<400> SEQUENCE: 91

```
Met Ser Ala Ser Gly Ala Leu Leu Pro Ala Ile Ala Ser Ala Ala Tyr
1               5                   10                  15

Ala Tyr Ala Thr Tyr Ala Tyr Ala Phe Glu Trp Ser His Ala Asn Gly
            20                  25                  30

Ile Asp Asn Val Asp Ala Arg Glu Trp Ile Gly Ala Leu Ser Leu Arg
        35                  40                  45

Leu Pro Ala Ile Ala Thr Thr Met Tyr Leu Leu Phe Cys Leu Val Gly
    50                  55                  60

Pro Arg Leu Met Ala Lys Arg Glu Ala Phe Asp Pro Lys Gly Phe Met
65                  70                  75                  80

Leu Ala Tyr Asn Ala Tyr Gln Thr Ala Phe Asn Val Val Leu Gly
                85                  90                  95

Met Phe Ala Arg Glu Ile Ser Gly Leu Gly Gln Pro Val Trp Gly Ser
                100                 105                 110

Thr Met Pro Trp Ser Asp Arg Lys Ser Phe Lys Ile Leu Leu Gly Val
            115                 120                 125

Trp Leu His Tyr Asn Asn Lys Tyr Leu Glu Leu Leu Asp Thr Val Phe
    130                 135                 140

Met Val Ala Arg Lys Lys Thr Lys Gln Leu Ser Phe Leu His Val Tyr
145                 150                 155                 160

His His Ala Leu Leu Ile Trp Ala Trp Trp Leu Val Cys His Leu Met
                165                 170                 175

Ala Thr Asn Asp Cys Ile Asp Ala Tyr Phe Gly Ala Ala Cys Asn Ser
                180                 185                 190

Phe Ile His Ile Val Met Tyr Ser Tyr Tyr Leu Met Ser Ala Leu Gly
                195                 200                 205

Ile Arg Cys Pro Trp Lys Arg Tyr Ile Thr Gln Ala Gln Met Leu Gln
                210                 215                 220

Phe Val Ile Val Phe Ala His Ala Val Phe Val Leu Arg Gln Lys His
225                 230                 235                 240

Cys Pro Val Thr Leu Pro Trp Ala Gln Met Phe Val Met Thr Asn Met
                245                 250                 255

Leu Val Leu Phe Gly Asn Phe Tyr Leu Lys Ala Tyr Ser Asn Lys Ser
                260                 265                 270

Arg Gly Asp Gly Ala Ser Ser Val Lys Pro Ala Glu Thr Thr Arg Ala
                275                 280                 285

Pro Ser Val Arg Arg Thr Arg Ser Arg Lys Ile Asp
                290                 295                 300
```

<210> SEQ ID NO 92
<211> LENGTH: 358
<212> TYPE: PRT
<213> ORGANISM: Thalassiosira pseudonana
<220> FEATURE:
<221> NAME/KEY: MISC_FEATURE
<222> LOCATION: (1)..(358)
<223> OTHER INFORMATION: polyunsaturated fatty acid elongase 2; GenBank Accession No. AAV67800

<400> SEQUENCE: 92

```
Met Cys Ser Ser Pro Pro Ser Gln Ser Lys Thr Thr Ser Leu Leu Ala
1               5                   10                  15

Arg Tyr Thr Thr Ala Ala Leu Leu Leu Leu Thr Leu Thr Trp Cys
            20                  25                  30

His Phe Ala Phe Pro Ala Ala Thr Ala Thr Pro Gly Leu Thr Ala Glu
                35                  40                  45
```

```
Met His Ser Tyr Lys Val Pro Leu Gly Leu Thr Val Phe Tyr Leu Leu
        50                  55                  60

Ser Leu Pro Ser Leu Lys Tyr Val Thr Asp Asn Tyr Leu Ala Lys Lys
 65                  70                  75                  80

Tyr Asp Met Lys Ser Leu Leu Thr Glu Ser Met Val Leu Tyr Asn Val
                 85                  90                  95

Ala Gln Val Leu Leu Asn Gly Trp Thr Val Tyr Ala Ile Val Asp Ala
            100                 105                 110

Val Met Asn Arg Asp His Pro Phe Ile Gly Ser Arg Ser Leu Val Gly
        115                 120                 125

Ala Ala Leu His Ser Gly Ser Ser Tyr Ala Val Trp Val His Tyr Cys
    130                 135                 140

Asp Lys Tyr Leu Glu Phe Phe Asp Thr Tyr Phe Met Val Leu Arg Gly
145                 150                 155                 160

Lys Met Asp Gln Val Ser Phe Leu His Ile Tyr His His Thr Thr Ile
                165                 170                 175

Ala Trp Ala Trp Trp Ile Ala Leu Arg Phe Ser Pro Gly Gly Asp Ile
            180                 185                 190

Tyr Phe Gly Ala Leu Leu Asn Ser Ile Ile His Val Leu Met Tyr Ser
        195                 200                 205

Tyr Tyr Ala Leu Ala Leu Leu Lys Val Ser Cys Pro Trp Lys Arg Tyr
    210                 215                 220

Leu Thr Gln Ala Gln Leu Leu Gln Phe Thr Ser Val Val Tyr Thr
225                 230                 235                 240

Gly Cys Thr Gly Tyr Thr His Tyr Tyr His Thr Lys His Gly Ala Asp
                245                 250                 255

Glu Thr Gln Pro Ser Leu Gly Thr Tyr Tyr Phe Cys Cys Gly Val Gln
            260                 265                 270

Val Phe Glu Met Val Ser Leu Phe Val Leu Phe Ser Ile Phe Tyr Lys
        275                 280                 285

Arg Ser Tyr Ser Lys Lys Asn Lys Ser Gly Gly Lys Asp Ser Lys Lys
    290                 295                 300

Asn Asp Asp Gly Asn Asn Glu Asp Gln Cys His Lys Ala Met Lys Asp
305                 310                 315                 320

Ile Ser Glu Gly Ala Lys Glu Val Val Gly His Ala Ala Lys Asp Ala
                325                 330                 335

Gly Lys Leu Val Ala Thr Ala Ser Lys Ala Val Lys Arg Lys Gly Thr
            340                 345                 350

Arg Val Thr Gly Ala Met
        355

<210> SEQ ID NO 93
<211> LENGTH: 515
<212> TYPE: PRT
<213> ORGANISM: Thraustochytrium aureum
<220> FEATURE:
<221> NAME/KEY: MISC_FEATURE
<222> LOCATION: (1)..(515)
<223> OTHER INFORMATION: delta 4-desaturase; GenBank Accession No.
      AAN75707

<400> SEQUENCE: 93

Met Thr Val Gly Phe Asp Glu Thr Val Thr Met Asp Thr Val Arg Asn
 1               5                  10                  15

His Asn Met Pro Asp Asp Ala Trp Cys Ala Ile His Gly Thr Val Tyr
                20                  25                  30
```

```
Asp Ile Thr Lys Phe Ser Lys Val His Pro Gly Gly Asp Ile Ile Met
         35                  40                  45

Leu Ala Ala Gly Lys Glu Ala Thr Ile Leu Phe Glu Thr Tyr His Ile
         50                  55                  60

Lys Gly Val Pro Asp Ala Val Leu Arg Lys Tyr Lys Val Gly Lys Leu
 65              70                  75                  80

Pro Gln Gly Lys Lys Gly Glu Thr Ser His Met Pro Thr Gly Leu Asp
                 85                  90                  95

Ser Ala Ser Tyr Tyr Ser Trp Asp Ser Glu Phe Tyr Arg Val Leu Arg
                100                 105                 110

Glu Arg Val Ala Lys Lys Leu Ala Glu Pro Gly Leu Met Gln Arg Ala
            115                 120                 125

Arg Met Glu Leu Trp Ala Lys Ala Ile Phe Leu Leu Ala Gly Phe Trp
    130                 135                 140

Gly Ser Leu Tyr Ala Met Cys Val Leu Asp Pro His Gly Gly Ala Met
145                 150                 155                 160

Val Ala Ala Val Thr Leu Gly Val Phe Ala Ala Phe Val Gly Thr Cys
                165                 170                 175

Ile Gln His Asp Gly Ser His Gly Ala Phe Ser Lys Ser Arg Phe Met
            180                 185                 190

Asn Lys Ala Ala Gly Trp Thr Leu Asp Met Ile Gly Ala Ser Ala Met
        195                 200                 205

Thr Trp Glu Met Gln His Val Leu Gly His His Pro Tyr Thr Asn Leu
    210                 215                 220

Ile Glu Met Glu Asn Gly Leu Ala Lys Val Lys Gly Ala Asp Val Asp
225                 230                 235                 240

Pro Lys Lys Val Asp Gln Glu Ser Asp Pro Asp Val Phe Ser Thr Tyr
                245                 250                 255

Pro Met Leu Arg Leu His Pro Trp His Arg Gln Arg Phe Tyr His Lys
            260                 265                 270

Phe Gln His Leu Tyr Ala Pro Leu Ile Phe Gly Phe Met Thr Ile Asn
        275                 280                 285

Lys Val Ile Ser Gln Asp Val Gly Val Val Leu Arg Lys Arg Leu Phe
    290                 295                 300

Gln Ile Asp Ala Asn Cys Arg Tyr Gly Ser Pro Trp Asn Val Ala Arg
305                 310                 315                 320

Phe Trp Ile Met Lys Leu Leu Thr Thr Leu Tyr Met Val Ala Leu Pro
                325                 330                 335

Met Tyr Met Gln Gly Pro Ala Gln Gly Leu Lys Leu Phe Phe Met Ala
            340                 345                 350

His Phe Thr Cys Gly Glu Val Leu Ala Thr Met Phe Ile Val Asn His
        355                 360                 365

Ile Ile Glu Gly Val Ser Tyr Ala Ser Lys Asp Ala Val Lys Gly Val
    370                 375                 380

Met Ala Pro Pro Arg Thr Val His Gly Val Thr Pro Met Gln Val Thr
385                 390                 395                 400

Gln Lys Ala Leu Ser Ala Glu Ser Thr Lys Ser Asp Ala Asp Lys
                405                 410                 415

Thr Thr Met Ile Pro Leu Asn Asp Trp Ala Ala Val Gln Cys Gln Thr
            420                 425                 430

Ser Val Asn Trp Ala Val Gly Ser Trp Phe Trp Asn His Phe Ser Gly
        435                 440                 445

Gly Leu Asn His Gln Ile Glu His His Cys Phe Pro Gln Asn Pro His
450                 455                 460
```

```
Thr Val Asn Val Tyr Ile Ser Gly Ile Val Lys Glu Thr Cys Glu Glu
465                 470                 475                 480

Tyr Gly Val Pro Tyr Gln Ala Glu Ile Ser Leu Phe Ser Ala Tyr Phe
                485                 490                 495

Lys Met Leu Ser His Leu Arg Thr Leu Gly Asn Glu Asp Leu Thr Ala
            500                 505                 510

Trp Ser Thr
        515

<210> SEQ ID NO 94
<211> LENGTH: 509
<212> TYPE: PRT
<213> ORGANISM: Schizochytrium aggregatum
<220> FEATURE:
<221> NAME/KEY: MISC_FEATURE
<222> LOCATION: (1)..(509)
<223> OTHER INFORMATION: delta 4-desaturase
<300> PUBLICATION INFORMATION:
<302> TITLE: DELTA 4-DESATURASE GENES AND USES THEREOF
<310> PATENT DOCUMENT NUMBER: WO  2002/090493
<311> PATENT FILING DATE: 2002-05-02
<312> PUBLICATION DATE: 2002-11-14
<313> RELEVANT RESIDUES: (1)..(509)

<400> SEQUENCE: 94

Met Thr Val Gly Gly Asp Glu Val Tyr Ser Met Ala Gln Val Arg Asp
1               5                   10                  15

His Asn Thr Pro Asp Asp Ala Trp Cys Ala Ile His Gly Glu Val Tyr
            20                  25                  30

Glu Leu Thr Lys Phe Ala Arg Thr His Pro Gly Gly Asp Ile Ile Leu
        35                  40                  45

Leu Ala Ala Gly Lys Glu Ala Thr Ile Leu Phe Glu Thr Tyr His Val
    50                  55                  60

Arg Pro Ile Ser Asp Ala Val Leu Arg Lys Tyr Arg Ile Gly Lys Leu
65                  70                  75                  80

Ala Ala Ala Gly Lys Asp Glu Pro Ala Asn Asp Ser Thr Tyr Tyr Ser
                85                  90                  95

Trp Asp Ser Asp Phe Tyr Lys Val Leu Arg Gln Arg Val Val Ala Arg
            100                 105                 110

Leu Glu Glu Arg Lys Ile Ala Arg Arg Gly Pro Glu Ile Trp Ile
        115                 120                 125

Lys Ala Ala Ile Leu Val Ser Gly Phe Trp Ser Met Leu Tyr Leu Met
    130                 135                 140

Cys Thr Leu Asp Pro Asn Arg Gly Ala Ile Leu Ala Ala Ile Ala Leu
145                 150                 155                 160

Gly Ile Val Ala Ala Phe Val Gly Thr Cys Ile Gln His Asp Gly Asn
                165                 170                 175

His Gly Ala Phe Ala Phe Ser Pro Phe Met Asn Lys Leu Ser Gly Trp
            180                 185                 190

Thr Leu Asp Met Ile Gly Ala Ser Ala Met Thr Trp Glu Met Gln His
        195                 200                 205

Val Leu Gly His His Pro Tyr Thr Asn Leu Ile Glu Met Glu Asn Gly
    210                 215                 220

Thr Gln Lys Val Thr His Ala Asp Val Asp Pro Lys Ala Asp Gln
225                 230                 235                 240

Glu Ser Asp Pro Asp Val Phe Ser Thr Tyr Pro Met Leu Arg Leu His
                245                 250                 255

Pro Trp His Arg Lys Arg Phe Tyr His Arg Phe Gln His Leu Tyr Ala
```

-continued

```
                260                 265                 270
Pro Leu Leu Phe Gly Phe Met Thr Ile Asn Lys Val Ile Thr Gln Asp
            275                 280                 285

Val Gly Val Val Leu Ser Lys Arg Leu Phe Gln Ile Asp Ala Asn Cys
        290                 295                 300

Arg Tyr Ala Ser Lys Ser Tyr Val Ala Arg Phe Trp Ile Met Lys Leu
305                 310                 315                 320

Leu Thr Val Leu Tyr Met Val Ala Leu Pro Val Tyr Thr Gln Gly Leu
                325                 330                 335

Val Asp Gly Leu Lys Leu Phe Phe Ile Ala His Phe Ser Cys Gly Glu
            340                 345                 350

Leu Leu Ala Thr Met Phe Ile Val Asn His Ile Ile Glu Gly Val Ser
        355                 360                 365

Tyr Ala Ser Lys Asp Ser Val Lys Gly Thr Met Ala Pro Pro Arg Thr
370                 375                 380

Val His Gly Val Thr Pro Met His Asp Thr Arg Asp Ala Leu Gly Lys
385                 390                 395                 400

Glu Lys Ala Ala Thr Lys His Val Pro Leu Asn Asp Trp Ala Ala Val
                405                 410                 415

Gln Cys Gln Thr Ser Val Asn Trp Ser Ile Gly Ser Trp Phe Trp Asn
            420                 425                 430

His Phe Ser Gly Gly Leu Asn His Gln Ile Glu His His Leu Phe Pro
        435                 440                 445

Gly Leu Thr His Thr Thr Tyr Val Tyr Ile Gln Asp Val Val Gln Ala
    450                 455                 460

Thr Cys Ala Glu Tyr Gly Val Pro Tyr Gln Ser Gln Ser Leu Phe
465                 470                 475                 480

Ser Ala Tyr Phe Lys Met Leu Ser His Leu Arg Ala Leu Gly Asn Glu
                485                 490                 495

Pro Met Pro Ser Trp Glu Lys Asp His Pro Lys Ser Lys
            500                 505
```

<210> SEQ ID NO 95
<211> LENGTH: 445
<212> TYPE: PRT
<213> ORGANISM: Pavlova lutheri
<220> FEATURE:
<221> NAME/KEY: MISC_FEATURE
<222> LOCATION: (1)..(445)
<223> OTHER INFORMATION: delta-4 desaturase; GenBank Accession No.
      AAQ98793

<400> SEQUENCE: 95

```
Met Pro Pro Ser Ala Ala Ser Glu Gly Gly Val Ala Glu Leu Arg Ala
1               5                   10                  15

Ala Glu Val Ala Ser Tyr Thr Arg Lys Ala Val Asp Glu Arg Pro Asp
            20                  25                  30

Leu Thr Ile Val Gly Asp Ala Val Tyr Asp Ala Lys Ala Phe Arg Asp
        35                  40                  45

Glu His Pro Gly Gly Ala His Phe Val Ser Leu Phe Gly Gly Arg Asp
    50                  55                  60

Ala Thr Glu Ala Phe Met Glu Tyr His Arg Arg Ala Trp Pro Lys Ala
65                  70                  75                  80

Arg Met Ser Lys Phe Phe Val Gly Ser Leu Asp Ala Ser Glu Lys Pro
                85                  90                  95

Thr Gln Ala Asp Ser Ala Tyr Leu Arg Leu Cys Ala Glu Val Asn Ala
            100                 105                 110
```

```
Leu Leu Pro Lys Gly Ser Gly Gly Phe Ala Pro Pro Ser Tyr Trp Leu
            115                 120                 125

Lys Ala Ala Ala Leu Val Val Ala Ala Val Ser Ile Glu Gly Tyr Met
        130                 135                 140

Leu Leu Arg Gly Lys Thr Leu Leu Leu Ser Val Phe Leu Gly Leu Val
145                 150                 155                 160

Phe Ala Trp Ile Gly Leu Asn Ile Gln His Asp Ala Asn His Gly Ala
                165                 170                 175

Leu Ser Arg His Ser Val Ile Asn Tyr Cys Leu Gly Tyr Ala Gln Asp
            180                 185                 190

Trp Ile Gly Gly Asn Met Val Leu Trp Leu Gln Glu His Val Val Met
        195                 200                 205

His His Leu His Thr Asn Asp Val Asp Ala Asp Pro Asp Gln Lys Ala
    210                 215                 220

His Gly Val Leu Arg Leu Lys Pro Thr Asp Gly Trp Met Pro Trp His
225                 230                 235                 240

Ala Leu Gln Gln Leu Tyr Ile Leu Pro Gly Glu Ala Met Tyr Ala Phe
                245                 250                 255

Lys Leu Leu Phe Leu Asp Ala Leu Glu Leu Leu Ala Trp Arg Trp Glu
            260                 265                 270

Gly Glu Lys Ile Ser Pro Leu Ala Arg Ala Leu Phe Ala Pro Ala Val
        275                 280                 285

Ala Cys Lys Leu Gly Phe Trp Ala Arg Phe Val Ala Leu Pro Leu Trp
    290                 295                 300

Leu Gln Pro Thr Val His Thr Ala Leu Cys Ile Cys Ala Thr Val Cys
305                 310                 315                 320

Thr Gly Ser Phe Tyr Leu Ala Phe Phe Phe Ile Ser His Asn Phe
                325                 330                 335

Asp Gly Val Gly Ser Val Gly Pro Lys Gly Ser Leu Pro Arg Ser Ala
            340                 345                 350

Thr Phe Val Gln Arg Gln Val Glu Thr Ser Ser Asn Val Gly Gly Tyr
        355                 360                 365

Trp Leu Gly Val Leu Asn Gly Gly Leu Asn Phe Gln Ile Glu His His
    370                 375                 380

Leu Phe Pro Arg Leu His His Ser Tyr Tyr Ala Gln Ile Ala Pro Val
385                 390                 395                 400

Val Arg Thr His Ile Glu Lys Leu Gly Phe Lys Tyr Arg His Phe Pro
                405                 410                 415

Thr Val Gly Ser Asn Leu Ser Ser Met Leu Gln His Met Gly Lys Met
            420                 425                 430

Gly Thr Arg Pro Gly Ala Glu Lys Gly Gly Lys Ala Glu
        435                 440                 445

<210> SEQ ID NO 96
<211> LENGTH: 433
<212> TYPE: PRT
<213> ORGANISM: Isochrysis galbana
<220> FEATURE:
<221> NAME/KEY: MISC_FEATURE
<222> LOCATION: (1)..(433)
<223> OTHER INFORMATION: delta-4 desaturase; GenBank Accession No.
      AAV33631

<400> SEQUENCE: 96

Met Cys Asn Ala Ala Gln Val Glu Thr Gln Ala Leu Arg Ala Lys Glu
1               5                   10                  15
```

```
Ala Ala Lys Pro Thr Trp Thr Lys Ile His Gly Arg Thr Val Asp Val
         20                  25                  30

Glu Thr Phe Arg His Pro Gly Gly Asn Ile Leu Asp Leu Phe Leu Gly
             35                  40                  45

Met Asp Ala Thr Thr Ala Phe Glu Thr Phe His Gly His His Lys Gly
 50                      55                      60

Ala Trp Lys Met Leu Lys Thr Leu Pro Glu Lys Glu Val Ala Ala Ala
 65                  70                  75                  80

Asp Ile Pro Ala Gln Lys Glu Glu His Val Ala Glu Met Thr Arg Leu
                 85                  90                  95

Met Ala Ser Trp Arg Glu Arg Gly Leu Phe Lys Pro Arg Pro Val Ala
                100                 105                 110

Ser Ser Ile Tyr Gly Leu Cys Val Ile Phe Ala Ile Ala Ala Ser Val
            115                 120                 125

Ala Cys Ala Pro Tyr Ala Pro Val Leu Ala Gly Ile Ala Val Gly Thr
        130                 135                 140

Cys Trp Ala Gln Cys Gly Phe Leu Gln His Met Gly Gly His Arg Glu
145                 150                 155                 160

Trp Gly Arg Thr Trp Ser Phe Ala Phe Gln His Leu Phe Glu Gly Leu
                165                 170                 175

Leu Lys Gly Gly Ser Ala Ser Trp Trp Arg Asn Arg His Asn Lys His
                180                 185                 190

His Ala Lys Thr Asn Val Leu Gly Glu Asp Gly Asp Leu Arg Thr Thr
            195                 200                 205

Pro Phe Phe Ala Trp Asp Pro Thr Leu Ala Lys Lys Val Pro Asp Trp
210                 215                 220

Ser Leu Arg Thr Gln Ala Phe Thr Phe Leu Pro Ala Leu Gly Ala Tyr
225                 230                 235                 240

Val Phe Val Phe Ala Phe Thr Val Arg Lys Tyr Ser Val Val Lys Arg
                245                 250                 255

Leu Trp His Glu Val Ala Leu Met Val Ala His Tyr Ala Leu Phe Ser
                260                 265                 270

Trp Ala Leu Ser Ala Ala Gly Ala Ser Leu Ser Ser Gly Leu Thr Phe
                275                 280                 285

Tyr Cys Thr Gly Tyr Ala Trp Gln Gly Ile Tyr Leu Gly Phe Phe Phe
290                 295                 300

Gly Leu Ser His Phe Ala Val Glu Arg Val Pro Ser Thr Ala Thr Trp
305                 310                 315                 320

Leu Glu Ser Thr Met Met Gly Thr Val Asp Trp Gly Gly Ser Ser Ala
                325                 330                 335

Phe Cys Gly Tyr Leu Ser Gly Phe Leu Asn Ile Gln Ile Glu His His
            340                 345                 350

Met Ala Pro Gln Met Pro Met Glu Asn Leu Arg Gln Ile Arg Ala Asp
        355                 360                 365

Cys Lys Ala Ala His Lys Phe Gly Leu Pro Tyr Arg Glu Leu Thr
370                 375                 380

Phe Val Ala Ala Thr Lys Leu Met Met Ser Gly Leu Tyr Arg Thr Gly
385                 390                 395                 400

Lys Asp Glu Leu Lys Leu Arg Ala Asp Arg Arg Lys Phe Thr Arg Ala
                405                 410                 415

Gln Ala Tyr Met Gly Ala Ala Ser Ala Leu Val Asp Thr Leu Lys Ala
                420                 425                 430

Asp
```

<210> SEQ ID NO 97
<211> LENGTH: 4
<212> TYPE: PRT
<213> ORGANISM: Artificial Sequence
<220> FEATURE:
<223> OTHER INFORMATION: NG motif

<400> SEQUENCE: 97

Lys Asn Gly Lys
1

<210> SEQ ID NO 98
<211> LENGTH: 5
<212> TYPE: PRT
<213> ORGANISM: Artificial Sequence
<220> FEATURE:
<223> OTHER INFORMATION: NG motif

<400> SEQUENCE: 98

Pro Glu Asn Gly Ala
1               5

<210> SEQ ID NO 99
<211> LENGTH: 7
<212> TYPE: PRT
<213> ORGANISM: Artificial Sequence
<220> FEATURE:
<223> OTHER INFORMATION: NG motif

<400> SEQUENCE: 99

Pro Cys Glu Asn Gly Thr Val
1               5

<210> SEQ ID NO 100
<211> LENGTH: 36
<212> TYPE: DNA
<213> ORGANISM: Artificial Sequence
<220> FEATURE:
<223> OTHER INFORMATION: primer EgEPAEloDom-5

<400> SEQUENCE: 100
gcggccgcac catggcggat agcccagtca tcaacc                          36

<210> SEQ ID NO 101
<211> LENGTH: 32
<212> TYPE: DNA
<213> ORGANISM: Artificial Sequence
<220> FEATURE:
<223> OTHER INFORMATION: primer oEUG el4-3

<400> SEQUENCE: 101
tgcggccgct tatgactttt tgtccccgtt cg                              32

<210> SEQ ID NO 102
<211> LENGTH: 5914
<212> TYPE: DNA
<213> ORGANISM: Artificial Sequence
<220> FEATURE:
<223> OTHER INFORMATION: plasmid pKR1062

<400> SEQUENCE: 102
ttgtaatacg actcactata gggcgaattg ggccctctag atgcatgctc gagcggccgc    60
cagtgtgatg gatatctgca gaattcaggg cggccgcacc atggcggata gcccagtcat   120
caacctcagc accatgtgga aacccctttc actgatggct ttggaccttg ccgttttggg   180
acatgtctgg aagcaggcac aacaggaggg cagcatttcg gcctatgctg attctgtttg   240

-continued

```
gactcctctc attatgtccg gtttatactt atcaatgatc ttcgtggggt gccgctggat    300
gaagaaccgt gaacccttg agatcaaaac atacatgttt gcgtataacc tgtatcagac    360
cttgatgaac ctttgcatcg tgttgggatt cttgtaccag gtgcatgcca ctgggatgcg    420
cttttgggga agtggtgtcg accgaagccc aaaaggtttg ggcattggct tcttcattta    480
tgcccactac cacaacaagt atgtggaata ttttgataca cttttatgg tgctgcgaaa    540 gaagaacaac cagatttctt tccttcacgt gtatcatcat gccctgttga catgggcttg    600
gtttgctgtt gtgtatttcg cacctggagg tgatggctgg tttggagctt gctacaattc    660
ttccatccat gtcctgatgt actcttacta cttgcttgca acttttggca tcagttgccc    720
atggaagaag atcttgacac agctccagat ggttcaattc tgtttctgtt ttacacattc    780
catttatgtg tggatttgcg ggtcagagat ctacccacgg cctctgactg ctttgcagtc    840
gttcgtgatg gtcaatatgt tggtgctgtt tggcaatttc tatgtcaagc aatactccca    900
aaagaacggc aagccggaga acggagccac ccctgagaac ggagcgaagc cgcaaccttg    960
cgagaacggc acgtggaaa agcgagagaa tgacaccgcc aacgttcggc ccgcccgtcc   1020
agctggactc ccgccggcca cgtactacga ctccctggca gtgtcgggc agggcaagga   1080 gcggctgttc accaccgatg aggtgaggcg gcacatcctc cccaccgatg gctggctgac   1140
gtgccacgaa ggagtctacg atgtcactga tttccttgcc aagcaccctg gtggcggtgt   1200
catcacgctg ggccttggaa gggactgcac aatcctcgtc gagtcatacc accctgctgg   1260
gcgcccggac aaggtgatgg agaagtaccg cattggtacg ctgcaggacc ccaagacgtt   1320
ctatgcttgg ggagagtccg atttctaccc tgagttgaag cgccgggccc ttgcaaggct   1380
gaaggaggct ggtcaggcgc ggcgcggcgg ccttggggtg aaggccctcc tggtgctcac   1440
cctcttcttc gtgtcgtggt acatgtgggt ggcccacaag tccttcctct gggccgccgt   1500
ctggggcttc gccggctccc acgtcgggct gagcatccag cacgacggca accacgcgc   1560 gttcagccgc agcacactgg tgaaccgcct ggcggggtgg ggcatggact tgatcggcgc   1620
gtcgtcaacg gtgtgggagt accagcacgt catcggccac caccagtaca ccaacctcgt   1680
gtcggacacg ctattcagtc tgcctgagaa cgatccggac gtcttctcca gctacccgct   1740
gatgcgcatg cacccggata cggcgtggca gccgcaccac cgcttccagc acctgttcgc   1800
gttcccactg ttcgccctga tgacaatcag caaggtgctg accagcgatt tcgctgtctg   1860
cctcagcatg aagaaggggt ccatcgactg ctcctccagg ctcgtcccac tggaggggca   1920
gctgctgttc tgggggggcca agctggcgaa cttcctgttg cagattgtgt tgccatgcta   1980
cctccacggg acagctatgg gcctggccct cttctctgtt gcccacctg tgtcggggga   2040 gtacctcgcg atctgcttca tcatcaacca catcagcgag tcttgtgagt ttatgaatac   2100
aagctttcaa accgccgccc ggaggacaga tgcttcag gcagcccatc aggcagcgga   2160
ggccaagaag gtgaagccca cccctccacc gaacgattgg gctgtgacac aggtccaatg   2220
ctgcgtgaat tggagatcag gtggcgtgtt ggccaatcac ctctctggag gcttgaacca   2280
ccagatcgag catcatctgt tccccagcat ctcgcatgcc aactacccca tcatcgcccg   2340
tgttgtgaag gaggtgtgcg aggagtatgg gttgccgtac aagaactacg tcacgttctg   2400
ggatgcagtc tgtggcatgg ttcagcacct ccggttgatg gtgctccac cggtgccaac   2460 gaacggggac aaaaagtcat aagcggccgc acctgaattc cagcacactg gcggccgtta   2520
ctagtggatc cgagctcggt accaagcttg atgcatagct tgagtattct aacgcgtcac   2580
ctaaatagct tggcgtaatc atggtcatag ctgtttcctg tgtgaaattg ttatccgctc   2640
```

```
acaattccac acaacatacg agccggaagc ataaagtgta aagcctgggg tgcctaatga   2700
gtgagctaac tcacattaat tgcgttgcgc tcactgcccg ctttccagtc gggaaacctg   2760
tcgtgccagc tgcattaatg aatcggccaa cgcgcgggga gaggcggttt gcgtattggg   2820
cgctcttccg cttcctcgct cactgactcg ctgcgctcgg tcgttcggct gcggcgagcg   2880
gtatcagctc actcaaaggc ggtaatacgg ttatccacag aatcagggga taacgcagga   2940
aagaacatgt gagcaaaagg ccagcaaaag gccaggaacc gtaaaaaggc cgcgttgctg   3000
gcgtttttcc ataggctccg ccccctgac gagcatcaca aaaatcgacg ctcaagtcag   3060
aggtggcgaa acccgacagg actataaaga taccaggcgt ttccccctgg aagctccctc   3120
gtgcgctctc ctgttccgac cctgccgctt accggatacc tgtccgcctt tctcccttcg   3180
ggaagcgtgg cgctttctca tagctcacgc tgtaggtatc tcagttcggt gtaggtcgtt   3240
cgctccaagc tgggctgtgt gcacgaaccc cccgttcagc ccgaccgctg cgccttatcc   3300
ggtaactatc gtcttgagtc aacccggta agacacgact tatcgccact ggcagcagcc   3360
actggtaaca ggattagcag agcgaggtat gtaggcggtg ctacagagtt cttgaagtgg   3420
tggcctaact acggctacac tagaagaaca gtatttggta tctgcgctct gctgaagcca   3480
gttaccttcg gaaaaagagt tggtagctct tgatccggca acaaaccac cgctggtagc   3540 ggtggttttt ttgtttgcaa gcagcagatt acgcgcagaa aaaaggatc tcaagaagat   3600 cctttgatct tttctacggg gtctgacgct cagtggaacg aaaactcacg ttaagggatt   3660
ttggtcatga gattatcaaa aaggatcttc acctagatcc ttttaaatta aaaatgaagt   3720
tttagcacgt gtcagtcctg ctcctcggcc acgaagtgca cgcagttgcc ggccgggtcg   3780
cgcagggcga actcccgccc ccacggctgc tcgccgatct cggtcatggc cggcccggag   3840
gcgtcccgga agttcgtgga cacgacctcc gaccactcgg cgtacagctc gtccaggccg   3900
cgcacccaca cccaggccag ggtgttgtcc ggcaccacct ggtcctggac cgcgctgatg   3960
aacagggtca cgtcgtcccg gaccacaccg gcgaagtcgt cctccacgaa gtcccgggag   4020
aacccgagcc ggtcggtcca gaactcgacc gctccggcga cgtcgcgcgc ggtgagcacc   4080
ggaacggcac tggtcaactt ggccatggtg gccctcctca cgtgctatta ttgaagcatt   4140
tatcagggtt attgtctcat gagcggatac atatttgaat gtatttagaa aaataaacaa   4200
ataggggttc cgcgcacatt tccccgaaaa gtgccacctg atgcggtgtg aaataccgca   4260
cagatgcgta aggagaaaat accgcatcag gaaattgtaa gcgttaataa ttcagaagaa   4320
ctcgtcaaga aggcgataga aggcgatgcg ctgcgaatcg ggagcggcga taccgtaaag   4380
cacgaggaag cggtcagccc attcgccgcc aagctcttca gcaatatcac gggtagccaa   4440
cgctatgtcc tgatagcggt ccgccacacc cagccggcca cagtcgatga atccagaaaa   4500
gcggccattt tccaccatga tattcggcaa gcaggcatcg ccatgggtca cgacgagatc   4560
ctcgccgtcg gcatgctcg ccttgagcct ggcgaacagt tcggctggcg cgagcccctg   4620
atgctcttcg tccagatcat cctgatcgac aagaccggct tccatccgag tacgtgctcg   4680
ctcgatgcga tgtttcgctt ggtggtcgaa tgggcaggta gccggatcaa gcgtatgcag   4740
ccgccgcatt gcatcagcca tgatggatac tttctcggca ggagcaaggt gagatgacag   4800
gagatcctgc cccggcactt cgcccaatag cagccagtcc cttcccgctt cagtgacaac   4860
gtcgagcaca gctgcgcaag gaacgcccgt cgtggccagc cacgatagcc gcgctgcctc   4920
gtcttgcagt tcattcaggg caccggacag gtcggtcttg acaaaaagaa ccgggcgccc   4980
ctgcgctgac agccggaaca cggcggcatc agagcagccg attgtctgtt gtgcccagtc   5040
```

```
atagccgaat agcctctcca cccaagcggc cggagaacct gcgtgcaatc catcttgttc    5100
aatcatgcga aacgatcctc atcctgtctc ttgatcagag cttgatcccc tgcgccatca    5160
gatccttggc ggcaagaaag ccatccagtt tactttgcag ggcttcccaa ccttaccaga    5220
gggcgcccca gctggcaatt ccggttcgct tgctgtccat aaaaccgccc agtctagcta    5280
tcgccatgta agcccactgc aagctacctg ctttctcttt gcgcttgcgt tttcccttgt    5340
ccagatagcc cagtagctga cattcatccg gggtcagcac cgtttctgcg gactggcttt    5400
ctacgtgaaa aggatctagg tgaagatcct ttttgataat ctcatgcctg acatttatat    5460
tccccagaac atcaggttaa tggcgttttt gatgtcattt tcgcggtggc tgagatcagc    5520
cacttcttcc ccgataacgg agaccggcac actggccata tcggtggtca tcatgcgcca    5580
gctttcatcc ccgatatgca ccaccgggta agttcacgg  gagactttat ctgacagcag    5640
acgtgcactg gccagggga  tcaccatccg tcgccccggc gtgtcaataa tatcactctg    5700
tacatccaca aacagacgat aacggctctc tcttttatag gtgtaaacct taaactgccg    5760
tacgtatagg ctgcgcaact gttgggaagg gcgatcggtg cgggcctctt cgctattacg    5820
ccagctggcg aaaggggat  gtgctgcaag gcgattaagt tgggtaacgc cagggttttc    5880
ccagtcacga cgttgtaaaa cgacggccag tgaa                                5914

<210> SEQ ID NO 103
<211> LENGTH: 45
<212> TYPE: DNA
<213> ORGANISM: Artificial Sequence
<220> FEATURE:
<223> OTHER INFORMATION: oligonucleotide EgEloD4Mut-5

<400> SEQUENCE: 103
caacttttgg catcagttgc ccttggaaga agatcttgac acagc                      45

<210> SEQ ID NO 104
<211> LENGTH: 45
<212> TYPE: DNA
<213> ORGANISM: Artificial Sequence
<220> FEATURE:
<223> OTHER INFORMATION: oligonucleotide EgEloD4Mut-3

<400> SEQUENCE: 104
gctgtgtcaa gatcttcttc caagggcaac tgatgccaaa agttg                      45

<210> SEQ ID NO 105
<211> LENGTH: 5914
<212> TYPE: DNA
<213> ORGANISM: Artificial Sequence
<220> FEATURE:
<223> OTHER INFORMATION: plasmid pLF115-7

<400> SEQUENCE: 105
ttgtaatacg actcactata gggcgaattg ggccctctag atgcatgctc gagcggccgc      60
cagtgtgatg gatatctgca gaattcaggg cggccgcacc atggcggata gcccagtcat     120
caacctcagc accatgtgga aaccccttc  actgatggct ttggaccttg ccgtttgggg     180
acatgtctgg aagcaggcac aacaggaggg cagcatttcg gcctatgctg attctgtttg     240
gactcctctc attatgtccg gtttatactt atcaatgatc ttcgtggggt gccgctggat     300
gaagaaccgt gaaccctttg agatcaaaac atacatgttt gcgtataacc tgtatcagac     360
cttgatgaac ctttgcatcg tgttgggatt cttgtaccag gtgcatgcca ctgggatgcg     420
cttttgggga agtggtgtcg accgaagccc aaaaggtttg gcattggct  tcttcattta     480
```

```
tgcccactac cacaacaagt atgtggaata ttttgataca cttttttatgg tgctgcgaaa    540
gaagaacaac cagatttctt tccttcacgt gtatcatcat gccctgttga catgggcttg    600
gtttgctgtt gtgtatttcg cacctggagg tgatggctgg tttggagctt gctacaattc    660
ttccatccat gtcctgatgt actcttacta cttgcttgca acttttggca tcagttgccc    720
ttggaagaag atcttgacac agctccagat ggttcaattc tgtttctgtt ttacacattc    780
catttatgtg tggatttgcg ggtcagagat ctacccacgg cctctgactg ctttgcagtc    840
gttcgtgatg gtcaatatgt tggtgctgtt tggcaatttc tatgtcaagc aatactccca    900
aaagaacggc aagccggaga acggagccac ccctgagaac ggagcgaagc cgcaaccttg    960
cgagaacggc acggtggaaa agcgagagaa tgacaccgcc aacgttcggc ccgcccgtcc   1020
agctggactc ccgccggcca cgtactacga ctccctggca gtgtcggggc agggcaagga   1080
gcggctgttc accaccgatg aggtgaggcg gcacatcctc cccaccgatg gctggctgac   1140
gtgccacgaa ggagtctacg atgtcactga tttccttgcc aagcacctg gtggcggtgt    1200
catcacgctg ggccttggaa gggactgcac aatcctcgtc gagtcatacc accctgctgg   1260
gcgcccggac aaggtgatgg agaagtaccg cattggtacg ctgcaggacc caagacgtt    1320
ctatgcttgg ggagagtccg atttctaccc tgagttgaag cgccgggccc ttgcaaggct   1380
gaaggaggct ggtcaggcgc ggcgcggcgg ccttggggtg aaggccctcc tggtgctcac   1440
cctcttcttc gtgtcgtggt acatgtgggt ggcccacaag tccttcctct gggccgccgt   1500
ctggggcttc gccggctccc acgtcgggct gagcatccag cacgacggca accacgcgc   1560
gttcagccgc agcacactgg tgaaccgcct ggcggggtgg ggcatggact tgatcggcgc   1620
gtcgtcaacg gtgtgggagt accagcacgt catcggccac caccagtaca ccaacctcgt   1680
gtcggacacg ctattcagtc tgcctgagaa cgatccggac gtcttctcca gctacccgct   1740
gatgcgcatg cacccggata cggcgtggca gccgcaccac cgcttccagc acctgttcgc   1800
gttcccactg ttcgccctga tgacaatcag caaggtgctg accagcgatt cgctgtctg    1860
cctcagcatg aagaagggt ccatcgactg ctcctccagg ctcgtcccac tggagggggca   1920
gctgctgttc tgggggggcca agctggcgaa cttcctgttg cagattgtgt tgccatgcta   1980
cctccacggg acagctatgg gcctggccct cttctctgtt gcccaccttg tgtcgggggga   2040
gtacctcgcg atctgcttca tcatcaacca catcagcgag tcttgtgagt ttatgaatac   2100
aagctttcaa accgccgccc ggaggacaga gatgcttcag gcagcccatc aggcagcgga   2160
ggccaagaag gtgaagccca cccctccacc gaacgattgg gctgtgacac aggtccaatg   2220
ctgcgtgaat tggagatcag gtggcgtgtt ggccaatcac ctctctggag gcttgaacca   2280
ccagatcgag catcatctgt tccccagcat ctcgcatgcc aactaccca tcatcgcccg    2340
tgttgtgaag gaggtgtgcg aggagtatgg gttgccgtac aagaactacg tcacgttctg   2400
ggatgcagtc tgtggcatgg ttcagcacct ccggttgatg ggtgctccac cggtgccaac   2460
gaacggggac aaaaagtcat aagcggccgc acctgaattc cagcacactg gcggccgtta   2520
ctagtggatc cgagctcggt accaagcttg atgcatagct tgagtattct aacgcgtcac   2580
ctaaatagct tggcgtaatc atggtcatag ctgtttcctg tgtgaaattg ttatccgctc   2640
acaattccac acaacatacg agccggaagc ataaagtgta aagcctgggg tgcctaatga   2700
gtgagctaac tcacattaat tgcgttgcgc tcactgcccg ctttccagtc gggaaacctg   2760
tcgtgccagc tgcattaatg aatcggccaa cgcgcgggga gaggcggttt gcgtattggg   2820
cgctcttccg cttcctcgct cactgactcg ctgcgctcgg tcgttcggct gcggcgagcg   2880
```

```
gtatcagctc actcaaaggc ggtaatacgg ttatccacag aatcagggga taacgcagga    2940
aagaacatgt gagcaaaagg ccagcaaaag gccaggaacc gtaaaaaggc cgcgttgctg    3000
gcgttttttcc ataggctccg ccccctgac gagcatcaca aaaatcgacg ctcaagtcag    3060
aggtggcgaa acccgacagg actataaaga taccaggcgt ttccccctgg aagctccctc    3120
gtgcgctctc ctgttccgac cctgccgctt accggatacc tgtccgcctt tctcccttcg    3180
ggaagcgtgg cgctttctca tagctcacgc tgtaggtatc tcagttcggt gtaggtcgtt    3240
cgctccaagc tgggctgtgt gcacgaaccc cccgttcagc ccgaccgctg cgccttatcc    3300
ggtaactatc gtcttgagtc aacccggta agacacgact tatcgccact ggcagcagcc    3360
actggtaaca ggattagcag agcgaggtat gtaggcggtg ctacagagtt cttgaagtgg    3420
tggcctaact acggctacac tagaagaaca gtatttggta tctgcgctct gctgaagcca    3480
gttaccttcg gaaaaagagt tggtagctct tgatccggca aacaaaccac cgctggtagc    3540
ggtggttttt ttgtttgcaa gcagcagatt acgcgcagaa aaaaggatc tcaagaagat    3600
cctttgatct tttctacggg gtctgacgct cagtggaacg aaaactcacg ttaagggatt    3660
ttggtcatga gattatcaaa aaggatcttc acctagatcc ttttaaatta aaaatgaagt    3720
tttagcacgt gtcagtcctg ctcctcggcc acgaagtgca cgcagttgcc ggccgggtcg    3780
cgcagggcga actcccgccc ccacggctgc tcgccgatct cggtcatggc cggcccggag    3840
gcgtcccgga agttcgtgga cacgacctcc gaccactcgg cgtacagctc gtccaggccg    3900
cgcacccaca cccaggccag ggtgttgtcc ggcaccacct ggtcctggac cgcgctgatg    3960
aacagggtca cgtcgtcccg gaccacaccg gcgaagtcgt cctccacgaa gtcccgggag    4020
aacccgagcc ggtcggtcca gaactcgacc gctccggcga cgtcgcgcgc ggtgagcacc    4080
ggaacggcac tggtcaactt ggccatggtg gccctcctca cgtgctatta ttgaagcatt    4140
tatcagggtt attgtctcat gagcggatac atatttgaat gtatttagaa aaataaacaa    4200
atagggggttc cgcgcacatt tccccgaaaa gtgccacctg atgcggtgtg aaataccgca    4260
cagatgcgta aggagaaaat accgcatcag gaaattgtaa gcgttaataa ttcagaagaa    4320
ctcgtcaaga aggcgataga aggcgatgcg ctgcgaatcg ggagcggcga taccgtaaag    4380
cacgaggaag cggtcagccc attcgccgcc aagctcttca gcaatatcac gggtagccaa    4440
cgctatgtcc tgatagcggt ccgccacacc cagccggcca cagtcgatga atccagaaaa    4500
gcggccattt tccaccatga tattcggcaa gcaggcatcg ccatgggtca cgacgagatc    4560
ctcgccgtcg gcatgctcg ccttgagcct ggcgaacagt tcggctggcg cgagcccctg    4620
atgctcttcg tccagatcat cctgatcgac aagaccggct tccatccgag tacgtgctcg    4680
ctcgatgcga tgtttcgctt ggtggtcgaa tgggcaggta gccggatcaa gcgtatgcag    4740
ccgccgcatt gcatcagcca tgatggatac tttctcggca ggagcaaggt gagatgacag    4800
gagatcctgc cccggcactt cgcccaatag cagccagtcc cttcccgctt cagtgacaac    4860
gtcgagcaca gctgcgcaag gaacgcccgt cgtggccagc cacgatagcc gcgctgcctc    4920
gtcttgcagt tcattcaggg caccggacag gtcggtcttg acaaaaagaa ccgggcgccc    4980
ctgcgctgac agccggaaca cggcggcatc agagcagccg attgtctgtt gtgcccagtc    5040
atagccgaat agcctctcca cccaagcggc cggagaacct gcgtgcaatc catcttgttc    5100
aatcatgcga aacgatcctc atcctgtctc ttgatcagag cttgatcccc tgcgccatca    5160
gatccttggc ggcaagaaag ccatccagtt tactttgcag gcttcccaa ccttaccaga    5220
gggcgcccca gctggcaatt ccggttcgct tgctgtccat aaaaccgccc agtctagcta    5280
```

```
tcgccatgta agcccactgc aagctacctg ctttctcttt gcgcttgcgt tttcccttgt   5340
ccagatagcc cagtagctga cattcatccg gggtcagcac cgtttctgcg gactggcttt   5400
ctacgtgaaa aggatctagg tgaagatcct ttttgataat ctcatgcctg acatttatat   5460
tccccagaac atcaggttaa tggcgttttt gatgtcattt tcgcggtggc tgagatcagc   5520
cacttcttcc ccgataacgg agaccggcac actggccata tcggtggtca tcatgcgcca   5580
gctttcatcc ccgatatgca ccaccgggta aagttcacgg gagactttat ctgacagcag   5640
acgtgcactg gccaggggga tcaccatccg tcgccccggc gtgtcaataa tatcactctg   5700
tacatccaca aacagacgat aacggctctc tcttttatag gtgtaaacct taaactgccg   5760
tacgtatagg ctgcgcaact gttgggaagg gcgatcggtg cgggcctctt cgctattacg   5820
ccagctggcg aaaggggggat gtgctgcaag gcgattaagt tgggtaacgc cagggttttc   5880
ccagtcacga cgttgtaaaa cgacggccag tgaa                               5914

<210> SEQ ID NO 106
<211> LENGTH: 2379
<212> TYPE: DNA
<213> ORGANISM: Euglena gracilis
<220> FEATURE:
<221> NAME/KEY: misc_feature
<222> LOCATION: (1)..(2379)
<223> OTHER INFORMATION: EgDHAsyn1*

<400> SEQUENCE: 106
atggcggata gcccagtcat caacctcagc accatgtgga aacccctttc actgatggct     60
ttggaccttg ccgttttggg acatgtctgg aagcaggcac aacaggaggg cagcatttcg    120
gcctatgctg attctgtttg gactcctctc attatgtccg gtttatactt atcaatgatc    180
ttcgtggggt gccgctggat gaagaaccgt gaacccttgg agatcaaaac atacatgttt    240
gcgtataacc tgtatcagac cttgatgaac ctttgcatcg tgttgggatt cttgtaccag    300
gtgcatgcca ctgggatgcg cttttgggga agtggtgtcg accgaagccc aaaaggtttg    360
ggcattggct tcttcattta tgcccactac acaacaagt atgtggaata ttttgataca    420 cttttttatgg tgctgcgaaa gaagaacaac cagatttctt tccttcacgt gtatcatcat    480
gccctgttga catgggcttg gtttgctgtt gtgtatttcg cacctggagg tgatggctgg    540
tttggagctt gctacaattc ttccatccat gtcctgatgt actcttacta cttgcttgca    600
acttttggca tcagttgccc ttggaagaag atcttgacac agctccagat ggttcaattc    660
tgtttctgtt ttacacattc catttatgtg tggatttgcg ggtcagagat ctacccacgg    720
cctctgactg ctttgcagtc gttcgtgatg gtcaatatgt tggtgctgtt tggcaatttc    780
tatgtcaagc aatactccca aaagaacggc aagccggaga acggagccac ccctgagaac    840
ggagcgaagc cgcaaccttg cgagaacggc acggtgaaaa agcagagaa tgacaccgcc    900 aacgttcggc ccgcccgtcc agctggactc ccgccggcca cgtactacga ctccctggca    960
gtgtcggggc agggcaagga gcggctgttc accaccgatg aggtgaggcg gcacatcctc   1020
cccaccgatg gctggctgac cgtgccacgaa ggagtctacg atgtcactga tttccttgcc   1080
aagcaccctg gtggcggtgt catcacgctg ggccttggaa gggactgcac aatcctcgtc   1140
gagtcatacc accctgctgg gcgcccggac aaggtgatgg agaagtaccg cattggtacg   1200
ctgcaggacc ccaagacgtt ctatgcttgg ggagagtccg atttctaccc tgagttgaag   1260
cgccgggccc ttgcaaggct gaaggaggct ggtcaggcgc ggcgcggcgg ccttggggtg   1320 aaggcccctcc tggtgctcac cctcttcttc gtgtcgtggt acatgtgggt ggcccacaag   1380
```

```
tccttcctct gggccgccgt ctggggcttc gccggctccc acgtcgggct gagcatccag    1440
cacgacggca accacggcgc gttcagccgc agcacactgg tgaaccgcct ggcggggtgg    1500
ggcatggact tgatcggcgc gtcgtcaacg gtgtgggagt accagcacgt catcggccac    1560
caccagtaca ccaacctcgt gtcggacacg ctattcagtc tgcctgagaa cgatccggac    1620
gtcttctcca gctacccgct gatgcgcatg cacccggata cggcgtggca gccgcaccac    1680
cgcttccagc acctgttcgc gttcccactg ttcgccctga tgacaatcag caaggtgctg    1740
accagcgatt tcgctgtctg cctcagcatg aagaaggggt ccatcgactg ctcctccagg    1800
ctcgtcccac tggaggggca gctgctgttc tgggggggcca gctggcgaaa cttcctgttg    1860
cagattgtgt tgccatgcta cctccacggg acagctatgg gcctggccct cttctctgtt    1920
gcccaccttg tgtcggggga gtacctcgcg atctgcttca tcatcaacca catcagcgag    1980
tcttgtgagt ttatgaatac aagctttcaa accgccgccc ggaggacaga gatgcttcag    2040
gcagcccatc aggcagcgga ggccaagaag gtgaagccca cccctccacc gaacgattgg    2100
gctgtgacac aggtccaatg ctgcgtgaat tggagatcag gtggcgtgtt ggccaatcac    2160
ctctctggag gcttgaacca ccagatcgag catcatctgt tccccagcat ctcgcatgcc    2220
aactacccca tcatcgcccg tgttgtgaag gaggtgtgcg aggagtatgg gttgccgtac    2280
aagaactacg tcacgttctg ggatgcagtc tgtggcatgg ttcagcacct ccggttgatg    2340
ggtgctccac cggtgccaac gaacggggac aaaaagtca                          2379

<210> SEQ ID NO 107
<211> LENGTH: 7783
<212> TYPE: DNA
<213> ORGANISM: Artificial Sequence
<220> FEATURE:
<223> OTHER INFORMATION: plasmid pY115

<400> SEQUENCE: 107
catggctctg ccaacgacg ctggcgagcg aatctgggct gccgtcaccg atcccgaaat      60
cctcattggc accttctcct acctgctcct gaagcctctc ctgcgaaact ctggtctcgt     120
ggacgagaag aaaggagcct accgaacctc catgatctgg tacaacgtcc tcctggctct     180
cttctctgcc ctgtccttct acgtgactgc caccgctctc ggctgggact acggtactgg     240
agcctggctg cgaagacaga ccggtgatac tccccagcct ctctttcagt gtccctctcc     300
tgtctgggac tccaagctgt tcacctggac tgccaaggcc ttctactatt ctaagtacgt     360
ggagtacctc gacaccgctt ggctggtcct caagggcaag cgagtgtcct ttctgcaggc     420
cttccatcac tttggagctc cctgggacgt ctacctcggc attgactgc acaacgaggg     480 tgtgtggatc ttcatgttct ttaactcgtt cattcacacc atcatgtaca cctactatgg     540
actgactgcc gctggctaca gttcaaggc caagcctctg atcactgcca tgcagatttg     600
ccagttcgtc ggtggctttc tcctggtctg ggactacatc aacgttccct gcttcaactc     660
tgacaagggc aagctgttct cctgggcttt caactacgcc tacgtcggat ctgtctttct     720
cctgttctgt cacttctttt accaggacaa cctggccacc aagaaatccg ctaaggctgg     780
taagcagctt tagcggccgc aagtgtggat ggggaagtga gtgcccggtt ctgtgtgcac     840
aattggcaat ccaagatgga tggattcaac acagggatat agcgagctac gtggtggtgc     900
gaggatatag caacggatat ttatgtttga cacttgagaa tgtacgatac aagcactgtc     960
caagtacaat actaaacata ctgtacatac tcatactcgt acccgggcaa cggtttcact    1020
tgagtgcagt ggctagtgct cttactcgta cagtgtgcaa tactgcgtat catagtcttt    1080
```

```
gatgtatatc gtattcattc atgttagttg cgtacgagcc ggaagcataa agtgtaaagc   1140
ctggggtgcc taatgagtga gctaactcac attaattgcg ttgcgctcac tgcccgcttt   1200
ccagtcggga aacctgtcgt gccagctgca ttaatgaatc ggccaacgcg cggggagagg   1260
cggtttgcgt attgggcgct cttccgcttc ctcgctcact gactcgctgc gctcggtcgt   1320
tcggctgcgg cgagcggtat cagctcactc aaaggcggta atacggttat ccacagaatc   1380
aggggataac gcaggaaaga acatgtgagc aaaaggccag caaaaggcca ggaaccgtaa   1440
aaaggccgcg ttgctggcgt ttttccatag gctccgcccc cctgacgagc atcacaaaaa   1500
tcgacgctca agtcagaggt ggcgaaaccc gacaggacta taaagatacc aggcgtttcc   1560
ccctggaagc tccctcgtgc gctctcctgt tccgaccctg ccgcttaccg gatacctgtc   1620
cgcctttctc ccttcgggaa gcgtggcgct ttctcatagc tcacgctgta ggtatctcag   1680
ttcggtgtag gtcgttcgct ccaagctggg ctgtgtgcac gaaccccccg ttcagcccga   1740
ccgctgcgcc ttatccggta actatcgtct tgagtccaac ccggtaagac acgacttatc   1800
gccactggca gcagccactg gtaacaggat tagcagagcg aggtatgtag gcggtgctac   1860
agagttcttg aagtggtggc ctaactacgg ctacactaga aggacagtat ttggtatctg   1920
cgctctgctg aagccagtta ccttcggaaa aagagttggt agctcttgat ccggcaaaca   1980
aaccaccgct ggtagcggtg gtttttttgt ttgcaagcag cagattacgc gcagaaaaaa   2040
aggatctcaa gaagatcctt tgatcttttc tacggggtct gacgctcagt ggaacgaaaa   2100
ctcacgttaa gggattttgg tcatgagatt atcaaaaagg atcttcacct agatcctttt   2160
aaattaaaaa tgaagtttta aatcaatcta agtatatat gagtaaactt ggtctgacag   2220
ttaccaatgc ttaatcagtg aggcaccat ctcagcgatc tgtctatttc gttcatccat   2280
agttgcctga ctccccgtcg tgtagataac tacgatacgg gagggcttac catctggccc   2340
cagtgctgca atgataccgc gagacccacg ctcaccggct ccagatttat cagcaataaa   2400
ccagccagcc ggaagggccg agcgcagaag tggtcctgca actttatccg cctccatcca   2460
gtctattaat tgttgccggg aagctagagt aagtagttcg ccagttaata gtttgcgcaa   2520
cgttgttgcc attgctacag gcatcgtggt gtcacgctcg tcgtttggta tggcttcatt   2580
cagctccggt tcccaacgat caaggcgagt tacatgatcc cccatgttgt gcaaaaaagc   2640
ggttagctcc ttcggtcctc cgatcgttgt cagaagtaag ttggccgcag tgttatcact   2700
catggttatg gcagcactgc ataattctct tactgtcatg ccatccgtaa gatgcttttc   2760
tgtgactggt gagtactcaa ccaagtcatt ctgagaatag tgtatgcggc gaccgagttg   2820
ctcttgcccg gcgtcaatac gggataatac cgcgccacat agcagaactt taaaagtgct   2880
catcattgga aaacgttctt cggggcgaaa actctcaagg atcttaccgc tgttgagatc   2940
cagttcgatg taacccactc gtgcacccaa ctgatcttca gcatctttta ctttcaccag   3000
cgtttctggg tgagcaaaaa caggaaggca aaatgccgca aaaagggaa taaggcgac   3060 acggaaatgt tgaatactca tactcttcct ttttcaatat tattgaagca tttatcaggg   3120
ttattgtctc atgagcggat acatatttga atgtatttag aaaaataaac aaataggggt   3180
tccgcgcaca tttccccgaa aagtgccacc tgacgcgccc tgtagcggcg cattaagcgc   3240
ggcgggtgtg gtggttacgc gcagcgtgac cgctacactt gccagcgccc tagcgcccgc   3300
tcctttcgct ttcttccctt cctttctcgc cacgttcgcc ggctttcccc gtcaagctct   3360
aaatcggggg ctccctttag ggttccgatt tagtgcttta cggcacctcg accccaaaaa   3420
acttgattag ggtgatggtt cacgtagtgg gccatcgccc tgatagacgg ttttcgccc   3480
```

-continued

```
tttgacgttg gagtccacgt tctttaatag tggactcttg ttccaaactg gaacaacact   3540
caaccctatc tcggtctatt cttttgattt ataagggatt ttgccgattt cggcctattg   3600
gttaaaaaat gagctgattt aacaaaaatt taacgcgaat tttaacaaaa tattaacgct   3660
tacaatttcc attcgccatt caggctgcgc aactgttggg aagggcgatc ggtgcgggcc   3720
tcttcgctat tacgccagct ggcgaaaggg ggatgtgctg caaggcgatt aagttgggta   3780
acgccagggt tttcccagtc acgacgttgt aaaacgacgg ccagtgaatt gtaatacgac   3840
tcactatagg gcgaattggg taccgggccc cccctcgagg tcgatggtgt cgataagctt   3900
gatatcgaat tcatgtcaca caaaccgatc ttcgcctcaa ggaaacctaa ttctacatcc   3960
gagagactgc cgagatccag tctacactga ttaattttcg ggccaataat ttaaaaaaat   4020
cgtgttatat aatattatat gtattatata tatacatcat gatgatactg acagtcatgt   4080
cccattgcta aatagacaga ctccatctgc cgcctccaac tgatgttctc aatatttaag   4140
gggtcatctc gcattgttta ataataaaca gactccatct accgcctcca aatgatgttc   4200
tcaaaatata ttgtatgaac ttattttttat tacttagtat tattagacaa cttacttgct   4260
ttatgaaaaa cacttcctat ttaggaaaca atttataatg gcagttcgtt catttaacaa   4320
tttatgtaga ataaatgtta taaatgcgta tgggaaatct taaatatgga tagcataaat   4380
gatatctgca ttgcctaatt cgaaatcaac agcaacgaaa aaaatccctt gtacaacata   4440
aatagtcatc gagaaatatc aactatcaaa gaacagctat tcacacgtta ctattgagat   4500
tattattgga cgagaatcac acactcaact gtctttctct cttctagaaa tacaggtaca   4560
agtatgtact attctcattg ttcatacttc tagtcatttc atcccacata ttccttggat   4620
ttctctccaa tgaatgacat tctatcttgc aaattcaaca attataataa gatataccaa   4680
agtagcggta tagtggcaat caaaaagctt ctctggtgtg cttctcgtat ttatttttat   4740
tctaatgatc cattaaaggt atatatttat ttcttgttat ataatccttt tgtttattac   4800
atgggctgga tacataaagg tattttgatt taattttttg cttaaattca atcccccctc   4860
gttcagtgtc aactgtaatg gtaggaaatt accatacttt tgaagaagca aaaaaaatga   4920
aagaaaaaaa aaatcgtatt tccaggttag acgttccgca gaatctagaa tgcggtatgc   4980
ggtacattgt tcttcgaacg taaaagttgc gctccctgag atattgtaca ttttttgcttt   5040
tacaagtaca agtacatcgt acaactatgt actactgttg atgcatccac aacagtttgt   5100
tttgtttttt tttgtttttt tttttttctaa tgattcatta ccgctatgta tacctacttg   5160
tacttgtagt aagccgggtt attggcgttc aattaatcat agacttatga atctgcacgg   5220
tgtgcgctgc gagttacttt tagcttatgc atgctacttg ggtgtaatat tgggatctgt   5280
tcggaaatca acggatgctc aatcgatttc gacagtaatt aattaagtca tacacaagtc   5340
agctttcttc gagcctcata taagtataag tagttcaacg tattagcact gtacccagca   5400
tctccgtatc gagaaacaca acaacatgcc ccattggaca gatcatgcgg atacacaggt   5460
tgtgcagtat catacatact cgatcagaca ggtcgtctga ccatcataca agctgaacaa   5520
gcgctccata cttgcacgct ctctatatac acagttaaat tacatatcca tagtctaacc   5580
tctaacagtt aatcttctgg taagcctccc agccagcctt ctggtatcgc ttggcctcct   5640
caataggatc tcggttctgg ccgtacagac ctcggccgac aattatgata tccgttccgg   5700
tagacatgac atcctcaaca gttcggtact gctgtccgag agcgtctccc ttgtcgtcaa   5760
gacccacccc gggggtcaga ataagccagt cctcagagtc gcccttaggt cggttctggg   5820
caatgaagcc aaccacaaac tcggggtcgg atcgggcaag ctcaatggtc tgcttggagt   5880
```

```
actcgccagt ggccagagag cccttgcaag acagctcggc cagcatgagc agacctctgg    5940
ccagcttctc gttgggagag gggactagga actccttgta ctgggagttc tcgtagtcag    6000
agacgtcctc cttcttctgt tcagagacag tttcctcggc accagctcgc aggccagcaa    6060
tgattccggt tccgggtaca ccgtgggcgt tggtgatatc ggaccactcg gcgattcggt    6120
gacaccggta ctggtgcttg acagtgttgc caatatctgc gaactttctg tcctcgaaca    6180
ggaagaaacc gtgcttaaga gcaagttcct tgaggggggag cacagtgccg gcgtaggtga    6240
agtcgtcaat gatgtcgata tgggttttga tcatgcacac ataaggtccg accttatcgg    6300
caagctcaat gagctccttg gtggtggtaa catccagaga agcacacagg ttggttttct    6360
tggctgccac gagcttgagc actcgagcgg caaaggcgga cttgtggacg ttagctcgag    6420
cttcgtagga gggcattttg gtggtgaaga ggagactgaa ataaatttag tctgcagaac    6480
tttttatcgg aaccttatct ggggcagtga agtatatgtt atggtaatag ttacgagtta    6540
gttgaactta tagatagact ggactatacg gctatcggtc caaattagaa agaacgtcaa    6600
tggctctctg ggcgtcgcct ttgccgacaa aaatgtgatc atgatgaaag ccagcaatga    6660
cgttgcagct gatattgttg tcggccaacc gcgccgaaaa cgcagctgtc agacccacag    6720
cctccaacga agaatgtatc gtcaaagtga tccaagcaca ctcatagttg gagtcgtact    6780
ccaaaggcgg caatgacgag tcagacagat actcgtcgac gtttaaacag tgtacgcaga    6840
tctactatag aggaacattt aaattgcccc ggagaagacg gccaggccgc ctagatgaca    6900
aattcaacaa ctcacagctg actttctgcc attgccacta gggggggggcc ttttatatg    6960 gccaagccaa gctctccacg tcggttgggc tgcacccaac aataaatggg tagggttgca    7020
ccaacaaagg gatgggatgg ggggtagaag atacgaggat aacggggctc aatggcacaa    7080
ataagaacga atactgccat taagactcgt gatccagcga ctgacaccat tgcatcatct    7140
aagggcctca aaactacctc ggaactgctg cgctgatctg gacaccacag aggttccgag    7200
cactttaggt tgcaccaaat gtcccaccag gtgcaggcag aaaacgctgg aacagcgtgt    7260
acagtttgtc ttaacaaaaa gtgagggcgc tgaggtcgag cagggtggtg tgacttgtta    7320
tagcctttag agctgcgaaa gcgcgtatgg atttggctca tcaggccaga ttgagggtct    7380
gtggacacat gtcatgttag tgtacttcaa tcgcccctg gatatagccc cgacaatagg    7440
ccgtggcctc atttttttgc cttccgcaca tttccattgc tcgatacccca caccttgctt    7500 ctcctgcact tgccaacctt aatactggtt tacattgacc aacatcttac aagcgggggg    7560
cttgtctagg gtatatataa acagtggctc tcccaatcgg ttgccagtct cttttttcct    7620
ttctttcccc acagattcga aatctaaact acacatcaca gaattccgag ccgtgagtat    7680
ccacgacaag atcagtgtcg agacgacgcg ttttgtgtaa tgacacaatc cgaaagtcgc    7740
tagcaacaca cactctctac acaaactaac ccagctctgg tac                      7783
```

<210> SEQ ID NO 108
<211> LENGTH: 9373
<212> TYPE: DNA
<213> ORGANISM: Artificial Sequence
<220> FEATURE:
<223> OTHER INFORMATION: plasmid pY141

<400> SEQUENCE: 108

```
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
```

-continued

```
aacatactgt acatactcat actcgtaccc ggcaacggtt tcacttgagt gcagtggcta    240
gtgctcttac tcgtacagtg tgcaatactg cgtatcatag tctttgatgt atatcgtatt    300
cattcatgtt agttgcgtac gagccggaag cataaagtgt aaagcctggg gtgcctaatg    360
agtgagctaa ctcacattaa ttgcgttgcg ctcactgccc gctttccagt cgggaaacct    420
gtcgtgccag ctgcattaat gaatcggcca acgcgcgggg agaggcggtt tgcgtattgg    480
gcgctcttcc gcttcctcgc tcactgactc gctgcgctcg tcgttcggc tgcggcgagc     540
ggtatcagct cactcaaagg cggtaatacg gttatccaca gaatcagggg ataacgcagg    600
aaagaacatg tgagcaaaag gccagcaaaa ggccaggaac cgtaaaaagg ccgcgttgct    660
ggcgttttc cataggctcc gccccctga cgagcatcac aaaaatcgac gctcaagtca      720
gaggtggcga acccgacag gactataaag ataccaggcg tttccccctg gaagctccct     780
cgtgcgctct cctgttccga ccctgccgct taccggatac ctgtccgcct ttctcccttc    840
gggaagcgtg gcgctttctc atagctcacg ctgtaggtat ctcagttcgg tgtaggtcgt    900
tcgctccaag ctgggctgtg tgcacgaacc ccccgttcag cccgaccgct gcgccttatc    960
cggtaactat cgtcttgagt ccaacccggt aagacacgac ttatcgccac tggcagcagc   1020
cactggtaac aggattagca gagcgaggta tgtaggcggt gctacagagt tcttgaagtg   1080
gtggcctaac tacggctaca ctagaaggac agtatttggt atctgcgctc tgctgaagcc   1140
agttaccttc ggaaaaagag ttggtagctc ttgatccggc aaacaaacca ccgctggtag   1200
cggtggtttt tttgtttgca agcagcagat tacgcgcaga aaaaaggat ctcaagaaga    1260
tcctttgatc ttttctacgg ggtctgacgc tcagtggaac gaaaactcac gttaagggat   1320
tttggtcatg agattatcaa aaaggatctt cacctagatc cttttaaatt aaaaatgaag   1380
ttttaaatca atctaaagta tatatgagta aacttggtct gacagttacc aatgcttaat   1440
cagtgaggca cctatctcag cgatctgtct atttcgttca tccatagttg cctgactccc   1500
cgtcgtgtag ataactacga tacgggaggg cttaccatct ggccccagtg ctgcaatgat   1560
accgcgagac ccacgctcac cggctccaga tttatcagca ataaaccagc cagccggaag   1620
ggccgagcgc agaagtggtc ctgcaacttt atccgcctcc atccagtcta ttaattgttg   1680
ccgggaagct agagtaagta gttcgccagt taatagtttg cgcaacgttg ttgccattgc   1740
tacaggcatc gtggtgtcac gctcgtcgtt tggtatggct tcattcagct ccggttccca   1800
acgatcaagg cgagttacat gatcccccat gttgtgcaaa aaagcggtta gctccttcgg   1860
tcctccgatc gttgtcagaa gtaagttggc cgcagtgtta tcactcatgg ttatggcagc   1920
actgcataat tctcttactg tcatgccatc cgtaagatgc ttttctgtga ctggtgagta   1980
ctcaaccaag tcattctgag aatagtgtat gcggcgaccg agttgctctt gcccggcgtc   2040
aatacgggat aataccgcgc cacatagcag aactttaaaa gtgctcatca ttggaaaacg   2100
ttcttcgggg cgaaaactct caaggatctt accgctgttg agatccagtt cgatgtaacc   2160
cactcgtgca cccaactgat cttcagcatc ttttactttc accagcgttt ctgggtgagc   2220
aaaaacagga aggcaaaatg ccgcaaaaaa gggaataagg gcgacacgga aatgttgaat   2280
actcatactc ttcctttttc aatattattg aagcatttat cagggttatt gtctcatgag   2340
cggatacata tttgaatgta tttagaaaaa taaacaaata ggggttccgc gcacatttcc   2400
ccgaaaagtg ccacctgacg cgccctgtag cggcgcatta agcgcggcgg gtgtggtggt   2460
tacgcgcagc gtgaccgcta cacttgccag cgccctagcg cccgctcctt tcgctttctt   2520
cccttccttt ctcgccacgt tcgccggctt tccccgtcaa gctctaaatc gggggctccc   2580
```

```
tttagggttc cgatttagtg ctttacggca cctcgacccc aaaaaacttg attagggtga   2640
tggttcacgt agtgggccat cgccctgata gacggttttt cgcccttga cgttggagtc   2700 cacgttcttt aatagtggac tcttgttcca aactggaaca acactcaacc ctatctcggt   2760
ctattctttt gatttataag ggattttgcc gatttcggcc tattggttaa aaaatgagct   2820
gatttaacaa aaattaacg cgaattttaa caaaatatta acgcttacaa tttccattcg   2880
ccattcaggc tgcgcaactg ttgggaaggg cgatcggtgc gggcctcttc gctattacgc   2940
cagctggcga aaggggatg tgctgcaagg cgattaagtt gggtaacgcc agggttttcc   3000
cagtcacgac gttgtaaaac gacggccagt gaattgtaat acgactcact atagggcgaa   3060
ttgggtaccg ggcccccct cgaggtcgat ggtgtcgata agcttgatat cgaattcatg   3120
tcacacaaac cgatcttcgc ctcaaggaaa cctaattcta catccgagag actgccgaga   3180
tccagtctac actgattaat tttcgggcca ataatttaaa aaaatcgtgt tatataatat   3240
tatatgtatt atatatatac atcatgatga tactgacagt catgtcccat tgctaaatag   3300
acagactcca tctgccgcct ccaactgatg ttctcaatat ttaaggggtc atctcgcatt   3360
gtttaataat aaacagactc catctaccgc ctccaaatga tgttctcaaa atatattgta   3420
tgaacttatt tttattactt agtattatta gacaacttac ttgctttatg aaaaacactt   3480
cctatttagg aaacaattta taatggcagt tcgttcattt aacaatttat gtagaataaa   3540
tgttataaat gcgtatggga aatcttaaat atggatagca taaatgatat ctgcattgcc   3600
taattcgaaa tcaacagcaa cgaaaaaaat cccttgtaca acataaatag tcatcgagaa   3660
atatcaacta tcaaagaaca gctattcaca cgttactatt gagattatta ttggacgaga   3720
atcacacact caactgtctt tctctcttct agaaatacag gtacaagtat gtactattct   3780
cattgttcat acttctagtc atttcatccc acatattcct tggatttctc tccaatgaat   3840
gacattctat cttgcaaatt caacaattat aataagatat accaaagtag cggtatagtg   3900
gcaatcaaaa agcttctctg gtgtgcttct cgtatttatt tttattctaa tgatccatta   3960
aaggtatata tttatttctt gttatataat ccttttgttt attacatggg ctggatacat   4020
aaaggtattt tgatttaatt ttttgcttaa attcaatccc ccctcgttca gtgtcaactg   4080
taatggtagg aaattaccat actttttgaag aagcaaaaaa aatgaaagaa aaaaaaaatc   4140
gtatttccag gttagacgtt ccgcagaatc tagaatgcgg tatgcggtac attgttcttc   4200
gaacgtaaaa gttgcgctcc ctgagatatt gtacattttt gcttttacaa gtacaagtac   4260
atcgtacaac tatgtactac tgttgatgca tccacaacag tttgttttgt ttttttttgt   4320 ttttttttt tctaatgatt cattaccgct atgtatacct acttgtactt gtagtaagcc   4380
gggttattgg cgttcaatta atcatagact tatgaatctg cacggtgtgc gctgcgagtt   4440
acttttagct tatgcatgct acttgggtgt aatattggga tctgttcgga aatcaacgga   4500
tgctcaatcg atttcgacag taattaatta agtcatacac aagtcagctt cttcgagcc   4560 tcatataagt ataagtagtt caacgtatta gcactgtacc cagcatctcc gtatcgagaa   4620
acacaacaac atgccccatt ggacagatca tgcggataca caggttgtgc agtatcatac   4680
atactcgatc agacaggtcg tctgaccatc atacaagctg aacaagcgct ccatacttgc   4740
acgctctcta tatacacagt taaattacat atccatagtc taacctctaa cagttaatct   4800
tctggtaagc ctcccagcca gccttctggt atcgcttggc ctcctcaata ggatctcggt   4860
tctggccgta cagacctcgg ccgacaatta tgatatccgt tccggtagac atgacatcct   4920
caacagttcg gtactgctgt ccgagagcgt ctcccttgtc gtcaagaccc accccggggg   4980
```

```
tcagaataag ccagtcctca gagtcgccct taggtcggtt ctgggcaatg aagccaacca    5040
caaactcggg gtcggatcgg gcaagctcaa tggtctgctt ggagtactcg ccagtggcca    5100
gagagccctt gcaagacagc tcggccagca tgagcagacc tctggccagc ttctcgttgg    5160
gagagsggac taggaactcc ttgtactggg agttctcgta gtcagagacg tcctccttct    5220
tctgttcaga gacagtttcc tcggcaccag ctcgcaggcc agcaatgatt ccggttccgg    5280
gtacaccgtg ggcgttggtg atatcggacc actcggcgat tcggtgacac cggtactggt    5340
gcttgacagt gttgccaata tctgcgaact ttctgtcctc gaacaggaag aaaccgtgct    5400
taagagcaag ttccttgagg gggagcacag tgccggcgta ggtgaagtcg tcaatgatgt    5460
cgatatgggt tttgatcatg cacacataag gtccgacctt atcggcaagc tcaatgagct    5520
ccttggtggt ggtaacatcc agagaagcac acaggttggt tttcttggct gccacgagct    5580
tgagcactcg agcggcaaag gcggacttgt ggacgttagc tcgagcttcg taggagggca    5640
ttttggtggt gaagaggaga ctgaaataaa tttagtctgc agaactttt atcggaacct    5700 tatctggggc agtgaagtat atgttatggt aatagttacg agttagttga acttatagat    5760
agactggact atacggctat cggtccaaat tagaaagaac gtcaatggct ctctgggcgt    5820 cgccttgcc gacaaaaatg tgatcatgat gaaagccagc aatgacgttg cagctgatat    5880
tgttgtcggc caaccgcgcc gaaaacgcag ctgtcagacc cacagcctcc aacgaagaat    5940
gtatcgtcaa agtgatccaa gcacactcat agttggagtc gtactccaaa ggcggcaatg    6000
acgagtcaga cagatactcg tcgacgttta acagtgtac gcagatctac tatagaggaa    6060
catttaaatt gccccggaga agacggccag gccgcctaga tgacaaattc aacaactcac    6120
agctgacttt ctgccattgc cactaggggg gggcctttt atatggccaa gccaagctct    6180
ccacgtcggt tgggctgcac ccaacaataa atgggtaggg ttgcaccaac aaagggatgg    6240 gatgggggt agaagatacg aggataacgg ggctcaatgg cacaaataag aacgaatact    6300
gccattaaga ctcgtgatcc agcgactgac accattgcat catctaaggg cctcaaaact    6360
acctcggaac tgctgcgctg atctggacac cacagaggtt ccgagcactt taggttgcac    6420
caaatgtccc accaggtgca ggcagaaaac gctggaacag cgtgtacagt ttgtcttaac    6480
aaaaagtgag ggcgctgagg tcgagcaggg tggtgtgact tgttatagcc tttagagctg    6540
cgaaagcgcg tatggatttg gctcatcagg ccagattgag ggtctgtgga cacatgtcat    6600
gttagtgtac ttcaatcgcc ccctggatat agccccgaca ataggccgtg gcctcatttt    6660
tttgccttcc gcacatttcc attgctcgat acccacacct tgcttctcct gcacttgcca    6720
accttaatac tggtttacat tgaccaacat cttacaagcg gggggcttgt ctagggtata    6780
tataaacagt ggctctccca atcggttgcc agtctctttt ttccttcctt tccccacaga    6840
ttcgaaatct aaactacaca tcacagaatt ccgagccgtg agtatccacg acaagatcag    6900
tgtcgagacg acgcgttttg tgtaatgaca caatccgaaa gtcgctagca acacacactc    6960
tctacacaaa ctaacccagc tctggtacca tggcggatag cccagtcatc aacctcagca    7020
ccatgtggaa acccctttca ctgatggctt tggaccttgc cgttttggga catgtctgga    7080
agcaggcaca acaggagggc agcatttcgg cctatgctga ttctgtttgg actcctctca    7140
ttatgtccgg tttatactta tcaatgatct tcgtggggtg ccgctggatg aagaaccgtg    7200
aaccctttga gatcaaaaca tacatgtttg cgtataacct gtatcagacc ttgatgaacc    7260
tttgcatcgt gttgggattc ttgtaccagg tgcatgccac tgggatgcgc ttttggggaa    7320
gtggtgtcga ccgaagccca aaaggtttgg gcattggctt cttcatttat gcccactacc    7380
```

```
acaacaagta tgtggaatat tttgatacac tttttatggt gctgcgaaag aagaacaacc    7440
agatttcttt ccttcacgtg tatcatcatg ccctgttgac atgggcttgg tttgctgttg    7500
tgtatttcgc acctggaggt gatggctggt ttggagcttg ctacaattct tccatccatg    7560
tcctgatgta ctcttactac ttgcttgcaa cttttggcat cagttgccct tggaagaaga    7620
tcttgacaca gctccagatg gttcaattct gtttctgttt tacacattcc atttatgtgt    7680
ggatttgcgg gtcagagatc tacccacggc ctctgactgc tttgcagtcg ttcgtgatgg    7740
tcaatatgtt ggtgctgttt ggcaatttct atgtcaagca atactcccaa aagaacggca    7800
agccggagaa cggagccacc cctgagaacg gagcgaagcc gcaaccttgc gagaacggca    7860
cggtggaaaa gcgagagaat gacaccgcca acgttcggcc cgcccgtcca gctggactcc    7920
cgccggccac gtactacgac tccctggcag tgtcggggca gggcaaggag cggctgttca    7980
ccaccgatga ggtgaggcgg cacatcctcc ccaccgatgg ctggctgacg tgccacgaag    8040
gagtctacga tgtcactgat ttccttgcca agcaccctgg tggcggtgtc atcacgctgg    8100
gccttggaag ggactgcaca atcctcgtcg agtcatacca ccctgctggg cgcccggaca    8160
aggtgatgga agagtaccgc attggtacgc tgcaggaccc caagacgttc tatgcttggg    8220
gagagtccga tttctaccct gagttgaagc gccgggccct tgcaaggctg aaggaggctg    8280
gtcaggcgcg gcgcggcggc cttggggtga aggccctcct ggtgctcacc ctcttcttcg    8340
tgtcgtggta catgtgggtg gcccacaagt ccttcctctg ggccgccgtc tggggcttcg    8400
ccggctccca cgtcgggctg agcatccagc acgacggcaa ccacggcgcg ttcagccgca    8460
gcacactggt gaaccgcctg gcggggtggg gcatggactt gatcggcgcg tcgtcaacgg    8520
tgtgggagta ccagcacgtc atcggccacc accagtacac caacctcgtg tcggacacgc    8580
tattcagtct gcctgagaac gatccggacg tcttctccag ctacccgctg atgcgcatgc    8640
acccggatac ggcgtggcag ccgcaccacc gcttccagca cctgttcgcg ttcccactgt    8700
tcgccctgat gacaatcagc aaggtgctga ccagcgattt cgctgtctgc ctcagcatga    8760
agaaggggtc catcgactgc tcctccaggc tcgtcccact ggaggggcag ctgctgttct    8820 gggggggccaa gctggcgaac ttcctgttgc agattgtgtt gccatgctac ctccacggga    8880
cagctatggg cctggccctc ttctctgttg cccaccttgt gtcggggggag tacctcgcga    8940 tctgcttcat catcaaccac atcagcgagt cttgtgagtt tatgaataca agcttttcaaa    9000 ccgccgcccg gaggacagag atgcttcagg cagcccatca ggcagcggag gccaagaagg    9060
tgaagcccac ccctccaccg aacgattggg ctgtgacaca ggtccaatgc tgcgtgaatt    9120
ggagatcagg tggcgtgttg gccaatcacc tctctggagg cttgaaccac cagatcgagc    9180
atcatctgtt ccccagcatc tcgcatgcca actacccccat catcgcccgt gttgtgaagg    9240
aggtgtgcga ggagtatggg ttgccgtaca agaactacgt cacgttctgg gatgcagtct    9300
gtggcatggt tcagcacctc cggttgatgg gtgctccacc ggtgccaacg aacggggaca    9360
aaaagtcata agc                                                       9373
```

<210> SEQ ID NO 109
<211> LENGTH: 22
<212> TYPE: DNA
<213> ORGANISM: Artificial Sequence
<220> FEATURE:
<223> OTHER INFORMATION: primer M13-28Rev

<400> SEQUENCE: 109
gtaatacgac tcactatagg gc      22

<210> SEQ ID NO 110
<211> LENGTH: 21
<212> TYPE: DNA
<213> ORGANISM: Artificial Sequence
<220> FEATURE:
<223> OTHER INFORMATION: oligonucleotide EaDHAsyn5'

<400> SEQUENCE: 110
gttgcagatg gtgcaattct g                                    21

<210> SEQ ID NO 111
<211> LENGTH: 20
<212> TYPE: DNA
<213> ORGANISM: Artificial Sequence
<220> FEATURE:
<223> OTHER INFORMATION: oligonucleotide EaDHAsyn5'2

<400> SEQUENCE: 111
cagcctacta cgatgccctg                                      20

<210> SEQ ID NO 112
<211> LENGTH: 20
<212> TYPE: DNA
<213> ORGANISM: Artificial Sequence
<220> FEATURE:
<223> OTHER INFORMATION: oligonucleotide EaDHAsyn5'3

<400> SEQUENCE: 112
gacgtcttcg gcacctatcc                                      20

<210> SEQ ID NO 113
<211> LENGTH: 21
<212> TYPE: DNA
<213> ORGANISM: Artificial Sequence
<220> FEATURE:
<223> OTHER INFORMATION: oligonucleotide EaDHAsyn5'4

<400> SEQUENCE: 113
ggaatggtgg agcacctcag g                                    21

<210> SEQ ID NO 114
<211> LENGTH: 20
<212> TYPE: DNA
<213> ORGANISM: Artificial Sequence
<220> FEATURE:
<223> OTHER INFORMATION: oligonucleotide EaDHAsyn3'

<400> SEQUENCE: 114
ctgaggtgct ccaccattcc                                      20

<210> SEQ ID NO 115
<211> LENGTH: 22
<212> TYPE: DNA
<213> ORGANISM: Artificial Sequence
<220> FEATURE:
<223> OTHER INFORMATION: oligonucleotide EaDHAsyn3'2

<400> SEQUENCE: 115
gagatgtggt tgatgatgaa gc                                   22

<210> SEQ ID NO 116
<211> LENGTH: 20
<212> TYPE: DNA
<213> ORGANISM: Artificial Sequence
<220> FEATURE:
<223> OTHER INFORMATION: oligonucleotide EaDHAsyn3'3

```
<400> SEQUENCE: 116
gacgtgctgg tactcccagg                                                     20

<210> SEQ ID NO 117
<211> LENGTH: 20
<212> TYPE: DNA
<213> ORGANISM: Artificial Sequence
<220> FEATURE:
<223> OTHER INFORMATION: oligonucleotide EaDHAsyn3'4

<400> SEQUENCE: 117
ctcccgcatg gtgaacttgc                                                     20

<210> SEQ ID NO 118
<211> LENGTH: 22
<212> TYPE: DNA
<213> ORGANISM: Artificial Sequence
<220> FEATURE:
<223> OTHER INFORMATION: oligonucleotide EaDHAsyn3'5

<400> SEQUENCE: 118
gaacaacgtg tcgacatact cc                                                  22

<210> SEQ ID NO 119
<211> LENGTH: 5607
<212> TYPE: DNA
<213> ORGANISM: Artificial Sequence
<220> FEATURE:
<223> OTHER INFORMATION: plasmid pLF117-2

<400> SEQUENCE: 119
gtacaaagtt ggcattataa gaaagcattg cttatcaatt tgttgcaacg aacaggtcac         60
tatcagtcaa aataaaatca ttatttgcca tccagctgat atccctata gtgagtcgta        120 ttacatggtc atagctgttt cctggcagct ctggcccgtg tctcaaaatc tctgatgtta       180
cattgcacaa gataaaaata tatcatcatg ttagaaaaac tcatcgagca tcaaatgaaa       240
ctgcaattta ttcatatcag gattatcaat accatatttt tgaaaaagcc gtttctgtaa       300
tgaaggagaa aactcaccga ggcagttcca taggatggca agatcctggt atcggtctgc       360
gattccgact cgtccaacat caatacaacc tattaatttc ccctcgtcaa aaataaggtt       420
atcaagtgag aaatcaccat gagtgacgac tgaatccggt gagaatggca aaagcttatg       480
catttctttc cagacttgtt caacaggcca gccattacgc tcgtcatcaa atcactcgc        540 atcaaccaaa ccgttattca ttcgtgattg cgcctgagcg agacgaaata cgcgatcgct       600
gttaaaagga caattacaaa caggaatcga atgcaaccgg cgcaggaaca ctgccagcgc       660
atcaacaata ttttcacctg aatcaggata ttcttctaat acctggaatg ctgttttccc       720
ggggatcgca gtggtgagta accatgcatc atcaggagta cggataaaat gcttgatggt       780
cggaagaggc ataaattccg tcagccagtt tagtctgacc atctcatctg taacatcatt       840
ggcaacgcta cctttgccat gtttcagaaa caactctggc gcatcgggct tcccatacaa       900
tcgatagatt gtcgcacctg attgcccgac attatcgcga gcccatttat acccatataa       960
atcagcatcc atgttggaat ttaatcgcgg cctcgagcaa gacgtttccc gttgaatatg      1020
gctcatagat cttttctcca tcactgatag ggagtggtaa aataactcca tcaatgatag      1080
agtgtcaaca acatgaccaa aatcccttaa cgtgagttac gcgtattaat tgcgttgcgc      1140
tcactgcccg ctttccagtc gggaaacctg tcgtgccagc tgcattaatg aatcggccaa      1200
cgcgcgggga gaggcggttt gcgtattggg cgctcttccg cttcctcgct cactgactcg      1260
```

| | | |
|---|---|---|
| ctgcgctcgg tcgttcggct gcggcgagcg gtatcagctc actcaaaggc ggtaatacgg | 1320 |
| ttatccacag aatcagggga taacgcagga agaacatgt gagcaaaagg ccagcaaaag | 1380 |
| gccaggaacc gtaaaaaggc cgcgttgctg gcgttttcc ataggctccg ccccctgac | 1440 |
| gagcatcaca aaaatcgacg ctcaagtcag aggtggcgaa acccgacagg actataaaga | 1500 |
| taccaggcgt ttccccctgg aagctccctc gtgcgctctc ctgttccgac cctgccgctt | 1560 |
| accggatacc tgtccgcctt tctcccttcg ggaagcgtgg cgctttctca atgctcacgc | 1620 |
| tgtaggtatc tcagttcggt gtaggtcgtt cgctccaagc tgggctgtgt gcacgaaccc | 1680 |
| cccgttcagc ccgaccgctg cgccttatcc ggtaactatc gtcttgagtc caacccggta | 1740 |
| agacacgact tatcgccact ggcagcagcc actggtaaca ggattagcag agcgaggtat | 1800 |
| gtaggcggtg ctacagagtt cttgaagtgg tggcctaact acggttacac tagaagaaca | 1860 |
| gtatttggta tctgcgctct gctgaagcca gttaccttcg gaaaaagagt tggtagctct | 1920 |
| tgatccggca aacaaaccac cgctggtagc ggtggttttt ttgtttgcaa gcagcagatt | 1980 |
| acgcgcagaa aaaaggatc tcaagaagat cctttgatct tttctacggg gtctgacgct | 2040 |
| cagggaacga cgcgtaccgc tagccaggaa gagtttgtag aaacgcaaaa aggccatccg | 2100 |
| tcaggatggc cttctgctta gtttgatgcc tggcagttta tggcgggcgt cctgcccgcc | 2160 |
| accctccggg ccgttgcttc acaacgttca aatccgctcc cggcggattt gtcctactca | 2220 |
| ggagagcgtt caccgacaaa caacagataa acgaaaggc ccagtcttcc gactgagcct | 2280 |
| ttcgttttat ttgatgcctg gcagttccct actctcgcgt taacgctagc atggatgttt | 2340 |
| tcccagtcac gacgttgtaa aacgacggcc agtcttaagc tcgggcccca aataatgatt | 2400 |
| ttattttgac tgatagtgac ctgttcgttg caacaaattg atgagcaatg cttttttata | 2460 |
| atgccaactt tgtacaaaaa agttggattt ttttcggtc tccatggccg aaggcaagag | 2520 |
| cgatgggcct gtggtgaccc ttcaaagcat gtggaaaccg cttgctctga tggcaataga | 2580 |
| tgtcggcata ttggtcaatg tccgccgcaa ggctttcact gagtttgatg ggcacagcaa | 2640 |
| cgttttcgca gatccagttt acattccatt tgtgatgaat ctcttctact tgaccatgat | 2700 |
| ctttgctggg tgccgttgga tgaagactcg cgaacccttt gagatcaagt catatatgtt | 2760 |
| tgcatacaat gcatatcaga caatgatgaa cttcctcatt gtcgtcgggt tcatgtatga | 2820 |
| ggtgcacagc acagggatgc gatattgggg gtccaggatc gacacctcca ccaagggctt | 2880 |
| gggcctcggt ttcctgatct atgcccacta ccacaacaaa tacgtggagt atgtcgacac | 2940 |
| gttgttcatg atcctgcgca agaaaaacaa ccagatctcg ttcctccacg tctaccacca | 3000 |
| ttcgcttttg acttgggcct ggtgggccgt ggtctactgg gccccaggag gagatgcctg | 3060 |
| gttcggagca tgctacaatt ccttcatcca cgtgctgatg tactcctact acctgtttgc | 3120 |
| aacgtttggc atcaggtgcc cctggaagaa gatgctgacc cagttgcaga tggtgcaatt | 3180 |
| ctgcttctgc tttgcccacg cgatgtatgt tggatggctg ggccatgaag tctacccgcg | 3240 |
| ctggttgacg gcgctacagg catttgtgat gctaaacatg ctggtgctgt tcggcaactt | 3300 |
| ctacatgaag tcgtactcca aggccagcaa gctggagccg gcctcccccg tgtccccgc | 3360 |
| ctccctcgcc cagaagccgt tcgagaacgc caaggtgaag cctggggggcc ccggcaagcc | 3420 |
| aagcgagatt gcgtcgctgc caccgccaat tcgaccagtc gggaacccac ctgcagccta | 3480 |
| ctacgatgcc ctggcgacct cgggcaccgg gcaggaccgc aagttcacca tgcgggaggt | 3540 |
| ggcccgccat attgtgccga ccgatggtgt gttggcgtgc catgacgtg tctacgacat | 3600 |
| caccgagttc ataggaaac atcctggcgg cgatgttatt tctctcggat tgggcaggga | 3660 |

```
ctccacaatc ctggttgagt cgtaccaccc tgccggaagg ccagacaagg tcatggaaaa    3720
gtaccgcatc gggacgctcc aggaccaccg cacgttctac gactggcagg cctccgcgtt    3780
ctacgccgag ctgaagcagc gggtggtgca gacgctaaag gaggccggcc aaccgcggcg    3840
tgggggcctg tcggtcaaag cggcgctggt catggcggcg ttcgcagcgt cgttctacct    3900
catggtgacc cagggatcct tcttctgggc cgccgtctgg ggcctcgccg gctcccacat    3960
tggcctcagc atccagcacg acgggaacca cggggctttc agtaagagtg gtcggctgaa    4020
ccgcctcgcg ggctggggca tggacgtcat cggggcctcc tcgacggcct gggagtacca    4080
gcacgtcatc gggcaccacc agtacaccaa cctggtatcg gatcccgagt tcgcgctgcc    4140
tgagaacgac ccggacgtct tcggcaccta tccgctgatg cggatgcatc cggacacccc    4200
ttggaagccg caccaccagc tgcagcatgt gtacgcgttc ccgctgttcg ccctgatgac    4260
catcagcaag gtcatcatca gcgacttcac gttctgcctc gccaagcggc gcgggccgat    4320
cgacttctcc gccaggctcg tgccacttga ggggcagatg ctcttctggg gggcgaagat    4380
catggggttc ctgatgcaga tagtcctgcc gtgctatctg catggcatcg cccatgggct    4440
ggcgctgttc atcacagccc acctggtgtc gggagagtac ctcgcggtct gcttcatcat    4500
caaccacatc tctgagtcat gcgactattt gaatccaagt tccgtcatcg ctgcgcggag    4560
gacgaaaatg ctgaagcagg cggagcagga ggccaaggca aagcagaagc accccacccc    4620
accgcccaac gactgggccg cgtctcaggt actgtgctgc gtaaactggc gctctggtgg    4680
ctatttctca aacccctct caggcgggct gaaccaccag atcgagcacc acctcttccc    4740
cagcatctca catgcgaact atccgaccat tgccccagtt gtgaaagggg tgtgcgagga    4800
gtacggcctc ccctacaaga actactccca gttctccgac gctctctatg gaatggtgga    4860
gcacctcagg gcgatgggca cgaagccggc agacaacgac aagctggcgc ccaccgcggg    4920
ctccctggag gacgtgtgcc cggtcttgag cgccgccgtt gctgcccaac tgacggaag    4980 caccgacggc agcgctgcgg gttgtccagc agtagccaca ctggcataaa gggcataatg    5040
agcatgccat catcactaga cgacgttgct caccttgttt tccatttgtg ccgtgccttg    5100
cggcccgtgt tctccatttg cgggcactag attcggtacc cagccctcct cacagctctg    5160
cgatttgagc cgtttggggc aacgctccgc tgacccttgt gcaggtcccc cgaccatccg    5220
ctccgaggaa tgcggtaaaa caaaacaaat aacaacagca tgaggcgtca atctctgcga    5280
tatgcggggc ttgctccagc tcacctggac cacttcgtcc gctgcgcagc tatagttttg    5340
ggccgcagct aggtctgcgg ttacttcctt ttttttctcc ggcgcagggc gcttggttct    5400 aagccttttcc tccaatcctc gagccccctc gacctgaccg tgtcttcctc tggctgaaag    5460
cggaggatga tttgtgcgtt gctcagaagg aacctccatc ggtggtggtt ttcgcatttc    5520
ccattgatgt ccaacagtgc tgccattcag tttgacctgc aaaaaaaaaa aaaaaaaaa     5580 aaaaaaaaa aaaacccaa ctttctt                                          5607
```

<210> SEQ ID NO 120
<211> LENGTH: 2523
<212> TYPE: DNA
<213> ORGANISM: Euglena anabaena

<400> SEQUENCE: 120

```
atggccgaag gcaagagcga tgggcctgtg gtgacccttc aaagcatgtg gaaaccgctt      60
gctctgatgg caatagatgt cggcatattg gtcaatgtcc gccgcaaggc tttcactgag     120
tttgatgggc acagcaacgt tttcgcagat ccagtttaca ttccatttgt gatgaatctc     180
```

-continued

```
ttctacttga ccatgatctt tgctgggtgc cgttggatga agactcgcga acccttt gag    240
atcaagtcat atatgtttgc atacaatgca tatcagacaa tgatgaactt cctcattgtc    300
gtcgggttca tgtatgaggt gcacagcaca gggatgcgat attgggggtc caggatcgac    360
acctccacca agggcttggg cctcggtttc ctgatctatg cccactacca caacaaatac    420
gtggagtatg tcgacacgtt gttcatgatc ctgcgcaaga aaacaaccca gatctcgttc    480
ctccacgtct accaccattc gcttttgact tgggcctggt gggccgtggt ctactgggcc    540
ccaggaggag atgcctggtt cggagcatgc tacaattcct tcatccacgt gctgatgtac    600
tcctactacc tgtttgcaac gtttggcatc aggtgcccct ggaagaagat gctgacccag    660
ttgcagatgg tgcaattctg cttctgcttt gcccacgcga tgtatgttgg atggctgggc    720
catgaagtct acccgcgctg gttgacggcg ctacaggcat ttgtgatgct aaacatgctg    780
gtgctgttcg gcaacttcta catgaagtcg tactccaagg ccagcaagct ggagccggcc    840
tcccccgtgt cccccgcctc cctcgcccag aagccgttcg agaacgccaa ggtgaagcct    900
gggggccccg gcaagccaag cgagattgcg tcgctgccac cgccaattcg accagtcggg    960
aacccacctg cagcctacta cgatgccctg gcgacctcgg gcaccgggca ggaccgcaag    1020
ttcaccatgc gggaggtggc ccgccatatt gtgccgaccg atgggtggtt ggcgtgccat    1080
gacggtgtct acgacatcac cgagttcata gggaaacatc ctggcggcga tgttatttct    1140
ctcggattgg gcagggactc cacaatcctg gttgagtcgt accaccctgc cggaaggcca    1200
gacaaggtca tggaaaagta ccgcatcggg acgctccagg accaccgcac gttctacgac    1260
tggcaggcct ccgcgttcta cgccgagctg aagcagcggg tggtgcagac gctaaaggag    1320
gccgccaac cgcggcgtgg gggcctgtcg gtcaaagcgg cgctggtcat ggcggcgttc    1380
gcagcgtcgt tctacctcat ggtgacccag ggatccttct tctgggccgc cgtctggggc    1440
ctcgccggct cccacattgg cctcagcatc cagcacgacg ggaaccacgg ggctttcagt    1500
aagagtggtc ggctgaaccg cctcgcgggc tggggcatgg acgtcatcgg ggcctcctcg    1560
acggcctggg agtaccagca cgtcatcggg caccaccagt acaccaacct ggtatcggat    1620
cccgagttcg cgctgcctga gaacgacccg gacgtcttcg gcacctatcc gctgatgcgg    1680
atgcatccgg acacccttg gaagccgcac caccagctgc agcatgtgta cgcgttcccg    1740
ctgttcgccc tgatgaccat cagcaaggtc atcatcagcg acttcacgtt ctgcctcgcc    1800
aagcggcgcg gccgatcga cttctccgcc aggctcgtgc cacttgaggg gcagatgctc    1860
ttctgggggg cgaagatcat ggggttcctg atgcagatag tcctgccgtg ctatctgcat    1920
ggcatcgccc atgggctggc gctgttcatc acagcccacc tggtgtcggg agagtacctc    1980
gcggtctgct tcatcatcaa ccacatctct gagtcatgcg actatttgaa tccaagttcc    2040
gtcatcgctg cgcggaggac ggaaatgctg aagcaggcgg agcaggaggc caaggcaaag    2100
cagaagcacc ccacccca gcccaacgac tgggccgcgt ctcaggtact gtgctgcgta    2160
aactggcgct ctggtggcta tttctcaaac cacctctcag gcgggctgaa ccaccagatc    2220
gagcaccacc tcttccccag catctcacat gcgaactatc cgaccattgc cccagttgtg    2280
aaagggggtgt gcgaggagta cggcctcccc tacaagaact actcccagtt ctccgacgct    2340
ctctatggaa tggtggagca cctcaggcg atgggcacga agccggcaga caacgacaag    2400
ctggcgccca ccgcgggctc cctggaggac gtgtgcccgg tcttgagcgc cgccgttgct    2460
gcccaacctg acggaagcac cgacggcagc gctgcgggtt gtccagcagt agccacactg    2520
gca                                                                  2523
```

```
<210> SEQ ID NO 121
<211> LENGTH: 841
<212> TYPE: PRT
<213> ORGANISM: Euglena anabaena

<400> SEQUENCE: 121

Met Ala Glu Gly Lys Ser Asp Gly Pro Val Val Thr Leu Gln Ser Met
1               5                   10                  15

Trp Lys Pro Leu Ala Leu Met Ala Ile Asp Val Gly Ile Leu Val Asn
            20                  25                  30

Val Arg Arg Lys Ala Phe Thr Glu Phe Asp Gly His Ser Asn Val Phe
        35                  40                  45

Ala Asp Pro Val Tyr Ile Pro Phe Val Met Asn Leu Phe Tyr Leu Thr
    50                  55                  60

Met Ile Phe Ala Gly Cys Arg Trp Met Lys Thr Arg Glu Pro Phe Glu
65                  70                  75                  80

Ile Lys Ser Tyr Met Phe Ala Tyr Asn Ala Tyr Gln Thr Met Met Asn
                85                  90                  95

Phe Leu Ile Val Val Gly Phe Met Tyr Glu Val His Ser Thr Gly Met
            100                 105                 110

Arg Tyr Trp Gly Ser Arg Ile Asp Thr Ser Thr Lys Gly Leu Gly Leu
        115                 120                 125

Gly Phe Leu Ile Tyr Ala His Tyr His Asn Lys Tyr Val Glu Tyr Val
    130                 135                 140

Asp Thr Leu Phe Met Ile Leu Arg Lys Lys Asn Asn Gln Ile Ser Phe
145                 150                 155                 160

Leu His Val Tyr His His Ser Leu Leu Thr Trp Ala Trp Trp Ala Val
                165                 170                 175

Val Tyr Trp Ala Pro Gly Gly Asp Ala Trp Phe Gly Ala Cys Tyr Asn
            180                 185                 190

Ser Phe Ile His Val Leu Met Tyr Ser Tyr Tyr Leu Phe Ala Thr Phe
        195                 200                 205

Gly Ile Arg Cys Pro Trp Lys Lys Met Leu Thr Gln Leu Gln Met Val
    210                 215                 220

Gln Phe Cys Phe Cys Phe Ala His Ala Met Tyr Val Gly Trp Leu Gly
225                 230                 235                 240

His Glu Val Tyr Pro Arg Trp Leu Thr Ala Leu Gln Ala Phe Val Met
                245                 250                 255

Leu Asn Met Leu Val Leu Phe Gly Asn Phe Tyr Met Lys Ser Tyr Ser
            260                 265                 270

Lys Ala Ser Lys Leu Glu Pro Ala Ser Pro Val Ser Pro Ala Ser Leu
        275                 280                 285

Ala Gln Lys Pro Phe Glu Asn Ala Lys Val Lys Pro Gly Gly Pro Gly
    290                 295                 300

Lys Pro Ser Glu Ile Ala Ser Leu Pro Pro Ile Arg Pro Val Gly
305                 310                 315                 320

Asn Pro Pro Ala Ala Tyr Tyr Asp Ala Leu Ala Thr Ser Gly Thr Gly
                325                 330                 335

Gln Asp Arg Lys Phe Thr Met Arg Glu Val Ala Arg His Ile Val Pro
            340                 345                 350

Thr Asp Gly Trp Leu Ala Cys His Asp Gly Val Tyr Asp Ile Thr Glu
        355                 360                 365

Phe Ile Gly Lys His Pro Gly Gly Asp Val Ile Ser Leu Gly Leu Gly
    370                 375                 380
```

```
Arg Asp Ser Thr Ile Leu Val Glu Ser Tyr His Pro Ala Gly Arg Pro
385                 390                 395                 400

Asp Lys Val Met Glu Lys Tyr Arg Ile Gly Thr Leu Gln Asp His Arg
                405                 410                 415

Thr Phe Tyr Asp Trp Gln Ala Ser Ala Phe Tyr Ala Glu Leu Lys Gln
            420                 425                 430

Arg Val Val Gln Thr Leu Lys Glu Ala Gly Pro Arg Arg Gly Gly
        435                 440                 445

Leu Ser Val Lys Ala Ala Leu Val Met Ala Ala Phe Ala Ala Ser Phe
450                 455                 460

Tyr Leu Met Val Thr Gln Gly Ser Phe Phe Trp Ala Ala Val Trp Gly
465                 470                 475                 480

Leu Ala Gly Ser His Ile Gly Leu Ser Ile Gln His Asp Gly Asn His
                485                 490                 495

Gly Ala Phe Ser Lys Ser Gly Arg Leu Asn Arg Leu Ala Gly Trp Gly
            500                 505                 510

Met Asp Val Ile Gly Ala Ser Ser Thr Ala Trp Glu Tyr Gln His Val
        515                 520                 525

Ile Gly His His Gln Tyr Thr Asn Leu Val Ser Asp Pro Glu Phe Ala
530                 535                 540

Leu Pro Glu Asn Asp Pro Asp Val Phe Gly Thr Tyr Pro Leu Met Arg
545                 550                 555                 560

Met His Pro Asp Thr Pro Trp Lys Pro His His Gln Leu Gln His Val
                565                 570                 575

Tyr Ala Phe Pro Leu Phe Ala Leu Met Thr Ile Ser Lys Val Ile Ile
            580                 585                 590

Ser Asp Phe Thr Phe Cys Leu Ala Lys Arg Arg Gly Pro Ile Asp Phe
        595                 600                 605

Ser Ala Arg Leu Val Pro Leu Glu Gly Gln Met Leu Phe Trp Gly Ala
610                 615                 620

Lys Ile Met Gly Phe Leu Met Gln Ile Val Leu Pro Cys Tyr Leu His
625                 630                 635                 640

Gly Ile Ala His Gly Leu Ala Leu Phe Ile Thr Ala His Leu Val Ser
                645                 650                 655

Gly Glu Tyr Leu Ala Val Cys Phe Ile Ile Asn His Ile Ser Glu Ser
            660                 665                 670

Cys Asp Tyr Leu Asn Pro Ser Ser Val Ile Ala Ala Arg Arg Thr Glu
        675                 680                 685

Met Leu Lys Gln Ala Glu Gln Glu Ala Lys Ala Lys Gln Lys His Pro
690                 695                 700

Thr Pro Pro Asn Asp Trp Ala Ala Ser Gln Val Leu Cys Cys Val
705                 710                 715                 720

Asn Trp Arg Ser Gly Gly Tyr Phe Ser Asn His Leu Ser Gly Gly Leu
                725                 730                 735

Asn His Gln Ile Glu His His Leu Phe Pro Ser Ile Ser His Ala Asn
            740                 745                 750

Tyr Pro Thr Ile Ala Pro Val Val Lys Gly Val Cys Glu Glu Tyr Gly
        755                 760                 765

Leu Pro Tyr Lys Asn Tyr Ser Gln Phe Ser Asp Ala Leu Tyr Gly Met
770                 775                 780

Val Glu His Leu Arg Ala Met Gly Thr Lys Pro Ala Asp Asn Asp Lys
785                 790                 795                 800

Leu Ala Pro Thr Ala Gly Ser Leu Glu Asp Val Cys Pro Val Leu Ser
```

```
                   805                 810                 815
Ala Ala Val Ala Ala Gln Pro Asp Gly Ser Thr Asp Gly Ser Ala Ala
            820                 825                 830

Gly Cys Pro Ala Val Ala Thr Leu Ala
        835                 840
```

<210> SEQ ID NO 122
<211> LENGTH: 19
<212> TYPE: DNA
<213> ORGANISM: Artificial Sequence
<220> FEATURE:
<223> OTHER INFORMATION: primer oYFBA1

<400> SEQUENCE: 122

| acgcagatct actatagag | 19 |
|---|---|

<210> SEQ ID NO 123
<211> LENGTH: 27
<212> TYPE: DNA
<213> ORGANISM: Artificial Sequence
<220> FEATURE:
<223> OTHER INFORMATION: primer oYFBA1-6

<400> SEQUENCE: 123

| agcggccgct ggtaccagag ctgggtt | 27 |
|---|---|

<210> SEQ ID NO 124
<211> LENGTH: 6992
<212> TYPE: DNA
<213> ORGANISM: Artificial Sequence
<220> FEATURE:
<223> OTHER INFORMATION: plasmid pY158

<400> SEQUENCE: 124

| ggccgcaagt gtggatgggg aagtgagtgc ccggttctgt gtgcacaatt ggcaatccaa | 60 |
|---|---|
| gatggatgga ttcaacacag ggatatagcg agctacgtgg tggtgcgagg atatagcaac | 120 |
| ggatatttat gtttgacact tgagaatgta cgatacaagc actgtccaag tacaatacta | 180 |
| aacatactgt acatactcat actcgtaccc ggcaacggtt tcacttgagt gcagtggcta | 240 |
| gtgctcttac tcgtacagtg tgcaatactg cgtatcatag tctttgatgt atatcgtatt | 300 |
| cattcatgtt agttgcgtac gagccggaag cataaagtgt aaagcctggg gtgcctaatg | 360 |
| agtgagctaa ctcacattaa ttgcgttgcg ctcactgccc gctttccagt cgggaaacct | 420 |
| gtcgtgccag ctgcattaat gaatcggcca acgcgcgggg agaggcggtt tgcgtattgg | 480 |
| gcgctcttcc gcttcctcgc tcactgactc gctgcgctcg tcgttcggc tgcggcgagc | 540 |
| ggtatcagct cactcaaagg cggtaatacg gttatccaca gaatcagggg ataacgcagg | 600 |
| aaagaacatg tgagcaaaag gccagcaaaa ggccaggaac cgtaaaaagg ccgcgttgct | 660 |
| ggcgttttc cataggctcc gcccccctga cgagcatcac aaaaatcgac gctcaagtca | 720 |
| gaggtggcga aacccgacag gactataaag ataccaggcg tttccccctg gaagctccct | 780 |
| cgtgcgctct cctgttccga ccctgccgct taccggatac ctgtccgcct ttctcccttc | 840 |
| gggaagcgtg gcgctttctc atagctcacg ctgtaggtat ctcagttcgg tgtaggtcgt | 900 |
| tcgctccaag ctgggctgtg tgcacgaacc ccccgttcag cccgaccgct gcgccttatc | 960 |
| cggtaactat cgtcttgagt ccaacccggt aagacacgac ttatcgccac tggcagcagc | 1020 |
| cactggtaac aggattagca gagcgaggta tgtaggcggt gctacagagt tcttgaagtg | 1080 |
| gtggcctaac tacggctaca ctagaaggac agtatttggt atctgcgctc tgctgaagcc | 1140 |

```
agttaccttc ggaaaaagag ttggtagctc ttgatccggc aaacaaacca ccgctggtag    1200
cggtggtttt tttgtttgca agcagcagat tacgcgcaga aaaaaaggat ctcaagaaga    1260
tcctttgatc ttttctacgg ggtctgacgc tcagtggaac gaaaactcac gttaagggat    1320
tttggtcatg agattatcaa aaaggatctt cacctagatc cttttaaatt aaaaatgaag    1380
ttttaaatca atctaaagta tatatgagta aacttggtct gacagttacc aatgcttaat    1440
cagtgaggca cctatctcag cgatctgtct atttcgttca tccatagttg cctgactccc    1500
cgtcgtgtag ataactacga tacgggaggg cttaccatct ggccccagtg ctgcaatgat    1560
accgcgagac ccacgctcac cggctccaga tttatcagca ataaaccagc cagccggaag    1620
ggccgagcgc agaagtggtc ctgcaacttt atccgcctcc atccagtcta ttaattgttg    1680
ccgggaagct agagtaagta gttcgccagt taatagtttg cgcaacgttg ttgccattgc    1740
tacaggcatc gtggtgtcac gctcgtcgtt tggtatggct tcattcagct ccggttccca    1800
acgatcaagg cgagttacat gatcccccat gttgtgcaaa aaagcggtta gctccttcgg    1860
tcctccgatc gttgtcagaa gtaagttggc cgcagtgtta tcactcatgg ttatggcagc    1920
actgcataat tctcttactg tcatgccatc cgtaagatgc ttttctgtga ctggtgagta    1980
ctcaaccaag tcattctgag aatagtgtat gcggcgaccg agttgctctt gcccggcgtc    2040
aatacgggat aataccgcgc cacatagcag aactttaaaa gtgctcatca ttggaaaacg    2100
ttcttcgggg cgaaaactct caaggatctt accgctgttg agatccagtt cgatgtaacc    2160
cactcgtgca cccaactgat cttcagcatc ttttactttc accagcgttt ctgggtgagc    2220
aaaaacagga aggcaaaatg ccgcaaaaaa gggaataagg gcgacacgga aatgttgaat    2280
actcatactc ttcctttttc aatattattg aagcatttat cagggttatt gtctcatgag    2340
cggatacata tttgaatgta tttagaaaaa taaacaaata ggggttccgc gcacatttcc    2400
ccgaaaagtg ccacctgacg cgccctgtag cggcgcatta agcgcggcgg gtgtggtggt    2460
tacgcgcagc gtgaccgcta cacttgccag cgccctagcg cccgctcctt tcgctttctt    2520
cccttccttt ctcgccacgt tcgccggctt tccccgtcaa gctctaaatc ggggggctccc    2580 tttagggttc cgatttagtg ctttacggca cctcgacccc aaaaaacttg attagggtga    2640
tggttcacgt agtgggccat cgccctgata cggtttttt cgcccttga cgttggagtc    2700 cacgttcttt aatagtggac tcttgttcca aactggaaca acactcaacc ctatctcggt    2760
ctattctttt gatttataag ggattttgcc gatttcggcc tattggttaa aaaatgagct    2820
gatttaacaa aaatttaacg cgaattttaa caaaatatta acgcttacaa tttccattcg    2880
ccattcaggc tgcgcaactg ttgggaaggg cgatcggtgc gggcctcttc gctattacgc    2940
cagctggcga aagggggatg tgctgcaagg cgattaagtt gggtaacgcc agggttttcc    3000
cagtcacgac gttgtaaaac gacggccagt gaattgtaat acgactcact atagggcgaa    3060
ttgggtaccg ggccccccct cgaggtcgat ggtgtcgata agcttgatat cgaattcatg    3120
tcacacaaac cgatcttcgc ctcaaggaaa cctaattcta catccgagag actgccgaga    3180
tccagtctac actgattaat tttcgggcca ataatttaaa aaaatcgtgt tatataatat    3240
tatatgtatt atatatatac atcatgatga tactgacagt catgtcccat tgctaaatag    3300
acagactcca tctgccgcct ccaactgatg ttctcaatat ttaagggtc atctcgcatt    3360 gtttaataat aaacagactc catctaccgc ctccaaatga tgttctcaaa atatattgta    3420
tgaacttatt tttattactt agtattatta gacaacttac ttgctttatg aaaaacactt    3480
cctatttagg aaacaattta taatggcagt tcgttcattt aacaattttat gtagaataaa    3540
```

-continued

```
tgttataaat gcgtatggga aatcttaaat atggatagca taaatgatat ctgcattgcc    3600
taattcgaaa tcaacagcaa cgaaaaaaat cccttgtaca acataaatag tcatcgagaa    3660
atatcaacta tcaaagaaca gctattcaca cgttactatt gagattatta ttggacgaga    3720
atcacacact caactgtctt tctctcttct agaaatacag gtacaagtat gtactattct    3780
cattgttcat acttctagtc atttcatccc acatattcct tggatttctc tccaatgaat    3840
gacattctat cttgcaaatt caacaattat aataagatat accaaagtag cggtatagtg    3900
gcaatcaaaa agcttctctg gtgtgcttct cgtatttatt tttattctaa tgatccatta    3960
aaggtatata tttatttctt gttatataat ccttttgttt attacatggg ctggatacat    4020
aaaggtattt tgatttaatt ttttgcttaa attcaatccc ccctcgttca gtgtcaactg    4080
taatggtagg aaattaccat acttttgaag aagcaaaaaa aatgaaagaa aaaaaaaatc    4140
gtatttccag gttagacgtt ccgcagaatc tagaatgcgg tatgcggtac attgttcttc    4200
gaacgtaaaa gttgcgctcc ctgagatatt gtacattttt gcttttacaa gtacaagtac    4260
atcgtacaac tatgtactac tgttgatgca tccacaacag tttgttttgt tttttttgt     4320 tttttttttt tctaatgatt cattaccgct atgtatacct acttgtactt gtagtaagcc    4380
gggttattgg cgttcaatta atcatagact tatgaatctg cacggtgtgc gctgcgagtt    4440
acttttagct tatgcatgct acttgggtgt aatattggga tctgttcgga atcaacgga     4500 tgctcaatcg atttcgacag taattaatta agtcatacac aagtcagctt cttcgagcc     4560 tcatataagt ataagtagtt caacgtatta gcactgtacc cagcatctcc gtatcgagaa    4620
acacaacaac atgccccatt ggacagatca tgcggataca caggttgtgc agtatcatac    4680
atactcgatc agacaggtcg tctgaccatc atacaagctg aacaagcgct ccatacttgc    4740
acgctctcta tatacacagt taaattacat atccatagtc taacctctaa cagttaatct    4800
tctggtaagc ctcccagcca gccttctggt atcgcttggc ctcctcaata ggatctcggt    4860
tctggccgta cagacctcgg ccgacaatta tgatatccgt tccggtagac atgacatcct    4920
caacagttcg gtactgctgt ccgagagcgt ctcccttgtc gtcaagaccc accccggggg    4980
tcagaataag ccagtcctca gagtcgccct taggtcggtt ctgggcaatg aagccaacca    5040
caaactcggg gtcggatcgg gcaagctcaa tggtctgctt ggagtactcg ccagtggcca    5100 gagagcccctt gcaagacagc tcggccagca tgagcagacc tctggccagc ttctcgttgg    5160
gagaggggac taggaactcc ttgtactggg agttctcgta gtcagagacg tcctccttct    5220
tctgttcaga gacagtttcc tcggcaccag ctcgcaggcc agcaatgatt ccggttccgg    5280
gtacaccgtg ggcgttggtg atatcggacc actcggcgat tcggtgacac cggtactggt    5340
gcttgacagt gttgccaata tctgcgaact ttctgtcctc gaacaggaag aaaccgtgct    5400
taagagcaag ttccttgagg gggagcacag tgccggcgta ggtgaagtcg tcaatgatgt    5460
cgatatgggt tttgatcatg cacacataag gtccgacctt atcggcaagc tcaatgagct    5520
ccttggtggt ggtaacatcc agagaagcac acaggttggt tttcttggct gccacgagct    5580
tgagcactcg agcggcaaag gcggacttgt ggacgttagc tcgagcttcg taggagggca    5640
ttttggtggt gaagaggaga ctgaaataaa tttagtctgc agaactttt atcggaacct     5700 tatctggggc agtgaagtat atgttatggt aatagttacg agttagttga acttatagat    5760
agactggact atacggctat cggtccaaat tagaaagaac gtcaatggct ctctgggcgt    5820
cgcctttgcc gacaaaaatg tgatcatgat gaaagccagc aatgacgttg cagctgatat    5880
tgttgtcggc caaccgcgcc gaaaacgcag ctgtcagacc cacagcctcc aacgaagaat    5940
```

```
gtatcgtcaa agtgatccaa gcacactcat agttggagtc gtactccaaa ggcggcaatg    6000
acgagtcaga cagatactcg tcgacgttta acagtgtac gcagatctac tatagaggaa    6060
catttaaatt gccccggaga agacggccag gccgcctaga tgacaaattc aacaactcac    6120
agctgacttt ctgccattgc cactaggggg gggccttttt atatggccaa gccaagctct    6180
ccacgtcggt tgggctgcac ccaacaataa atgggtaggg ttgcaccaac aaagggatgg    6240 gatgggggt agaagatacg aggataacgg ggctcaatgg cacaaataag aacgaatact    6300
gccattaaga ctcgtgatcc agcgactgac accattgcat catctaaggg cctcaaaact    6360
acctcggaac tgctgcgctg atctggacac cacagaggtt ccgagcactt taggttgcac    6420
caaatgtccc accaggtgca ggcagaaaac gctggaacag cgtgtacagt ttgtcttagc    6480
aaaaagtgaa ggcgctgagg tcgagcaggg tggtgtgact tgtttatagcc tttagagctg    6540 cgaaagcgcg tatggatttg gctcatcagg ccagattgag ggtctgtgga cacatgtcat    6600
gttagtgtac ttcaatcgcc ccctggatat agccccgaca ataggccgtg gcctcatttt    6660
tttgccttcc gcacatttcc attgctcgat acccacacct tgcttctcct gcacttgcca    6720
accttaatac tggtttacat tgaccaacat cttacaagcg gggggcttgt ctagggtata    6780
tataaacagt ggctctccca atcggttgcc agtctctttt ttccttctt tccccacaga    6840 ttcgaaatct aaactacaca tcacagaatt ccgagccgtg agtatccacg acaagatcag    6900
tgtcgagacg acgcgttttg tgtaatgaca caatccgaaa gtcgctagca acacacactc    6960
tctacacaaa ctaacccagc tctggtacca gc                                  6992

<210> SEQ ID NO 125
<211> LENGTH: 8707
<212> TYPE: DNA
<213> ORGANISM: Artificial Sequence
<220> FEATURE:
<223> OTHER INFORMATION: plasmid pY159

<400> SEQUENCE: 125
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
aacatactgt acatactcat actcgtaccc ggcaacggtt tcacttgagt gcagtggcta     240
gtgctcttac tcgtacagtg tgcaatactg cgtatcatag tctttgatgt atatcgtatt     300
cattcatgtt agttgcgtac gagccggaag cataaagtgt aaagcctggg gtgcctaatg     360
agtgagctaa ctcacattaa ttgcgttgcg ctcactgccc gctttccagt cgggaaacct     420
gtcgtgccag ctgcattaat gaatcggcca acgcgcgggg agaggcggtt tgcgtattgg     480
gcgctcttcc gcttcctcgc tcactgactc gctgcgctcg tcgttcggc tgcggcgagc     540 ggtatcagct cactcaaagg cggtaatacg gttatccaca gaatcagggg ataacgcagg     600
aaagaacatg tgagcaaaag gccagcaaaa ggccaggaac cgtaaaaagg ccgcgttgct     660
ggcgtttttc cataggctcc gcccccctga cgagcatcac aaaaatcgac gctcaagtca     720
gaggtggcga aacccgacag gactataaag ataccaggcg tttccccctg gaagctccct     780
cgtgcgctct cctgttccga ccctgccgct taccggatac ctgtccgcct ttctcccttc     840
gggaagcgtg gcgctttctc atagctcacg ctgtaggtat ctcagttcgg tgtaggtcgt     900
tcgctccaag ctgggctgtg tgcacgaacc cccgttcag cccgaccgct gcgccttatc     960
cggtaactat cgtcttgagt ccaacccggt aagacacgac ttatcgccac tggcagcagc    1020
```

```
cactggtaac aggattagca gagcgaggta tgtaggcggt gctacagagt tcttgaagtg   1080
gtggcctaac tacggctaca ctagaaggac agtatttggt atctgcgctc tgctgaagcc   1140
agttaccttc ggaaaaagag ttggtagctc ttgatccggc aaacaaacca ccgctggtag   1200
cggtggtttt tttgtttgca agcagcagat tacgcgcaga aaaaaggat ctcaagaaga    1260 tcctttgatc ttttctacgg ggtctgacgc tcagtggaac gaaaactcac gttaagggat   1320
tttggtcatg agattatcaa aaaggatctt cacctagatc cttttaaatt aaaaatgaag   1380
ttttaaatca atctaaagta tatatgagta aacttggtct gacagttacc aatgcttaat   1440
cagtgaggca cctatctcag cgatctgtct atttcgttca tccatagttg cctgactccc   1500
cgtcgtgtag ataactacga tacgggaggg cttaccatct ggccccagtg ctgcaatgat   1560
accgcgagac ccacgctcac cggctccaga tttatcagca ataaaccagc cagccggaag   1620
ggccgagcgc agaagtggtc ctgcaacttt atccgcctcc atccagtcta ttaattgttg   1680
ccgggaagct agagtaagta gttcgccagt taatagtttg cgcaacgttg ttgccattgc   1740
tacaggcatc gtggtgtcac gctcgtcgtt tggtatggct tcattcagct ccggttccca   1800
acgatcaagg cgagttacat gatcccccat gttgtgcaaa aaagcggtta gctccttcgg   1860
tcctccgatc gttgtcagaa gtaagttggc cgcagtgtta tcactcatgg ttatggcagc   1920
actgcataat tctcttactg tcatgccatc cgtaagatgc ttttctgtga ctggtgagta   1980
ctcaaccaag tcattctgag aatagtgtat gcggcgaccg agttgctctt gcccggcgtc   2040
aatacgggat aataccgcgc cacatagcag aactttaaaa gtgctcatca ttggaaaacg   2100
ttcttcgggg cgaaaactct caaggatctt accgctgttg agatccagtt cgatgtaacc   2160
cactcgtgca cccaactgat cttcagcatc ttttactttc accagcgttt ctgggtgagc   2220
aaaaacagga aggcaaaatg ccgcaaaaaa gggaataagg gcgacacgga aatgttgaat   2280
actcatactc ttcctttttc aatattattg aagcatttat cagggttatt gtctcatgag   2340
cggatacata tttgaatgta tttagaaaaa taaacaaata ggggttccgc gcacatttcc   2400
ccgaaaagtg ccacctgacg cgccctgtag cggcgcatta agcgcggcgg gtgtggtggt   2460
tacgcgcagc gtgaccgcta cacttgccag cgccctagcg cccgctcctt tcgctttctt   2520
cccttccttt ctcgccacgt tcgccggctt tccccgtcaa gctctaaatc ggggggctccc   2580 tttagggttc cgatttagtg ctttacggca cctcgacccc aaaaaacttg attagggtga   2640
tggttcacgt agtgggccat cgccctgata gacggttttt cgccctttga cgttggagtc   2700
cacgttcttt aatagtggac tcttgttcca aactggaaca acactcaacc ctatctcggt   2760
ctattctttt gatttataag ggattttgcc gatttcggcc tattggttaa aaaatgagct   2820
gatttaacaa aaatttaacg cgaattttaa caaaatatta acgcttacaa tttccattcg   2880
ccattcaggc tgcgcaactg ttgggaaggg cgatcggtgc gggcctcttc gctattacgc   2940
cagctggcga aaggggatg tgctgcaagg cgattaagtt gggtaacgcc agggttttcc   3000
cagtcacgac gttgtaaaac gacggccagt gaattgtaat acgactcact atagggcgaa   3060
ttgggtaccg ggccccccct cgaggtcgat ggtgtcgata gcttgatat cgaattcatg   3120 tcacacaaac cgatcttcgc ctcaaggaaa cctaattcta catccgagag actgccgaga   3180
tccagtctac actgattaat tttcgggcca ataatttaaa aaaatcgtgt tatataaat   3240 tatatgtatt atatatatac atcatgatga tactgacagt catgtcccat tgctaaatag   3300
acagactcca tctgccgcct ccaactgatg ttctcaatat ttaaggggtc atctcgcatt   3360
gtttaataat aaacagactc catctaccgc ctccaaatga tgttctcaaa atatattgta   3420
```

```
tgaacttatt tttattactt agtattatta gacaacttac ttgctttatg aaaaacactt    3480
cctatttagg aaacaattta taatggcagt tcgttcattt aacaatttat gtagaataaa    3540
tgttataaat gcgtatggga aatcttaaat atggatagca taaatgatat ctgcattgcc    3600
taattcgaaa tcaacagcaa cgaaaaaaat cccttgtaca acataaatag tcatcgagaa    3660
atatcaacta tcaaagaaca gctattcaca cgttactatt gagattatta ttggacgaga    3720
atcacacact caactgtctt tctctcttct agaaatacag gtacaagtat gtactattct    3780
cattgttcat acttctagtc atttcatccc acatattcct tggatttctc tccaatgaat    3840
gacattctat cttgcaaatt caacaattat aataagatat accaaagtag cggtatagtg    3900
gcaatcaaaa agcttctctg gtgtgcttct cgtatttatt tttattctaa tgatccatta    3960
aaggtatata tttatttctt gttatataat cctttgttt attacatggg ctggatacat     4020
aaaggtattt tgatttaatt ttttgcttaa attcaatccc ccctcgttca gtgtcaactg    4080
taatggtagg aaattaccat acttttgaag aagcaaaaaa aatgaaagaa aaaaaaaatc    4140
gtatttccag gttagacgtt ccgcagaatc tagaatgcgg tatgcggtac attgttcttc    4200
gaacgtaaaa gttgcgctcc ctgagatatt gtacattttt gcttttacaa gtacaagtac    4260
atcgtacaac tatgtactac tgttgatgca tccacaacag tttgttttgt tttttttgt    4320 ttttttttt tctaatgatt cattaccgct atgtatacct acttgtactt gtagtaagcc    4380
gggttattgg cgttcaatta atcatagact tatgaatctg cacggtgtgc gctgcgagtt    4440
acttttagct tatgcatgct acttgggtgt aatattggga tctgttcgga atcaacgga    4500 tgctcaatcg atttcgacag taattaatta agtcatacac aagtcagctt tcttcgagcc    4560
tcatataagt ataagtagtt caacgtatta gcactgtacc cagcatctcc gtatcgagaa    4620
acacaacaac atgccccatt ggacagatca tgcggataca caggttgtgc agtatcatac    4680
atactcgatc agacaggtcg tctgaccatc atacaagctg aacaagcgct ccatacttgc    4740
acgctctcta tatacacagt taaattacat atccatagtc taacctctaa cagttaatct    4800
tctggtaagc ctcccagcca gccttctggt atcgcttggc ctcctcaata ggatctcggt    4860
tctggccgta cagacctcgg ccgacaatta tgatatccgt tccggtagac atgacatcct    4920
caacagttcg gtactgctgt ccgagagcgt ctcccttgtc gtcaagaccc accccggggg    4980
tcagaataag ccagtcctca gagtcgccct taggtcggtt ctgggcaatg aagccaacca    5040
caaactcggg gtcggatcgg gcaagctcaa tggtctgctt ggagtactcg ccagtggcca    5100
gagagccctt gcaagacagc tcggccagca tgagcagacc tctggccagc ttctcgttgg    5160
gagaggggac taggaactcc ttgtactggg agttctcgta gtcagagacg tcctccttct    5220
tctgttcaga gacagtttcc tcggcaccag ctcgcaggcc agcaatgatt ccggttccgg    5280
gtacaccgtg ggcgttggtg atatcggacc actcggcgat tcggtgacac cggtactggt    5340
gcttgacagt gttgccaata tctgcgaact ttctgtcctc gaacaggaag aaaccgtgct    5400
taagagcaag ttccttgagg gggagcacag tgccggcgta ggtgaagtcg tcaatgatgt    5460
cgatatgggt tttgatcatg cacacataag gtccgacctt atcggcaagc tcaatgagct    5520
ccttggtggt ggtaacatcc agagaagcac acaggttggt tttcttggct gccacgagct    5580
tgagcactcg agcggcaaag gcggacttgt ggacgttagc tcgagcttcg taggagggca    5640
ttttggtggt gaagaggaga ctgaaataaa tttagtctgc agaacttttt atcggaacct    5700
tatctggggc agtgaagtat atgttatggt aatagttacg agttagttga acttatagat    5760
agactggact atacggctat cggtccaaat tagaaagaac gtcaatggct ctctgggcgt    5820
```

```
cgcctttgcc gacaaaaatg tgatcatgat gaaagccagc aatgacgttg cagctgatat    5880
tgttgtcggc caaccgcgcc gaaaacgcag ctgtcagacc cacagcctcc aacgaagaat    5940
gtatcgtcaa agtgatccaa gcacactcat agttggagtc gtactccaaa ggcggcaatg    6000
acgagtcaga cagatactcg tcgacgttta aacagtgtac gcagatctac tatagaggaa    6060
catttaaatt gccccggaga agacggccag gccgcctaga tgacaaattc aacaactcac    6120
agctgacttt ctgccattgc cactaggggg gggcctttt atatggccaa gccaagctct    6180
ccacgtcggt tgggctgcac ccaacaataa atgggtaggg ttgcaccaac aaagggatgg    6240
gatgggggt agaagatacg aggataacgg ggctcaatgg cacaaataag aacgaatact    6300
gccattaaga ctcgtgatcc agcgactgac accattgcat catctaaggg cctcaaaact    6360
acctcggaac tgctgcgctg atctggacac cacagaggtt ccgagcactt taggttgcac    6420
caaatgtccc accaggtgca ggcagaaaac gctggaacag cgtgtacagt ttgtcttagc    6480
aaaaagtgaa ggcgctgagg tcgagcaggg tggtgtgact tgtttatagcc tttagagctg    6540
cgaaagcgcg tatggatttg gctcatcagg ccagattgag ggtctgtgga cacatgtcat    6600
gttagtgtac ttcaatcgcc ccctggatat agccccgaca ataggccgtg gcctcatttt    6660
tttgccttcc gcacatttcc attgctcgat acccacacct tgcttctcct gcacttgcca    6720
accttaatac tggtttacat tgaccaacat cttacaagcg gggggcttgt ctagggtata    6780
tataaacagt ggctctccca atcggttgcc agtctctttt ttcctttctt tccccacaga    6840
ttcgaaatct aaactacaca tcacagaatt ccgagccgtg agtatccacg acaagatcag    6900
tgtcgagacg acgcgttttg tgtaatgaca caatccgaaa gtcgctagca acacacactc    6960
tctacacaaa ctaacccagc tctggtacca gcggccatca caagtttgta caaaaaagct    7020
gaacgagaaa cgtaaaatga tataaatatc aatatattaa attagatttt gcataaaaaa    7080
cagactacat aatactgtaa aacacaacat atccagtcat attggcggcc gcattaggca    7140
ccccaggctt tacactttat gcttccggct cgtataatgt gtggattttg agttaggatc    7200
cgtcgagatt ttcaggagct aaggaagcta aaatggagaa aaaaatcact ggatatacca    7260
ccgttgatat atcccaatgg catcgtaaag aacattttga ggcatttcag tcagttgctc    7320
aatgtaccta taaccagacc gttcagctgg atattacggc cttttttaaag accgtaaaga    7380
aaaataagca caagttttat ccggccttta ttcacattct tgcccgcctg atgaatgctc    7440
atccggaatt ccgtatggca atgaaagacg gtgagctggt gatatgggat agtgttcacc    7500
cttgttacac cgttttccat gagcaaactg aaacgttttc atcgctctgg agtgaatacc    7560
acgacgattt ccggcagttt ctacacatat attcgcaaga tgtggcgtgt tacggtgaaa    7620
acctggccta tttccctaaa gggtttattg agaatatgtt tttcgtctca gccaatccct    7680
gggtgagttt caccagtttt gatttaaacg tggccaatat ggacaacttc ttcgccccg    7740
ttttcaccat gggcaaatat tatacgcaag cgacaaggt gctgatgccg ctggcgattc    7800
aggttcatca tgccgtttgt gatggcttcc atgtcggcag aatgcttaat gaattacaac    7860
agtactgcga tgagtggcag ggcggggcgt aaacgcgtgg atccggctta ctaaaagcca    7920
gataacagta tgcgtatttg cgcgctgatt tttgcggtat aagaatatat actgatatgt    7980
atacccgaag tatgtcaaaa agaggtatgc tatgaagcag cgtattacag tgacagttga    8040
cagcgacagc tatcagttgc tcaaggcata tatgatgtca atatctccgg tctggtaagc    8100
acaaccatgc agaatgaagc ccgtcgtctg cgtgccgaac gctggaaagc ggaaaatcag    8160
gaagggatgg ctgaggtcgc ccggtttatt gaaatgaacg gctctttgc tgacgagaac    8220
```

```
aggggctggt gaaatgcagt ttaaggttta cacctataaa agagagagcc gttatcgtct    8280
gtttgtggat gtacagagtg atattattga cacgcccggg cgacggatgg tgatcccct    8340
ggccagtgca cgtctgctgt cagataaagt ctcccgtgaa ctttacccgg tggtgcatat    8400
cggggatgaa agctggcgca tgatgaccac cgatatggcc agtgtgccgg tctccgttat    8460
cggggaagaa gtggctgatc tcagccaccg cgaaaatgac atcaaaaacg ccattaacct    8520
gatgttctgg ggaatataaa tgtcaggctc ccttatacac agccagtctg caggtcgacc    8580
atagtgactg gatatgttgt gttttacagc attatgtagt ctgttttta tgcaaaatct    8640
aatttaatat attgatattt atatcatttt acgtttctcg ttcagctttc ttgtacaaag    8700
tggtgat                                                             8707

<210> SEQ ID NO 126
<211> LENGTH: 10158
<212> TYPE: DNA
<213> ORGANISM: Artificial Sequence
<220> FEATURE:
<223> OTHER INFORMATION: plasmid pY166

<400> SEQUENCE: 126
cttgtacaaa gtggtgatgg ccgcaagtgt ggatggggaa gtgagtgccc ggttctgtgt      60
gcacaattgg caatccaaga tggatggatt caacacaggg atatagcgag ctacgtggtg     120
gtgcgaggat atagcaacgg atatttatgt ttgacacttg agaatgtacg atacaagcac     180
tgtccaagta caatactaaa catactgtac atactcatac tcgtacccgg caacggtttc     240
acttgagtgc agtggctagt gctcttactc gtacagtgtg caatactgcg tatcatagtc     300
tttgatgtat atcgtattca ttcatgttag ttgcgtacga gccggaagca taaagtgtaa     360
agcctggggt gcctaatgag tgagctaact cacattaatt gcgttgcgct cactgcccgc     420
tttccagtcg ggaaacctgt cgtgccagct gcattaatga atcggccaac gcgcggggag     480
aggcggtttg cgtattgggc gctcttccgc ttcctcgctc actgactcgc tgcgctcggt     540
cgttcggctg cggcgagcgg tatcagctca ctcaaaggcg gtaatacggt tatccacaga     600
atcaggggat aacgcaggaa agaacatgtg agcaaaaggc cagcaaaagg ccaggaaccg     660
taaaaaggcc gcgttgctgg cgttttttcca taggctccgc ccccctgacg agcatcacaa     720
aaatcgacgc tcaagtcaga ggtggcgaaa cccgacagga ctataaagat accaggcgtt     780
tccccctgga agctccctcg tgcgctctcc tgttccgacc ctgccgctta ccggatacct     840
gtccgccttt ctcccttcgg gaagcgtggc gctttctcat agctcacgct gtaggtatct     900
cagttcggtg taggtcgttc gctccaagct gggctgtgtg cacgaacccc ccgttcagcc     960
cgaccgctgc gccttatccg gtaactatcg tcttgagtcc aacccggtaa gacacgactt    1020
atcgccactg gcagcagcca ctggtaacag gattagcaga gcgaggtatg taggcggtgc    1080
tacagagttc ttgaagtggt ggcctaacta cggctacact agaaggacag tatttggtat    1140
ctgcgctctg ctgaagccag ttaccttcgg aaaaagagtt ggtagctctt gatccggcaa    1200
acaaaccacc gctggtagcg gtggtttttt tgtttgcaag cagcagatta cgcgcagaaa    1260
aaaaggatct caagaagatc ctttgatctt ttctacgggg tctgacgctc agtggaacga    1320
aaactcacgt taagggattt tggtcatgag attatcaaaa aggatcttca cctagatcct    1380
tttaaattaa aaatgaagtt ttaaatcaat ctaaagtata tatgagtaaa cttggtctga    1440
cagttaccaa tgcttaatca gtgaggcacc tatctcagcg atctgtctat ttcgttcatc    1500
catagttgcc tgactccccg tcgtgtagat aactacgata cgggagggct taccatctgg    1560
```

-continued

```
ccccagtgct gcaatgatac cgcgagaccc acgctcaccg gctccagatt tatcagcaat    1620
aaaccagcca gccggaaggg ccgagcgcag aagtggtcct gcaactttat ccgcctccat    1680
ccagtctatt aattgttgcc gggaagctag agtaagtagt tcgccagtta atagtttgcg    1740
caacgttgtt gccattgcta caggcatcgt ggtgtcacgc tcgtcgtttg gtatggcttc    1800
attcagctcc ggttcccaac gatcaaggcg agttacatga tcccccatgt tgtgcaaaaa    1860
agcggttagc tccttcggtc ctccgatcgt tgtcagaagt aagttggccg cagtgttatc    1920
actcatggtt atggcagcac tgcataattc tcttactgtc atgccatccg taagatgctt    1980
ttctgtgact ggtgagtact caaccaagtc attctgagaa tagtgtatgc ggcgaccgag    2040
ttgctcttgc ccggcgtcaa tacgggataa taccgcgcca catagcagaa ctttaaaagt    2100
gctcatcatt ggaaaacgtt cttcggggcg aaaactctca aggatcttac cgctgttgag    2160
atccagttcg atgtaaccca ctcgtgcacc caactgatct tcagcatctt ttactttcac    2220
cagcgtttct gggtgagcaa aaacaggaag gcaaaatgcc gcaaaaaagg gaataagggc    2280
gacacggaaa tgttgaatac tcatactctt ccttttcaa tattattgaa gcatttatca    2340
gggttattgt ctcatgagcg gatacatatt tgaatgtatt tagaaaaata aacaaatagg    2400
ggttccgcgc acatttcccc gaaaagtgcc acctgacgcg ccctgtagcg gcgcattaag    2460
cgcggcgggt gtggtggtta cgcgcagcgt gaccgctaca cttgccagcg ccctagcgcc    2520
cgctcctttc gctttcttcc cttcctttct cgccacgttc gccggctttc cccgtcaagc    2580
tctaaatcgg gggctccctt tagggttccg atttagtgct ttacggcacc tcgaccccaa    2640
aaaacttgat tagggtgatg gttcacgtag tgggccatcg ccctgataga cggttttcg    2700
cccttttgacg ttggagtcca cgttctttaa tagtggactc ttgttccaaa ctggaacaac    2760
actcaaccct atctcggtct attctttga tttataaggg attttgccga tttcggccta    2820
ttggttaaaa aatgagctga tttaacaaaa attttaacgcg aattttaaca aaatattaac    2880
gcttacaatt tccattcgcc attcaggctg cgcaactgtt gggaagggcg atcggtgcgg    2940
gcctcttcgc tattacgcca gctggcgaaa gggggatgtg ctgcaaggcg attaagttgg    3000
gtaacgccag ggttttccca gtcacgacgt tgtaaaacga cggccagtga attgtaaatac    3060
gactcactat agggcgaatt gggtaccggg ccccccctcg aggtcgatgg tgtcgataag    3120
cttgatatcg aattcatgtc acacaaaccg atcttcgcct caaggaaacc taattctaca    3180
tccgagagac tgccgagatc cagtctacac tgattaattt tcgggccaat aatttaaaaa    3240
aatcgtgtta tataatatta tatgtattat atatatacat catgatgata ctgacagtca    3300
tgtcccattg ctaaatagac agactccatc tgccgcctcc aactgatgtt ctcaatattt    3360
aagggggtcat ctcgcattgt ttaataataa acagactcca tctaccgcct ccaaatgatg    3420
ttctcaaaat atattgtatg aacttatttt tattacttag tattattaga caacttactt    3480
gctttatgaa aaacacttcc tatttaggaa acaatttata atggcagttc gttcatttaa    3540
caatttatgt agaataaatg ttataaatgc gtatgggaaa tcttaaatat ggatagcata    3600
aatgatatct gcattgccta attcgaaatc aacagcaacg aaaaaaatcc cttgtacaac    3660
ataaatagtc atcgagaaat atcaactatc aaagaacagc tattcacacg ttactattga    3720
gattattatt ggacgagaat cacacactca actgtctttc tctcttctag aaatacaggt    3780
acaagtatgt actattctca ttgttcatac ttctagtcat ttcatcccac atattccttg    3840
gatttctctc caatgaatga cattctatct tgcaaattca acaattataa taagatatac    3900
caaagtagcg gtatagtggc aatcaaaaag cttctctggt gtgcttctcg tatttatttt    3960
```

-continued

```
tattctaatg atccattaaa ggtatatatt tatttcttgt tatataatcc ttttgtttat    4020
tacatgggct ggatacataa aggtattttg atttaatttt ttgcttaaat tcaatccccc    4080
ctcgttcagt gtcaactgta atggtaggaa attaccatac ttttgaagaa gcaaaaaaaa    4140
tgaaagaaaa aaaaaatcgt atttccaggt tagacgttcc gcagaatcta gaatgcggta    4200
tgcggtacat tgttcttcga acgtaaaagt tgcgctccct gagatattgt acattttgc     4260 ttttacaagt acaagtacat cgtacaacta tgtactactg ttgatgcatc cacaacagtt    4320
tgttttgttt tttttttgttt tttttttttc taatgattca ttaccgctat gtatacctac   4380
ttgtacttgt agtaagccgg gttattggcg ttcaattaat catagactta tgaatctgca    4440
cggtgtgcgc tgcgagttac ttttagctta tgcatgctac ttgggtgtaa tattgggatc    4500
tgttcggaaa tcaacggatg ctcaatcgat ttcgacagta attaattaag tcatacacaa    4560
gtcagctttc ttcgagcctc atataagtat aagtagttca acgtattagc actgtaccca    4620
gcatctccgt atcgagaaac acaacaacat gccccattgg acagatcatg cggatacaca    4680
ggttgtgcag tatcatacat actcgatcag acaggtcgtc tgaccatcat acaagctgaa    4740
caagcgctcc atacttgcac gctctctata tacacagtta aattacatat ccatagtcta    4800
acctctaaca gttaatcttc tggtaagcct cccagccagc cttctggtat cgcttggcct    4860
cctcaatagg atctcggttc tggccgtaca gacctcggcc gacaattatg atatccgttc    4920
cggtagacat gacatcctca acagttcggt actgctgtcc gagagcgtct cccttgtcgt    4980
caagacccac cccgggggtc agaataagcc agtcctcaga gtcgccctta ggtcggttct    5040
gggcaatgaa gccaaccaca aactcggggt cggatcgggc aagctcaatg gtctgcttgg    5100
agtactcgcc agtggccaga gagcccttgc aagacagctc ggccagcatg agcagacctc    5160
tggccagctt ctcgttggga gagggacta ggaactcctt gtactgggag ttctcgtagt     5220
cagagacgtc ctccttcttc tgttcagaga cagtttcctc ggcaccagct cgcaggccag    5280
caatgattcc ggttccgggt acaccgtggg cgttggtgat atcggaccac tcggcgattc    5340
ggtgacaccg gtactggtgc ttgacagtgt tgccaatatc tgcgaacttt ctgtcctcga    5400
acaggaagaa accgtgctta agagcaagtt ccttgagggg gagcacagtg ccggcgtagg    5460
tgaagtcgtc aatgatgtcg atatgggttt tgatcatgca cacataaggt ccgaccttat    5520
cggcaagctc aatgagctcc ttggtggtgg taacatccag agaagcacac aggttggttt    5580
tcttggctgc cacgagcttg agcactcgag cggcaaaggc ggacttgtgg acgttagctc    5640
gagcttcgta ggagggcatt ttggtggtga agaggagact gaaataaatt tagtctgcag    5700 aacttttat cggaacctta tctggggcag tgaagtatat gttatggtaa tagttacgag     5760
ttagttgaac ttatagatag actggactat acggctatcg gtccaaatta gaagaacgt     5820 caatggctct ctgggcgtcg cctttgccga caaaaatgtg atcatgatga aagccagcaa    5880
tgacgttgca gctgatattg ttgtcggcca accgcgccga aaacgcagct gtcagaccca    5940
cagcctccaa cgaagaatgt atcgtcaaag tgatccaagc acactcatag ttggagtcgt    6000
actccaaagg cggcaatgac gagtcagaca gatactcgtc gacgtttaaa cagtgtacgc    6060
agatctacta tagaggaaca tttaaattgc cccggagaag acggccaggc cgcctagatg    6120
acaaattcaa caactcacag ctgactttct gccattgcca ctaggggggg gccttttat     6180 atggccaagc caagctctcc acgtcggttg ggctgcaccc aacaataaat gggtagggtt    6240
gcaccaacaa agggatggga tgggggtag aagatacgag gataacgggg ctcaatggca     6300
caaataagaa cgaatactgc cattaagact cgtgatccag cgactgacac cattgcatca    6360
```

```
tctaagggcc tcaaaactac ctcggaactg ctgcgctgat ctggacacca cagaggttcc    6420
gagcacttta ggttgcacca aatgtcccac caggtgcagg cagaaaacgc tggaacagcg    6480
tgtacagttt gtcttagcaa aaagtgaagg cgctgaggtc gagcagggtg tgtgacttg    6540
ttatagcctt tagagctgcg aaagcgcgta tggatttggc tcatcaggcc agattgaggg    6600
tctgtggaca catgtcatgt tagtgtactt caatcgcccc ctggatatag ccccgacaat    6660
aggccgtggc ctcattttt tgccttccgc acatttccat tgctcgatac ccacaccttg    6720
cttctcctgc acttgccaac cttaatactg gtttacattg accaacatct tacaagcggg    6780
gggcttgtct agggtatata taaacagtgg ctctcccaat cggttgccag tctctttttt    6840
cctttctttc cccacagatt cgaaatctaa actacacatc acagaattcc gagccgtgag    6900
tatccacgac aagatcagtg tcgagacgac gcgttttgtg taatgacaca atccgaaagt    6960
cgctagcaac acacactctc tacacaaact aacccagctc tggtaccagc ggccatcaca    7020
agtttgtaca aaaaagttgg atttttttc ggtctccatg gccgaaggca agagcgatgg    7080
gcctgtggtg acccttcaaa gcatgtggaa accgcttgct ctgatggcaa tagatgtcgg    7140
catattggtc aatgtccgcc gcaaggcttt cactgagttt gatgggcaca gcaacgtttt    7200
cgcagatcca gtttacattc catttgtgat gaatctcttc tacttgacca tgatctttgc    7260
tgggtgccgt tggatgaaga ctcgcgaacc ctttgagatc aagtcatata tgtttgcata    7320
caatgcatat cagacaatga tgaacttcct cattgtcgtc gggttcatgt atgaggtgca    7380
cagcacaggg atgcgatatt gggggtccag gatcgacacc tccaccaagg gcttgggcct    7440
cggtttcctg atctatgccc actaccacaa caaatacgtg gagtatgtcg acacgttgtt    7500
catgatcctg cgcaagaaaa acaaccgat ctcgttcctc cacgtctacc accattcgct    7560
tttgacttgg gcctggtggg ccgtggtcta ctgggcccca ggaggagatg cctggttcgg    7620
agcatgctac aattccttca tccacgtgct gatgtactcc tactacctgt ttgcaacgtt    7680
tggcatcagg tgcccctgga agaagatgct gacccagttg cagatggtgc aattctgctt    7740
ctgctttgcc cacgcgatgt atgttggatg gctgggccat gaagtctacc cgcgctggtt    7800
gacggcgcta caggcatttg tgatgctaaa catgctggtc ctgttcggca acttctacat    7860
gaagtcgtac tccaaggcca gcaagctgga gccggcctcc ccgtgtccc ccgcctccct    7920
cgcccagaag ccgttcgaga cgcaaggt gaagcctggg ggccccggca agccaagcga    7980
gattgcgtcg ctgccaccgc caattcgacc agtcgggaac ccacctgcag cctactacga    8040
tgccctggcg acctcgggca ccgggcagga ccgcaagttc accatgcggg aggtggcccg    8100
ccatattgtg ccgaccgatg ggtggttggc gtgccatgac ggtgtctacg acatcaccga    8160
gttcataggg aaacatcctg gcggcgatgt tattctctc ggattgggca gggactccac    8220
aatcctggtt gagtcgtacc accctgccgg aaggccagac aaggtcatgg aaaagtaccg    8280
catcgggacg ctccaggacc accgcacgtt ctacgactgg caggcctccg cgttctacgc    8340
cgagctgaag cagcgggtgg tgcagacgct aaaggaggcc ggccaaccgc ggcgtggggg    8400
cctgtcggtc aaagcggcgc tggtcatggc ggcgttcgca gcgtcgttct acctcatggt    8460
gacccaggga tccttcttct gggccgccgt ctggggcctc gccggctccc acattggcct    8520
cagcatccag cacgacggga accacggggc tttcagtaag agtggtcggc tgaaccgcct    8580
cgcgggctgg ggcatggacg tcatcggggc ctcctcgacg gcctgggagt accagcacgt    8640
catcgggcac caccagtaca ccaacctggt atcggatccc gagttcgcgc tgcctgagaa    8700
cgacccggac gtcttcggca cctatccgct gatgcggatg catccggaca ccccttggaa    8760
```

-continued

```
gccgcaccac cagctgcagc atgtgtacgc gttcccgctg ttcgccctga tgaccatcag    8820
caaggtcatc atcagcgact tcacgttctg cctcgccaag cggcgcgggc cgatcgactt    8880
ctccgccagg ctcgtgccac ttgaggggca gatgctcttc tgggggggcga agatcatggg    8940 gttcctgatg cagatagtcc tgccgtgcta tctgcatggc atcgcccatg gctggcgct    9000 gttcatcaca gcccacctgg tgtcgggaga gtacctcgcg gtctgcttca tcatcaacca    9060
catctctgag tcatgcgact atttgaatcc aagttccgtc atcgctgcgc ggaggacgga    9120
aatgctgaag caggcggagc aggaggccaa ggcaaagcag aagcacccca ccccaccgcc    9180
caacgactgg gccgcgtctc aggtactgtg ctgcgtaaac tggcgctctg gtggctattt    9240
ctcaaaccac ctctcaggcg ggctgaacca ccagatcgag caccacctct tccccagcat    9300
ctcacatgcg aactatccga ccattgcccc agttgtgaaa ggggtgtgcg aggagtacgg    9360
cctcccctac aagaactact cccagttctc cgacgctctc tatggaatgg tggagcacct    9420
cagggcgatg ggcacgaagc cggcagacaa cgacaagctg gcgcccaccg cgggctccct    9480
ggaggacgtg tgcccggtct tgagcgccgc cgttgctgcc caacctgacg gaagcaccga    9540
cggcagcgct gcgggttgtc cagcagtagc cacactggca taaagggcat aatgagcatg    9600
ccatcatcac tagacgacgt tgctcacctt gttttccatt tgtgccgtgc cttgcggccc    9660
gtgttctcca tttgcgggca ctagattcgg tacccagccc tcctcacagc tctgcgattt    9720
gagccgtttg gggcaacgct ccgctgaccc ttgtgcaggt cccccgacca tccgctccga    9780
ggaatgcggt aaaacaaaac aaataacaac agcatgaggc gtcaatctct gcgatatgcg    9840
gggcttgctc cagctcacct ggaccacttc gtccgctgcg cagctatagt tttgggccgc    9900
agctaggtct gcggttactt cctttttttt ctccggcgca gggcgcttgg ttctaagcct    9960
ttcctccaat cctcgagccc cctcgacctg accgtgtctt cctctggctg aaagcggagg   10020
atgatttgtg cgttgctcag aaggaacctc atcggtggt ggttttcgca tttcccattg    10080
atgtccaaca gtgctgccat tcagtttgac ctgcaaaaaa aaaaaaaaaa aaaaaaaaaa   10140
aaaaaaaaac ccaactttt                                                10158
```

<210> SEQ ID NO 127
<211> LENGTH: 912
<212> TYPE: DNA
<213> ORGANISM: Euglena gracilis
<220> FEATURE:
<221> NAME/KEY: CDS
<222> LOCATION: (1)..(912)
<223> OTHER INFORMATION: synthetic C20 elongase (codon-optimized)

<400> SEQUENCE: 127

```
atg gct gac tct ccc gtc atc aac ctc tcc acc atg tgg aag cct ctg         48
Met Ala Asp Ser Pro Val Ile Asn Leu Ser Thr Met Trp Lys Pro Leu
1               5                   10                  15 tcg ctc atg gcc ttg gat ctt gct gtt ctg gga cac gtc tgg aag cag         96
Ser Leu Met Ala Leu Asp Leu Ala Val Leu Gly His Val Trp Lys Gln
            20                  25                  30 gca caa cag gag ggc tcc atc tcg gct tac gcc gac tct gtg tgg act        144
Ala Gln Gln Glu Gly Ser Ile Ser Ala Tyr Ala Asp Ser Val Trp Thr
        35                  40                  45 ccc ctc atc atg tcc ggt ctg tac ctc tcc atg atc ttc gtg gga tgt        192
Pro Leu Ile Met Ser Gly Leu Tyr Leu Ser Met Ile Phe Val Gly Cys
    50                  55                  60 cga tgg atg aag aac cga gag ccc ttc gaa atc aag acc tac atg ttt        240
Arg Trp Met Lys Asn Arg Glu Pro Phe Glu Ile Lys Thr Tyr Met Phe
65                  70                  75                  80
```

```
gcc tac aac ctg tac cag acc ctc atg aac ctt tgc att gtg ctg ggc      288
Ala Tyr Asn Leu Tyr Gln Thr Leu Met Asn Leu Cys Ile Val Leu Gly
            85                  90                  95 ttc ctc tac cag gtc cac gct acc ggt atg cga ttc tgg gga tct ggc      336
Phe Leu Tyr Gln Val His Ala Thr Gly Met Arg Phe Trp Gly Ser Gly
            100                 105                 110 gtg gac cga tcg ccc aag ggt ctg gga att ggc ttt tc atc tat gcc       384
Val Asp Arg Ser Pro Lys Gly Leu Gly Ile Gly Phe Phe Ile Tyr Ala
            115                 120                 125 cat tac cac aac aag tac gtc gag tac ttc gac aca ctc ttc atg gtg      432
His Tyr His Asn Lys Tyr Val Glu Tyr Phe Asp Thr Leu Phe Met Val
    130                 135                 140 ctg cgg aaa aag aac aac cag att tcc ttt ctt cac gtc tac cat cac      480
Leu Arg Lys Lys Asn Asn Gln Ile Ser Phe Leu His Val Tyr His His
145                 150                 155                 160 gct ctg ctc acc tgg gct tgg ttt gcc gtg gtc tac ttc gct cct gga      528
Ala Leu Leu Thr Trp Ala Trp Phe Ala Val Val Tyr Phe Ala Pro Gly
                165                 170                 175 ggt gac ggc tgg ttt gga gcc tgc tac aat tcc tcc att cat gtc ctg      576
Gly Asp Gly Trp Phe Gly Ala Cys Tyr Asn Ser Ser Ile His Val Leu
            180                 185                 190 atg tac tct tac tat ctg ctt gcc acc ttc ggc atc tcc tgt ccc tgg      624
Met Tyr Ser Tyr Tyr Leu Leu Ala Thr Phe Gly Ile Ser Cys Pro Trp
            195                 200                 205 aaa aag atc ctc acc cag ctg caa atg gtt cag ttc tgc ttt tgc ttc      672
Lys Lys Ile Leu Thr Gln Leu Gln Met Val Gln Phe Cys Phe Cys Phe
            210                 215                 220 acc cac tcg atc tac gtg tgg att tgc ggt tcc gaa atc tac cct cga      720
Thr His Ser Ile Tyr Val Trp Ile Cys Gly Ser Glu Ile Tyr Pro Arg
225                 230                 235                 240 ccc ttg act gct ctc cag tcc ttc gtg atg gtc aac atg ctg gtt ctc      768
Pro Leu Thr Ala Leu Gln Ser Phe Val Met Val Asn Met Leu Val Leu
                245                 250                 255 ttt ggc aac ttc tac gtc aag cag tat tct cag aag aat gga aag ccc      816
Phe Gly Asn Phe Tyr Val Lys Gln Tyr Ser Gln Lys Asn Gly Lys Pro
            260                 265                 270 gag aac ggt gcc act cct gag aac ggt gcc aag cct cag ccc tgc gag      864
Glu Asn Gly Ala Thr Pro Glu Asn Gly Ala Lys Pro Gln Pro Cys Glu
            275                 280                 285 aac ggc acc gtc gag aag cga gag aac gac act gcc aac gtt cga taa      912
Asn Gly Thr Val Glu Lys Arg Glu Asn Asp Thr Ala Asn Val Arg
            290                 295                 300

<210> SEQ ID NO 128
<211> LENGTH: 303
<212> TYPE: PRT
<213> ORGANISM: Euglena gracilis

<400> SEQUENCE: 128

Met Ala Asp Ser Pro Val Ile Asn Leu Ser Thr Met Trp Lys Pro Leu
1               5                   10                  15

Ser Leu Met Ala Leu Asp Leu Ala Val Leu Gly His Val Trp Lys Gln
            20                  25                  30

Ala Gln Gln Glu Gly Ser Ile Ser Ala Tyr Ala Asp Ser Val Trp Thr
        35                  40                  45

Pro Leu Ile Met Ser Gly Leu Tyr Leu Ser Met Ile Phe Val Gly Cys
    50                  55                  60

Arg Trp Met Lys Asn Arg Glu Pro Phe Glu Ile Lys Thr Tyr Met Phe
65                  70                  75                  80

Ala Tyr Asn Leu Tyr Gln Thr Leu Met Asn Leu Cys Ile Val Leu Gly
```

```
                85                  90                  95
Phe Leu Tyr Gln Val His Ala Thr Gly Met Arg Phe Trp Gly Ser Gly
                    100                 105                 110
Val Asp Arg Ser Pro Lys Gly Leu Gly Ile Gly Phe Ile Tyr Ala
                115                 120                 125
His Tyr His Asn Lys Tyr Val Glu Tyr Phe Asp Thr Leu Phe Met Val
            130                 135                 140
Leu Arg Lys Lys Asn Asn Gln Ile Ser Phe Leu His Val Tyr His His
145                 150                 155                 160
Ala Leu Leu Thr Trp Ala Trp Phe Ala Val Val Tyr Phe Ala Pro Gly
                165                 170                 175
Gly Asp Gly Trp Phe Gly Ala Cys Tyr Asn Ser Ser Ile His Val Leu
            180                 185                 190
Met Tyr Ser Tyr Tyr Leu Leu Ala Thr Phe Gly Ile Ser Cys Pro Trp
                195                 200                 205
Lys Lys Ile Leu Thr Gln Leu Gln Met Val Gln Phe Cys Phe Cys Phe
    210                 215                 220
Thr His Ser Ile Tyr Val Trp Ile Cys Gly Ser Glu Ile Tyr Pro Arg
225                 230                 235                 240
Pro Leu Thr Ala Leu Gln Ser Phe Val Met Val Asn Met Leu Val Leu
                245                 250                 255
Phe Gly Asn Phe Tyr Val Lys Gln Tyr Ser Gln Lys Asn Gly Lys Pro
                260                 265                 270
Glu Asn Gly Ala Thr Pro Glu Asn Gly Ala Lys Pro Gln Pro Cys Glu
            275                 280                 285
Asn Gly Thr Val Glu Lys Arg Glu Asn Asp Thr Ala Asn Val Arg
    290                 295                 300

<210> SEQ ID NO 129
<211> LENGTH: 3632
<212> TYPE: DNA
<213> ORGANISM: Artificial Sequence
<220> FEATURE:
<223> OTHER INFORMATION: Plasmid pEgC20ES

<400> SEQUENCE: 129
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgagctcggt acctcgcgaa     420
tgcatctaga tccatggctg actctcccgt catcaacctc tccaccatgt ggaagcctct     480
gtcgctcatg gccttggatc ttgctgttct gggacacgtc tggaagcagg cacaacagga     540
gggctccatc tcggcttacg ccgactctgt gtggactccc ctcatcatgt ccggtctgta     600
cctctccatg atcttcgtgg gatgtcgatg gatgaagaac cgagagccct tcgaaatcaa     660
gacctacatg tttgcctaca acctgtacca gaccctcatg aacctttgca ttgtgctggg     720
cttcctctac caggtccacg ctaccggtat gcgattctgg ggatctggcg tggaccgatc     780
gcccaagggt ctgggaattg ctttttcat ctatgcccat taccacaaca agtacgtcga     840
gtacttcgac acactcttca tggtgctgcg gaaaaagaac aaccagattt cctttcttca     900
```

```
cgtctaccat cacgctctgc tcacctgggc ttggtttgcc gtggtctact tcgctcctgg    960
aggtgacggc tggtttggag cctgctacaa ttcctccatt catgtcctga tgtactctta   1020
ctatctgctt gccaccttcg gcatctcctg tccctggaaa aagatcctca cccagctgca   1080
aatggttcag ttctgctttt gcttcaccca ctcgatctac gtgtggattt gcggttccga   1140
aatctaccct cgaccttga ctgctctcca gtccttcgtg atggtcaaca tgctggttct   1200
ctttggcaac ttctacgtca agcagtattc tcagaagaat ggaaagcccg agaacggtgc   1260
cactcctgag aacggtgcca agcctcagcc ctgcgagaac ggcaccgtcg agaagcgaga   1320
gaacgacact gccaacgttc gataagcggc cgcatcggat cccgggcccg tcgactgcag   1380
aggcctgcat gcaagcttgg cgtaatcatg gtcatagctg tttcctgtgt gaaattgtta   1440
tccgctcaca attccacaca acatacgagc cggaagcata aagtgtaaag cctggggtgc   1500
ctaatgagtg agctaactca cattaattgc gttgcgctca ctgcccgctt tccagtcggg   1560
aaacctgtcg tgccagctgc attaatgaat cggccaacgc gcggggagag gcggtttgcg   1620
tattgggcgc tcttccgctt cctcgctcac tgactcgctg cgctcggtcg ttcggctgcg   1680
gcgagcggta tcagctcact caaaggcggt aatacggtta tccacagaat caggggataa   1740
cgcaggaaag aacatgtgag caaaaggcca gcaaaaggcc aggaaccgta aaaaggccgc   1800
gttgctggcg ttttttccata ggctccgccc ccctgacgag catcacaaaa atcgacgctc   1860
aagtcagagg tggcgaaacc cgacaggact ataaagatac caggcgtttc ccctggaag   1920
ctccctcgtg cgctctcctg ttccgaccct gccgcttacc ggatacctgt ccgcctttct   1980
cccttcggga agcgtggcgc tttctcatag ctcacgctgt aggtatctca gttcggtgta   2040
ggtcgttcgc tccaagctgg gctgtgtgca cgaacccccc gttcagcccg accgctgcgc   2100
cttatccggt aactatcgtc ttgagtccaa cccggtaaga cacgacttat cgccactggc   2160
agcagccact ggtaacagga ttagcagagc gaggtatgta ggcggtgcta cagagttctt   2220
gaagtggtgg cctaactacg gctacactag aagaacagta tttggtatct gcgctctgct   2280
gaagccagtt accttcggaa aaagagttgg tagctcttga tccggcaaac aaaccaccgc   2340
tggtagcggt ggtttttttg tttgcaagca gcagattacg cgcagaaaaa aaggatctca   2400
agaagatcct ttgatctttt ctacggggtc tgacgctcag tggaacgaaa actcacgtta   2460
agggattttg gtcatgagat tatcaaaaag gatcttcacc tagatccttt taaattaaaa   2520
atgaagtttt aaatcaatct aaagtatata tgagtaaact tggtctgaca gttaccaatg   2580
cttaatcagt gaggcaccta tctcagcgat ctgtctattt cgttcatcca tagttgcctg   2640
actccccgtc gtgtagataa ctacgatacg ggagggctta ccatctggcc ccagtgctgc   2700
aatgataccg cgagacccac gctcaccggc tccagattta tcagcaataa accagccagc   2760
cggaagggcc gagcgcagaa gtggtcctgc aactttatcc gcctccatcc agtctattaa   2820
ttgttgccgg gaagctagag taagtagttc gccagttaat agtttgcgca acgttgttgc   2880
cattgctaca ggcatcgtgg tgtcacgctc gtcgtttggt atggcttcat tcagctccgg   2940
ttcccaacga tcaaggcgag ttacatgatc ccccatgttg tgcaaaaaag cggttagctc   3000
cttcggtcct ccgatcgttg tcagaagtaa gttggccgca gtgttatcac tcatggttat   3060
ggcagcactg cataattctc ttactgtcat gccatccgta agatgctttt ctgtgactgg   3120
tgagtactca accaagtcat tctgagaata gtgtatgcgg cgaccgagtt gctcttgccc   3180
ggcgtcaata cgggataata ccgcgccaca tagcagaact ttaaaagtgc tcatcattgg   3240
aaaacgttct cggggcgaa aactctcaag gatcttaccg ctgttgagat ccagttcgat   3300
```

-continued

```
gtaacccact cgtgcaccca actgatcttc agcatctttt actttcacca gcgtttctgg    3360
gtgagcaaaa acaggaaggc aaaatgccgc aaaaaaggga ataagggcga cacggaaatg    3420
ttgaatactc atactcttcc tttttcaata ttattgaagc atttatcagg gttattgtct    3480
catgagcgga tacatatttg aatgtattta gaaaaataaa caaatagggg ttccgcgcac    3540
atttccccga aaagtgccac ctgacgtcta agaaaccatt attatcatga cattaaccta    3600
taaaaatagg cgtatcacga ggccctttcg tc                                  3632
```

<210> SEQ ID NO 130
<211> LENGTH: 900
<212> TYPE: DNA
<213> ORGANISM: Euglena anabaena
<220> FEATURE:
<221> NAME/KEY: CDS
<222> LOCATION: (1)..(900)
<223> OTHER INFORMATION: synthetic C20 elongase (codon-optimized)

<400> SEQUENCE: 130

```
atg gcc gag ggc aag tcc gac ggt ccc gtc gtt acc ctc cag tcc atg        48
Met Ala Glu Gly Lys Ser Asp Gly Pro Val Val Thr Leu Gln Ser Met
 1               5                  10                  15 tgg aag ccc ctg gct ctc atg gcc atc gac gtc ggc atc ctg gtc aac        96
Trp Lys Pro Leu Ala Leu Met Ala Ile Asp Val Gly Ile Leu Val Asn
            20                  25                  30 gtg cga cgg aag gcc ttc acc gag ttc gac gga cac tcg aac gtc ttc       144
Val Arg Arg Lys Ala Phe Thr Glu Phe Asp Gly His Ser Asn Val Phe
        35                  40                  45 gcc gat ccc gtg tac att ccc ttt gtc atg aac ctg ttc tac ctc acc       192
Ala Asp Pro Val Tyr Ile Pro Phe Val Met Asn Leu Phe Tyr Leu Thr
    50                  55                  60 atg atc ttt gct ggc tgc cga tgg atg aag act cga gaa ccc ttc gag       240
Met Ile Phe Ala Gly Cys Arg Trp Met Lys Thr Arg Glu Pro Phe Glu
65                  70                  75                  80 atc aag tcc tac atg ttt gcc tac aac gct tac cag aca atg atg aac       288
Ile Lys Ser Tyr Met Phe Ala Tyr Asn Ala Tyr Gln Thr Met Met Asn
                85                  90                  95 ttt ctc att gtg gtc ggc ttc atg tat gag gtt cac tcc acc ggt atg       336
Phe Leu Ile Val Val Gly Phe Met Tyr Glu Val His Ser Thr Gly Met
            100                 105                 110 cga tac tgg gga tcc aga atc gac act tct acc aag ggc ttg gga ctg       384
Arg Tyr Trp Gly Ser Arg Ile Asp Thr Ser Thr Lys Gly Leu Gly Leu
        115                 120                 125 ggt ttc ctc atc tat gcc cat tac cac aac aag tac gtg gag tac gtc       432
Gly Phe Leu Ile Tyr Ala His Tyr His Asn Lys Tyr Val Glu Tyr Val
    130                 135                 140 gac acc ctg ttc atg att ctg cgg aag aaa aac aat cag atc tcg ttc       480
Asp Thr Leu Phe Met Ile Leu Arg Lys Lys Asn Asn Gln Ile Ser Phe
145                 150                 155                 160 ctt cac gtt tac cac cat tcc ctc ctc act tgg gca tgg tgg gct gtg       528
Leu His Val Tyr His His Ser Leu Leu Thr Trp Ala Trp Trp Ala Val
                165                 170                 175 gtc tac tgg gct cct ggc gga gat gcc tgg ttc ggt gcc tgt tac aac       576
Val Tyr Trp Ala Pro Gly Gly Asp Ala Trp Phe Gly Ala Cys Tyr Asn
            180                 185                 190 tcc ttc atc cac gtt ctc atg tac tcc tac tat ctg ttt gcc acc ttc       624
Ser Phe Ile His Val Leu Met Tyr Ser Tyr Tyr Leu Phe Ala Thr Phe
        195                 200                 205 ggc att cga tgt ccc tgg aaa aag atg ctc acc cag ttg caa atg gtc       672
Gly Ile Arg Cys Pro Trp Lys Lys Met Leu Thr Gln Leu Gln Met Val
    210                 215                 220
```

-continued

```
cag ttc tgc ttt tgc ttc gct cat gcc atg tac gtt gga tgg ctt ggt      720
Gln Phe Cys Phe Cys Phe Ala His Ala Met Tyr Val Gly Trp Leu Gly
225                 230                 235                 240 cac gag gtg tac cct cga tgg ctc act gct ctg cag gcc ttt gtg atg      768
His Glu Val Tyr Pro Arg Trp Leu Thr Ala Leu Gln Ala Phe Val Met
                245                 250                 255 ctc aac atg ctg gtc ctc ttt ggc aac ttc tac atg aag tct tac tcc      816
Leu Asn Met Leu Val Leu Phe Gly Asn Phe Tyr Met Lys Ser Tyr Ser
            260                 265                 270 aag gcg agc aag ctc gaa cca gcc tct ccc gtg tcg cct gcc tct ctt      864
Lys Ala Ser Lys Leu Glu Pro Ala Ser Pro Val Ser Pro Ala Ser Leu
        275                 280                 285 gct cag aag ccc ttc gag aac gcc aag gtc aag taa                      900
Ala Gln Lys Pro Phe Glu Asn Ala Lys Val Lys
    290                 295

<210> SEQ ID NO 131
<211> LENGTH: 299
<212> TYPE: PRT
<213> ORGANISM: Euglena anabaena

<400> SEQUENCE: 131

Met Ala Glu Gly Lys Ser Asp Gly Pro Val Thr Leu Gln Ser Met
1               5                   10                  15

Trp Lys Pro Leu Ala Leu Met Ala Ile Asp Val Gly Ile Leu Val Asn
                20                  25                  30

Val Arg Arg Lys Ala Phe Thr Glu Phe Asp Gly His Ser Asn Val Phe
            35                  40                  45

Ala Asp Pro Val Tyr Ile Pro Phe Val Met Asn Leu Phe Tyr Leu Thr
    50                  55                  60

Met Ile Phe Ala Gly Cys Arg Trp Met Lys Thr Arg Glu Pro Phe Glu
65                  70                  75                  80

Ile Lys Ser Tyr Met Phe Ala Tyr Asn Ala Tyr Gln Thr Met Met Asn
                85                  90                  95

Phe Leu Ile Val Val Gly Phe Met Tyr Glu Val His Ser Thr Gly Met
            100                 105                 110

Arg Tyr Trp Gly Ser Arg Ile Asp Thr Ser Thr Lys Gly Leu Gly Leu
        115                 120                 125

Gly Phe Leu Ile Tyr Ala His Tyr His Asn Lys Tyr Val Glu Tyr Val
    130                 135                 140

Asp Thr Leu Phe Met Ile Leu Arg Lys Lys Asn Asn Gln Ile Ser Phe
145                 150                 155                 160

Leu His Val Tyr His His Ser Leu Leu Thr Trp Ala Trp Trp Ala Val
                165                 170                 175

Val Tyr Trp Ala Pro Gly Gly Asp Ala Trp Phe Gly Ala Cys Tyr Asn
            180                 185                 190

Ser Phe Ile His Val Leu Met Tyr Ser Tyr Tyr Leu Phe Ala Thr Phe
        195                 200                 205

Gly Ile Arg Cys Pro Trp Lys Lys Met Leu Thr Gln Leu Gln Met Val
    210                 215                 220

Gln Phe Cys Phe Cys Phe Ala His Ala Met Tyr Val Gly Trp Leu Gly
225                 230                 235                 240

His Glu Val Tyr Pro Arg Trp Leu Thr Ala Leu Gln Ala Phe Val Met
                245                 250                 255

Leu Asn Met Leu Val Leu Phe Gly Asn Phe Tyr Met Lys Ser Tyr Ser
            260                 265                 270
```

```
Lys Ala Ser Lys Leu Glu Pro Ala Ser Pro Val Ser Pro Ala Ser Leu
    275                 280                 285

Ala Gln Lys Pro Phe Glu Asn Ala Lys Val Lys
    290                 295

<210> SEQ ID NO 132
<211> LENGTH: 3620
<212> TYPE: DNA
<213> ORGANISM: Artificial Sequence
<220> FEATURE:
<223> OTHER INFORMATION: Plasmid pEaC20ES

<400> SEQUENCE: 132
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg     120 ttggcgggtg tcgggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaagggg ggatgtgctg caaggcgatt aagttgggta acgccagggt     360
tttcccagtc acgacgttgt aaaacgacgg ccagtgaatt cgagctcggt acctcgcgaa     420
tgcatctaga tccatggccg agggcaagtc cgacggtccc gtcgttaccc tccagtccat     480
gtggaagccc ctggctctca tggccatcga cgtcggcatc ctggtcaacg tgcgacggaa     540
ggccttcacc gagttcgacg gacactcgaa cgtcttcgcc gatcccgtgt acattccctt     600
tgtcatgaac ctgttctacc tcaccatgat ctttgctggc tgccgatgga tgaagactcg     660
agaacccttc gagatcaagt cctacatgtt tgcctacaac gcttaccaga caatgatgaa     720 cttttctcatt gtggtcggct tcatgtatga ggttcactcc accggtatgc gatactgggg     780
atccagaatc gacacttcta ccaagggctt gggactgggt ttcctcatct atgcccatta     840
ccacaacaag tacgtggagt acgtcgacac cctgttcatg attctgcgga gaaaaaacaa     900
tcagatctcg ttccttcacg tttaccacca ttccctgctc acttgggcat ggtgggctgt     960
ggtctactgg gctcctggcg gagatgcctg gttcggtgcc tgttacaact ccttcatcca    1020
cgttctcatg tactcctact atctgttttg caccttcggc attcgatgtc cctggaaaaa    1080
gatgctcacc cagttgcaaa tggtccagtt ctgcttttgc ttcgctcatg ccatgtacgt    1140
tggatggctt ggtcacgagg tgtaccctcg atggctcact gctctgcagg cctttgtgat    1200
gctcaacatg ctggtcctct ttggcaactt ctacatgaag tcttactcca aggcgagcaa    1260
gctcgaacca gcctctcccg tgtcgcctgc ctctcttgct cagaagccct cgagaacgc    1320 caaggtcaag taagcggccg catcggatcc cgggcccgtc gactgcagag gcctgcatgc    1380
aagcttggcg taatcatggt catagctgtt cctgtgtga aattgttatc cgctcacaat    1440
tccacacaac atacgagccg gaagcataaa gtgtaaagcc tggggtgcct aatgagtgag    1500
ctaactcaca ttaattgcgt tgcgctcact gcccgctttc cagtcgggaa acctgtcgtg    1560
ccagctgcat taatgaatcg gccaacgcgc ggggagaggc ggtttgcgta ttgggcgctc    1620
ttccgcttcc tcgctcactg actcgctgcg ctcggtcgtt cggctgcggc gagcggtatc    1680
agctcactca aaggcggtaa tacggttatc cacagaatca ggggataacg caggaaagaa    1740
catgtgagca aaaggccagc aaaaggccag gaaccgtaaa aaggccgcgt tgctggcgtt    1800
tttccatagg ctccgccccc ctgacgagca tcacaaaaat cgacgctcaa gtcagaggtg    1860
gcgaaacccg acaggactat aaagatacca ggcgtttccc cctggaagct ccctcgtgcg    1920
```

```
ctctcctgtt ccgaccctgc cgcttaccgg atacctgtcc gcctttctcc cttcgggaag    1980
cgtggcgctt tctcatagct cacgctgtag gtatctcagt tcggtgtagg tcgttcgctc    2040
caagctgggc tgtgtgcacg aaccccccgt tcagcccgac cgctgcgcct tatccggtaa    2100
ctatcgtctt gagtccaacc cggtaagaca cgacttatcg ccactggcag cagccactgg    2160
taacaggatt agcagagcga ggtatgtagg cggtgctaca gagttcttga agtggtggcc    2220
taactacggc tacactagaa gaacagtatt tggtatctgc gctctgctga agccagttac    2280
cttcggaaaa agagttggta gctcttgatc cggcaaacaa accaccgctg gtagcggtgg    2340
tttttttgtt tgcaagcagc agattacgcg cagaaaaaaa ggatctcaag aagatccttt    2400
gatcttttct acggggtctg acgctcagtg aacgaaaac tcacgttaag ggattttggt    2460
catgagatta tcaaaaagga tcttcaccta gatcctttta aattaaaaat gaagttttaa    2520
atcaatctaa agtatatatg agtaaacttg gtctgacagt taccaatgct taatcagtga    2580
ggcacctatc tcagcgatct gtctatttcg ttcatccata gttgcctgac tccccgtcgt    2640
gtagataact acgatacggg agggcttacc atctggcccc agtgctgcaa tgataccgcg    2700
agacccacgc tcaccggctc cagatttatc agcaataaac cagccagccg aagggccga    2760 gcgcagaagt ggtcctgcaa ctttatccgc ctccatccag tctattaatt gttgccggga    2820
agctagagta agtagttcgc cagttaatag tttgcgcaac gttgttgcca ttgctacagg    2880
catcgtggtg tcacgctcgt cgtttggtat ggcttcattc agctccggtt cccaacgatc    2940
aaggcgagtt acatgatccc ccatgttgtg caaaaaagcg gttagctcct tcggtcctcc    3000
gatcgttgtc agaagtaagt tggccgcagt gttatcactc atggttatgg cagcactgca    3060
taattctctt actgtcatgc catccgtaag atgcttttct gtgactggtg agtactcaac    3120
caagtcattc tgagaatagt gtatgcggcg accgagttgc tcttgcccgg cgtcaatacg    3180
ggataatacc gcgccacata gcagaacttt aaaagtgctc atcattggaa acgttcttc    3240 ggggcgaaaa ctctcaagga tcttaccgct gttgagatcc agttcgatgt aacccactcg    3300
tgcacccaac tgatcttcag catcttttac tttcaccagc gtttctgggt gagcaaaaac    3360
aggaaggcaa aatgccgcaa aaaagggaat aagggcgaca cggaaatgtt gaatactcat    3420
actcttcctt tttcaatatt attgaagcat ttatcagggt tattgtctca tgagcggata    3480
catatttgaa tgtatttaga aaaataaaca aataggggtt ccgcgcacat ttccccgaaa    3540
agtgccacct gacgtctaag aaaccattat tatcatgaca ttaacctata aaaataggcg    3600
tatcacgagg ccctttcgtc                                                3620
```

<210> SEQ ID NO 133
<211> LENGTH: 1936
<212> TYPE: DNA
<213> ORGANISM: Yarrowia lipolytica
<220> FEATURE:
<221> NAME/KEY: CDS
<222> LOCATION: (283)..(1539)
<300> PUBLICATION INFORMATION:
<302> TITLE: A DELTA-12 DESATURASE GENE SUITABLE FOR ALTERING LEVELS OF
      POLYUNSATURATED FATTY ACIDS IN OLEAGINOUS YEASTS
<310> PATENT DOCUMENT NUMBER: U.S. 7,214,491
<311> PATENT FILING DATE: 2004-05-06
<312> PUBLICATION DATE: 2007-05-08
<313> RELEVANT RESIDUES: (1)..(1936)
<300> PUBLICATION INFORMATION:
<302> TITLE: A DELTA-12 DESATURASE GENE SUITABLE FOR ALTERING LEVELS OF
      POLYUNSATURATED FATTY ACIDS IN OLEAGINOUS YEASTS
<310> PATENT DOCUMENT NUMBER: WO 2004/104167
<311> PATENT FILING DATE: 2004-05-07
<312> PUBLICATION DATE: 2004-12-02
<313> RELEVANT RESIDUES: (1)..(1936)

<400> SEQUENCE: 133

```
cgtagttata tacaagaggt agatgcgtgc tggtgttaga ggggctctca ggattaggag      60
gaaaatttga cattggccct caacatataa cctcgggtgt gcctctgttt accctcagct     120
tttgcttgtc cccaagtcag tcacgccagg ccaaaaaggt tggtggattg acagggagaa     180
aaaaaaaagc ctagtgggtt taaactcgag gtaagacatt gaaatatata ccggtcggca     240
tcctgagtcc ctttctcgta ttccaacaga ccgaccatag aa atg gat tcg acc        294
                                                Met Asp Ser Thr
                                                 1 acg cag acc aac acc ggc acc ggc aag gtg gcc gtg cag ccc ccc acg       342
Thr Gln Thr Asn Thr Gly Thr Gly Lys Val Ala Val Gln Pro Pro Thr
 5                  10                  15                  20 gcc ttc att aag ccc att gag aag gtg tcc gag ccc gtc tac gac acc       390
Ala Phe Ile Lys Pro Ile Glu Lys Val Ser Glu Pro Val Tyr Asp Thr
                 25                  30                  35 ttt ggc aac gag ttc act cct cca gac tac tct atc aag gat att ctg       438
Phe Gly Asn Glu Phe Thr Pro Pro Asp Tyr Ser Ile Lys Asp Ile Leu
             40                  45                  50 gat gcc att ccc cag gag tgc tac aag cgg tcc tac gtt aag tcc tac       486
Asp Ala Ile Pro Gln Glu Cys Tyr Lys Arg Ser Tyr Val Lys Ser Tyr
         55                  60                  65 tcg tac gtg gcc cga gac tgc ttc ttt atc gcc gtt ttt gcc tac atg       534
Ser Tyr Val Ala Arg Asp Cys Phe Phe Ile Ala Val Phe Ala Tyr Met
     70                  75                  80 gcc tac gcg tac ctg cct ctt att ccc tcg gct tcc ggc cga gct gtg       582
Ala Tyr Ala Tyr Leu Pro Leu Ile Pro Ser Ala Ser Gly Arg Ala Val
 85                  90                  95                 100 gcc tgg gcc atg tac tcc att gtc cag ggt ctg ttt ggc acc ggt ctg       630
Ala Trp Ala Met Tyr Ser Ile Val Gln Gly Leu Phe Gly Thr Gly Leu
                105                 110                 115 tgg gtt ctt gcc cac gag tgt ggc cac tct gct ttc tcc gac tct aac       678
Trp Val Leu Ala His Glu Cys Gly His Ser Ala Phe Ser Asp Ser Asn
            120                 125                 130 acc gtc aac aac gtc acc gga tgg gtt ctg cac tcc tcc atg ctg gtc       726
Thr Val Asn Asn Val Thr Gly Trp Val Leu His Ser Ser Met Leu Val
        135                 140                 145 cct tac tac gcc tgg aag ctg acc cac tcc atg cac cac aag tcc act       774
Pro Tyr Tyr Ala Trp Lys Leu Thr His Ser Met His His Lys Ser Thr
    150                 155                 160 ggt cac ctc acc cgt gat atg gtg ttt gtg ccc aag gac cga aag gag       822
Gly His Leu Thr Arg Asp Met Val Phe Val Pro Lys Asp Arg Lys Glu
165                 170                 175                 180 ttt atg gag aac cga ggc gcc cat gac tgg tct gag ctt gct gag gac       870
Phe Met Glu Asn Arg Gly Ala His Asp Trp Ser Glu Leu Ala Glu Asp
                185                 190                 195 gct ccc ctc atg acc ctc tac ggc ctc atc acc cag cag gtg ttt gga       918
Ala Pro Leu Met Thr Leu Tyr Gly Leu Ile Thr Gln Gln Val Phe Gly
            200                 205                 210 tgg cct ctg tat ctg ctg tct tac gtt acc gga cag aag tac ccc aag       966
Trp Pro Leu Tyr Leu Leu Ser Tyr Val Thr Gly Gln Lys Tyr Pro Lys
        215                 220                 225 ctc aac aaa tgg gct gtc aac cac ttc aac ccc aac gcc ccg ctg ttt      1014
Leu Asn Lys Trp Ala Val Asn His Phe Asn Pro Asn Ala Pro Leu Phe
    230                 235                 240 gag aag aag gac tgg ttc aac atc tgg atc tct aac gtc ggt att ggt      1062
Glu Lys Lys Asp Trp Phe Asn Ile Trp Ile Ser Asn Val Gly Ile Gly
245                 250                 255                 260 atc acc atg tcc gtc atc gca tac tcc atc aac cga tgg ggc ctg gct      1110
```

```
Ile Thr Met Ser Val Ile Ala Tyr Ser Ile Asn Arg Trp Gly Leu Ala
             265                 270                 275 tcc gtc acc ctc tac tac ctg atc ccc tac ctg tgg gtc aac cac tgg     1158
Ser Val Thr Leu Tyr Tyr Leu Ile Pro Tyr Leu Trp Val Asn His Trp
             280                 285                 290 ctc gtg gcc atc acc tac ctg cag cac acc gac ccc act ctg ccc cac     1206
Leu Val Ala Ile Thr Tyr Leu Gln His Thr Asp Pro Thr Leu Pro His
             295                 300                 305 tac cac gcc gac cag tgg aac ttc acc cga gga gcc gcc acc atc         1254
Tyr His Ala Asp Gln Trp Asn Phe Thr Arg Gly Ala Ala Thr Ile
         310                 315                 320 gac cga gag ttt ggc ttc atc ggc tcc ttc tgc ttc cat gac atc atc     1302
Asp Arg Glu Phe Gly Phe Ile Gly Ser Phe Cys Phe His Asp Ile Ile
325                 330                 335                 340 gag acc cac gtt ctg cac cac tac gtg tct cga att ccc ttc tac aac     1350
Glu Thr His Val Leu His His Tyr Val Ser Arg Ile Pro Phe Tyr Asn
                345                 350                 355 gcc cga atc gcc act gag aag atc aag aag gtc atg ggc aag cac tac     1398
Ala Arg Ile Ala Thr Glu Lys Ile Lys Lys Val Met Gly Lys His Tyr
             360                 365                 370 cga cac gac gac acc aac ttc atc aag tct ctt tac act gtc gcc cga     1446
Arg His Asp Asp Thr Asn Phe Ile Lys Ser Leu Tyr Thr Val Ala Arg
             375                 380                 385 acc tgc cag ttt gtt gaa ggt aag gaa ggc att cag atg ttt aga aac     1494
Thr Cys Gln Phe Val Glu Gly Lys Glu Gly Ile Gln Met Phe Arg Asn
             390                 395                 400 gtc aat gga gtc gga gtt gct cct gac ggc ctg cct tct aaa aag         1539
Val Asn Gly Val Gly Val Ala Pro Asp Gly Leu Pro Ser Lys Lys
405                 410                 415 tagagctaga aatgttattt gattgtgttt taactgaaca gcaccgagcc cgaggctaag   1599
ccaagcgaag ccgaggggtt gtgtagtcca tggacgtaac gagtaggcga tatcaccgca   1659
ctcggcactg cgtgtctgcg ttcatgggcg aagtcacatt acgctgacaa ccgttgtagt   1719 ttcccttag tatcaatact gttacaagta ccggtctcgt actcgtactg atacgaatct    1779
gtgggaagaa gtcacccttta tcagaccttc atactgatgt ttcggatatc aatagaactg  1839
gcatagagcc gttaaagaag tttcacttaa tcactccaac cctcctactt gtagattcaa   1899
gcagatcgat aagatggatt tgatggtcag tgctagc                            1936
```

<210> SEQ ID NO 134
<211> LENGTH: 419
<212> TYPE: PRT
<213> ORGANISM: Yarrowia lipolytica

<400> SEQUENCE: 134

```
Met Asp Ser Thr Thr Gln Thr Asn Thr Gly Thr Gly Lys Val Ala Val
1               5                   10                  15

Gln Pro Pro Thr Ala Phe Ile Lys Pro Ile Glu Lys Val Ser Glu Pro
             20                  25                  30

Val Tyr Asp Thr Phe Gly Asn Glu Phe Thr Pro Pro Asp Tyr Ser Ile
         35                  40                  45

Lys Asp Ile Leu Asp Ala Ile Pro Gln Glu Cys Tyr Lys Arg Ser Tyr
     50                  55                  60

Val Lys Ser Tyr Ser Tyr Val Ala Arg Asp Cys Phe Phe Ile Ala Val
65                   70                  75                  80

Phe Ala Tyr Met Ala Tyr Ala Tyr Leu Pro Leu Ile Pro Ser Ala Ser
                 85                  90                  95

Gly Arg Ala Val Ala Trp Ala Met Tyr Ser Ile Val Gln Gly Leu Phe
```

```
                    100                 105                 110
Gly Thr Gly Leu Trp Val Leu Ala His Glu Cys Gly His Ser Ala Phe
            115                 120                 125

Ser Asp Ser Asn Thr Val Asn Asn Val Thr Gly Trp Val Leu His Ser
        130                 135                 140

Ser Met Leu Val Pro Tyr Tyr Ala Trp Lys Leu Thr His Ser Met His
145                 150                 155                 160

His Lys Ser Thr Gly His Leu Thr Arg Asp Met Val Phe Val Pro Lys
                165                 170                 175

Asp Arg Lys Glu Phe Met Glu Asn Arg Gly Ala His Asp Trp Ser Glu
            180                 185                 190

Leu Ala Glu Asp Ala Pro Leu Met Thr Leu Tyr Gly Leu Ile Thr Gln
        195                 200                 205

Gln Val Phe Gly Trp Pro Leu Tyr Leu Leu Ser Tyr Val Thr Gly Gln
    210                 215                 220

Lys Tyr Pro Lys Leu Asn Lys Trp Ala Val Asn His Phe Asn Pro Asn
225                 230                 235                 240

Ala Pro Leu Phe Glu Lys Lys Asp Trp Phe Asn Ile Trp Ile Ser Asn
                245                 250                 255

Val Gly Ile Gly Ile Thr Met Ser Val Ile Ala Tyr Ser Ile Asn Arg
            260                 265                 270

Trp Gly Leu Ala Ser Val Thr Leu Tyr Tyr Leu Ile Pro Tyr Leu Trp
        275                 280                 285

Val Asn His Trp Leu Val Ala Ile Thr Tyr Leu Gln His Thr Asp Pro
    290                 295                 300

Thr Leu Pro His Tyr His Ala Asp Gln Trp Asn Phe Thr Arg Gly Ala
305                 310                 315                 320

Ala Ala Thr Ile Asp Arg Glu Phe Gly Phe Ile Gly Ser Phe Cys Phe
                325                 330                 335

His Asp Ile Ile Glu Thr His Val Leu His His Tyr Val Ser Arg Ile
            340                 345                 350

Pro Phe Tyr Asn Ala Arg Ile Ala Thr Glu Lys Ile Lys Lys Val Met
        355                 360                 365

Gly Lys His Tyr Arg His Asp Asp Thr Asn Phe Ile Lys Ser Leu Tyr
    370                 375                 380

Thr Val Ala Arg Thr Cys Gln Phe Val Glu Gly Lys Glu Gly Ile Gln
385                 390                 395                 400

Met Phe Arg Asn Val Asn Gly Val Gly Val Ala Pro Asp Gly Leu Pro
                405                 410                 415

Ser Lys Lys

<210> SEQ ID NO 135
<211> LENGTH: 7904
<212> TYPE: DNA
<213> ORGANISM: Artificial Sequence
<220> FEATURE:
<223> OTHER INFORMATION: Plasmid pZuFmEgC20ES

<400> SEQUENCE: 135
catggctgac tctcccgtca tcaacctctc caccatgtgg aagcctctgt cgctcatggc      60
cttggatctt gctgttctgg acacgtctg gaagcaggca caacaggagg ctccatctc     120 ggcttacgcc gactctgtgt ggactcccct catcatgtcc ggtctgtacc tctccatgat    180
cttcgtggga tgtcgatgga tgaagaaccg agagcccttc gaaatcaaga cctacatgtt    240
tgcctacaac ctgtaccaga ccctcatgaa cctttgcatt gtgctgggct tcctctacca    300
```

```
ggtccacgct accggtatgc gattctgggg atctggcgtg gaccgatcgc ccaagggtct    360
gggaattggc ttttcatct atgcccatta ccacaacaag tacgtcgagt acttcgacac     420
actcttcatg gtgctgcgga aaagaacaa ccagatttcc tttcttcacg tctaccatca    480
cgctctgctc acctgggctt ggtttgccgt ggtctacttc gctcctggag gtgacggctg    540
gtttggagcc tgctacaatt cctccattca tgtcctgatg tactcttact atctgcttgc    600
caccttcggc atctcctgtc cctggaaaaa gatcctcacc cagctgcaaa tggttcagtt    660
ctgcttttgc ttcacccact cgatctacgt gtggatttgc ggttccgaaa tctaccctcg    720
acccttgact gctctccagt ccttcgtgat ggtcaacatg ctggttctct ttggcaactt    780
ctacgtcaag cagtattctc agaagaatgg aaagcccgag aacggtgcca ctcctgagaa    840
cggtgccaag cctcagccct gcgagaacgg caccgtcgag aagcgagaga cgacactgc    900
caacgttcga taagcggccg caagtgtgga tggggaagtg agtgcccggt tctgtgtgca    960
caattggcaa tccaagatgg atggattcaa cacaggata tagcgagcta cgtggtggtg    1020
cgaggatata gcaacggata tttatgtttg acacttgaga atgtacgata caagcactgt    1080
ccaagtacaa tactaaacat actgtacata ctcatactcg tacccgggca acggtttcac    1140
ttgagtgcag tggctagtgc tcttactcgt acagtgtgca atactgcgta tcatagtctt    1200
tgatgtatat cgtattcatt catgttagtt gcgtacgagc cggaagcata aagtgtaaag    1260
cctggggtgc ctaatgagtg agctaactca cattaattgc gttgcgctca ctgcccgctt    1320
tccagtcggg aaacctgtcg tgccagctgc attaatgaat cggccaacgc gcggggagag    1380
gcggtttgcg tattgggcgc tcttccgctt cctcgctcac tgactcgctg cgctcggtcg    1440
ttcggctgcg gcgagcggta tcagctcact caaaggcggt aatacggtta ccacagaat    1500
caggggataa cgcaggaaag aacatgtgag caaaaggcca gcaaaaggcc aggaaccgta    1560
aaaaggccgc gttgctggcg ttttttccata ggctccgccc ccctgacgag catcacaaaa    1620
atcgacgctc aagtcagagg tggcgaaacc cgacaggact ataaagatac caggcgtttc    1680
cccctggaag ctccctcgtg cgctctcctg ttccgaccct gccgcttacc ggatacctgt    1740
ccgcctttct cccttcggga agcgtggcgc tttctcatag ctcacgctgt aggtatctca    1800
gttcggtgta ggtcgttcgc tccaagctgg gctgtgtgca cgaacccccc gttcagcccg    1860
accgctgcgc cttatccggt aactatcgtc ttgagtccaa cccggtaaga cacgacttat    1920
cgccactggc agcagccact ggtaacagga ttagcagagc gaggtatgta ggcggtgcta    1980
cagagttctt gaagtggtgg cctaactacg gctacactag aaggacagta tttggtatct    2040
gcgctctgct gaagccagtt accttcggaa aaagagttgg tagctcttga tccggcaaac    2100
aaaccaccgc tggtagcggt ggtttttttg tttgcaagca gcagattacg cgcagaaaaa    2160
aaggatctca agaagatcct ttgatctttt ctacggggtc tgacgctcag tggaacgaaa    2220
actcacgtta agggattttg gtcatgagat tatcaaaaag gatcttcacc tagatccttt    2280
taaattaaaa atgaagtttt aaatcaatct aaagtatata tgagtaaact ggtctgaca    2340
gttaccaatg cttaatcagt gaggcaccta tctcagcgat ctgtctattt cgttcatcca    2400
tagttgcctg actccccgtc gtgtagataa ctacgatacg ggagggctta ccatctggcc    2460
ccagtgctgc aatgataccg cgagacccac gctcaccggc tccagattta tcagcaataa    2520
accagccagc cggaagggcc gagcgcagaa gtggtcctgc aactttatcc gcctccatcc    2580
agtctattaa ttgttgccgg gaagctagag taagtagttc gccagttaat agtttgcgca    2640
acgttgttgc cattgctaca ggcatcgtgg tgtcacgctc gtcgtttggt atggcttcat    2700
```

```
tcagctccgg ttcccaacga tcaaggcgag ttacatgatc ccccatgttg tgcaaaaaag    2760
cggttagctc cttcggtcct ccgatcgttg tcagaagtaa gttggccgca gtgttatcac    2820
tcatggttat ggcagcactg cataattctc ttactgtcat gccatccgta agatgctttt    2880
ctgtgactgg tgagtactca accaagtcat tctgagaata gtgtatgcgg cgaccgagtt    2940
gctcttgccc ggcgtcaata cgggataata ccgcgccaca tagcagaact ttaaaagtgc    3000
tcatcattgg aaaacgttct tcggggcgaa aactctcaag gatcttaccg ctgttgagat    3060
ccagttcgat gtaacccact cgtgcaccca actgatcttc agcatctttt actttcacca    3120
gcgtttctgg gtgagcaaaa acaggaaggc aaaatgccgc aaaaaaggga ataagggcga    3180
cacggaaatg ttgaatactc atactcttcc tttttcaata ttattgaagc atttatcagg    3240
gttattgtct catgagcgga tacatatttg aatgtattta gaaaaataaa caaatagggg    3300
ttccgcgcac atttccccga aaagtgccac ctgacgcgcc ctgtagcggc gcattaagcg    3360
cggcgggtgt ggtggttacg cgcagcgtga ccgctacact tgccagcgcc ctagcgcccg    3420
ctcctttcgc tttcttccct tcctttctcg ccacgttcgc cggctttccc cgtcaagctc    3480
taaatcgggg gctccctttta gggttccgat ttagtgcttt acggcacctc gaccccaaaa    3540
aacttgatta gggtgatggt tcacgtagtg ggccatcgcc ctgatagacg gttttcgcc    3600 ctttgacgtt ggagtccacg ttctttaata gtggactctt gttccaaact ggaacaacac    3660
tcaaccctat ctcggtctat tcttttgatt tataagggat tttgccgatt tcggcctatt    3720
ggttaaaaaa tgagctgatt taacaaaaat ttaacgcgaa ttttaacaaa atattaacgc    3780
ttacaatttc cattcgccat tcaggctgcg caactgttgg gaagggcgat cggtgcgggc    3840
ctcttcgcta ttacgccagc tggcgaaagg gggatgtgct gcaaggcgat taagttgggt    3900
aacgccaggg ttttcccagt cacgacgttg taaaacgacg gccagtgaat tgtaatacga    3960
ctcactatag ggcgaattgg gtaccgggcc cccctcgag gtcgatggtg tcgataagct    4020
tgatatcgaa ttcatgtcac acaaaccgat cttcgcctca aggaaaccta attctacatc    4080
cgagagactg ccgagatcca gtctacactg attaattttc gggccaataa tttaaaaaaa    4140
tcgtgttata taatattata tgtattatat atatacatca tgatgatact gacagtcatg    4200
tcccattgct aaatagacag actccatctg ccgcctccaa ctgatgttct caatatttaa    4260
ggggtcatct cgcattgttt aataataaac agactccatc taccgcctcc aaatgatgtt    4320
ctcaaaatat attgtatgaa cttattttta ttacttagta ttattagaca acttacttgc    4380
tttatgaaaa acacttccta tttaggaaac aatttataat ggcagttcgt tcatttaaca    4440
atttatgtag aataaatgtt ataaatgcgt atgggaaatc ttaaatatgg atagcataaa    4500
tgatatctgc attgcctaat tcgaaatcaa cagcaacgaa aaaaatccct tgtacaacat    4560
aaatagtcat cgagaaatat caactatcaa agaacagcta ttcacacgtt actattgaga    4620
ttattattgg acgagaatca cacactcaac tgtctttctc tcttctagaa atacaggtac    4680
aagtatgtac tattctcatt gttcatactt ctagtcattt catcccacat attccttgga    4740
tttctctcca atgaatgaca ttctatcttg caaattcaac aattataata agatataccaa   4800 aagtagcgt atagtggcaa tcaaaaagct tctctggtgt gcttctcgta tttattttta    4860
ttctaatgat ccattaaagg tatatattta tttcttgtta tataatcctt tgtttatta    4920 catgggctgg atacataaag gtattttgat ttaattttt gcttaaattc aatcccccct    4980
cgttcagtgt caactgtaat ggtaggaaat taccatactt ttgaagaagc aaaaaaaatg    5040
aaagaaaaaa aaaatcgtat ttccaggtta gacgttccgc agaatctaga atgcggtatg    5100
```

```
cggtacattg ttcttcgaac gtaaaagttg cgctccctga gatattgtac attttttgctt    5160 ttacaagtac aagtacatcg tacaactatg tactactgtt gatgcatcca caacagtttg    5220
ttttgttttt ttttgttttt ttttttttcta atgattcatt accgctatgt atacctactt    5280
gtacttgtag taagccgggt tattggcgtt caattaatca tagacttatg aatctgcacg    5340
gtgtgcgctg cgagttactt ttagcttatg catgctactt gggtgtaata ttgggatctg    5400
ttcggaaatc aacggatgct caatcgattt cgacagtaat taattaagtc atacacaagt    5460
cagctttctt cgagcctcat ataagtataa gtagttcaac gtattagcac tgtacccagc    5520
atctccgtat cgagaaacac aacaacatgc cccattggac agatcatgcg gatacacagg    5580
ttgtgcagta tcatacatac tcgatcagac aggtcgtctg accatcatac aagctgaaca    5640
agcgctccat acttgcacgc tctctatata cacagttaaa ttacatatcc atagtctaac    5700
ctctaacagt taatcttctg gtaagcctcc cagccagcct tctggtatcg cttggcctcc    5760
tcaataggat ctcggttctg gccgtacaga cctcggccga caattatgat atccgttccg    5820
gtagacatga catcctcaac agttcggtac tgctgtccga gagcgtctcc cttgtcgtca    5880
agacccaccc cggggtcag aataagccag tcctcagagt cgcccttagg tcggttctgg    5940
gcaatgaagc caaccacaaa ctcggggtcg gatcgggcaa gctcaatggt ctgcttggag    6000
tactcgccag tggccagaga gcccttgcaa gacagctcgg ccagcatgag cagacctctg    6060
gccagcttct cgttgggaga ggggactagg aactccttgt actgggagtt ctcgtagtca    6120
gagacgtcct ccttcttctg ttcagagaca gtttcctcgg caccagctcg caggccagca    6180
atgattccgg ttccgggtac accgtgggcg ttggtgatat cggaccactc ggcgattcgg    6240
tgacaccggt actggtgctt gacagtgttg ccaatatctg cgaactttct gtcctcgaac    6300
aggaagaaac cgtgcttaag agcaagttcc ttgaggggga gcacagtgcc ggcgtaggtg    6360
aagtcgtcaa tgatgtcgat atgggttttg atcatgcaca cataaggtcc gaccttatcg    6420
gcaagctcaa tgagctcctt ggtggtggta acatccagag aagcacacag gttggttttc    6480
ttggctgcca cgagcttgag cactcgagcg gcaaaggcgg acttgtggac gttagctcga    6540
gcttcgtagg agggcatttt ggtggtgaag aggagactga aataaattta gtctgcagaa    6600 cttttttatcg gaaccttatc tggggcagtg aagtatatgt tatggtaata gttacgagtt    6660
agttgaactt atagatagac tggactatac ggctatcggt ccaaattaga agaacgtca    6720 atggctctct gggcgtcgcc tttgccgaca aaaatgtgat catgatgaaa gccagcaatg    6780
acgttgcagc tgatattgtt gtcggccaac cgcgccgaaa acgcagctgt cagacccaca    6840
gcctccaacg aagaatgtat cgtcaaagtg atccaagcac actcatagtt ggagtcgtac    6900
tccaaaggcg gcaatgacga gtcagacaga tactcgtcga cgtttaaaca gtgtacgcag    6960
atctactata gaggaacatt taaattgccc cggagaagac ggccaggccg cctagatgac    7020
aaattcaaca actcacagct gactttctgc cattgccact aggggggggc ttttttatat    7080
ggccaagcca agctctccac gtcggttggg ctgcacccaa caataaatgg gtagggttgc    7140
accaacaaag ggatgggatg gggggtagaa gatacgagga taacgggggct caatggcaca    7200 aataagaacg aatactgcca ttaagactcg tgatccagcg actgacacca ttgcatcatc    7260
taagggcctc aaaactacct cggaactgct gcgctgatct ggacaccaca gaggttccga    7320
gcactttagg ttgcaccaaa tgtcccacca ggtgcaggca gaaaacgctg aacagcgtg    7380 tacagttgt cttaacaaaa agtgagggcg ctgaggtcga gcagggtggt gtgacttgtt    7440
atagccttta gagctgcgaa agcgcgtatg gatttggctc atcaggccag attgagggtc    7500
```

```
tgtggacaca tgtcatgtta gtgtacttca atcgccccct ggatatagcc ccgacaatag    7560
gccgtggcct cattttttg ccttccgcac atttccattg ctcgataccc acaccttgct     7620
tctcctgcac ttgccaacct taatactggt ttacattgac caacatctta caagcggggg    7680
gcttgtctag ggtatatata aacagtggct ctcccaatcg gttgccagtc tcttttttcc    7740
tttctttccc cacagattcg aaatctaaac tacacatcac agaattccga gccgtgagta    7800
tccacgacaa gatcagtgtc gagacgacgc gttttgtgta atgacacaat ccgaaagtcg    7860
ctagcaacac acactctcta cacaaactaa cccagctctg gtac                    7904
```

<210> SEQ ID NO 136
<211> LENGTH: 7892
<212> TYPE: DNA
<213> ORGANISM: Artificial Sequence
<220> FEATURE:
<223> OTHER INFORMATION: Plasmid pZuFmEaC20ES

<400> SEQUENCE: 136

```
catggccgag ggcaagtccg acggtcccgt cgttaccctc cagtccatgt ggaagcccct      60
ggctctcatg gccatcgacg tcggcatcct ggtcaacgtg cgacggaagg ccttcaccga     120
gttcgacgga cactcgaacg tcttcgccga tcccgtgtac attccctttg tcatgaacct    180
gttctacctc accatgatct tgctggctg ccgatggatg aagactcgag aacccttcga     240
gatcaagtcc tacatgtttg cctacaacgc ttaccagaca atgatgaact ttctcattgt    300
ggtcggcttc atgtatgagg ttcactccac cggtatgcga tactggggat ccagaatcga    360
cacttctacc aagggcttgg gactgggttt cctcatctat gcccattacc acaacaagta    420
cgtggagtac gtcgacaccc tgttcatgat tctgcggaag aaaaacaatc agatctcgtt    480
ccttcacgtt taccaccatt ccctgctcac ttgggcatgg tgggctgtgg tctactgggc    540
tcctggcgga gatgcctggt cggtgcctg ttacaactcc ttcatccacg ttctcatgta     600
ctcctactat ctgtttgcca ccttcggcat tcgatgtccc tggaaaaaga tgctcaccca    660
gttgcaaatg gtccagttct gctttttgct tcgctcatgcc atgtacgttg gatggcttgg    720
tcacgaggtg taccctcgat ggctcactgc tctgcaggcc tttgtgatgc tcaacatgct    780
ggtcctcttt ggcaacttct acatgaagtc ttactccaag gcgagcaagc tcgaaccagc    840
ctctcccgtg tcgcctgcct ctcttgctca gaagcccttc gagaacgcca aggtcaagta    900
agcggccgca agtgtggatg gggaagtgag tgcccggttc tgtgtgcaca attggcaatc    960
caagatggat ggattcaaca cagggatata gcgagctacg tggtggtgcg aggatatagc   1020
aacggatatt tatgtttgac acttgagaat gtacgataca agcactgtcc aagtacaata   1080
ctaaacatac tgtacatact catactcgta cccgggcaac ggtttcactt gagtgcagtg   1140
gctagtgctc ttactcgtac agtgtgcaat actgcgtatc atagtctttg atgtatatcg   1200
tattcattca tgttagttgc gtacgagccg gaagcataaa gtgtaaagcc tggggtgcct   1260
aatgagtgag ctaactcaca ttaattgcgt tgcgctcact gcccgctttc cagtcgggaa   1320
acctgtcgtg ccagctgcat taatgaatcg gccaacgcgc ggggagaggc ggtttgcgta   1380
ttgggcgctc ttccgcttcc tcgctcactg actcgctgcg ctcggtcgtt cggctgcggc   1440
gagcggtatc agctcactca aaggcggtaa tacggttatc cacagaatca ggggataacg   1500
caggaaagaa catgtgagca aaaggccagc aaaaggccag gaaccgtaaa aaggccgcgt   1560
tgctggcgtt tttccatagg ctccgccccc ctgacgagca tcacaaaaat cgacgctcaa   1620
gtcagaggtg gcgaaacccg acaggactat aaagatacca ggcgtttccc cctggaagct   1680
```

```
ccctcgtgcg ctctcctgtt ccgaccctgc cgcttaccgg ataccgtcc gcctttctcc    1740 cttcgggaag cgtggcgctt tctcatagct cacgctgtag gtatctcagt tcggtgtagg    1800
tcgttcgctc caagctgggc tgtgtgcacg aaccccccgt tcagcccgac cgctgcgcct    1860
tatccggtaa ctatcgtctt gagtccaacc cggtaagaca cgacttatcg ccactggcag    1920
cagccactgg taacaggatt agcagagcga ggtatgtagg cggtgctaca gagttcttga    1980
agtggtggcc taactacggc tacactagaa ggacagtatt tggtatctgc gctctgctga    2040
agccagttac cttcggaaaa agagttggta gctcttgatc cggcaaacaa accaccgctg    2100
gtagcggtgg ttttttttgtt tgcaagcagc agattacgcg cagaaaaaaa ggatctcaag    2160
aagatccttt gatcttttct acggggtctg acgctcagtg gaacgaaaac tcacgttaag    2220
ggattttggt catgagatta tcaaaaagga tcttcaccta gatccttta aattaaaaat    2280 gaagttttaa atcaatctaa agtatatatg agtaaacttg gtctgacagt taccaatgct    2340
taatcagtga ggcacctatc tcagcgatct gtctatttcg ttcatccata gttgcctgac    2400
tccccgtcgt gtagataact acgatacggg agggcttacc atctggcccc agtgctgcaa    2460
tgataccgcg agacccacgc tcaccggctc cagatttatc agcaataaac cagccagccg    2520
gaagggccga gcgcagaagt ggtcctgcaa ctttatccgc ctccatccag tctattaatt    2580
gttgccggga agctagagta agtagttcgc cagttaatag tttgcgcaac gttgttgcca    2640
ttgctacagg catcgtggtg tcacgctcgt cgtttggtat ggcttcattc agctccggtt    2700
cccaacgatc aaggcgagtt acatgatccc ccatgttgtg caaaaaagcg gttagctcct    2760
tcggtcctcc gatcgttgtc agaagtaagt tggccgcagt gttatcactc atggttatgg    2820
cagcactgca taattctctt actgtcatgc catccgtaag atgcttttct gtgactggtg    2880
agtactcaac caagtcattc tgagaatagt gtatgcggcg accgagttgc tcttgcccgg    2940
cgtcaatacg ggataatacc gcgccacata gcagaacttt aaaagtgctc atcattggaa    3000
aacgttcttc ggggcgaaaa ctctcaagga tcttaccgct gttgagatcc agttcgatgt    3060
aacccactcg tgcacccaac tgatcttcag catcttttac tttcaccagc gtttctgggt    3120
gagcaaaaac aggaaggcaa aatgccgcaa aaaagggaat aagggcgaca cggaaatgtt    3180
gaatactcat actcttcctt tttcaatatt attgaagcat ttatcagggt tattgtctca    3240
tgagcggata catatttgaa tgtatttaga aaaataaaca ataggggtt ccgcgcacat    3300 ttccccgaaa agtgccacct gacgcgccct gtagcggcgc attaagcgcg gcgggtgtgg    3360
tggttacgcg cagcgtgacc gctacacttg ccagcgccct agcgcccgct cctttcgctt    3420
tcttcccttc ctttctcgcc acgttcgccg gctttcccg tcaagctcta aatcgggggc    3480
tccctttagg gttccgattt agtgctttac ggcacctcga ccccaaaaaa cttgattagg    3540
gtgatggttc acgtagtggg ccatcgccct gatagacggt ttttcgccct ttgacgttgg    3600
agtccacgtt ctttaatagt ggactcttgt tccaaactgg aacaacactc aaccctatct    3660
cggtctattc ttttgattta agggattt tgccgatttc ggcctattgg ttaaaaaatg    3720
agctgattta acaaaaattt aacgcgaatt ttaacaaaat attaacgctt acaatttcca    3780
ttcgccattc aggctgcgca actgttggga agggcgatcg gtgcgggcct cttcgctatt    3840
acgccagctg gcgaaagggg gatgtgctgc aaggcgatta agttgggtaa cgccagggtt    3900
ttcccagtca cgacgttgta aaacgacggc cagtgaattg taatacgact cactataggg    3960
cgaattgggt accgggcccc cctcgaggt cgatggtgtc gataagcttg atatcgaatt    4020
catgtcacac aaaccgatct tcgcctcaag gaaacctaat tctacatccg agagactgcc    4080
```

-continued

```
gagatccagt ctacactgat taattttcgg gccaataatt taaaaaaatc gtgttatata    4140
atattatatg tattatatat atacatcatg atgatactga cagtcatgtc ccattgctaa    4200
atagacagac tccatctgcc gcctccaact gatgttctca atatttaagg ggtcatctcg    4260
cattgtttaa taataaacag actccatcta ccgcctccaa atgatgttct caaaatatat    4320
tgtatgaact tattttttatt acttagtatt attagacaac ttacttgctt tatgaaaaac    4380
acttcctatt taggaaacaa tttataatgg cagttcgttc atttaacaat ttatgtagaa    4440
taaatgttat aaatgcgtat gggaaatctt aaatatggat agcataaatg atatctgcat    4500
tgcctaattc gaaatcaaca gcaacgaaaa aaatcccttg tacaacataa atagtcatcg    4560
agaaatatca actatcaaag aacagctatt cacacgttac tattgagatt attattggac    4620
gagaatcaca cactcaactg tctttctctc ttctagaaat acaggtacaa gtatgtacta    4680
ttctcattgt tcatacttct agtcatttca tcccacatat tccttggatt tctctccaat    4740
gaatgacatt ctatcttgca aattcaacaa ttataataag atataccaaa gtagcggtat    4800
agtggcaatc aaaaagcttc tctggtgtgc ttctcgtatt tattttttatt ctaatgatcc    4860
attaaaggta tatatttatt tcttgttata taatcctttt gtttattaca tgggctggat    4920
acataaaggt attttgattt aattttttgc ttaaattcaa tcccccctcg ttcagtgtca    4980
actgtaatgg taggaaatta ccatactttt gaagaagcaa aaaaaatgaa agaaaaaaaa    5040
aatcgtattt ccaggttaga cgttccgcag aatctagaat gcggtatgcg gtacattgtt    5100
cttcgaacgt aaaagttgcg ctccctgaga tattgtacat ttttgctttt acaagtacaa    5160
gtacatcgta caactatgta ctactgttga tgcatccaca acagtttgtt ttgttttttt    5220
ttgttttttt tttttctaat gattcattac cgctatgtat acctacttgt acttgtagta    5280
agccgggtta ttggcgttca attaatcata gacttatgaa tctgcacggt gtgcgctgcg    5340
agttacttttt agcttatgca tgctacttgg gtgtaatatt gggatctgtt cggaaatcaa    5400
cggatgctca atcgatttcg acagtaatta attaagtcat acacaagtca gctttcttcg    5460
agcctcatat aagtataagt agttcaacgt attagcactg tacccagcat ctccgtatcg    5520
agaaacacaa caacatgccc cattggacag atcatgcgga tacacaggtt gtgcagtatc    5580
atacatactc gatcagacag gtcgtctgac catcatacaa gctgaacaag cgctccatac    5640
ttgcacgctc tctatataca cagttaaatt acatatccat agtctaacct ctaacagtta    5700
atcttctggt aagcctccca gccagccttc tggtatcgct tggcctcctc aataggatct    5760
cggttctggc cgtacagacc tcggccgaca attatgatat ccgttccggt agacatgaca    5820
tcctcaacag ttcggtactg ctgtccgaga gcgtctccct tgtcgtcaag acccaccccg    5880
ggggtcagaa taagccagtc ctcagagtcg cccttaggtc ggttctgggc aatgaagcca    5940
accacaaact cggggtcgga tcgggcaagc tcaatggtct gcttggagta ctcgccagtg    6000
gccagagagc ccttgcaaga cagctcggcc agcatgagca gacctctggc cagcttctcg    6060
ttgggagagg ggactaggaa ctccttgtac tgggagttct cgtagtcaga gacgtcctcc    6120
ttcttctgtt cagagacagt ttcctcggca ccagctcgca ggccagcaat gattccggtt    6180
ccgggtacac cgtgggcgtt ggtgatatcg gaccactcgg cgattcggtg acaccggtac    6240
tggtgcttga cagtgttgcc aatatctgcg aactttctgt cctcgaacag gaagaaaccg    6300
tgcttaagag caagttcctt gagggggagc acagtgccgg cgtaggtgaa gtcgtcaatg    6360
atgtcgatat gggttttgat catgcacaca taaggtccga cccttatcggc aagctcaatg    6420
agctccttgg tggtggtaac atccagagaa gcacacaggt tggttttctt ggctgccacg    6480
```

```
-continued agcttgagca ctcgagcggc aaaggcggac ttgtggacgt tagctcgagc ttcgtaggag    6540 ggcatttttgg tggtgaagag gagactgaaa taaatttagt ctgcagaact tttatcgga     6600 accttatctg gggcagtgaa gtatatgtta tggtaatagt tacgagttag ttgaacttat    6660
agatagactg gactatacgg ctatcggtcc aaattagaaa gaacgtcaat ggctctctgg    6720
gcgtcgcctt tgccgacaaa aatgtgatca tgatgaaagc cagcaatgac gttgcagctg    6780
atattgttgt cggccaaccg cgccgaaaac gcagctgtca gacccacagc ctccaacgaa    6840
gaatgtatcg tcaaagtgat ccaagcacac tcatagttgg agtcgtactc caaaggcggc    6900
aatgacgagt cagacagata ctcgtcgacg tttaaacagt gtacgcagat ctactataga    6960
ggaacattta aattgccccg gagaagacgg ccaggccgcc tagatgacaa attcaacaac    7020
tcacagctga ctttctgcca ttgccactag gggggggcct ttttatatgg ccaagccaag    7080
ctctccacgt cggttgggct gcacccaaca ataaatgggt agggttgcac caacaaaggg    7140
atgggatggg gggtagaaga tacgaggata acggggctca atggcacaaa taagaacgaa    7200
tactgccatt aagactcgtg atccagcgac tgacaccatt gcatcatcta agggcctcaa    7260
aactacctcg gaactgctgc gctgatctgg acaccacaga ggttccgagc actttaggtt    7320
gcaccaaatg tcccaccagg tgcaggcaga aaacgctgga acagcgtgta cagtttgtct    7380
taacaaaaag tgagggcgct gaggtcgagc agggtggtgt gacttgttat agcctttaga    7440
gctgcgaaag cgcgtatgga tttggctcat caggccagat tgagggtctg tggacacatg    7500
tcatgttagt gtacttcaat cgcccctgg atatagcccc gacaataggc cgtggcctca     7560 ttttttttgcc ttccgcacat ttccattgct cgatacccac accttgcttc tcctgcactt   7620 gccaaccttta atactggttt acattgacca acatcttaca agcgggggc ttgtctaggg    7680 tatatataaa cagtggctct cccaatcggt tgccagtctc ttttttcctt tctttcccca    7740
cagattcgaa atctaaacta cacatcacag aattccgagc cgtgagtatc cacgacaaga    7800
tcagtgtcga gacgacgcgt tttgtgtaat gacacaatcc gaaagtcgct agcaacacac    7860
actctctaca caaactaacc cagctctggt ac                                    7892
```